(12) United States Patent
Ellsworth et al.

(10) Patent No.: US 9,604,964 B2
(45) Date of Patent: Mar. 28, 2017

(54) DIHYDROPYRAZOLE GPR40 MODULATORS

(71) Applicant: BRISTOL-MYERS SQUIBB COMPANY, Princeton, NJ (US)

(72) Inventors: Bruce A. Ellsworth, Princeton, NJ (US); Jun Shi, Pennington, NJ (US); William R. Ewing, Yardley, PA (US); Elizabeth A. Jurica, Robbinsville, NJ (US); Andres S. Hernandez, Lawrenceville, NJ (US); Ximao Wu, Princeton Junction, NJ (US); Zhengxiang Gu, Piscataway, NJ (US); Zhenqiu Hong, Princeton, NJ (US); Stephen P. O'Connor, Asbury Park, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 123 days.

(21) Appl. No.: 14/442,670

(22) PCT Filed: Nov. 15, 2013

(86) PCT No.: PCT/US2013/070216
§ 371 (c)(1),
(2) Date: May 13, 2015

(87) PCT Pub. No.: WO2014/078611
PCT Pub. Date: May 22, 2014

(65) Prior Publication Data
US 2016/0297797 A1    Oct. 13, 2016

Related U.S. Application Data

(60) Provisional application No. 61/727,262, filed on Nov. 16, 2012.

(51) Int. Cl.
| | | |
|---|---|---|
| C07D 401/12 | (2006.01) |
| C07D 401/14 | (2006.01) |
| C07D 405/12 | (2006.01) |
| C07D 405/14 | (2006.01) |
| C07D 417/14 | (2006.01) |
| C07D 403/12 | (2006.01) |
| C07D 451/06 | (2006.01) |
| A61K 45/06 | (2006.01) |
| A61K 31/4545 | (2006.01) |
| A61K 31/4155 | (2006.01) |
| C07D 413/14 | (2006.01) |
| C07D 401/10 | (2006.01) |
| C07D 487/08 | (2006.01) |

(Continued)

(52) U.S. Cl.
CPC ........ *C07D 401/12* (2013.01); *A61K 31/4155* (2013.01); *A61K 31/454* (2013.01); *A61K 31/4545* (2013.01); *A61K 31/46* (2013.01);
*A61K 31/497* (2013.01); *A61K 31/506* (2013.01); *A61K 31/55* (2013.01); *A61K 45/06* (2013.01); *C07D 401/10* (2013.01); *C07D 401/14* (2013.01); *C07D 403/12* (2013.01); *C07D 405/12* (2013.01); *C07D 405/14* (2013.01); *C07D 413/14* (2013.01); *C07D 417/14* (2013.01); *C07D 451/06* (2013.01); *C07D 471/08* (2013.01); *C07D 487/08* (2013.01)

(58) Field of Classification Search
None
See application file for complete search history.

(56) References Cited

U.S. PATENT DOCUMENTS

| | | |
|---|---|---|
| 5,614,492 A | 3/1997 | Habener |
| 8,236,812 B2 | 8/2012 | Honigberg et al. |

(Continued)

FOREIGN PATENT DOCUMENTS

| | | |
|---|---|---|
| EP | 1 637 522 A1 | 3/2006 |
| EP | 1 743 894 A1 | 1/2007 |

(Continued)

OTHER PUBLICATIONS

Arbeeny, C. et al., "The Metabolic Syndrome: From Pathophysiology to Novel Treatment Strategies", Curr. Med. Chem.—Imm., Endoc. & Metab. Agents, vol. 1, No. 1, pp. 1-24 (2001).

(Continued)

*Primary Examiner* — Nyeemah A Grazier
(74) *Attorney, Agent, or Firm* — Barry H. Jacobsen; Yong Lu

(57) ABSTRACT

The present invention provides compounds of Formula (I): (Formula (I), or a stereoisomer, or a pharmaceutically acceptable salt thereof, wherein all of the variables are as defined herein. These compounds are GPR40 G protein-coupled receptor modulators which may be used as medicaments.

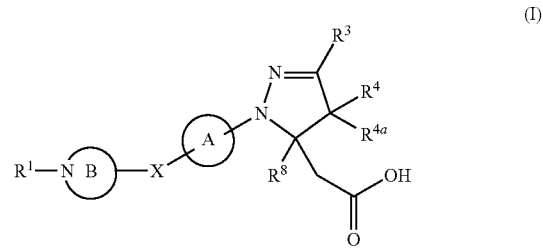

12 Claims, 2 Drawing Sheets

(51) Int. Cl.
*A61K 31/454* (2006.01)
*A61K 31/46* (2006.01)
*A61K 31/497* (2006.01)
*A61K 31/506* (2006.01)
*A61K 31/55* (2006.01)
*C07D 471/08* (2006.01)

(56) References Cited

U.S. PATENT DOCUMENTS

| | | | |
|---|---|---|---|
| 8,236,821 B2 | 8/2012 | McElroy et al. | |
| 8,288,404 B2 | 10/2012 | Ellsworth et al. | |
| 8,791,091 B2 | 7/2014 | Turdi et al. | |
| 9,133,163 B2 * | 9/2015 | Ellsworth | C07D 401/12 |
| 2016/0280659 A1 * | 9/2016 | Hernandez | C07D 403/12 |

FOREIGN PATENT DOCUMENTS

| | | |
|---|---|---|
| EP | 1743888 | 1/2007 |
| JP | 2011001349 A * | 1/2011 |
| WO | WO2004/099192 A2 | 11/2004 |
| WO | WO 2005/012249 | 2/2005 |
| WO | WO 2009/115515 | 9/2009 |
| WO | WO 2012/068529 | 5/2012 |

OTHER PUBLICATIONS

Barlind, J.G. et al., "Identification and design of a novel series of MGAT2 inhibitors", Bioorganic & Medicinal Chemistry Letters, vol. 23, pp. 2721-2726 (2013).

Bundgaard, H., Chapter 5: "Design and Application of Prodrugs", A Textbook of Drug Design and Development, pp. 113-191, Krogsgaard-Larsen, P. et al., eds., Harwood Academic Publishers, publ. (1991).

Bundgaard, H., ed., Design of Prodrugs, Elsevier Science Publishers B.V., publ. (1985).

Bundgaard, H., "Prodrugs as a means to improve the delivery of peptide drugs", Advanced Drug Delivery Reviews, vol. 8, pp. 1-38 (1992).

De Benassuti, L. et al., "Oxygenated monoterpenes as dipolarophiles for nitrilimine cycloadditions", Tetrahedron, vol. 60, pp. 4627-4633 (2004).

Edfalk, S. et al., "*Gpr40* is Expressed in Enteroendocrine Cells and Mediates Free Fatty Acid Stimulation of Incretin Secretion", Diabetes, vol. 57, pp. 2280-2287 (2008).

Elangbam, C.S., "Review Paper: Current Strategies in the Development of Anti-obesity Drugs and Their Safety Concerns", Vet. Pathol., vol. 46, No. 1, pp. 10-24 (2009).

Ford, E.S. et al., "Prevalence of the Metabolic Syndrome Among US Adults: Findings from the Third National Health and Nutrition Examination Survey", Journal of the American Medical Association, vol. 287, No. 3, pp. 356-359 (2002).

Fyfe, M.C.T. et al., "Glucokinase Activators as Potential Antidiabetic Agents Possessing Superior Glucose-Lowering Efficacy", Drugs of the Future, vol. 34, No. 8, pp. 641-653 (2009).

Garanti, L. et al., "Diastereoselective cycloadditions of nitrilimines to enantiopure acrylamides", Tetrahedron: Asymmetry, vol. 13, pp. 1285-1289 (2002).

Itoh, Y. et al., "Free fatty acids regulate insulin secretion from pancreatic β cells through GPR40", Nature, vol. 422, pp. 173-176 (2003).

Jones, D., "Novel pharmacotherapies for obesity poised to enter market", Nature Reviews: Drug Discovery, vol. 8, pp. 833-834 (2009).

Kakeya, N. et al., "Studies on Prodrugs of Cephalosporins. I. Synthesis and Biological Properties of Glycyloxybenzoyloxymethyl and Glycylaminobenzoyloxymethyl Esters of 7β-[2-(2-Aminothiazol-4-yl)-(Z)-2-methoxyiminoacetamido]-3-methyl-3-cephem-4-carboxylic Acid", Chem. Pharm. Bull., vol. 32, No. 2, pp. 692-698 (1984).

Larock, R.C., Comprehensive Organic Transformations: A Guide to Functional Group Preparations, pp. xiii-xxviii, Vch Publishers, Inc., publ. (1989).

Lewis, Sr., R.J., Hawley's Condensed Chemical Dictionary, Thirteenth Edition, John Wiley & Sons, Inc., publ. (1997).

Luo, S. et al., "The Cotton Centromere Contains a Ty3-*gypsy*-like LTR Retroelement", PLoS ONE, vol. 7, No. 4, pp. 1-10 (2012).

Manyem, S. et al., "Solution-Phase Parallel Synthesis of a Library of $\Delta^2$-Pyrazolines", J. Comb. Chem., vol. 9, No. 1, pp. 20-28 (2007).

Melnikova, I. et al., "Anti-obesity therapies", Nature Reviews Drug Discovery, 5, pp. 369-370 (2006).

Mizuno, C.S. et al., "Type 2 Diabetes and Oral Antihyperglycemic Drugs", Current Medicinal Chemistry, vol. 15, No. 1, pp. 61-74 (2008).

Mohler, M.L. et al., "Recent and Emerging Anti-Diabetes Targets", Medicinal Research Reviews, vol. 29, No. 1, pp. 125-195 (2009).

Molteni, G., "The first case of diastereoselective cycloadditions of enantiopure nitrilimines in aqueous media", Tetrahedron: Asymmetry, vol. 15, pp. 1077-1079 (2004).

NCBI Reference Sequence No. NM_005303, Kristinsson, H. et al., Feb. 20, 2014.

NCBI Reference Sequence No. NM_194057, Shen, X. et al., May 24, 2014.

Nielsen, N.M. et al., "Glycolamide Esters as Biolabile Prodrugs of Carboxylic Acid Agents: Synthesis, Stability, Bioconversion, and Physicochemical Properties", Journal of Pharmaceutical Sciences, vol. 77, No. 4, pp. 285-298 (1988).

Obici, S., "Minireview: Molecular Targets for Obesity Therapy in the Brain", Endocrinology, vol. 150, No. 6, pp. 2512-2517 (2009).

Semmelhack, M.F., ed., Comprehensive Organic Synthesis: Selectivity, Strategy & Efficiency in Modern Organic Chemistry, vol. 4: "Additions to and Substitutions at C—C π-Bonds", pp. v-vi, Pergamon Press, Inc., publ. (1991).

Shimizu, T. et al., "The Reaction of N-Aryl-C-ethoxycarbonylnitrilimine with Olefins", Bull. Chem. Soc. Jpn., vol. 57, No. 3, pp. 787-790 (1984).

Shimpukade, B. et al., "Discovery of a Potent and Selective GPR120 Agonist", Journal of Medicinal Chemistry, vol. 55, pp. 4511-4515 (2012).

Sibi, M.P. et al., "An Entry to a Chiral Dihydropyrazole Scaffold: Enantioselective [3 + 2] Cycloaddition of Nitrile (mines", J. Am. Chem. Soc., vol. 127, No. 23, pp. 8276-8277 (2005).

Sibi, M.P. et al., "Nitrile Ylides: Diastereoselective Cycloadditions using Chiral Oxzolidinones without Lewis Acid", Organic Letters, vol. 11, No. 23, pp. 5366-5369 (2009).

Simpkins, L.M. et al., "Potent non-nitrile dipeptidic dipeptidyl peptidase Iv inhibitors", Bioorganic & Medicinal Chemistry Letters, vol. 17, pp. 6476-6480 (2007).

Smith, M.B. et al., Mar.'s Advanced Organic Chemistry: Reactions, Mechanisms, and Structure, Sixth Edition, John Wiley & Sons, Inc. (2007).

Tan, C.P. et al., "Selective Small-Molecule Agonists of G Protein-Coupled Receptor 40 Promote Glucose-Dependent Insulin Secretion and Reduce Blood Glucose in Mice", Diabetes, vol. 57, pp. 2211-2219 (2008).

Testa, B. et al., Hydrolysis in Drug and Prodrug Metabolism: Chemistry, Biochemistry, and Enzymology, pp. xi-xx, Wiley-VCH GmbH & Co., publ. (2003).

Tortolani, D.R. et al., "A Convenient Synthesis to N-Aryl-Substituted 4-Piperidones", Organic Letters, vol. 1, No. 8, pp. 1261-1262 (1999).

Widder, K.J. et al., eds., Section III: "Prodrugs", Methods in Enzymology, vol. 112, pp. 309-396, Academic Press, Inc., publ. (1985).

Yamashima, T., "A putative link of PUFA, GPR40 and adult-born hippocampal neurons for memory", Progress in Neurobiology, vol. 84, pp. 105-115 (2008).

* cited by examiner

Glucose excursion curve in rats from an acute combination study of Example 81, Isomer 2 with BMS DPP4i.

Plasma GLP-1 levels upon administration to rats from a combination study of Example 81, Isomer 2 with BMS DPP4i

DIHYDROPYRAZOLE GPR40 MODULATORS

CROSS-REFERENCE TO RELATED APPLICATIONS

The present application is a 371 of International Application No. PCT/US2013/070216 filed on Nov. 15, 2013, which claims priority benefit of U.S. provisional application Ser. No. 61/727,262, filed Nov. 16, 2012; each of which is fully incorporated by reference herein.

FIELD OF THE INVENTION

The present invention provides novel carboxylic acid substituted dihydropyrazole compounds, and their analogues thereof, which are GPR40 G protein-coupled receptor modulators, compositions containing them, and methods of using them, for example, for the treatment or prophylaxis of diabetes and related conditions.

BACKGROUND OF THE INVENTION

Diabetes mellitus is a progressively debilitating disorder of epidemic proportions leading to various micro- and macrovascular complications and morbidity. The most common type of diabetes, type 2 diabetes, is characterized by increasing insulin resistance associated with inadequate insulin secretion after a period of compensatory hyperinsulinemia. Free fatty acids (FFAs) are evidenced to influence insulin secretion from β cells primarily by enhancing glucose-stimulated insulin secretion (GSIS). G-protein coupled receptors (GPCRs) expressed in β cells are known to modulate the release of insulin in response to changes in plasma glucose levels. GPR40, also known as fatty acid receptor 1 (FFAR1), is a membrane-bound FFA receptor which is preferentially expressed in the pancreatic islets and specifically in β cells and mediates medium to long chain fatty acid induced insulin secretion. GPR40 is also expressed in enteroendocrine cells wherein activation promotes the secretion of gut incretin hormones, such as GLP-1, GIP, CCK and PYY. To decrease medical burden of type 2 diabetes through enhanced glycemic control, GPR40 modulator compounds hold the promise of exerting an incretin effect to promote GSIS as well as potential combination with a broad range of antidiabetic drugs.

The present invention relates to novel substituted dihydropyrazole compounds which have the ability to modulate GPR40. Such compounds are therefore potentially useful for the treatment or prophylaxis of diabetes and related conditions.

SUMMARY OF THE INVENTION

The present invention provides substituted dihydropyrazole compounds, and their analogues thereof, which are useful as GPR40 modulators, including stereoisomers, tautomers, pharmaceutically acceptable salts, or solvates thereof.

The present invention also provides processes and intermediates for making the compounds of the present invention or stereoisomers, tautomers, pharmaceutically acceptable salts, or solvates thereof.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of multiple diseases or disorders associated with GPR40, such as diabetes and related conditions, microvascular complications associated with diabetes, the macrovascular complications associated with diabetes, cardiovascular diseases, Metabolic Syndrome and its component conditions, disorders of glucose metabolism, obesity and other maladies.

The compounds of the invention may be used in therapy.

The compounds of the invention may be used for the manufacture of a medicament for the treatment and/or prophylaxis of multiple diseases or disorders associated with GPR40.

The compounds of the invention can be used alone, in combination with other compounds of the present invention, or in combination with one or more other agent(s).

Other features and advantages of the invention will be apparent from the following detailed description and claims.

BRIEF DESCRIPTION OF THE DRAWINGS

The invention is illustrated by reference to the accompanying drawings described below.

DETAILED DESCRIPTION OF THE INVENTION

I. Compounds of the Invention

Figure 1:
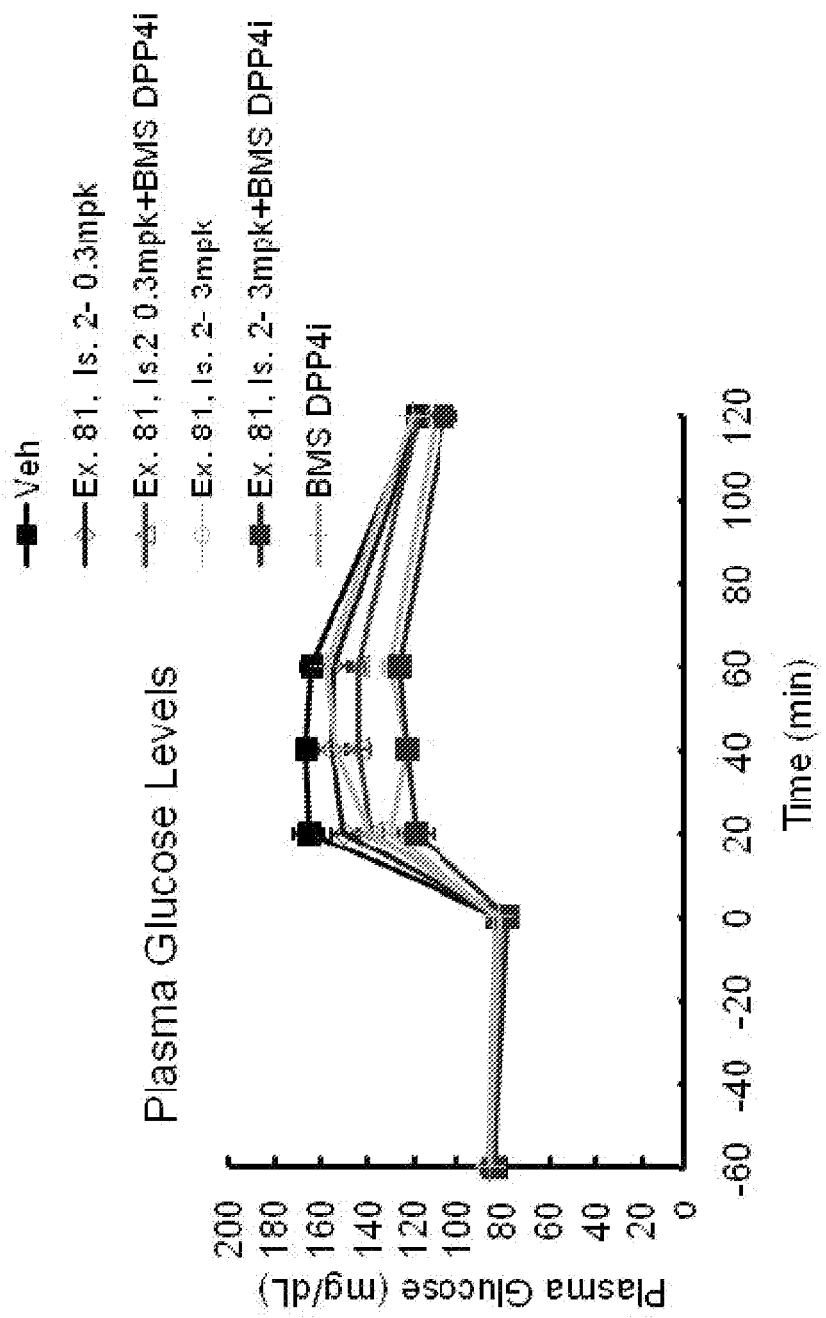
FIG. 1 shows a glucose excursion curve in rats an acute combination study of Example 81, Isomer 2 with BMS DPP4i.

In a first aspect, the present disclosure provides, inter alia, a compound of Formula (I):

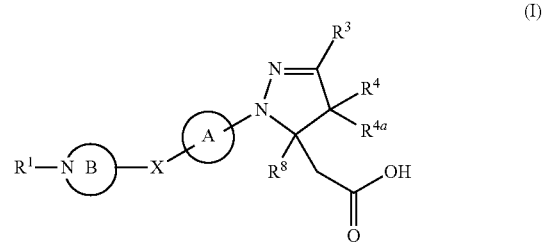

or a stereoisomer, a tautomer, a pharmaceutically acceptable salt, or a solvate thereof, wherein:

X is independently selected from: a bond, O, S, NH, N($C_{1-4}$ alkyl), $CH_2$, $CH_2CH_2$, CH($C_{1-4}$ alkyl), $OCH_2$, $CH_2O$, $OCH_2CH_2$, and $CH_2CH_2O$;

ring A is independently

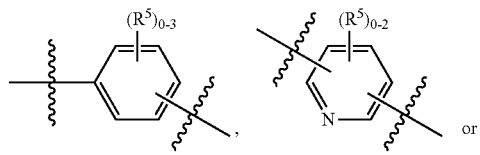

or

-continued

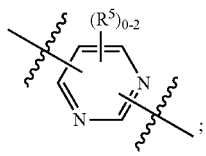

ring B is independently a 4- to 7-membered saturated heterocycle containing carbon atoms, the nitrogen atom shown in the ring B and 0-1 additional heteroatom selected from N, O, and S; and ring B is substituted with 0-4 $R^2$;

$R^1$ is independently $CO_2R^9$, $SO_2R^9$,

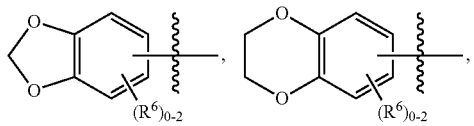

phenyl, benzyl, naphthyl or a 5- to 10-membered heteroaryl containing carbon atoms and 1-4 heteroatoms selected from N, $NR^{11}$, O, and S; wherein said phenyl, benzyl, naphthyl and heteroaryl are each substituted with 0-3 $R^6$;

$R^2$, at each occurrence, is independently selected from: =O, OH, halogen, $C_{1-6}$ alkyl substituted with 0-1 $R^{12}$, $C_{1-6}$ alkoxy substituted with 0-1 $R^{12}$, $C_{1-4}$ haloalkyl substituted with 0-1 $R^{12}$, $C_{1-4}$ haloalkoxy substituted with 0-1 $R^{12}$, —$(CH_2)_m$—$C_{3-6}$ carbocycle substituted with 0-1 $R^{12}$, and —$(CH_2)_m$-(5- to 10-membered heteroaryl containing carbon atoms and 1-4 heteroatoms selected from N, $NR^{11}$, O, and S); wherein said heteroaryl is substituted with 0-1 $R^{12}$;

when two $R^2$ groups are attached to two different carbon atoms, they may combine to form a 1- to 3-membered carbon atom bridge over ring B;

when two $R^2$ groups are attached to the same carbon, they may combine, together with the carbon atom to which they are attached, to form a 3- to 6-membered carbon atom containing spiro ring;

$R^3$ is independently selected from: H, halogen, CN, OH, $CO_2H$, $C_{1-6}$ alkyl, $C_{2-6}$ alkenyl, $C_{2-6}$ alkynyl, $C_{1-6}$ haloalkyl, —$N(C_{1-4}$ alkyl$)SO_2Ph$, $OR^9$, $SR^9$, $C(O)OR^9$, $CO_2R^9$, $S(O)R^9$, $SO_2R^9$, $CONHR^9$, $CON(C_{1-4}$ alkyl$)_2$, —$(O)_n$—$(CH_2)_m$-(phenyl substituted with 0-2 $R^{10}$), —$(O)_n$—$(CH_2)_m$-(5- to 10-membered heteroaryl containing carbon atoms and 1-4 heteroatoms selected from N, $NR^{11}$, O, and S; wherein said heteroaryl is substituted with 0-2 $R^{10}$);

$R^4$ is independently selected from: H, $C_{1-6}$ alkyl substituted with 0-1 $R^c$, $C_{1-6}$ alkoxy, and —$(CH_2)_m$—$C_{3-6}$ carbocycle substituted with 0-2 $R^c$;

$R^{4a}$ is independently selected from: H, halogen, $C_{1-6}$ alkyl, $C_{1-6}$ alkoxy, and —$(CH_2)_m$—$C_{3-6}$ carbocycle;

$R^5$, at each occurrence, is independently selected from: halogen, $C_{1-6}$ alkyl, and $C_{1-6}$ alkoxy;

$R^6$, at each occurrence, is independently selected from: halogen, OH, $C_{1-4}$ alkylthio, CN, $SO_2(C_{1-2}$ alkyl), $N(C_{1-4}$ alkyl$)_2$, $C_{1-4}$ haloalkyl, $C_{1-4}$ haloalkoxy, $C_{1-8}$ alkyl substituted with 0-1 $R^7$, $C_{1-6}$ alkoxy substituted with 0-1 $R^7$, —$(O)_n$—$(CH_2)_m$—$(C_{3-10}$ carbocycle substituted with 0-2 $R^7$), and —$(CH_2)_m$-(5- to 10-membered heteroaryl containing carbon atoms and 1-4 heteroatoms selected from N, $NR^{11}$, O, and S; wherein said heteroaryl is substituted with 0-2 $R^7$;

$R^7$, at each occurrence, is independently selected from: halogen, OH, $C_{1-4}$ alkyl, $C_{2-4}$ alkenyl, $C_{1-4}$ alkoxy, $C_{1-4}$ alkylthio, $C_{1-4}$ haloalkyl, $C_{1-4}$ haloalkoxy, $SCF_3$, CN, $NO_2$, $NH_2$, $NH(C_{1-4}$ alkyl), $N(C_{1-4}$ alkyl$)_2$, $SO_2(C_{1-2}$ alkyl), and phenyl;

$R^8$ is independently selected from: H and $C_{1-4}$ alkyl;

$R^9$, at each occurrence, is independently selected from: $C_{1-6}$ alkyl, $C_{1-4}$ haloalkyl, —$(CH_2)_m$—$(C_{3-6}$ cycloalkyl substituted with 0-2 $R^{10}$), and —$(CH_2)_m$-(phenyl substituted with 0-2 $R^{10}$);

$R^{10}$ and $R^{12}$, at each occurrence, is independently selected from: OH, halogen, CN, $C_{1-4}$ alkyl, $C_{1-4}$ alkoxy, $C_{1-4}$ haloalkyl, $C_{1-4}$ haloalkoxy, $SCF_3$, $NO_2$, $CO_2(C_{1-4}$ alkyl), $SO_2(C_{1-4}$ alkyl), and tetrazolyl;

$R^{11}$, at each occurrence, is independently selected from: H, $C_{1-4}$ alkyl and benzyl;

$R^c$, at each occurrence, is independently selected from: OH, $C_{1-4}$ alkoxy, halogen, $CF_3$, $OCF_3$, and CN;

m, at each occurrence, is independently 0, 1, or 2; and n, at each occurrence, is independently 0 or 1.

In a second aspect, the present disclosure provides a compound of Formula (1a):

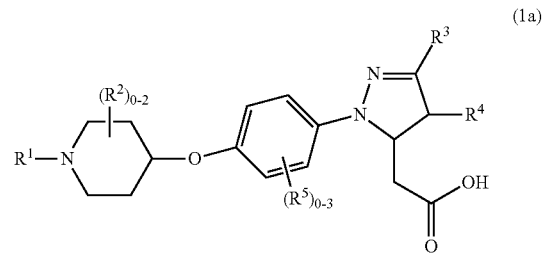

or a stereoisomer, a tautomer, a pharmaceutically acceptable salt, or a solvate thereof, wherein:

$R^1$ is independently phenyl substituted with 0-3 $R^6$ or pyridinyl substituted with 0-3 $R^6$;

$R^2$ is, at each occurrence, independently halogen or $C_{1-4}$ alkyl;

$R^3$ is independently selected from: $CF_3$, 4-halo-Ph, 4-CN-Ph, 4-$CO_2(C_{1-2}$ alkyl)-Ph, 2-halo-4-CN-Ph, and pyrimidin-2-yl;

$R^4$ is independently $C_{1-4}$ alkyl or cyclopropylmethyl;

$R^5$ is, at each occurrence, independently halogen; and $R^6$, at each occurrence, is independently selected from: OH, halogen, CN, $C_{1-4}$ alkyl, and $C_{1-4}$ alkoxy.

In a third aspect, the present disclosure provides the compound of the first aspect wherein the compound of the second aspect is excluded.

In a fourth aspect, the present disclosure provides a compound of Formula (I), wherein $R^{4a}$ is hydrogen and $R^8$ is hydrogen, further characterized by Formula (II):

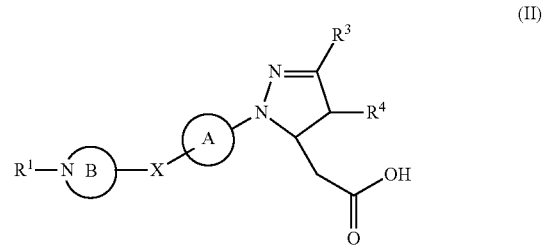

or a stereoisomer, a tautomer, a pharmaceutically acceptable salt, or a solvate thereof, wherein:

X is independently selected from: a bond, O, S, NH, N(C$_{1-4}$ alkyl), CH$_2$, CH$_2$CH$_2$, CH(C$_{1-4}$ alkyl), OCH$_2$, CH$_2$O, OCH$_2$CH$_2$, and CH$_2$CH$_2$O;

ring A is independently

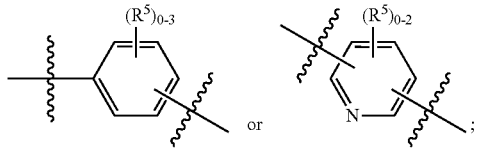

or ring B is independently a 4- to 7-membered saturated heterocycle containing carbon atoms and the nitrogen atom shown in ring B; and ring B is substituted with 0-4 R$^2$;

R$^1$ is independently CO$_2$(C$_{1-4}$ alkyl), CO$_2$Bn,

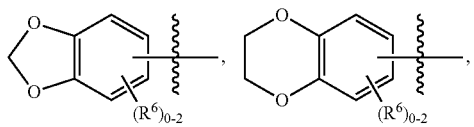

phenyl, benzyl, naphthyl or a 5- to 10-membered heteroaryl containing carbon atoms and 1-4 heteroatoms selected from N, NR$^{11}$, O, and S; wherein said phenyl, benzyl, naphthyl and heteroaryl are each substituted with 0-3 R$^6$;

R$^2$, at each occurrence, is independently selected from: =O, OH, halogen, C$_{1-6}$ alkyl substituted with 0-1 R$^{12}$, C$_{1-6}$ alkoxy substituted with 0-1 R$^{12}$, C$_{1-4}$ haloalkyl, C$_{1-4}$ haloalkoxy, and benzyl;

when two R$^2$ groups are attached to two different carbon atoms, they may combine to form a 1- to 3-membered carbon atom bridge over ring B;

when two R$^2$ groups are attached to the same carbon, they may combine, together with the carbon atom to which they are attached, to form a 3- to 6-membered carbon atom containing spiro ring;

R$^3$ is independently selected from: H, halogen, CN, SO$_2$(C$_{1-4}$ alkyl), CONH(C$_{1-4}$ alkyl), CON(C$_{1-4}$ alkyl)$_2$, C$_{1-4}$ alkyl, C$_{1-4}$ alkoxy, C$_{1-4}$ alkylthio, C$_{1-4}$ haloalkyl, C$_{1-4}$ haloalkoxy, —N(C$_{1-4}$ alkyl)SO$_2$Ph, —(O)$_n$—(CH$_2$)$_m$-(phenyl substituted with 0-2 R$^{10}$), and —(O)$_n$—(CH$_2$)$_m$-(a 5- to 10-membered heteroaryl containing carbon atoms and 1-4 heteroatoms selected from N, NR$^{11}$, O, and S; wherein said heteroaryl is substituted with 0-2 R$^{10}$);

R$^4$ is independently selected from: H, halogen, C$_{1-4}$ alkyl, C$_{1-4}$ alkoxy, and —(CH$_2$)$_m$—C$_{3-6}$ carbocycle;

R$^5$, at each occurrence, is independently selected from: halogen, C$_{1-6}$ alkyl, and C$_{1-6}$ alkoxy;

R$^6$, at each occurrence, is independently selected from: halogen, OH, C$_{1-4}$ alkylthio, CN, SO$_2$(C$_{1-2}$ alkyl), N(C$_{1-4}$ alkyl)$_2$, C$_{1-4}$ haloalkyl, C$_{1-4}$ haloalkoxy, C$_{1-6}$ alkyl substituted with 0-1 R$^7$, C$_{1-4}$ alkoxy substituted with 0-1 R$^7$, —(O)$_n$—(CH$_2$)$_m$—(C$_{3-6}$ carbocycle substituted with 0-2 R$^7$), —(CH$_2$)$_m$— (naphthyl substituted with 0-2 R$^7$), and —(CH$_2$)$_m$-(5- to 10-membered heteroaryl containing carbon atoms and 1-4 heteroatoms selected from N, NR$^{11}$, O, and S; wherein said heteroaryl is substituted with 0-2 R$^7$;

R$^7$, at each occurrence, is independently selected from: halogen, OH, C$_{1-4}$ alkyl, C$_{2-4}$ alkenyl, C$_{1-4}$ alkoxy, C$_{1-4}$ alkylthio, C$_{1-4}$ haloalkyl, C$_{1-4}$ haloalkoxy, SCF$_3$, CN, NO$_2$, NH$_2$, NH(C$_{1-4}$ alkyl), N(C$_{1-4}$ alkyl)$_2$, SO$_2$(C$_{1-2}$ alkyl), and phenyl;

R$^{10}$ and R$^{12}$, at each occurrence, are independently selected from: OH, halogen, CN, C$_{1-4}$ alkyl, C$_{1-4}$ alkoxy, C$_{1-4}$ haloalkyl, C$_{1-4}$ haloalkoxy, SCF$_3$, NO$_2$, CO$_2$(C$_{1-4}$ alkyl), SO$_2$(C$_{1-4}$ alkyl), and tetrazolyl;

R$^{11}$, at each occurrence, is independently selected from: H, C$_{1-4}$ alkyl and benzyl;

m, at each occurrence, is independently 0, 1, or 2; and n, at each occurrence, is independently 0 or 1.

In a fifth aspect, the present disclosure provides the compound of the fourth aspect wherein the compound of the second aspect is excluded.

In a sixth aspect, the present disclosure includes a compound of Formula (I) or (II), or a stereoisomer, a tautomer, a pharmaceutically acceptable salt, or a solvate thereof, within the scope of any of the first, third, fourth and fifth aspects, wherein:

X is independently selected from: a bond, O, NH, N(CH$_3$), CH$_2$, CH$_2$CH$_2$, CH(CH$_3$), OCH$_2$, CH$_2$O, OCH$_2$CH$_2$, and CH$_2$CH$_2$O;

ring A is independently

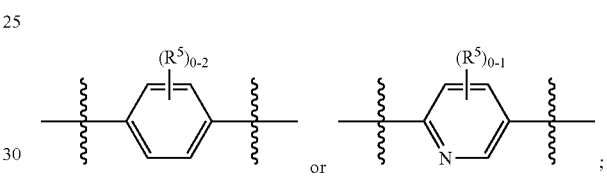

ring B is independently selected from:

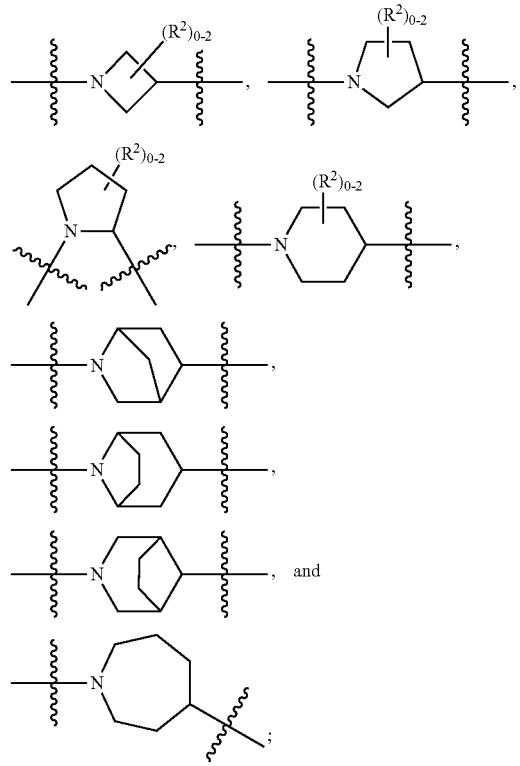

$R^1$ is independently $CO_2(C_{1-4}$ alkyl), $CO_2Bn$,

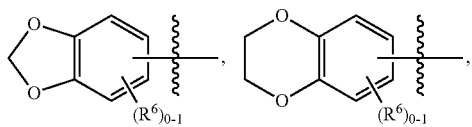

phenyl substituted with 0-3 $R^6$ or a heteroaryl substituted with 0-2 $R^6$; wherein said heteroaryl is selected from: furanyl, oxazolyl, thiazolyl, pyrazolyl, oxadiazolyl, pyridinyl, pyrimidinyl, pyrazinyl,

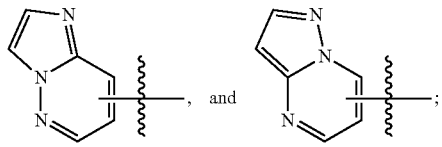

$R^2$, at each occurrence, is independently selected from: =O, OH, halogen, $C_{1-4}$ alkyl substituted with 0-1 $R^{12}$, $C_{1-4}$ alkoxy substituted with 0-1 $R^{12}$, and benzyl;

$R^3$ is independently selected from: H, halogen, CN, $SO_2$($C_{1-4}$ alkyl), $CONH(C_{1-4}$ alkyl), $CON(C_{1-4}$ alkyl)$_2$, —N($C_{1-4}$ alkyl)$SO_2Ph$, $C_{1-6}$ alkyl, $C_{1-6}$ alkoxy, $C_{1-4}$ haloalkyl, $C_{1-4}$ haloalkoxy, phenyl, benzyl, phenoxy, benzoxy, oxazolyl, 1-$C_{1-4}$ alkyl-pyrazolyl, triazolyl, tetrazolyl, pyridinyl, —O-pyridinyl, pyrimidinyl, —O-pyrimidinyl, and

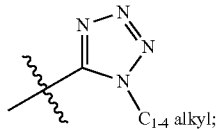

wherein each said ring moiety is each substituted with 0-2 $R^{10}$;

$R^4$ is independently selected from: H, halogen, $C_{1-4}$ alkyl, and —$(CH_2)_m$—$C_{3-6}$ carbocycle; and $R^6$, at each occurrence, is independently selected from: halogen, OH, $C_{1-6}$ alkyl substituted with 0-1 OH, $C_{1-4}$ alkoxy, $C_{1-4}$ alkylthio, $C_{1-4}$ haloalkyl, $C_{1-4}$ haloalkoxy, CN, $SO_2(C_{1-2}$ alkyl), $N(C_{1-4}$ alkyl)$_2$, $C_{3-6}$ cycloalkyl, —O—$C_{3-6}$ cycloalkyl, benzyl, and oxazolyl.

In a seventh aspect, the present disclosure provides a compound of Formula (1b):

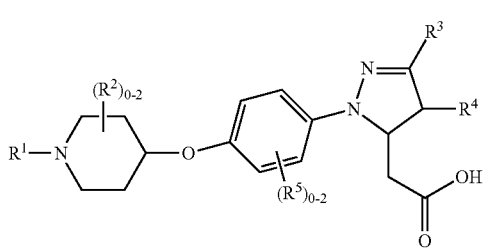

(1b)

or a stereoisomer, tautomer, a pharmaceutically acceptable salt, or a solvate thereof, wherein:

$R^1$ is independently phenyl substituted with 0-3 $R^6$ or pyridinyl substituted with 0-3 $R^6$;

$R^2$ is, at each occurrence, independently halogen or $C_{1-4}$ alkyl;

$R^3$ is independently selected from: $CF_3$, 4-halo-Ph, 4-CN-Ph, 4-$CO_2(C_{1-2}$ alkyl)-Ph, 2-halo-4-CN-Ph, and pyrimidin-2-yl;

$R^4$ is independently $C_{1-4}$ alkyl or cyclopropylmethyl;

$R^5$ is, at each occurrence, independently halogen;

$R^6$, at each occurrence, is independently selected from: OH, halogen, CN, $C_{1-4}$ alkyl, and $C_{1-4}$ alkoxy.

In an eighth aspect, the present disclosure provides the compound of the first aspect wherein the compound of the seventh aspect is excluded.

In a ninth aspect, the present disclosure includes a compound of Formula (I) or (II), or a stereoisomer, a tautomer, a pharmaceutically acceptable salt, or a solvate thereof, within the scope of any of the first, third, fourth, fifth, sixth and eighth aspects, wherein:

$R^1$ is independently

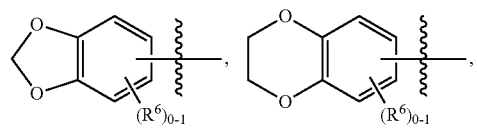

phenyl substituted with 0-3 $R^6$ or a heteroaryl substituted with 0-2 $R^6$; wherein said heteroaryl is selected from: thiazolyl, pyridinyl, pyrimidinyl, pyrazinyl,

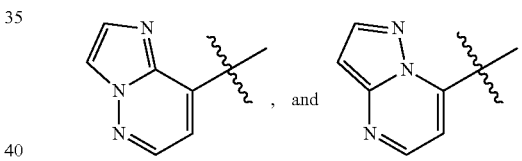

In a tenth aspect, the present disclosure includes a compound of Formula (I) or (II), or a stereoisomer, a tautomer, a pharmaceutically acceptable salt, or a solvate thereof, within the scope of any of the first, third, fourth, fifth, sixth, eighth and ninth aspects, wherein:

X is independently selected from: 0, $N(CH_3)$, $CH_2$, $CH_2O$, and $CH_2CH_2O$;

ring A is

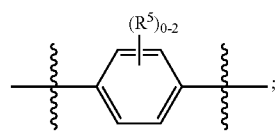

ring B is independently selected from:

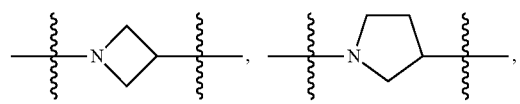

-continued

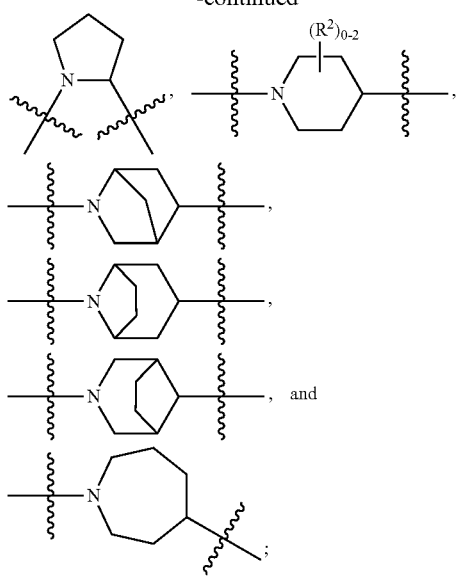

R¹ is independently phenyl substituted with 0-3 R⁶, pyridinyl substituted with 0-2 R⁶, pyrazinyl substituted with 0-2 R⁶, pyrimidinyl substituted with 0-2 R⁶, thiazolyl substituted with 0-2 R⁶,

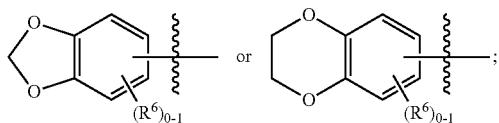

R², at each occurrence, is independently selected from: OH, halogen, $C_{1-4}$ alkyl substituted with 0-1 $R^{12}$, $C_{1-4}$ alkoxy substituted with 0-1 $C_{1-4}$ alkoxy, benzyl, and tetrazolylmethyl;

R³ is independently selected from: H, halogen, CN, $C_{1-4}$ alkyl, $C_{1-4}$ alkoxy, $C_{1-4}$ haloalkyl, $C_{1-4}$ haloalkoxy, phenyl, benzyl, phenoxy, benzoxy, —N($C_{1-4}$ alkyl)SO₂Ph, 1-$C_{1-4}$ alkyl-pyrazolyl, triazolyl, tetrazolyl, pyridinyl, —O-pyridinyl, pyrimidinyl, and —O-pyrimidinyl; wherein said phenyl, benzyl, phenoxy and pyridinyl are each substituted with 0-2 $R^{10}$;

R⁴ is independently $C_{1-4}$ alkyl or —CH₂—$C_{3-6}$ cycloalkyl;

R⁶, at each occurrence, is independently selected from: halogen, CN, $C_{1-4}$ alkyl, $C_{1-4}$ alkoxy, $C_{1-4}$ haloalkyl, $C_{1-4}$ haloalkoxy, $C_{3-6}$ cycloalkyl, —O—$C_{3-6}$ cycloalkyl, benzyl, and oxazolyl;

R¹⁰, at each occurrence, is independently selected from: halogen, CN, $C_{1-4}$ alkyl, $C_{1-4}$ alkoxy, $C_{1-4}$ haloalkyl, $C_{1-4}$ haloalkoxy, and CO₂($C_{1-2}$ alkyl); and R¹² is independently selected from: OH, CN, and $C_{1-4}$ alkoxy.

In an eleventh aspect, the present disclosure includes a compound of Formula (I) or (II), or a stereoisomer, a tautomer, a pharmaceutically acceptable salt, or a solvate thereof, within the scope of any of the first, third, fourth, fifth, sixth, eighth, ninth and tenth aspects, wherein:

X is O;
ring A is

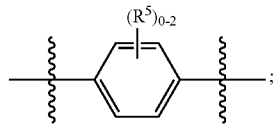

ring B is independently selected from:

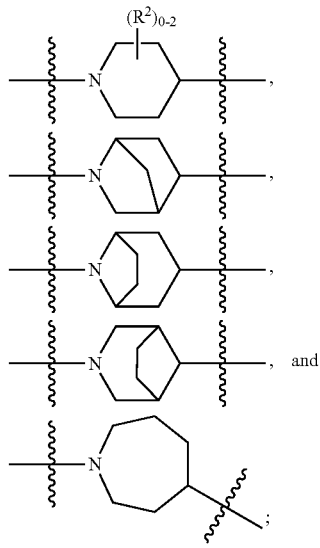

R², at each occurrence, is independently selected from: halogen, $C_{1-4}$ alkyl substituted with 0-1 $R^{12}$, $C_{1-4}$ alkoxy, and benzyl;

R³ is independently selected from: CN, $C_{1-4}$ haloalkyl, 4-halo-Ph, 4-CN-Ph, 4-CO₂($C_{1-2}$ alkyl)-Ph, 2-halo-4-CN-Ph, 3-halo-4-halo-Ph, 3-CN-4-CN-Ph, and pyrimidinyl;

R⁴ is independently $C_{1-4}$ alkyl or —CH₂—$C_{3-6}$ cycloalkyl;

R⁵ is independently halogen or $C_{1-4}$ alkyl;

R⁶, at each occurrence, is independently selected from: halogen, CN, $C_{1-4}$ alkyl, $C_{1-4}$ alkoxy, cyclopentoxy, and oxazolyl; and R¹² is independently selected from: OH, CN, and $C_{1-4}$ alkoxy.

In a twelfth aspect, the present invention provides a compound selected from the exemplified examples or a stereoisomer, a tautomer, a pharmaceutically acceptable salt, or a solvate thereof.

In another aspect, the present invention provides a compound selected from any subset list of compounds or a single compound from the exemplified examples within the scope of any of the above aspects.

In another aspect, the present disclosure includes a compound of Formula (I) or a stereoisomer, a tautomer, a pharmaceutically acceptable salt, or a solvate thereof, wherein:

X is independently selected from: a bond, O, S, NH, N($C_{1-4}$ alkyl), CH₂, CH₂CH₂, CH($C_{1-4}$ alkyl), OCH₂, CH₂O, OCH₂CH₂, and CH₂CH₂O;

ring A is independently

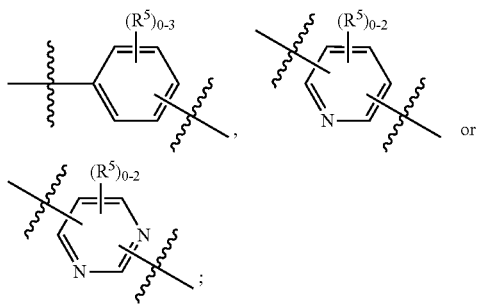

ring B is independently a 4- to 7-membered saturated heterocycle containing carbon atoms, the nitrogen atom shown in the ring B and 0-1 additional heteroatom selected from N, O, and S; and ring B is substituted with 0-4 $R^2$;

$R^1$ is independently $CO_2R^9$, phenyl, benzyl, naphthyl or a 5- to 10-membered heteroaryl containing carbon atoms and 1-4 heteroatoms selected from N, $NR^{11}$, O, and S; wherein said phenyl, benzyl, naphthyl and heteroaryl are each substituted with 0-3 $R^6$;

$R^2$, at each occurrence, is independently selected from: =O, OH, halogen, $C_{1-4}$ alkyl, $C_{1-4}$ alkoxy, and —$(CH_2)_m$—$C_{3-6}$ carbocycle;

two $R^2$ groups may combine, together with the carbon atoms to which they are attached, to form a bridged ring;

$R^3$ is independently selected from: H, halogen, CN, OH, $CO_2H$, $C_{1-4}$ alkyl, $C_{1-4}$ alkenyl, $C_{1-4}$ alkynyl, $C_{1-4}$ haloalkyl, $OR^9$, $SR^9$, $C(O)OR^9$, $CO_2R^9$, $S(O)R^9$, $SO_2R^9$, $CONHR^9$, $CON(C_{1-4}\ alkyl)_2$, —$(O)_n$—$(CH_2)_m$-phenyl, —$(CH_2)_m$-(5- to 10-membered heteroaryl containing carbon atoms and 1-4 heteroatoms selected from N, $NR^{11}$, O, and S); wherein said phenyl and heteroaryl are substituted with 0-2 $R^{10}$;

$R^4$ is independently selected from: H, $C_{1-4}$ alkyl substituted with 0-1 $R^c$, and —$(CH_2)_m$—$C_{3-6}$ carbocycle substituted with 0-2 $R^c$;

$R^{4a}$ is independently selected from: H, halogen, $C_{1-4}$ alkyl, and —$(CH_2)_m$—$C_{3-6}$ carbocycle;

$R^5$, at each occurrence, is independently selected from: halogen and $C_{1-4}$ alkyl;

$R^6$, at each occurrence, is independently selected from: halogen, OH, $C_{1-4}$ alkylthio, CN, $SO_2(C_{1-2}\ alkyl)$, $N(C_{1-4}\ alkyl)_2$, $C_{1-4}$ haloalkyl, $C_{1-4}$ haloalkoxy, $C_{1-6}$ alkyl substituted with 0-1 $R^7$, $C_{1-4}$ alkoxy substituted with 0-1 $R^7$, —$(O)_n$—$(CH_2)_m$—$(C_{3-10}$ carbocycle substituted with 0-2 $R^7$), and —$(CH_2)_m$-(5- to 10-membered heteroaryl containing carbon atoms and 1-4 heteroatoms selected from N, $NR^{11}$, O, and S; wherein said heteroaryl is substituted with 0-2 $R^7$;

$R^7$, at each occurrence, is independently selected from: halogen, OH, $C_{1-4}$ alkyl, $C_{2-4}$ alkenyl, $C_{1-4}$ alkoxy, $C_{1-4}$ alkylthio, $C_{1-4}$ haloalkyl, $C_{1-4}$ haloalkoxy, $SCF_3$, CN, $NO_2$, $NH_2$, $NH(C_{1-4}\ alkyl)$, $N(C_{1-4}\ alkyl)_2$, $SO_2(C_{1-2}\ alkyl)$, and phenyl;

$R^8$ is independently selected from: H and $C_{1-4}$ alkyl;

$R^9$, at each occurrence, is independently selected from: $C_{1-4}$ alkyl, $C_{1-4}$ haloalkyl and —$(CH_2)_m$-phenyl;

$R^{10}$, at each occurrence, is independently selected from: halogen, CN, $C_{1-4}$ haloalkyl, $C_{1-4}$ haloalkoxy, $SCF_3$, $NO_2$, and $CO_2(C_{1-4}\ alkyl)$;

$R^{11}$, at each occurrence, is independently selected from: H, $C_{1-4}$ alkyl and benzyl;

$R^c$, at each occurrence, is independently selected from: OH, $C_{1-4}$ alkoxy, halogen, $CF_3$, $OCF_3$, and CN;

m, at each occurrence, is independently 0, 1, or 2; and n, at each occurrence, is independently 0 or 1.

In another aspect, the present disclosure provides a compound of Formula (I) or (II): or a stereoisomer, a tautomer, a pharmaceutically acceptable salt, or a solvate thereof, wherein:

X is independently selected from: a bond, O, S, NH, $N(C_{1-4}\ alkyl)$, $CH_2$, $CH_2CH_2$, $CH(C_{1-4}\ alkyl)$, $OCH_2$, $CH_2O$, $OCH_2CH_2$, and $CH_2CH_2O$;

ring A is independently

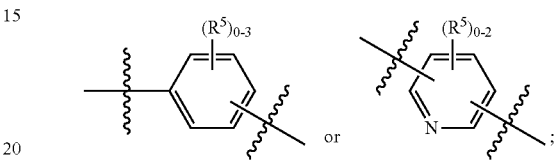

ring B is independently a 4- to 7-membered saturated heterocycle containing carbon atoms and the nitrogen atom shown in ring B; and ring B is substituted with 0-4 $R^2$;

$R^1$ is independently $CO_2(C_{1-4}\ alkyl)$, $CO_2Bn$, phenyl, benzyl, naphthyl or a 5- to 10-membered heteroaryl containing carbon atoms and 1-4 heteroatoms selected from N, $NR^{11}$, O, and S; wherein said phenyl, benzyl, naphthyl and heteroaryl are each substituted with 0-3 $R^6$;

$R^2$, at each occurrence, is independently selected from: =O, OH, halogen, $C_{1-4}$ alkyl, $C_{1-4}$ alkoxy, and benzyl;

two $R^2$ groups may combine, together with the carbon atoms to which they are attached, to form a bridged ring;

$R^3$ is independently selected from: H, halogen, CN, $SO_2(C_{1-4}\ alkyl)$, $CONH(C_{1-4}\ alkyl)$, $CON(C_{1-4}\ alkyl)_2$, $C_{1-4}$ alkyl, $C_{1-4}$ alkoxy, $C_{1-4}$ alkylthio, $C_{1-4}$ haloalkyl, $C_{1-4}$ haloalkoxy, phenyl, benzyl, phenoxy, and a 5- to 10-membered heteroaryl containing carbon atoms and 1-4 heteroatoms selected from N, $NR^{11}$, O, and S; wherein said phenyl, benzyl, phenoxy and heteroaryl is substituted with 0-2 $R^{10}$;

$R^4$ is independently selected from: H, halogen, $C_{1-4}$ alkyl, and —$(CH_2)_m$—$C_{3-6}$ carbocycle;

$R^5$, at each occurrence, is independently selected from: halogen and $C_{1-4}$ alkyl;

$R^6$, at each occurrence, is independently selected from: halogen, OH, $C_{1-4}$ alkylthio, CN, $SO_2(C_{1-2}\ alkyl)$, $N(C_{1-4}\ alkyl)_2$, $C_{1-4}$ haloalkyl, $C_{1-4}$ haloalkoxy, $C_{1-6}$ alkyl substituted with 0-1 $R^7$, $C_{1-4}$ alkoxy substituted with 0-1 $R^7$, —$(CH_2)_m$—$(C_{3-6}$ cycloalkyl), —$O(CH_2)_m$—$(C_{3-6}$ cycloalkyl), —$(CH_2)_m$-(phenyl substituted with 0-2 $R^7$), —$O(CH_2)_m$-(phenyl substituted with 0-2 $R^7$), —$(CH_2)_m$-(naphthyl substituted with 0-2 $R^7$), and —$(CH_2)_m$-(5- to 10-membered heteroaryl containing carbon atoms and 1-4 heteroatoms selected from N, $NR^{11}$, O, and S; wherein said heteroaryl is substituted with 0-2 $R^7$;

$R^7$, at each occurrence, is independently selected from: halogen, OH, $C_{1-4}$ alkyl, $C_{2-4}$ alkenyl, $C_{1-4}$ alkoxy, $C_{1-4}$ alkylthio, $C_{1-4}$ haloalkyl, $C_{1-4}$ haloalkoxy, $SCF_3$, CN, $NO_2$, $NH_2$, $NH(C_{1-4}\ alkyl)$, $N(C_{1-4}\ alkyl)_2$, $SO_2(C_{1-2}\ alkyl)$, and phenyl;

$R^{10}$, at each occurrence, is independently selected from: halogen, CN, $C_{1-4}$ haloalkyl, $C_{1-4}$ haloalkoxy, $SCF_3$, $NO_2$, and $CO_2(C_{1-4}\ alkyl)$;

$R^{11}$, at each occurrence, is independently selected from: H, $C_{1-4}$ alkyl and benzyl; and m, at each occurrence, is independently 0, 1, or 2.

In another aspect, the present disclosure includes a compound of Formula (I) or (II), or a stereoisomer, a tautomer, a pharmaceutically acceptable salt, or a solvate thereof, wherein:

X is independently selected from: a bond, O, NH, N(CH$_3$), CH$_2$, CH$_2$CH$_2$, CH(CH$_3$), OCH$_2$, CH$_2$O, OCH$_2$CH$_2$, and CH$_2$CH$_2$O;

ring A is independently

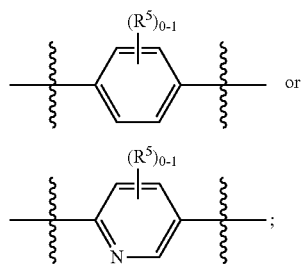

ring B is independently selected from:

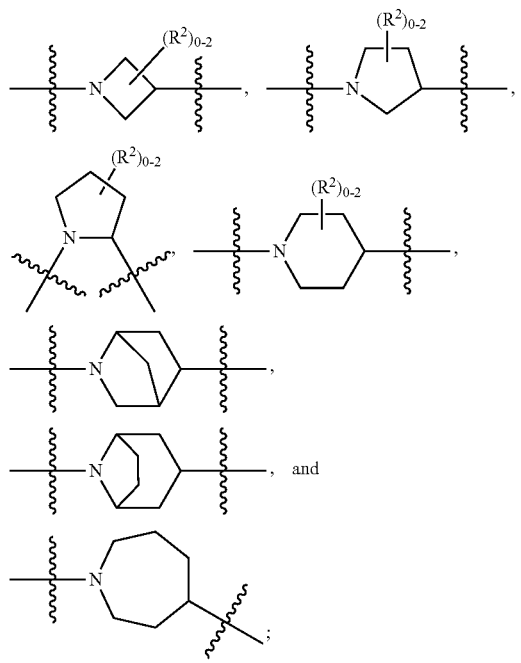

R$^1$ is independently CO$_2$(C$_{1-4}$ alkyl), CO$_2$Bn, phenyl substituted with 0-3 R$^6$ or a heteroaryl substituted with 0-2 R$^6$; wherein said heteroaryl is selected from: furanyl, oxazolyl, thiazolyl, pyrazolyl, oxadiazolyl, pyridinyl, pyrimidinyl and pyrazinyl;

R$^2$, at each occurrence, is independently selected from: =O, OH, halogen, C$_{1-4}$ alkyl, C$_{1-4}$ alkoxy, and benzyl;

R$^3$ is independently selected from: H, halogen, CN, SO$_2$(C$_{1-4}$ alkyl), CONH(C$_{1-4}$ alkyl), CON(C$_{1-4}$ alkyl)$_2$, C$_{1-4}$ alkyl, C$_{1-4}$ alkoxy, C$_{1-4}$ haloalkyl, C$_{1-4}$ haloalkoxy, 4-halo-Ph, 4-CN-Ph, 4-CO$_2$(C$_{1-4}$ alkyl)-Ph, benzyl, phenoxy, oxazolyl, pyrimidinyl, and

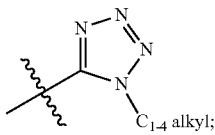

R$^4$ is independently selected from: H, halogen, C$_{1-4}$ alkyl, and —(CH$_2$)$_m$—C$_{3-6}$ carbocycle; and R$^6$, at each occurrence, is independently selected from: halogen, OH, C$_{1-6}$ alkyl substituted with 0-1 OH, C$_{1-4}$ alkoxy, C$_{1-4}$ alkylthio, C$_{1-4}$ haloalkyl, C$_{1-4}$ haloalkoxy, CH$_2$OH, CN, SO$_2$(C$_{1-2}$ alkyl), N(C$_{1-4}$ alkyl)$_2$, —O—C$_{3-6}$ cycloalkyl, and benzyl.

In another aspect, the present disclosure includes a compound of Formula (I) or (II), or a stereoisomer, a tautomer, a pharmaceutically acceptable salt, or a solvate thereof, wherein:

R$^1$ is independently phenyl substituted with 0-3 R$^6$ or a heteroaryl substituted with 0-2 R$^6$; wherein said heteroaryl is selected from: pyridinyl, pyrimidinyl and pyrazinyl.

In another aspect, the present disclosure includes a compound of Formula (I) or (II), or a stereoisomer, a tautomer, a pharmaceutically acceptable salt, or a solvate thereof, X is independently selected from: O, N(CH$_3$), CH$_2$, CH$_2$O, and CH$_2$CH$_2$O;

ring A is

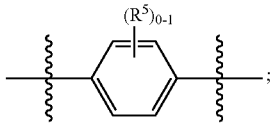

ring B is independently selected from:

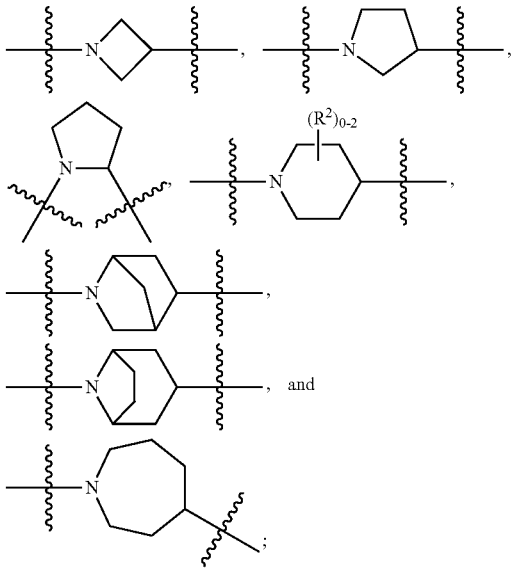

R$^1$ is independently phenyl substituted with 0-3 R$^6$, pyridinyl substituted with 0-2 R$^6$, or pyrazinyl substituted with 0-2 R$^6$;

R$^2$, at each occurrence, is independently selected from: OH, halogen, C$_{1-4}$ alkyl, C$_{1-4}$ alkoxy, and benzyl;

$R^3$ is independently selected from: H, halogen, CN, $C_{1-4}$ alkoxy, $CF_3$, $CF_2CF_3$, phenyl, 4-halo-Ph, 4-CN-Ph, 4-$CO_2$($C_{1-2}$ alkyl)-Ph, 2-halo-4-CN-Ph, 3-halo-4-halo-Ph, 3-CN-4-CN-Ph, benzyl, phenoxy, and pyrimidin-2-yl;

$R^4$ is independently $C_{1-4}$ alkyl or —$CH_2$—$C_{3-6}$ cycloalkyl; and $R^6$, at each occurrence, is independently selected from: halogen, CN, $CF_3$, $OCF_3$, $C_{1-4}$ alkyl, $C_{1-4}$ alkoxy, and —O—$C_{3-6}$ cycloalkyl.

In another aspect, the present disclosure includes a compound of Formula (I) or (II), or a stereoisomer, a tautomer, a pharmaceutically acceptable salt, or a solvate thereof, wherein:

X is O;

ring A is

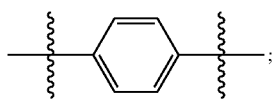 [SMILES: *c1ccc(*)cc1]

ring B is independently selected from:

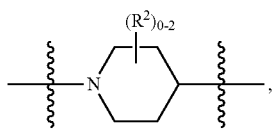

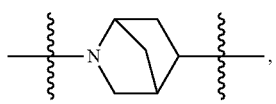

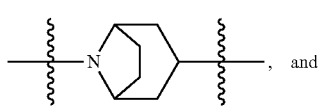, and

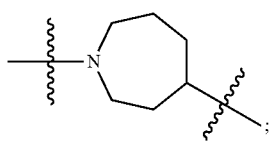;

$R^2$, at each occurrence, is independently selected from: halogen, $C_{1-4}$ alkyl, $C_{1-4}$ alkoxy, and benzyl;

$R^3$ is independently selected from: $CF_3$, 4-halo-Ph, 4-CN-Ph, 4-$CO_2$($C_{1-2}$ alkyl)-Ph, 2-halo-4-CN-Ph, 3-halo-4-halo-Ph, 3-CN-4-CN-Ph, and pyrimidin-2-yl;

$R^4$ is independently $C_{1-4}$ alkyl or —$CH_2$—$C_{3-6}$ cycloalkyl; and $R^6$, at each occurrence, is independently selected from: halogen, CN, $C_{1-4}$ alkyl, $C_{1-4}$ alkoxy, and cyclopentoxy.

In another aspect, the present disclosure includes a compound of Formula (IIIa):

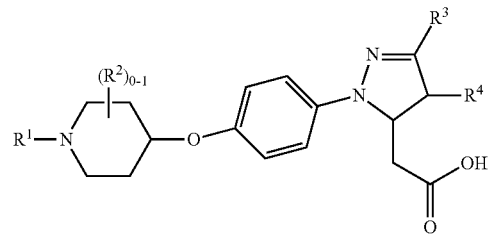

(IIIa)

or a stereoisomer, a tautomer, a pharmaceutically acceptable salt, or a solvate thereof, wherein:

$R^1$ is independently phenyl substituted with 0-3 $R^6$ or pyridinyl substituted with 0-2 $R^6$;

$R^2$ is independently halogen or $C_{1-4}$ alkyl;

$R^3$ is independently selected from: $CF_3$, 4-halo-Ph, 4-CN-Ph, 4-$CO_2$($C_{1-2}$ alkyl)-Ph, 2-halo-4-CN-Ph, and pyrimidin-2-yl;

$R^4$ is independently $C_{1-4}$ alkyl or cyclopropylmethyl; and $R^6$, at each occurrence, is independently selected from: halogen, CN, $C_{1-4}$ alkyl, and $C_{1-4}$ alkoxy.

In another embodiment, X is independently selected from: a bond, O, $CH_2$, $CH_2CH_2$, CH($C_{1-4}$ alkyl), $OCH_2$, $CH_2O$, $OCH_2CH_2$, and $CH_2CH_2O$.

In another embodiment, X is independently selected from: O, $CH_2$, $CH_2CH_2$, CH($C_{1-4}$ alkyl), $CH_2O$, and $CH_2CH_2O$.

In another embodiment, X is O.

In another embodiment, X is independently selected from: $CH_2$, $CH_2CH_2$, and CH($C_{1-4}$ alkyl).

In another embodiment, X is independently selected from: $CH_2O$, and $CH_2CH_2O$.

In another embodiment, ring A is independently

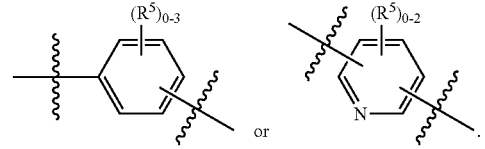

In another embodiment, ring A is independently

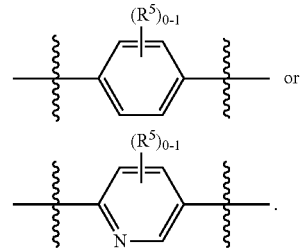

In another embodiment, ring A is

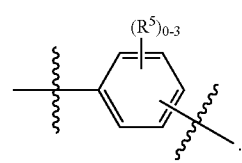

In another embodiment, ring A is

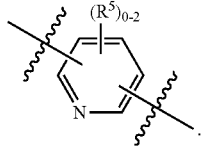

In another embodiment, ring A is

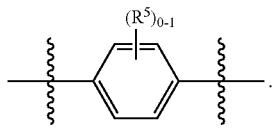

In another embodiment, ring A is

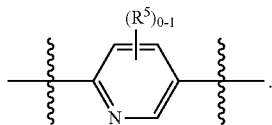

In another embodiment, ring B is independently a 4- to 7-membered saturated heterocycle containing carbon atoms and the nitrogen atom shown in ring B; and ring B is substituted with 0-4 $R^2$.

In another embodiment, ring B is independently selected from:

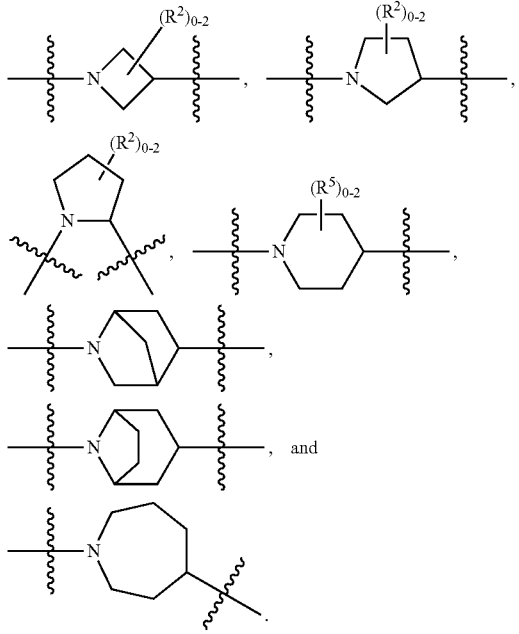

In another embodiment, ring B is independently selected from:

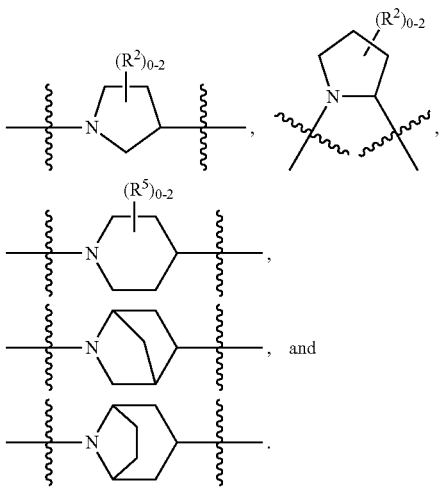

In another embodiment, ring B is independently

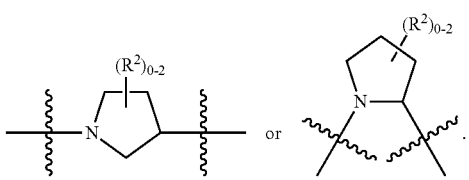

In another embodiment, ring B is independently

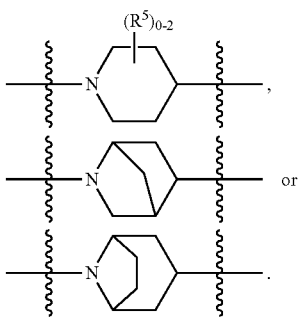

In another embodiment, ring B is

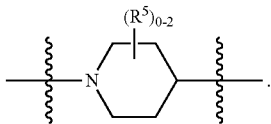

In another embodiment, $R^1$ is independently $CO_2(C_{1-4}$ alkyl), $CO_2Bn$, phenyl substituted with 0-3 $R^6$ or a heteroaryl substituted with 0-2 $R^6$; wherein said heteroaryl is selected from: furanyl, oxazolyl, thiazolyl, pyrazolyl, oxadiazolyl, pyridinyl, pyrimidinyl and pyrazinyl.

In another embodiment, $R^1$ is independently $CO_2(C_{1-4}$ alkyl), $CO_2Bn$, phenyl substituted with 0-3 $R^6$ or a heteroaryl substituted with 0-2 $R^6$; wherein said heteroaryl is selected from: furanyl, oxazolyl, thiazolyl, pyrazolyl, oxadiazolyl, pyridinyl, pyrimidinyl and pyrazinyl.

In another embodiment, $R^1$ is independently phenyl substituted with 0-3 $R^6$, pyridinyl substituted with 0-2 $R^6$, or pyrazinyl substituted with 0-2 $R^6$.

In another embodiment, $R^1$ is independently phenyl substituted with 0-3 $R^6$ or pyridinyl substituted with 0-2 $R^6$.

In another embodiment, $R^1$ is phenyl substituted with 0-3 $R^6$.

In another embodiment, $R^1$ is pyridinyl substituted with 0-2 $R^6$.

In another embodiment, $R^2$, at each occurrence, is independently selected from: =O, OH, halogen, $C_{1-4}$ alkyl, $C_{1-4}$ alkoxy, and benzyl.

In another embodiment, $R^2$, at each occurrence, is independently selected from: OH, halogen, $C_{1-4}$ alkyl, $C_{1-4}$ alkoxy, and benzyl.

In another embodiment, $R^2$, at each occurrence, is independently selected from: halogen, $C_{1-4}$ alkyl, $C_{1-4}$ alkoxy, and benzyl.

In another embodiment, $R^2$, at each occurrence, is independently selected from: halogen and $C_{1-4}$ alkyl.

In another embodiment, two $R^2$ groups may combine, together with the carbon atoms to which they are attached, to form a bridged ring.

In another embodiment, $R^3$ is independently selected from: H, halogen, CN, $SO_2(C_{1-4}$ alkyl$)$, $CONH(C_{1-4}$ alkyl$)$, $CON(C_{1-4}$ alkyl$)_2$, $C_{1-4}$ alkyl, $C_{1-4}$ alkoxy, $C_{1-4}$ alkylthio, $C_{1-4}$ haloalkyl, $C_{1-4}$ haloalkoxy, phenyl, benzyl, phenoxy, and a 5- to 10-membered heteroaryl containing carbon atoms and 1-4 heteroatoms selected from N, $NR^{11}$, O, and S; wherein said phenyl, benzyl, phenoxy and heteroaryl is substituted with 0-2 $R^{10}$.

In another embodiment, $R^3$ is independently selected from: H, halogen, CN, $SO_2(C_{1-4}$ alkyl$)$, $CONH(C_{1-4}$ alkyl$)$, $CON(C_{1-4}$ alkyl$)_2$, $C_{1-4}$ alkyl, $C_{1-4}$ alkoxy, $C_{1-4}$ haloalkyl, $C_{1-4}$ haloalkoxy, 4-halo-Ph, 4-CN-Ph, 4-$CO_2(C_{1-4}$ alkyl$)$-Ph, benzyl, phenoxy, oxazolyl, pyrimidinyl, and

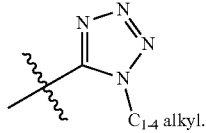

In another embodiment, $R^3$ is independently selected from: H, halogen, CN, $C_{1-4}$ alkoxy, $CF_3$, $CF_2CF_3$, phenyl, 4-halo-Ph, 4-CN-Ph, 4-$CO_2(C_{1-2}$ alkyl$)$-Ph, 2-halo-4-CN-Ph, 3-halo-4-halo-Ph, 3-CN-4-CN-Ph, benzyl, phenoxy, and pyrimidin-2-yl.

In another embodiment, $R^3$ is independently selected from: H, halogen, CN, $C_{1-4}$ alkoxy, $CF_3$, and $CF_2CF_3$.

In another embodiment, $R^3$ is CN, $CF_3$, and $CF_2CF_3$.

In another embodiment, $R^3$ is independently selected from: phenyl, 4-halo-Ph, 4-CN-Ph, 4-$CO_2(C_{1-2}$ alkyl$)$-Ph, 2-halo-4-CN-Ph, 3-halo-4-halo-Ph, 3-CN-4-CN-Ph, benzyl, phenoxy, and pyrimidin-2-yl.

In another embodiment, $R^4$ is independently $C_{1-4}$ alkyl or —$CH_2$—$C_{3-6}$ cycloalkyl.

In another embodiment, $R^4$ is $C_{1-4}$ alkyl.

In another embodiment, $R^4$ is independently —$CH_2$—$C_{3-6}$ cycloalkyl.

In another embodiment, $R^6$, at each occurrence, is independently selected from: halogen, OH, $C_{1-6}$ alkyl substituted with 0-1 OH, $C_{1-4}$ alkoxy, $C_{1-4}$ alkylthio, $C_{1-4}$ haloalkyl, $C_{1-4}$ haloalkoxy, $CH_2OH$, CN, $SO_2(C_{1-2}$ alkyl$)$, $N(C_{1-4}$ alkyl$)_2$, —O—$C_{3-6}$ cycloalkyl, and benzyl.

In another embodiment, $R^6$, at each occurrence, is independently selected from: halogen, CN, $CF_3$, $OCF_3$, $C_{1-4}$ alkyl, $C_{1-4}$ alkoxy, and —O—$C_{3-6}$ cycloalkyl.

In another embodiment, $R^6$, at each occurrence, is independently selected from: halogen, CN, $C_{1-4}$ alkyl, and $C_{1-4}$ alkoxy.

In another embodiment, $R^1$ is phenyl substituted with 0-3 $R^6$.

In another embodiment, $R^1$ is phenyl substituted with 0-2 $R^6$.

In another embodiment, $R^1$ is phenyl substituted with 0-1 $R^6$.

In another embodiment, $R^1$ is pyridinyl substituted with 0-2 $R^6$.

In another embodiment, $R^1$ is pyridinyl substituted with 0-1 $R^6$.

In another embodiment, $R^2$ is independently halogen.

In another embodiment, $R^2$ is independently $C_{1-4}$ alkyl.

In another embodiment, $R^3$ is $CF_3$.

In another embodiment, $R^3$ is independently selected from: 4-halo-Ph, 4-CN-Ph, 4-$CO_2(C_{1-2}$ alkyl$)$-Ph, 2-halo-4-CN-Ph, and pyrimidin-2-yl.

In another embodiment, $R^3$ is independently selected from: 4-halo-Ph, 4-CN-Ph, 4-$CO_2(C_{1-2}$ alkyl$)$-Ph, and 2-halo-4-CN-Ph.

In another embodiment, $R^4$ is $C_{1-4}$ alkyl.

In another embodiment, $R^4$ is cyclopropylmethyl.

In another embodiment, $R^6$, at each occurrence, is independently selected from: halogen, $C_{1-4}$ alkyl, and $C_{1-4}$ alkoxy.

In another embodiment, $R^6$, at each occurrence, is independently selected from: halogen and $C_{1-4}$ alkyl.

In another embodiment, $R^6$, at each occurrence, is independently selected from: halogen and $C_{1-4}$ alkoxy.

In another embodiment, the compounds of the present invention have hGPR40 $EC_{50}$ values ≤10 µM.

In another embodiment, the compounds of the present invention have hGPR40 $EC_{50}$ values ≤5 µM.

In another embodiment, the compounds of the present invention have hGPR40 $EC_{50}$ values ≤1 µM.

In another embodiment, the compounds of the present invention have hGPR40 $EC_{50}$ values ≤0.5 µM.

In another embodiment, the compounds of the present invention have hGPR40 $EC_{50}$ values ≤0.2 µM.

In another embodiment, the compounds of the present invention have hGPR40 $EC_{50}$ values 0.1 µM.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention or a stereoisomer, a tautomer, a pharmaceutically acceptable salt, or a solvate thereof.

In another embodiment, the present invention provides an intermediate for making a compound of the present invention or a stereoisomer, a tautomer, a pharmaceutically acceptable salt, or a solvate thereof.

In another embodiment, the present invention provides a pharmaceutical composition further comprising additional therapeutic agent(s). Examples of additional therapeutic agent(s), according to the present invention include, but are not limited to, anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, treatments for heart failure, treatments for peripheral arterial disease and anti-inflammatory agents.

In a preferred embodiment, the present invention provides pharmaceutical composition, wherein the additional therapeutic agents are, for example, a dipeptidyl peptidase-IV (DPP4) inhibitor (for example a member selected from saxagliptin, sitagliptin, vildagliptin, linagliptin, alogliptin, and "BMS DPP4i"), and/or a sodium-glucose transporter-2 (SGLT2) inhibitor (for example a member selected from dapagliflozin, canagliflozin, empagliflozin and remagliflozin).

In a preferred embodiment, the present invention provides pharmaceutical composition, wherein the additional therapeutic agents are, for example, a DPP4 inhibitor (for example a member selected from saxagliptin, sitagliptin, vildagliptin, linagliptin, alogliptin, and "BMS DPP4i").

In a preferred embodiment, the present invention provides pharmaceutical composition, wherein the additional therapeutic agents are, for example, an SGLT2 inhibitor (for example a member selected from dapagliflozin, canagliflozin, empagliflozin and remagliflozin).

In another embodiment, the present invention provides a method for the treatment and/or prophylaxis of multiple diseases or disorders associated with GPR40, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

Examples of diseases or disorders associated with the activity of the GPR40 that can be prevented, modulated, or treated according to the present invention include, but are not limited to, diabetes, hyperglycemia, impaired glucose tolerance, gestational diabetes, insulin resistance, hyperinsulinemia, retinopathy, neuropathy, nephropathy, diabetic kidney disease, acute kidney injury, cardiorenal syndrome, acute coronary syndrome, delayed wound healing, atherosclerosis and its sequelae, abnormal heart function, congestive heart failure, myocardial ischemia, stroke, Metabolic Syndrome, hypertension, obesity, fatty liver disease, dislipidemia, dyslipidemia, hyperlipidemia, hypertriglyceridemia, hypercholesterolemia, low high-density lipoprotein (HDL), high low-density lipoprotein (LDL), non-cardiac ischemia, pancreatitis, lipid disorders, neurodegenerative disease, cognitive impairment, dementia, and liver diseases such as NASH (Non-Alcoholic SteatoHepatitis), NAFLD (Non-Alcoholic Fatty Liver Disease) and liver cirrhosis.

In another embodiment, the present invention provides a method for the treatment and/or prophylaxis of diabetes, hyperglycemia, gestational diabetes, obesity, dyslipidemia, hypertension and cognitive impairment, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of diabetes, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of hyperglycemia, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of obesity, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of dyslipidemia, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of hypertension, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a method for the treatment and/or prophylaxis of cognitive impairment, comprising administering to a patient in need of such treatment and/or prophylaxis a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment and/or prophylaxis of multiple diseases or disorders associated with GPR40.

In another embodiment, the present invention also provides the use of a compound of the present invention for the manufacture of a medicament for the treatment and/or prophylaxis of multiple diseases or disorders associated with GPR40.

In another embodiment, the present invention provides a method for the treatment and/or prophylaxis of multiple diseases or disorders associated with GPR40, comprising: administering to a patient in need thereof a therapeutically effective amount of a first and second therapeutic agent, wherein the first therapeutic agent is a compound of the present invention. Preferably, the second therapeutic agent, for example, a DPP4 inhibitor (for example a member selected from saxagliptin, sitagliptin, vildagliptin, linagliptin and alogliptin).

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment and/or prophylaxis of multiple diseases or disorders associated with GPR40.

Where desired, the compound of the present invention may be used in combination with one or more other types of antidiabetic agents and/or one or more other types of therapeutic agents which may be administered orally in the same dosage form, in a separate oral dosage form or by injection. The other type of antidiabetic agent that may be optionally employed in combination with the GPR40 receptor modulator of the present invention may be one, two, three or more antidiabetic agents or antihyperglycemic agents which may be administered orally in the same dosage form, in a separate oral dosage form, or by injection to produce an additional pharmacological benefit.

The antidiabetic agents used in the combination with the GPR40 receptor modulator of the present invention include, but are not limited to, insulin secretagogues or insulin sensitizers, other GPR40 receptor modulators, or other antidiabetic agents. These agents include, but are not limited to, DPP4 inhibitors (for example, sitagliptin, saxagliptin, alogliptin, linagliptin and vildagliptin), biguanides (for example, metformin and phenformin), sulfonyl ureas (for example, glyburide, glimepiride and glipizide), glucosidase inhibitors (for example, acarbose, miglitol), PPARγ agonists such as thiazolidinediones (for example, rosiglitazone and pioglitazone), PPAR α/γ dual agonists (for example, muraglitazar, tesaglitazar and aleglitazar), glucokinase activators, GPR119 receptor modulators (for example, MBX-2952, PSN821, and APD597), GPR120 receptor modulators (for example, as described in Shimpukade, B. et al. *J. Med. Chem.* 2012, 55 (9), 4511-4515), SGLT2 inhibitors (for example, dapagliflozin, canagliflozin, empagliflozin and remagliflozin), MGAT inhibitors (for example, as described in Barlind, J. G. et al. *Bioorg. Med. Chem. Lett.* 2013, 23 (9), 2721-2726; or US20130143843A1), amylin analogs such as pramlintide, and/or insulin.

The GPR40 receptor modulator of the present invention may also be optionally employed in combination with agents for treating complication of diabetes. These agents include PKC inhibitors and/or AGE inhibitors.

The GPR40 receptor modulator of the present invention may also be optionally employed in combination with one or more hypophagic and/or weight-loss agents such as diethylpropion, phendimetrazine, phentermine, orlistat, sibutramine, lorcaserin, pramlintide, topiramate, MCHR1 receptor antagonists, oxyntomodulin, naltrexone, Amylin peptide, NPY Y5 receptor modulators, NPY Y2 receptor modulators, NPY Y4 receptor modulators, cetilistat, 5HT2c receptor modulators, and the like. The GPR40 receptor modulator of the present invention may also be employed in combination with an agonist of the glucagon-like peptide-1 receptor (GLP-1 R), such as exenatide, liraglutide, GLP-1 (1-36) amide, GLP-1(7-36) amide, GLP-1(7-37), which may be administered via injection, intranasal, or by transdermal or buccal devices.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of stereoisomeric forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "alkyl" or "alkylene" is intended to include both branched and straight-chain saturated aliphatic hydrocarbon groups having the specified number of carbon atoms. For example, "$C_1$ to $C_6$ alkyl" or "$C_{1-6}$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

The term "alkoxy" or "alkyloxy" refers to an —O-alkyl group. For example, "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. For example, "$C_3$ to $C_6$ cycloalkyl" or "$C_{3-6}$ cycloalkyl" is intended to include $C_3$, $C_4$, $C_5$, and $C_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. $C_{4-6}$ cycloalkenyl is intended to include $C_4$, $C_5$, and $C_6$ cycloalkenyl groups. Example cycloalkenyl groups include, but are not limited to, cyclobutenyl, cyclopentenyl, and cyclohexenyl.

As used herein, "carbocycle," "carbocyclyl," or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, indanyl, and tetrahydronaphthyl. When the term "carbocycle" is used, it is intended to include "aryl." A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or bicyclic aromatic hydrocarbons, including, for example, phenyl, and naphthyl. Aryl moieties are well known and described, for example, in *Hawley's Condensed Chemical Dictionary* (13th ed.), R. J. Lewis, ed., J. Wiley & Sons, Inc., New York, 1997. "$C_{6-10}$ aryl" refers to phenyl and naphthyl.

The term "benzyl," as used herein, refers to a methyl group on which one of the hydrogen atoms is replaced by a phenyl group.

As used herein, the term "heterocycle," "heterocyclyl," or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, imidazopyridazinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolopyrimidinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, pyrimidinyl, pyrazinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, imidazolopyridinyl, imidazopyridazinyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, pyrazolopyridinyl and pyrazolopyrimidinyl.

Examples of 5- to 6-membered heterocycles include, but are not limited to, pyridinyl, furanyl, thienyl, pyrrolyl, pyrazolyl, pyrazinyl, piperazinyl, piperidinyl, pyrimidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Examples of 5- to 6-membered heteroaryls include, but are not limited to, pyridinyl, furanyl, thienyl, pyrrolyl, pyrazolyl, pyrazinyl, imidazolyl, imidazolidinyl, tetrazolyl, isoxazolyl, oxazolyl, oxadiazolyl, oxazolidinyl, thiadiazinyl, thiadiazolyl, thiazolyl, triazinyl, and triazolyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Examples of 5- to 6-membered heteroaryls include, but are not limited to, pyridinyl, furanyl, thienyl, pyrrolyl, pyrazolyl, pyrazinyl, imidazolyl, imidazolidinyl, tetrazolyl, isoxazolyl, oxazolyl, oxadiazolyl, oxazolidinyl, thiadiazinyl, thiadiazolyl, thiazolyl, triazinyl, and triazolyl.

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counter ion" is used to represent a negatively charged species such as chloride, bromide, hydroxide, acetate, and sulfate or a positively charged species such as sodium (Na+), potassium (K+), calcium (Ca$^{2+}$)ammonium (R$_n$NH$_m$+ where n=0-4 and m=0-4) and the like.

When a dotted ring is used within a ring structure, this indicates that the ring structure may be saturated, partially saturated or unsaturated.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. and Greene, T. W. *Protecting Groups in Organic Synthesis*, 4th Edition, Wiley (2007) and *The Peptides: Analysis, Synthesis, Biology*, Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent.

Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington: The Science and Practice of Pharmacy*, 22$^{nd}$ Edition, Allen, L. V. Jr., Ed.; Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) *Design of Prodrugs*, Bundgaard, H., ed., Elsevier (1985), and *Methods in Enzymology*, 112:309-396, Widder, K. et al., eds., Academic Press (1985);

b) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988);

e) Kakeya, N. et al., *Chem. Pharm. Bull.*, 32:692 (1984); and f) Rautio, J (Editor). *Prodrugs and Targeted Delivery (Methods and Principles in Medicinal Chemistry)*, Vol 47, Wiley-VCH, 2011.

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK ($2^{nd}$ edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, $3^{rd}$ edition, Academic Press, San Diego, Calif. (2008).

The present invention also includes isotopically-labeled compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as $^2H$ (also represented as 'D' for deuterium) and $^3H$, carbon such as $^{11}C$, $^{13}C$, and $^{14}C$, nitrogen, such as $^{13}N$ and $^{15}N$, oxygen, such as $^{15}O$, $^{17}O$, and $^{18}O$. Certain isotopically-labeled compounds of the invention, for example, those incorporating a radioactive isotope, are useful in drug and/or substrate tissue distribution studies. The radioactive isotopes tritium, $^3H$, and carbon-14, $^{14}C$, are particularly useful for this purpose in view of their ease of incorporation and ready means of detection. Substitution with heavier isotopes such as deuterium, $^2H$, may afford certain therapeutic advantages resulting from greater metabolic stability, for example, increase in vivo half-life or reduced dosage requirements, and hence may be preferred in some circumstances. Substitution with positron emitting isotopes, such as $^{11}C$, $^{15}O$, $^{18}F$, and $^{13}N$, can be useful in Positron Emission Topography (PET) studies for examining substrate receptor occupancy. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or min, "h" for hour or h, "rt" for room temperature, "RT" for retention time, "atm" for atmosphere, "psi" for pounds per square inch, "conc." for concentrate, "aq" for "aqueous", "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1H$" for proton, "δ" for delta, "s" for singlet, "d" for doublet, "t" for triplet, "q" for quartet, "m" for multiplet, "br" for broad, "Hz" for hertz, and "a", "(3", "R", "S", "E", and "Z" are stereochemical designations familiar to one skilled in the art.

Me methyl
Et ethyl
Pr propyl
i-Pr isopropyl
Bu butyl
i-Bu isobutyl
t-Bu tert-butyl
Ph phenyl
Bn benzyl
Hex hexanes
MeOH methanol
EtOH ethanol
i-PrOH or IPA isopropanol
AcOH or HOAc acetic acid
$Ag_2CO_3$ silver carbonate
AgOAc silver acetate
ADDP 1,1'-(azodicarbonyl)dipiperidine
DEAD diethyl azodicarboxylate
DBAD di-tert-butyl azodicarboxylate
$PPh_3$ triphenylphosphine
$PBu_3$ tributylphosphine
$CDCl_3$ deutero-chloroform
$CHCl_3$ chloroform
cDNA complimentary DNA
DMF dimethyl formamide
DMSO dimethyl sulfoxide
EDTA ethylenediaminetetraacetic acid
EtOAc ethyl acetate
$Et_2O$ diethyl ether
$AlCl_3$ aluminum chloride
Boc tert-butyloxycarbonyl
DCM dichloromethane
$CH_2Cl_2$ dichloromethane
$CH_3CN$ or ACN acetonitrile
$Cs_2CO_3$ cesium carbonate
HCl hydrochloric acid
$H_2SO_4$ sulfuric acid
$K_2CO_3$ potassium carbonate
KCN potassium cyanide
mCPBA or m-CPBA meta-chloroperbenzoic acid Pd/C palladium on carbon
PhSO₂Cl benzenesulfonyl chloride
i-Pr₂NEt diisopropylethylamine
Pd(dppf)Cl₂ [1,1'-bis(diphenylphosphino)ferrocene]dichloropalladium
Pd₂(dba)₃ tris(dibenzylideneacetone)dipalladium
Sphos 2-dicyclohexylphosphino-2',6'-dimethoxybiphenyl
Sphos pre.cat. chloro(2-dicyclohexylphosphino-2',6'-dimethoxy-1,1'-biphenyl)[2-(2-aminoethylphenyl)]palladium(II)-methyl-t-butyl ether adduct
LiHMDS lithium bis(trimethylsilyl)amide
9-BBN 9-borabicyclo[3.3.1]nonane
BBr₃ boron tribromide
H₂O₂ hydrogen peroxide
DIEA or Hünig's base N,N-Diisopropylethylamine
PS polystyrene
SiO₂ silica oxide
SnCl₂ tin(II) chloride
Selectfluro® 1-Chloromethyl-4-fluoro-1,4-diazoniabicyclo[2.2.2]octane bis(tetrafluoroborate)
L-selectride lithium tri-sec-butyl(hydrido)borate
TBAF tetra-n-butylammonium fluoride
TEA triethylamine
TFA trifluoroacetic acid
TFAA trifluoroacetic anhydride
THF tetrahydrofuran
TMSCl chlorotrimethylsilane
TBSOTf tert-butyldimethylsilyl trifluoromethanesulfonate
TBSCl tert-butyldimethylsilyl chloride
TMSCHN₂ trimethylsilyldiazomethane
KOAc potassium acetate
MgSO₄ magnesium sulfate
MsCl methanesulfonyl chloride
MsOH or MSA methylsulfonic acid
NaCl sodium chloride
NaH sodium hydride
NaHCO₃ sodium bicarbonate
NaOH sodium hydroxide
Na₂SO₃ sodium sulfite
Na₂S₂O₃ sodium thiosulphate
Na₂SO₄ sodium sulfate
NH₃ ammonia
NH₄Cl ammonium chloride
NH₄OH ammonium hydroxide
LG leaving group
PG protecting group The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

Synthesis

The compounds of Formula (I) may be prepared by the exemplary processes described in the following schemes and working examples, as well as relevant published literature procedures that are used by one skilled in the art. Exemplary reagents and procedures for these reactions appear hereinafter and in the working examples. Protection and deprotection in the processes below may be carried out by procedures generally known in the art (see, for example, Wuts, P. G. M. and Greene, T. W. *Protecting Groups in Organic Synthesis,* 4th Edition, Wiley (2007)). General methods of organic synthesis and functional group transformations are found in: Trost, B. M. and Fleming, I., eds., *Comprehensive Organic Synthesis: Selectivity, Strategy & Efficiency in Modern Organic Chemistry*, Pergamon Press, New York, N.Y. (1991); Smith, M. B. and March, J., *March's Advanced Organic Chemistry: Reactions, Mechanisms, and Structure.* 6th Edition, Wiley & Sons, New York, N.Y. (2007); Katritzky, A. R. and Taylor, R. J. K., eds., *Comprehensive Organic Functional Groups Transformations II,* 2nd Edition, Elsevier Science Inc., Tarrytown, N.Y. (2004); Larock, R. C., *Comprehensive Organic Transformations*, VCH Publishers, Inc., New York, N.Y. (1999), and references therein.

Methods for synthesis of a large variety of substituted dihydropyrazole compounds useful as starting materials for the preparation of compounds of the present invention are well known in the art. For examples of methods useful for the preparation of dihydropyrazole materials see the following references and citations therein: Katritzky et al., eds., *Comprehensive Heterocyclic Chemistry*, Pergamon Press Inc., New York (1996); Sibi, M. P. et al., Organic Letters, 11(23): 5366 (2009); Sibi, M. P. et al., *J. Am. Chem. Soc.* 127(23): 8276 (2005); Manyem, S. et al., *J. Comb. Chem.* 9: 20 (2007); Garanti, L. et al., *Tetrahedron: Asymmetry,* 13: 1285 (2002); Molteni, G. *Tetrahedron: Asymmetry,* 15: 1077 (2004); Benassuti, L. D. et al., *Tetrahedron,* 60:4627 (2004); Shimizu, T. et al. *Bull. Chem. Soc. Jpn.,* 57: 787 (1984).

Compounds of Formula (I) can be prepared as shown in Scheme 1. Conversion of hydrazine A, which contains a LG such as =F, Cl, Br and the like, to hydrazide B with trifluoroacetic anhydride followed by treatment with a phenylsulfonyl chloride forms hydrazonoyl chloride C. Hydrazonoyl chloride C can undergo a [3+2] cycloaddition with an α,β-unsaturated carbonyl compound where Y is a chiral auxiliary, such as (4S)-phenyloxazolidinone and the like, or alkoxy group to give dihydropyrazole D as depicted in Scheme 1. Reduction of the carbonyl group in D, via a reducing agent, e.g., NaBH₄ or LiBH₄, leads to hydroxyl E. Activation of the hydroxyl group of E, via methanesulfonyl chloride, for example, and displacement with a cyanide reagent, e.g., sodium cyanide, potassium cyanide or trimethylsilylcyanide, leads to nitrile F. Nitrile F can be converted to methyl ester G by acidic methanolysis. Intermediate G can be converted to boronate H by metal catalyzed borylation, e.g, catalyzed by Pd(dppf)Cl₂. Cleavage of the boronate group in H, via oxidation with, for example, H₂O₂, leads to phenol M. Displacement of the hydroxyl group in L (synthesis shown vide infra) with phenol M, via e.g. PBu₃ and ADDP, or PPh₃ and DEAD, or PPh₃ and DBAD, generates intermediate N. Intermediate N can be converted to compounds of Formula (I) by hydrolysis, via a hydroxide reagent, e.g, LiOH or NaOH. Intermediate L can be synthesized from amine J. Conversion of the amine J to intermediate K via metal catalyzed amination or SN_{Ar} reaction, e.g. Pd (0), Cu(I) or heat with base. Activation of X group in K, via toluenesulfonyl chloride, for example, leads to intermediate L.

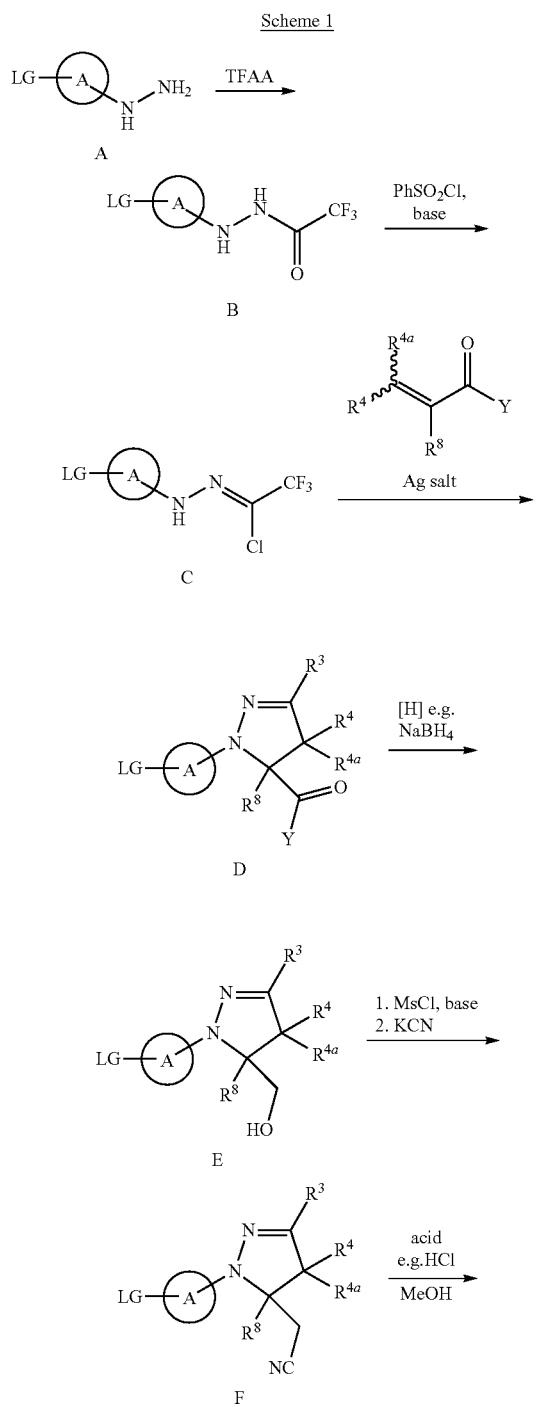

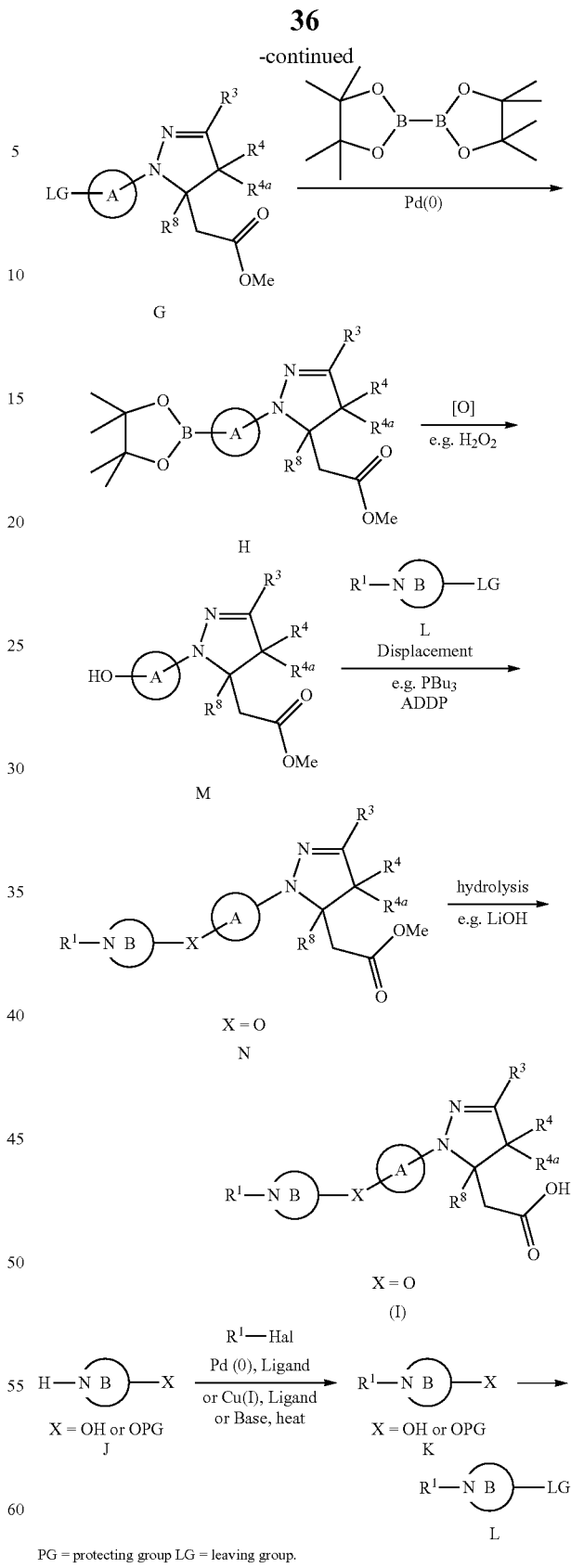

Alternatively, compounds of Formula (I) may be synthesized starting with amine O; treatment of O with MeI affords ammonium salt P. Conversion of P to Q with R¹NH₂ and base (as described, for example, in David R. Tortolani, Michael A. Poss, Organic Letters, 1999, Vol. 1, No. 8, 1261-1263) followed by treatment with reductant, e.g. L-selectride, forms alcohol S as shown in Scheme 2. Transformation of the hydroxyl group in S to leaving group gives intermediate L, via methanesulfonyl chloride, for example. Intermediate L could be converted to compounds of Formula (I) according to the synthetic steps described in Scheme 1.

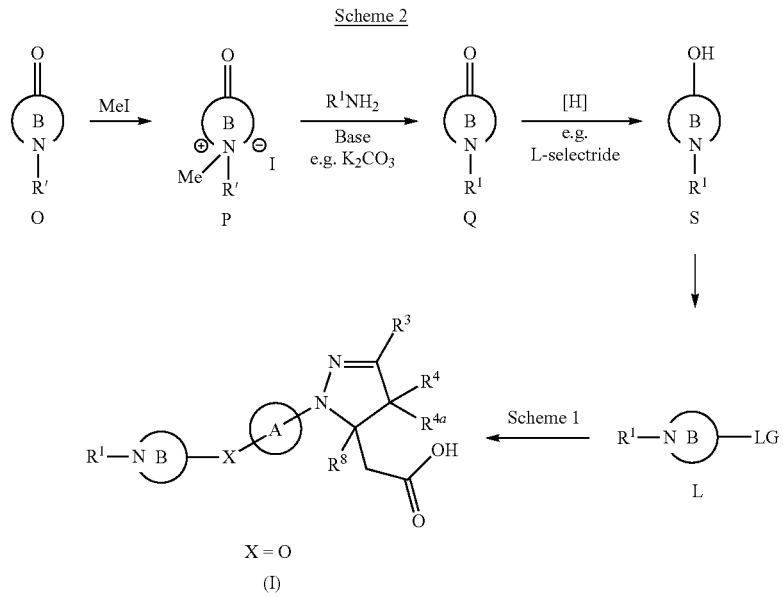

Alternatively, compounds of Formula (I) can be synthesized via coupling T and U to afford intermediate V via metal catalyzed amination or $SN_{Ar}$ reaction, e.g. Pd (0), Cu(I) or heat with base as depicted in Scheme 3. Acid mediated deprotection of V followed by olefination, for example Wittig reaction, e.g. methyltriphenylphosphonium bromide and nBuLi, forms olefin W. Coupling W and F by treatment with Pd(dppf)Cl$_2$ and 9-BBN generates Y. Nitrile Y can be converted to the methyl ester N by acidic methanolysis. Intermediate N could be converted to compounds of Formula (I) by hydrolysis, via a hydroxide reagent, e.g, LiOH or NaOH.

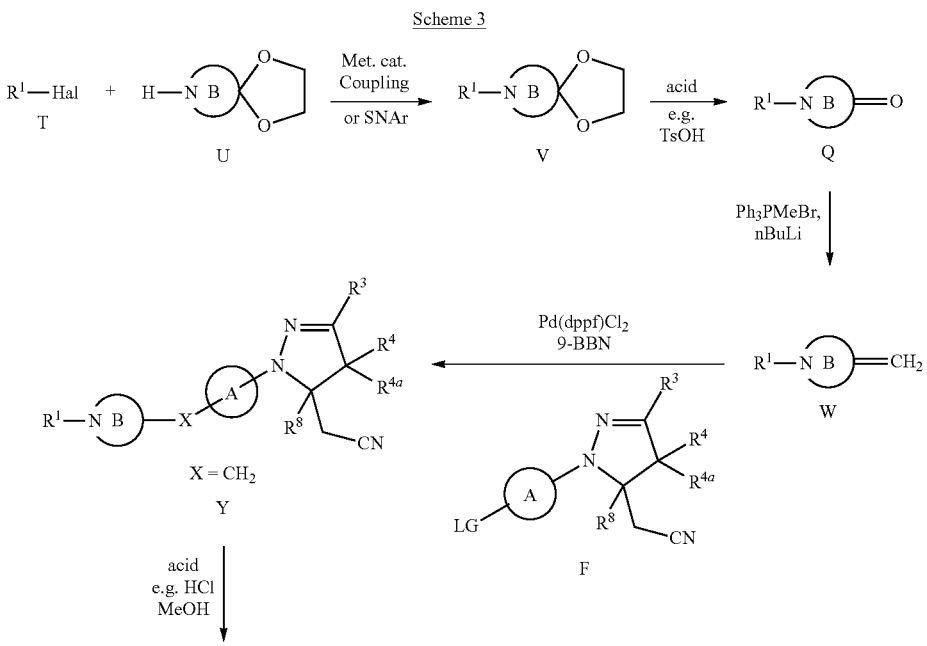

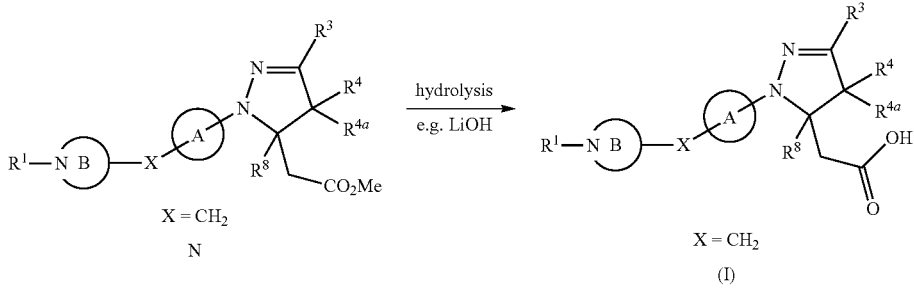

Alternatively, compounds of Formula (I) can be synthesized via reaction of intermediate C with a substituted acrylate AA in the presence of a Ag salt to provide dihydropyrazole AB as depicted in Scheme 4. The methyl ester AB can be hydrolyzed, via LiOH, for example, to afford carboxylic acid AC. Carboxylic acid AC can be converted to ester AD, via Arndt-Eistert homologation. Intermediate AD could be converted to compounds of Formula (I) by according to the synthetic steps described in Scheme 1 or Scheme 3.

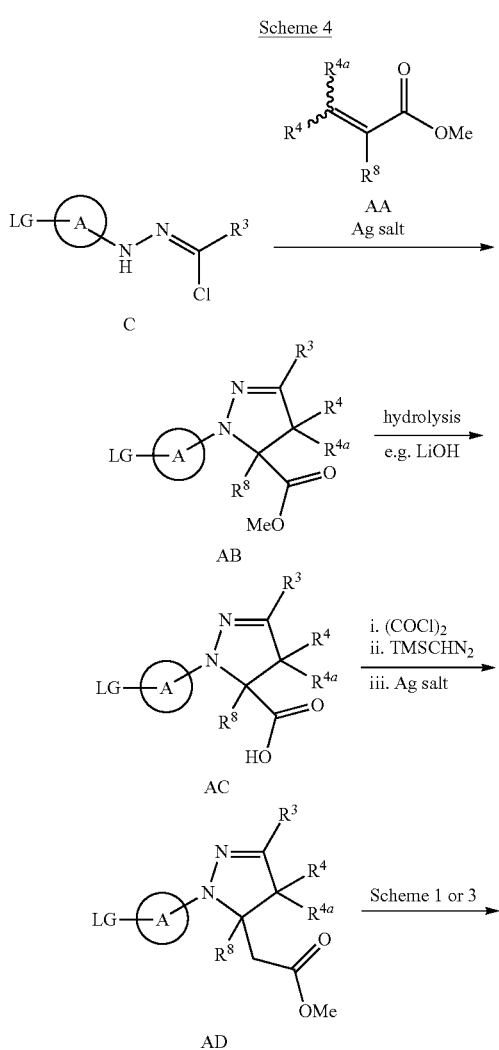

Scheme 4

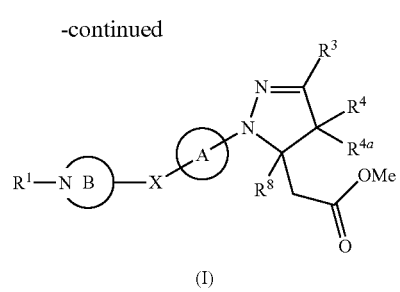

The compound of the instant invention herein described may have asymmetric centers. For example, the chiral carbon atoms in Formula (I) or Formula (II), as indicated below, exist in either as S or R configuration.

Thus, the stereoisomeric configurations of each compound of Formula (I) or Formula (II) are considered part of the invention. In structures where the stereochemistry of an intermediate or final compound is not indicated, it has not been determined.

IV. Biology

Diabetes mellitus is a serious disease afflicting over 100 million people worldwide. It is diagnosed as a group of disorders characterized by abnormal glucose homeostasis resulting in elevated blood glucose. Diabetes is a syndrome with interrelated metabolic, vascular, and neuropathic components. The metabolic abnormality is generally characterized by hyperglycemia and alterations in carbohydrate, fat and protein metabolism caused by absent or reduced insulin secretion and/or ineffective insulin secretion. The vascular syndrome consists of abnormalities in the blood vessels leading to cardiovascular, retinal and renal complications. Abnormalities in the peripheral and autonomic nervous systems are also part of diabetic syndrome. Strikingly, diabetes is the fourth leading cause of global death by disease, the largest cause of kidney failure in developed countries, the leading cause of vision loss in industrialized countries and has the greatest prevalence increase in developing countries.

Type 2 diabetes, which accounts for 90% of diabetes cases, is characterized by increasing insulin resistance associated with inadequate insulin secretion after a period of compensatory hyperinsulinemia. The reasons for β cell secondary failure are not completely understood. Acquired pancreatic islet damage or exhaustion and/or genetic factors causing susceptibility to islet secretory insufficiency have been hypothesized.

Free fatty acids (FFAs) are evidenced to influence insulin secretion from β cells primarily by enhancing glucose-stimulated insulin secretion (GSIS). Although glucose is recognized as the major stimulator of insulin secretion from β cells, other stimuli, such as amino acids, hormones, and FFAs, also regulate insulin secretion. Thus, under normal settings, insulin secretion from β cells in response to food intake is evoked by the collective stimuli of nutrients, such as glucose, amino acids, and FFAs, and hormones like the incretin glucagon-like peptide 1 (GLP-1). Fatty acids are also known to stimulate the secretion of several gut satiety hormones, including cholocystokinine (CCK), GLP-1, and peptide YY (PYY).

G-protein coupled receptors (GPCRs) expressed in β cells are known to modulate the release of insulin in response to changes in plasma glucose levels. GPR40, also known as fatty acid receptor 1 (FFAR1), is a membrane-bound FFA receptor which is preferentially expressed in the pancreatic islets and specifically in β cells. GPR40 (e.g., human GPR40, RefSeq mRNA ID NM_005303; e.g., mouse GPR40 RefSeq mRNA ID NM_194057) is a GPCR located at chromosome 19q13.12. GPR40 is activated by medium to long chain fatty acids and thereby triggering a signaling cascade that results in increased levels of $[Ca^{2+}]_i$ in β cells and subsequent stimulation of insulin secretion (Itoh et al., *Nature*, 422:173-176 (2003)). Selective small molecule agonists of GPR40 have been shown to promote GSIS and reduce blood glucose in mice (Tan et al., *Diabetes*, 57:2211-2219 (2008)). Briefly, when activators of GPR40 are administered to either normal mice or mice that are prone to diabetes due to genetic mutation, prior to a glucose tolerance test, improvements in glucose tolerance are observed. A short-lived increase in plasma insulin levels are also observed in these treated mice. It has also been shown that GPR40 agonists restore GSIS in pancreatic β-cells from the neonatal STZ rats suggesting that GPR40 agonists will be efficacious in diabetics with compromised β-cell function and mass. Fatty acids are known to stimulate the secretion of several gut satiety hormones, including cholocystokinine (CCK), GLP-1, and peptide YY (PYY), and GPR40 has been shown to colocalize with cells that secrete such hormones (Edfalk et al., *Diabetes*, 57:2280-2287 (2008) Luo et al. *PLOSone*, 7:1-12 (2012)). Fatty acids are also known to play a role in neuronal development and function, and GPR40 has been reported as a potential modulator of the fatty acid effects on neurons (Yamashima, T., *Progress in Neurobiology*, 84:105-115 (2008)).

Given the increase in the worldwide patient population afflicted by type 2 diabetes, there is a need for novel therapies which are effective with minimal adverse events.

To decrease medical burden of type 2 diabetes through enhanced glycemic control, GPR40 modulator compounds of the present invention are being investigated here for their incretin effect to promote GSIS as well as the potential combination with a broad range of anti-diabetic drugs.

The term "modulator" refers to a chemical compound with capacity to either enhance (e.g., "agonist" activity) or partially enhance (e.g., "partial agonist" activity) or inhibit (e.g., "antagonist" activity or "inverse agonist" activity) a functional property of biological activity or process (e.g., enzyme activity or receptor binding); such enhancement or inhibition may be contingent on the occurrence of a specific event, such as activation of a signal transduction pathway, receptor internalization, and/or may be manifest only in particular cell types.

It is also desirable and preferable to find compounds with advantageous and improved characteristics compared with known anti-diabetic agents, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood drug concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) improved therapeutic index with less propensity for hypoglycemia.

As used herein, the term "patient" encompasses all mammalian species.

As used herein, the term "subject" refers to any human or non-human organism that could potentially benefit from treatment with a GPR40 modulator. Exemplary subjects include human beings of any age with risk factors for metabolic disease. Common risk factors include, but are not limited to, age, sex, weight, family history, or signs of insulin resistance such as acanthosis nigricans, hypertension, dislipidemia, or polycystic ovary syndrome (PCOS).

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or "prevention" cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to modulate GPR40 and/or to prevent or treat the disorders listed herein. When applied to a combination, the term refers to combined amounts of the active ingredients that result in the preventive or therapeutic effect, whether administered in combination, serially, or simultaneously.

In Vitro GPR40 Assays

FDSS-based Intracellular Calcium Assay

Cell lines expressing GPR40 are generated using the pDEST 3×flag gene expression system and are cultured in culture medium comprising the following components: F12 (Gibco #11765), 10% lipid deprived fetal bovine serum, 250 µg/ml zeocin and 500 µg/ml G418. To conduct the fluorescent imaging plate reader (FLIPR)-based calcium flux assay to measure intracellular $Ca^{2+}$ response, cells expressing GPR40 are plated on 384 well plates (BD Biocoat #356697) at a density of 20,000 cells/20 µL medium per well in phenol red and serum-free DMEM (Gibco #21063-029) and incubated overnight. Using BD kit #s 80500-310 or -301, the cells are incubated with 20 µL per well of Hank's buffered salt solution with 1.7 mM probenecid and Fluo-3 at 37° C. for 30 min. Compounds are dissolved in DMSO and diluted to desired concentrations with assay buffer and added to the cells as 3× solution (20 µL per well). Run fluorescence/luminescence reader FDSS (Hamamatsu) to read intracellular $Ca^{2+}$ response.

The exemplified Examples disclosed below were tested in the Human GRP40 In Vitro assay described above and found having hGRP40 modulating activity.

GPR40 IP-One HTRF Assays in HEK293/GPR40 Inducible Cell Lines

Human, mouse and rat GPR40-mediated intracellular IP-One HTRF assays were established using human embryonic kidney HEK293 cells stably transfected with a tetracycline-inducible human, mouse or rat GPR40 receptor. Cells were routinely cultured in growth medium containing DMEM (Gibco Cat. #:12430-047), 10% qualified FBS (Sigma, Cat. #: F2442), 200 µg/mL hygromycin (Invitrogen, Cat. #: 16087-010) and 1.5 µg/mL blasticidin (Invitrogen, Cat. # R210-01). About 12-15 million cells were passed into a T175 tissue culture flask (BD Falcon 353112) with growth medium and incubated for 16-18 hours (overnight) at 370 C with 5% CO2. The next day, assay medium was exchanged with growth medium containing 1000 ng/mL of tetracycline (Fluka Analytical, Cat. #87128) to induce GPR40 expression for 18-24 hours at 370 C incubator with 5% CO2. After induction, the cells were washed with PBS (Gibco, Cat. #14190-036) and detached with Cell Stripper (Cellgro, Cat. #25-056-CL). 10-20 mL growth medium were added to the flask and cells were collected in 50 mL tubes (Falcon, Cat.#:352098) and spun at 1000 RPM for 5 minutes. Culture medium was aspirated and the cells were resuspended in 10 mL of 1×IP-One Stimulation Buffer from the Cisbio IP-One kit (Cisbio, Cat. #62IPAPEJ). The cells were diluted to 1.4×106 cells/mL in Stimulation Buffer.

Test compounds were 3-fold, 11-point serially diluted in DMSO in a REMP assay plate (Matrix Cat. #: 4307) by BioCel (Agilent). The compounds were transferred into an Echo plate (LABCYTE, Cat. #: LP-0200) and 20 nL of diluted compounds were transferred to an assay plate (proxiplate from Perkin Elmer, Cat. #6008289) by Echo acoustic nano dispenser (LABCYTE, model ECHO550). 14 µL of the diluted cells were then added to the assay plate by Thermo (SN 836 330) Combi Drop and incubated at room temperature for 45 minutes. Then 3 µL of IP1 coupled to dye D2 from the Cisbio IP-One kit were added to the assay plate followed by 3 µL of Lumi4TM-Tb cryptate K from the kit. The plate was further incubated at room for 1 hour before reading on the Envision (Perkin Elmer Model2101) with an HTRF protocol. Activation data for the test compound over a range of concentrations was plotted as percentage activation of the test compound (100%=maximum response). After correcting for background [(sample read-mean of low control)/(mean of high control–mean of low control)] (low control is DMSO without any compound), EC50 values were determined. The EC50 is defined as the concentration of test compound which produces 50% of the maximal response and was quantified using the 4 parameter logistic equation to fit the data. The maximal Y value observed (% Ymax) was calculated relative to a BMS standard reference compound at a final concentration of 0.625 µM.

Some of the exemplified Examples disclosed below were tested in the Human GRP40 In Vitro assay described above and found having hGRP40 modulating activity reported as hGPR40 IP1 $EC_{50}$.

In Vivo GPR40 Assays

Acute Oral Glucose Tolerance Test

Ten week old C57BL6 mice were housed individually and fasted for 5 hours on the day of study. Tail vein sampling was performed from nicked tails to obtain plasma samples. Baseline plasma samples were taken at t=0. Mice were orally treated with vehicle or compounds co-administered with glucose (2 g/kg). Sampling thereafter from tails of treated mice at 20, 40, 60, 120 and 180 min provided data used for generating glucose excursion curves from which 0-180 min blood glucose excursion profiles were generated. The area under the curve (AUC) allowed for assessment of glucose lowering by compound treatments. Blood samples were collected in EDTA-treated tubes (microvette CB300, Sarstedt, Numbrecht, Germany), stored on ice and spun @ 6000 rpm for 10 minutes. Plasma glucose was analyzed on the same day using an AU680 Clinical Chemistry Analyzer (Beckman Coulter, Brea, Calif.). Statistical analysis is a one way ANOVA with Dunnett's post hoc test or two-way student's t test where appropriate. P values less than 0.05 were considered statistically significant. Glucose reduction is reported as a % change in AUC (0-180 min) from the vehicle treatment group. For example, "Acute oral glucose tolerance: −50% @ 0.3 mg/kg" represents the results of a study as described above, whereupon administration of 0.3 mg/kg of the specified example results in a 50% reduction in glucose AUC (0-180 min) relative to vehicle treated animals.

Acute Oral Glucose Tolerance Test in Rats

Male Sprague Dawley rats (CRL, Wilmington Mass.) were used. Rats were delivered to the vivarium and acclimated for 1 week. Rats were fasted from 5 PM on the night before study. Overnight fasted rats were 180-200 grams at time of study. Tail vein sampling was performed to obtain baseline plasma samples. Rats were randomized to treatment groups based on fasting plasma glucose readings determined by Accu-Chek® glucometer (Roche, Indianapolis, Ind.). Rats were dosed at 4 mL/Kg body weight with 40% PEG400 (Sigma, St. Louis, Mo.) 10% Cremophore (Sigma, St. Louis, Mo.) and 50% distilled water with or without compounds. For rats that received BMS DPP4i combined with GPR40 agonist, administration was performed by co-dosing compounds. Plasma samples were collected one hour after compound dosing to determine baseline changes in glucose and active GLP-1 levels in the presence and absence of BMS DPP4i. Sampling thereafter from tail veins provided time point data to calculate $AUC_{0-120}$, glucose as a marker of two hour glucose lowering efficacy. Blood samples were collected in EDTA-treated tubes (microvette CB300, Sarstedt, Numbrecht, Germany), stored on ice and spun @ 6000 rpm for 10 minutes. Plasma glucose was analyzed on the same day using an AU680 Clinical Chemistry Analyzer (Beckman Coulter, Brea, Calif.). Statistical analysis is a one way ANOVA with Dunnett's post hoc test or two-way student's t test where appropriate. P values less than 0.05 were considered statistically significant. Glucose reduction is reported as a % change in AUC (0-120 min) from the vehicle treatment group. Fasting hormone responses are the difference from basal levels 1 hour post dose. Active GLP-1 levels (GLP-1 (7-36) amide and GLP-1 (7-37)) were measured by ELISA (Millipore, Billerica, Mass.).

BMS DPP4i—Reference Compound

BMS DPP4i is disclosed in Simpkins, L. et al. *Bioorganic Medicinal Chemistry Letters* 2007, 17(23), 6476-80 (compound 48) and in WO2005012249 (Example 3). BMS DPP4i has the following formula:

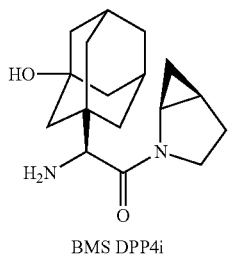 [SMILES: N[C@H](C(=O)N1CC[C@@H]2C[C@@H]21)C12CC3CC(CC(O)(C3)C1)C2]

BMS DPP4i

Figure 2:
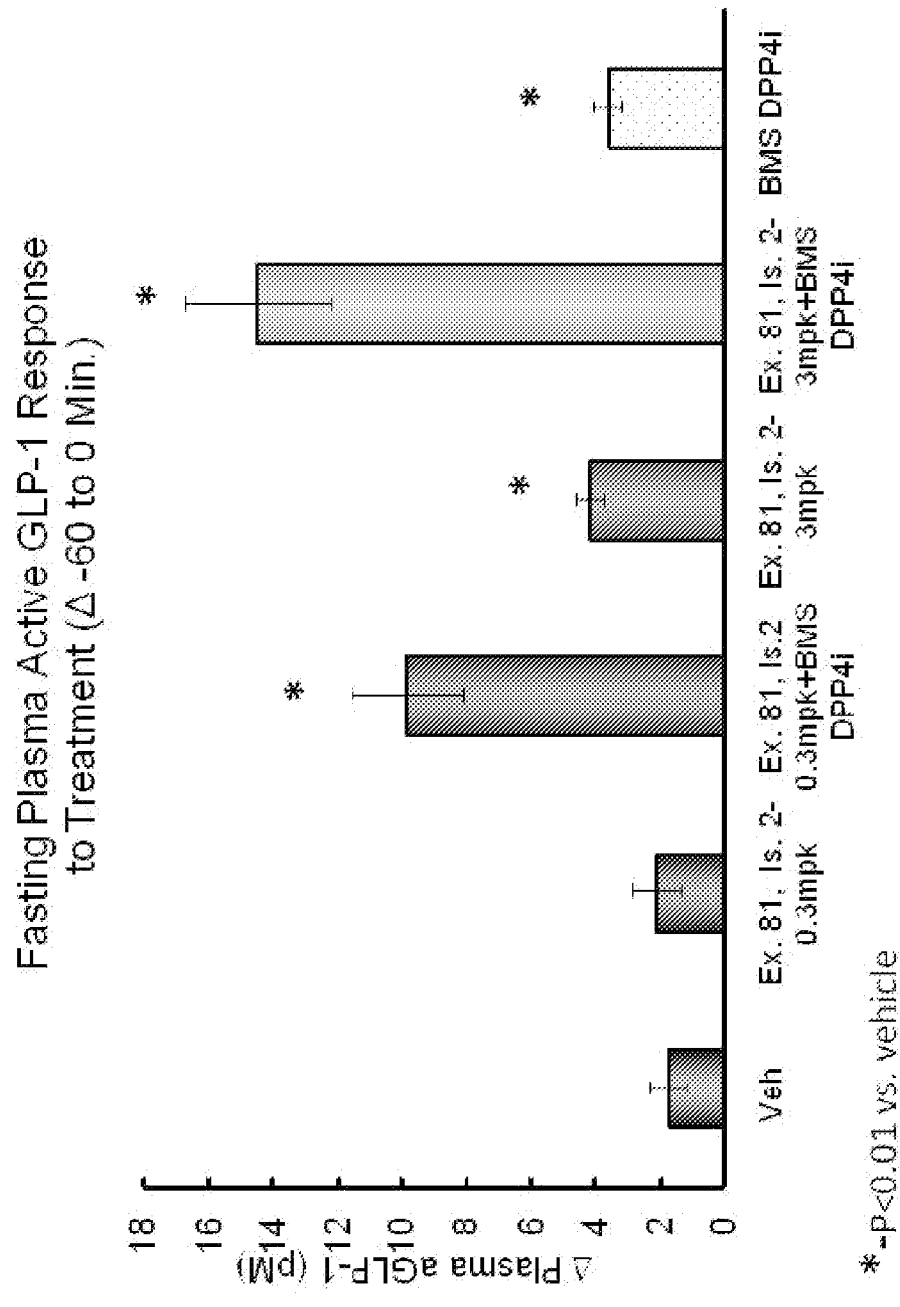
FIG. 2 shows plasma GLP-1 levels upon administration to rats from a combination study of Example 81, Isomer 2 with BMS DPP4i.

BMS DPP4i was administered to rats alone, and in combination with Example 81, Isomer 2 of the present invention, at 10 mg/kg, as depicted in FIG. 1 and FIG. 2. As depicted in FIG. 1, the combination of BMS DPP4i with Example 81, Isomer 2 demonstrated greater reductions in plasma glucose during an oral glucose tolerance test than either Example 81, Isomer 2 or BMS DPP4i alone. As depicted in FIG. 2, the combination of BMS DPP4i with Example 81, Isomer 2 shows greater increases in active GLP-1 during an oral glucose tolerance test than either Example 81, Isomer 2 or BMS DPP4i alone.

The compounds of the present invention possess activity as modulators of GPR40, and, therefore, may be used in the treatment of diseases associated with GPR40 activity. Via modulation of GPR40, the compounds of the present invention may preferably be employed to modulate the production/secretion of insulin and/or gut hormones, such as GLP-1, GIP, PYY, CCK and amylin.

Accordingly, the compounds of the present invention can be administered to mammals, preferably humans, for the treatment of a variety of conditions and disorders, including, but not limited to, treating, preventing, or slowing the progression of diabetes and related conditions, microvascular complications associated with diabetes, macrovascular complications associated with diabetes, cardiovascular diseases, Metabolic Syndrome and its component conditions, inflammatory diseases and other maladies. Consequently, it is believed that the compounds of the present invention may be used in preventing, inhibiting, or treating diabetes, hyperglycemia, impaired glucose tolerance, gestational diabetes, insulin resistance, hyperinsulinemia, retinopathy, neuropathy, nephropathy, diabetic kidney disease, acute kidney injury, cardiorenal syndrome, acute coronary syndrome, delayed wound healing, atherosclerosis and its sequelae (acute coronary syndrome, myocardial infarction, angina pectoris, peripheral vascular disease, intermittent claudication, myocardial ischemia, stroke, heart failure), Metabolic Syndrome, hypertension, obesity, fatty liver disease, dyslipidemia, hyperlipidemia, hypertriglyceridemia, hypercholesterolemia, low HDL, high LDL, vascular restenosis, peripheral arterial disease, lipid disorders, liver diseases such as NASH (Non-Alcoholic SteatoHepatitis), NAFLD (Non-Alcoholic Fatty Liver Disease) and liver cirrhosis, neurodegenerative disease, cognitive impairment, dementia, and treatment of side-effects related to diabetes, lipodystrophy and osteoporosis from corticosteroid treatment.

Metabolic Syndrome or "Syndrome X" is described in Ford et al., *J. Am. Med. Assoc.*, 287:356-359 (2002) and Arbeeny et al., *Curr. Med. Chem.—Imm., Endoc. & Metab. Agents*, 1:1-24 (2001).

GPR40 is expressed in neuronal cells, and is associated with development and maintenance of neuronal health in brain, as described in Yamashima, T. *Progress in Neurobiology* 2008, 84, 105-115.

V. Pharmaceutical Compositions, Formulations and Combinations

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V. Jr. et al. *Remington: The Science and Practice of Pharmacy* (2 *Volumes*), 22nd Edition (2012), Pharmaceutical Press.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more other therapeutic agent(s), e.g., an antidiabetic agent or other pharmaceutically active material.

The compounds of the present invention may be employed in combination with other GPR40 modulators or one or more other suitable therapeutic agents useful in the treatment of the aforementioned disorders including: anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, or cognition promoting agents, appetite suppressants, treatments for heart failure, treatments for peripheral arterial disease and anti-inflammatory agents.

Where desired, the compound of the present invention may be used in combination with one or more other types of antidiabetic agents and/or one or more other types of therapeutic agents which may be administered orally in the same dosage form, in a separate oral dosage form or by injection. The other type of antidiabetic agent that may be optionally employed in combination with the GPR40 receptor modulator of the present invention may be one, two, three or more antidiabetic agents or antihyperglycemic agents which may be administered orally in the same dosage form, in a separate oral dosage form, or by injection to produce an additional pharmacological benefit.

The antidiabetic agents used in the combination with the compound of the present invention include, but are not limited to, insulin secretagogues or insulin sensitizers, other GPR40 receptor modulators, or other antidiabetic agents. These agents include, but are not limited to, dipeptidyl peptidase IV inhibitors (DPP4i; for example, sitagliptin, saxagliptin, alogliptin, vildagliptin), biguanides (for example, metformin, phenformin), sulfonyl ureas (for example, gliburide, glimepiride, glipizide), glucosidase inhibitors (for example, acarbose, miglitol), PPARγ agonists such as thiazolidinediones (for example, rosiglitazone, pioglitazone), PPAR α/γ dual agonists (for example, muraglitazar, tesaglitazar, aleglitazar), glucokinase activators (as described in Fyfe, M. C. T. et al., Drugs of the Future, 34(8):641-653 (2009) and incorporated herein by reference), other GPR40 receptor modulators (e.g. TAK-875), GPR119 receptor modulators (for example, MBX-2952, PSN821, APD597), GPR120 receptor modulators (for example, as described in Shimpukade, B. et al. J. Med. Chem. 2012, 55 (9), 4511-4515), sodium-glucose transporter-2 (SGLT2) inhibitors (for example dapagliflozin, canagliflozin, empagliflozin, remagliflozin), 11b-HSD-1 inhibitors (for example MK-0736, BI35585, BMS-823778, and LY2523199), MGAT inhibitors (for example, as described in Barlind, J. G. et al. Bioorg. Med. Chem. Lett. 2013, 23(9), 2721-2726; or US20130143843A1), amylin analogs such as pramlintide, and/or insulin. Reviews of current and emerging therapies for the treatment of diabetes can be found in: Mohler, M. L. et al., Medicinal Research Reviews, 29(1):125-195 (2009), and Mizuno, C. S. et al., Current Medicinal Chemistry, 15:61-74 (2008).

The GPR40 receptor modulator of formula I may also be optionally employed in combination with agents for treating complication of diabetes. These agents include PKC inhibitors and/or AGE inhibitors.

The GPR40 receptor modulator of formula I way also be optionally employed in combination with one or more hypophagic agents such as diethylpropion, phendimetrazine, phentermine, orlistat, sibutramine, lorcaserin, pramlintide, topiramate, MCHR1 receptor antagonists, oxyntomodulin, naltrexone, Amylin peptide, NPY Y5 receptor modulators, NPY Y2 receptor modulators, NPY Y4 receptor modulators, cetilistat, 5HT2c receptor modulators, and the like. The compound of structure I may also be employed in combination with an agonist of the glucagon-like peptide-1 receptor (GLP-1 R), such as exenatide, liraglutide, GPR-1(1-36) amide, GLP-1(7-36) amide, GLP-1(7-37) (as disclosed in U.S. Pat. No. 5,614,492 to Habener, the disclosure of which is incorporated herein by reference), which may be administered via injection, intranasal, or by transdermal or buccal devices. Reviews of current and emerging therapies for the treatment of obesity can be found in: Melnikova, I. et al., Nature Reviews Drug Discovery, 5:369-370 (2006); Jones, D., Nature Reviews: Drug Discovery, 8:833-834 (2009);

Obici, S., *Endocrinology*, 150(6):2512-2517 (2009); and Elangbam, C. S., *Vet. Pathol.*, 46(1):10-24 (2009).

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the GPR40 receptor. Such compounds may be provided in a commercial kit, for example, for use in pharmaceutical research involving GPR40 or anti-diabetic activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving GPR40.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment and/or prophylaxis of multiple diseases or disorders associated with GPR40 (as defined previously). In another embodiment, the package insert states that the pharmaceutical composition can be used in combination (as defined previously) with a second therapeutic agent for the treatment and/or prophylaxis of multiple diseases or disorders associated with GPR40. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof.

VI. Examples

The following Examples are offered as illustrative, as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the schemes and other methods disclosed herein or may be prepared using the same.

Hplc/Ms and Preparatory/Analytical Hplc Methods Employed in Characterization or Purification of Examples Analytical HPLC/MS (unless otherwise noted) was performed on Shimadzu SCL-10A liquid chromatographs and Waters MICROMASS® ZQ Mass Spectrometers (Desolvation Gas: Nitrogen; Desolvation Temp. 250° C.; Ion Source Temp: 120° C.; Positive Electrospray conditions) using the following method:

Linear Gradient of 0% to 100% solvent B over 2 min, with 1 minute hold at 100% B;

UV visualization at 220 nm;

Column: PHENOMENEX® Luna C18 (2) 30 mm×4.60 mm; 5 m particle (Heated to Temp. 40° C.);

Flow rate: 5 mL/min;

Solvent A: 10% ACN, 90% Water, 0.1% TFA; or, 10% MeOH, 90% water, 0.1% TFA; and

Solvent B: 90% ACN, 10% Water, 0.1% TFA; or, 90% MeOH, 10% water, 0.1% TFA.

Preparatory HPLC (unless otherwise noted) was performed on a Shimadzu SCL-10A liquid chromatograph with a linear gradient of 20-100% Solvent B over 10 or 30 min, with either a 2 or 5 min (respectively) hold at 100% Solvent B;

UV visualization at 220 nm;

Column: PHENOMENEX® Luna Axia 5u C18 30×100 mm;

Flow rate: 20 mL/min;

Solvent A: 10% ACN, 90% water, 0.1% trifluoroacetic Acid; and

Solvent B: 90% ACN, 10% water, 0.1% trifluoroacetic Acid.

Preparative LC/MS (unless otherwise noted) with the following conditions:

Gradient: 25-100% B over 25 minutes, then a 5-minute hold at 100% B;

Column: Waters XBridge C18, 19×250 mm, 5-μm particles;

Guard Column: Waters XBridge C18, 19×10 mm, 5-μm particles;

Mobile Phase A: 5:95 acetonitrile:water with 10-mM ammonium acetate;

Mobile Phase B: 95:5 acetonitrile:water with 10-mM ammonium acetate;

Flow rate: 20 mL/min.

Analytical HPLC (unless otherwise noted) was performed to determine compound purity on a Shimadzu SIL-10A using the following method (Unless otherwise stated, retention times listed in Examples refer the retention times of Column 1):

orthogonal method:

Linear Gradient of 10% to 100% solvent B over 15 min;

UV visualization at 220 nm and 254 nm;

Column 1: SunFire C18 3.5 μm, 4.6×150 mm;

Column 2: Xbridge Phenyl 3.5 m, 4.6×150 mm;

Flow rate: 1 mL/min (for both columns);

Solvent A: 5% MeCN-95% H2O-0.05% TFA; and

Solvent B: 95% MeCN-5% H2O-0.05% TFA.

Or

Zorbax Method

Linear Gradient of stated starting percentage to 100% solvent B over 8 min;

UV visualization at 220 nm;

Column: Zorbax SB C18 3.5 μm, 4.6×75 mm;

Flow rate: 2.5 mL/min;

Solvent A: 10% MeOH-90% H2O-0.2% $H_3PO_4$; and

Solvent B: 90% MeOH-10% H2O-00.2% $H_3PO_4$.

Or

Analytical LC/MS method

Gradient: 0-100% B over 3 minutes, then a 0.75-minute hold at 100% B;

UV visualization at 220 nm;

Column: Waters Acquity UPLC BEH C18, 2.1×50 mm, 1.7-μm particles;

Mobile Phase A: 5:95 acetonitrile:water with 10 mM ammonium acetate; or 5:95 acetonitrile:water with 0.05% TFA;

Mobile Phase B: 95:5 acetonitrile:water with 10 mM ammonium acetate; or 95:5 acetonitrile:water with 0.05% TFA;

Temperature: 50° C.;

Flow: 1.11 mL/min.

Preparatory chiral SFC chromatography (unless otherwise noted) was performed on a Berger Multigram II SFC chromatograph using the following method:

UV visualization at 220 nm;

Column: Chiralpak AD-H SFC, 250×21 mm ID, 5 μm;

Flow rate: 60.0 mL/min, 150 bar backpressure; and

Mobile Phase: 60/40, $CO_2$/MeOH.

Analytical chiral SFC chromatography (unless otherwise noted) was performed on an Aurora Analytical SFC chromatography using the following method:

UV visualization at 220 nm;

Column: Chiralpak AD-H, 250×4.6 mm ID, 5 μm;

Flow rate: 3 mL/min, 150 bar backpressure; and

Mobile Phase: 60/40, $CO_2$/MeOH.

NMR Employed in Characterization of Examples $^1$H NMR spectra (unless otherwise noted) were obtained with JEOL or Bruker FOURIER® transform spectrometers operating at 400 MHz or 500 MHz. $^1$H-nOe experiments were performed in some cases for regiochemistry elucidation with a 400 MHz Bruker FOURIER® Transform spectrometer.

Spectral data are reported as chemical shift (multiplicity, number of hydrogens, coupling constants in Hz) and are reported in ppm (δ units) relative to either an internal standard (tetramethyl silane=0 ppm) for $^1$H NMR spectra, or are referenced to the residual solvent peak (2.49 ppm for $CD_3SOCD_2H$, 3.30 ppm for $CD_2HOD$, 1.94 for $CHD_2CN$, 7.26 ppm for $CHCl_3$, 5.32 ppm for $CDHCl_2$).

EXAMPLE 1

2-((4S,5S)-1-(4-((1-(2-fluoro-5-methoxyphenyl)piperidin-4-yl)oxy)phenyl)-4-methyl-3-(trifluoromethyl)-4,5-dihydro-1H-pyrazol-5-yl)acetic acid, HCl

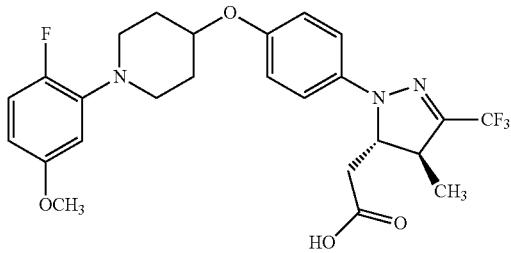 [SMILES: COc1ccc(F)c(N2CCC(Oc3ccc(N4N=C(C(F)(F)F)[C@@H](C)[C@@H]4CC(=O)O)cc3)CC2)c1]

1A. 1-(2-fluoro-5-methoxyphenyl)piperidin-4-ol: A mixture of 2-bromo-1-fluoro-4-methoxybenzene (650 mg, 3.2 mmol), piperidin-4-ol (800 mg, 7.9 mmol) and 2-dicyclohexylphosphino-2',6'-dimethoxy-1,1'-biphenyl (52 mg, 0.13 mmol) in THF (3.2 mL) was purged with argon. Tris (dibenzylideneacetone)dipalladium (0) (58 mg, 0.063 mmol) was added and followed by lithium bis(trimethylsilyl)amide (1 N in THF, 15.2 mL, 15.2 mmol). The mixture was purged with argon at rt for several min and then heated at 70° C. for 2.5 h. The reaction mixture was diluted with aqueous NaHCO$_3$ and was extracted with EtOAc. The organic extract was washed with H$_2$O, brine, dried (MgSO$_4$) and concentrated. Purification via silica gel chromatography gave the desired product as an oil (330 mg, 46% yield). LC-MS Anal. Calc'd for C$_{12}$H$_{16}$FNO$_2$: 225.26, found [M+H] 226.2. $^1$H NMR (400 MHz, CDCl$_3$) δ ppm 6.92 (1 H, dd, J=12.09, 8.79 Hz), 6.51 (1 H, dd, J=7.15, 3.30 Hz), 6.40 (1 H, dt, J=8.79, 3.02 Hz), 3.85 (1 H, td, J=8.52, 4.40 Hz), 3.76 (3 H, s), 3.27-3.46 (2 H, m), 2.74-2.91 (2 H, m), 1.95-2.14 (2 H, m), 1.75 (2 H, dtd, J=12.85, 9.10, 9.10, 3.57 Hz), 1.45 (1 H, d, J=4.40 Hz).

1B. 1-(2-fluoro-5-methoxyphenyl)piperidin-4-yl 4-methylbenzenesulfonate: To 1-(2-fluoro-5-methoxyphenyl)piperidin-4-ol (1.0 g, 4.4 mmol) and 4-methylbenzene-1-sulfonyl chloride (1.7 g, 8.9 mmol) in CH$_2$Cl$_2$ (10 mL) at rt, pyridine (3.5 g, 44 mmol) was added dropwise. The reaction was stirred at rt for 16 h. The reaction mixture was diluted with EtOAc, washed with H$_2$O, brine, dried (MgSO$_4$) and concentrated. Purification via silica gel chromatography gave the desired product (light yellow solid, 1.5 g, 87% yield). LC-MS Anal. Calc'd for C$_{19}$H$_{22}$FNO$_4$S: 379.45, found [M+H] 380.1. $^1$H NMR (400 MHz, CDCl$_3$) δ 7.91-7.76 (m, J=8.2 Hz, 2H), 7.40-7.30 (m, J=8.2 Hz, 2H), 6.91 (dd, J=12.1, 8.8 Hz, 1H), 6.52-6.33 (m, 2H), 4.79-4.58 (m, 1H), 3.75 (s, 3H), 3.22 (ddd, J=11.8, 7.4, 3.8 Hz, 2H), 2.91 (ddd, J=11.8, 7.4, 3.8 Hz, 2H), 2.46 (s, 3H), 2.05-1.84 (m, 4H).

1C N'-(4-Bromophenyl)-2,2,2-trifluoroacetohydrazide. To a stirred suspension of (4-bromophenyl)hydrazine hydrochloride (100 g, 447 mmol) in DCM (1500 mL) at rt was added dropwise a solution of TFAA (68.4 mL, 492 mmol) in DCM (150 mL). The reaction mixture was stirred at rt for 2 h and TFAA (45 mL, 324 mmol) was added slowly to the reaction mixture. After 5 min, no more solids left and the reaction was judged complete by LCMS. The reaction mixture was concentrated to half volume, and the mixture was diluted with hexane (~1 L), resulting in an off white crystalline precipitate. The mixture was filtered and the solids were rinsed with hexanes. The resulting solid was dried under high-vac 12 h at 50° C. to give N'-(4-bromophenyl)-2,2,2-trifluoroacetohydrazide (103 g, 364 mmol, 81% yield) as an off white crystalline compound. The mother liquor was concentrated and redissolved in DCM and 3 g N'-(4-bromophenyl)-2,2,2-trifluoroacetohydrazide was added. The mixture was stirred for 20 min and hexane was added to give a suspension, which was filtrated and dried to give an additional 6.3 g (+4.96% yield) of N'-(4-bromophenyl)-2,2,2-trifluoroacetohydrazide as an off white crystalline compound. LCMS: RT=2.52 min (86.6%), m/z calc'd 282, 284, obs 305, 307 [M+Na]. $^1$H NMR (400 MHz, CDCl$_3$) δ 8.10 (br. s., 1H), 7.46-7.33 (m, 2H), 6.79-6.67 (m, 2H), 6.06 (br. s., 1H).

1D (Z)—N'-(4-Bromophenyl)-2,2,2-trifluoroacetohydrazonoyl chloride. To a solution of N'-(4-bromophenyl)-2,2,2-trifluoroacetohydrazide (111.3 g, 393 mmol) in EtOAc (1500 mL) at rt was added dropwise benzenesulfonyl chloride (53.8 mL, 413 mmol). The mixture was cooled to 0° C. and Hunig's Base (72.8 mL, 413 mmol) was added dropwise. The resulting mixture was stirred at rt overnight, and the reaction was judged complete as monitored by LCMS. The mixture was diluted with EtOAc and the organic layer was washed with water (3×2 L). The combined organic extracts were dried over sodium sulfate, filtered and concentrated to give (Z)—N'-(4-bromophenyl)-2,2,2-trifluoroacetohydrazonoyl chloride (119 g, 393 mmol, 100% yield) as a yellow liquid, which was used for next step without further purification. Analytical HPLC: RT=3.93 min (83.1%). $^1$H NMR (400 MHz, CDCl$_3$) δ 8.00 (br. s., 1H), 7.51-7.36 (m, 2H), 7.11-6.94 (m, 2H).

1E (S,E)-3-But-2-enoyl-4-phenyloxazolidin-2-one. To a solution of (S)-(+)-4-phenyl-2-oxazolidinone (84.4 g, 517 mmol), lithium chloride (22.81 g, 538 mmol) and triethylamine (79 mL, 564 mmol) in THF (1200 mL) in a 5 L 3-neck flask at −5° C. was added crotonic anhydride (76 mL, 512 mmol) over 5 min. The reaction temperature increased slightly during the addition. The mixture was allowed to warm to rt, resulting in a white milky solution. The reaction mixture was stirred at rt overnight. Upon completion, as monitored by LCMS, the reaction mixture was quenched with 0.2M aqueous HCl (600 mL) to give an aqueous layer of pH~7. The two layers were seperated and the aqueous layer was extracted with EtOAc (400 mL). The combined EtOAc and THF layers were washed with brine, and dried over Na$_2$SO$_4$ and concentrated to give an light brown oil (200 mL). To the oil was added MeOH (200 mL). Crystals formed slowly at the beginning and then precipitated over 15 min. The product was collected by filtration and rinsed with MeOH (200 mL) to give white solid. More product was collected from the MeOH filtrate, and the materials were combined and dried to give 101.6 g of (S,E)-3-But-2-enoyl-4-phenyloxazolidin-2-one as white crystals.

1F. (S)-3-((4S,5R)-1-(4-Bromophenyl)-4-methyl-3-(trifluoromethyl)-4,5-dihydro-1H-pyrazole-5-carbonyl)-4-phenyloxazolidin-2-one. To A solution of (Z)—N'-(4-bromophenyl)-2,2,2-trifluoroacetohydrazonoyl chloride (94.3 g, 313 mmol) and (S,E)-3-But-2-enoyl-4-phenyloxazolidin-2-one (65.1 g, 282 mmol) in 1,4-dioxane (782 mL) under N$_2$ atm was added silver carbonate (103 g, 375 mmol) and the mixture was stirred at 50° C. overnight. The reaction was monitored via LCMS and starting material was not detected. The reaction mixture was filtered through Celite, and the filter cake was washed with EtOAc. The filtrate was concentrated to give an oil, which was purified via silica gel chromatography to give a yellow oil. The residue was purified via crystallization from hexanes-ether (7; 3) to give (S)-3-((4S,5R)-1-(4-bromophenyl)-4-methyl-3-(trifluoromethyl)-4,5-dihydro-1H-pyrazole-5-carbonyl)-4-phenyloxazolidin-2-one (72 g, 145 mmol, 46.4% yield) as a white cystalline compound. $^1$H NMR (400 MHz, CDCl$_3$) δ 7.47-7.31 (m, 5H), 7.29-7.20 (m, 3H), 6.93-6.81 (m, 2H), 5.81 (d, J=2.2 Hz, 1H), 5.39 (dd, J=8.8, 4.2 Hz, 1H), 4.82 (t, J=9.0 Hz, 1H), 4.43 (dd, J=9.2, 4.2 Hz, 1H), 3.16 (dd, J=7.0, 1.5 Hz, 1H), 1.50 (d, J=7.0 Hz, 3H).

1G. ((4S,5R)-1-(4-Bromophenyl)-4-methyl-3-(trifluoromethyl)-4,5-dihydro-1H-pyrazol-5-yl)methanol. To a solution of (S)-3-((4S,5R)-1-(4-bromophenyl)-4-methyl-3-(trifluoromethyl)-4,5-dihydro-1H-pyrazole-5-carbonyl)-4-phenyloxazolidin-2-one (93.8 g, 189 mmol) in THF (1420 mL) was added a solution of NaBH$_4$ (7.15 g, 189 mmol) in water (56.8 mL) in two portions. The first portion was slowly added over 5 min and the internal temperature raised from 20.5° C. to 28.9° C., and the second portion was added more rapidly. The resulting mixture was stirred at rt for 4 h. The reaction mixture was cooled to 2° C., and 10% KHSO$_4$ (180 mL) was added while maintaining internal temperature <10° C. The resulting mixture was stirred for 30 min and the mixture was evaporated. The residue was diluted with EtOAc (900 mL) and water (900 mL). The layers were extracted and the organic layer was washed with brine. The organic layer was dried over Na$_2$SO$_4$ and the solution was filtered and evaporated to give 102 g of a white semi-solid that was purified via silica gel chromatography to give 85 g of ((4S,5R)-1-(4-bromophenyl)-4-methyl-3-(trifluoromethyl)-4,5-dihydro-1H-pyrazol-5-yl)methanol as a white solid. LCMS: RT=3.64 min (93.6%), m/z calc'd 336, 338, obs 337, 339 [M+H]. $^1$H NMR (400 MHz, CDCl$_3$) δ 7.46-7.35 (m, 2H), 7.10-6.95 (m, 2H), 4.07 (q, J=4.6 Hz, 1H), 3.90-3.69 (m, 2H), 3.55-3.39 (m, 1H), 1.63-1.49 (m, 1H), 1.36 (dd, J=7.2, 0.6 Hz, 3H).

1H. ((4S,5R)-1-(4-Bromophenyl)-4-methyl-3-(trifluoromethyl)-4,5-dihydro-1H-pyrazol-5-yl)methyl methanesulfonate. To a cooled (0-5° C.) solution of ((4S,5R)-1-(4-bromophenyl)-4-methyl-3-(trifluoromethyl)-4,5-dihydro-1H-pyrazol-5-yl)methanol (85 g, 252 mmol) in THF (750 mL) was added triethylamine (70.3 mL, 504 mmol) and methanesulfonyl chloride (22.59 mL, 290 mmol). A white precipitate was observed. The mixture was stirred at rt for 30 min, and the reaction was judged complete as monitored by LCMS. The mixture was diluted with EtOAc (250 mL) and sat'd aqueous NaHCO$_3$. The layers were extracted, and the aqueous layer was back extracted with EtOAc. The combined organic layers were washed successively with water and brine. The organic layer was dried over MgSO$_4$, and the solution was filtered and evaporated to give ((4S,5R)-1-(4-bromophenyl)-4-methyl-3-(trifluoromethyl)-4,5-dihydro-1H-pyrazol-5-yl)methyl methanesulfonate (103 g, 248 mmol, 98% yield). LCMS: r.t. 3.60 min (94.7%), m/z calc'd 414, 416, obs 415, 417 [M+H].

1I. 2-((4S,5S)-1-(4-Bromophenyl)-4-methyl-3-(trifluoromethyl)-4,5-dihydro-1H-pyrazol-5-yl)acetonitrile. A suspension of KCN (9.89 g, 147 mmol) in DMSO (700 mL) was heated to 60° C. for 1 h and cooled to 40° C. To this mixture was added a solution of ((4S,5R)-1-(4-bromophenyl)-4-methyl-3-(trifluoromethyl)-4,5-dihydro-1H-pyrazol-5-yl)methyl methanesulfonate (51 g, 123 mmol) in 50 mL of DMSO. The mixture was heated at 40° C. for 9 h, and was judged complete as monitored by LCMS. The reaction mixture was cooled in an ice bath and stirred overnight. The reaction mixture was diluted with ice (450 g), EtOAc (500 mL), and sat'd aqueous NaHCO$_3$ solution (250 mL). The mixture was stirred for 15 min and the layers were separated. The aqueous layer was extracted with EtOAc (200 mL) and the combined organic layers were washed with brine. The organic layer was dried over MgSO$_4$, filtered and evaporated to give 2-((4S,5S)-1-(4-bromophenyl)-4-methyl-3-(trifluoromethyl)-4,5-dihydro-1H-pyrazol-5-yl)acetonitrile (39 g, 113 mmol, 92% yield) as a slight reddish oil. LCMS: RT=3.55 min (88.3%), m/z calc'd 345, 347, obs 368, 380 [M+Na]. $^1$H NMR (400 MHz, CDCl$_3$) δ 7.53-7.39 (m, 2H), 7.07-6.92 (m, 2H), 4.36-4.24 (m, 1H), 3.56-3.31 (m, 1H), 2.78 (dd, J=16.9, 3.5 Hz, 1H), 2.50 (dd, J=16.9, 9.0 Hz, 1H), 1.48-1.36 (m, 3H).

1J. Methyl 2-((4S,5S)-1-(4-bromophenyl)-4-methyl-3-(trifluoromethyl)-4,5-dihydro-1H-pyrazol-5-yl)acetate: To a cooled (0° C.) solution of methanol (1 L) and dichloromethane (1.5 L) was added acetyl chloride (0.33 L, 4.7 mol) over 45 min. The resulting mixture was stirred for 1 h, and 2-((4S,5S)-1-(4-bromophenyl)-4-methyl-3-(trifluoromethyl)-4,5-dihydro-1H-pyrazol-5-yl)acetonitrile (90 g, 0.26 mol) was added, and the mixture was stirred for 2 h at rt. The reaction mixture was evaporated in vacuo, and the residue was treated with a solution of HCl/methanol/dichloromethane as generated above. The reaction mixture was stirred overnight at rt. The reaction mixture was evaporated in vacuo, and the residue was dissolved in HCl/methanol that was formed separately by mixing methanol with acetyl chloride as above (1 L methanol treated with 0.33 L of acetyl chloride at 0° C. for 45 min) The reaction mixture was stirred at rt overnight, and was heated at 40° C. for 1 h. The reaction mixture was diluted with 1 L of acetonitrile, and the mixture was evaporated in vacuo. The residue was dissolved in ethyl acetate, and the mixture was washed successively with 2× sat'd aqueous NaHCO$_3$ and brine. The combined organic layers were dried over Na$_2$SO$_3$, the mixture was filtered, and the solution was evaporated. The residue was purified via silica chromatography to give 80.5 g of methyl 2-((4S,5S)-1-(4-bromophenyl)-4-methyl-3-(trifluoromethyl)-4,5-dihydro-1H-pyrazol-5-yl)acetate as a light yellow oil. LC-MS Anal. Calc'd for C$_{14}$H$_{14}$BrF$_3$N$_2$O$_2$: 378.02, found [M+H] 379.5, 381.5. $^1$H NMR (400 MHz, CDCl$_3$) δ 7.43-7.37 (m, 2 H), 7.01-6.94 (m, 2 H), 4.45-4.37 (m, 1 H), 3.72 (s, 3 H), 3.23-3.15 (m, 1 H), 2.79 (dd, J=3.0, 16.3 Hz, 1 H), 2.41 (dd, J=10.3, 16.3 Hz, 1 H), 1.34 (d, J=7.0 Hz, 3 H). $^{13}$C NMR (300 MHz, CDCl$_3$) δ 170.57, 142.50, 132.29, 129.58, 123.02, 119.45, 115.78, 113.60, 77.43, 65.06, 52.08, 45.52, 34.81, 17.70. $^{19}$F-NMR (400 MHz, CDCl$_3$) δ −63.25

1K. Methyl 2-((4S,5S)-4-methyl-1-(4-(4,4,5,5-tetramethyl-1,3,2-dioxaborolan-2-yl)phenyl)-3-(trifluoromethyl)-4,5-dihydro-1H-pyrazol-5-yl)acetate: A mixture of methyl 2-((4S,5S)-1-(4-bromophenyl)-4-methyl-3-(trifluoromethyl)-4,5-dihydro-1H-pyrazol-5-yl)acetate (1.517 g, 4.0 mmol), 4,4,4',4',5,5,5',5'-octamethyl-2,2'-bi(1,3,2-dioxaborolane) (1.63 g, 6.4 mmol), potassium acetate (1.26 g, 12.8 mmol) and 1,1'-(diphenylphosphino)ferrocene)palladium dichloride (0.16 g, 0.20 mmol) in DMF (8 mL) was purged with argon. The reaction mixture was heated at 80° C. for 2 h. The reaction mixture was diluted with EtOAc, washed with H$_2$O, brine, dried (MgSO$_4$) and concentrated. Purification via silica gel chromatography gave the desired product as a gum (2.36 g). The crude product was used without further purification.

1L. Methyl 2-((4S,5S)-1-(4-hydroxyphenyl)-4-methyl-3-(trifluoromethyl)-4,5-dihydro-1H-pyrazol-5-yl)acetate: To a solution of methyl 2-((4S,5S)-4-methyl-1-(4-(4,4,5,5-tetramethyl-1,3,2-dioxaborolan-2-yl)phenyl)-3-(trifluoromethyl)-4,5-dihydro-1H-pyrazol-5-yl)acetate in ethyl acetate (75 mL), was added hydrogen peroxide (30 wt % in water, 15 mL) dropwise. The reaction mixture was stirred at rt. After 1 h, additional hydrogen peroxide solution (6.5 mL)

and 15 mL EtOAc were added. After the mixture was stirred at rt for 7 h, the reaction mixture was cooled with an ice-water bath and the reaction was slowly quenched with aqueous sodium sulfite. The mixture was extracted with EtOAc. The organic extracts were washed with brine, dried (MgSO$_4$) and concentrated. Purification via silica gel chromatography gave the desired product as an oil (1.1 g, 85% yield). LC-MS Anal. Calc'd for C$_{14}$H$_{15}$F$_3$N$_2$O$_3$: 316.28, found [M+H] 317.2.

1M. Methyl 2-((4S,5S)-1-(4-((1-(2-fluoro-5-methoxyphenyl)piperidin-4-yl)oxy)phenyl)-4-methyl-3-(trifluoromethyl)-4,5-dihydro-1H-pyrazol-5-yl)acetate: To 1-(2-fluoro-5-methoxyphenyl)piperidin-4-yl 4-methylbenzenesulfonate (1.22 g, 2.96 mmol) and methyl 2-((4S,5S)-1-(4-hydroxyphenyl)-4-methyl-3-(trifluoromethyl)-4,5-dihydro-1H-pyrazol-5-yl)acetate (0.94 g, 3.0 mmol) in DMF (7 mL), cesium carbonate (2.22 g, 6.81 mmol) was added. The reaction mixture was heated at 60° C. for 16 h. The reaction mixture was cooled to rt and treated with methyl iodide (698 mg, 4.92 mmol) and stirred at rt for 1 h. The reaction mixture was diluted with EtOAc, washed with H$_2$O, brine, dried (MgSO$_4$) and concentrated. Purification via silica gel chromatography gave the desired product as a gum (660 mg, 42% yield). LC-MS Anal. Calc'd for C$_{26}$H$_{29}$F$_4$N$_3$O$_4$: 523.52, found [M+H] 524.2. $^1$H NMR (400 MHz, CDCl$_3$) δ 7.12-6.99 (m, 2H), 6.99-6.83 (m, 3H), 6.53 (dd, J=7.1, 3.3 Hz, 1H), 6.41 (dt, J=8.8, 3.3 Hz, 1H), 4.38 (tt, J=7.1, 3.6 Hz, 2H), 3.81-3.73 (m, 3H), 3.72-3.67 (m, 3H), 3.33 (ddd, J=11.4, 7.6, 3.6 Hz, 2H), 3.26-3.12 (m, 1H), 2.97 (ddd, J=11.7, 8.1, 3.3 Hz, 2H), 2.80 (dd, J=15.9, 3.3 Hz, 1H), 2.49-2.33 (m, 1H), 2.19-2.04 (m, 2H), 2.04-1.87 (m, 2H), 1.34 (d, J=6.6 Hz, 3H).

Example 1: To a solution of methyl 2-((4S,5S)-1-(4-((1-(2-fluoro-5-methoxyphenyl)piperidin-4-yl)oxy)phenyl)-4-methyl-3-(trifluoromethyl)-4,5-dihydro-1H-pyrazol-5-yl)acetate (533 mg, 1.02 mmol) in THF (20 mL) was added lithium hydroxide (1 N in water, 1.43 mL, 1.43 mmol) and the reaction was stirred at rt. After 16 h, additional lithium hydroxide (1 N, 2.64 mL, 2.64 mmol) was added. The reaction mixture was stirred at rt for an additional 3 h. The reaction mixture was cooled with an ice-water bath, and the solution was acidified with 1 N HCl. The mixture was extracted with CH$_2$Cl$_2$. The extracts were dried (MgSO$_4$) and concentrated, and the residue was purified via RP-Prep HPLC. The product-containing fractions were evaporated, and the residue was treated with CH$_3$CN and 1 N HCl and lyophilized to give 2-((4S,5S)-1-(4-((1-(2-fluoro-5-methoxyphenyl)piperidin-4-yl)oxy)phenyl)-4-methyl-3-(trifluoromethyl)-4,5-dihydro-1H-pyrazol-5-yl)acetic acid, HCl as a light yellow solid (480 mg, 84% yield). LC-MS Anal. Calc'd for C$_{25}$H$_{27}$F$_4$N$_3$O$_4$: 509.19, found [M+H] 510.2. $^1$H NMR (500 MHz, CD$_3$CN) δ ppm 7.13-7.07 (m, 2H), 7.07-7.03 (m, 1H), 7.01-6.96 (m, 2H), 6.74 (dd, J=7.2, 3.0 Hz, 1H), 6.61 (dt, J=8.9, 3.3 Hz, 1H), 5.67 (br.s, 1H), 4.53-4.47 (m, 1H), 4.47-4.42 (m, 1H), 3.79 (s, 3H), 3.46 (ddd, J=11.6, 7.6, 3.6 Hz, 2H), 3.40-3.32 (m, 1H), 3.11 (ddd, J=11.9, 8.2, 3.3 Hz, 2H), 2.75 (dd, J=16.5, 3.0 Hz, 1H), 2.52 (dd, J=16.5, 9.6 Hz, 1H), 2.21-2.13 (m, 2H), 2.00 (s, 1H), 1.96-1.89 (m, 2H), 1.33 (d, J=7.2 Hz, 3H) Analytical HPLC(Orthogonal method): RT=9.1 min, HI: 97%. hGPR40 EC$_{50}$=114 nM. hGPR40 IP1 EC$_{50}$=17 nM. Acute oral glucose tolerance: – 47% @ 0.3 mg/kg.

EXAMPLE 2

2-((4S,5S)-1-(4-((8-(2-fluoro-5-methoxyphenyl)-8-azabicyclo[3.2.1]octan-3-yl)oxy)phenyl)-4-methyl-3-(trifluoromethyl)-4,5-dihydro-1H-pyrazol-5-yl) acetic acid, HCl

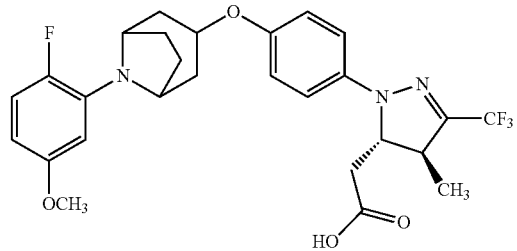 [SMILES: COc1ccc(F)c(N2C3CCC2CC(Oc2ccc(N4N=C(C(F)(F)F)[C@@H](C)[C@@H]4CC(=O)O)cc2)C3)c1]

2A. 8-benzyl-8-azaspiro[bicyclo[3.2.1]octane-3,2'-[1,3]dioxolane]: To a round bottom flask fitted with a Dean-Stark trap was added 8-benzyl-8-azabicyclo[3.2.1]octan-3-one (8.60 g, 40 mmol), ethane-1,2-diol (8.08 mL, 145 mmol), p-toluenesulfonic acid monohydrate (0.76 g, 4.0 mmol) and toluene (100 mL). The reaction mixture was heated at reflux. Additional ethane-1,2-diol (6 mL, 108 mmol) was added after 6 h. The reaction was refluxed for 23 h, cooled and diluted with EtOAc. The organic liquid was washed with sat. aqueous NaHCO$_3$, H$_2$O, brine, dried (MgSO$_4$) and concentrated. Purification via silica gel chromatography gave the desired product as an oil (1.87 g, 18% yield) and recovered 3 g the starting material 8 benzyl-8-azabicyclo[3.2.1]octan-3-one. LC-MS Anal. Calc'd for C$_{16}$H$_{21}$NO$_2$:259.34, found [M+H] 260.2.

2B. 8-azaspiro[bicyclo[3.2.1]octane-3,2'-[1,3]dioxolane]: A mixture of 8-benzyl-8-azaspiro[bicyclo[3.2.1]octane-3,2'-[1,3]dioxolane] (1.86 g, 7.17 mmol) and 20% palladium hydroxide on carbon (0.96 g) in MeOH (100 mL) was stirred at rt under H$_2$ atmosphere (1 atm, balloon) for 18 h. The mixture was filtered through Celite and the filtrate was concentrated to give a brown solid (1.21 g, 100% yield). LC-MS Anal. Calc'd for C$_9$H$_{15}$NO$_2$:169.22, found [M+H] 170.1.

2C. 8-(2-fluoro-5-methoxyphenyl)-8-azaspiro[bicyclo[3.2.1]octane-3,2'-[1,3]dioxolane]: A mixture of 2-bromo-1-fluoro-4-methoxybenzene (1.70 g, 8.27 mmol), 8-azaspiro[bicyclo[3.2.1]octane-3,2'-[1,3]dioxolane] (1 g, 5.91 mmol) and 2-dicyclohexylphosphino-2',6'-dimethoxy-1,1'-biphenyl (0.12 g, 0.29 mmol) in THF (7 mL) was purged with argon. Tris(dibenzylideneacetone)dipalladium (0) (0.11 g, 0.12 mmol) was added and followed by lithium bis(trimethylsilyl)amide (1 N in THF, 7.1 mL, 7.1 mmol). The resulting mixture was purged with argon for several min and the mixture was heated at 70° C. for 2.5 h. The reaction mixture was quenched with aqueous NaHCO$_3$, extracted with EtOAc. The extracts were washed with H$_2$O, brine, dried (MgSO$_4$) and concentrated. Purification via silica gel chromatography gave 8-(2-fluoro-5-methoxyphenyl)-8-azaspiro[bicyclo[3.2.1]octane-3,2'-[1,3]dioxolane] as an oil (890 mg, 51% yield). LC-MS Anal. Calc'd for C$_{16}$H$_{20}$FNO$_3$ 293.333, found [M+H] 294.2.

2D. 8-(2-fluoro-5-methoxyphenyl)-8-azabicyclo[3.2.1] octan-3-one: To a solution of 8-(2-fluoro-5-methoxyphenyl)-8-azaspiro[bicyclo[3.2.1]octane-3,2'-[1,3]dioxolane] (1.1 g, 3.6 mmol) in acetone (50 mL) and water (22 mL) was added p-toluenesulfonic acid monohydrate (1.0 g, 5.4 mmol). The reaction mixture was heated at 60° C. for 2 h, and the volatile organics were removed in vacuo. The resulting mixture was treated with 600 mg solid NaHCO$_3$, and the solution was extracted with EtOAc. The extracts were washed with sat. NaHCO$_3$, H$_2$O, brine, dried (MgSO$_4$) and concentrated. Purification via silica gel chromatography gave 8-(2-fluoro-5-methoxyphenyl)-8-azabicyclo[3.2.1]octan-3-one as an oil (843 mg, 94% yield). LC-MS Anal. Calc'd for C$_{14}$H$_{16}$FNO$_2$ 249.28 found [M+H] 250.1.

2E. 8-(2-fluoro-5-methoxyphenyl)-8-azabicyclo[3.2.1]octan-3-ol Isomer A and Isomer B: To 8-(2-fluoro-5-methoxyphenyl)-8-azabicyclo[3.2.1]octan-3-one (920 mg, 3.7 mmol) in MeOH (14 mL) and THF (3.5 mL) at 0° C., sodium borohydride (420 mg, 11 mmol) was added portions over 10 min. The reaction was stirred at 0° C. for 2 h 30 min. The reaction mixture was cooled with ice-water bath, quenched with 20 mL sat. NaHCO$_3$. MeOH and THF were evaporated. The residue was extracted with EtOAc. The extracts were washed with H$_2$O, brine, dried (MgSO$_4$) and concentrated. Purification via silica gel chromatography gave 2E (Isomer A) as a white solid (472 mg, 51% yield), LC-MS Anal. Calc'd for C$_{14}$H$_{18}$FNO$_2$:251.30, found [M+H] 252.2; and 2E (Isomer B) as a white solid (273 mg, 29.4% yield), LC-MS Anal. Calc'd for C$_{14}$H$_{18}$FNO$_2$ 251.30, found [M+H] 252.2.

2F. 8-(2-fluoro-5-methoxyphenyl)-8-azabicyclo[3.2.1]octan-3-yl 4-methylbenzenesulfonate: To 8-(2-fluoro-5-methoxyphenyl)-8-azabicyclo[3.2.1]octan-3-ol (Isomer A) (40 mg, 0.16 mmol) and 4-methylbenzene-1-sulfonyl chloride (48 mg, 0.26 mmol) in CH$_2$Cl$_2$ (0.4 mL), pyridine (0.13 mL, 1.6 mmol) was added dropwise. The reaction mixture was stirred at rt and additional 4-methylbenzene-1-sulfonyl chloride (20 mg, 0.11 mmol) was added after 21 h. After stirring for 24 h, the reaction mixture was diluted with EtOAc, and the organic layer was washed with H$_2$O, brine, dried (MgSO$_4$) and concentrated. Purification via silica gel chromatography gave 8-(2-fluoro-5-methoxyphenyl)-8-azabicyclo[3.2.1]octan-3-yl 4-methylbenzenesulfonate as a gum (30 mg, 46% yield), LC-MS Anal. Calc'd for C$_{15}$H$_{20}$FNO$_4$S, 329.39, found [M+H] 330.2.

2G. Methyl 2-((4S,5S)-1-(4-((8-(2-fluoro-5-methoxyphenyl)-8-azabicyclo[3.2.1]octan-3-yl)oxy)phenyl)-4-methyl-3-(trifluoromethyl)-4,5-dihydro-1H-pyrazol-5-yl)acetate: To 8-(2-fluoro-5-methoxyphenyl)-8-azabicyclo[3.2.1]octan-3-yl 4-methylbenzenesulfonate (29.5 mg, 0.073 mmol) and methyl 2-((4S,5S)-1-(4-hydroxyphenyl)-4-methyl-3-(trifluoromethyl)-4,5-dihydro-1H-pyrazol-5-yl)acetate (23 mg, 0.073 mmol) (1J) in DMF (0.3 mL), cesium carbonate (47 mg, 0.15 mmol) was added. The reaction mixture was heated at 65° C. for 16 h, and was cooled to rt. To the mixture was added iodomethane (60 mg) and the solution was stirred at rt for 1.5 h. The reaction mixture was diluted with EtOAc, washed with H$_2$O, brine, dried (MgSO$_4$) and concentrated. Purification via silica gel chromatography gave 2G as a gum (11 mg, 28% yield), LC-MS Anal. Calc'd for C$_{28}$H$_{31}$F$_4$N$_3$O$_4$ 549.56, found [M+H] 550.3.

Example 2: To methyl 2-((4S,5S)-1-(4-((8-(2-fluoro-5-methoxyphenyl)-8-azabicyclo[3.2.1]octan-3-yl)oxy)phenyl)-4-methyl-3-(trifluoromethyl)-4,5-dihydro-1H-pyrazol-5-yl)acetate (28 mg, 0.051 mmol) in THF (4 mL), lithium hydroxide (1 N, 0.26 mL, 0.26 mmol) was added. The reaction mixture was stirred at rt for 6 h and 30 min. The mixture was cooled with ice-water bath, acidified with TFA and concentrated. The residue was purified via RP-prep HPLC. The product-containing fractions were evaporated and the residue was treated with CH$_3$CN/1 N HCl and lyophilized to give 2-((4S,5S)-1-(4-((8-(2-fluoro-5-methoxyphenyl)-8-azabicyclo[3.2.1]octan-3-yl)oxy)phenyl)-4-methyl-3-(trifluoromethyl)-4,5-dihydro-1H-pyrazol-5-yl)acetic acid, HCl as a grey solid (20 mg, 68% yield). LC-MS Anal. Calc'd for C$_{27}$H$_{29}$F$_4$N$_3$O$_4$ 535.21, found [M+H] 536.3. $^1$H NMR (500 MHz, CD$_3$CN) δ ppm 7.11-7.05 (m, 1 H), 6.96 (d, J=8.9 Hz, 2 H), 6.86 (d, J=8.9 Hz, 2 H), 6.73-6.67 (m, 2H), 4.67 (m, 1 H), 4.45-4.30 (m, 3 H), 3.73 (s, 3 H), 3.28-3.18 (m, 2 H), 1.87-2.64 (m, 7 H), 1.1-1.3 (m, 5 H), Analytical HPLC: RT=9.8 min, HI: 99%. hGPR40 EC$_{50}$=644 nM.

EXAMPLE 3

2-((4S,5S)-1-(4-((1-(5-ethoxy-2-fluorophenyl)-3-methylpiperidin-4-yl)methyl)phenyl)-4-methyl-3-(trifluoromethyl)-4,5-dihydro-1H-pyrazol-5-yl)acetic acid, HCl (Isomers 1, 2, 3 and 4)

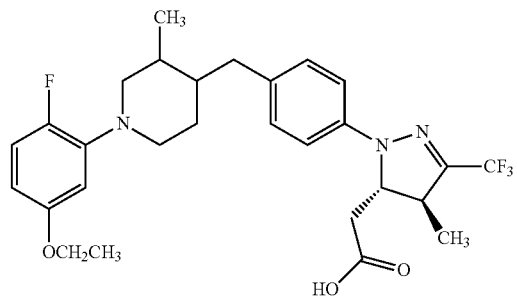 [SMILES: CCOc1ccc(F)c(N2CCC(Cc3ccc(N4N=C(C(F)(F)F)[C@@H](C)[C@@H]4CC(=O)O)cc3)C(C)C2)c1]

3A. 8-benzyl-6-methyl-1,4-dioxa-8-azaspiro[4.5]decane: To a round bottom flask fitted with a Dean-Stark trap was added 1-benzyl-3-methylpiperidin-4-one (3.05 g, 15 mmol), ethane-1,2-diol (6.3 mL, 110 mmol), p-toluenesulfonic acid monohydrate (1.1 g, 6 mmol) and toluene (60 mL). The reaction was heated at 120° C. for 25 h. The reaction mixture was diluted with EtOAc, washed with sat. aqueous NaHCO$_3$, water, brine, dried (MgSO$_4$) and concentrated. Purification via silica gel chromatography gave 8-benzyl-6-methyl-1,4-dioxa-8-azaspiro[4.5]decane as an oil, (3.6 g, 97% yield). LC-MS Anal. Calc'd for C$_{15}$H$_{21}$NO$_2$ 247.33, found [M+H] 248.2.

3B. 6-methyl-1,4-dioxa-8-azaspiro[4.5]decane: A mixture of 8-benzyl-6-methyl-1,4-dioxa-8-azaspiro[4.5]decane (3.6 g, 15 mmol) and palladium hydroxide on carbon (20 wt. %, 1.94 g) in MeOH (180 mL) was stirred at rt under H$_2$ atmosphere (1 atm, balloon) for 24 h. The mixture was filtered through celite and the filtrate was concentrated to give 6-methyl-1,4-dioxa-8-azaspiro[4.5]decane as an oil (2.18 g, 95% yield). LC-MS Anal. Calc'd for C$_8$H$_{15}$NO$_2$ 157.21, found [M+H] 158.2.

3C. 8-(5-ethoxy-2-fluorophenyl)-6-methyl-1,4-dioxa-8-azaspiro[4.5]decane: A mixture of 2-bromo-4-ethoxy-1-fluorobenzene (654 mg, 3.0 mmol), 6-methyl-1,4-dioxa-8-azaspiro[4.5]decane (563 mg, 3.6 mmol) and 2-dicyclohexylphosphino-2',6'-dimethoxy-1,1'-biphenyl (74 mg, 0.18 mmol) in THF (4 mL) was purged with argon. Tris(dibenzylideneacetone)dipalladium (0) (55 mg, 0.06 mmol) was added and followed by lithium bis(trimethylsilyl)amide (1 N in THF, 3.88 mL, 3.88 mmol). The mixture was purged with argon for several min and then heated at 70° C. for 3 h. The reaction was quenched with aqueous NaHCO$_3$, diluted with EtOAc, washed with water, brine, dried (MgSO$_4$) and concentrated. Purification via silica gel chromatography gave 8-(5-ethoxy-2-fluorophenyl)-6-methyl-1,4-dioxa-8-azaspiro[4.5]decane as an oil (387 mg, 44% yield). LC-MS Anal. Calc'd for $C_{16}H_{22}FNO_3$ 295.35, found [M+H] 296.2.

3D. 1-(5-ethoxy-2-fluorophenyl)-3-methylpiperidin-4-one: To a solution of 8-(5-ethoxy-2-fluorophenyl)-6-methyl-1,4-dioxa-8-azaspiro[4.5]decane (645 mg, 2.43 mmol) in acetone (35 mL) and water (15 mL) was added p-toluenesulfonic acid monohydrate (700 mg, 3.6 mmol). The reaction mixture was heated at 60° C. for 3 h 30 min and volatile organics were evaporated in vacuo. The resulting mixture was treated with 400 mg solid $NaHCO_3$ and was extracted with EtOAc. The organic extracts were washed with sat. $NaHCO_3$, water, brine, dried ($MgSO_4$) and concentrated. Purification via silica gel chromatography gave 1-(5-ethoxy-2-fluorophenyl)-3-methylpiperidin-4-one as an oil (520 mg, 90% yield). LC-MS Anal. Calc'd for $C_{14}H_{18}FNO_2$ 251.13, found [M+H] 252.2.

3E. 1-(5-ethoxy-2-fluorophenyl)-3-methyl-4-methylenepiperidine: To (methyl)triphenylphosphonium bromide (940 mg, 2.6 mmol) in THF (6 mL) at 0° C., N-butyllithium (1.7 mL, 2.6 mmol) was added. The reaction mixture was stirred at 0° C. for 30 min. To this solution was added 1-(5-ethoxy-2-fluorophenyl)-3-methylpiperidin-4-one (472 mg, 1.88 mmol) in THF (4 mL). The reaction mixture was stirred at rt for 2 h and the reaction was quenched with aqueous $NH_4Cl$. The mixture was diluted with EtOAc, washed with $H_2O$, brine, dried ($MgSO_4$) and concentrated. Purification via silica gel chromatography gave 1-(5-ethoxy-2-fluorophenyl)-3-methyl-4-methylenepiperidine as an oil (364 mg, 78% yield). LC-MS Anal. Calc'd for $C_{15}H_{20}FNO$, 249.324, found [M+H] 250.1.

3F. 2-((4S,5S)-1-(4-((1-(5-ethoxy-2-fluorophenyl)-3-methylpiperidin-4-yl)methyl)phenyl)-4-methyl-3-(trifluoromethyl)-4,5-dihydro-1H-pyrazol-5-yl)acetonitrile (Isomers 1 and 2, Isomers 3 and 4): To 1-(5-ethoxy-2-fluorophenyl)-3-methyl-4-methylenepiperidine (321 mg, 1.29 mmol) in THF (0.6 mL) under argon 9-borabicyclo[3.3.1]nonane (2.57 mL, 1.29 mmol) (0.5 M in THF) was added. The reaction mixture was heated at 70° C. for 1 h 30 min. After cooling to rt, 2-((4S,5S)-1-(4-bromophenyl)-4-methyl-3-(trifluoromethyl)-4,5-dihydro-1H-pyrazol-5-yl)acetonitrile (Example 1I, 446 mg, 1.29 mmol), DMF (2.4 mL), water (0.24 mL), potassium carbonate (360 mg, 2.6 mmol) and 1,1'-bis(diphenylphosphino)ferrocenepalladium(II) dichloride (53 mg, 0.064 mmol) were added. The reaction mixture was purged with argon for several min and heated at 60° C. for 3 h 30 min. The reaction mixture was diluted with EtOAc, washed with water, brine, dried ($MgSO_4$) and concentrated. Purification via silica gel chromatography gave a gum. Further purification via RP-Prep HPLC to give 3F as a mixture of Isomer 1 and Isomer 2 (white solid, 104 mg, 16% yield) and a mixture of Isomer 3 and Isomer 4 (white solid, 258 mg, 38.8% yield). LC-MS Anal. Calc'd for $C_{28}H_{32}F_4N_4O$, 516.57, found [M+H] 517.2.

3G. Methyl 2-((4S,5S)-1-(4-((1-(5-ethoxy-2-fluorophenyl)-3-methylpiperidin-4-yl)methyl)phenyl)-4-methyl-3-(trifluoromethyl)-4,5-dihydro-1H-pyrazol-5-yl)acetate (Isomers 1 and 2): To MeOH (20 mL) at 0° C. acetyl chloride (5.42 mL, 76 mmol) was added dropwise. The solution was stirred at rt for 30 min. The solution was added to 2-((4S,5S)-1-(4-((1-(5-ethoxy-2-fluorophenyl)-3-methylpiperidin-4-yl)methyl)phenyl)-4-methyl-3-(trifluoromethyl)-4,5-dihydro-1H-pyrazol-5-yl)acetonitrile (Isomers 1 and 2) (130 mg, 0.252 mmol) and the reaction vessel was sealed and stirred at 40° C. for 31 h. The reaction mixture was concentrated. The residue was treated with 3 N HCl/MeOH/MeOAc (made by combining 20 mL MeOH and 5.43 mL acetyl chloride as above) and the mixture was heated at 40° C. for additional 28 h. The reaction mixture was concentrated, diluted with EtOAc, washed with aqueous $NaHCO_3$, water, brine, dried ($MgSO_4$) and concentrated. Purification via silica gel chromatography gave 3G (Isomer 1 and 2) as an oil (110 mg, 80% yield). LC-MS Anal. Calc'd for $C_{29}H_{35}F_4N_3O_3$ 549.60, found [M+H] 550.3.

3H. Methyl 2-((4S,5S)-1-(4-((1-(5-ethoxy-2-fluorophenyl)-3-methylpiperidin-4-yl)methyl)phenyl)-4-methyl-3-(trifluoromethyl)-4,5-dihydro-1H-pyrazol-5-yl)acetate (Isomers 3 and 4): To MeOH (20 mL) at 0° C. acetyl chloride (5.42 mL, 76 mmol) was added dropwise. The solution was stirred at rt for 30 min. The solution was added to 2-((4S,5S)-1-(4-((1-(5-ethoxy-2-fluorophenyl)-3-methylpiperidin-4-yl)methyl)phenyl)-4-methyl-3-(trifluoromethyl)-4,5-dihydro-1H-pyrazol-5-yl)acetonitrile (isomers 3 and 4) (150 mg, 0.29 mmol) and the reaction vessel was sealed and stirred at 40° C. for 48 h. The reaction mixture was concentrated. The residue was treated with 3 N HCl/MeOH/MeOAc (made by combining 20 mL MeOH and 5.43 mL acetyl chloride as above) and heated at 40° C. for additional 22 h. The reaction mixture was concentrated, diluted with EtOAc, washed with aqueous $NaHCO_3$, water, brine, dried ($MgSO_4$) and concentrated. Purification via silica gel chromatography gave 3H (Isomer 3 and 4) (126 mg, 79% yield). LC-MS Anal. Calc'd for $C_{29}H_{35}F_4N_3O_3$ 549.60, found [M+H] 550.3.

Example 3 (Isomers 1 and 2): To methyl 2-((4S,5S)-1-(4-((1-(5-ethoxy-2-fluorophenyl)-3-methylpiperidin-4-yl)methyl)phenyl)-4-methyl-3-(trifluoromethyl)-4,5-dihydro-1H-pyrazol-5-yl)acetate (110 mg, 0.200 mmol) (Isomers 1 and 2) in THF (4 mL), lithium hydroxide (1 N in water, 0.42 mL, 0.42 mmol) was added. The reaction mixture was stirred at rt for 16 h. The reaction mixture was cooled with ice-water bath and was acidified with 1 mL 1 N HCl and concentrated. The residue was diluted with EtOAc. The EtOAc layer was dried ($MgSO_4$), filtered. The filtrate was treated with 0.1 mL 4 N HCl in dioxane and concentrated to give a solid. Purification via chiral Prep. SFC gave Example 3 (Isomer 1) (light yellow solid, 42 mg, 36% yield). LC-MS Anal. Calc'd for $C_{28}H_{33}F_4N_3O_3$: 535.25, found [M+H] 536.2. $^1$H NMR (500 MHz, $CD_3CN$) δ ppm 7.96 (s, 1 H), 7.27-7.23 (m, 1 H), 7.18 (d, J=8.6 Hz, 2 H), 7.09 (d, J=8.6 Hz, 2 H), 7.02-6.97 (m, 1 H), 4.52-4.47 (m, 1H), 4.10-4.02 (m, 2 H), 3.60-3.25 (m, 5 H), 3.13-3.08 (m, 1 H), 2.80-2.75 (m, 1 H), 2.54-2.31 (m, 3 H), 2.05-1.50 (m, 3H), 1.40-1.30 (m, 7 H), 1.13 (d, J=6.3 Hz, 3 H). Analytical HPLC (Orthogonal method): RT=9.0 min, HI: 98%. hGPR40 $EC_{50}$=3219 nM. Example 3 (Isomer 2) (light yellow solid, 43 mg, 37% yield). LC-MS Anal. Calc'd for $C_{28}H_{33}F_4N_3O_3$ 535.25, found [M+H] 536.2. $^1$H NMR (500 MHz, $CD_3CN$) δ ppm 7.96 (s, 1 H), 7.27-7.23 (m, 1 H), 7.18 (d, J=8.6 Hz, 2 H), 7.09 (d, J=8.6 Hz, 2H), 7.02-6.97 (m, 1 H), 4.52-4.47 (m, 1 H), 4.10-4.02 (m, 2 H), 3.60-3.25 (m, 5 H), 3.13-3.08 (m, 1 H), 2.80-2.75 (m, 1 H), 2.54-2.31 (m, 3 H), 2.05-1.50 (m, 3 H), 1.40-1.30 (m, 7 H), 1.13 (d, J=6.3 Hz, 3 H). Analytical HPLC (Orthogonal method): RT=9.0 min, HI: 98%. hGPR40 $EC_{50}$=471 nM.

Example 3 (Isomers 3 and 4): To methyl 2-((4S,5S)-1-(4-((1-(5-ethoxy-2-fluorophenyl)-3-methylpiperidin-4-yl)methyl)phenyl)-4-methyl-3-(trifluoromethyl)-4,5-dihydro-1H-pyrazol-5-yl)acetate (125 mg, 0.23 mmol) (Isomers 3 and 4) in THF (4.5 mL), lithium hydroxide (1 N in water, 0.48 mL, 0.48 mmol) was added. The reaction mixture was stirred at rt for 16 h. The reaction mixture was cooled with ice-water bath and acidified with 1 mL 1 N HCl and concentrated. The residue was diluted with EtOAc. The EtOAc layer was dried (MgSO$_4$), filtered. The filtrate was treated with 0.1 mL 4 N HCl in dioxane and concentrated to give a solid. Purification via chiral Prep. SFCgave Example 3 (Isomer 3) (light yellow solid, 57 mg, 43% yield). LC-MS Anal. Calc'd for $C_{28}H_{33}F_4N_3O_3$: 535.25, found [M+H] 536.2. $^1$H NMR (500 MHz, CD$_3$CN) δ ppm 7.67 (s, 1 H), 7.29-7.22 (m, 1 H), 7.20 (d, J=8.5 Hz, 2 H), 7.09 (d, J=8.5 Hz, 2 H), 6.99-6.93 (m, 1 H), 4.50-4.45 (m, 1 H), 4.00-3.90 (m, 2 H), 3.60-3.20 (m, 5 H), 2.70-2.40 (m, 5 H), 2.05-1.50 (m, 2 H), 1.30-1.01 (m, 11 H). Analytical HPLC (Orthogonal method): RT=4.9 min, HI: 98%. hGPR40 EC$_{50}$=1136 nM. Example 3 (Isomer 4) (light yellow solid, 54 mg, 41% yield). LC-MS Anal. Calc'd for $C_{28}H_{33}F_4N_3O_3$535.25, found [M+H] 536.2. $^1$H NMR (500 MHz, CD$_3$CN) δ ppm 7.67 (s, 1 H), 7.29-7.22 (m, 1 H), 7.20 (d, J=8.5 Hz, 2 H), 7.09 (d, J=8.5 Hz, 2 H), 6.99-6.93 (m, 1 H), 4.50-4.45 (m, 1 H), 4.00-3.90 (m, 2 H), 3.60-3.20 (m, 5 H), 2.70-2.40 (m, 5 H), 2.05-1.50 (m, 2 H), 1.30-1.01 (m, 11 H). Analytical HPLC (Orthogonal method): RT=4.9 min, HI: 98%. hGPR40 EC$_{50}$=672 nM.

EXAMPLE 4

2-((4S,5S)-1-(4-((1-(5-chloro-2,3-dihydrobenzofuran-6-yl)piperidin-4-yl)oxy)phenyl)-4-methyl-3-(trifluoromethyl)-4,5-dihydro-1H-pyrazol-5-yl)acetic acid, HCl

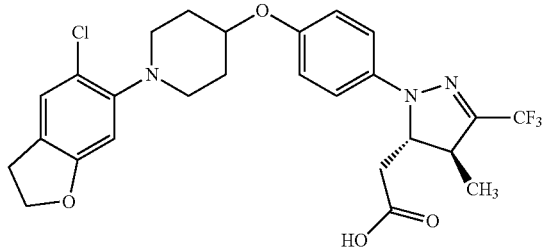 [SMILES: C[C@@H]1C(C(F)(F)F)=NN(c2ccc(OC3CCN(c4cc5c(cc4Cl)CCO5)CC3)cc2)[C@H]1CC(=O)O]

4A. 8-(5-chloro-2,3-dihydrobenzofuran-6-yl)-1,4-dioxa-8-azaspiro[4.5]decane: A mixture of 6-bromo-5-chloro-2,3-dihydrobenzofuran (135 mg, 0.58 mmol), 1,4-dioxa-8-azaspiro[4.5]decane (250 mg, 1.7 mmol) and 2-dicyclohexylphosphino-2',6'-dimethoxy-1,1'-biphenyl (10 mg, 0.023 mmol) in THF (0.58 mL) was purged with argon. Tris(dibenzylideneacetone)dipalladium (0) (11 mg, 0.012 mmol) was added and followed by lithium bis(trimethylsilyl)amide (1.62 mL, 1.62 mmol) (1 N in THF). The mixture was purged with argon for several min and then heated at 70° C. for 1 h 10 min. The reaction was quenched with aqueous NaHCO$_3$, diluted with EtOAc, washed with water, brine, dried (MgSO$_4$) and concentrated. Purification via silica gel chromatography gave 8-(5-chloro-2,3-dihydrobenzofuran-6-yl)-1,4-dioxa-8-azaspiro[4.5]decane as a gummy solid (55 mg, 32% yield). LC-MS Anal. Calc'd for $C_{15}H_{18}ClNO_3$ 295.10, found [M+H] 296.1.

4B. 1-(5-chloro-2,3-dihydrobenzofuran-6-yl)piperidin-4-one: To a solution of 8-(5-chloro-2,3-dihydrobenzofuran-6-yl)-1,4-dioxa-8-azaspiro[4.5]decane (55 mg, 0.19 mmol) in acetone (2.6 mL) and water (1.1 mL) was added p-toluenesulfonic acid monohydrate (53 mg, 0.28 mmol). The reaction was heated at 60° C. for 3 h 30 min. Acetone was evaporated. The reaction mixture was treated with 50 mg solid NaHCO$_3$, diluted with EtOAc, washed with sat. NaHCO$_3$, water, brine, dried (MgSO$_4$) and concentrated. Purification via silica gel chromatography gave 1-(5-chloro-2,3-dihydrobenzofuran-6-yl)piperidin-4-one (38 mg, 81% yield). LC-MS Anal. Calc'd for $C_{13}H_{14}ClNO_2$ 251.71, found [M+H] 251.2.

4C. 1-(5-chloro-2,3-dihydrobenzofuran-6-yl)piperidin-4-ol: To 1-(5-chloro-2,3-dihydrobenzofuran-6-yl)piperidin-4-one (38 mg, 0.15 mmol) in MeOH (1.2 mL) and THF (0.48 mL) at 0° C., sodium borohydride (17 mg, 0.45 mmol) was added portionwise. The reaction was stirred at 0° C. for 10 min and at rt for 1 h. The reaction mixture was cooled with ice-water bath, quenched with 1 mL sat. NaHCO$_3$. MeOH and THF were evaporated. The residue was extracted with EtOAc. The extracts were washed with water, brine, dried (MgSO$_4$) and concentrated to give 1-(5-chloro-2,3-dihydrobenzofuran-6-yl)piperidin-4-ol as a white solid (39 mg, 100% yield), which was used without further purification. LC-MS Anal. Calc'd for $C_{13}H_{16}ClNO_2$ 253.09, found [M+H] 254.1.

4E. 1-(5-chloro-2,3-dihydrobenzofuran-6-yl)piperidin-4-yl 4-methylbenzenesulfonate: To 1-(5-chloro-2,3-dihydrobenzofuran-6-yl)piperidin-4-ol (39 mg, 0.15 mmol) and 4-methylbenzene-1-sulfonyl chloride (46.9 mg, 0.25 mmol) in CH$_2$Cl$_2$ (0.4 mL), pyridine (0.12 mL, 1.54 mmol) was added dropwise. The reaction mixture was stirred at rt. After 17 h, 4-methylbenzene-1-sulfonyl chloride (47 mg, 0.25 mmol) was added and the reaction was stirred at rt for additional 7 h. The reaction mixture was diluted with EtOAc, and the organic layer was washed with water, brine, dried (MgSO$_4$) and concentrated. Purification via silica gel chromatography gave 1-(5-chloro-2,3-dihydrobenzofuran-6-yl)piperidin-4-yl 4-methylbenzenesulfonate (white solid, 53 mg, 85% yield). LC-MS Anal. Calc'd for $C_{20}H_{22}ClNO_4S$, 407.10, found [M+H] 408.1.

4F. Methyl 2-((4S,5S)-1-(4-((1-(5-chloro-2,3-dihydrobenzofuran-6-yl)piperidin-4-yl)oxy)phenyl)-4-methyl-3-(trifluoromethyl)-4,5-dihydro-1H-pyrazol-5-yl)acetate: To 1-(5-chloro-2,3-dihydrobenzofuran-6-yl)piperidin-4-yl 4-methylbenzenesulfonate (53 mg, 0.13 mmol) and methyl 2-((4S,5S)-1-(4-hydroxyphenyl)-4-methyl-3-(trifluoromethyl)-4,5-dihydro-1H-pyrazol-5-yl)acetate (1J, 53 mg, 0.17 mmol) in DMF (0.4 mL) cesium carbonate (85 mg, 0.26 mmol) was added. The reaction mixture was heated at 55° C. for 18 h. The mixture was cooled to rt and treated with 2 drops MeI and stirred at rt for 2 h. The reaction mixture was diluted with EtOAc, washed with water, brine dried (MgSO$_4$) and concentrated. Purification via silica gel chromatography gave methyl 2-((4S,5S)-1-(4-((1-(5-chloro-2,3-dihydrobenzofuran-6-yl)piperidin-4-yl)oxy)phenyl)-4-methyl-3-(trifluoromethyl)-4,5-dihydro-1H-pyrazol-5-yl)acetate (gum, 33 mg, 46% yield). LC-MS Anal. Calc'd for $C_{27}H_{29}ClF_3N_3O_4$ 551.99, found [M+H] 552.3.

Example 4: To methyl 2-((4S,5S)-1-(4-((1-(5-chloro-2,3-dihydrobenzofuran-6-yl)piperidin-4-yl)oxy)phenyl)-4-methyl-3-(trifluoromethyl)-4,5-dihydro-1H-pyrazol-5-yl)acetate (51 mg, 0.06 mmol) in THF (3 mL), lithium hydroxide (1 N 0.36 mL, 0.36 mmol) was added. The reaction mixture was stirred at rt for 4 h 30 min. The mixture was cooled with ice-water bath, acidified with 1 N HCl. THF was evaporated. The mixture was extracted with EtOAc and the extract was concentrated. Purification via RP-Prep HPLC gave 2-((4S,5S)-1-(4-((1-(5-chloro-2,3-dihydrobenzofuran-6-yl)piperidin-4-yl)oxy)phenyl)-4-methyl-3-(trifluoromethyl)-4,5-dihydro-1H-pyrazol-5-yl)acetic acid, HCl (light yellow solid, 22 mg, 63% yield). LC-MS Anal. Calc'd for $C_{26}H_{27}ClF_3N_3O_4$: 537.96, found [M+H] 538.3. $^1$H NMR (500 MHz, $CD_3CN$) δ ppm 7.60-7.30 (m, 2 H), 7.11 (d, J=8.8 Hz, 2 H), 7.02 (d, J=8.8 Hz, 2 H), 4.90- (m, 3 H), 4.00-3.70 (m, 2 H), 3.60-3.24 (m, 5 H), 2.75-2.40 (m, 4 H), 2.30-2.10 (m, 2 H), 1.50-1.30 (m, 4 H), 1.18-1.12 (m, 1 H). Analytical HPLC (Orthogonal method): RT=9.5 min, HI: 97%. hGPR40 $EC_{50}$=1044 nM.

EXAMPLE 5

2-((4S,5S)-4-methyl-1-(4-((1-(5-propylpyrimidin-2-yl)piperidin-4-yl)oxy)phenyl)-3-(trifluoromethyl)-4,5-dihydro-1H-pyrazol-5-yl)acetic acid, TFA salt

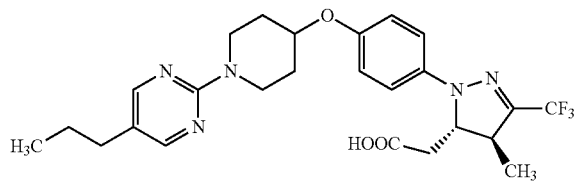 [SMILES: CCCc1cnc(N2CCC(Oc3ccc(N4N=C(C(F)(F)F)[C@@H](C)[C@@H]4CC(=O)O)cc3)CC2)nc1]

5A. 1-(5-propylpyrimidin-2-yl)piperidin-4-ol: The mixture of piperidin-4-ol (17 g, 168 mmol), 2-chloro-5-propylpyrimidine (26.3 g, 168 mmol) and potassium carbonate (69.7 g, 504 mmol) in DMF (150 mL) was stirred at 100° C. for 15 h. The reaction mixture was cooled to rt and EtOAc (300 mL) and $H_2O$ (200 mL) was added. The organic layer was collected, washed with $H_2O$ (3×), sat. aqueous $NaHCO_3$ (3×) and brine (3×). After drying over $Na_2SO_4$ and concentration, 1-(5-propylpyrimidin-2-yl)piperidin-4-ol: The mixture of piperidin-4-ol as a yellow solid (22 g, 94 mmol, 56% yield) was obtained. LC-MS Anal. Calc'd for $C_{12}H_{19}N_3O$, 221.15, found [M+H] 222.0.

5B. Methyl 2-((4S,5S)-4-methyl-1-(4-((1-(5-propylpyrimidin-2-yl)piperidin-4-yl)oxy)phenyl)-3-(trifluoromethyl)-4,5-dihydro-1H-pyrazol-5-yl)acetate: In a one-dram vial was added triphenylphosphine (58 mg, 0.22 mmol), DMF (0.3 mL) and (E)-diethyl diazene-1,2-dicarboxylate (0.03 mL, 0.19 mmol). The reaction mixture was stirred for 5 min before the addition of methyl 2-((4S,5S)-1-(4-hydroxyphenyl)-4-methyl-3-(trifluoromethyl)-4,5-dihydro-1H-pyrazol-5-yl)acetate (1J, 50 mg, 0.16 mmol) and 1-(5-propylpyrimidin-2-yl)piperidin-4-ol (35 mg, 0.16 mmol). The reaction vessel was heated at 100° C. for 4 h. After cooling the mixture to rt, 2 mL EtOAc and 2 mL water were added. The organic layer was collected and the aqueous layer was extracted with EtOAc (2×). The combined extracts were dried ($Na_2SO_4$) and concentrated. The crude product was purified by chromatography (silica gel, hexanes-EtOAc gradient 0 to 40% EtOAc) to give methyl 2-((4S,5S)-4-methyl-1-(4-((1-(5-propylpyrimidin-2-yl)piperidin-4-yl)oxy)phenyl)-3-(trifluoromethyl)-4,5-dihydro-1H-pyrazol-5-yl)acetate as a yellow solid (50 mg, 0.08 mmol, 52% yield). LC-MS Anal. Calc'd for $C_{26}H_{32}F_3N_5O_3$ 519.24, found [M+H] 520.2.

Example 5: In one-dram vial was added methyl 2-((4S,5S)-4-methyl-1-(4-((1-(5-propylpyrimidin-2-yl)piperidin-4-yl)oxy)phenyl)-3-(trifluoromethyl) -4,5-dihydro-1H-pyrazol-5-yl)acetate (50 mg, 0.096 mmol), lithium hydroxide (0.58 mL, 1M in $H_2O$, 0.58 mmol) and THF (0.6 mL) and the mixture was stirred at rt overnight. The reaction mixture was acidified by addition of 1N HCl and the solvent was evaporated. Purification via RP-Prep HPLC gave 2-((4S,5S)-4-methyl-1-(4-((1-(5-propylpyrimidin-2-yl)piperidin-4-yl)oxy)phenyl)-3-(trifluoromethyl)-4,5-dihydro-1H-pyrazol-5-yl)acetic acid, TFA salt as a yellow oil (12 mg, 0.02 mmol, 19% yield). $^1$H NMR (500 MHz, $CDCl_3$) δ 8.40 (s, 2H), 7.06 (d, J=9.1 Hz, 2H), 6.90 (d, J=8.8 Hz, 2H), 4.56 (t, J=4.1 Hz, 1H), 4.39 (d, J=9.9 Hz, 1H), 4.16-4.03 (m, 2H), 4.01-3.89 (m, 3H), 3.21 (dd, J=5.4, 3.7 Hz, 1H), 2.83 (dd, J=16.5, 3.0 Hz, 1H), 2.58-2.35 (m, 3H), 2.01 (d, J=3.3 Hz, 4H), 1.63 (sxt, J=7.4 Hz, 2H), 1.34 (d, J=7.2 Hz, 3H), 0.98 (t, J=7.3 Hz, 3H). LC-MS Anal. Calc'd for $C_{25}H_{30}F_3N_5O_3$ 505.23, found [M+H] 506.3. Analytical HPLC (Orthogonal method, 0% Solvent B start): RT=10.1 min, HI: 100%. hGPR40 $EC_{50}$=5808 nM.

EXAMPLE 6

2-((4S,5S)-4-methyl-3-(trifluoromethyl)-1-(4-((1-(5-(trifluoromethyl)pyridin-2-yl)piperidin-4-yl)oxy)phenyl)-4,5-dihydro-1H-pyrazol-5-yl)acetic acid, TFA salt

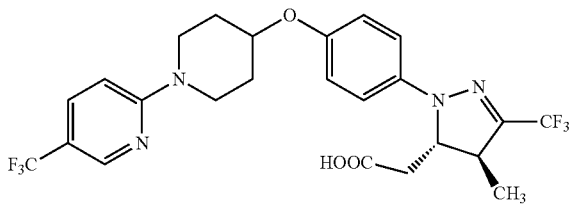 [SMILES: C[C@@H]1C(C(F)(F)F)=NN(c2ccc(OC3CCN(c4ccc(C(F)(F)F)cn4)CC3)cc2)[C@H]1CC(=O)O]

Example 6 (white solid, 12 mg) was prepared following the procedure for Example 5. LC-MS Anal. Calc'd for $C_{25}H_{24}F_6N_4O_3$ 530.46, found [M+H] 531.2. $^1$H NMR (500 MHz, $CDCl_3$) δ 8.41 (s, 1H), 7.81 (dd, J=9.4, 2.5 Hz, 1H), 7.12-7.03 (m, 2H), 6.98-6.86 (m, 3H), 4.57 (t, J=4.3 Hz, 1H), 4.39 (d, J=9.9 Hz, 1H), 3.98-3.75 (m, 4H), 3.22 (d, J=1.7 Hz, 1H), 2.83 (dd, J=16.5, 3.3 Hz, 1H), 2.46 (dd, J=16.5, 10.2 Hz, 1H), 2.10-1.95 (m, 4H), 1.35 (d, J=6.9 Hz, 3H). Analytical HPLC (Orthogonal method, 0% Solvent B start): RT=11.4 min, HI: 95%. hGPR40 $EC_{50}$=7517 nM.

EXAMPLE 7

2-((4S,5S)-1-(4-((1-(5-chloropyrimidin-2-yl)piperidin-4-yl)oxy)phenyl)-4-methyl-3-(trifluoromethyl)-4,5-dihydro-1H-pyrazol-5-yl)acetic acid, TFA salt

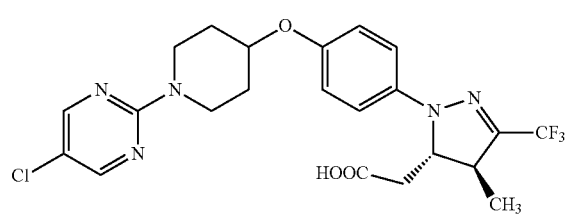 [SMILES: C[C@@H]1C(C(F)(F)F)=NN(c2ccc(OC3CCN(c4ncc(Cl)cn4)CC3)cc2)[C@H]1CC(=O)O]

Example 7 (yellow solid, 14 mg) was prepared following the procedure for Example 5. LC-MS Anal. Calc'd for $C_{22}H_{23}ClF_3N_5O_3$ 497.14, found [M+H] 498.2. $^1$H NMR (500 MHz, $CDCl_3$) δ 8.34 (s, 2H), 7.06 (d, J=8.8 Hz, 2H), 6.92 (d, J=8.8 Hz, 2H), 4.58-4.48 (m, 1H), 4.40 (d, J=10.5 Hz, 1H), 4.11-3.96 (m, 2H), 3.91-3.75 (m, 2H), 3.22 (br. s., 1H), 2.86 (dd, J=16.5, 2.5 Hz, 1H), 2.47 (dd, J=16.6, 10.3 Hz, 1H), 2.06-1.79 (m, 4H), 1.35 (d, J=7.2 Hz, 3H). Analytical HPLC (Orthogonal method, 0% Solvent B start): RT=12.9 min, HI: 99%. hGPR40 EC$_{50}$=4480 nM.

EXAMPLE 8

2-((4S,5S)-1-(4-((1-(2,3-difluoro-5-methoxyphenyl)-3-methylpiperidin-4-yl)oxy)phenyl)-4-methyl-3-(trifluoromethyl)-4,5-dihydro-1H-pyrazol-5-yl)acetic acid, HCl (Isomer 1 and Isomer 2)

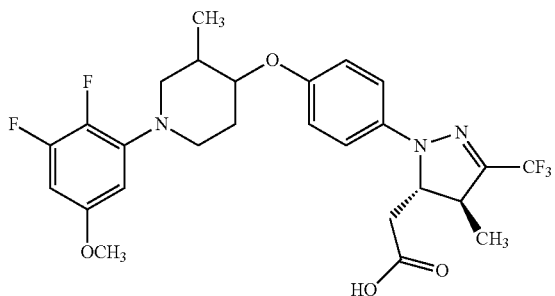 [SMILES: COc1cc(F)c(F)c(N2CCC(Oc3ccc(N4N=C(C(F)(F)F)[C@@H](C)[C@@H]4CC(=O)O)cc3)C(C)C2)c1]

8A. 4-((tert-butyldimethylsilyl)oxy)-1-(2,3-difluoro-5-methoxyphenyl)-3-methylpiperidine: A mixture of 1,2,3-trifluoro-5-methoxybenzene (530 mg, 3.3 mmol) and 4-((tert-butyldimethylsilyl)oxy)-3-methylpiperidine (300 mg, 1.3 mmol) in DMSO (3 mL) was heated at 140° C. for 20 h. The reaction mixture was quenched with aqueous NaHCO$_3$ and extracted with EtOAc. The organic extract was washed with H$_2$O and brine, dried (Na$_2$SO$_4$) and concentrated. Purification via silica gel chromatography gave 4-((tert-butyldimethylsilyl)oxy)-1-(2,3-difluoro-5-methoxyphenyl)-3-methylpiperidine as a yellow oil (230 mg, 47% yield). LC-MS Anal. Calc'd for C$_{19}$H$_{31}$F$_2$NO$_2$Si, 371.21, found [M+H] 372.1.

8B. 1-(2,3-difluoro-5-methoxyphenyl)-3-methylpiperidin-4-ol: To a solution of cis-4-((tert-butyldimethylsilyl)oxy)-1-(2,3-difluoro-5-methoxyphenyl)-3-methylpiperidine (230 mg, 0.61 mmol) in THF (1 mL) was added 1M tetrabutylammonium fluoride (3 mL, 3 mmol) and stirred at rt for 8 h. The reaction mixture was quenched with aqueous NaHCO$_3$ and extracted with EtOAc. The organic extract was washed with H$_2$O and brine, dried (Na$_2$SO$_4$) and concentrated. Purification via silica gel chromatography gave 1-(2,3-difluoro-5-methoxyphenyl)-3-methylpiperidin-4-ol as an oil (105 mg, 65% yield). LC-MS Anal. Calc'd for C$_{13}$H$_{17}$F$_2$NO$_2$ 257.12, found [M+H] 258.0.

8C. Methyl 2-((4S,5S)-1-(4-(((3R,4R)-1-(2,3-difluoro-5-methoxyphenyl)-3-methylpiperidin-4-yl)oxy)phenyl)-4-methyl-3-(trifluoromethyl)-4,5-dihydro-1H-pyrazol-5-yl)acetate: To triphenylphosphine (140 mg, 0.53 mmol) in DMF (4 mL)) was added (E)-diethyl diazene-1,2-dicarboxylate (0.072 mL, 0.46 mmol) and methyl 2-((4S,5S)-1-(4-hydroxyphenyl)-4-methyl-3-(trifluoromethyl)-4,5-dihydro-1H-pyrazol-5-yl)acetate (1J, 120 mg, 0.38 mmol) and then the mixture was stirred for 5 min followed by the addition of 1-(2,3-difluoro-5-methoxyphenyl)-3-methylpiperidin-4-ol (98 mg, 0.38 mmol) and then stirred at rt overnight. The reaction mixture was quenched with aqueous NaHCO$_3$ and extracted with EtOAc. The organic extract was washed with H$_2$O and then brine, dried (Na$_2$SO$_4$) and concentrated. Purification via silica gel chromatography gave methyl 2-((4S,5S)-1-(4-(((3R,4R)-1-(2,3-difluoro-5-methoxyphenyl)-3-methylpiperidin-4-yl)oxy)phenyl)-4-methyl-3-(trif- luoromethyl)-4,5-dihydro-1H-pyrazol-5-yl)acetate as an oil (40 mg, 19% yield). LC-MS Anal. Calc'd for C$_{27}$H$_{30}$F$_5$N$_3$O$_4$ 555.22, found [M+H] 556.0.

Example 8 (Isomer 1) and (Isomer 2): To a stirred solution of methyl 2-((4S,5S)-1-(4-(((3R,4R)-1-(2,3-difluoro-5-methoxyphenyl)-3-methylpiperidin-4-yl)oxy)phenyl)-4-methyl-3-(trifluoromethyl)-4,5-dihydro-1H-pyrazol-5-yl)acetate (55 mg, 0.099 mmol) in THF (1 mL) and H$_2$O (0.10 mL) was added 2M lithium hydroxide (0.074 mL, 0.15 mmol). The mixture was stirred at rt for 3 h and then diluted with EtOAc and acidified with 6N HCl. The organic layer was dried (Na$_2$SO$_4$) and concentrated. They were separated by to provide 4 isomers. The resulting product was separated via chiral Prep. SFC to yield two diastereomers as yellow oil: 2-((4S,5S)-1-(4-((1-(2,3-difluoro-5-methoxyphenyl)-3-methylpiperidin-4-yl)oxy)phenyl)-4-methyl-3-(trifluoromethyl)-4,5-dihydro-1H-pyrazol-5-yl)acetic acid, HCl (11 mg, 19% yield, Isomer 1): LC-MS Anal. Calc'd for C$_{26}$H$_{28}$F$_5$N$_3$O$_4$ 541.20, found [M+H] 542.2. $^1$H NMR (500 MHz, CDCl$_3$) δ 7.13-6.99 (m, 2H), 6.96-6.85 (m, 2H), 6.40-6.15 (m, 2H), 4.45-4.32 (m, 1H), 3.94-3.81 (m, 1H), 3.74 (s, 3H), 3.48-3.39 (m, 2H), 3.26-3.18 (m, 1H), 2.85 (dd, J=16.4, 2.9 Hz, 2H), 2.65-2.58 (m, 1H), 2.49-2.39 (m, 1H), 2.20-2.09 (m, 2H), 1.86-1.75 (m, 1H), 1.35 (d, J=7.2 Hz, 3H), 1.12 (d, J=6.6 Hz, 3H). Analytical HPLC (Orthogonal method, 10% Solvent B start): RT=11.7 min, HI: 95%. hGPR40 EC$_{50}$=796 nM. 2-((4S,5S)-1-(4-((1-(2,3-difluoro-5-methoxyphenyl)-3-methylpiperidin-4-yl)oxy)phenyl)-4-methyl-3-(trifluoromethyl)-4,5-dihydro-1H-pyrazol-5-yl) acetic acid, HCl (16 mg, 26% yield, Isomer 2): LC-MS Anal. Calc'd for C$_{26}$H$_{28}$F$_5$N$_3$O$_4$ 541.20, found [M+H] 542.2. $^1$H NMR (500 MHz, CDCl$_3$) δ 7.13-6.99 (m, 2H), 6.96-6.85 (m, 2H), 6.40-6.15 (m, 2H), 4.45-4.32 (m, 1H), 3.94-3.81 (m, 1H), 3.74 (s, 3H), 3.48-3.39 (m, 2H), 3.26-3.18 (m, 1H), 2.85 (dd, J=16.4, 2.9 Hz, 2H), 2.65-2.58 (m, 1H), 2.49-2.39 (m, 1H), 2.20-2.09 (m, 2H), 1.86-1.75 (m, 1H), 1.35 (d, J=7.2 Hz, 3H), 1.12 (d, J=6.6 Hz, 3H). Analytical HPLC (Orthogonal method, 10% Solvent B start): RT=11.7 min, HI: 95%. hGPR40 EC$_{50}$=237 nM.

EXAMPLE 9

2-((4S,5S)-1-(4-((1-(2-fluoro-5-isopropoxyphenyl)piperidin-4-yl)oxy)phenyl)-4-methyl-3-(trifluoromethyl)-4,5-dihydro-1H-pyrazol-5-yl)acetic acid, HCl

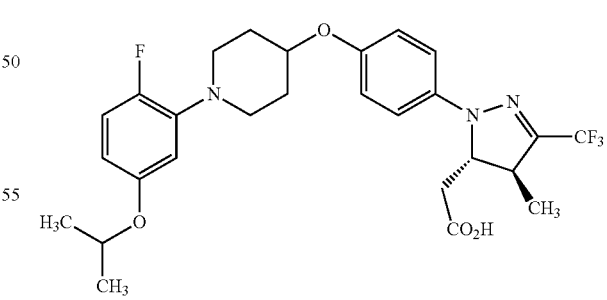

9A. 1-(2-fluoro-5-isopropoxyphenyl)piperidin-4-ol: To 1,2-difluoro-4-isopropoxybenzene (950 mg, 5.52 mmol) and piperidin-4-ol (1.1 g, 11 mmol) was added DMSO (7 mL). The mixture was heated at 140° C. overnight. The reaction mixture was quenched with aqueous NaHCO$_3$ and extracted with EtOAc. The organic extract was washed with H$_2$O and then brine, dried (Na$_2$SO$_4$) and concentrated. Purification via silica gel chromatography gave 1-(2-fluoro-5-isopropoxyphenyl)piperidin-4-ol as a yellow oil (666 mg, 70% yield). LC-MS Anal. Calc'd for $C_{14}H_{20}FNO_2$ 253.15, found [M+H] 254.2.

9B. Methyl 2-((4S,5S)-1-(4-((1-(2-fluoro-5-isopropoxyphenyl)piperidin-4-yl)oxy)phenyl)-4-methyl-3-(trifluoromethyl)-4,5-dihydro-1H-pyrazol-5-yl)acetate: A mixture of triphenylphosphine (123 mg, 0.47 mmol) and (E)-diethyl diazene-1,2-dicarboxylate (0.064 mL, 0.40 mmol) in DMF (0.5 mL) was stirred for 5 min. and methyl 2-((4S,5S)-1-(4-hydroxyphenyl)-4-methyl-3-(trifluoromethyl)-4,5-dihydro-1H-pyrazol-5-yl)acetate (1J, 101 mg, 0.32 mmol) in DMF (0.2 mL) was added, followed by the addition of 1-(2-fluoro-5-isopropoxyphenyl)piperidin-4-ol (85 mg, 0.34 mmol) in DMF (0.25 mL). The reaction mixture was stirred at rt overnight. The reaction mixture was quenched with aqueous $NaHCO_3$ and extracted with EtOAc. The organic extract was washed with $H_2O$ and then brine, dried ($Na_2SO_4$) and concentrated. Purification via silica gel chromatography gave methyl 2-((4S,5S)-1-(4-((1-(2-fluoro-5-isopropoxyphenyl)piperidin-4-yl)oxy)phenyl)-4-methyl-3-(trifluoromethyl)-4,5-dihydro-1H-pyrazol-5-yl)acetate as an oil (62 mg, 33% yield). LC-MS Anal. Calc'd for $C_{28}H_{33}F_4N_3O_4$ 551.24, found [M+H] 552.0.

Example 9 (white solid, 13 mg) was prepared following the same procedure for Example 8. LC-MS Anal. Calc'd for $C_{27}H_{31}F_4N_3O_4$ 537.23, found [M+H] 537.9. $^1H$ NMR (500 MHz, $CDCl_3$) δ 7.07 (d, J=9.1 Hz, 4H), 6.93 (d, J=9.1 Hz, 2H), 6.75-6.65 (m, 1H), 4.57-4.51 (m, 1H), 4.50-4.43 (m, 1H), 4.42-4.37 (m, 1H), 3.80-3.69 (m, 2H), 3.38-3.29 (m, 2H), 3.27-3.17 (m, 1H), 2.88-2.80 (m, 1H), 2.50-2.42 (m, 1H), 2.40-2.30 (m, 2H), 2.18-2.08 (m, 2H), 1.40-1.28 (m, 10H). Analytical HPLC (Orthogonal method, 10% Solvent B start): RT=10.4 min, HI: 95%. hGPR40 $EC_{50}$=374 nM.

EXAMPLE 10

2-((4S,5S)-1-(4-((1-(5-ethoxy-2,3-difluorophenyl)-3-methylpiperidin-4-yl)oxy)phenyl)-4-methyl-3-(trifluoromethyl)-4,5-dihydro-1H-pyrazol-5-yl)acetic acid, HCl (Isomer 1 and Isomer 2)

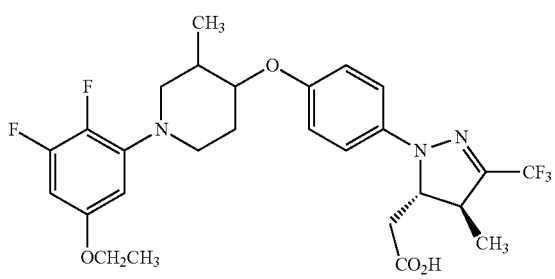 [SMILES: CCOc1cc(F)c(F)c(N2CCC(Oc3ccc(N4N=C(C(F)(F)F)[C@@H](C)[C@@H]4CC(=O)O)cc3)C(C)C2)c1]

10A. cis-4-((tert-butyldimethylsilyl)oxy)-1-(5-ethoxy-2,3-difluorophenyl)-3-methylpiperidine: A mixture of 5-ethoxy-1,2,3-trifluorobenzene (403 mg, 2.29 mmol) and cis-4-((tert-butyldimethylsilyl)oxy)-3-methylpiperidine (350 mg, 1.53 mmol) in DMSO (2 mL) was heated at 140° C. for 18 h. The reaction mixture was quenched with $H_2O$ and extracted with EtOAc. The organic extract was washed with $H_2O$ and then brine, dried ($Na_2SO_4$) and concentrated. Purification via silica gel chromatography gave cis-4-((tert-butyldimethylsilyl)oxy)-1-(5-ethoxy-2,3-difluorophenyl)-3-methylpiperidine as a yellow oil (340 mg, 58% yield). LC-MS Anal. Calc'd for $C_{20}H_{33}F_2NO_2Si$, 385.22, found [M+H] 386.0.

Example 10 (Isomer 1 and Isomer 2): Isomer 1 (white solid, 13 mg) and Isomer 2 (white solid, 17 mg) were prepared following the procedure for Example 8. 2-((4S,5S)-1-(4-((1-(5-ethoxy-2,3-difluorophenyl)-3-methylpiperidin-4-yl)oxy)phenyl)-4-methyl-3-(trifluoromethyl)-4,5-dihydro-1H-pyrazol-5-yl)acetic acid, HCl (Isomer 1): LC-MS Anal. Calc'd for $C_{27}H_{30}F_5N_3O_4$ 555.22, found [M+H] 555.9. $^1H$ NMR (500 MHz, $CDCl_3$) δ 7.04-7.09 (m, 2H), 6.85-6.91 (m, 2H), 6.22-6.33 (m, 2H), 4.31-4.37 (m, 1H), 3.94 (q, J=7.1 Hz, 2H), 3.82 (d, J=3.8 Hz, 1H), 3.38-3.47 (m, 2H), 3.22-3.31 (m, 1H), 2.89 (q, J=7.4 Hz, 3H), 2.81 (br. s., 1H), 2.72 (dd, J=15.5, 2.9 Hz, 1H), 2.59 (dd, J=12.2, 9.5 Hz, 1H), 2.29 (dd, J=15.4, 10.2 Hz, 1H), 2.08-2.18 (m, 2H), 1.75-1.85 (m, 1H), 1.39 (t, J=7.0 Hz, 3H), 1.21 (d, J=6.0 Hz, 1H), 1.11 (d, J=6.6 Hz, 3H). Analytical HPLC (Orthogonal method, 10% Solvent B start): RT=11.7 min, HI: 97%. hGPR40 $EC_{50}$=1203 nM. 2-((4S,5S)-1-(4-((1-(5-ethoxy-2,3-difluorophenyl)-3-methylpiperidin-4-yl)oxy)phenyl)-4-methyl-3-(trifluoromethyl)-4,5-dihydro-1H-pyrazol-5-yl)acetic acid, HCl (Isomer 2): LC-MS Anal. Calc'd for $C_{27}H_{30}F_5N_3O_4$ 555.2, found [M+H] 555.9. $^1H$ NMR (500 MHz, $CDCl_3$) δ 7.04-7.09 (m, 2H), 6.85-6.91 (m, 2H), 6.22-6.33 (m, 2H), 4.31-4.37 (m, 1H), 3.94 (q, J=7.1 Hz, 2H), 3.82 (d, J=3.8 Hz, 1H), 3.38-3.47 (m, 2H), 3.22-3.31 (m, 1H), 2.89 (q, J=7.4 Hz, 3H), 2.81 (br. s., 1H), 2.72 (dd, J=15.5, 2.9 Hz, 1H), 2.59 (dd, J=12.2, 9.5 Hz, 1H), 2.29 (dd, J=15.4, 10.2 Hz, 1H), 2.08-2.18 (m, 2H), 1.75-1.85 (m, 1H), 1.39 (t, J=7.0 Hz, 3H), 1.21 (d, J=6.0 Hz, 1H), 1.11 (d, J=6.6 Hz, 3H). Analytical HPLC (Orthogonal method, 10% Solvent B start): RT=11.7 min, HI: 97%. hGPR40 $EC_{50}$=315 nM.

EXAMPLE 11

2-((4S,5S)-1-(4-((1-(2-fluoro-5-(2,2,2-trifluoroethoxy)phenyl)-3-methylpiperidin-4-yl)oxy)phenyl)-4-methyl-3-(trifluoromethyl)-4,5-dihydro-1H-pyrazol-5-yl)acetic acid, HCl

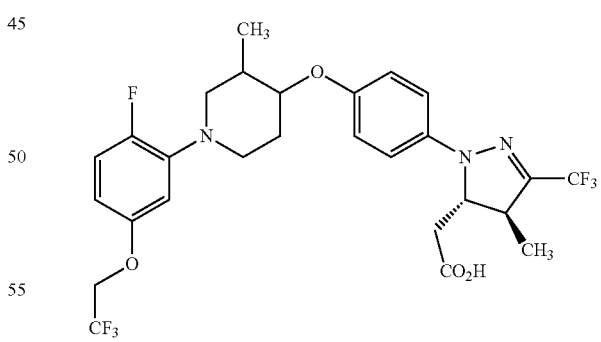

11A. 1,2-difluoro-4-(2,2,2-trifluoroethoxy)benzene: A mixture of 3,4-difluorophenol (2 g, 15.3 mmol), 1,1,1-trifluoro-2-iodoethane (4.84 g, 23.1 mmol) and potassium carbonate (4.3 g, 30.7 mmol) in DMF (10 mL) was heated at 100° C. overnight. The reaction mixture was quenched with aqueous $NaHCO_3$ and extracted with EtOAc. The organic extract was washed with $H_2O$ and then brine, dried ($Na_2SO_4$) and concentrated. Purification via silica gel chromatography gave 1,2-difluoro-4-(2,2,2-trifluoroethoxy)benzene as a yellow oil (1.63 g, 50% yield). ¹H NMR (500 MHz, CDCl₃) δ 7.17-7.08 (m, 1H), 6.80 (ddd, J=11.4, 6.5, 3.0 Hz, 1H), 6.66 (dtd, J=9.1, 3.2, 1.7 Hz, 1H), 4.37-4.24 (m, 2H).

11B. cis-4-((tert-butyldimethylsilyl)oxy)-1-(2-fluoro-5-(2,2,2-trifluoroethoxy)phenyl)-3-methylpiperidine: The mixture of cis-4-((tert-butyldimethylsilyl)oxy)-3-methylpiperidine (400 mg, 2.62 mmol), 1,2-difluoro-4-(2,2,2-trifluoroethoxy)benzene (555 mg, 2.62 mmol) and sodium bicarbonate (146 mg, 1.74 mmol) in DMSO (2 mL) was heated at 140° C. for 18 h. The reaction mixture was quenched with aqueous NaHCO₃ and extracted with EtOAc. The organic extract was washed with H₂O, brine, dried (Na₂SO₄) and concentrated. Purification via silica gel chromatography gave cis-4-((tert-butyldimethylsilyl)oxy)-1-(2-fluoro-5-(2,2,2-trifluoroethoxy)phenyl)-3-methylpiperidine as a yellow oil (240 mg, 33% yield). LC-MS Anal. Calc'd for $C_{20}H_{31}F_4NO_2Si$, 421.21, found [M+H] 422.0.

11C. cis-1-(2-fluoro-5-(2,2,2-trifluoroethoxy)phenyl)-3-methylpiperidin-4-ol: To a solution of cis-4-((tert-butyldimethylsilyl)oxy)-1-(2-fluoro-5-(2,2,2-trifluoroethoxy)phenyl)-3-methylpiperidine (240 mg, 0.57 mmol) in THF (1 mL) was added 1M tetrabutylammonium fluoride (0.683 mL, 0.68 mmol) and the mixture was stirred at rt for 28 h. The reaction mixture was quenched with aqueous NH₄Cl and extracted with EtOAc. The organic extract was washed with H₂O and then brine, dried (Na₂SO₄) and concentrated. Purification via silica gel chromatography gave cis-1-(2-fluoro-5-(2,2,2-trifluoroethoxy)phenyl)-3-methylpiperidin-4-ol as a yellow oil (92 mg, 53% yield). LC-MS Anal. Calc'd for $C_{14}H_{17}F_4NO_2$ 307.12, found [M+H] 308.0.

11D. Methyl 2-((4S,5S)-1-(4-((-1-(2-fluoro-5-(2,2,2-trifluoroethoxy)phenyl)-trans-3-methylpiperidin-4-yl)oxy)phenyl)-4-methyl-3-(trifluoromethyl)-4,5-dihydro-1H-pyrazol-5-yl)acetate: To a mixture of methyl 2-((4S,5S)-1-(4-hydroxyphenyl)-4-methyl-3-(trifluoromethyl)-4,5-dihydro-1H-pyrazol-5-yl)acetate (1J, 54 mg, 0.16 mmol), 1-(2-fluoro-5-(2,2,2-trifluoroethoxy)phenyl)-cis-3-methylpiperidin-4-ol (40 mg, 0.13 mmol) and triphenylphosphine (51 mg, 0.20 mmol) in THF (0.8 mL) was added (E)-di-tert-butyl diazene-1,2-dicarboxylate (45 mg, 0.20 mmol). The reaction mixture was stirred overnight at rt. The reaction mixture was quenched with aqueous NaHCO₃ and extracted with EtOAc. The organic extract was washed with H₂O and then brine, dried (Na₂SO₄) and concentrated. Purification via silica gel chromatography gave methyl 2-((4S,5S)-1-(4-((-1-(2-fluoro-5-(2,2,2-trifluoroethoxy)phenyl)-trans-3-methylpiperidin-4-yl)oxy)phenyl)-4-methyl-3-(trifluoromethyl)-4,5-dihydro-1H-pyrazol-5-yl)acetate as a yellow oil (16 mg, 19% yield). LC-MS Anal. Calc'd for $C_{28}H_{30}F_7N_3O_4$ 605.21, found [M+H] 606.2.

Example 11: To a suspension of methyl 2-((4S,5S)-1-(4-((3R,4R)-1-(2-fluoro-5-(2,2,2-trifluoroethoxy)phenyl)-3-methylpiperidin-4-yl)oxy)phenyl)-4-methyl-3-(trifluoromethyl)-4,5-dihydro-1H-pyrazol-5-yl)acetate (16 mg, 0.026 mmol) in THF (0.25 mL) and H₂O (0.1 mL) was added 2M lithium hydroxide (0.20 mL, 0.04 mmol) and the mixture was stirred at rt for 3 h. The mixture was diluted with EtOAc and acidified with 2N HCl. The organic layer was collected, dried (Na₂SO₄) and concentrated. The resulting product was separated via chiral Prep. SFC to yield 2-((4S,5S)-1-(4-((1-(2-fluoro-5-(2,2,2-trifluoroethoxy)phenyl)-3-methylpiperidin-4-yl)oxy)phenyl)-4-methyl-3-(trifluoromethyl)-4,5-dihydro-1H-pyrazol-5-yl)acetic acid, HCl as a white solid (5 mg, 29% yield). LC-MS Anal. Calc'd for $C_{27}H_{28}F_7N_3O_4$ 591.20, found [M+H] 592.0. ¹H NMR (500 MHz, CDCl₃) δ 7.05 (d, J=8.8 Hz, 2H), 6.92 (d, J=8.8 Hz, 3H), 6.65-6.74 (m, 1H), 6.39-6.51 (m, 1H), 4.37-4.45 (m, 1H), 4.24-4.35 (m, 2H), 3.81-3.92 (m, 1H), 3.40-3.52 (m, 2H), 3.15-3.26 (m, 1H), 2.80-2.94 (m, 2H), 2.59-2.71 (m, 1H), 2.39-2.51 (m, 1H), 2.17-2.26 (m, 2H), 1.35 (d, J=7.2 Hz, 3H), 1.26 (t, J=7.2 Hz, 2H), 1.13 (d, J=5.8 Hz, 3H). Analytical HPLC (Orthogonal method, 10% Solvent B start): RT=11.2 min, HI: 97%. hGPR40 EC₅₀=1084 nM.

EXAMPLE 12

2-((4S,5S)-1-(4-((1-(2-fluoro-5-isopropoxyphenyl)-3-methylpiperidin-4-yl)oxy)phenyl)-4-methyl-3-(trifluoromethyl)-4,5-dihydro-1H-pyrazol-5-yl)acetic acid, HCl

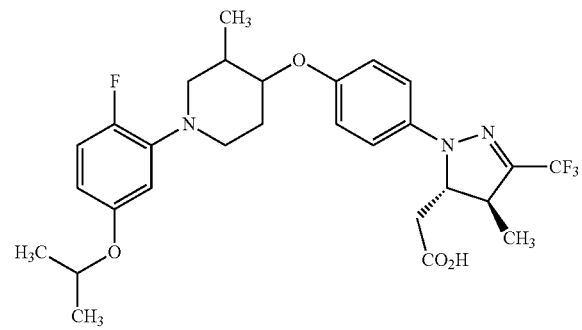 [SMILES: CC(C)Oc1ccc(F)c(N2CCC(Oc3ccc(N4N=C(C(F)(F)F)[C@@H](C)[C@@H]4CC(=O)O)cc3)C(C)C2)c1]

12A. 4-((tert-butyldimethylsilyl)oxy)-1-(2-fluoro-5-isopropoxyphenyl)-3-methylpiperidine: A mixture of 4-((tert-butyldimethylsilyl)oxy)-3-methylpiperidine (250 mg, 1.09 mmol), 1,2-difluoro-4-isopropoxybenzene (225 mg, 1.30 mmol) and sodium bicarbonate (92 mg, 1.09 mmol) in DMSO (1 mL) was heated at 140° C. for 28 h. The reaction mixture was quenched with H₂O and extracted with EtOAc. The organic extract was washed with H₂O and then brine, dried (Na₂SO₄) and concentrated. Purification via silica gel chromatography gave the desired product as an oil (50 mg, 12.0% yield). LC-MS Anal. Calc'd for $C_{21}H_{36}FNO_2Si$, 381.25, found [M+H] 382.0.

12B. 1-(2-fluoro-5-isopropoxyphenyl)-3-methylpiperidin-4-ol: To a solution of 4-((tert-butyldimethylsilyl)oxy)-1-(2-fluoro-5-isopropoxyphenyl)-3-methylpiperidine (80 mg, 0.21 mmol) in THF (1 mL) was added 1M tetrabutylammonium fluoride (1.0 mL, 1.04 mmol) and the mixture was stirred at rt for 28 h. The reaction mixture was quenched with aqueous NH₄Cl and extracted with EtOAc. The organic extract was washed with H₂O and then brine, dried (Na₂SO₄) and concentrated. Purification via silica gel chromatography gave the desired product as a yellow oil (25 mg, 45% yield). LC-MS Anal. Calc'd for $C_{15}H_{22}FNO_2$ 267.16, found [M+H] 268.0.

12C. Methyl 2-((4S,5S)-1-(4-((1-(2-fluoro-5-isopropoxyphenyl)-3-methylpiperidin-4-yl)oxy)phenyl)-4-methyl-3-(trifluoromethyl)-4,5-dihydro-1H-pyrazol-5-yl)acetate: A mixture of methyl 2-((4S,5S)-1-(4-hydroxyphenyl)-4-methyl-3-(trifluoromethyl)-4,5-dihydro-1H-pyrazol-5-yl)acetate (1J, 30 mg, 0.09 mmol), 1-(2-fluoro-5-isopropoxyphenyl)-3-methylpiperidin-4-ol (25 mg, 0.09 mmol) and triphenylphosphine (37 mg, 0.14 mmol) in THF (0.8 mL) was sonicated for 10 min. before (E)-di-tert-butyl 1,2-dicarboxylate (32 mg, 0.14 mmol) was added. The mixture was stirred at rt overnight. The reaction mixture was quenched with aqueous NaHCO₃ and extracted with EtOAc. The organic extract was washed with H₂O and then brine, dried (Na₂SO₄) and concentrated. Purification via silica gel chromatography gave the desired product as a yellow oil (26 mg, 49% yield). LC-MS Anal. Calc'd for $C_{29}H_{35}F_4N_3O_4$ 565.26, found [M+H] 566.0.

Example 12: To a suspension of methyl 2-((4S,5S)-1-(4-((1-(2-fluoro-5-isopropoxyphenyl)-3-methylpiperidin-4-yl)oxy)phenyl)-4-methyl-3-(trifluoromethyl)-4,5-dihydro-1H-pyrazol-5-yl)acetate (26 mg, 0.05 mmol) in THF (0.25 mL) and H₂O (0.03 mL) was added 2M lithium hydroxide (0.04 mL, 0.07 mmol) and the mixture was stirred at rt for 3 h. The reaction was diluted with EtOAc and acidified with 6N HCl. The organic layer was collected and the aqueous layer was extracted with CH₂Cl₂ twice. The combined organic was dried (Na₂SO₄) and concentrated. The resulting product was separated via chiral Prep. SFC to yield 2-((4S,5S)-1-(4-((1-(2-fluoro-5-isopropoxyphenyl)-3-methylpiperidin-4-yl)oxy)phenyl)-4-methyl-3-(trifluoromethyl)-4,5-dihydro-1H-pyrazol-5-yl)acetic acid, HCl (oil, 6 mg, 21%). LC-MS Anal. Calc'd for $C_{28}H_{33}F_4N_3O_4$: 551.2, found [M+H] 552.1. ¹H NMR (500 MHz, CDCl₃) δ ppm 7.05 (d, J=8.8 Hz, 2H), 6.83-6.97 (m, 3H), 6.50 (dd, J=7.4, 3.0 Hz, 1H), 6.30-6.44 (m, 1H), 4.32-4.51 (m, 2H), 3.83 (d, J=3.8 Hz, 1H), 3.36-3.47 (m, 2H), 3.12-3.27 (m, 1H), 2.72-2.89 (m, 2H), 2.56 (dd, J=12.0, 9.8 Hz, 1H), 2.45 (dd, J=16.4, 10.3 Hz, 1H), 2.09-2.21 (m, 2H), 1.73-1.90 (m, 1H), 1.29-1.37 (m, 9H), 1.22-1.27 (m, 2H), 1.11 (d, J=6.6 Hz, 3H). Analytical HPLC (Orthogonal method, 10% Solvent B start): RT=11.2 min, HI: 99%. hGPR40 EC₅₀=311 nM. hGPR40 IP1 EC₅₀=253 nM.

EXAMPLE 13

2-((4S,5S)-4-methyl-1-(4-((1-(thiazol-2-yl)piperidin-4-yl)oxy)phenyl)-3-(trifluoromethyl)-4,5-dihydro-1H-pyrazol-5-yl)acetic acid, HCl

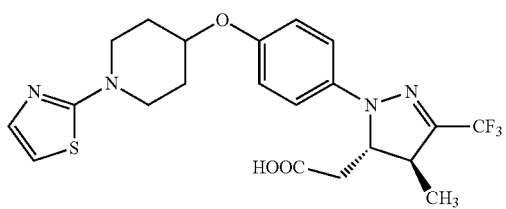 [SMILES: C[C@@H]1C(C(F)(F)F)=NN(c2ccc(OC3CCN(c4nccs4)CC3)cc2)[C@H]1CC(=O)O]

13A. 1-(thiazol-2-yl)piperidin-4-ol: A mixture of piperidin-4-ol (154 mg, 1.52 mmol), 2-bromothiazole (250 mg, 1.524 mmol) and cesium carbonate (497 mg, 1.52 mmol) in toluene (1 mL) was heated at 95° C. overnight. The reaction mixture was concentrated to remove solvent, and then was diluted with EtOAc to which was then added aqueous NaHCO₃. The organic layer was collected and was washed with H₂O and then brine, dried (Na₂SO₄) and concentrated. Purification via silica gel chromatography gave the desired product as a yellow oil (140 mg, 50% yield). LC-MS Anal. Calc'd for $C_8H_{12}N_2OS$, 184.07, found [M+H] 185.1.

13B. Methyl 2-((4S,5S)-4-methyl-1-(4-((1-(thiazol-2-yl)piperidin-4-yl)oxy)phenyl)-3-(trifluoromethyl)-4,5-dihydro-1H-pyrazol-5-yl)acetate: A mixture of triphenylphosphine (137 mg, 0.52 mmol), (E)-di-tert-butyl diazene-1,2-dicarboxylate (120 mg, 0.52 mmol), 1-(thiazol-2-yl)piperidin-4-ol (80 mg, 0.43 mmol) and methyl 2-((4S,5S)-1-(4-hydroxyphenyl)-4-methyl-3-(trifluoromethyl)-4,5-dihydro-1H-pyrazol-5-yl)acetate (1J, 143 mg, 0.43 mmol) in THF (0.8 mL) was stirred at rt overnight. The reaction mixture was quenched with aqueous NaHCO₃ and extracted with EtOAc. The organic extract was washed with H₂O and then brine, dried (Na₂SO₄) and concentrated. Purification via silica gel chromatography gave the desired product as white solid (50 mg, 24% yield). LC-MS Anal. Calc'd for $C_{22}H_{25}F_3N_4O_3S$, 482.16, found [M+H] 483.0.

EXAMPLE 13

To a suspension of methyl 2-((4S,5S)-4-methyl-1-(4-((1-(thiazol-2-yl)piperidin-4-yl)oxy)phenyl)-3-(trifluoromethyl)-4,5-dihydro-1H-pyrazol-5-yl)acetate (50 mg, 0.10 mmol) in THF (0.5 mL) and H₂O (0.1 mL) was added 2M lithium hydroxide (0.034 mL, 0.07 mmol) and the mixture was stirred at rt for 3 h. The reaction mixture was diluted with EtOAc and acidified with 6N HCl. The organic layer was collected and the aqueous layer was extracted with CH₂Cl₂. The combined organic extracts were dried (Na₂SO₄) and concentrated. Purification via RP-Prep HPLC yielded 2-((4S,5S)-4-methyl-1-(4-((1-(thiazol-2-yl)piperidin-4-yl)oxy)phenyl)-3-(trifluoromethyl)-4,5-dihydro-1H-pyrazol-5-yl)acetic acid, HCl as white solid (10 mg, 19% yield). LC-MS Anal. Calc'd for LC-MS Anal. Calc'd for $C_{21}H_{23}F_3N_4O_3S$, 468.14, found [M+H] 469.0. ¹H NMR (500 MHz, CD₃Cl) δ ppm 7.35 (d, J=4.1 Hz, 1H), 7.02-7.13 (m, 2H), 6.80-6.96 (m, 2H), 6.61 (d, J=4.4 Hz, 1H), 4.54-4.66 (m, 1H), 4.34-4.46 (m, 1H), 3.85 (d, J=3.6 Hz, 2H), 3.66-3.78 (m, 2H), 3.49 (s, 1H), 3.15-3.26 (m, 1H), 2.81 (dd, J=16.4, 3.4 Hz, 1H), 2.45 (d, J=9.6 Hz, 1H), 2.09 (d, J=5.0 Hz, 4H), 1.35 (d, J=6.9 Hz, 3H). Analytical HPLC (Orthogonal method, 10% Solvent B start): RT=7.4 min, HI: 99%. hGPR40 EC₅₀=1695 nM.

EXAMPLE 14

2-((4S,5S)-1-(4-((1-((benzyloxy)carbonyl)piperidin-4-yl)oxy)phenyl)-4-methyl-3-(trifluoromethyl)-4,5-dihydro-1H-pyrazol-5-yl)acetic acid

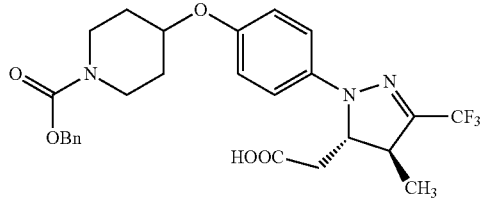 [SMILES: C[C@@H]1C(C(F)(F)F)=NN(c2ccc(OC3CCN(C(=O)OCc4ccccc4)CC3)cc2)[C@H]1CC(=O)O]

14A. Benzyl 4-(4-((4S,5S)-5-(2-methoxy-2-oxoethyl)-4-methyl-3-(trifluoromethyl)-4,5-dihydro-1H-pyrazol-1-yl)phenoxy)piperidine-1-carboxylate: A mixture of triphenylphosphine (54 mg, 0.20 mmol), (E)-di-tert-butyl diazene-1,2-dicarboxylate (47 mg, 0.20 mmol), benzyl 4-hydroxypiperidine-1-carboxylate (40 mg, 0.17 mmol) and methyl 2-((4S,5S)-1-(4-hydroxyphenyl)-4-methyl-3-(trifluoromethyl)-4,5-dihydro-1H-pyrazol-5-yl)acetate (1J, 60 mg, 0.17 mmol) in THF (0.8 mL) was stirred at rt overnight. The reaction mixture was quenched with aqueous NaHCO₃ and extracted with EtOAc. The organic extract was washed with H₂O and then brine, dried (Na₂SO₄) and concentrated. Purification via silica gel chromatography gave the desired product as a white oil (24 mg, 26% yield). LC-MS Anal. Calc'd for $C_{27}H_{30}F_3N_3O_5$ 533.21, found [M+H] 534.0.

EXAMPLE 14

To a solution of benzyl 4-(4-((4S,5S)-5-(2-methoxy-2-oxoethyl)-4-methyl-3-(trifluoromethyl)-4,5-dihydro-1H-pyrazol-1-yl)phenoxy)piperidine-1-carboxylate (24 mg, 0.05 mmol) in THF (0.5 mL) and $H_2O$ (0.1 mL) was added 2M lithium hydroxide (0.03 mL, 0.07 mmol) and the mixture was stirred at rt for 3 h. The reaction mixture was diluted with EtOAc and acidified with 6N HCl. The organic layer was collected and the aqueous layer was extracted with $CH_2Cl_2$ twice. The combined organic extracts were dried ($Na_2SO_4$) and concentrated to give 2-((4S,5S)-1-(4-((1-((benzyloxy)carbonyl)piperidin-4-yl)oxy)phenyl)-4-methyl-3-(trifluoromethyl)-4,5-dihydro-1H-pyrazol-5-yl)acetic acid as a white oil (8 mg, 33%). LC-MS Anal. Calc'd for $C_{26}H_{28}F_3N_3O_5$ 519.20, found [M+H] 520.0. $^1$H NMR (500 MHz, $CDCl_3$) δ 7.29-7.43 (m, 5H), 7.00-7.09 (m, 2H), 6.82-6.94 (m, 2H), 5.14 (s, 2H), 4.34-4.46 (m, 1H), 3.70-3.82 (m, 2H), 3.39-3.53 (m, 2H), 3.22 (ddd, J=7.0, 3.7, 1.1 Hz, 1H), 2.84 (dd, J=16.5, 3.0 Hz, 1H), 2.44 (dd, J=16.5, 10.5 Hz, 1H), 1.85-1.96 (m, 2H), 1.78 (br. s., 2H), 1.35 (d, J=6.9 Hz, 3H), 1.26 (t, J=7.2 Hz, 2H). Analytical HPLC (Orthogonal method, 10% Solvent B start): RT=10.3 min, HI: 97%. hGPR40 $EC_{50}$=4267 nM.

EXAMPLE 15

2-((4S,5S)-1-(4-((1-(tert-butoxycarbonyl)piperidin-4-yl)oxy)phenyl)-4-methyl-3-(trifluoromethyl)-4,5-dihydro-1H-pyrazol-5-yl)acetic acid

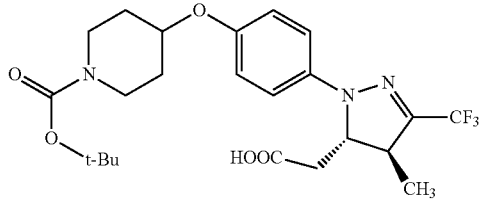 [SMILES: C[C@@H]1C(C(F)(F)F)=NN(c2ccc(OC3CCN(C(=O)OC(C)(C)C)CC3)cc2)[C@H]1CC(=O)O]

15A. tert-Butyl 4-(4-((4S,5S)-5-(2-methoxy-2-oxoethyl)-4-methyl-3-(trifluoromethyl)-4,5-dihydro-1H-pyrazol-1-yl)phenoxy)piperidine-1-carboxylate: A mixture of methyl 2-((4S,5S)-1-(4-hydroxyphenyl)-4-methyl-3-(trifluoromethyl)-4,5-dihydro-1H-pyrazol-5-yl)acetate (1J, 35 mg, 0.11 mmol), tert-butyl 4-hydroxypiperidine-1-carboxylate (27 mg, 0.13 mmol) and triphenylphosphine (35 mg, 0.13 mmol) in THF (0.8 mL) was stirred for 5 min. before (E)-di-tert-butyl diazene-1,2-dicarboxylate (31 mg, 0.13 mmol) was added and the mixture was then stirred at rt overnight. The reaction mixture was quenched with aqueous $NaHCO_3$ and extracted with EtOAc. The organic extract was washed with $H_2O$ and then brine, dried ($Na_2SO_4$) and concentrated. Purification via silica gel chromatography gave the desired product as a white oil (20 mg, 33% yield). LC-MS Anal. Calc'd for $C_{24}H_{32}F_3N_3O_5$ 499.23, found [M+H] 500.0.

Example 15: To a solution of tert-butyl 4-(4-((4S,5S)-5-(2-methoxy-2-oxoethyl)-4-methyl-3-(trifluoromethyl)-4,5-dihydro-1H-pyrazol-1-yl)phenoxy)piperidine-1-carboxylate (20 mg, 0.04 mmol) in THF (0.5 mL) and $H_2O$ (0.1 mL) was added 2M lithium hydroxide (0.034 mL, 0.068 mmol) and the mixture was stirred at rt for 3 h. The reaction was acidified with 6 N HCl and was extracted with EtOAc. The organic layer was collected and the aqueous layer was extracted with $CH_2Cl_2$ twice. The combined organic extracts were dried ($Na_2SO_4$) and concentrated. Purification via RP-Prep HPLC gave 2-((4S,5S)-1-(4-((1-(tert-butoxycarbonyl)piperidin-4-yl)oxy)phenyl)-4-methyl-3-(trifluoromethyl)-4,5-dihydro-1H-pyrazol-5-yl)acetic acid as a yellow oil (10 mg, 49%). LC-MS Anal. Calc'd for $C_{23}H_{30}F_3N_3O_5$ 485.21, found [M+H] 486.0. $^1$H NMR (500 MHz, $CDCl_3$) δ 7.04 (d, J=7.4 Hz, 2H), 6.82-6.94 (m, 2H), 4.31-4.44 (m, 2H), 3.63-3.74 (m, 2H), 3.27-3.39 (m, 2H), 3.21 (br. s., 1H), 2.83 (dd, J=16.5, 1.4 Hz, 1H), 2.44 (dd, J=16.1, 10.9 Hz, 1H), 1.82-1.92 (m, 3H), 1.65-1.76 (m, 2H), 1.46 (d, J=1.4 Hz, 9H), 1.26 (dt, J=7.2, 1.6 Hz, 3H). Analytical HPLC (Orthogonal method, 10% Solvent B start): RT=10.0 min, HI: 98%. hGPR40 $EC_{50}$=1717 nM.

EXAMPLE 16

2-((4S,5S)-1-(4-((1-(2,3-difluoro-5-methoxyphenyl)piperidin-4-yl)oxy)phenyl)-4-methyl-3-(trifluoromethyl)-4,5-dihydro-1H-pyrazol-5-yl)acetic acid, HCl

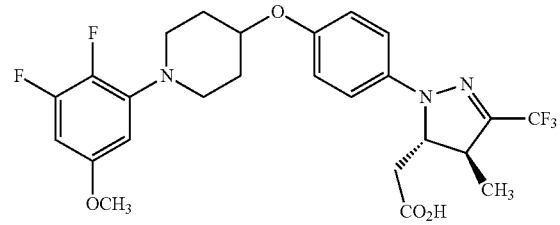 [SMILES: COc1cc(F)c(F)c(N2CCC(Oc3ccc(N4N=C(C(F)(F)F)[C@@H](C)[C@@H]4CC(=O)O)cc3)CC2)c1]

16A. 1-(2,3-difluoro-5-methoxyphenyl)piperidin-4-ol: To 1,2,3-trifluoro-5-methoxybenzene (1 g, 6.17 mmol) was added piperidin-4-ol (1.87 g, 18.51 mmol) and DMSO (10 mL). The reaction was capped and placed in a 140° C. oil bath for 3 hours. The reaction mixture was filtered and the solids rinsed into the filtrate with 2 mL of EtOAc. The filtrate was added to 50 mL of water and 50 mL of EtOAc, the mixture was well stirred, allowed to settle, and then the lower aqueous layer was removed. The EtOAc layer was washed with an additional 3×50 mL of water. The EtOAc layer was passed through a 30 mm id×40 mm silica gel plug using a total of 200 mL of EtOAc. The filtrate was concentrated in vacuo to give the product as a tan solid (1.02 g, 68% yield). LC-MS Anal. Calc'd for $C_{12}H_{15}F_2NO_2$ 243.11, found [M+H] 244.1. $^1$H NMR (500 MHz, $CDCl_3$) δ 6.33 (dd, J=5.8, 3.0 Hz, 1H), 6.27-6.17 (m, 1H), 3.97-3.80 (m, 1H), 3.75 (s, 3H), 3.53-3.19 (m, 2H), 3.02-2.78 (m, 2H), 2.04 (d, J=9.9 Hz, 2H), 1.84-1.69 (m, 2H), 1.61-1.40 (m, 1H).

16B. Methyl 2-((4S,5S)-1-(4-((1-(2,3-difluoro-5-methoxyphenyl)piperidin-4-yl)oxy)phenyl)-4-methyl-3-(trifluoromethyl)-4,5-dihydro-1H-pyrazol-5-yl)acetate: To a solution of triphenylphosphine (107 mg, 0.407 mmol) and DMF (1 mL) was added (E)-diethyl diazene-1,2-dicarboxylate (0.055 mL, 0.349 mmol) and the mixture was stirred at rt for 5 min. This mixture was added to the thick amber oil methyl 2-((4S,5S)-1-(4-hydroxyphenyl)-4-methyl-3-(trifluoromethyl)-4,5-dihydro-1H-pyrazol-5-yl)acetate (1J, 92 mg, 0.291 mmol) and the mixture was stirred for 5 minutes. To this amber solution was added 1-(2,3-difluoro-5-methoxyphenyl)piperidin-4-ol (77 mg, 0.317 mmol) and the mixture was stirred for 5 hours. The reaction mixture was quenched with 5 mL of water and 20 mL of EtOAc. The organic layer was washed with 3×5 mL of additional water and then the solvent from the organic layer was removed in vacuo. The residue was purified via silica gel chromatography to give the desired product as a pale amber oil (39 mg, 24% yield). LC-MS Anal. Calc'd for $C_{26}H_{28}F_5N_3O_4$ 541.20, found [M+H] 542.2.

Example 16: To methyl 2-((4S,5S)-1-(4-((1-(2,3-difluoro-5-methoxyphenyl)piperidin-4-yl)oxy)phenyl)-4-methyl-3-(trifluoromethyl)-4,5-dihydro-1H-pyrazol-5-yl)acetate (39 mg, 0.072 mmol) and THF (1 mL) added water (0.1 mL) and then lithium hydroxide (2 M aqueous) (0.090 mL, 0.18 mmol). After 3 h the reaction mixture was added to 10 mL of EtOAc and then 5 mL of hexane was added. The mixture was shaken and then allowed to settle. An emulsion had formed. 2-3 mL of the upper hexane layer were removed leaving 2-3 mL of an emulsion at the top of the mixture. 3 drops of 2 N aqueous HCl were added causing the emulsion to break and a white cloudiness to now appear in the lower aqueous layer. The remaining hexane layer was removed. The aqueous layer was pH 2 (pH paper). The aqueous layer was extracted with 5×3 mL of $CH_2Cl_2$, the combined extracts dried with $Na_2SO_4$, filtered, and concentrated in vacuo to provide 2-((4S,5S)-1-(4-((1-(2,3-difluoro-5-methoxyphenyl)piperidin-4-yl)oxy)phenyl)-4-methyl-3-(trifluoromethyl)-4,5-dihydro-1H-pyrazol-5-yl)acetic acid, HCl (tan foam, 34 mg, 82% yield). LC-MS Anal. Calc'd for $C_{25}H_{26}F_5N_3O_4$ 527.18, found [M+H] 528.2. $^1$H NMR (500 MHz, CDCl$_3$) δ 7.12-7.02 (m, 2H), 6.98-6.88 (m, 2H), 6.40-6.22 (m, 2H), 4.40 (dt, J=10.5, 3.3 Hz, 2H), 3.84-3.67 (m, 5H), 3.35 (ddd, J=11.6, 7.9, 3.3 Hz, 2H), 3.23 (td, J=3.6, 2.5 Hz, 1H), 3.01 (ddd, J=11.6, 7.9, 3.3 Hz, 2H), 2.86 (dd, J=16.5, 3.0 Hz, 1H), 2.46 (dd, J=16.5, 10.5 Hz, 1H), 2.19-2.05 (m, 2H), 2.03-1.80 (m, 4H), 1.36 (d, J=7.2 Hz, 3H). Analytical HPLC (Orthogonal method, 10% Solvent B start): RT=10.8 min, HI: 99%. hGPR40 EC$_{50}$=273 nM. hGPR40 IP1 EC$_{50}$=133 nM.

EXAMPLE 17

2-((4S,5S)-1-(4-((1-(5-ethoxy-2,3-difluorophenyl)piperidin-4-yl)oxy)phenyl)-4-methyl-3-(trifluoromethyl)-4,5-dihydro-1H-pyrazol-5-yl)acetic acid, HCl

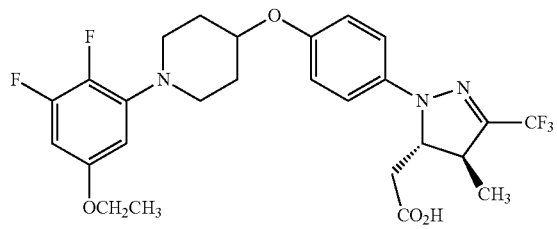 [SMILES: CCOc1cc(F)c(F)c(N2CCC(Oc3ccc(N4N=C(C(F)(F)F)[C@@H](C)[C@@H]4CC(=O)O)cc3)CC2)c1]

17A. 5-ethoxy-1,2,3-trifluorobenzene: To 3,4,5-trifluorophenol (5 g, 33.8 mmol) and potassium carbonate (11.7 g, 84 mmol) in acetone (33 mL) was added bromoethane (3.8 mL, 50.6 mmol). The mixture was reluxed for 16 hours under nitrogen. The reaction was filtered and the solids were washed with 5 mL of $CH_2Cl_2$ to provide a slightly cloudy filtrate which was concentrated to remove the $CH_2Cl_2$ and then was filtered to provide product (4.5 g, 76% yield) as a faintly yellow liquid. $^1$H NMR (500 MHz, CDCl3) δ 6.50 (dd, J=9.5, 5.6 Hz, 2H), 3.96 (q, J=6.9 Hz, 2H), 1.41 (t, J=7.0 Hz, 3H).

Example 17 (pale tan foam, 52 mg) was prepared following the procedure for Example 16. LC-MS Anal. Calc'd for $C_{26}H_{28}F_5N_3O_4$ 541.20, found [M+H] 542.2. $^1$H NMR (500 MHz, CDCl3) δ 7.14-7.02 (m, 2H), 7.00-6.88 (m, 2H), 6.40-6.21 (m, 2H), 4.47-4.33 (m, 2H), 3.96 (q, J=7.2 Hz, 2H), 3.35 (ddd, J=11.6, 7.8, 3.2 Hz, 2H), 3.28-3.15 (m, 1H), 3.00 (ddd, J=11.8, 7.9, 3.4 Hz, 2H), 2.87 (dd, J=16.5, 3.0 Hz, 1H), 2.47 (dd, J=16.5, 10.5 Hz, 1H), 2.19-2.05 (m, 2H), 2.02-1.79 (m, 2H), 1.46-1.30 (m, 6H). Analytical HPLC (Orthogonal method, 10% Solvent B start): RT=13.4 min, HI: 98%. hGPR40 EC$_{50}$=286 nM. hGPR40 IP1 EC$_{50}$=294 nM.

EXAMPLE 18

2-((4S,5S)-1-(4-((1-(2,3-difluoro-5-isobutoxyphenyl)piperidin-4-yl)oxy)phenyl)-4-methyl-3-(trifluoromethyl)-4,5-dihydro-1H-pyrazol-5-yl)acetic acid, HCl

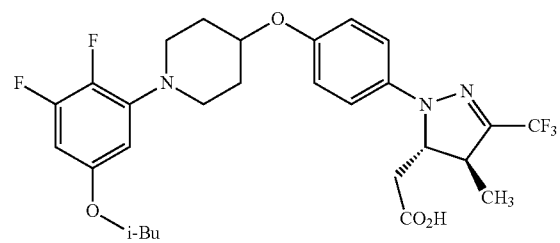

Example 18 (sticky, off-white foam, 24 mg) was prepared following the procedure for Example 16. LC-MS Anal. Calc'd for $C_{28}H_{32}F_5N_3O_4$ 569.23, found [M+H] 570.2. $^1$H NMR (500 MHz, CDCl3) δ 7.15-7.01 (m, 2H), 6.99-6.85 (m, 2H), 6.38-6.24 (m, 2H), 4.46-4.35 (m, 2H), 3.64 (d, J=6.6 Hz, 2H), 3.35 (ddd, J=11.5, 7.8, 3.3 Hz, 2H), 3.26-3.18 (m, 1H), 3.01 (ddd, J=11.7, 7.8, 3.6 Hz, 2H), 2.87 (dd, J=16.5, 3.0 Hz, 1H), 2.47 (dd, J=16.5, 10.5 Hz, 1H), 2.19-2.07 (m, 2H), 2.02-1.87 (m, 2H), 1.36 (d, J=7.2 Hz, 3H), 1.02 (d, J=6.6 Hz, 6H). Analytical HPLC (Orthogonal method, 10% Solvent B start): RT=8.5 min, HI: 98%. hGPR40 EC$_{50}$=4763 nM.

EXAMPLE 19

2-((4S,5S)-1-(4-((1-(5-(cyclopentyloxy)-2,3-difluorophenyl)piperidin-4-yl)oxy)phenyl)-4-methyl-3-(trifluoromethyl)-4,5-dihydro-1H-pyrazol-5-yl)acetic acid, HCl

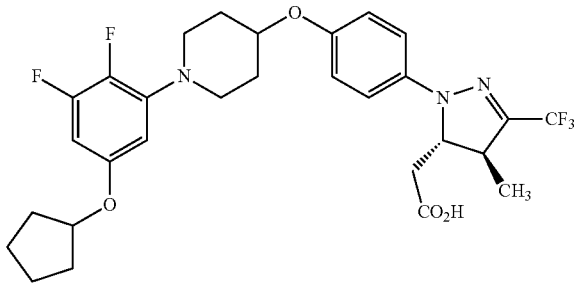 [SMILES: C[C@@H]1C(C(F)(F)F)=NN(c2ccc(OC3CCN(c4cc(OC5CCCC5)cc(F)c4F)CC3)cc2)[C@H]1CC(=O)O]

Example 19 (pale yellow oily foam, 10 mg) was prepared following the procedure for Example 16. LC-MS Anal.

Calc'd for $C_{29}H_{32}F_5N_3O_4$: 581.23, found [M+H] 582.2. $^1$H NMR (500 MHz, CDCl3) δ 7.13-7.02 (m, 2H), 6.98-6.86 (m, 2H), 6.38-6.09 (m, 2H), 4.64 (tt, J=5.7, 2.7 Hz, 1H), 4.47-4.33 (m, 2H), 4.13 (q, J=7.2 Hz, 1H), 3.35 (br. s., 3H), 3.23 (ddd, J=6.9, 3.8, 1.1 Hz, 2H), 3.00 (t, J=8.1 Hz, 3H), 2.87 (dd, J=16.5, 3.0 Hz, 2H), 2.47 (dd, J=16.5, 10.5 Hz, 2H), 2.10 (d, J=4.1 Hz, 4H), 2.03-1.94 (m, 4H), 1.92-1.87 (m, 3H), 1.86-1.83 (m, 2H), 1.82-1.72 (m, 5H), 1.69-1.54 (m, 4H), 1.36 (d, J=6.9 Hz, 5H). Analytical HPLC (Orthogonal method, 10% Solvent B start): RT=12.0 min, HI: 96%. hGPR40 $EC_{50}$=4819 nM.

EXAMPLE 20

2-((4S,5S)-4-methyl-3-(trifluoromethyl)-1-(4-((1-(4-(trifluoromethyl)pyrimidin-2-yl)piperidin-4-yl)oxy)phenyl)-4,5-dihydro-1H-pyrazol-5-yl)acetic acid

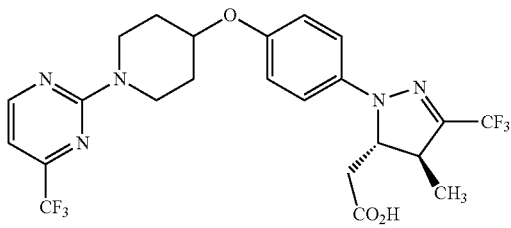 [SMILES: C[C@@H]1C(C(F)(F)F)=NN(c2ccc(OC3CCN(c4nccc(C(F)(F)F)n4)CC3)cc2)[C@H]1CC(=O)O]

Example 20 (colorless oil, 16 mg) was prepared following the procedure in Example 16 using 1-(4-(trifluoromethyl)pyrimidin-2-yl)piperidin-4-ol in place of 1-(5-ethoxy-2,3-difluorophenyl)piperidin-4-ol. LC-MS Anal. Calc'd for $C_{23}H_{23}F_6N_5O_3$ 531.17, found [M+H] 532.2. $^1$H NMR (500 MHz, CDCl3) δ 8.50 (d, J=4.7 Hz, 1H), 7.07 (d, J=8.8 Hz, 2H), 6.94 (d, J=8.8 Hz, 2H), 6.75 (d, J=5.0 Hz, 1H), 4.55-4.49 (m, 1H), 4.41 (d, J=10.2 Hz, 1H), 4.26-4.07 (m, 2H), 3.90-3.65 (m, 2H), 3.31-3.14 (m, 1H), 2.87 (dd, J=16.5, 2.8 Hz, 1H), 2.47 (dd, J=16.5, 10.2 Hz, 1H), 2.00 (td, J=8.6, 3.7 Hz, 2H), 1.90-1.75 (m, 2H), 1.36 (d, J=6.9 Hz, 3H). Analytical HPLC (Orthogonal method, 10% Solvent B start): RT=11.4 min, HI: 95%. hGPR40 $EC_{50}$=1420 nM.

EXAMPLE 21

2-((4S,5S)-1-(4-((1-(2-cyano-5-methoxyphenyl)piperidin-4-yl)oxy)phenyl)-4-methyl-3-(trifluoromethyl)-4,5-dihydro-1H-pyrazol-5-yl)acetic acid, TFA

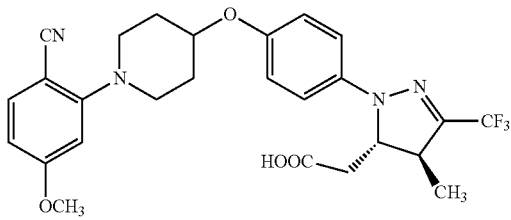 [SMILES: COc1ccc(C#N)c(N2CCC(Oc3ccc(N4N=C(C(F)(F)F)[C@@H](C)[C@@H]4CC(=O)O)cc3)CC2)c1]

21A. 2-(4-hydroxypiperidin-1-yl)-4-methoxybenzonitrile: A reaction mixture of 2-fluoro-4-methoxybenzonitrile (0.5 g, 3.31 mmol) and piperidin-4-ol (1.0 g, 9.92 mmol) in Acetonitrile (3.31 mL) with $K_2CO_3$ (1.37 g, 9.92 mmol) was stirred at 70° C. for 16 h. Cooled to room temperature. Diluted with water and extracted with methylene chloride. The organic extract was washed with brine, dried over $Mg_2SO_4$, and concentrated in vacuo to give 0.77 g yellow oil. Purification via silica gel chromatography gave (0.77 g, 3.24 mmol, 98% yield) as a clear, colorless oil. LC-MS Anal. Calc'd for $C_{13}H_{16}N_2O_2$ 232.12, found [M+H] 233.0.

Example 21 (amber oil, 71 mg) was prepared following the procedure for Example 1. LC-MS Anal. Calc'd for $C_{26}H_{27}F_3N_4O_4$ 516.20, found [M+H] 517.1. $^1$H NMR (400 MHz, CDCl$_3$) δ 10.17 (br. s., 1H), 7.65 (d, J=8.2 Hz, 1H), 7.18-6.89 (m, 5H), 6.82 (d, J=2.2 Hz, 1H), 4.61 (br. s., 1H), 4.40 (d, J=9.9 Hz, 1H), 3.97 (t, J=9.6 Hz, 2H), 3.88 (s, 3H), 3.50-3.32 (m, 2H), 3.31-3.14 (m, J=5.8, 3.6 Hz, 1H), 2.86 (dd, J=16.5, 2.7 Hz, 1H), 2.59-2.39 (m, J=16.5, 10.4 Hz, 1H), 2.38-2.24 (m, 2H), 2.24-2.09 (m, 2H), 1.35 (d, J=7.1 Hz, 3H). Analytical HPLC (Orthogonal method, 0% Solvent B start): RT=9.3 min, HI: 98%. hGPR40 $EC_{50}$=680 nM.

EXAMPLE 22

2-(1-(4-((1-(2-fluoro-5-methoxyphenyl)piperidin-4-yl)oxy)phenyl)-4-methyl-3-(pyrimidin-2-yl)-4,5-dihydro-1H-pyrazol-5-yl)acetic acid, TFA Isomer 1 and Isomer 2

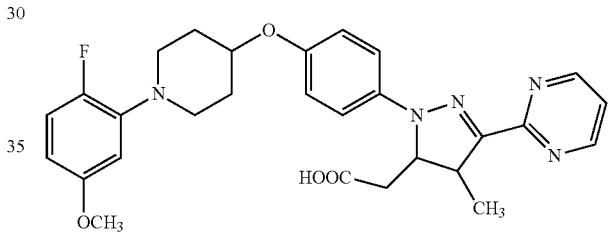

Example 22 (red oil, 11 mg) was prepared following the procedure for Example 1 using methyl but-2-enoate instead of 1E with chiral preparative SFC separation. Isomer 1: LC-MS Anal. Calc'd for $C_{28}H_{30}FN_5O_4$ 519.23, found [M+H] 520.2. $^1$H NMR (500 MHz, CDCl$_3$) δ 8.86 (d, J=4.7 Hz, 2H), 7.30 (d, J=4.7 Hz, 2H), 7.22 (t, J=4.8 Hz, 1H), 7.00-6.94 (m, 3H), 6.63 (dd, J=7.3, 2.9 Hz, 1H), 6.47 (dt, J=8.9, 3.1 Hz, 1H), 4.60 (dt, J=11.0, 2.5 Hz, 1H), 4.45-4.39 (m, 1H), 3.80 (s, 3H), 3.74 (qd, J=7.1, 2.5 Hz, 1H), 3.41 (ddd, J=11.6, 8.0, 3.6 Hz, 2H), 3.04 (ddd, J=11.6, 7.7, 3.3 Hz, 2H), 2.92 (dd, J=16.0, 2.8 Hz, 1H), 2.51 (dd, J=16.0, 11.0 Hz, 1H), 2.17 (td, J=8.5, 3.9 Hz, 2H), 2.06-1.97 (m, 2H), 1.43 (d, J=7.2 Hz, 3H). Analytical HPLC (Zorbax method, 0% Solvent B start): RT=5.1 min, HI: 98%. hGPR40 $EC_{50}$=2038 nM. Isomer 2: LC-MS Anal. Calc'd for $C_{28}H_{30}FN_5O_4$ 519.23, found [M+H] 520.2. $^1$H NMR (500 MHz, CDCl$_3$) δ 8.87 (d, J=4.7 Hz, 2H), 7.30 (d, J=9.1 Hz, 2H), 7.23 (t, J=5.0 Hz, 1H), 7.02 (dd, J=12.0, 8.9 Hz, 1H), 6.96 (d, J=8.8 Hz, 2H), 6.80 (dd, J=6.7, 2.9 Hz, 1H), 6.58 (dt, J=8.8, 3.0 Hz, 1H), 4.60 (d, J=11.0 Hz, 1H), 4.48 (dt, J=6.1, 3.1 Hz, 1H), 3.80 (s, 3H), 3.75-3.68 (m, 1H), 3.59-3.51 (m, 2H), 3.21-3.11 (m, 2H), 2.92 (dd, J=16.1, 2.6 Hz, 1H), 2.51 (dd, J=$1_{6.0}$, 11.0 Hz, 1H), 2.30-2.21 (m, 2H), 2.12-2.02 (m, 2H), 1.43 (d, J=7.2 Hz, 3H). Analytical HPLC (Zorbax method, 0% Solvent B start): RT=5.0 min, HI: 92%. hGPR40 $EC_{50}$=5570 nM.

EXAMPLE 23

2-((4S,5S)-1-(4-((1-(2-fluoro-5-methoxyphenyl)azepan-4-yl)oxy)phenyl)-4-methyl-3-(trifluoromethyl)-4,5-dihydro-1H-pyrazol-5-yl)acetic acid

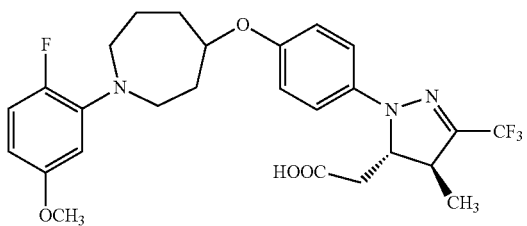 [SMILES: COc1ccc(F)c(N2CCCC(Oc3ccc(N4N=C(C(F)(F)F)[C@@H](C)[C@@H]4CC(=O)O)cc3)CC2)c1]

Example 23 (sticky orange oil, 13 mg) was prepared following the procedure for Example 1 using methyl but-2-enoate instead of 1E with chiral preparative SFC separation. LC-MS Anal. Calc'd for $C_{26}H_{29}F_4N_3O_4$ 523.21, found [M+H] 524.2. $^1$H NMR (500 MHz, $CDCl_3$) δ 7.08-7.02 (m, 2H), 6.93-6.84 (m, 3H), 6.37 (dd, J=7.4, 3.0 Hz, 1H), 6.20 (dt, J=8.8, 3.0 Hz, 1H), 4.43-4.36 (m, J=10.2 Hz, 1H), 4.11-4.04 (m, 1H), 4.00 (t, J=6.3 Hz, 2H), 3.76 (s, 3H), 3.68-3.60 (m, 1H), 3.28-3.19 (m, 2H), 2.84 (dd, J=16.5, 3.0 Hz, 1H), 2.45 (dd, J=16.5, 10.2 Hz, 1H), 2.24-2.12 (m, 2H), 2.03-1.95 (m, 1H), 1.94-1.88 (m, 1H), 1.88-1.80 (m, 1H), 1.77-1.67 (m, 1H), 1.36 (d, J=6.9 Hz, 3H). Analytical HPLC (Zorbax method, 0% Solvent B start): RT=7.6 min, HI: 97%. hGPR40 $EC_{50}$=3021 nM.

EXAMPLE 25

2-((4S,5S)-1-(4-((1-(5-ethoxy-2-fluorophenyl)-3-ethylpiperidin-4-yl)oxy)phenyl)-4-methyl-3-(trifluoromethyl)-4,5-dihydro-1H-pyrazol-5-yl)acetic acid, HCl (Isomers 1 and 2)

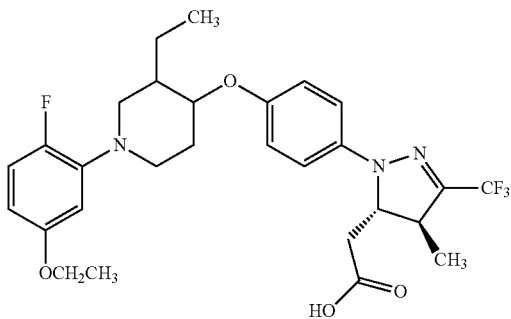 [SMILES: CCOc1ccc(F)c(N2CCC(Oc3ccc(N4N=C(C(F)(F)F)[C@@H](C)[C@@H]4CC(=O)O)cc3)C(CC)C2)c1]

25A. ethyl 1-benzyl-3-ethyl-4-oxopiperidine-3-carboxylate: To a solution of ethyl 1-benzyl-4-oxopiperidine-3-carboxylate (1.0 g, 3.8 mmol) in ACN (9.6 mL) was added KOtBu (1 N in THF) (5.7 mL, 5.7 mmol) and iodoethane (0.46 mL, 5.7 mmol). The reaction mixture was stirred at rt overnight. The reaction mixture was poured into sat. $NH_4Cl$ and extracted with EtOAc. The organic layers was washed with brine, dried over $Na_2SO_4$ and concentrated to give a colorless oil as a crude material as ethyl 1-benzyl-3-ethyl-4-oxopiperidine-3-carboxylate (0.90 g, 3.11 mmol, 81% yield). LC-MS Anal. Calc'd for $C_{17}H_{23}NO_3$ 289.17, found [M+H] 290.0.

25B. 1-benzyl-3-ethylpiperidin-4-one: To a sealed vial containing ethyl 1-benzyl-3-ethyl-4-oxopiperidine-3-carboxylate (800 mg, 2.8 mmol) was added 6 N HCl (8 mL, 48 mmol). The reaction mixture was heated at 100° C. for 16 h. To the reaction mixture was poured cold 5 N NaOH to adjust the pH~8 and the mixture was extracted with EtOAc. The organic layer was washed with brine, dried over $Na_2SO_4$, and concentrated. Purification via silica gel chromatography gave a colorless oil (0.31 g, 1.427 mmol, 51.6% yield). LC-MS Anal. Calc'd for $C_{14}H_{19}NO$, 217.15, found [M+H] 218.0. $^1$H NMR (400 MHz, $CDCl_3$) δ ppm 7.27 (s, 5H), 3.64-3.31 (m, 2H), 3.02-2.70 (m, 2H), 2.53-2.39 (m, 2H), 2.34-2.25 (m, 2H), 2.18 (dd, J=11.0, 9.5 Hz, 1H), 1.39-0.98 (m, 2H), 0.79 (t, J=7.5 Hz, 3H).

25C. 1-benzyl-3-ethyl-1-methyl-4-oxopiperidin-1-ium, iodide salt: To a solution of 1-benzyl-3-ethylpiperidin-4-one (0.46 g, 2.10 mmol) in acetone (2.10 mL) was added methyl iodide (0.16 mL, 2.60 mmol). The reaction mixture was stirred at rt overnight. The solvents were removed and the residue was dried in vacuo to give a light yellow foam as 1-benzyl-3-ethyl-1-methyl-4-oxopiperidin-1-ium, iodide salt (0.58 g, 1.60 mmol, 76% yield). LC-MS Anal. Calc'd for $C_{15}H_{22}NO$, 232.17, found [M+H] 232.0.

25D. 1-(5-ethoxy-2-fluorophenyl)-3-ethylpiperidin-4-one: To a solution of 5-ethoxy-2-fluoroaniline (100 mg, 0.64 mmol) in EtOH (1.3 mL)/water (0.6 mL) was added 1-benzyl-3-ethyl-1-methyl-4-oxopiperidin-1-ium, iodide salt (301 mg, 0.84 mmol) and $K_2CO_3$ (13 mg, 0.097 mmol). The reaction mixture was heated at 100° C. overnight. The reaction mixture was poured into water and was extracted with dichloromethane. The organic layer was washed with brine, dried over $Na_2SO_4$, and concentrated via vaccum. Purification via silica gel chromatography gave a colorless oil 1-(5-ethoxy-2-fluorophenyl)-3-ethylpiperidin-4-one (155 mg, 0.58 mmol, 91% yield). $^1$H NMR (500 MHz, $CD_3Cl$) δ ppm 6.95 (dd, J=12.1, 8.8 Hz, 1H), 6.53 (dd, J=7.4, 3.0 Hz, 1H), 6.44 (dt, J=8.8, 3.2 Hz, 1H), 4.14-3.88 (m, 2H), 3.74-3.48 (m, 2H), 3.25-3.11 (m, 1H), 2.92 (dd, J=11.8, 9.4 Hz, 1H), 2.69 (dddd, J=14.2, 10.0, 5.8, 1.4 Hz, 1H), 2.60-2.40 (m, 2H), 2.07-1.77 (m, 1H), 1.46-1.29 (m, 4H), 1.04-0.83 (m, 3H).

25E. 1-(5-ethoxy-2-fluorophenyl)-cis-3-ethylpiperidin-4-ol: To a 0° C. solution of 1-(5-ethoxy-2-fluorophenyl)-3-ethylpiperidin-4-one (0.51 g, 1.92 mmol) in MeOH (7.7 mL) was added $NaBH_4$ (0.084 g, 2.2 mmol). After 1 h, the reaction was quenched via addition of 1.5 M $K_2HPO_4$ and the mixture was concentrated to remove MeOH. The resulting mixture was diluted with water and extracted with dichloromethane. The organic layer was washed with brine, dried with $Na_2SO_4$, and concentrated. The residue was dissolved in EtOAc and filtered through a plug of silica gel. Purification via silica gel chromatography gave 1-(5-ethoxy-2-fluorophenyl)-cis-3-ethylpiperidin-4-ol (180 mg, 0.673 mmol, 35.0% yield). $^1$H NMR (400 MHz, $CD_3Cl$) δ ppm 6.90 (dd, J=12.1, 8.8 Hz, 1H), 6.55 (dd, J=7.3, 3.0 Hz, 1H), 6.39 (dt, J=8.8, 3.2 Hz, 1H), 4.08-3.85 (m, 3H), 3.31-2.96 (m, 3H), 2.82 (t, J=11.0 Hz, 1H), 2.02-1.72 (m, 3H), 1.59-1.33 (m, 5H), 0.99 (t, J=7.5 Hz, 3H).

25F. methyl 2-(1-(4-((1-(5-ethoxy-2-fluorophenyl)-3-ethylpiperidin-4-yl)oxy)phenyl)-4-methyl-3-(trifluoromethyl)-4,5-dihydro-1H-pyrazol-5-yl)acetate: To a solution of methyl 2-((4S,5S)-1-(4-hydroxyphenyl)-4-methyl-3-(trifluoromethyl)-4,5-dihydro-1H-pyrazol-5-yl)acetate (1J, 56 mg, 0.18 mmol), $PPh_3$ (70 mg, 0.27 mmol), and di-tert-butylazodicarboxylate (61 mg, 0.27 mmol) in toluene (0.88 mL) was added 1-(5-ethoxy-2-fluorophenyl)-cis-3-ethylpiperidin-4-ol (57 mg, 0.21 mmol). The reaction mixture was stirred at 60° C. for 2.5 h. The reaction mixture was loaded onto to a silica gel column for purification, followed by RP-Prep HPLC. The purified material was dissolved in EtOAc and was extracted with sat. NaHCO$_3$. The organic layers were washed with brine and dried over Na$_2$SO$_4$. The organic layer was concentrated to give methyl 2-(1-(4-((1-(5-ethoxy-2-fluorophenyl)-3-ethylpiperidin-4-yl)oxy)phenyl)-4-methyl-3-(trifluoromethyl)-4,5-dihydro-1H-pyrazol-5-yl)acetate (42 mg, 0.074 mmol, 41.9% yield) as a colorless foam. LC-MS Anal. Calc'd for C$_{29}$H$_{35}$F$_4$N$_3$O$_4$: 565.26. found [M+H] 566.2.

Example 25 (Isomers 1 and 2): To methyl 2-((4S,5S)-1-(4-((1-(5-ethoxy-2-fluorophenyl)-3-ethylpiperidin-4-yl)oxy)phenyl)-4-methyl-3-(trifluoromethyl)-4,5-dihydro-1H-pyrazol-5-yl)acetate (42 mg, 0.074 mmol) in THF (1.4 mL)/water (0.14 mL), lithium hydroxide (1 N in water, 0.22 mL, 0.22 mmol) was added. The reaction mixture was stirred at rt for 1 h. The reaction mixture was diluted with water and acidified with 1 N HCl. The mixture was extracted with CH$_2$Cl$_2$. The organic extracts were dried (MgSO$_4$) and concentrated to afford a diastereomeric mixture. The diastereomers were separated by chiral Prep. SFC to provide 2 isomers. Example 25 (Isomer 1) was obtained as a colorless foam (17.5 mg, 39.0%). LC-MS Anal. Calc'd for C$_{28}$H$_{33}$F$_4$N$_3$O$_4$: 551.24, found [M+H] 552.1. $^1$H NMR (400 MHz, CD$_3$CN) δ ppm 7.86-7.72 (m, 1H), 7.25-7.15 (m, 1H), 7.12-7.02 (m, 2H), 7.01-6.94 (m, 2H), 6.93-6.84 (m, 1H), 4.48-4.38 (m, 1H), 4.29-4.19 (m, 1H), 4.04 (d, J=7.1 Hz, 2H), 3.73-3.51 (m, 3H), 3.38-3.24 (m, 2H), 3.03-2.91 (m, 1H), 2.71 (d, J=3.0 Hz, 1H), 2.51 (d, J=9.6 Hz, 3H), 2.32 (br. s., 3H), 1.37 (t, J=6.9 Hz, 3H), 1.33-1.22 (m, 3H), 0.94 (t, J=7.6 Hz, 3H). Analytical HPLC (Orthogonal method): RT=11.3 min, HI: 97%. hGPR40 EC$_{50}$=1019 nM. Example 25 (Isomer 2) was obtained as a colorless foam (17.0 mg, 37.1%). LC-MS Anal. Calc'd for C$_{28}$H$_{33}$F$_4$N$_3$O$_4$ 551.24, found [M+H] 552.1. $^1$H NMR (400 MHz, CD$_3$CN) δ ppm 7.97-7.83 (m, 1H), 7.27-7.16 (m, 1H), 7.13-7.04 (m, 2H), 7.03-6.88 (m, 3H), 4.50-4.38 (m, 1H), 4.32-4.18 (m, 1H), 4.05 (d, J=7.1 Hz, 2H), 3.77-3.54 (m, 4H), 3.44-3.22 (m, 3H), 3.04-2.89 (m, 1H), 2.71 (d, J=3.3 Hz, 1H), 2.65-2.56 (m, 1H), 2.51 (d, J=9.6 Hz, 1H), 2.42-2.26 (m, 2H), 1.38 (t, J=6.9 Hz, 3H), 1.33-1.23 (m, 3H), 0.94 (t, J=7.5 Hz, 3H). Analytical HPLC (Orthogonal method): RT=11.3 min, HI: 95%. hGPR40 EC$_{50}$=113 nM. hGPR40 IP1 EC$_{50}$=21 nM. Acute oral glucose tolerance: −38% @ 0.3 mg/kg.

EXAMPLE 26

2-((4S,5S)-1-(4-((1-(5-ethoxy-2-fluorophenyl)-3-isopropylpiperidin-4-yl)oxy)phenyl)-4-methyl-3-(trifluoromethyl)-4,5-dihydro-1H-pyrazol-5-yl)acetic acid, HCl, (Isomers 1 and 2)

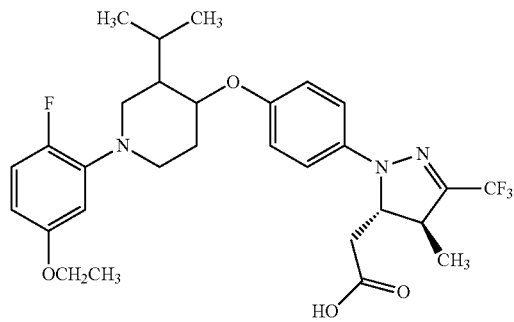 [SMILES: CCOc1ccc(F)c(N2CCC(Oc3ccc(N4N=C(C(F)(F)F)[C@@H](C)[C@@H]4CC(=O)O)cc3)C(C(C)C)C2)c1]

Example 26 (Isomer 1) (beige foam, 20 mg) was prepared following the procedure for Example 25. LC-MS Anal. Calc'd for C$_{29}$H$_{35}$F$_4$N$_3$O$_4$: 565.26, found [M+H] 566.0. $^1$H NMR (500 MHz, CD$_3$CN) δ ppm 7.85-7.74 (m, 1H), 7.25-7.15 (m, 1H), 7.11-7.04 (m, 2H), 6.99 (d, J=9.1 Hz, 2H), 6.94-6.85 (m, 1H), 4.47-4.38 (m, 2H), 4.04 (d, J=6.9 Hz, 2H), 3.65-3.53 (m, 3H), 3.41-3.28 (m, 2H), 2.76-2.67 (m, 1H), 2.54-2.44 (m, 1H), 2.37-2.22 (m, 4H), 1.37 (t, J=7.0 Hz, 3H), 1.30 (d, J=6.9 Hz, 3H), 1.00 (d, J=7.2 Hz, 3H), 0.90 (d, J=6.9 Hz, 3H). Analytical HPLC (Orthogonal method): RT=11.5 min, HI: 100%. hGPR40 EC$_{50}$=1904 nM.

Example 26 (Isomer 2) (beige foam, 21.0 mg) was prepared following the procedure for Example 25. LC-MS Anal. Calc'd for C$_{29}$H$_{35}$F$_4$N$_3$O$_4$: 565.24, found [M+H] 566.0. $^1$H NMR (500 MHz, CD$_3$CN) δ ppm 8.03-7.87 (m, 1H), 7.29-7.18 (m, 1H), 7.12-7.04 (m, 2H), 7.02-6.98 (m, 2H), 6.97-6.91 (m, 1H), 4.53-4.36 (m, 2H), 4.05 (q, J=6.9 Hz, 2H), 3.64 (d, J=3.3 Hz, 3H), 3.47-3.38 (m, 1H), 3.37-3.27 (m, 1H), 2.73 (dd, J=16.5, 3.0 Hz, 2H), 2.56-2.45 (m, 1H), 2.44-2.23 (m, 4H), 1.38 (t, J=7.0 Hz, 3H), 1.30 (d, J=7.2 Hz, 3H), 1.00 (d, J=7.2 Hz, 3H), 0.90 (d, J=7.2 Hz, 3H). Analytical HPLC (Orthogonal method): RT=11.5 min, HI: 100%. hGPR40 EC$_{50}$=82 nM.

EXAMPLE 27

2-((4S,5S)-1-(4-((1-(5-ethoxy-2-fluorophenyl)-3-isobutylpiperidin-4-yl)oxy)phenyl)-4-methyl-3-(trifluoromethyl)-4,5-dihydro-1H-pyrazol-5-yl)acetic acid, HCl (Isomers 1 and 2)

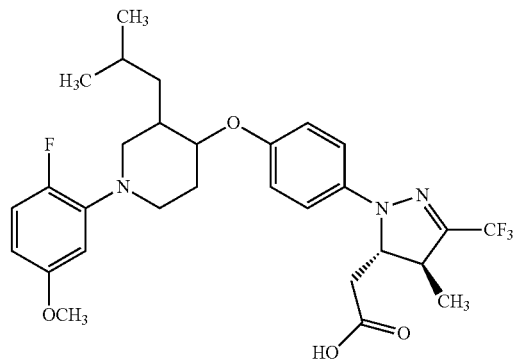 [SMILES: COc1ccc(F)c(N2CCC(Oc3ccc(N4N=C(C(F)(F)F)[C@@H](C)[C@@H]4CC(=O)O)cc3)C(CC(C)C)C2)c1]

Example 27 (Isomer 1) (beige foam, 38 mg) was prepared following the procedure for Example 25. LC-MS Anal. Calc'd for C$_{30}$H$_{37}$F$_4$N$_3$O$_4$: 579.27, found [M+H] 580.3. $^1$H NMR (500 MHz, CD$_3$CN) δ ppm 7.92-7.66 (m, 1H), 7.30-7.13 (m, 1H), 7.13-7.04 (m, 2H), 7.02-6.95 (m, 2H), 6.92-6.85 (m, 1H), 4.53-4.38 (m, 1H), 4.20-4.12 (m, 1H), 4.04 (d, J=7.1 Hz, 2H), 3.73-3.46 (m, 3H), 3.40-3.18 (m, 2H), 2.94 (dd, J=12.5, 7.2 Hz, 3H), 2.73 (dd, J=16.4, 3.3 Hz, 1H), 2.51 (d, J=9.6 Hz, 1H), 2.31 (m., 1H), 1.74-1.53 (m, 2H), 1.37 (t, J=7.1 Hz, 3H), 1.31-1.21 (m, 3H), 0.92 (dd, J=7.3, 6.3 Hz, 6H). Analytical HPLC (Orthogonal method): RT=14.6 min, HI: 96%. hGPR40 EC$_{50}$=412 nM. hGPR40 IP1 EC$_{50}$=90 nM.

Example 27 (Isomer 2) (beige foam, 21 mg) was prepared following the procedure for Example 25. LC-MS Anal. Calc'd for C$_{30}$H$_{37}$F$_4$N$_3$O$_4$: 579.27, found [M+H] 580.4. $^1$H NMR (500 MHz, CD$_3$CN) δ ppm 7.77-7.57 (m, 1H), 7.23-7.12 (m, 1H), 7.10-7.02 (m, 2H), 7.00-6.92 (m, 2H), 6.89-6.80 (m, 1H), 4.47-4.35 (m, 1H), 4.20-4.10 (m, 1H), 4.04 (d, J=7.1 Hz, 2H), 3.66-3.54 (m, 2H), 3.53-3.42 (m, 1H), 3.37-3.27 (m, 1H), 3.25-3.13 (m, 1H), 2.70 (m, 1H), 2.54-2.43 (m, 1H), 2.33-2.23 (m, 4H), 1.74-1.54 (m, 2H), 1.37 (t, J=6.9 Hz, 3H), 1.30 (d, J=7.1 Hz, 3H), 0.92 (t, J=6.3 Hz, 6H). Analytical HPLC (Orthogonal method): RT=14.8 min, HI: 100%. hGPR40 $EC_{50}$=34 nM. hGPR40 IP1 $EC_{50}$=84 nM.

EXAMPLE 28

2-((4S,5S)-1-(4-((3-benzyl-1-(5-ethoxy-2-fluorophenyl)piperidin-4-yl)oxy)phenyl)-4-methyl-3-(trifluoromethyl)-4,5-dihydro-1H-pyrazol-5-yl)acetic acid, HCl (Isomers 1 and 2)

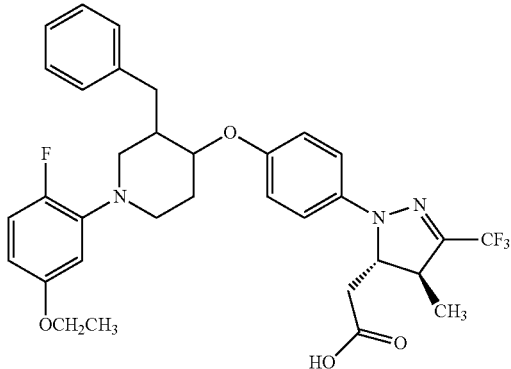 [SMILES: CCOc1ccc(F)c(N2CCC(Oc3ccc(N4N=C(C(F)(F)F)[C@@H](C)[C@@H]4CC(=O)O)cc3)C(Cc3ccccc3)C2)c1]

Example 28 (Isomer 1) (white solid, 96 mg) was prepared following the procedure for Example 25. LC-MS Anal. Calc'd for $C_{33}H_{35}F_4N_3O_4$: 613.26, found [M+H] 614.2. $^1$H NMR (400 MHz, $CD_3CN$) δ ppm 7.62 (br. s., 1H), 7.34-7.25 (m, 2H), 7.25-7.19 (m, 3H), 7.15 (dd, J=12.2, 9.1 Hz, 1H), 7.11-7.05 (m, 2H), 7.02-6.94 (m, 2H), 6.85 (dt, J=9.0, 3.1 Hz, 1H), 4.48-4.40 (m, 1H), 4.34-4.24 (m, 1H), 3.99 (q, J=7.0 Hz, 2H), 3.69-3.49 (m, 2H), 3.44 (dd, J=12.3, 3.1 Hz, 1H), 3.38-3.28 (m, 2H), 3.28-3.19 (m, 1H), 2.92 (br. s., 1H), 2.78-2.61 (m, 2H), 2.50 (dd, J=16.5, 9.5 Hz, 1H), 2.42-2.25 (m, 2H), 1.39-1.26 (m, 6H). Analytical HPLC (Orthogonal method): RT=14.2 min, HI: 100%. hGPR40 $EC_{50}$=132 nM.

Example 28 (Isomer 2) (beige foam, 93 mg) was prepared following the procedure for Example 25. LC-MS Anal. Calc'd for $C_{33}H_{35}F_4N_3O_4$: 613.26, found [M+H] 614.3. $^1$H NMR (400 MHz, $CD_3CN$) δ ppm 7.77-7.57 (m, 1H), 7.23-7.12 (m, 1H), 7.10-7.02 (m, 2H), 7.00-6.92 (m, 2H), 6.89-6.80 (m, 1H), 4.47-4.35 (m, 1H), 4.20-4.10 (m, 1H), 4.04 (d, J=7.1 Hz, 2H), 3.66-3.54 (m, 2H), 3.53-3.42 (m, 1H), 3.37-3.27 (m, 1H), 3.25-3.13 (m, 1H), 2.70 (m, 1H), 2.54-2.43 (m, 1H), 2.33-2.23 (m, 4H), 1.74-1.54 (m, 2H), 1.37 (t, J=6.9 Hz, 3H), 1.30 (d, J=7.1 Hz, 3H), 0.92 (t, J=6.3 Hz, 6H). Analytical HPLC (Orthogonal method): RT=14.3 min, HI: 99%. hGPR40 $EC_{50}$=1317 nM. hGPR40 IP1 $EC_{50}$=230 nM.

EXAMPLE 29

2-((4S,5S)-1-(4-(((3R,4R)-1-(5-ethoxy-2-fluorophenyl)-3-methylpiperidin-4-yl)oxy)phenyl)-4-methyl-3-(trifluoromethyl)-4,5-dihydro-1H-pyrazol-5-yl) acetic acid, HCl salt

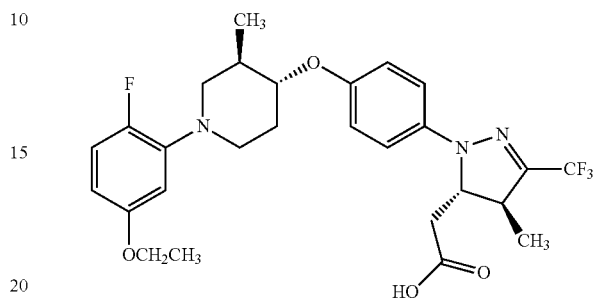

29A. 5-ethoxy-2-fluoroaniline: To a solution of (5-ethoxy-2-fluorophenyl)boronic acid (10.1 g, 55.0 mmol) in MeOH (220 mL) was added 14.8 M aqueous $NH_4OH$ (18.6 mL, 275 mmol), and then cuprous oxide (1.57 g, 11.0 mmol). The reaction mixture was stirred under air for 7 h. The reaction mixture was concentrated. The crude material was dissolved in EtOAc/Hex (2:1). The material was filtered through Celite and concentrated. The crude material was purified by flash chromatography to provide 5-ethoxy-2-fluoroaniline (4.10 g, 26.4 mmol, 48% yield) as a brown oil. LC-MS Anal. Calc'd for $C_8H_{20}FNO$, 155.17, found [M+H] 156.1. $^1$H NMR (400 MHz, $CDCl_3$) δ 6.86 (dd, J=10.9, 8.8 Hz, 1H), 6.32 (dd, J=7.5, 2.9 Hz, 1H), 6.20 (dt, J=8.8, 3.3 Hz, 1H), 3.94 (q, J=6.9 Hz, 2H), 3.68 (br. s., 2H), 1.37 (t, J=6.9 Hz, 3H).

29B. 1-benzyl-1,3-dimethyl-4-oxopiperidin-1-ium, iodide salt: To a solution of 1-benzyl-3-methylpiperidin-4-one (14.0 g, 68.9 mmol) in acetone (68.9 mL) at rt was added MeI (8.61 mL, 138 mmol) dropwise. The reaction mixture was concentrated to obtain 1-benzyl-1,3-dimethyl-4-oxopiperidin-1-ium, iodide salt (24 g, 69.5 mmol, 101% yield) as a light yellow foam. LC-MS Anal. Calc'd for $C_{14}H_{20}NO$: 218.15, found [M+H] 219.2.

29C. 1-(5-ethoxy-2-fluorophenyl)-3-methylpiperidin-4-one: To a solution of 5-ethoxy-2-fluoroaniline (7.87 g, 50.7 mmol) in EtOH (103 mL) was added $K_2CO_3$ (1.05 g, 7.61 mmol), 1-benzyl-1,3-dimethyl-4-oxopiperidin-1-ium, iodide salt (26.3 g, 76.0 mmol), and water (46.6 mL). The reaction mixture was heated to 95° C. overnight. The reaction mixture was cooled to rt and diluted with EtOAc/water. The layers were separated and the aqueous layer was extracted with EtOAc (2×). The combined organic layers were washed with brine, dried ($MgSO_4$) and concentrated. The crude product was purified by flash chromatography to provide 1-(5-ethoxy-2-fluorophenyl)-3-methylpiperidin-4-one (10.12 g, 40.3 mmol, 79% yield) as a colorless oil, which solidified overnight. LC-MS Anal. Calc'd for $C_{14}H_{18}FNO_2$ 251.13, found [M+H] 252.2. $^1$H NMR (400 MHz, $CDCl_3$) δ 6.95 (dd, J=12.1, 8.8 Hz, 1H), 6.52 (dd, J=7.5, 2.9 Hz, 1H), 6.44 (dt, J=8.8, 3.2 Hz, 1H), 3.98 (q, J=7.3 Hz, 2H), 3.75-3.64 (m, 2H), 3.12 (td, J=11.7, 3.5 Hz, 1H), 2.85-2.69 (m, 3H), 2.49 (dt, J=14.1, 3.3 Hz, 1H), 1.40 (t, J=6.9 Hz, 3H), 1.09 (d, J=6.1 Hz, 3H).

29D. (cis)-1-(5-ethoxy-2-fluorophenyl)-3-methylpiperidin-4-ol: To a solution of 1-(5-ethoxy-2-fluorophenyl)-3- methylpiperidin-4-one (4.920 g, 19.58 mmol) in THF (98 mL) at −78° C. was added a 1 M solution of L-Selectride (23.49 mL, 23.49 mmol) in THF. After 1 h, the reaction mixture was quenched with 1 M aqueous NaOH (23.49 mL, 23.49 mmol) and warmed to 0° C. 30% aqueous $H_2O_2$ (7.40 mL, 72.4 mmol) was added dropwise and the reaction mixture was warmed to rt and stirred for 1 h. The reaction mixture was diluted with EtOAc/water and the layers were separated. The aqueous layer was extracted with EtOAc (2×). The combined organic layers were washed with brine, dried ($MgSO_4$) and concentrated. The crude product was purified by flash chromatography to provide (cis)-1-(5-ethoxy-2-fluorophenyl)-3-methylpiperidin-4-ol (4.453 g, 17.58 mmol, 90% yield) as a colorless oil. LC-MS Anal. Calc'd for $C_{14}H_{20}FNO_2$: 253.31, found [M+H] 254.0. $^1$H NMR (500 MHz, $CDCl_3$) δ 6.89 (dd, J=12.1, 8.8 Hz, 1H), 6.52 (dd, J=7.3, 2.9 Hz, 1H), 6.37 (dt, J=8.8, 3.2 Hz, 1H), 3.97 (q, J=7.1 Hz, 2H), 3.90 (br. s., 1H), 3.13-3.02 (m, 2H), 3.02-2.95 (m, 1H), 2.84 (dd, J=11.4, 9.8 Hz, 1H), 2.05 (dqt, J=10.1, 6.7, 3.6 Hz, 1H), 2.00-1.91 (m, 1H), 1.91-1.83 (m, 1H), 1.50 (br. s., 1H), 1.38 (t, J=6.9 Hz, 3H), 1.03 (d, J=6.9 Hz, 3H)

29E. (3R,4S)-1-(5-ethoxy-2-fluorophenyl)-3-methylpiperidin-4-ol: (cis)-1-(5-ethoxy-2-fluorophenyl)-3-methylpiperidin-4-ol (29.15 g, 115 mmol) was purified by chiral SFC chromatography. (3R,4S)-1-(5-ethoxy-2-fluorophenyl)-3-methylpiperidin-4-ol (13.54 g, 53.50 mmol, 47% yield) was obtained as a colorless oil after concentration. LC-MS Anal. Calc'd for $C_{14}H_{18}FNO_2$: 251.13, found [M+H] 252.2. $^1$H NMR (400 MHz, $CDCl_3$) δ 6.95 (dd, J=12.1, 8.8 Hz, 1H), 6.52 (dd, J=7.5, 2.9 Hz, 1H), 6.44 (dt, J=8.8, 3.2 Hz, 1H), 3.98 (q, J=7.3 Hz, 2H), 3.75-3.64 (m, 2H), 3.12 (td, J=11.7, 3.5 Hz, 1H), 2.85-2.69 (m, 3H), 2.49 (dt, J=14.1, 3.3 Hz, 1H), 1.40 (t, J=6.9 Hz, 3H), 1.09 (d, J=6.1 Hz, 3H).

29F. methyl 2-((4S,5S)-1-(4-(((3R,4R)-1-(5-ethoxy-2-fluorophenyl)-3-methylpiperidin-4-yl)oxy)phenyl)-4-methyl-3-(trifluoromethyl)-4,5-dihydro-1H-pyrazol-5-yl)acetate: To a solution of (3R,4S)-1-(5-ethoxy-2-fluorophenyl)-3-methylpiperidin-4-ol (2.48 g, 9.78 mmol), methyl 2-((4S,5S)-1-(4-hydroxyphenyl)-4-methyl-3-(trifluoromethyl)-4,5-dihydro-1H-pyrazol-5-yl)acetate (1J, 3.09 g, 9.78 mmol), and $Bu_3P$ (3.86 mL, 15.6 mmol) in toluene (122 mL) was added (E)-diazene-1,2-diylbis(piperidin-1-ylmethanone) (3.95 g, 15.6 mmol). The reaction mixture was sonicated for 2 h. The reaction mixture was poured into hexanes and filtered. The crude product was purified by flash chromatography to provide methyl 2-((4S,5S)-1-(4-(((3R,4R)-1-(5-ethoxy-2-fluorophenyl)-3-methylpiperidin-4-yl)oxy)phenyl)-4-methyl-3-(trifluoromethyl)-4,5-dihydro-1H-pyrazol-5-yl)acetate (2.60 g, 4.70 mmol, 48% yield) as a colorless oil. LC-MS Anal. Calc'd for $C_{28}H_{33}F_4N_3O_4$: 551.57, found [M+H] 552.4. $^1$H NMR (500 MHz, $CDCl_3$) δ 7.07-7.00 (m, 2H), 6.95-6.86 (m, 3H), 6.51 (dd, J=7.3, 2.9 Hz, 1H), 6.39 (dt, J=8.8, 3.0 Hz, 1H), 4.39 (dt, J=10.1, 3.1 Hz, 1H), 3.98 (q, J=7.0 Hz, 2H), 3.83 (td, J=9.1, 4.3 Hz, 1H), 3.71 (s, 3H), 3.48-3.36 (m, 2H), 3.22-3.14 (m, 1H), 2.85-2.74 (m, 2H), 2.57 (dd, J=12.1, 9.6 Hz, 1H), 2.41 (dd, J=16.1, 10.3 Hz, 1H), 2.20-2.08 (m, 2H), 1.88-1.76 (m, 1H), 1.40 (t, J=7.0 Hz, 3H), 1.34 (d, J=7.2 Hz, 3H), 1.11 (d, J=6.6 Hz, 3H).

Example 29: To a solution of methyl 2-((4S,5S)-1-(4-(((3R,4R)-1-(5-ethoxy-2-fluorophenyl)-3-methylpiperidin-4-yl)oxy)phenyl)-4-methyl-3-(trifluoromethyl)-4,5-dihydro-1H-pyrazol-5-yl)acetate (2.57 g, 4.66 mmol) in THF (85 mL) and water (8.5 mL) was added a 1 M aqueous solution of LiOH (58.2 mL, 23.3 mmol) and the reaction mixture was stirred at rt until complete for 1 h. The reaction mixture was concentrated to remove the THF and hexanes was added. An emulsion formed. The layers were separated as much as possible. Brine was added to the emulsion and the layers separated completely. The combined aqueous layer and brine aqueous layer was acidified to pH 2 with 1 M aqueous HCl. The product was extracted with $CH_2Cl_2$ (3×) and the combined organic layers were dried ($MgSO_4$) and concentrated to provide 2-((4S,5S)-1-(4-(((3R,4R)-1-(5-ethoxy-2-fluorophenyl)-3-methylpiperidin-4-yl)oxy)phenyl)-4-methyl-3-(trifluoromethyl)-4,5-dihydro-1H-pyrazol-5-yl)acetic acid (2.4720 g, 4.60 mmol, 99% yield) as a white foam. To a solution of 2-((4S,5S)-1-(4-(((3R,4R)-1-(5-ethoxy-2-fluorophenyl)-3-methylpiperidin-4-yl)oxy)phenyl)-4-methyl-3-(trifluoromethyl)-4,5-dihydro-1H-pyrazol-5-yl)acetic acid (7.72 g, 14.4 mmol) in acetonitrile (50 mL) was added 3 N aqueous HCl (9.57 mL, 28.7 mmol). The solution was concentrated. 2-((4S,5S)-1-(4-(((3R,4R)-1-(5-ethoxy-2-fluorophenyl)-3-methylpiperidin-4-yl)oxy)phenyl)-4-methyl-3-(trifluoromethyl)-4,5-dihydro-1H-pyrazol-5-yl)acetic acid, HCl (8.08 g, 14.0 mmol, 97% yield) was isolated as an off-white solid. LC-MS Anal. Calc'd for $C_{27}H_{31}F_4N_3O_4$: 537.55, found [M+H] 538.3. $^1$H NMR (400 MHz, $CD_3CN$) δ 7.99 (br. s., 1H), 7.24 (ddd, J=12.0, 9.3, 1.2 Hz, 1H), 7.12-7.04 (m, 2H), 7.02-6.93 (m, 3H), 4.47-4.38 (m, 1H), 4.18 (td, J=10.0, 4.1 Hz, 1H), 4.04 (q, J=6.9 Hz, 2H), 3.78-3.65 (m, 2H), 3.62 (dd, J=12.4, 4.1 Hz, 1H), 3.42 (td, J=11.8, 4.4 Hz, 1H), 3.37-3.27 (m, 1H), 2.83 (br. s., 1H), 2.73 (dd, J=16.5, 3.0 Hz, 1H), 2.54-2.38 (m, 2H), 2.36-2.28 (m, 1H), 1.37 (t, J=7.0 Hz, 3H), 1.30 (d, J=7.2 Hz, 3H), 1.11 (d, J=6.9 Hz, 3H). Analytical HPLC (Orthogonal method) RT=13.3 min, HI: 97%. hGPR40 $EC_{50}$=154 nM. hGPR40 IP1 $EC_{50}$=11 nM. Acute oral glucose tolerance: −52% @ 0.3 mg/kg (average of two experiments).

EXAMPLE 30

2-((4S,5S)-1-(4-(((3S,4S)-1-(5-ethoxy-2-fluorophenyl)-3-methylpiperidin-4-yl)oxy)phenyl)-4-methyl-3-(trifluoromethyl)-4,5-dihydro-1H-pyrazol-5-yl)acetic acid

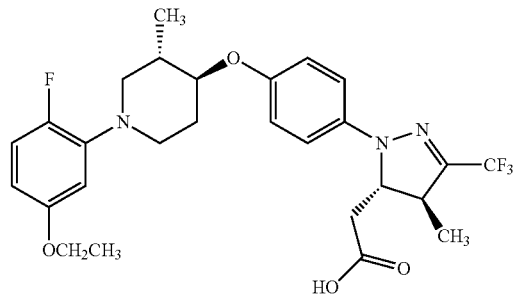 [SMILES: CCOc1ccc(F)c(N2CC[C@H](Oc3ccc(N4N=C(C(F)(F)F)[C@@H](C)[C@@H]4CC(=O)O)cc3)[C@@H](C)C2)c1]

Example 30 (off white solid, 26.8 mg) was prepared following the procedure for Example 25. LC-MS Anal. Calc'd for $C_{27}H_{31}F_4N_3O_4$: 537.55, found [M+H] 538.3. $^1$H NMR (500 MHz, $CD_3CN$) δ 7.09-7.03 (m, 2H), 6.97-6.90 (m, 3H), 6.53 (dd, J=7.4, 3.0 Hz, 1H), 6.43 (dt, J=8.9, 3.3 Hz, 1H), 4.46-4.38 (m, 1H), 3.98 (q, J=6.9 Hz, 2H), 3.92 (td, J=9.2, 4.4 Hz, 1H), 3.43-3.36 (m, 2H), 3.36-3.29 (m, 1H), 2.87-2.77 (m, 1H), 2.72 (dd, J=16.4, 3.2 Hz, 1H), 2.58 (dd, J=12.1, 9.9 Hz, 1H), 2.48 (dd, J=16.4, 9.5 Hz, 1H), 2.20-2.11 (m, 1H), 2.06-1.97 (m, 1H), 1.74-1.63 (m, 1H), 1.36-1.31

(m, 3H), 1.30 (d, J=6.9 Hz, 3H), 1.07 (d, J=6.6 Hz, 3H). Analytical HPLC (Orthogonal method): 13.3 min, HI: 97%. hGPR40 EC$_{50}$=1200 nM.

EXAMPLE 31

2-((4S,5S)-1-(4-((1-(5-ethoxy-2-fluorophenyl)-3-methoxypiperidin-4-yl)oxy)phenyl)-4-methyl-3-(trifluoromethyl)-4,5-dihydro-1H-pyrazol-5-yl)acetic acid, HCl (Isomers 1 and 2)

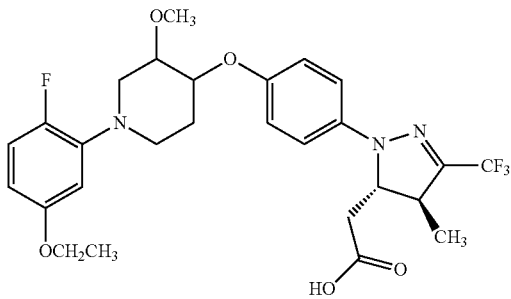 [SMILES: CCOc1ccc(F)c(N2CCC(Oc3ccc(N4N=C(C(F)(F)F)[C@@H](C)[C@@H]4CC(=O)O)cc3)C(OC)C2)c1]

Example 31 (Isomers and 2) were prepared following the procedures for Examples 29 and 30. Example 31 (Isomer 1) (light yellow solid, 48 mg). LC-MS Anal. Calc'd for C$_{27}$H$_{31}$F$_4$N$_3$O$_5$ 553.55, found [M+H] 554.3. $^1$H NMR (500 MHz, CD$_3$CN) δ 7.45-7.40 (m, 1 H), 7.11-6.95 (m, 5 H), 6.80-6.70 (m, 1 H), 4.40-4.30 (m, 2 H), 4.00-3.95 (m, 2 H), 3.90-3.80 (m, 1 H), 3.66-3.50 (m, 2 H), 3.41 (s, 3 H), 3.39-3.20 (m, 3 H), 2.70-2.65 (m, 1 H), 2.45-2.10 (m, 3 H, m), 1.32-1.29 (t, J=7.0 Hz, 3 H), 1.26-1.23 (m, 4 H). Analytical HPLC (Orthogonal method): RT=9.5 min, HI: 97%. hGPR40 EC$_{50}$=473 nM. hGPR40 IP1 EC$_{50}$=13 nM. Example 31 (Isomer 2) (light yellow solid, 50 mg). LC-MS Anal. Calc'd for C$_{27}$H$_{31}$F$_4$N$_3$O$_5$ 553.55, found [M+H] 554.3. $^1$H NMR (500 MHz, CD$_3$CN) δ 7.45-7.40 (m, 1 H), 7.11-6.95 (m, 5 H), 6.80-6.70 (m, 1 H), 4.40-4.30 (m, 2 H), 4.00-3.95 (m, 2 H), 3.90-3.80 (m, 1 H), 3.66-3.50 (m, 2 H), 3.41 (s, 3 H), 3.39-3.20 (m, 3 H), 2.70-2.65 (m, 1 H), 2.45-2.10 (m, 3 H, m), 1.32-1.29 (t, J=7.0 Hz, 3 H), 1.26-1.23 (m, 4 H). Analytical HPLC (Orthogonal method): RT=9.5 min, HI: 96%. hGPR40 EC$_{50}$=910 nM.

EXAMPLE 32

2-((4S,5S)-1-(4-((1-(5-ethoxy-2-fluorophenyl)piperidin-4-yl)oxy)phenyl)-4-methyl-3-(trifluoromethyl)-4,5-dihydro-1H-pyrazol-5-yl)acetic acid, HCl

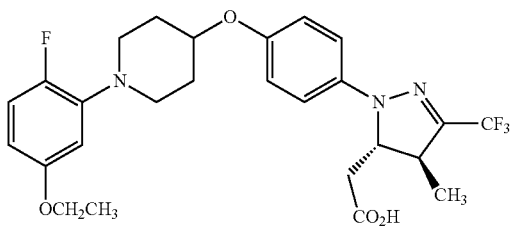 [SMILES: CCOc1ccc(F)c(N2CCC(Oc3ccc(N4N=C(C(F)(F)F)[C@@H](C)[C@@H]4CC(=O)O)cc3)CC2)c1]

32A. 2-bromo-4-ethoxy-1-fluorobenzene: A mixture of 3-bromo-4-fluorophenol (2 g, 10.47 mmol), potassium carbonate (1.74 g, 12.57 mmol) and bromoethane (4 mL, 52.4 mmol) and acetonitrile (10.5 mL) was heated at 60° C. overnight. Sat. aqueous NaHCO$_3$ (50 mL) was added slowly to the reaction mixture. The mixture was extracted with EtOAc (2×50 mL), and the combined organic extracts were washed with water (100 mL) and brine (100 mL), and dried (Na$_2$SO$_4$), filtered, and concentrated to afford 2-bromo-4-ethoxy-1-fluorobenzene (clear oil, 1.9 g, 8.67 mmol, 83% yield). $^1$H NMR (400 MHz, CDCl$_3$) δ 7.05 (dt, J=6.1, 3.4 Hz, 1H), 7.03-6.98 (m, 1H), 6.82-6.76 (m, 1H), 3.98 (q, J=7.0 Hz, 2H), 1.40 (t, J=7.0 Hz, 3H).

32B. 1-(5-ethoxy-2-fluorophenyl)piperidin-4-ol: A mixture of piperidin-4-ol (460 mg, 4.5 mmol), 2-bromo-4-ethoxy-1-fluorobenzene (495 mg, 2.26 mmol) and Sphos pre.cat. (15 mg, 0.023 mmol) in THF (4.5 mL) was purged with argon and lithium bis(trimethylsilyl)amide (9.0 mL, 9.04 mmol) was added. The reaction mixture was heated at 70° C. for 2.5 h. Sat. aqueous NaHCO$_3$ (10 mL) was added slowly to the reaction mixture. The mixture was extracted with EtOAc (2×10 mL), and the combined organic extracts were washed with water (20 mL) and brine (20 mL), and dried (Na$_2$SO$_4$), filtered, and concentrated. Purification via silica gel chromatography gave 1-(5-ethoxy-2-fluorophenyl)piperidin-4-ol (yellow oil, 254 mg, 1.051 mmol, 46.5% yield). LC-MS Anal. Calc'd for C$_{13}$H$_{18}$FNO$_2$ 239.13, found [M+H] 240.2.

Example 32 was prepared following the procedure for Example 1. LC-MS Anal. Calc'd for C$_{26}$H$_{29}$F$_4$N$_3$O$_4$ 523.52, found [M+H] 524.1. $^1$H NMR (400 MHz, CD$_3$CN) δ ppm 8.00 (dd, J=5.9, 2.6 Hz, 1H), 7.29 (dd, J=12.2, 9.2 Hz, 1H), 7.14-7.08 (m, 2H), 7.06-6.98 (m, 3H), 4.70 (br. s., 1H), 4.51-4.40 (m, 1H), 4.08 (q, J=6.9 Hz, 2H), 3.91 (t, J=9.9 Hz, 2H), 3.65-3.50 (m, 2H), 3.44-3.29 (m, 1H), 2.76 (dd, J=16.4, 3.1 Hz, 1H), 2.62 (br. s., 2H), 2.56-2.48 (m, 1H), 2.38-2.23 (m, 2H), 1.40 (t, J=7.0 Hz, 3H), 1.33 (d, J=7.3 Hz, 3H). Analytical HPLC (Orthogonal method, 10% Solvent B start): RT=11.8 min, HI: 100%. hGPR40 EC$_{50}$=217 nM.

Example 33 and Example 35 to Example 56 were prepared following the procedure for Example 32.

EXAMPLE 33

2-((4S,5S)-1-(4-((1-(2-chloro-5-methoxyphenyl)piperidin-4-yl)oxy)phenyl)-4-methyl-3-(trifluoromethyl)-4,5-dihydro-1H-pyrazol-5-yl)acetic acid

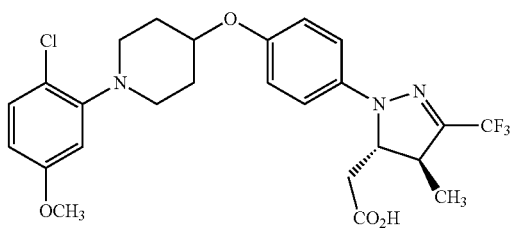 [SMILES: COc1ccc(Cl)c(N2CCC(Oc3ccc(N4N=C(C(F)(F)F)[C@@H](C)[C@@H]4CC(=O)O)cc3)CC2)c1]

Example 33 (1.2 mg): LC-MS Anal. Calc'd for C$_{25}$H$_{27}$ClF$_3$N$_3$O$_4$ 525.95, found [M+H] 526.1. $^1$H NMR (500 MHz, 1:1 MeOD:CDCl$_3$) δ ppm 7.24 (d, J=8.9 Hz, 1H), 7.13-7.04 (m, 2H), 6.94 (d, J=8.9 Hz, 2H), 6.66 (d, J=3.0 Hz, 1H), 6.54 (dd, J=8.7, 2.7 Hz, 1H), 4.51-4.37 (m, 3H), 3.79 (s, 3H), 3.31-3.18 (m, 3H), 2.98-2.90 (m, 2H), 2.82-2.70 (m, 1H), 2.34-2.20 (m, 1H), 2.18-2.07 (m, 2H), 2.04-1.85 (m, 2H), 1.32 (d, J=7.4 Hz, 3H). Analytical HPLC (Analytical LC/MS method, 0% Solvent B start): RT=2.4 min, HI: 100%. hGPR40 $EC_{50}$=103 nM.

EXAMPLE 35

2-((4S,5S)-1-(4-((1-(2,5-dichlorophenyl)piperidin-4-yl)oxy)phenyl)-4-methyl-3-(trifluoromethyl)-4,5-dihydro-1H-pyrazol-5-yl)acetic acid

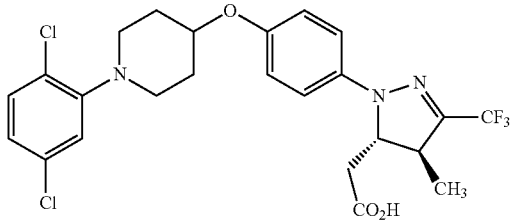 [SMILES: C[C@@H]1C(C(F)(F)F)=NN(c2ccc(OC3CCN(c4cc(Cl)ccc4Cl)CC3)cc2)[C@H]1CC(=O)O]

Example 35 (2.2 mg): LC-MS Anal. Calc'd for $C_{24}H_{24}Cl_2F_3N_3O_3$ 530.37, found [M+H] 530.0. $^1$H NMR (500 MHz, 1:1 MeOD:CDCl$_3$) δ ppm 7.29 (d, J=8.4 Hz, 1H), 7.14-7.05 (m, 3H), 7.01-6.92 (m, 3H), 4.48-4.38 (m, 3H), 3.31-3.20 (m, 2H), 2.95 (ddd, J=11.5, 8.1, 3.2 Hz, 2H), 2.77 (dd, J=15.9, 3.0 Hz, 1H), 2.33 (dd, J=15.9, 10.9 Hz, 1H), 2.18-2.07 (m, 2H), 2.03-1.93 (m, 2H), 1.33 (d, J=6.9 Hz, 3H). Analytical HPLC (Analytical LC/MS method, 0% Solvent B start): RT=2.7 min, HI: 100%. hGPR40 $EC_{50}$=254 nM.

EXAMPLE 36

2-((4S,5S)-1-(4-((1-(2-fluoro-5-methylphenyl)piperidin-4-yl)oxy)phenyl)-4-methyl-3-(trifluoromethyl)-4,5-dihydro-1H-pyrazol-5-yl)acetic acid

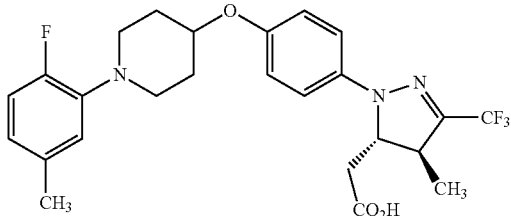

Example 36 (5.9 mg): LC-MS Anal. Calc'd for $C_{25}H_{27}F_4N_3O_3$ 493.50, found [M+H] 494.2. $^1$H NMR (500 MHz, 1:1 MeOD:CDCl$_3$) δ ppm 7.10-7.06 (m, 2H), 6.96-6.92 (m, 2H), 6.89 (dd, J=12.4, 8.4 Hz, 1H), 6.84 (dd, J=8.4, 2.0 Hz, 1H), 6.78-6.73 (m, 1H), 4.47-4.36 (m, 2H), 3.32-3.21 (m, 2H), 2.96 (ddd, J=11.5, 8.3, 3.5 Hz, 2H), 2.77 (dd, J=15.9, 3.0 Hz, 1H), 2.36-2.31 (m, 2H), 2.29 (s, 3H), 2.16-2.08 (m, 2H), 2.00-1.89 (m, 2H), 1.33 (d, J=7.4 Hz, 3H). Analytical HPLC (Analytical LC/MS method, 0% Solvent B start): RT=1.9 min, HI: 97%. hGPR40 $EC_{50}$=440 nM. hGPR40 IP1 $EC_{50}$=86 nM.

EXAMPLE 37

2-((4S,5S)-1-(4-((1-(2-chlorophenyl)piperidin-4-yl)oxy)phenyl)-4-methyl-3-(trifluoromethyl)-4,5-dihydro-1H-pyrazol-5-yl)acetic acid

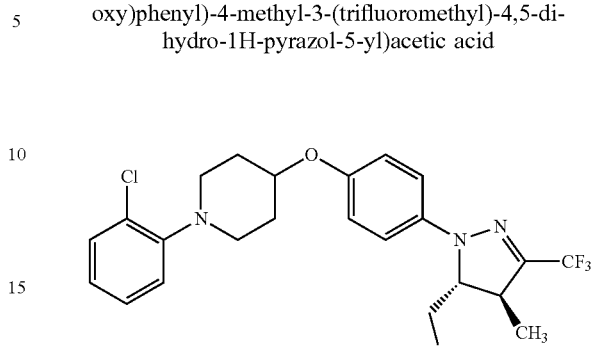

Example 37 (3.3 mg): LC-MS Anal. Calc'd for $C_{24}H_{25}ClF_3N_3O_3$ 495.93, found [M+H] 496.1. $^1$H NMR (500 MHz, 1:1 MeOD:CDCl$_3$) δ ppm 7.35 (dd, J=7.9, 1.5 Hz, 1H), 7.23 (td, J=7.7, 1.5 Hz, 1H), 7.14-7.06 (m, 3H), 7.03-6.91 (m, 3H), 4.48-4.38 (m, 2H), 3.31-3.20 (m, 3H), 2.99-2.90 (m, 2H), 2.77 (dd, J=15.9, 3.0 Hz, 1H), 2.32 (dd, J=15.6, 10.7 Hz, 1H), 2.20-2.07 (m, 2H), 2.04-1.87 (m, 2H), 1.33 (d, J=6.9 Hz, 3H). Analytical HPLC (Analytical LC/MS method, 0% Solvent B start): RT=2.4 min, HI: 98%. hGPR40 $EC_{50}$=448 nM.

EXAMPLE 38

2-((4S,5S)-1-(4-((1-(2,5-difluorophenyl)piperidin-4-yl)oxy)phenyl)-4-methyl-3-(trifluoromethyl)-4,5-dihydro-1H-pyrazol-5-yl)acetic acid

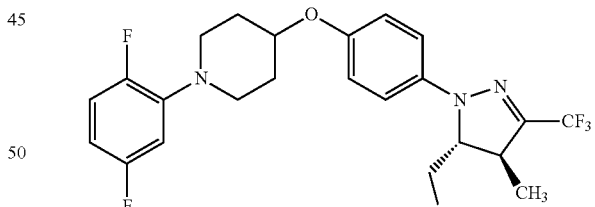

Example 38 (2.8 mg): LC-MS Anal. Calc'd for $C_{24}H_{24}F_5N_3O_3$ 497.46, found [M+H] 498.1. $^1$H NMR (500 MHz, 1:1 MeOD:CDCl$_3$) δ ppm 7.09 (d, J=8.9 Hz, 2H), 7.01-6.90 (m, 3H), 6.73 (ddd, J=10.3, 7.1, 3.0 Hz, 1H), 6.66-6.57 (m, 1H), 4.49-4.37 (m, 3H), 3.28-3.19 (m, 2H), 3.04-2.95 (m, 2H), 2.76 (dd, J=15.4, 3.0 Hz, 1H), 2.29 (dd, J=15.6, 10.7 Hz, 1H), 2.21-2.10 (m, 2H), 2.02-1.84 (m, 2H), 1.32 (d, J=6.9 Hz, 3H). Analytical HPLC (Analytical LC/MS method, 0% Solvent B start): RT=2.4 min, HI: 100%. hGPR40 $EC_{50}$=475 nM.

EXAMPLE 39

2-((4S,5S)-4-methyl-1-(4-((1-(o-tolyl)piperidin-4-yl)oxy)phenyl)-3-(trifluoromethyl)-4,5-dihydro-1H-pyrazol-5-yl)acetic acid

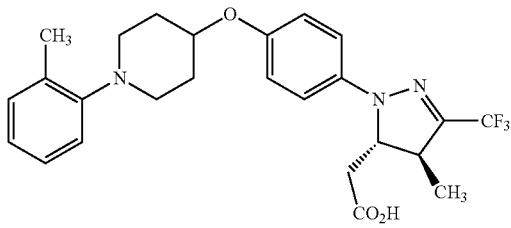 [SMILES: Cc1ccccc1N1CCC(Oc2ccc(N3N=C(C(F)(F)F)[C@@H](C)[C@@H]3CC(=O)O)cc2)CC1]

Example 39 (8.6 mg): LC-MS Anal. Calc'd for $C_{25}H_{28}F_3N_3O_3$ 475.51, found [M+H] 476.2. $^1$H NMR (500 MHz, 1:1 MeOD:CDCl$_3$) δ ppm 7.19-7.12 (m, 2H), 7.10-7.03 (m, 3H), 6.98-6.92 (m, 3H), 4.46-4.35 (m, 2H), 3.31-3.21 (m, 2H), 3.18-3.10 (m, 2H), 2.85-2.72 (m, 2H), 2.31 (s, 3H), 2.16-2.09 (m, 2H), 2.00-1.88 (m, 2H), 1.33 (d, J=7.4 Hz, 3H). Analytical HPLC (Analytical LC/MS method, 0% Solvent B start): RT=1.8 min, HI: 96%. hGPR40 EC$_{50}$=498 nM.

EXAMPLE 40

2-((4S,5S)-1-(4-((1-(3-methoxyphenyl)piperidin-4-yl)oxy)phenyl)-4-methyl-3-(trifluoromethyl)-4,5-dihydro-1H-pyrazol-5-yl)acetic acid

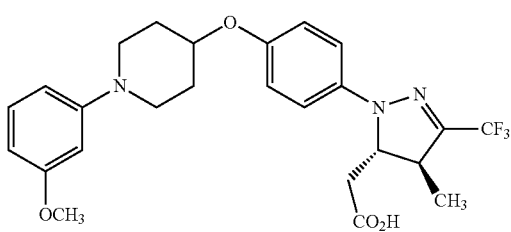 [SMILES: COc1cccc(N2CCC(Oc3ccc(N4N=C(C(F)(F)F)[C@@H](C)[C@@H]4CC(=O)O)cc3)CC2)c1]

Example 40 (1.2 mg): LC-MS Anal. Calc'd for $C_{25}H_{28}F_3N_3O_4$ 491.51, found [M+H] 492.2. $^1$H NMR (500 MHz, 1:1 MeOD:CDCl$_3$) δ ppm 7.16 (t, J=8.2 Hz, 1H), 7.09 (d, J=8.9 Hz, 2H), 6.97-6.88 (m, 2H), 6.61 (dd, J=8.4, 2.0 Hz, 1H), 6.53 (t, J=2.2 Hz, 1H), 6.44 (dd, J=7.9, 2.0 Hz, 1H), 4.48-4.37 (m, 2H), 3.79 (s, 3H), 3.59-3.46 (m, 2H), 3.25 (d, J=4.0 Hz, 1H), 3.14-3.04 (m, 2H), 2.76 (dd, J=15.9, 3.0 Hz, 1H), 2.26 (dd, J=15.4, 10.9 Hz, 1H), 2.15-2.05 (m, 2H), 1.97-1.84 (m, 2H), 1.32 (d, J=6.9 Hz, 3H). Analytical HPLC (Analytical LC/MS method, 0% Solvent B start): RT=1.7 min, HI: 97%. hGPR40 EC$_{50}$=620 nM. hGPR40 IP1 EC$_{50}$=107 nM.

EXAMPLE 41

2-((4S,5S)-1-(4-((1-(3-fluoropyridin-2-yl)piperidin-4-yl)oxy)phenyl)-4-methyl-3-(trifluoromethyl)-4,5-dihydro-1H-pyrazol-5-yl)acetic acid

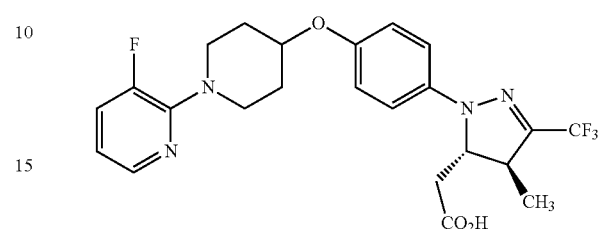

Example 41 (5.6 mg): LC-MS Anal. Calc'd for $C_{23}H_{24}F_4N_4O_3$ 480.46, found [M+H] 481.1. $^1$H NMR (500 MHz, 1:1 MeOD:CDCl$_3$) δ ppm 7.96-7.93 (m, 1H), 7.32 (ddd, J=13.4, 7.9, 1.5 Hz, 1H), 7.14-7.05 (m, 2H), 7.00-6.89 (m, 2H), 6.82 (ddd, J=7.9, 5.0, 3.0 Hz, 1H), 4.53-4.39 (m, 3H), 3.88-3.72 (m, 2H), 3.32-3.21 (m, 2H), 2.77 (dd, J=15.9, 2.5 Hz, 1H), 2.32 (dd, J=15.6, 10.7 Hz, 1H), 2.10 (ddd, J=9.8, 6.8, 3.7 Hz, 2H), 1.89 (dt, J=12.9, 4.0 Hz, 2H), 1.33 (d, J=6.9 Hz, 3H). Analytical HPLC (Analytical LC/MS method, 0% Solvent B start): RT=1.9 min, HI: 100%. hGPR40 EC$_{50}$=628 nM.

EXAMPLE 42

2-((4S,5S)-1-(4-((1-(2-fluoro-6-methylphenyl)piperidin-4-yl)oxy)phenyl)-4-methyl-3-(trifluoromethyl)-4,5-dihydro-1H-pyrazol-5-yl)acetic acid

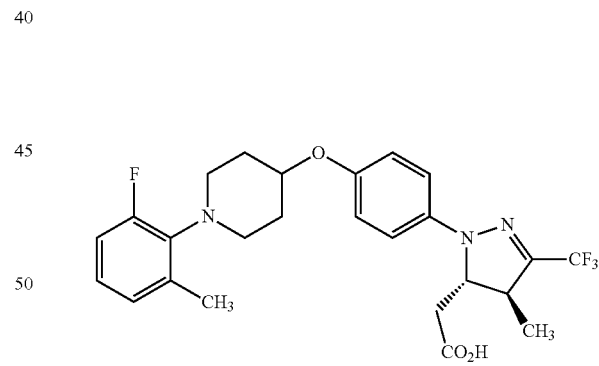

Example 42 (1.2 mg): LC-MS Anal. Calc'd for $C_{25}H_{27}F_4N_3O_3$ 493.50, found [M+H] 494.1. $^1$H NMR (500 MHz, 1:1 MeOD:CDCl$_3$) δ ppm 7.07 (d, J=8.4 Hz, 2H), 7.00-6.93 (m, 4H), 6.89-6.79 (m, 1H), 4.46-4.32 (m, 2H), 3.29-3.03 (m, 5H), 2.78 (dd, J=16.1, 2.7 Hz, 1H), 2.41-2.36 (m, 1H), 2.34 (s, 3H), 2.08 (br. s., 2H), 1.85 (d, J=7.4 Hz, 2H), 1.34 (d, J=6.9 Hz, 3H). Analytical HPLC (Analytical LC/MS method, 0% Solvent B start): RT=2.6 min, HI: 100%. hGPR40 EC$_{50}$=796 nM.

EXAMPLE 43

2-((4S,5S)-1-(4-((1-(2,5-dimethylphenyl)piperidin-4-yl)oxy)phenyl)-4-methyl-3-(trifluoromethyl)-4,5-dihydro-1H-pyrazol-5-yl)acetic acid

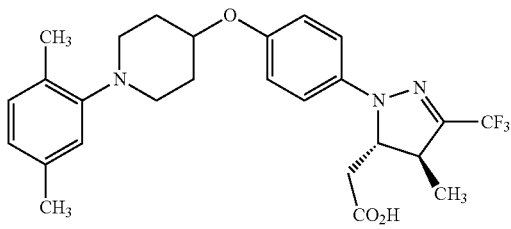 [SMILES: Cc1ccc(C)c(N2CCC(Oc3ccc(N4N=C(C(F)(F)F)[C@@H](C)[C@@H]4CC(=O)O)cc3)CC2)c1]

Example 43 (8.3 mg): LC-MS Anal. Calc'd for $C_{26}H_{30}F_3N_3O_3$ 489.54, found [M+H] 490.2. $^1$H NMR (500 MHz, 1:1 MeOD:CDCl$_3$) δ ppm 7.12-7.06 (m, 2H), 7.04 (d, J=7.4 Hz, 1H), 6.97-6.93 (m, 2H), 6.87 (s, 1H), 6.77 (d, J=7.4 Hz, 1H), 4.46-4.34 (m, 2H), 3.24 (dd, J=5.4, 4.0 Hz, 1H), 3.17-3.09 (m, 2H), 2.85-2.73 (m, 3H), 2.33 (dd, J=16.1, 10.7 Hz, 1H), 2.29 (s, 3H), 2.26 (s, 3H), 2.12 (dd, J=11.9, 3.0 Hz, 2H), 1.96-1.87 (m, 2H), 1.33 (d, J=6.9 Hz, 3H). Analytical HPLC (Analytical LC/MS method, 0% Solvent B start): RT=1.9 min, HI: 98%. hGPR40 $EC_{50}$=1074 nM.

EXAMPLE 44

2-((4S,5S)-1-(4-((1-(2,6-dimethylphenyl)piperidin-4-yl)oxy)phenyl)-4-methyl-3-(trifluoromethyl)-4,5-dihydro-1H-pyrazol-5-yl)acetic acid

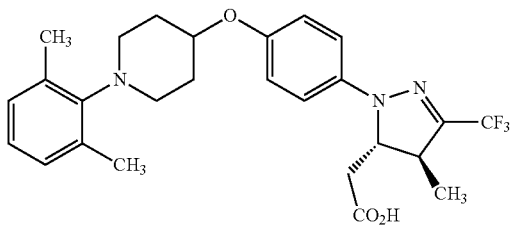 [SMILES: Cc1cccc(C)c1N1CCC(Oc2ccc(N3N=C(C(F)(F)F)[C@@H](C)[C@@H]3CC(=O)O)cc2)CC1]

Example 44 (5.7 mg): LC-MS Anal. Calc'd for $C_{26}H_{30}F_3N_3O_3$ 489.54, found [M+H] 490.1. $^1$H NMR (500 MHz, 1:1 MeOD:CDCl$_3$) δ ppm 7.12-7.06 (m, 2H), 7.03-6.88 (m, 5H), 4.45-4.31 (m, 3H), 3.28-3.08 (m, 5H), 2.78 (dd, J=16.3, 3.0 Hz, 1H), 2.34 (s, 3H), 2.32 (s, 3H), 2.08 (dt, J=8.2, 3.8 Hz, 2H), 1.85 (dtd, J=12.7, 8.8, 4.0 Hz, 2H), 1.33 (d, J=6.9 Hz, 3H). Analytical HPLC (Analytical LC/MS method, 0% Solvent B start): RT=2.5 min, HI: 99%. hGPR40 $EC_{50}$=1338 nM.

EXAMPLE 45

2-((4S,5S)-1-(4-((1-(4-methoxypyridin-2-yl)piperidin-4-yl)oxy)phenyl)-4-methyl-3-(trifluoromethyl)-4,5-dihydro-1H-pyrazol-5-yl)acetic acid

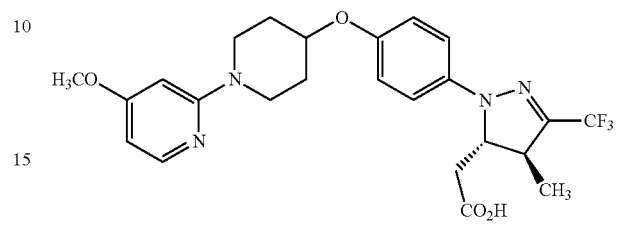

Example 45 (4.2 mg): LC-MS Anal. Calc'd for $C_{24}H_{27}F_3N_4O_4$ 492.50, found [M+H] 493.1. $^1$H NMR (500 MHz, 1:1 MeOD:CDCl$_3$) δ ppm 7.91 (d, J=5.9 Hz, 1H), 7.14-7.04 (m, 2H), 6.97-6.90 (m, 2H), 6.31 (dd, J=5.9, 2.0 Hz, 1H), 6.24 (d, J=2.0 Hz, 1H), 4.48 (tt, J=7.4, 3.5 Hz, 1H), 4.42 (d, J=10.4 Hz, 1H), 3.84 (s, 4H), 3.88-3.81 (m, 1H), 3.47-3.37 (m, 2H), 3.24 (dd, J=5.4, 4.0 Hz, 1H), 2.77 (dd, J=15.9, 3.0 Hz, 1H), 2.32 (dd, J=15.6, 10.7 Hz, 1H), 2.10-1.98 (m, 2H), 1.93-1.79 (m, 2H), 1.33 (d, J=6.9 Hz, 3H). Analytical HPLC (Analytical LC/MS method, 0% Solvent B start): RT=1.6 min, HI: 100%. hGPR40 $EC_{50}$=1523 nM.

EXAMPLE 46

2-((4S,5S)-1-(4-((1-(2-methoxyphenyl)piperidin-4-yl)oxy)phenyl)-4-methyl-3-(trifluoromethyl)-4,5-dihydro-1H-pyrazol-5-yl)acetic acid

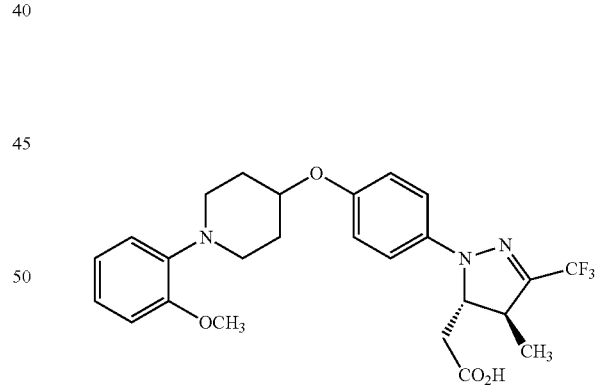

Example 46 (3.6 mg): LC-MS Anal. Calc'd for $C_{25}H_{28}F_3N_3O_4$ 491.51, found [M+H] 492.1. $^1$H NMR (500 MHz, 1:1 MeOD:CDCl$_3$) δ ppm 7.10-7.06 (m, 2H), 7.04-7.00 (m, 2H), 6.96-6.89 (m, 4H), 4.49-4.34 (m, 2H), 3.91 (s, 3H), 3.32-3.20 (m, 2H), 2.95-2.88 (m, 3H), 2.77 (dd, J=15.9, 3.0 Hz, 1H), 2.30 (dd, J=15.6, 10.7 Hz, 1H), 2.17-2.08 (m, 2H), 1.97 (dt, J=12.9, 4.0 Hz, 2H), 1.32 (d, J=6.9 Hz, 3H). Analytical HPLC (Analytical LC/MS method, 0% Solvent B start): RT=1.6 min, HI: 99%. hGPR40 $EC_{50}$=1697 nM.

EXAMPLE 47

2-((4S,5S)-1-(4-((1-(2-methoxypyridin-4-yl)piperidin-4-yl)oxy)phenyl)-4-methyl-3-(trifluoromethyl)-4,5-dihydro-1H-pyrazol-5-yl)acetic acid

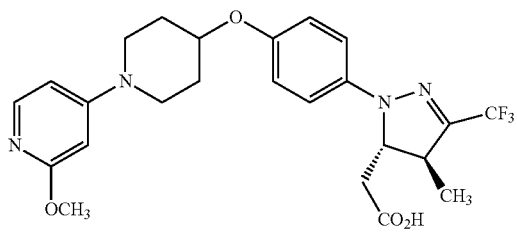 [SMILES: COc1cc(N2CCC(Oc3ccc(N4N=C(C(F)(F)F)[C@@H](C)[C@@H]4CC(=O)O)cc3)CC2)ccn1]

Example 47 (4.8 mg): LC-MS Anal. Calc'd for $C_{24}H_{27}F_3N_4O_4$ 492.50, found [M+H] 493.1. $^1$H NMR (500 MHz, 1:1 MeOD:CDCl$_3$) δ ppm 7.76 (d, J=6.4 Hz, 1H), 7.13-7.03 (m, 2H), 6.98-6.88 (m, 2H), 6.52 (dd, J=6.4, 2.0 Hz, 1H), 6.14 (d, J=2.5 Hz, 1H), 4.51 (tt, J=6.9, 3.5 Hz, 1H), 4.42 (d, J=10.4 Hz, 1H), 3.88 (s, 3H), 3.72-3.64 (m, 2H), 3.37 (td, J=8.7, 4.0 Hz, 2H), 3.25 (dd, J=5.9, 4.0 Hz, 1H), 2.76 (dd, J=15.9, 2.5 Hz, 1H), 2.32 (dd, J=15.9, 10.4 Hz, 1H), 2.09-1.98 (m, 2H), 1.92-1.77 (m, 2H), 1.33 (d, J=6.9 Hz, 3H). Analytical HPLC (Analytical LC/MS method, 0% Solvent B start): RT=1.6 min, HI: 99%. hGPR40 EC$_{50}$=1910 nM.

EXAMPLE 48

2-((4S,5S)-1-(4-((1-(3-fluorophenyl)piperidin-4-yl)oxy)phenyl)-4-methyl-3-(trifluoromethyl)-4,5-dihydro-1H-pyrazol-5-yl)acetic acid

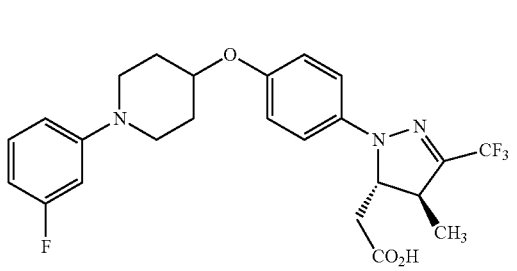 [SMILES: C[C@@H]1C(C(F)(F)F)=NN(c2ccc(OC3CCN(c4cccc(F)c4)CC3)cc2)[C@H]1CC(=O)O]

Example 48 (7.4 mg): LC-MS Anal. Calc'd for $C_{24}H_{25}F_4N_3O_3$ 479.47, found [M+H] 480.1. $^1$H NMR (500 MHz, 1:1 MeOD:CDCl$_3$) δ ppm 7.23-7.16 (m, 1H), 7.10-7.05 (m, 2H), 7.00-6.90 (m, 2H), 6.74 (dd, J=8.2, 2.2 Hz, 1H), 6.65 (dt, J=12.6, 2.1 Hz, 1H), 6.50 (td, J=8.1, 2.2 Hz, 1H), 4.49-4.36 (m, 2H), 3.59-3.45 (m, 2H), 3.24 (dd, J=5.4, 4.0 Hz, 1H), 3.12 (ddd, J=12.4, 8.4, 3.5 Hz, 2H), 2.77 (dd, J=15.9, 3.0 Hz, 1H), 2.34 (dd, J=15.9, 10.4 Hz, 1H), 2.14-2.02 (m, 2H), 1.95-1.81 (m, 2H), 1.33 (d, J=6.9 Hz, 3H). Analytical HPLC (Analytical LC/MS method, 0% Solvent B start): RT=2.1 min, HI: 93%. hGPR40 EC$_{50}$=2272 nM.

EXAMPLE 49

2-((4S,5S)-1-(4-((1-(4-fluorophenyl)piperidin-4-yl)oxy)phenyl)-4-methyl-3-(trifluoromethyl)-4,5-dihydro-1H-pyrazol-5-yl)acetic acid

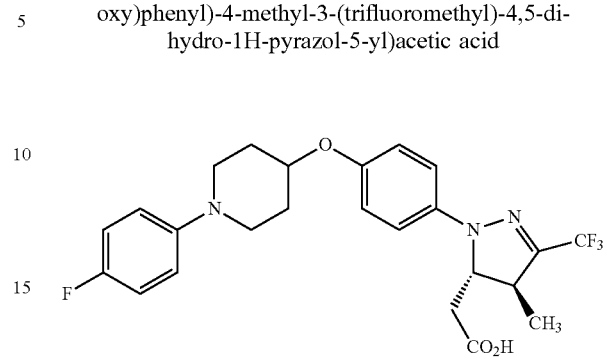

Example 49 (1.8 mg): LC-MS Anal. Calc'd for $C_{24}H_{25}F_4N_3O_3$ 479.47, found [M+H] 480.2. $^1$H NMR (500 MHz, 1:1 MeOD:CDCl$_3$) δ ppm 7.11-7.04 (m, 2H), 7.01-6.88 (m, 6H), 4.45-4.34 (m, 2H), 3.44-3.36 (m, 2H), 3.24 (dd, J=5.4, 4.0 Hz, 1H), 3.06-2.99 (m, 2H), 2.77 (dd, J=15.9, 2.5 Hz, 1H), 2.33 (dd, J=15.9, 10.4 Hz, 1H), 2.15-2.06 (m, 2H), 1.97-1.88 (m, 2H), 1.33 (d, J=6.9 Hz, 3H). Analytical HPLC (Analytical LC/MS method, 0% Solvent B start): RT=1.7 min, HI: 98%. hGPR40 EC$_{50}$=2646 nM.

EXAMPLE 50

2-((4S,5S)-1-(4-((1-(3-chlorophenyl)piperidin-4-yl)oxy)phenyl)-4-methyl-3-(trifluoromethyl)-4,5-dihydro-1H-pyrazol-5-yl)acetic acid

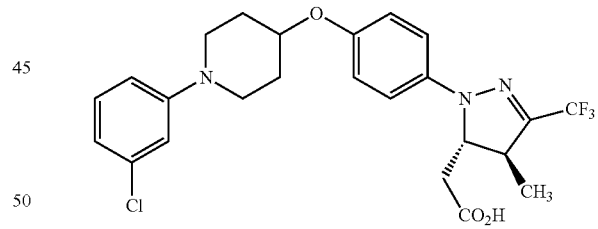

Example 50 (7.4 mg): LC-MS Anal. Calc'd for $C_{24}H_{25}ClF_3N_3O_3$ 495.93, found [M+H] 496.1. $^1$H NMR (500 MHz, 1:1 MeOD:CDCl$_3$) δ ppm 7.17 (t, J=8.2 Hz, 1H), 7.08 (d, J=8.9 Hz, 2H), 6.97-6.91 (m, 3H), 6.87 (dd, J=8.2, 2.2 Hz, 1H), 6.78 (dd, J=7.9, 1.5 Hz, 1H), 4.48-4.39 (m, 2H), 3.58-3.45 (m, 2H), 3.25 (dd, J=5.4, 4.0 Hz, 1H), 3.12 (ddd, J=12.4, 8.4, 3.5 Hz, 2H), 2.77 (dd, J=15.9, 3.0 Hz, 1H), 2.34 (dd, J=16.1, 10.7 Hz, 1H), 2.17-2.04 (m, 2H), 1.97-1.84 (m, 2H), 1.33 (d, J=7.4 Hz, 3H). Analytical HPLC (Analytical LC/MS method, 0% Solvent B start): RT=2.2 min, HI: 97%. hGPR40 EC$_{50}$=2839 nM.

EXAMPLE 51

2-((4S,5S)-1-(4-((1-(4-methoxy-2,6-dimethylphenyl)piperidin-4-yl)oxy)phenyl)-4-methyl-3-(trifluoromethyl)-4,5-dihydro-1H-pyrazol-5-yl)acetic acid

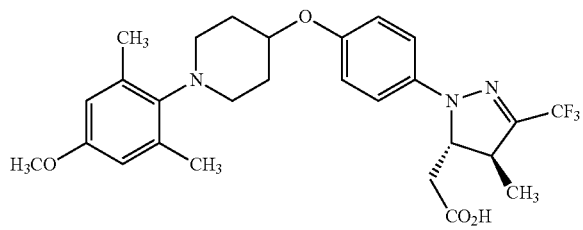 [SMILES: COc1cc(C)c(N2CCC(Oc3ccc(N4N=C(C(F)(F)F)[C@@H](C)[C@@H]4CC(=O)O)cc3)CC2)c(C)c1]

Example 51 (0.9 mg): LC-MS Anal. Calc'd for $C_{27}H_{32}F_3N_3O_4$ 519.56, found [M+H] 520.1. $^1$H NMR (500 MHz, 1:1 MeOD:CDCl$_3$) δ ppm 7.10-7.04 (m, 2H), 6.99-6.93 (m, 2H), 6.60-6.48 (m, 2H), 4.46-4.32 (m, 2H), 3.76-3.72 (m, 3H), 3.28-3.07 (m, 5H), 2.78 (dd, J=16.3, 3.0 Hz, 1H), 2.41-2.36 (m, 1H), 2.36-2.33 (m, 2H), 2.31 (s, 3H), 2.08 (br. s., 3H), 1.87 (br. s., 2H), 1.34 (d, J=6.9 Hz, 3H). Analytical HPLC (Analytical LC/MS method, 0% Solvent B start): RT=2.3 min, HI: 97%. hGPR40 $EC_{50}$=3063 nM.

EXAMPLE 52

2-((4S,5S)-1-(4-((1-(3-fluoro-4-methoxyphenyl)piperidin-4-yl)oxy)phenyl)-4-methyl-3-(trifluoromethyl)-4,5-dihydro-1H-pyrazol-5-yl)acetic acid

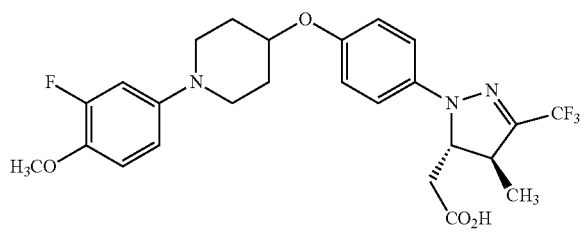 [SMILES: COc1ccc(N2CCC(Oc3ccc(N4N=C(C(F)(F)F)[C@@H](C)[C@@H]4CC(=O)O)cc3)CC2)cc1F]

Example 52 (4.4 mg): LC-MS Anal. Calc'd for $C_{25}H_{27}F_4N_3O_4$ 509.50, found [M+H] 510.1. $^1$H NMR (500 MHz, 1:1 MeOD:CDCl$_3$) δ ppm 7.07 (d, J=8.9 Hz, 2H), 6.97-6.91 (m, 3H), 6.79 (dd, J=14.1, 2.7 Hz, 1H), 6.71 (ddd, J=8.8, 2.8, 1.2 Hz, 1H), 4.45-4.37 (m, 2H), 3.84 (s, 3H), 3.41-3.35 (m, 2H), 3.23 (d, J=3.5 Hz, 1H), 3.05-2.97 (m, 2H), 2.77 (dd, J=16.1, 2.7 Hz, 1H), 2.33 (dd, J=15.9, 10.4 Hz, 1H), 2.14-2.05 (m, 2H), 1.97-1.86 (m, 2H), 1.33 (d, J=6.9 Hz, 3H). Analytical HPLC (Analytical LC/MS method, 0% Solvent B start): RT=1.7 min, HI: 97%. hGPR40 $EC_{50}$=3621 nM.

EXAMPLE 53

2-((4S,5S)-1-(4-((1-(6-methoxypyrazin-2-yl)piperidin-4-yl)oxy)phenyl)-4-methyl-3-(trifluoromethyl)-4,5-dihydro-1H-pyrazol-5-yl)acetic acid

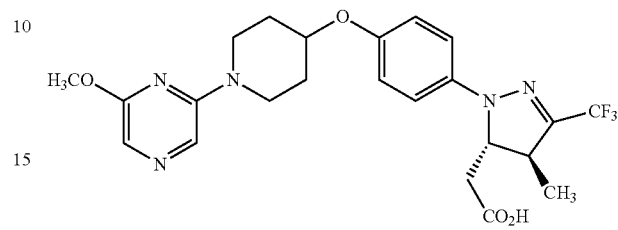

Example 53 (6.5 mg): LC-MS Anal. Calc'd for $C_{23}H_{26}F_3N_5O_4$ 493.48, found [M+H] 494.1. $^1$H NMR (500 MHz, 1:1 MeOD:CDCl$_3$) δ ppm 7.37 (s, 1H), 7.08 (d, J=8.9 Hz, 2H), 7.00-6.90 (m, 2H), 4.53 (td, J=7.2, 3.5 Hz, 1H), 4.43 (d, J=10.4 Hz, 1H), 3.96-3.91 (m, 2H), 3.90 (s, 3H), 3.61-3.48 (m, 3H), 3.25 (br. s., 1H), 2.77 (d, J=15.9 Hz, 1H), 2.34 (dd, J=15.6, 10.7 Hz, 1H), 2.16-2.00 (m, 2H), 1.94-1.76 (m, 2H), 1.33 (d, J=6.9 Hz, 3H). Analytical HPLC (Analytical LC/MS method, 0% Solvent B start): RT=1.9 min, HI: 100%. hGPR40 $EC_{50}$=4204 nM.

EXAMPLE 54

2-((4S,5S)-1-(4-((1-(2-fluoro-6-methoxyphenyl)piperidin-4-yl)oxy)phenyl)-4-methyl-3-(trifluoromethyl)-4,5-dihydro-1H-pyrazol-5-yl)acetic acid

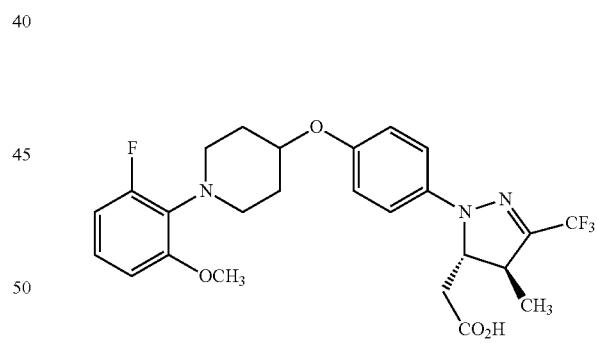

Example 54 (0.5 mg): LC-MS Anal. Calc'd for $C_{25}H_{27}F_4N_3O_4$ 509.50, found [M+H] 510.1. $^1$H NMR (500 MHz, 1:1 MeOD:CDCl$_3$) δ ppm 7.11 (d, J=8.9 Hz, 2H), 6.98 (td, J=8.3, 6.2 Hz, 1H), 6.93 (d, J=8.9 Hz, 2H), 6.73-6.61 (m, 2H), 4.44 (d, J=10.4 Hz, 1H), 4.37-4.28 (m, 3H), 3.86 (s, 3H), 3.31-3.18 (m, 2H), 3.14-3.08 (m, 2H), 2.74 (d, J=12.4 Hz, 1H), 2.24-2.13 (m, 1H), 2.06 (d, J=12.9 Hz, 2H), 1.92-1.81 (m, 2H), 1.31 (d, J=6.9 Hz, 3H). Analytical HPLC (Analytical LC/MS method, 0% Solvent B start): RT=1.8 min, HI: 100%. hGPR40 $EC_{50}$=5896 nM.

EXAMPLE 55

2-((4S,5S)-1-(4-((1-(5-chloropyrazin-2-yl)piperidin-4-yl)oxy)phenyl)-4-methyl-3-(trifluoromethyl)-4,5-dihydro-1H-pyrazol-5-yl)acetic acid

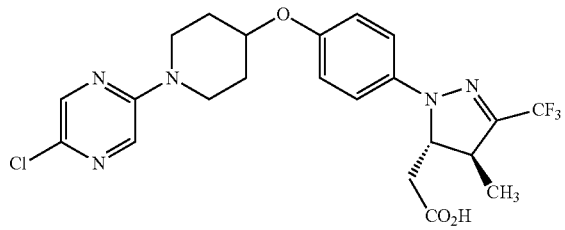 [SMILES: C[C@@H]1C(C(F)(F)F)=NN(c2ccc(OC3CCN(c4cnc(Cl)cn4)CC3)cc2)[C@H]1CC(=O)O]

Example 55 (2.3 mg): LC-MS Anal. Calc'd for $C_{22}H_{23}ClF_3N_5O_3$ 497.90, found [M+H] 498.1. $^1$H NMR (500 MHz, 1:1 MeOD:CDCl$_3$) δ ppm 7.67-7.61 (m, 1H), 7.12-7.05 (m, 2H), 6.94 (d, J=8.9 Hz, 2H), 4.53 (tt, J=6.9, 3.5 Hz, 1H), 4.43 (d, J=10.4 Hz, 1H), 3.94-3.84 (m, 2H), 3.60-3.50 (m, 2H), 3.25 (dd, J=5.4, 4.0 Hz, 2H), 2.77 (dd, J=15.9, 3.0 Hz, 1H), 2.33 (dd, J=15.9, 10.4 Hz, 1H), 2.08-1.97 (m, 2H), 1.91-1.79 (m, 2H), 1.33 (d, J=7.4 Hz, 3H). Analytical HPLC (Analytical LC/MS method, 0% Solvent B start): RT=2.3 min, HI: 98%. hGPR40 EC$_{50}$=6252 nM.

EXAMPLE 56

2-((4S,5S)-1-(4-((1-(4-chlorophenyl)piperidin-4-yl)oxy)phenyl)-4-methyl-3-(trifluoromethyl)-4,5-dihydro-1H-pyrazol-5-yl)acetic acid

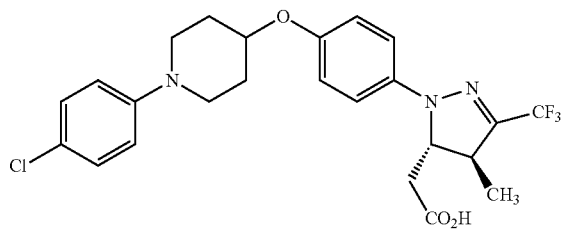 [SMILES: C[C@@H]1C(C(F)(F)F)=NN(c2ccc(OC3CCN(c4ccc(Cl)cc4)CC3)cc2)[C@H]1CC(=O)O]

Example 56 (9 mg). LC-MS Anal. Calc'd for $C_{24}H_{25}ClF_3N_3O_3$ 495.93, found [M+H] 496.1. $^1$H NMR (500 MHz, 1:1 MeOD:CDCl$_3$) δ ppm 7.19 (d, J=8.9 Hz, 2H), 7.07 (d, J=9.4 Hz, 2H), 6.99-6.89 (m, 4H), 4.42 (dt, J=7.3, 3.5 Hz, 2H), 3.50-3.41 (m, 2H), 3.24 (dd, J=5.4, 4.0 Hz, 1H), 3.08 (ddd, J=12.3, 8.5, 3.5 Hz, 2H), 2.77 (dd, J=16.3, 3.0 Hz, 1H), 2.34 (dd, J=15.9, 10.4 Hz, 1H), 2.17-2.02 (m, 2H), 1.98-1.78 (m, 2H), 1.33 (d, J=6.9 Hz, 3H). Analytical HPLC (Analytical LC/MS method, 0% Solvent B start): RT=1.9 min, HI: 94%. hGPR40 EC$_{50}$=6268 nM.

EXAMPLE 57

2-((4S,5S)-1-(4-((3-fluoro-1-(2-fluoro-5-methoxyphenyl)piperidin-4-yl)oxy)phenyl)-4-methyl-3-(trifluoromethyl)-4,5-dihydro-1H-pyrazol-5-yl)acetic acid, HCl (Isomers 1, 2, 3 and 4)

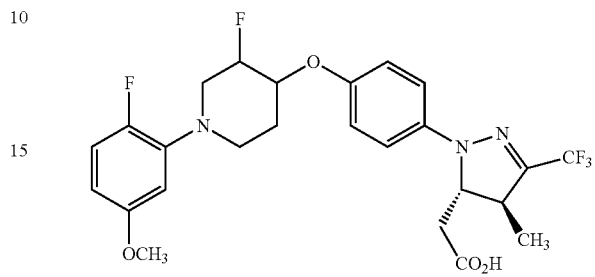

57A. benzyl 4-((trimethylsilyl)oxy)-5,6-dihydropyridine-1(2H)-carboxylate: To a solution of benzyl 4-oxopiperidine-1-carboxylate (1.27 g, 5.44 mmol) in DMF (4 mL) was added chlorotrimethylsilane (0.83 mL, 6.53 mmol) followed by triethylamine (1.52 mL, 10.89 mmol). The resulting heterogeneous mixture was warmed to 80° C. and stirred for 16 h. The cooled mixture was diluted with hexanes (50 mL), wahsed with sat. NaHCO$_3$ (30 mL) and brine (30 mL), then dried over MgSO$_4$, filtered and concentrated to afford benzyl 4-((trimethylsilyl)oxy)-5,6-dihydropyridine-1(2H)-carboxylate (1.5 g, 4.91 mmol, 90% yield) as a clear oil. $^1$H NMR (400 MHz, CDCl$_3$) δ 7.22-7.08 (m, 5H), 4.98-4.94 (m, 2H), 4.60 (br. s., 1H), 3.77 (q, J=2.3 Hz, 2H), 3.42 (t, J=5.6 Hz, 2H), 1.94 (br. s., 2H), 0.04-0.04 (m, 9H).

57B. benzyl 3-fluoro-4-oxopiperidine-1-carboxylate: To a solution of benzyl 4-((trimethylsilyl)oxy)-5,6-dihydropyridine-1(2H)-carboxylate (1.52 g, 4.98 mmol) in acetonitrile (31 mL) at rt was added Selectfluro® (2.1 g, 6.0 mmol) portionwise over 10 min. The mixture was stirred for 2 h, then concentrated to dryness and partitioned between EtOAc and brine. The aqueous layer was extracted with EtOAc and the combined organic phases were washed with brine, dried over MgSO$_4$, filtered and concentrated. Purification via silica chromatography gave benzyl 3-fluoro-4-oxopiperidine-1-carboxylate (1.2 g, 4.78 mmol, 96% yield) as a solid. $^1$H NMR (400 MHz, CDCl$_3$) δ 7.51-7.30 (m, 5H), 5.27-5.16 (m, 2H), 4.97-4.70 (m, 1H), 4.47 (br. s., 1H), 4.33-4.18 (m, 1H), 3.59-3.28 (m, 2H), 2.72-2.41 (m, 2H).

57C. benzyl 3-fluoro-4-hydroxypiperidine-1-carboxylate: To a solution of benzyl 3-fluoro-4-oxopiperidine-1-carboxylate (880 mg, 3.50 mmol) in MeOH (7 mL) was added sodium borohydride (130 mg, 3.50 mmol) slowly. After 1 h, 10% KHSO$_4$ (10 mL) was added slowly to the reaction mixture. The mixture was extracted with EtOAc (2×30 mL), and the combined organic extracts were dried (Na$_2$SO$_4$), filtered, and concentrated. Purification via silica gel chromatography gave benzyl 3-fluoro-4-hydroxypiperidine-1-carboxylate (870 mg, 3.44 mmol, 98% yield). $^1$H NMR (400 MHz, CDCl$_3$) δ ppm 7.47-7.27 (m, 5H), 5.13 (s, 2H), 4.75-4.52 (m, 1H), 4.07-3.68 (m, 3H), 3.61-3.04 (m, 2H), 2.22 (d, J=5.0 Hz, 1H), 1.93-1.63 (m, 2H).

57D. benzyl 4-((tert-butyldimethylsilyl)oxy)-3-fluoropiperidine-1-carboxylate: To a solution of benzyl 3-fluoro-4-hydroxypiperidine-1-carboxylate (410 mg, 1.62 mmol) in DCM (1.62 mL) and triethylamine (670 μl, 4.86 mmol) was added tert-butyldimethylsilyl trifluoromethanesulfonate (390 µl, 1.70 mmol) at 0° C. After 1 h, sat. aq NaHCO$_3$ (10 mL) was added slowly to the reaction mixture. The mixture was extracted with EtOAc (2×30 mL), and the combined organic extracts were dried (Na$_2$SO$_4$), filtered, and concentrated to afford benzyl 4-((tert-butyldimethylsilyl)oxy)-3-fluoropiperidine-1-carboxylate (450 mg, 1.22 mmol, 76% yield). $^1$H NMR (400 MHz, CDCl$_3$) δ ppm 7.36-7.20 (m, 5H), 5.05 (s, 2H), 4.43-4.22 (m, 1H), 4.07-3.96 (m, 1H), 3.88-3.62 (m, 2H), 3.59-3.24 (m, 2H), 1.75-1.50 (m, 2H), 0.84 (s, 9H), 0.02-0.05 (m, 6H).

57E. 4-((tert-butyldimethylsilyl)oxy)-3-fluoropiperidine: A mixture of benzyl 4-((tert-butyldimethylsilyl)oxy)-3-fluoropiperidine-1-carboxylate (440 mg, 1.20 mmol) and Pd on activated carbon (127 mg, 0.120 mmol) in MeOH (12 mL) was purged with H$_2$ for 30 min and stirred under a H$_2$ balloon at rt for 1 h. The mixture was filtered through Celite®, washed with EtOAc (30 mL) and MeOH (30 mL) and concentrated to afford 4-((tert-butyldimethylsilyl)oxy)-3-fluoropiperidine (270 mg, 1.16 mmol, 97% yield) as a clear oil. $^1$H NMR (400 MHz, CDCl$_3$) δ ppm 4.50-4.27 (m, 1H), 3.97-3.77 (m, 1H), 3.19-3.05 (m, 1H), 2.93 (ddd, J=13.1, 6.3, 4.1 Hz, 1H), 2.82-2.65 (m, 2H), 2.62-2.46 (m, 1H), 1.73-1.50 (m, 2H), 0.88 (s, 9H), 0.00 (d, J=3.8 Hz, 6H).

57F. 4-(4-((tert-butyldimethylsilyl)oxy)-3-fluoropiperidin-1-yl)-5-chloro-2-methoxypyridine: A mixture of 4-((tert-butyldimethylsilyl)oxy)-3-fluoropiperidine (194 mg, 0.83 mmol), 4-bromo-5-chloro-2-methoxypyridine (185 mg, 0.83 mmol) and Sphos pre.cat. (6 mg, 8 µmol) in THF (1.7 mL) was purged with argon and lithium bis(trimethylsilyl)amide (1 mL, 1.0 mmol) was added. The reaction mixture was heated at 70° C. for 2 h. Sat. aqueous NaHCO$_3$ (10 mL) was added slowly to the reaction mixture. The mixture was extracted with EtOAc (2×10 mL), and the combined organic extracts were washed with water (20 mL) and brine (20 mL), and dried (Na$_2$SO$_4$), filtered, and concentrated. Purification via silica gel chromatography gave 4-(4-((tert-butyldimethylsilyl)oxy)-3-fluoropiperidin-1-yl)-5-chloro-2-methoxypyridine (182 mg, 0.49 mmol, 58% yield). LC-MS Anal. Calc'd for C$_{17}$H$_{28}$ClFN$_2$O$_2$Si, 374.16, found [M+H] 374.9.

57G. 1-(5-chloro-2-methoxypyridin-4-yl)-3-fluoropiperidin-4-ol: To a mixture of 4-(4-((tert-butyldimethylsilyl)oxy)-3-fluoropiperidin-1-yl)-5-chloro-2-methoxypyridine (192 mg, 0.51 mmol) in THF (1.0 mL) was added TBAF (0.6 mL, 0.61 mmol). The reaction was stirred at 23° C. for 2 h. Sat. aqueous NaHCO$_3$ (10 mL) was added slowly to the reaction mixture. The mixture was extracted with EtOAc (2×10 mL), and the combined organic extracts were washed with water (20 mL) and brine (20 mL), and dried (Na$_2$SO$_4$), filtered, and concentrated. Purification via silica gel chromatography gave 1-(5-chloro-2-methoxypyridin-4-yl)-3-fluoropiperidin-4-ol (110 mg, 0.42 mmol, 82% yield) as a white foam. LC-MS Anal. Calc'd for C$_{11}$H$_{24}$ClFN$_2$O$_2$ 260.07, found [M+H] 261.0.

57H. 3-fluoro-1-(2-fluoro-5-methoxyphenyl)piperidin-4-yl 4-methylbenzenesulfonate: To a solution of 3-fluoro-1-(2-fluoro-5-methoxyphenyl)piperidin-4-ol (74 mg, 0.30 mmol), 4-methylbenzene-1-sulfonyl chloride (290 mg, 1.52 mmol) and N,N-dimethylpyridin-4-amine (4 mg, 0.03 mmol) in DCM (600 µl), pyridine (245 µl, 3.04 mmol) was added dropwise. The reaction mixture was stirred at rt for 20 h. The reaction mixture was diluted with EtOAc and the organic layer was washed successively with H$_2$O and brine. The organic layer was dried and concentrated. Purification by chromatography gave 3-fluoro-1-(2-fluoro-5-methoxyphenyl)piperidin-4-yl 4-methylbenzenesulfonate (waxy solid, 74 mg, 0.19 mmol, 61% yield). LC-MS Anal. Calc'd for C$_{19}$H$_{21}$F$_2$NO$_4$S, 397.12, found [M+H] 398.0.

57I. methyl 2-((4S,5S)-1-(4-((3-fluoro-1-(2-fluoro-5-methoxyphenyl)piperidin-4-yl)oxy)phenyl)-4-methyl-3-(trifluoromethyl)-4,5-dihydro-1H-pyrazol-5-yl)acetate: A solution of 3-fluoro-1-(2-fluoro-5-methoxyphenyl)piperidin-4-yl 4-methylbenzenesulfonate (96 mg, 0.24 mmol), methyl 2-((4S,5S)-1-(4-hydroxyphenyl)-4-methyl-3-(trifluoromethyl)-4,5-dihydro-1H-pyrazol-5-yl)acetate (1J, 80 mg, 0.25 mmol) and cesium carbonate (160 mg, 0.48 mmol) in DMF (0.48 mL) was heated at 60° C. for 48 h. The reaction mixture was diluted with EtOAc (10 mL), and the organic layer was washed with water (10 mL) three times and brine (10 mL). The organic layer was dried (Na$_2$SO$_4$), filtered, and concentrated. Purification by chromatography and RP-Prep HPLC afforded a diastereomeric mixture. The diastereomers were separated by chiral Prep. SFC to provide 4 isomers.

Isomer 1: LC-MS Anal. Calc'd for C$_{26}$H$_{28}$F$_5$N$_3$O$_4$ 541.20, found [M+H] 542.2.

Isomer 2: LC-MS Anal. Calc'd for C$_{26}$H$_{28}$F$_5$N$_3$O$_4$ 541.20, found [M+H] 542.2.

Isomer 3: LC-MS Anal. Calc'd for C$_{26}$H$_{28}$F$_5$N$_3$O$_4$ 541.20, found [M+H] 542.2.

Isomer 3: LC-MS Anal. Calc'd for C$_{26}$H$_{28}$F$_5$N$_3$O$_4$ 541.20, found [M+H] 542.2.

Four isomers of Example 57 were prepared following the procedure for Example 1.

Example 57 (Isomer 1, yellow solid, 0.9 mg): LC-MS Anal. Calc'd for C$_{25}$H$_{26}$F$_5$N$_3$O$_4$ 527.49, found [M+H] 528.1. $^1$H NMR (400 MHz, CD$_3$CN) δ ppm 7.13-7.09 (m, 3H), 7.08-7.01 (m, 2H), 6.95 (dd, J=7.2, 3.1 Hz, 1H), 6.68 (dt, J=9.0, 3.3 Hz, 1H), 5.04-4.84 (m, 1H), 4.58-4.42 (m, 2H), 3.80 (s, 3H), 3.79-3.68 (m, 1H), 3.53-3.43 (m, 2H), 3.40-3.25 (m, 2H), 3.13 (ddd, J=12.3, 9.3, 3.0 Hz, 1H), 2.76 (dd, J=16.4, 3.1 Hz, 1H), 2.53 (dd, J=16.6, 9.5 Hz, 1H), 2.35 (dd, J=8.9, 4.1 Hz, 1H), 1.33 (d, J=7.0 Hz, 3H). Analytical HPLC (Orthogonal method, 30% Solvent B start): RT=11.5 min, HI: 99%. hGPR40 EC$_{50}$=292 nM.

Example 57 (Isomer 2, yellow solid, 1.2 mg): LC-MS Anal. Calc'd for C$_{25}$H$_{26}$F$_5$N$_3$O$_4$ 527.49, found [M+H] 528.1. $^1$H NMR (400 MHz, CD$_3$CN) δ ppm 7.14-7.07 (m, 3H), 7.07-7.02 (m, 2H), 6.99 (dd, J=7.2, 2.9 Hz, 1H), 6.69 (dt, J=9.0, 3.2 Hz, 1H), 5.06-4.87 (m, 1H), 4.58-4.42 (m, 2H), 3.80 (s, 3H), 3.78-3.70 (m, 1H), 3.53-3.45 (m, 1H), 3.42-3.26 (m, 2H), 3.15 (ddd, J=12.3, 9.4, 3.4 Hz, 1H), 2.76 (dd, J=16.4, 3.1 Hz, 1H), 2.52 (dd, J=16.6, 9.5 Hz, 1H), 2.41-2.31 (m, 1H), 2.08-2.01 (m, 1H), 1.33 (d, J=7.0 Hz, 3H). Analytical HPLC (Orthogonal method, 30% Solvent B start): RT=11.4 min, HI: 99%. hGPR40 EC$_{50}$=119 nM.

Example 57 (Isomer 3, yellow solid, 0.9 mg): LC-MS Anal. Calc'd for C$_{25}$H$_{26}$F$_5$N$_3$O$_4$ 527.49, found [M+H] 528.1. $^1$H NMR (400 MHz, CD$_3$CN) δ ppm 7.18-7.00 (m, 6H), 6.78-6.69 (m, 1H), 5.11-4.91 (m, 1H), 4.61-4.50 (m, 1H), 4.50-4.42 (m, 1H), 3.81 (s, 3H), 3.80-3.72 (m, 1H), 3.58-3.48 (m, 1H), 3.36 (dt, J=12.2, 7.6 Hz, 2H), 3.21 (ddd, J=12.3, 9.3, 3.3 Hz, 2H), 2.76 (dd, J=16.6, 3.3 Hz, 1H), 2.53 (dd, J=16.6, 9.5 Hz, 1H), 2.39 (dd, J=9.0, 4.5 Hz, 1H), 2.18-2.04 (m, 1H), 1.33 (d, J=7.0 Hz, 3H). Analytical HPLC (Orthogonal method, 30% Solvent B start): RT=11.6 min, HI: 100%. hGPR40 EC$_{50}$=716 nM.

Example 57 (Isomer 4, yellow solid, 1.2 mg): LC-MS Anal. Calc'd for C$_{25}$H$_{26}$F$_5$N$_3$O$_4$ 527.49, found [M+H] 528.0. $^1$H NMR (400 MHz, CD$_3$CN) δ ppm 7.26-7.20 (m, 1H), 7.19-7.15 (m, 1H), 7.14-7.09 (m, 2H), 7.08-7.02 (m, 2H), 6.83-6.75 (m, 1H), 5.16-4.96 (m, 1H), 4.62-4.53 (m, 1H), 4.51-4.43 (m, 1H), 3.81 (s, 3H), 3.89-3.74 (m, 1H), 3.63-3.53 (m, 1H), 3.48-3.22 (m, 4H), 2.76 (dd, J=16.4, 3.1

Hz, 1H), 2.53 (dd, J=16.6, 9.5 Hz, 1H), 2.42 (td, J=9.3, 4.5 Hz, 1H), 2.20-2.07 (m, 1H), 1.33 (d, J=7.0 Hz, 3H). Analytical HPLC (Orthogonal method, 30% Solvent B start): RT=11.4 min, HI: 97%. hGPR40 EC$_{50}$=66 nM. hGPR40 IP1 EC$_{50}$=11 nM.

EXAMPLE 58

2-((4S,5S)-1-(4-((1-(3-chloropyridin-2-yl)piperidin-4-yl)oxy)phenyl)-4-methyl-3-(trifluoromethyl)-4,5-dihydro-1H-pyrazol-5-yl)acetic acid, HCl

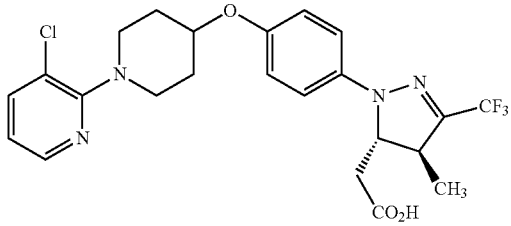 [SMILES: C[C@@H]1C(C(F)(F)F)=NN(c2ccc(OC3CCN(c4ncccc4Cl)CC3)cc2)[C@H]1CC(=O)O]

58A. methyl 2-((4S,5S)-1-(4-((1-(3-chloropyridin-2-yl)piperidin-4-yl)oxy)phenyl)-4-methyl-3-(trifluoromethyl)-4,5-dihydro-1H-pyrazol-5-yl)acetate: To a stirred solution of triphenylphosphine (43 mg, 0.16 mmol) and (E)-diethyl diazene-1,2-dicarboxylate (22 μl, 0.14 mmol) in THF (118 μl) at rt was added methyl 2-((4S,5S)-1-(4-hydroxyphenyl)-4-methyl-3-(trifluoromethyl)-4,5-dihydro-1H-pyrazol-5-yl)acetate (37 mg, 0.12 mmol) followed by 1-(3-chloropyridin-2-yl)piperidin-4-ol (synthesized following the procedure for Example 32 (25 mg, 0.12 mmol). The reaction mixture was stirred at 50° C. for 30 min. The solvent was evaporated and the residue was purified. Purification by chromatography gave methyl 2-((4S,5S)-1-(4-((1-(3-chloropyridin-2-yl)piperidin-4-yl)oxy)phenyl)-4-methyl-3-(trifluoromethyl)-4,5-dihydro-1H-pyrazol-5-yl)acetate (54 mg, 0.11 mmol, 90% yield). LC-MS Anal. Calc'd for C$_{24}$H$_{26}$ClF$_3$N$_4$O$_3$ 510.17, found [M+H] 511.1.

Example 58 (yellow oil, 9.5 mg) was prepared following the procedure for Example 32. LC-MS Anal. Calc'd for C$_{23}$H$_{24}$ClF$_3$N$_4$O$_3$ 496.15, found [M+H] 497.0. $^1$H NMR (400 MHz, CD$_3$CN) δ ppm 8.26-8.10 (m, 2H), 7.19 (dd, J=7.8, 6.3 Hz, 1H), 7.10 (d, J=9.0 Hz, 2H), 7.04-6.94 (m, 2H), 4.63 (dt, J=6.8, 3.4 Hz, 1H), 4.51-4.39 (m, 1H), 4.01-3.85 (m, 2H), 3.81-3.58 (m, 2H), 3.35 (dd, J=5.5, 4.5 Hz, 1H), 2.76 (dd, J=16.4, 3.1 Hz, 1H), 2.52 (dd, J=16.3, 9.5 Hz, 1H), 2.26-2.11 (m, 2H), 2.08-2.01 (m, 2H), 1.32 (d, J=7.0 Hz, 3H). Analytical HPLC (Orthogonal method, 30% Solvent B start): RT=12.4 min, HI: 99%. hGPR40 EC$_{50}$=293 nM.

Example 59 to Example 64 were prepared following the procedure for Example 58.

EXAMPLE 59

2-((4S,5S)-1-(4-((1-(2-chloro-5-fluorophenyl)piperidin-4-yl)oxy)phenyl)-4-methyl-3-(trifluoromethyl)-4,5-dihydro-1H-pyrazol-5-yl)acetic acid, HCl

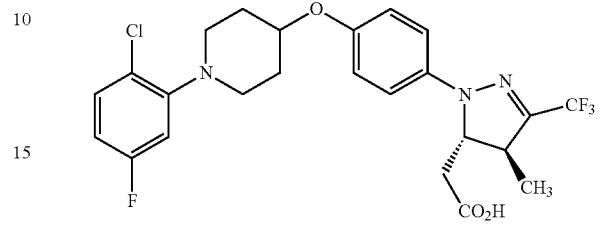

Example 59 (white foam, 7 mg): LC-MS Anal. Calc'd for C$_{24}$H$_{24}$ClF$_4$N$_3$O$_3$ 513.14, found [M+H] 514.0. $^1$H NMR (400 MHz, CD$_3$CN) δ ppm 7.85 (br. s., 1H), 7.57 (dd, J=8.9, 5.6 Hz, 1H), 7.18-7.08 (m, 3H), 7.05-6.99 (m, 2H), 4.64 (br. s., 1H), 4.50-4.41 (m, 1H), 3.85 (br. s., 2H), 3.46-3.28 (m, 3H), 2.75 (dd, J=16.6, 2.5 Hz, 1H), 2.62-2.39 (m, 3H), 2.16 (d, J=9.3 Hz, 2H), 1.33 (d, J=7.0 Hz, 3H). Analytical HPLC (Orthogonal method, 50% Solvent B start): RT=10.2 min, HI: 100%. hGPR40 EC$_{50}$=361 nM.

EXAMPLE 60

2-((4S,5S)-1-(4-((1-(2-chloro-5-methylphenyl)piperidin-4-yl)oxy)phenyl)-4-methyl-3-(trifluoromethyl)-4,5-dihydro-1H-pyrazol-5-yl)acetic acid, HCl

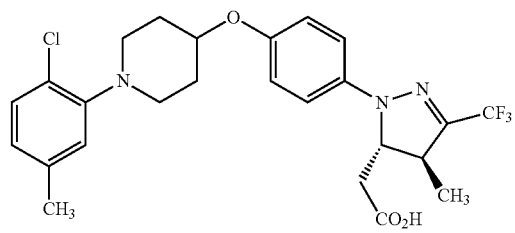 [SMILES: Cc1ccc(Cl)c(N2CCC(Oc3ccc(N4N=C(C(F)(F)F)[C@@H](C)[C@@H]4CC(=O)O)cc3)CC2)c1]

Example 60 (clear oil, 6 mg): LC-MS Anal. Calc'd for C$_{25}$H$_{27}$ClF$_3$N$_3$O$_3$ 509.17, found [M+H] 510.0. $^1$H NMR (400 MHz, CD$_3$CN) δ ppm 8.21 (br. s., 1H), 7.52 (d, J=8.3 Hz, 1H), 7.36 (d, J=8.3 Hz, 1H), 7.16-7.10 (m, 2H), 7.08-7.02 (m, 2H), 4.74 (br. s., 1H), 4.51-4.41 (m, 1H), 4.15 (br. s., 2H), 3.63 (br. s., 2H), 3.42-3.31 (m, 1H), 2.81-2.65 (m, 3H), 2.53 (dd, J=16.6, 9.5 Hz, 1H), 2.42 (s, 3H), 2.32 (d, J=13.3 Hz, 2H), 1.33 (d, J=7.0 Hz, 3H). Analytical HPLC (Orthogonal method, 30% Solvent B start): RT=11.7 min, HI: 99%. hGPR40 EC$_{50}$=364 nM.

EXAMPLE 61

2-((4S,5S)-1-(4-((1-(3-fluoro-6-methylpyridin-2-yl)piperidin-4-yl)oxy)phenyl)-4-methyl-3-(trifluoromethyl)-4,5-dihydro-1H-pyrazol-5-yl)acetic acid, HCl

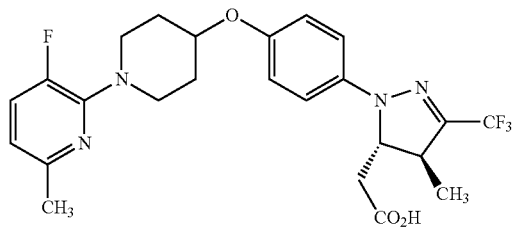 [SMILES: Cc1ccc(F)c(N2CCC(Oc3ccc(N4N=C(C(F)(F)F)[C@@H](C)[C@@H]4CC(=O)O)cc3)CC2)n1]

Example 61 (yellow solid, 35 mg): LC-MS Anal. Calc'd for $C_{24}H_{26}F_4N_4O_3$ 494.19, found [M+H] 495.1. $^1$H NMR (400 MHz, CD$_3$CN) δ ppm 7.71 (dd, J=13.1, 8.3 Hz, 1H), 7.14-7.06 (m, 2H), 7.02-6.93 (m, 2H), 6.80 (dd, J=8.2, 3.4 Hz, 1H), 4.67-4.55 (m, 1H), 4.49-4.40 (m, 1H), 4.08-3.94 (m, 2H), 3.84-3.68 (m, 2H), 3.46-3.29 (m, 1H), 2.76 (dd, J=16.4, 3.1 Hz, 1H), 2.69 (s, 3H), 2.51 (dd, J=16.3, 9.5 Hz, 1H), 2.27-2.11 (m, 2H), 2.02-1.83 (m, 2H), 1.32 (d, J=7.0 Hz, 3H). Analytical HPLC (Orthogonal method, 30% Solvent B start): RT=7.6 min, HI: 99%. hGPR40 EC$_{50}$=366 nM.

EXAMPLE 62

2-((4S,5S)-1-(4-((1-(2-chloro-4-fluorophenyl)piperidin-4-yl)oxy)phenyl)-4-methyl-3-(trifluoromethyl)-4,5-dihydro-1H-pyrazol-5-yl)acetic acid, HCl

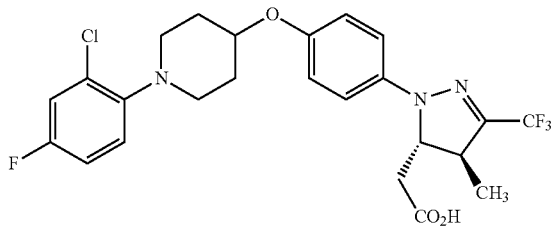 [SMILES: C[C@@H]1C(C(F)(F)F)=NN(c2ccc(OC3CCN(c4ccc(F)cc4Cl)CC3)cc2)[C@H]1CC(=O)O]

Example 62 (white foam, 3 mg): LC-MS Anal. Calc'd for $C_{24}H_{24}ClF_4N_3O_3$ 513.14, found [M+H] 514.0. $^1$H NMR (400 MHz, CD$_3$CN) δ ppm 8.08 (d, J=4.5 Hz, 1H), 7.42-7.36 (m, 1H), 7.30 (dd, J=12.2, 8.9 Hz, 1H), 7.16-7.08 (m, 2H), 7.05-6.98 (m, 2H), 4.68-4.60 (m, 1H), 4.50-4.42 (m, 1H), 3.81-3.69 (m, 2H), 3.46-3.32 (m, 3H), 2.81-2.67 (m, 1H), 2.58-2.42 (m, 2H), 2.19 (br. s., 1H), 1.98-1.92 (m, 2H), 1.33 (d, J=7.0 Hz, 3H). Analytical HPLC (Orthogonal method (column 2), 50% Solvent B start): RT=10.0 min, HI: 97%. hGPR40 EC$_{50}$=382 nM.

EXAMPLE 63

2-((4S,5S)-1-(4-((1-(4-chloro-2-fluorophenyl)piperidin-4-yl)oxy)phenyl)-4-methyl-3-(trifluoromethyl)-4,5-dihydro-1H-pyrazol-5-yl)acetic acid, HCl

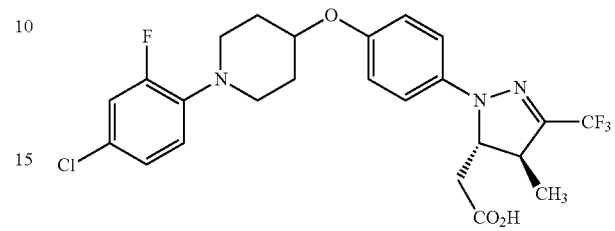

Example 63 (white foam, 15 mg): LC-MS Anal. Calc'd for $C_{24}H_{24}ClF_4N_3O_3$ 513.14, found [M+H] 514.0. $^1$H NMR (400 MHz, CD$_3$CN) δ ppm 8.42 (dd, J=6.7, 2.6 Hz, 1H), 7.58-7.48 (m, 1H), 7.38 (dd, J=12.0, 9.0 Hz, 1H), 7.16-7.09 (m, 2H), 7.07-6.99 (m, 2H), 4.75-4.66 (m, 1H), 4.51-4.36 (m, 1H), 3.97-3.82 (m, 2H), 3.62-3.48 (m, 2H), 3.44-3.28 (m, 1H), 2.76 (dd, J=16.4, 3.1 Hz, 1H), 2.66-2.47 (m, 3H), 2.36-2.22 (m, 2H), 1.33 (d, J=7.0 Hz, 3H). Analytical HPLC (Orthogonal method (column 2), 50% Solvent B start): RT=6.8 min, HI: 99%. hGPR40 EC$_{50}$=398 nM.

EXAMPLE 64

2-((4S,5S)-1-(4-((1-(5-chloro-2-fluorophenyl)piperidin-4-yl)oxy)phenyl)-4-methyl-3-(trifluoromethyl)-4,5-dihydro-1H-pyrazol-5-yl)acetic acid, HCl

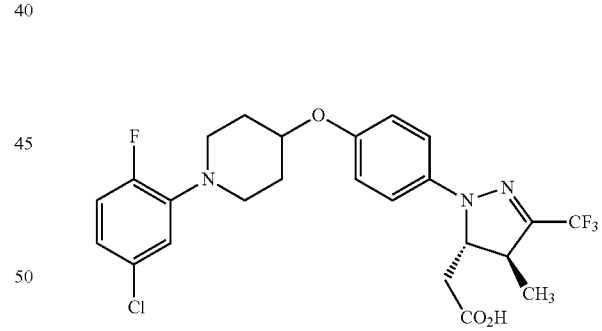

Example 64 (white foam, 9 mg): LC-MS Anal. Calc'd for $C_{24}H_{24}ClF_4N_3O_3$ 513.14, found [M+H] 514.0. $^1$H NMR (400 MHz, CD$_3$CN) δ ppm 7.98 (d, J=8.3 Hz, 1H), 7.60 (dd, J=9.0, 5.5 Hz, 1H), 7.24-7.17 (m, 1H), 7.15-7.09 (m, 2H), 7.06-7.00 (m, 2H), 4.73-4.63 (m, 1H), 4.51-4.40 (m, 1H), 4.04-3.90 (m, 2H), 3.56-3.43 (m, 2H), 3.41-3.30 (m, 1H), 2.76 (dd, J=16.4, 3.1 Hz, 1H), 2.62-2.47 (m, 3H), 2.31-2.18 (m, 2H), 1.33 (d, J=7.3 Hz, 3H). Analytical HPLC (Orthogonal method, 50% Solvent B start): RT=13.3 min, HI: 98%. hGPR40 EC$_{50}$=512 nM.

EXAMPLE 65

2-((4S,5S)-1-(4-((1-(5-ethyl-2-fluorophenyl)piperidin-4-yl)oxy)phenyl)-4-methyl-3-(trifluoromethyl)-4,5-dihydro-1H-pyrazol-5-yl)acetic acid, HCl

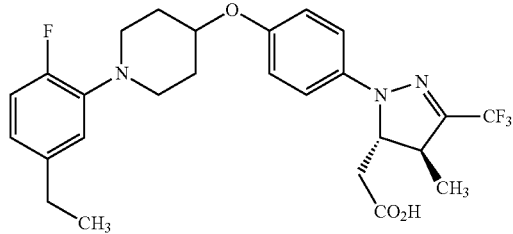 [SMILES: CCc1ccc(F)c(N2CCC(Oc3ccc(N4N=C(C(F)(F)F)[C@@H](C)[C@@H]4CC(=O)O)cc3)CC2)c1]

Example 65 (grey solid, 26 mg) was prepared following the procedure for Example 32. LC-MS Anal. Calc'd for $C_{26}H_{29}F_4N_3O_3$ 507.22, found [M+H] 508.1. $^1$H NMR (400 MHz, $CD_3CN$) δ ppm 8.23 (dd, J=7.4, 1.9 Hz, 1H), 7.45-7.38 (m, 1H), 7.30 (dd, J=12.5, 8.5 Hz, 1H), 7.15-7.07 (m, 2H), 7.06-6.99 (m, 2H), 4.72 (br. s., 1H), 4.51-4.41 (m, 1H), 3.94 (br. s., 2H), 3.61 (br. s., 2H), 3.45-3.31 (m, 1H), 2.81-2.61 (m, 4H), 2.52 (dd, J=16.4, 9.7 Hz, 2H), 2.33 (br. s., 2H), 1.32 (d, J=7.3 Hz, 3H), 1.25 (t, J=7.7 Hz, 3H). Analytical HPLC (Orthogonal method, 10% Solvent B start): RT=13.5 min, HI: 100%. hGPR40 $EC_{50}$=583 nM. hGPR40 IP1 $EC_{50}$=297 nM.

EXAMPLE 66

2-((4S,5S)-1-(4-((1-(2-fluoro-5-isopropylphenyl)piperidin-4-yl)oxy)phenyl)-4-methyl-3-(trifluoromethyl)-4,5-dihydro-1H-pyrazol-5-yl)acetic acid, HCl

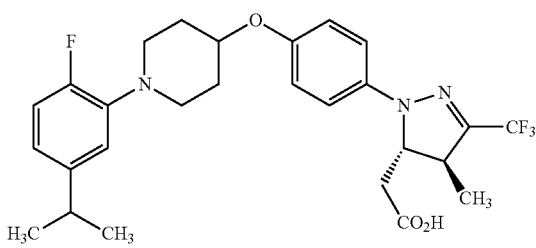

Example 66 (grey solid, 10 mg) was prepared following the procedure for Example 32. LC-MS Anal. Calc'd for $C_{27}H_{31}F_4N_3O_3$ 521.23, found [M+H] 522.2. $^1$H NMR (400 MHz, $CD_3CN$) δ ppm 8.29 (dd, J=7.3, 1.8 Hz, 1H), 7.47-7.40 (m, 1H), 7.30 (dd, J=12.4, 8.7 Hz, 1H), 7.18-7.10 (m, 2H), 7.07-7.00 (m, 2H), 4.72 (br. s., 1H), 4.53-4.40 (m, 1H), 4.07-3.87 (m, 2H), 3.59 (d, J=11.3 Hz, 2H), 3.44-3.31 (m, 1H), 3.07-2.94 (m, 1H), 2.81-2.58 (m, 3H), 2.52 (dd, J=16.6, 9.5 Hz, 1H), 2.33 (br. s., 2H), 1.33 (d, J=7.3 Hz, 3H), 1.27 (d, J=7.0 Hz, 6H). Analytical HPLC (Orthogonal method, 10% Solvent B start): RT=13.9 min, HI: 100%. hGPR40 $EC_{50}$=600 nM.

EXAMPLE 67

2-((4S,5S)-1-(4-(((1R,4S)-2-(2-fluoro-5-methoxyphenyl)-3-oxo-2-azabicyclo[2.2.1]heptan-5-yl)oxy)phenyl)-4-methyl-3-(trifluoromethyl)-4,5-dihydro-1H-pyrazol-5-yl)acetic acid

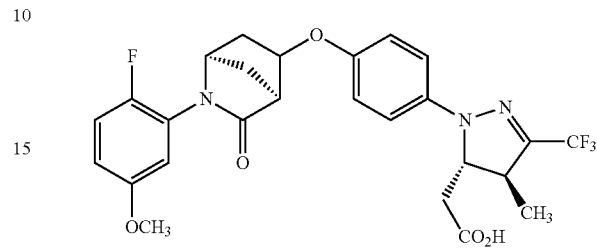

67A. (1R,4S)-2-(2-fluoro-5-methoxyphenyl)-2-azabicyclo[2.2.1]hept-5-en-3-one: To a suspension of 2-bromo-1-fluoro-4-methoxybenzene (1 g, 4.9 mmol) and (1R,4S)-2-azabicyclo[2.2.1]hept-5-en-3-one (0.48 g, 4.4 mmol) in Toluene (9 mL) was added $N_1,N_2$-dimethylethane-1,2-diamine (0.19 mL, 1.8 mmol) and potassium carbonate (1.23 g, 8.9 mmol). The mixture was evacuated and refilled with $N_2$ for three times. copper(I) iodide (0.17 g, 0.89 mmol) was added and the reaction mixture was heated to 100° C. for 20 h. The mixture was filtered through Celite and concentrated. Purification via silica gel chromatography gave (1R,4S)-2-(2-fluoro-5-methoxyphenyl)-2-azabicyclo[2.2.1]hept-5-en-3-one (900 mg, 3.86 mmol, 87% yield). LC-MS Anal. Calc'd for $C_{13}H_{12}FNO_2$ 233.09, found [M+H] 234.1.

67B. (1R,4S)-2-(2-fluoro-5-methoxyphenyl)-5-hydroxy-2-azabicyclo[2.2.1]heptan-3-one: To a solution of (1R,4S)-2-(2-fluoro-5-methoxyphenyl)-2-azabicyclo[2.2.1]hept-5-en-3-one (286 mg, 1.24 mmol) in THF (1.2 mL) and water (1.23 mL) was added diacetoxymercury (469 mg, 1.47 mmol). The reaction mixture was stirred for 16 h at rt. Then, 3M NaOH (1.5 mL, 4.41 mmol) was added, followed by 0.5 M $NaBH_4$ in 3M NaOH (1.5 mL, 0.74 mmol). Then, NaCl was added to the reaction mixture to saturate the water layer. The resulting mixture was then extracted with EtOAc (2×10 mL), and the combined organic extracts were washed with water (20 mL) and brine (20 mL), and dried ($Na_2SO_4$), filtered, and concentrated. Purification by chromatography gave (1R,4S)-2-(2-fluoro-5-methoxyphenyl)-5-hydroxy-2-azabicyclo[2.2.1]heptan-3-one (140 mg, 0.56 mmol, 45% yield). LC-MS Anal. Calc'd for $C_{13}H_{14}FNO_3$ 251.10, found [M+H] 252.1.

Example 67 (clear oil, 1.9 mg) was prepared following the procedure for Example 1. LC-MS Anal. Calc'd for $C_{26}H_{25}F_4N_3O_5$ 535.17, found [M+H] 536.0. $^1$H NMR (400 MHz, $CD_3CN$) δ ppm 7.20-7.07 (m, 3H), 7.05-6.94 (m, 3H), 6.83 (dt, J=9.0, 3.5 Hz, 1H), 4.82 (d, J=6.8 Hz, 1H), 4.50-4.42 (m, 1H), 4.40 (br. s., 1H), 3.80 (s, 3H), 3.42-3.32 (m, 1H), 3.08 (s, 1H), 2.83-2.71 (m, 1H), 2.63-2.47 (m, 1H), 2.36-2.26 (m, 1H), 2.17 (d, J=9.8 Hz, 1H), 1.99 (s, 1H), 1.88 (d, J=13.6 Hz, 1H), 1.33 (d, J=7.0 Hz, 3H). Analytical HPLC (Orthogonal method, 30% Solvent B start): RT=11.9 min, HI: 99%. hGPR40 $EC_{50}$=6411 nM.

EXAMPLE 68

2-((4S,5S)-1-(4-(((1S,4R)-2-(2-fluoro-5-methoxy-phenyl)-3-oxo-2-azabicyclo[2.2.1]heptan-5-yl)oxy)phenyl)-4-methyl-3-(trifluoromethyl)-4,5-dihydro-1H-pyrazol-5-yl)acetic acid

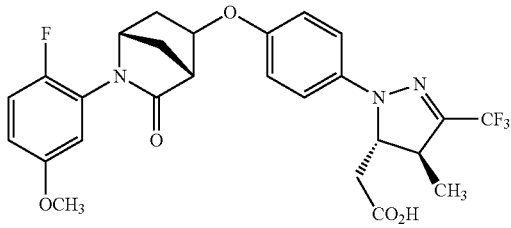 [SMILES: COc1ccc(F)c(N2C(=O)[C@@H]3C[C@H]2CC3Oc2ccc(N3N=C(C(F)(F)F)[C@@H](C)[C@@H]3CC(=O)O)cc2)c1]

Example 68 (waxy solid, 6.7 mg) was prepared following the procedure for Example 67. LC-MS Anal. Calc'd for $C_{26}H_{25}F_4N_3O_5$ 535.17, found [M+H] 536.2. $^1$H NMR (400 MHz, $CD_3CN$) δ ppm 7.19-7.07 (m, 3H), 7.04-6.94 (m, 3H), 6.83 (dt, J=8.9, 3.5 Hz, 1H), 4.81 (d, J=6.5 Hz, 1H), 4.51-4.43 (m, 1H), 4.40 (br. s., 1H), 3.80 (s, 3H), 3.44-3.31 (m, 1H), 3.07 (s, 1H), 2.79-2.72 (m, 1H), 2.64-2.47 (m, 1H), 2.33-2.25 (m, 1H), 2.17 (d, J=9.8 Hz, 1H), 1.99 (s, 1H), 1.92-1.85 (m, 1H), 1.33 (d, J=7.0 Hz, 3H). Analytical HPLC (Orthogonal method, 10% Solvent B start): RT=12.8 min, HI: 97%. hGPR40 $EC_{50}$=5044 nM.

EXAMPLE 69

2-((4S,5S)-1-(4-(((1R,4R)-2-(2-fluoro-5-methoxy-phenyl)-2-azabicyclo[2.2.1]heptan-5-yl)oxy)phenyl)-4-methyl-3-(trifluoromethyl)-4,5-dihydro-1H-pyrazol-5-yl)acetic acid, HCl

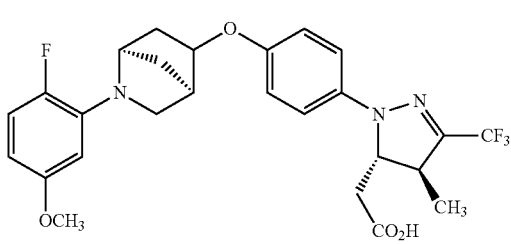 [SMILES: COc1ccc(F)c(N2C[C@H]3C[C@@H]2CC3Oc2ccc(N3N=C(C(F)(F)F)[C@@H](C)[C@@H]3CC(=O)O)cc2)c1]

69A. (1R,4R)-2-(2-fluoro-5-methoxyphenyl)-2-azabicyclo[2.2.1]heptan-5-ol: To a solution of (1R,4S)-2-(2-fluoro-5-methoxyphenyl)-5-hydroxy-2-azabicyclo[2.2.1]heptan-3-one (prepared following the procedure for Example 67) (110 mg, 0.44 mmol) in $LiAlH_4$ in THF (1M, 2.2 mL, 2.2 mmol) at 23° C. was added $LiAlH_4$ in THF (2.2 mL, 2.2 mmol) and the reaction mixture was warmed up to 50° C. and stirred for 1 h. The reaction was monitored by LCMS and desired mass was found. Then, sat. aqueous sodium potassium tartrate (10 mL) was added slowly over 10 min to the reaction mixture at 0° C. The mixture was then extracted with EtOAc (2×30 mL), and the combined organic extracts were dried ($Na_2SO_4$), filtered, and concentrated. Purification via silica gel chromatography gave (1R,4R)-2-(2-fluoro-5-methoxyphenyl)-2-azabicyclo[2.2.1]heptan-5-ol (20 mg, 0.084 mmol, 19.25% yield). LC-MS Anal. Calc'd for $C_{13}H_{16}FNO_2$ 237.12, found [M+H] 238.1.

Example 69 (slight yellow oil, 1.8 mg) was prepared following the procedure for Example 67. LC-MS Anal. Calc'd for $C_{26}H_{27}F_4N_3O_4$ 521.19, found [M+H] 522.1. $^1$H NMR (400 MHz, $CD_3CN$) δ ppm 7.17 (dd, J=12.3, 9.0 Hz, 1H), 7.11-7.05 (m, 2H), 6.96-6.89 (m, 2H), 6.81 (dd, J=6.8, 2.8 Hz, 1H), 6.76-6.69 (m, 1H), 4.55 (d, J=5.8 Hz, 1H), 4.44 (br. s., 2H), 3.82 (s, 3H), 3.81-3.75 (m, 1H), 3.40-3.29 (m, 2H), 2.90 (br. s., 1H), 2.74 (dd, J=16.6, 3.0 Hz, 2H), 2.51 (dd, J=16.3, 9.5 Hz, 2H), 2.18-2.08 (m, 2H), 1.33 (d, J=7.0 Hz, 3H). Analytical HPLC (Orthogonal method (column 2), 10% Solvent B start): RT=11.3 min, HI: 100%. hGPR40 $EC_{50}$=847 nM.

EXAMPLE 70

2-((4S,5S)-1-(4-(((1S,4S)-2-(2-fluoro-5-methoxy-phenyl)-2-azabicyclo[2.2.1]heptan-5-yl)oxy)phenyl)-4-methyl-3-(trifluoromethyl)-4,5-dihydro-1H-pyrazol-5-yl)acetic acid, HCl

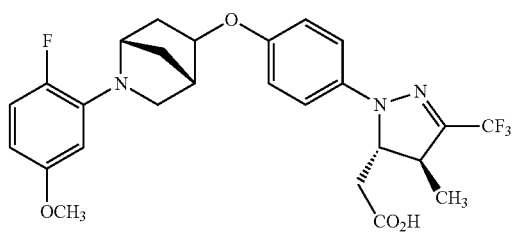 [SMILES: COc1ccc(F)c(N2C[C@@H]3C[C@H]2CC3Oc2ccc(N3N=C(C(F)(F)F)[C@@H](C)[C@@H]3CC(=O)O)cc2)c1]

Example 70 (grey solid, 1.5 mg) was prepared following the procedure for Example 67. LC-MS Anal. Calc'd for $C_{26}H_{27}F_4N_3O_4$ 521.19, found [M+H] 522.2. $^1$H NMR (400 MHz, $CD_3CN$) δ ppm 7.32-7.21 (m, 1H), 7.15-7.06 (m, 2H), 7.01 (dd, J=6.5, 3.0 Hz, 1H), 6.97-6.85 (m, 3H), 4.60 (d, J=6.3 Hz, 1H), 4.50 (br. s., 1H), 4.48-4.41 (m, 1H), 3.84 (s, 3H), 3.81 (dd, J=4.1, 2.1 Hz, 1H), 3.48 (d, J=11.5 Hz, 3H), 3.41-3.28 (m, 1H), 2.79-2.68 (m, 2H), 2.58-2.46 (m, 2H), 2.34-2.14 (m, 1H), 1.85-1.77 (m, 2H), 1.33 (d, J=7.0 Hz, 3H). Analytical HPLC (Orthogonal method (column 2), 10% Solvent B start): RT=12.6 min, HI: 90%. hGPR40 $EC_{50}$=1001 nM.

EXAMPLE 71

2-((4S,5S)-1-(4-((1-(3-ethylphenyl)piperidin-4-yl)oxy)phenyl)-4-methyl-3-(trifluoromethyl)-4,5-dihydro-1H-pyrazol-5-yl)acetic acid, HCl

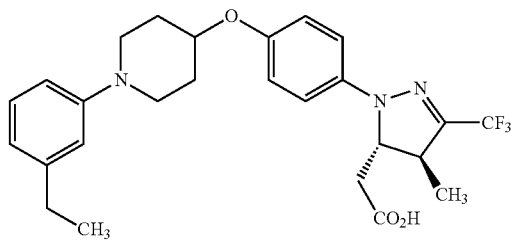 [SMILES: CCc1cccc(N2CCC(Oc3ccc(N4N=C(C(F)(F)F)[C@@H](C)[C@@H]4CC(=O)O)cc3)CC2)c1]

Example 71 (grey solid, 29 mg) was prepared following the procedure for Example 32. LC-MS Anal. Calc'd for $C_{26}H_{30}F_3N_3O_3$ 489.22, found [M+H] 490.0. $^1$H NMR (400 MHz, $CD_3CN$) δ ppm 7.98-7.67 (m, 2H), 7.49 (t, J=7.9 Hz, 1H), 7.40 (d, J=7.5 Hz, 1H), 7.18-7.04 (m, 3H), 4.74 (br. s., 1H), 4.54-4.42 (m, 2H), 3.80 (br. s., 2H), 3.46 (br. s., 2H), 3.38-3.28 (m, 2H), 2.86-2.66 (m, 5H), 2.53 (dd, J=16.6, 9.5 Hz, 2H), 1.33 (d, J=7.0 Hz, 3H), 1.27 (t, J=7.5 Hz, 3H). Analytical HPLC (Orthogonal method (column 2), 10% Solvent B start): RT=10.1 min, HI: 90%. hGPR40 $EC_{50}$=1182 nM. hGPR40 IP1 $EC_{50}$=224 nM.

EXAMPLE 72

2-((4S,5S)-4-methyl-1-(4-((1-phenylpiperidin-4-yl)oxy)phenyl)-3-(trifluoromethyl)-4,5-dihydro-1H-pyrazol-5-yl)acetic acid, HCl

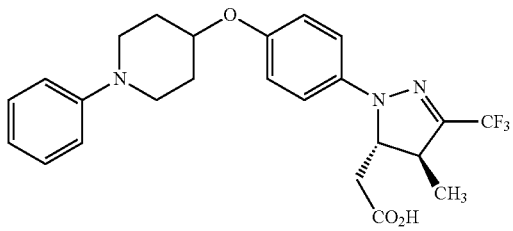 [SMILES: C[C@@H]1C(C(F)(F)F)=NN(c2ccc(OC3CCN(c4ccccc4)CC3)cc2)[C@H]1CC(=O)O]

Example 72 (slightly yellow foam, 46 mg) was prepared following the procedure for Example 58. LC-MS Anal. Calc'd for $C_{24}H_{26}F_3N_3O_3$ 461.48, found [M+H] 462.1. $^1$H NMR (400 MHz, $CD_3CN$) δ ppm 7.95 (d, J=7.3 Hz, 2H), 7.70-7.46 (m, 3H), 7.22-6.94 (m, 4H), 4.72 (br. s., 1H), 4.53-4.39 (m, 1H), 3.78 (br. s., 2H), 3.49 (br. s., 1H), 3.36 (td, J=5.6, 1.3 Hz, 1H), 2.92-2.69 (m, 3H), 2.53 (dd, J=16.6, 9.5 Hz, 3H), 2.23 (br. s., 1H), 1.32 (d, J=7.0 Hz, 3H). Analytical HPLC (Orthogonal method, 30% Solvent B start): RT=6.3 min, HI: 97%. hGPR40 $EC_{50}$=1932 nM.

EXAMPLE 73

2-((4S,5S)-1-(4-((1-(3-isopropylphenyl)piperidin-4-yl)oxy)phenyl)-4-methyl-3-(trifluoromethyl)-4,5-dihydro-1H-pyrazol-5-yl)acetic acid, HCl

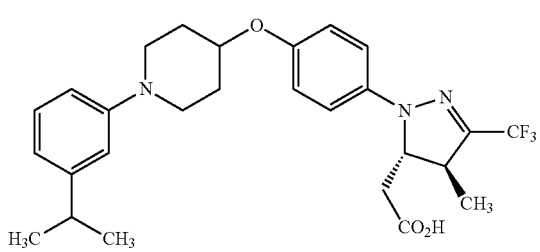 [SMILES: CC(C)c1cccc(N2CCC(Oc3ccc(N4N=C(C(F)(F)F)[C@@H](C)[C@@H]4CC(=O)O)cc3)CC2)c1]

Example 73 (grey solid, 29 mg) was prepared following the procedure for Example 32. LC-MS Anal. Calc'd for $C_{27}H_{32}F_3N_3O_3$ 503.24, found [M+H] 504.1. $^1$H NMR (400 MHz, $CD_3CN$) δ ppm 7.84 (s, 1H), 7.74 (d, J=8.0 Hz, 1H), 7.54-7.47 (m, 1H), 7.46-7.40 (m, 1H), 7.17-7.10 (m, 2H), 7.06 (br. s., 2H), 4.72 (br. s., 1H), 4.53-4.38 (m, 1H), 3.77 (d, J=7.3 Hz, 2H), 3.48 (br. s., 2H), 3.36 (td, J=5.7, 1.4 Hz, 1H), 3.11-2.96 (m, 1H), 2.76 (dd, J=16.4, 3.1 Hz, 2H), 2.52 (dd, J=16.6, 9.5 Hz, 2H), 2.33-2.15 (m, 2H), 1.32 (d, J=7.0 Hz, 3H), 1.29 (d, J=7.0 Hz, 6H). Analytical HPLC (Orthogonal method, 10% Solvent B start): RT=9.5 min, HI: 100%. hGPR40 $EC_{50}$=2121 nM.

EXAMPLE 74

2-((4S,5S)-4-methyl-1-(4-((1-(pyridin-2-yl)piperidin-4-yl)oxy)phenyl)-3-(trifluoromethyl)-4,5-dihydro-1H-pyrazol-5-yl)acetic acid, HCl

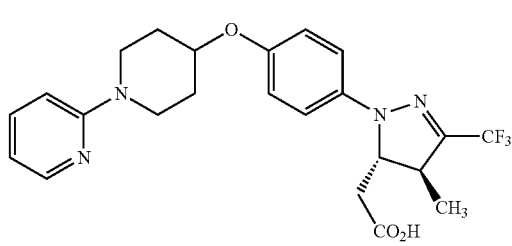 [SMILES: C[C@@H]1C(C(F)(F)F)=NN(c2ccc(OC3CCN(c4ccccn4)CC3)cc2)[C@H]1CC(=O)O]

Example 74 (clear oil, 2.5 mg) was prepared following the procedure for Example 58. LC-MS Anal. Calc'd for $C_{23}H_{25}F_3N_4O_3$ 462.19, found [M+H] 462.9. $^1$H NMR (400 MHz, $CD_3CN$) δ ppm 8.03-7.88 (m, 1H), 7.20 (d, J=9.3 Hz, 1H), 7.14-7.07 (m, 2H), 7.04-6.96 (m, 2H), 6.90 (t, J=6.7 Hz, 1H), 4.64 (tt, J=6.7, 3.5 Hz, 1H), 4.51-4.40 (m, 1H), 4.14-3.98 (m, 2H), 3.81 (ddd, J=13.7, 7.3, 3.8 Hz, 2H), 3.41-3.29 (m, 2H), 2.76 (dd, J=16.4, 3.1 Hz, 1H), 2.52 (dd, J=16.4, 9.4 Hz, 1H), 2.22-2.04 (m, 2H), 1.94-1.84 (m, 2H), 1.33 (d, J=7.0 Hz, 3H). Analytical HPLC (Orthogonal method, 30% Solvent B start): RT=4.9 min, HI: 99%. hGPR40 $EC_{50}$=2606 nM.

EXAMPLE 75

2-((4S,5S)-4-methyl-1-(4-((1-(pyridin-3-yl)piperidin-4-yl)oxy)phenyl)-3-(trifluoromethyl)-4,5-dihydro-1H-pyrazol-5-yl)acetic acid, HCl

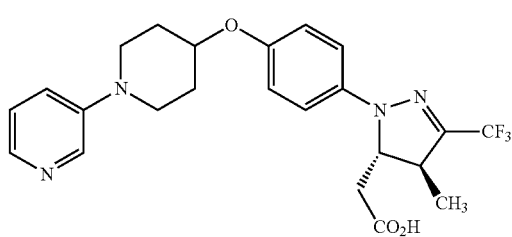 [SMILES: C[C@@H]1C(C(F)(F)F)=NN(c2ccc(OC3CCN(c4cccnc4)CC3)cc2)[C@H]1CC(=O)O]

Example 75 (clear oil, 2.2 mg) was prepared following the procedure for Example 58. LC-MS Anal. Calc'd for $C_{23}H_{25}F_3N_4O_3$ 462.19, found [M+H] 463.1. $^1$H NMR (400 MHz, $CD_3CN$) δ ppm 8.21 (d, J=2.8 Hz, 1H), 8.02-7.92 (m, 2H), 7.76 (dd, J=9.0, 5.5 Hz, 1H), 7.16-7.07 (m, 2H), 7.02-6.94 (m, 2H), 4.65-4.52 (m, 1H), 4.51-4.39 (m, 1H), 3.79-3.66 (m, 2H), 3.49-3.32 (m, 3H), 2.75 (dd, J=16.4, 3.1 Hz, 2H), 2.52 (dd, J=16.4, 9.7 Hz, 2H), 2.14-2.06 (m, 1H), 1.90-1.80 (m, 1H), 1.33 (d, J=7.0 Hz, 3H). Analytical HPLC (Orthogonal method, 30% Solvent B start): RT=5.0 min, HI: 100%. hGPR40 $EC_{50}$=7680 nM.

EXAMPLE 76

2-((4S,5S)-1-(4-((1-(3-chloro-6-methoxypyridin-2-yl)piperidin-4-yl)oxy)phenyl)-4-methyl-3-(trifluoromethyl)-4,5-dihydro-1H-pyrazol-5-yl)acetic acid, HCl

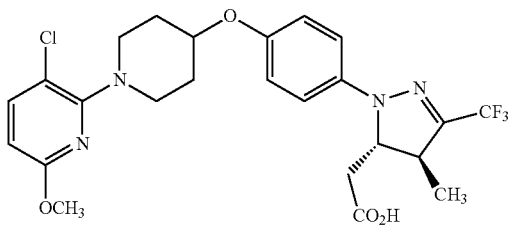 [SMILES: COc1ccc(Cl)c(N2CCC(Oc3ccc(N4N=C(C(F)(F)F)[C@@H](C)[C@@H]4CC(=O)O)cc3)CC2)n1]

Example 76 (yellow solid, 12 mg) was prepared following the procedure for Example 58. LC-MS Anal. Calc'd for $C_{24}H_{26}ClF_3N_4O_4$ 526.16, found [M+H] 527.0. $^1$H NMR (400 MHz, $CD_3CN$) δ ppm 7.88 (d, J=8.5 Hz, 1H), 7.14-7.08 (m, 2H), 7.06-6.99 (m, 2H), 6.94 (d, J=8.8 Hz, 1H), 6.28 (br. s., 1H), 4.69 (dt, J=6.0, 2.9 Hz, 1H), 4.50-4.40 (m, 1H), 4.00 (s, 3H), 3.98-3.90 (m, 2H), 3.76-3.62 (m, 2H), 3.45-3.28 (m, 1H), 2.76 (dd, J=16.6, 3.0 Hz, 1H), 2.65-2.47 (m, 3H), 2.36-2.25 (m, 2H), 1.33 (d, J=7.0 Hz, 3H). Analytical HPLC (Orthogonal method, 40% Solvent B start): RT=11.8 min, HI: 100%. hGPR40 $EC_{50}$=649 nM.

EXAMPLE 77

2-((4S,5S)-1-(4-((1-(5-chloro-2-methoxypyridin-4-yl)piperidin-4-yl)oxy)phenyl)-4-methyl-3-(trifluoromethyl)-4,5-dihydro-1H-pyrazol-5-yl)acetic acid, HCl

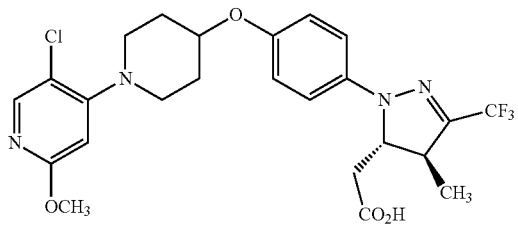 [SMILES: COc1cc(N2CCC(Oc3ccc(N4N=C(C(F)(F)F)[C@@H](C)[C@@H]4CC(=O)O)cc3)CC2)c(Cl)cn1]

Example 77 (white solid, 4 mg) was prepared following the procedure for Example 81 (Isomer 2). LC-MS Anal. Calc'd for $C_{24}H_{26}ClF_3N_4O_4$ 526.16, found [M+H] 526.8. $^1$H NMR (400 MHz, $CD_3CN$) δ ppm 7.97 (s, 1H), 7.11 (d, J=9.0 Hz, 2H), 7.04-6.96 (m, 2H), 6.49 (s, 1H), 4.67-4.58 (m, 1H), 4.51-4.42 (m, 1H), 4.10 (s, 3H), 3.83 (ddd, J=12.7, 8.5, 3.6 Hz, 3H), 3.61-3.52 (m, 3H), 3.42-3.32 (m, 2H), 2.76 (dd, J=16.4, 3.1 Hz, 1H), 2.52 (dd, J=16.3, 9.5 Hz, 1H), 2.26-2.10 (m, 2H), 1.33 (d, J=7.0 Hz, 3H). Analytical HPLC (Orthogonal method, 40% Solvent B start): RT=11.3 min, HI: 100%. hGPR40 $EC_{50}$=110 nM. hGPR40 IP1 $EC_{50}$=20 nM. Acute oral glucose tolerance: −38% @ 0.3 mg/kg.

EXAMPLE 78

2-((4S,5S)-1-(4-((1-(4-chloro-6-methoxypyridin-2-yl)piperidin-4-yl)oxy)phenyl)-4-methyl-3-(trifluoromethyl)-4,5-dihydro-1H-pyrazol-5-yl)acetic acid, HCl

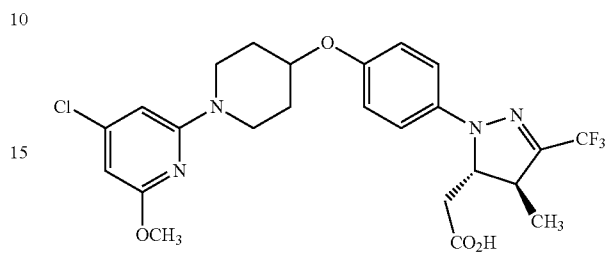

Example 78 (white solid, 1 mg) was prepared following the procedure for Example 58. LC-MS Anal. Calc'd for $C_{24}H_{26}ClF_3N_4O_4$ 526.16, found [M+H] 526.8. $^1$H NMR (400 MHz, $CD_3CN$) δ ppm 8.84 (d, J=2.0 Hz, 1H), 8.28 (d, J=2.3 Hz, 1H), 7.16-7.09 (m, 2H), 7.08-7.02 (m, 2H), 4.70 (br. s., 1H), 4.46 (d, J=9.5 Hz, 1H), 4.12 (s, 3H), 4.03 (d, J=11.8 Hz, 2H), 3.55 (br. s., 2H), 3.37 (br. s., 2H), 2.76 (dd, J=16.4, 3.1 Hz, 2H), 2.62-2.50 (m, 3H), 2.29 (br. s., 3H), 1.33 (d, J=6.8 Hz, 3H). Analytical HPLC (Orthogonal method, 40% Solvent B start): RT=13.6 min, HI: 98%. hGPR40 $EC_{50}$=1990 nM.

EXAMPLE 79

2-((4S,5S)-1-(4-((1-(5-fluoro-2-methoxypyridin-4-yl)piperidin-4-yl)oxy)phenyl)-4-methyl-3-(trifluoromethyl)-4,5-dihydro-1H-pyrazol-5-yl)acetic acid, HCl

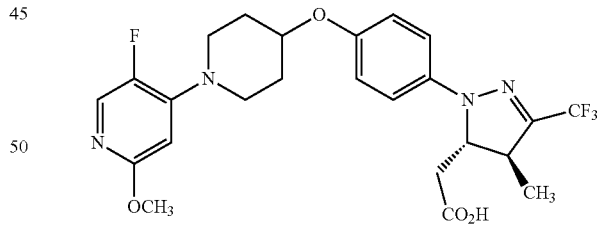

Example 79 (white foam, 5 mg) was prepared following the procedure for Example 58. LC-MS Anal. Calc'd for $C_{24}H_{26}F_4N_4O_4$ 510.19, found [M+H] 511.0. $^1$H NMR (400 MHz, $CD_3CN$) δ ppm 7.83 (d, J=8.3 Hz, 1H), 7.11 (d, J=9.3 Hz, 2H), 7.03-6.96 (m, 2H), 6.36 (d, J=7.3 Hz, 1H), 4.68-4.59 (m, 1H), 4.49-4.42 (m, 1H), 4.08 (s, 3H), 3.99-3.90 (m, 2H), 3.68 (ddd, J=13.7, 7.7, 3.5 Hz, 2H), 3.42-3.32 (m, 1H), 2.76 (dd, J=16.4, 3.1 Hz, 1H), 2.52 (dd, J=16.6, 9.5 Hz, 1H), 2.18-2.08 (m, 2H), 1.94-1.84 (m, 2H), 1.33 (d, J=7.0 Hz, 3H). HPLC (Orthogonal method, 30% Solvent B start): RT=7.6 min, HI: 98%. hGPR40 $EC_{50}$=163 nM. hGPR40 IP1 $EC_{50}$=94 nM.

EXAMPLE 80

2-((4S,5S)-1-(4-((1-(4-fluoro-6-methoxypyridin-2-yl)piperidin-4-yl)oxy)phenyl)-4-methyl-3-(trifluoromethyl)-4,5-dihydro-1H-pyrazol-5-yl)acetic acid, HCl

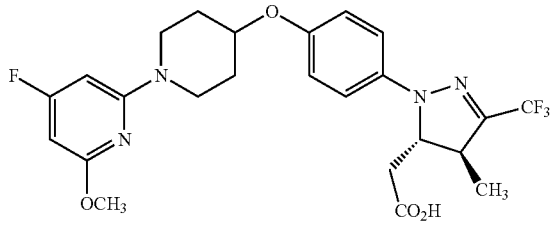 [SMILES: COc1cc(F)cc(N2CCC(Oc3ccc(N4N=C(C(F)(F)F)[C@@H](C)[C@@H]4CC(=O)O)cc3)CC2)n1]

Example 80 (white solid, 9 mg) was prepared following the procedure for Example 58. LC-MS Anal. Calc'd for $C_{24}H_{26}F_4N_4O_4$ 510.19, found [M+H] 511.0. $^1$H NMR (400 MHz, $CD_3CN$) δ ppm 8.72 (dd, J=8.4, 2.9 Hz, 1H), 8.24 (d, J=2.8 Hz, 1H), 7.17-7.08 (m, 2H), 7.08-7.00 (m, 2H), 4.76-4.69 (m, 1H), 4.49-4.43 (m, 1H), 4.12 (s, 3H), 4.09-4.01 (m, 2H), 3.59 (d, J=11.5 Hz, 2H), 3.37 (ddd, J=7.0, 4.3, 1.5 Hz, 2H), 2.76 (dd, J=16.4, 3.1 Hz, 1H), 2.63-2.48 (m, 3H), 2.30 (d, J=13.1 Hz, 2H), 1.36-1.31 (m, 3H). HPLC (Orthogonal method, 40% Solvent B start): RT=12.2 min, HI: 99%. hGPR40 $EC_{50}$=2559 nM.

EXAMPLE 81

2-((4S,5S)-1-(4-((1-(5-chloro-2-methoxypyridin-4-yl)-3-methylpiperidin-4-yl)oxy)phenyl)-4-methyl-3-(trifluoromethyl)-4,5-dihydro-1H-pyrazol-5-yl)acetic acid Isomer 1:

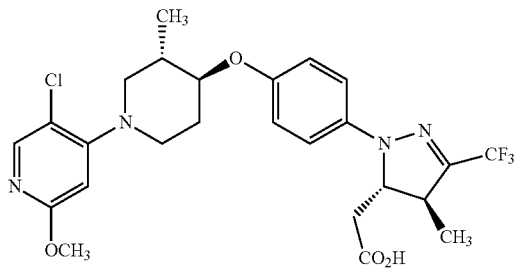

Isomer 2:

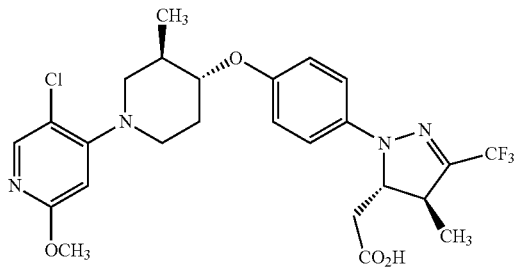 [SMILES: CCOc1cc(N2CC[C@@H](Oc3ccc(N4N=C(C(F)(F)F)[C@@H](C)[C@@H]4CC(=O)O)cc3)[C@H](C)C2)c(Cl)cn1]

81A. 4-bromo-5-chloropyridin-2-amine: To a stirred solution of 4-bromopyridin-2-amine (30 g, 173 mmol) in DMF (350 mL) at −20° C. was added 1-chloropyrrolidine-2,5-dione (24 g, 182 mmol). The reaction mixture was allowed to stir at rt for 24 h. The reaction mixture was poured into a cold solution of 1M NaOH (300 mL) and the mixture was extracted with $Et_2O$ (2×400 mL). The combined extracts were washed with water (3×200 mL), brine (200 mL), dried over $Na_2SO_4$, filtered and concentrated. The crude material was recrystallized from DCM which afforded 4-bromo-5-chloropyridin-2-amine as red solid (22 g, 106 mmol, 61% yield). LC-MS Anal. Calc'd for $C_5H_4BrClN_2$ 205.93, found [M+H] 206.9. $^1$H NMR (400 MHz, $CDCl_3$) δ 8.08 (s, 1H), 6.81 (s, 1H), 4.49 (br. s., 2H).

81B. 4-bromo-5-chloro-2-methoxypyridine: To MeOH (390 mL) was added chlorotrimethylsilane (49 mL, 386 mmol) at 0° C., and the solution was warmed to rt and stirred for 30 min. To the resulting solution was added 4-bromo-5-chloropyridin-2-amine (20 g, 96 mmol), and the mixture was stirred for 15 min. To the reaction mixture was added sodium nitrite (2.7 g, 40 mmol) and the solution was stirred at 50° C. for 3 h. The reaction mixture was evaporated in vacuo, and the residue was diluted with EtOAc. The pH of the aqueous layer was adjusted to pH=~12 via addition of 1 N NaOH, and the solution was extracted 3× with EtOAc. The combined organic layers were concentrated, and the residue was purified via recrystallization from MeOH and $H_2O$ to give 4-bromo-5-chloro-2-methoxypyridine as white crystalline needles (18 g, 81 mmol, 84% yield). LC-MS Anal. Calc'd for $C_6H_5BrClNO$, 220.92, found [M+H] 223.9. $^1$H NMR (400 MHz, $CDCl_3$) δ 8.18 (s, 1H), 7.08 (s, 1H), 3.94 (s, 4H).

81C. rac-1-benzyl-3-cis-methylpiperidin-4-ol: To a solution of 1-benzyl-3-methylpiperidin-4-one (24.8 g, 122 mmol) in THF (102 mL) at −78° C. was added dropwise 1 M solution of L-Selectride (183 mL, 183 mmol) in THF. The reaction was stirred at −78° C. for 1 h 30 min. To this solution were added EtOH (22 mL), water (55 mL) and 1 M NaOH (55 mL). The reaction mixture was warmed to 0° C. and 30% aqueous $H_2O_2$ (55 mL) was added dropwise. The reaction mixture was warmed to rt with stirring for 2 h. The reaction mixture was diluted with EtOAc and the insoluble white solid was filtered. The filtrate was washed with sat. $NaHCO_3$, $H_2O$/brine, brine, dried ($MgSO_4$) and concentrated to give the crude product as an oil. Purification via silica gel chromatography gave rac-(3R,4S)-1-benzyl-3-cis-methylpiperidin-4-ol as a white solid (22.2 g, 88% yield). $^1$H NMR (500 MHz, $CDCl_3$) δ 7.40-7.20 (m, 5H), 3.84 (s, 1H), 3.55 (s, 2H), 2.60-1.73 (m, 7H), 0.97 (d, 3H).

81D. rac-1-benzyl-4-cis-((tert-butyldimethylsilyl)oxy)-3-methylpiperidine: To a solution of rac-1-benzyl-3-cis-methylpiperidin-4-ol (21.9 g, 107 mmol) in $CH_2Cl_2$ (107 mL) and triethylamine (45 mL, 320 mmol) at 0° C. was added tert-butyldimethylsilyl trifluoromethanesulfonate (29 mL, 130 mmol). The reaction mixture was stirred at 0° C. for 1 h. Sat. aqueous $NaHCO_3$ (180 mL) was added slowly to the reaction mixture. The solution was concentrated, diluted with EtOAc, washed with $H_2O$, brine, dried ($MgSO_4$) and concentrated. Purification via silica gel chromatography gave rac-1-benzyl-4-cis-((tert-butyldimethylsilyl)oxy)-3-methylpiperidine as an oil (32 g, 92% yield). LC-MS Anal. Calc'd for $C_{19}H_{33}NOSi$, 319.56, found [M+H] 320.3. $^1$H NMR (400 MHz, $CDCl_3$) δ 7.33-7.19 (m, 5H), 3.73 (d, J=3.3 Hz, 1H), 3.45 (br. s., 2H), 2.44 (br. s., 1H), 2.34 (br. s., 2H), 2.12 (t, J=9.9 Hz, 1H), 1.84-1.50 (m, 3H), 0.92-0.84 (m, 9H), 0.82 (d, J=7.0 Hz, 3H), 0.00 (s, 6H).

81E. rac-cis-4-((tert-butyldimethylsilyl)oxy)-3-methylpiperidine: A mixture of rac-1-benzyl-4-cis-((tert-butyldimethylsilyl)oxy)-3-methylpiperidine (16 g, 49 mmol) and 10% palladium on carbon (3.2 g) in MeOH (500 mL) was stirred at rt under hydrogen atmosphere (1 atm, balloon) for 24 h. The mixture was filtered through celite and the filtrate was concentrated to give rac-4-cis-((tert-butyldimethylsilyl)oxy)-3-methylpiperidine as an oil (11.3 g, 100% yield). $^1$H NMR (500 MHz, CDCl$_3$) δ 3.80 (s, 1H), 2.90 (m, 1H), 2.70-2.50 (m, 4H), 1.60-1.50 (m, 3H), 0.86 (s, 9H), 0.80 (d, 3H), 0.00 (s, 6H).

81F. rac-4-(cis-4-((tert-butyldimethylsilyl)oxy)-3-methylpiperidin-1-yl)-5-chloro-2-methoxypyridine: A mixture of 4-bromo-5-chloro-2-methoxypyridine (9.7 g, 44 mmol), rac-4-cis-((tert-butyldimethylsilyl)oxy)-3-methylpiperidine (10 g, 44 mmol), and K$_2$CO$_3$ (12 g, 87 mmol) in DMSO (15 mL) was vigorously stirred at 110° C. overnight. The reaction mixture was diluted with water and extracted with EtOAc. The organic extract was washed with H$_2$O, brine, dried (MgSO$_4$) and concentrated. Purification via silica gel chromatography gave rac-4-(cis-4-((tert-butyldimethylsilyl)oxy)-3-methylpiperidin-1-yl)-5-chloro-2-methoxypyridine as an oil (14.3 g, 77% yield). LC-MS Anal. Calc'd for C$_{18}$H$_{31}$ClN$_2$O$_2$Si: 370.18, found [M+H] 371.2. $^1$H NMR (400 MHz, CDCl$_3$) δ 7.88 (s, 1H), 6.21 (s, 1H), 3.83-3.79 (m, 4H), 3.19 (dtd, J=11.7, 3.9, 1.8 Hz, 1H), 3.07-2.99 (m, 2H), 2.78 (t, J=11.0 Hz, 1H), 1.93-1.81 (m, 1H), 1.81-1.74 (m, 1H), 1.73-1.63 (m, 1H), 0.89-0.82 (m, 12H), 0.00 (s, 6H).

81G. rac-1-(5-chloro-2-methoxypyridin-4-yl)-3-cis-methylpiperidin-4-ol: To a mixture of rac-4-(cis-4-((tert-butyldimethylsilyl)oxy)-3-methylpiperidin-1-yl)-5-chloro-2-methoxypyridine (10 g, 27 mmol)) in THF (27 mL) was added TBAF (81 mL, 81 mmol). The reaction was stirred at 23° C. for 16 h. To the reaction mixture was slowly added sat. aq NaHCO$_3$ (100 mL) and the resulting mixture was extracted with EtOAc (2×100 mL), and the combined organic extracts were washed with water (50 mL) and brine (50 mL), and dried (Na$_2$SO$_4$), filtered, and concentrated. Purification via silica gel chromatography gave rac-1-(5-chloro-2-methoxypyridin-4-yl)-3-cis-methylpiperidin-4-ol as white foam (7 g, 99% yield). LC-MS Anal. Calc'd for C$_{12}$H$_{17}$ClN$_2$O$_2$:256.10, found [M+H] 257.0. $^1$H NMR (400 MHz, CDCl$_3$) δ 7.98 (s, 1H), 6.30 (s, 1H), 3.99-3.94 (m, 1H), 3.91 (s, 3H), 3.30-3.21 (m, 1H), 3.18-3.09 (m, 2H), 2.93 (dd, J=11.5, 10.0 Hz, 1H), 2.08 (qd, J=6.8, 3.1 Hz, 1H), 2.02-1.87 (m, 2H), 1.42 (d, J=3.8 Hz, 1H), 1.06 (d, J=7.0 Hz, 3H).

81H. methyl 2-((4S,5S)-1-(4-((1-(5-chloro-2-methoxypyridin-4-yl)-3-trans-methylpiperidin-4-yl)oxy)phenyl)-4-methyl-3-(trifluoromethyl)-4,5-dihydro-1H-pyrazol-5-yl) acetate: To a solution of methyl 2-((4S,5S)-1-(4-hydroxyphenyl)-4-methyl-3-(trifluoromethyl)-4,5-dihydro-1H-pyrazol-5-yl)acetate (1J, 111 mg, 0.35 mmol) and rac-1-(5-chloro-2-methoxypyridin-4-yl)-3-cis-methylpiperidin-4-ol (100 mg, 0.39 mmol) in THF (130 μl) was added triphenylphosphine (143 mg, 0.55 mmol). The reaction vessel was then lowered into a sonication bath and sonicated for several minutes (to allow for mixing) giving a clear and highly viscous solution. While sonicating, (E)-diethyl diazene-1,2-dicarboxylate (74 μL, 0.47 mmol) was added dropwise to the reaction mixture, and the reaction mixture was sonicated for 120 min. To the reaction mixture was slowly added sat. aq NaHCO$_3$ (10 mL), and the mixture was extracted with EtOAc (2×10 mL), and the combined organic extracts were washed with water (20 mL) and brine (20 mL), and dried (Na$_2$SO$_4$), filtered, and concentrated. Purification by chromatography gave methyl 2-((4S,5S)-1-(4-((-1-(5-chloro-2-methoxypyridin-4-yl)-3-trans-methylpiperidin-4-yl)oxy)phenyl)-4-methyl-3-(trifluoromethyl)-4,5-dihydro-1H-pyrazol-5-yl)acetate (65 mg, 0.12 mmol, 30% yield) as white foam. LC-MS Anal. Calc'd for C$_{26}$H$_{30}$ClF$_3$N$_4$O$_4$: 554.19, found [M+H] 555.1. $^1$H NMR (400 MHz, CDCl$_3$) δ 8.00 (s, 1H), 7.11-7.04 (m, 2H), 6.98-6.89 (m, 2H), 6.29 (s, 1H), 4.41 (d, J=10.1 Hz, 1H), 3.91 (s, 3H), 3.77-3.71 (m, 4H), 3.54 (dd, J=12.0, 2.4 Hz, 2H), 3.28-3.17 (m, 1H), 2.94-2.64 (m, 3H), 2.43 (dd, J=16.0, 10.2 Hz, 1H), 2.20 (dd, J=8.8, 3.8 Hz, 2H), 1.92-1.77 (m, 1H), 1.36 (d, J=7.1 Hz, 3H), 1.19-1.13 (m, 3H).

Example 81 (Isomers 1 and 2): To a stirred solution of methyl 2-((4S,5S)-1-(4-((1-(5-chloro-2-methoxypyridin-4-yl)-3-methylpiperidin-4-yl)oxy)phenyl)-4-methyl-3-(trifluoromethyl)-4,5-dihydro-1H-pyrazol-5-yl)acetate (65 mg, 0.12 mmol) in THF (0.53 mL) and water (53 μL) at rt was added 1N LiOH solution (350 μL, 0.35 mmol). The reaction mixture was stirred at rt for 1 h. The reaction mixture was cooled to 0° C. and a solution of 3N HCl (0.4 mL) was added. The reaction mixture was warmed to rt. The solvent was evaporated and the residue was disolved in CH$_3$CN, filtered. Purification by RP-Prep HPLC afforded a diastereomeric mixture. The diastereomers were separated by chiral Prep. SFC. Product-containing fractions were evaporated and the residue was dissolved in DCM and was treated with 3N HCl (3 mL). The resulting mixture was concentrated to provide Example 81, Isomer 1 and Isomer 2 as single stereoisomers. Example 81, Isomer 1 (white foam, 20 mg) LC-MS Anal. Calc'd for C$_{25}$H$_{28}$ClF$_3$N$_4$O$_4$ 540.18, found [M+H] 541.0. $^1$H NMR (400 MHz, CD$_3$CN) δ ppm 8.02-7.92 (m, 1H), 7.18-7.05 (m, 2H), 7.03-6.92 (m, 2H), 6.48 (s, 1H), 4.51-4.40 (m, 1H), 4.25 (br.s, 1H), 4.16 (td, J=8.5, 4.0 Hz, 1H), 4.11 (s, 3H), 3.99 (dd, J=13.2, 3.6 Hz, 2H), 3.43-3.32 (m, 2H), 3.16 (dd, J=13.3, 9.5 Hz, 1H), 2.77 (dd, J=16.4, 3.1 Hz, 1H), 2.52 (dd, J=16.4, 9.7 Hz, 1H), 2.31-2.21 (m, 1H), 2.16-2.04 (m, 1H), 1.82-1.68 (m, 1H), 1.33 (d, J=7.0 Hz, 3H), 1.13 (d, J=6.8 Hz, 3H). HPLC (Orthogonal method, 30% Solvent B start): RT=11.9 min, HI: 97%. hGPR40 EC$_{50}$=319 nM. Example 81, Isomer 2 (white foam, 20 mg) LC-MS Anal. Calc'd for C$_{25}$H$_{28}$ClF$_3$N$_4$O$_4$ 540.18, found [M+H] 541.0. $^1$H NMR (400 MHz, CD$_3$CN) δ ppm 8.02-7.92 (m, 1H), 7.18-7.05 (m, 2H), 7.03-6.92 (m, 2H), 6.50 (br.s, 1H), 6.48 (s, 1H), 4.51-4.40 (m, 1H), 4.16 (td, J=8.5, 4.0 Hz, 1H), 4.11 (s, 3H), 3.99 (dd, J=13.2, 3.6 Hz, 2H), 3.43-3.32 (m, 2H), 3.16 (dd, J=13.3, 9.5 Hz, 1H), 2.77 (dd, J=16.4, 3.1 Hz, 1H), 2.52 (dd, J=16.4, 9.7 Hz, 1H), 2.31-2.21 (m, 1H), 2.16-2.04 (m, 1H), 1.82-1.68 (m, 1H), 1.33 (d, J=7.0 Hz, 3H), 1.13 (d, J=6.8 Hz, 3H). HPLC (Orthogonal method, 30% Solvent B start): RT=11.9 min, HI: 97%. hGPR40 EC$_{50}$=71 nM.

81I. (3R,4S)-1-(5-chloro-2-methoxypyridin-4-yl)-3-methylpiperidin-4-ol: rac-1-(5-chloro-2-methoxypyridin-4-yl)-3-cis-methylpiperidin-4-ol (81G, 9.6 g, 37.5 mmol) isomers were separated by chiral Prep. SFC to provide (3R,4S)-1-(5-chloro-2-methoxypyridin-4-yl)-3-methylpiperidin-4-ol (white foam, 4 g, 15.6 mmol) as a single enantiomer. LC-MS Anal. Calc'd for C$_{12}$H$_{17}$ClN$_2$O$_2$:256.10, found [M+H] 257.0. $^1$H NMR (400 MHz, CDCl$_3$) δ 7.98 (s, 1H), 6.30 (s, 1H), 3.99-3.94 (m, 1H), 3.91 (s, 3H), 3.30-3.21 (m, 1H), 3.18-3.09 (m, 2H), 2.93 (dd, J=11.5, 10.0 Hz, 1H), 2.08 (qd, J=6.8, 3.1 Hz, 1H), 2.02-1.87 (m, 2H), 1.42 (d, J=3.8 Hz, 1H), 1.06 (d, J=7.0 Hz, 3H).

81J. 2-((4S,5S)-1-(4-(((3R,4R)-1-(5-chloro-2-methoxypyridin-4-yl)-3-methylpiperidin-4-yl)oxy)phenyl)-4-methyl-3-(trifluoromethyl)-4,5-dihydro-1H-pyrazol-5-yl) acetate: To a solution of methyl 2-((4S,5S)-1-(4-hydroxyphenyl)-4-methyl-3-(trifluoromethyl)-4,5-dihydro-1H-pyrazol-5-yl)acetate (1J, 4.6 g, 15 mmol) and (3R,4S)-1-(5-chloro-2-methoxypyridin-4-yl)-3-methylpiperidin-4-ol (3.4 g, 13 mmol) in toluene (166 mL) was added tributylphosphine (5.5 mL, 21 mmol). While stirring, (E)-diazene-1,2-diylbis(piperidin-1-ylmethanone) (5.4 g, 21 mmol) was added portionwise to the reaction mixture, and the resulting mixture was heated at 50° C. for 120 min. The mixture was cooled to rt and 150 mL of hexanes was added to the mixture and a white precipitate formed. The mixture was filtered, and the filtrate was concentrated and was purified via silica gel chromatography to give methyl 2-((4S,5S)-1-(4-(((3R,4R)-1-(5-chloro-2-methoxypyridin-4-yl)-3-methylpiperidin-4-yl)oxy)phenyl)-4-methyl-3-(trifluoromethyl)-4,5-dihydro-1H-pyrazol-5-yl)acetate (4.7 g, 8.5 mmol, 64% yield). LC-MS Anal. Calc'd for $C_{26}H_{30}ClF_3N_4O_4$ 554.19, found [M+H] 555.2. $^1$H NMR (400 MHz, $CDCl_3$) δ ppm 8.00 (s, 1H), 7.15-7.04 (m, 2H), 7.01-6.89 (m, 2H), 6.30 (s, 1H), 4.49-4.36 (m, 1H), 3.91 (s, 4H), 3.73 (s, 3H), 3.62-3.49 (m, 2H), 3.28-3.15 (m, 1H), 2.95-2.85 (m, 1H), 2.82 (dd, J=16.2, 3.2 Hz, 1H), 2.67 (dd, J=12.3, 9.0 Hz, 1H), 2.43 (dd, J=16.1, 10.3 Hz, 1H), 2.26-2.12 (m, 2H), 1.91-1.78 (m, 1H), 1.36 (d, J=7.0 Hz, 3H), 1.16 (d, J=6.6 Hz, 3H).

Example 81, Isomer 2 (neutral form): To a stirred solution of methyl 2-((4S,5S)-1-(4-(((3R,4R)-1-(5-chloro-2-methoxypyridin-4-yl)-3-methylpiperidin-4-yl)oxy)phenyl)-4-methyl-3-(trifluoromethyl)-4,5-dihydro-1H-pyrazol-5-yl) acetate (5.5 g, 9.9 mmol) in THF (90 mL) and water (9 mL) at rt was added 2N LiOH solution (12 mL, 24 mmol). The reaction mixture was stirred at rt for 16 h and 1N HCl (25 mL, 25 mmol) was added at 0° C. to pH=4-5. The solvent was evaporated and the residue was extracted 3× with EtOAc. The organic extracts were dried over $Na_2SO_4$; the solution was filtered and concentrated. The residue was recrystallized from isopropanol to give Example 81, Isomer 2 (neutral form) as white solid (4.3 g, 7.7 mmol, 78% yield). LC-MS Anal. Calc'd for $C_{25}H_{28}ClF_3N_4O_4$ 540.18, found [M+H] 541.0. $^1$H NMR (500 MHz, DMSO-d6) δ ppm 12.52 (br. s., 1H), 8.01 (s, 1H), 7.05 (d, J=9.1 Hz, 2H), 6.96 (d, J=9.1 Hz, 2H), 6.40 (s, 1H), 4.49-4.33 (m, 1H), 4.02 (td, J=8.8, 4.1 Hz, 1H), 3.80 (s, 3H), 3.56-3.39 (m, 2H), 3.37-3.29 (m, 1H), 2.94-2.85 (m, 1H), 2.72-2.66 (m, 1H), 2.64 (dd, J=16.1, 2.9 Hz, 1H), 2.49-2.41 (m, 1H), 2.22-2.05 (m, 1H), 2.01-1.86 (m, 1H), 1.68-1.50 (m, 1H), 1.25 (d, J=7.2 Hz, 3H), 1.03 (d, J=6.9 Hz, 3H). HPLC (Orthogonal method, 30% Solvent B start): RT=11.9 min, HI: 97%. hGPR40 $EC_{50}$=71 nM. hGPR40 IP1 $EC_{50}$=9 nM. Acute oral glucose tolerance: −54% @ 0.3 mg/kg.

EXAMPLE 82

2-((4S,5S)-1-(4-(((3S,4S)-1-(5-chloro-2-ethoxypyridin-4-yl)-3-methylpiperidin-4-yl)oxy)phenyl)-4-methyl-3-(trifluoromethyl)-4,5-dihydro-1H-pyrazol-5-yl)acetic acid, HCl

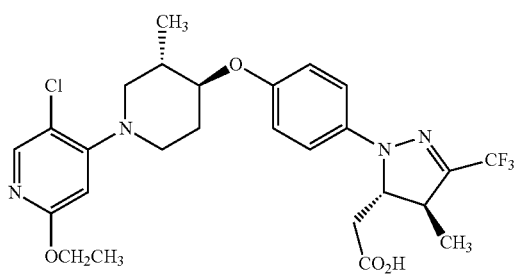

Example 82 (white foam, 15 mg) was prepared following the procedure for Example 81. LC-MS Anal. Calc'd for $C_{26}H_{30}ClF_3N_4O_4$ 554.19, found [M+H] 555.0. $^1$H NMR (400 MHz, $CD_3CN$) δ ppm 7.98 (s, 1H), 7.09 (d, J=9.0 Hz, 2H), 6.97 (d, J=9.0 Hz, 2H), 6.34 (s, 1H), 4.50-4.40 (m, 1H), 4.30 (q, J=7.0 Hz, 2H), 4.00 (td, J=9.0, 4.1 Hz, 1H), 3.61-3.49 (m, 2H), 3.41-3.31 (m, 1H), 2.96-2.86 (m, 1H), 2.79-2.63 (m, 2H), 2.51 (dd, J=16.6, 9.5 Hz, 1H), 2.19-1.93 (m, 2H), 1.79-1.67 (m, 1H), 1.37-1.31 (m, 6H), 1.12 (dd, J=6.5, 4.0 Hz, 3H). HPLC (Orthogonal method, 30% Solvent B start): RT=13.5 min, HI: 100%. hGPR40 $EC_{50}$=760 nM.

EXAMPLE 83

2-((4S,5S)-1-(4-(((3R,4R)-1-(5-chloro-2-ethoxypyridin-4-yl)-3-methylpiperidin-4-yl)oxy)phenyl)-4-methyl-3-(trifluoromethyl)-4,5-dihydro-1H-pyrazol-5-yl)acetic acid, HCl

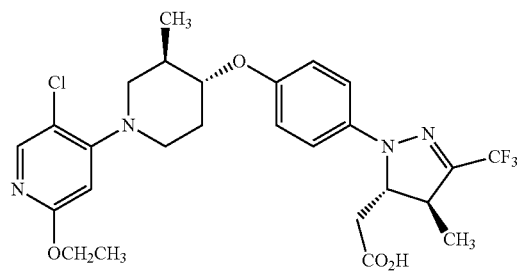

Example 83 (white foam, 15 mg) was prepared following the procedure for Example 81. LC-MS Anal. Calc'd for $C_{26}H_{30}ClF_3N_4O_4$ 554.19, found [M+H] 555.0. $^1$H NMR (400 MHz, $CD_3CN$) δ ppm 7.98 (s, 1H), 7.11-7.06 (m, 2H), 6.99-6.95 (m, 2H), 6.34 (s, 1H), 4.49-4.41 (m, 1H), 4.30 (q, J=7.0 Hz, 2H), 4.01 (td, J=8.9, 4.3 Hz, 1H), 3.61-3.49 (m, 2H), 3.40-3.31 (m, 1H), 2.96-2.87 (m, 1H), 2.79-2.67 (m, 2H), 2.51 (dd, J=16.6, 9.5 Hz, 1H), 2.19-1.93 (m, 2H), 1.78-1.67 (m, 1H), 1.37-1.30 (m, 6H), 1.12 (dd, J=6.3, 3.5 Hz, 3H). HPLC (Orthogonal method, 30% Solvent B start): RT=13.5 min, HI: 100%. hGPR40 $EC_{50}$=224 nM.

EXAMPLE 84

2-((4S,5S)-1-(4-(((3S,4S)-1-(2-ethoxy-5-fluoropyridin-4-yl)-3-methylpiperidin-4-yl)oxy)phenyl)-4-methyl-3-(trifluoromethyl)-4,5-dihydro-1H-pyrazol-5-yl)acetic acid, HCl

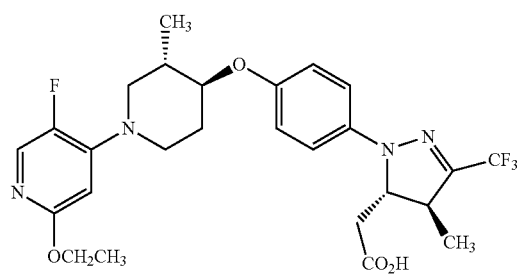 [SMILES: CCOc1cc(N2CC[C@H](Oc3ccc(N4N=C(C(F)(F)F)[C@@H](C)[C@@H]4CC(=O)O)cc3)[C@@H](C)C2)c(F)cn1]

Example 84 (white foam, 20 mg) was prepared following the procedure for Example 81. LC-MS Anal. Calc'd for $C_{26}H_{30}F_4N_4O_4$ 538.22, found [M+H] 539.2. $^1$H NMR (400 MHz, $CD_3CN$) δ ppm 7.85-7.69 (m, 1H), 7.17-7.04 (m, 2H), 7.02-6.89 (m, 2H), 6.29-6.12 (m, 1H), 4.44 (d, J=9.0 Hz, 1H), 4.26 (q, J=7.0 Hz, 2H), 4.00 (td, J=9.0, 3.9 Hz, 1H), 3.71-3.58 (m, 2H), 3.34 (d, J=5.5 Hz, 1H), 3.07-2.93 (m, 2H), 2.86-2.65 (m, 2H), 2.46 (dd, J=16.2, 9.7 Hz, 1H), 2.21-2.12 (m, 1H), 2.02 (dt, J=4.8, 2.5 Hz, 1H), 1.73-1.58 (m, 1H), 1.38-1.29 (m, 6H), 1.09 (d, J=6.5 Hz, 3H). HPLC (Orthogonal method, 30% Solvent B start): RT=7.5 min, HI: 99%. hGPR40 $EC_{50}$=2575 nM.

EXAMPLE 85

2-((4S,5S)-1-(4-(((3R,4R)-1-(2-ethoxy-5-fluoropyridin-4-yl)-3-methylpiperidin-4-yl)oxy)phenyl)-4-methyl-3-(trifluoromethyl)-4,5-dihydro-1H-pyrazol-5-yl)acetic acid, HCl

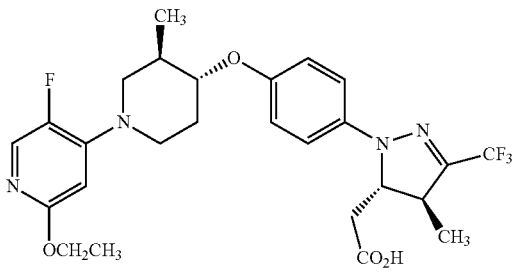 [SMILES: CCOc1cc(N2CC[C@@H](Oc3ccc(N4N=C(C(F)(F)F)[C@@H](C)[C@@H]4CC(=O)O)cc3)[C@H](C)C2)c(F)cn1]

Example 85 (white foam, 20 mg) was prepared following the procedure for Example 81. LC-MS Anal. Calc'd for $C_{26}H_{30}F_4N_4O_4$ 538.22, found [M+H] 539.2. $^1$H NMR (400 MHz, $CD_3CN$) δ ppm 7.85-7.69 (m, 1H), 7.17-7.04 (m, 2H), 7.02-6.89 (m, 2H), 6.29-6.12 (m, 1H), 4.44 (d, J=9.0 Hz, 1H), 4.26 (q, J=7.0 Hz, 2H), 4.00 (td, J=9.0, 3.9 Hz, 1H), 3.71-3.58 (m, 2H), 3.34 (d, J=5.5 Hz, 1H), 3.07-2.93 (m, 2H), 2.86-2.65 (m, 2H), 2.46 (dd, J=16.2, 9.7 Hz, 1H), 2.21-2.12 (m, 1H), 2.02 (dt, J=4.8, 2.5 Hz, 1H), 1.73-1.58 (m, 1H), 1.38-1.29 (m, 6H), 1.09 (d, J=6.5 Hz, 3H). HPLC (Orthogonal method, 30% Solvent B start): RT=7.6 min, HI: 100%. hGPR40 $EC_{50}$=277 nM.

EXAMPLE 86

2-(1-(4-((1-(5-chloro-2-methoxypyridin-4-yl)-3-methylpiperidin-4-yl)oxy)phenyl)-4-ethyl-3-(trifluoromethyl)-4,5-dihydro-1H-pyrazol-5-yl)acetic acid (Isomers 1, 2 and 3)

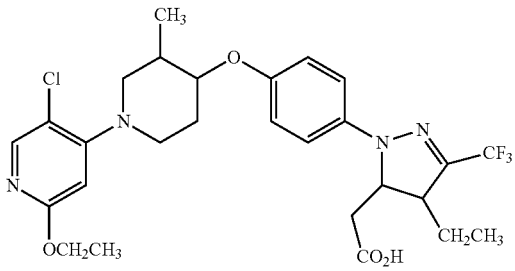 [SMILES: CCOc1cc(N2CCC(Oc3ccc(N4N=C(C(F)(F)F)C(CC)C4CC(=O)O)cc3)C(C)C2)c(Cl)cn1]

86A. 2,2,2-trifluoro-N'-(4-methoxyphenyl)acetohydrazide: To a stirred suspension of (4-methoxyphenyl)hydrazine (6 g, 43.4 mmol) in THF (150 mL) at 0° C. was added TFAA (6.0 mL, 43.4 mmol) dropwise. The resulting mixture was stirred at 0° C. for 2 h. LCMS showed the completion of the reaction. The mixture was then concentrated and purified by chromatography afforded 2,2,2-trifluoro-N'-(4-methoxyphenyl)acetohydrazide (9 g, 38.4 mmol, 89% yield) as red solid. LC-MS Anal. Calc'd for $C_9H_9F_3N_2O_2$ 234.06, found [M+H] 235.0.

86B. (Z)-2,2,2-trifluoro-N'-(4-methoxyphenyl)acetohydrazonoyl chloride: To a stirred solution of 2,2,2-trifluoro-N'-(4-methoxyphenyl)acetohydrazide (5 g, 21.4 mmol) in EtOAc (100 mL) at 0° C. was added benzenesulfonyl chloride (3.4 mL, 25.6 mmol) followed by N-ethyl-N-isopropylpropan-2-amine (5.6 mL, 32.0 mmol) dropwise. The resulting mixture was then warmed up to rt and stirred at rt for 12 h. LCMS showed the completion of the reaction. Then, sat. aq $NaHCO_3$ (50 mL) was added slowly to the reaction mixture. The mixture was then extracted with EtOAc (2×50 mL), and the combined organic extracts were dried ($Na_2SO_4$), filtered, and concentrated. Purification by chromatography gave (Z)-2,2,2-trifluoro-N'-(4-methoxyphenyl)acetohydrazonoyl chloride (3 g, 11.9 mmol, 56% yield) as red oil. LC-MS Anal. Calc'd for $C_9H_8ClF_3N_2O$, 252.03, found [M−H] 251.0.

86C. methyl 4-ethyl-1-(4-methoxyphenyl)-3-(trifluoromethyl)-4,5-dihydro-1H-pyrazole-5-carboxylate: To a mixture of (Z)-2,2,2-trifluoro-N'-(4-methoxyphenyl)acetohydrazonoyl chloride (3.4 g, 13.46 mmol) and (E)-methyl pent-2-enoate (1.5 g, 13.5 mmol) in 1,4-Dioxane (27 mL) was added silver carbonate (3.7 g, 13.5 mmol). The mixture was purged with Ar three times. Then, the mixture was heat to 65° C. for overnight. The mixture was filtered through celite and washed with DCM. The combined filtrates were concentrated. Purification by chromatography gave methyl 4-ethyl-1-(4-methoxyphenyl)-3-(trifluoromethyl)-4,5-dihydro-1H-pyrazole-5-carboxylate (2.1 g, 6.4 mmol, 47% yield) as a yellow oil. LC-MS Anal. Calc'd for $C_{15}H_{17}F_3N_2O_3$ 330.12, found [M+H] 331.1.

86D. 4-ethyl-1-(4-methoxyphenyl)-3-(trifluoromethyl)-4,5-dihydro-1H-pyrazol-5-yl)methanol: Dissolved methyl 4-ethyl-1-(4-methoxyphenyl)-3-(trifluoromethyl)-4,5-dihydro-1H-pyrazole-5-carboxylate (2.3 g, 6.96 mmol) in EtOH (23.2 mL) and THF (11.61 mL) and added $NaBH_4$ (0.53 g, 13.93 mmol) slowly into the solution at 23° C. After 1 hour, 10% $KHSO_4$ (10 mL) was added slowly to the reaction mixture. The mixture was then extracted with EtOAc (2×30 mL), and the combined organic extracts were dried ($Na_2SO_4$), filtered, and concentrated. Purification via silica gel chromatography gave 4-ethyl-1-(4-methoxyphenyl)-3-(trifluoromethyl)-4,5-dihydro-1H-pyrazol-5-yl)methanol (1.8 g, 5.95 mmol, 86% yield) as an oil. LC-MS Anal. Calc'd for $C_{14}H_{17}F_3N_2O_2$ 302.12, found [M+H] 303.0.

86E. 4-ethyl-1-(4-methoxyphenyl)-3-(trifluoromethyl)-4,5-dihydro-1H-pyrazol-5-yl)methyl methanesulfonate: To a solution of 4-ethyl-1-(4-methoxyphenyl)-3-(trifluoromethyl)-4,5-dihydro-1H-pyrazol-5-yl)methanol (2.2 g, 7.28 mmol) in dichloromethane (14.5 mL) added triethylamine (5.0 mL, 36.4 mmol) and methanesulfonyl chloride (1.7 mL, 21.8 mmol) at 0° C. and stirred for 30 mins. LCMS showed that the reaction was completed. TLC (1:2 EtOAc:Hexanes) showed starting material were completely consumed. Then, sat. $NaHCO_3$ (200 mL) was added slowly to the reaction mixture. The mixture was then extracted with EtOAc (2×200 mL), and the combined organic extracts were dried (Na₂SO₄), filtered, and concentrated. Purification via silica gel chromatography gave (4-ethyl-1-(4-methoxyphenyl)-3-(trifluoromethyl)-4,5-dihydro-1H-pyrazol-5-yl)methyl methanesulfonate (2.4 g, 6.31 mmol, 87% yield) as a white foam. LC-MS Anal. Calc'd for $C_{15}H_{19}F_3N_2O_4S$, 380.10, found [M+H] 381.0.

86F. 2-(4-ethyl-1-(4-methoxyphenyl)-3-(trifluoromethyl)-4,5-dihydro-1H-pyrazol-5-yl)acetonitrile: A solution of 4-ethyl-1-(4-methoxyphenyl)-3-(trifluoromethyl)-4,5-dihydro-1H-pyrazol-5-yl)methyl methanesulfonate (1.24 g, 3.26 mmol) in DMSO (6.5 mL)) was treated with cyanopotassium (0.32 g, 4.89 mmol) and stirred at 40° C. under Ar. Reaction was monitored by LC/MS. After 16 h, LCMS showed completion. After cooling to rt, it was diluted with NaHCO₃ (~200 mL) and EtOAc (200 mL). After separation of the layers, the aqueous layer was then extracted with EtOAc (3×200 mL). The combined organic extracts were washed with water (3×), brine, dried (Na₂SO₄), and concentrated. Purification via silica gel chromatography gave 2-(4-ethyl-1-(4-methoxyphenyl)-3-(trifluoromethyl)-4,5-dihydro-1H-pyrazol-5-yl)acetonitrile as an oil. LC-MS Anal. Calc'd for $C_{15}H_{16}F_3N_3O$, 311.13, found [M+H] 312.0.

86G. 2-(4-ethyl-1-(4-hydroxyphenyl)-3-(trifluoromethyl)-4,5-dihydro-1H-pyrazol-5-yl)acetonitrile: To a stirred solution of 2-(4-ethyl-1-(4-methoxyphenyl)-3-(trifluoromethyl)-4,5-dihydro-1H-pyrazol-5-yl)acetonitrile (900 mg, 2.89 mmol) in DCM (14 mL) at −78° C. was added tribromoborane (547 μl, 5.78 mmol). After the addition was complete, the reaction mixture was stirred at −78° C. for 15 min and then allowed to warm up to 0° C. over a 2 h period. LCMS showed no starting material. The reaction mixture was quenched at 0° C. with dry MeOH (10 mL) and then allowed to warm up to rt. The mixture was evaporated and, the residue was partitioned between 0.1M HCl (20 mL) and CH₂Cl₂ (40 mL). The aqueous layer was extracted with CH₂Cl₂ (2×20 mL) and, the combined organic layers were dried (Na₂SO₄) and concentrated. Purification via silica gel chromatography gave 2-(4-ethyl-1-(4-hydroxyphenyl)-3-(trifluoromethyl)-4,5-dihydro-1H-pyrazol-5-yl)acetonitrile (600 mg, 2.02 mmol, 70% yield) as a yellow oil. LC-MS Anal. Calc'd for $C_{14}H_{14}F_3N_3O$, 297.11, found [M+H] 298.0.

86H. 2-(1-(4-((-1-(5-chloro-2-methoxypyridin-4-yl)-3-methylpiperidin-4-yl)oxy)phenyl)-4-ethyl-3-(trifluoromethyl)-4,5-dihydro-1H-pyrazol-5-yl)acetonitrile: To a solution of 2-(4-ethyl-1-(4-hydroxyphenyl)-3-(trifluoromethyl)-4,5-dihydro-1H-pyrazol-5-yl)acetonitrile (174 mg, 0.58 mmol) and (3R,4S)-1-(5-chloro-2-methoxypyridin-4-yl)-3-methylpiperidin-4-ol (150 mg, 0.58 mmol) in THF (195μ) was added triphenylphosphine (215 mg, 0.82 mmol). The reaction vessel was then lowered into a sonication bath and sonicated for several minutes (to allow for mixing) giving a clear and highly viscous solution. While sonicating, (E)-di-tert-butyl diazene-1,2-dicarboxylate (161 mg, 0.70 mmol) was added dropwise to the reaction mixture, and the reaction mixture was sonicated for 120 min. LCMS showed the desired mass of product. Then, sat. aq NaHCO₃ (10 mL) was added slowly to the reaction mixture. The mixture was then extracted with EtOAc (2×10 mL), and the combined organic extracts were washed with water (20 mL) and brine (20 mL), and dried (Na₂SO₄), filtered, and concentrated. Purification by chromatography gave 2-((4S,5S)-1-(4-((-1-(5-chloro-2-methoxypyridin-4-yl)-3-methylpiperidin-4-yl)oxy)phenyl)-4-ethyl-3-(trifluoromethyl)-4,5-dihydro-1H-pyrazol-5-yl) acetonitrile (80 mg, 0.15 mmol, 26% yield) an oil. LC-MS Anal. Calc'd for $C_{26}H_{29}ClF_3N_5O_2$ 535.20, found [M+H] 536.0.

Example 86 (Isomers 1, 2 and 3): To a solution of 3.6 M HCl in MeOH/MeOAc (326 μL, 1.174 mmol) was added to 2-(1-(4-((-1-(5-chloro-2-methoxypyridin-4-yl)-3-methylpiperidin-4-yl)oxy)phenyl)-4-ethyl-3-(trifluoromethyl)-4,5-dihydro-1H-pyrazol-5-yl)acetonitrile (37 mg, 0.069 mmol) and the reaction stirred at rt for 48 h. The reaction mixture was diluted with acetonitrile and was evaporated to remove methanol and acetonitrile. The residue was dissolved in ethyl acetate and washed with a saturated aqueous NaHCO₃ (2×100 mL), water, and brine. The organic layer was then dried (Na₂SO₄), filtered, and concentrated. The residue was dissolved in THF (124 μl) and Water (13 μl) at rt was added 2M LiOH (345 μl, 0.69 mmol). The reaction mixture was stirred at rt for 1 h and LCMS showed no starting material. Then, 3N HCl (0.4 mL) was added at 0° C. and warmed up to rt. The solvent was evaporated and the residue was dissolved in CH₃CN, filtered. Purification by RP-Prep HPLC afforded a diastereomeric mixture. The diastereomers were separated by chiral Prep. SFC to provide Example 86, Isomers 1, 2 and 3 as single stereoisomers, prepared following the procedure for Example 81. Example 86, Isomer 1 (off-white solid, 5 mg): LC-MS Anal. Calc'd for $C_{26}H_{30}ClF_3N_4O_4$ 554.19, found [M+H] 555.1. ¹H NMR (400 MHz, CD₃CN) δ ppm 8.00 (s, 1H), 7.13-7.06 (m, 2H), 7.02-6.94 (m, 2H), 6.38 (s, 1H), 4.60 (d, J=9.3 Hz, 1H), 4.01 (td, J=8.9, 4.3 Hz, 1H), 3.87 (s, 3H), 3.59-3.50 (m, 2H), 3.31 (dd, J=3.5, 2.3 Hz, 1H), 2.97-2.87 (m, 1H), 2.76-2.66 (m, 2H), 2.52 (dd, J=16.2, 9.4 Hz, 1H), 2.25-2.16 (m, 1H), 2.10-2.02 (m, 1H), 1.79-1.58 (m, 4H), 1.12 (d, J=6.8 Hz, 3H), 0.95 (t, J=7.5 Hz, 3H). HPLC (Orthogonal method, 30% Solvent B start): RT=12.5 min, HI: 98%. hGPR40 EC₅₀=73 nM. Example 86, Isomer 2 (off-white solid, 5 mg): LC-MS Anal. Calc'd for $C_{26}H_{30}ClF_3N_4O_4$ 554.19, found [M+H] 555.1. ¹H NMR (400 MHz, CD₃CN) δ ppm 7.89 (s, 1H), 7.01-6.94 (m, 2H), 6.91-6.83 (m, 2H), 6.27 (s, 1H), 4.49 (d, J=9.3 Hz, 1H), 3.89 (td, J=8.9, 4.2 Hz, 1H), 3.76 (s, 3H), 3.51-3.39 (m, 2H), 3.20 (dd, J=3.7, 2.1 Hz, 1H), 2.86-2.78 (m, 1H), 2.64-2.54 (m, 2H), 2.41 (dd, J=16.3, 9.5 Hz, 1H), 2.14-2.06 (m, 1H), 1.96 (dd, J=12.4, 5.8 Hz, 1H), 1.71-1.48 (m, 3H), 1.01 (d, J=6.6 Hz, 3H), 0.87-0.80 (m, 3H). HPLC (Orthogonal method, 30% Solvent B start): RT=12.5 min, HI: 96%. hGPR40 EC₅₀=599 nM. Example 86, Isomer 3 (off-white solid, 5 mg): LC-MS Anal. Calc'd for $C_{26}H_{30}ClF_3N_4O_4$ 554.19, found [M+H] 555.1. ¹H NMR (400 MHz, CD₃CN) δ ppm 8.00 (s, 1H), 7.13-7.06 (m, 2H), 7.01-6.92 (m, 2H), 6.38 (s, 1H), 4.60 (d, J=9.8 Hz, 1H), 4.01 (td, J=8.8, 4.1 Hz, 1H), 3.87 (s, 3H), 3.60-3.50 (m, 2H), 3.31 (dd, J=3.5, 2.0 Hz, 1H), 2.97-2.86 (m, 1H), 2.75-2.65 (m, 2H), 2.52 (dd, J=16.3, 9.3 Hz, 1H), 2.25-2.17 (m, 1H), 2.07 (d, J=6.5 Hz, 1H), 1.81-1.59 (m, 3H), 1.12 (d, J=6.5 Hz, 3H), 0.95 (t, J=7.5 Hz, 3H). HPLC (Orthogonal method, 30% Solvent B start): RT=12.5 min, HI: 95%. hGPR40 EC₅₀=1932 nM.

EXAMPLE 87

2-((4S,5S)-1-(4-(((3R,4R)-1-(5-chloro-2-d3-methoxypyridin-4-yl)-3-methylpiperidin-4-yl)oxy)phenyl)-4-methyl-3-(trifluoromethyl)-4,5-dihydro-1H-pyrazol-5-yl)acetic acid, HCl

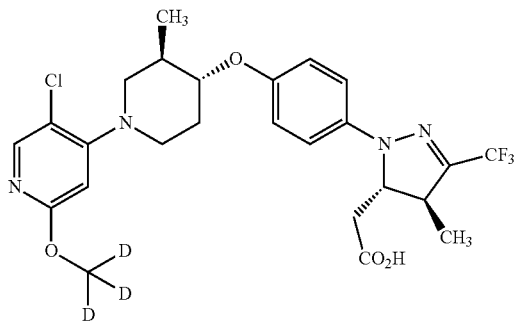 [SMILES: [2H]C([2H])([2H])Oc1cc(N2CC[C@@H](Oc3ccc(N4N=C(C(F)(F)F)[C@@H](C)[C@@H]4CC(=O)O)cc3)[C@H](C)C2)c(Cl)cn1]

Example 87 (white foam, 60 mg) was prepared following the procedure for Example 81. LC-MS Anal. Calc'd for $C_{25}H_{25}D_3ClF_3N_4O_4$ 543.19, found [M+H] 544.2. $^1$H NMR (400 MHz, $CD_3CN$) δ ppm 7.96 (s, 1H), 7.11 (d, J=9.0 Hz, 2H), 6.99 (d, J=8.8 Hz, 2H), 6.48 (s, 1H), 4.54-4.41 (m, 1H), 4.16 (td, J=8.4, 4.0 Hz, 1H), 3.98 (dd, J=12.7, 3.6 Hz, 2H), 3.43-3.34 (m, 2H), 3.16 (dd, J=13.2, 9.7 Hz, 2H), 2.76 (dd, J=16.3, 3.0 Hz, 1H), 2.53 (dd, J=16.3, 9.5 Hz, 1H), 2.33-2.20 (m, 1H), 2.12 (br. s., 1H), 1.82-1.71 (m, 1H), 1.33 (d, J=7.0 Hz, 3H), 1.13 (d, J=6.8 Hz, 3H). HPLC (Orthogonal method, 30% Solvent B start): RT=11.6 min, HI: 100%. hGPR40 $EC_{50}$=74 nM. hGPR40 IP1 $EC_{50}$=6 nM.

EXAMPLE 88

2-((4S,5S)- and (4R,5R)-4-ethyl-1-(4-((1-(2-fluoro-5-methoxyphenyl)piperidin-4-yl)oxy)phenyl)-3-(trifluoromethyl)-4,5-dihydro-1H-pyrazol-5-yl)acetic acid (Isomers 1 and 2)

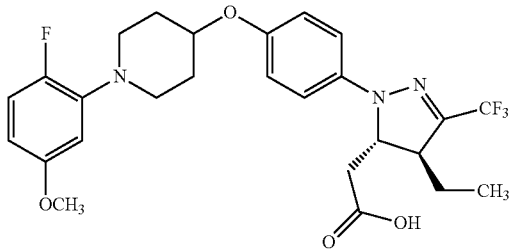 [SMILES: CC[C@@H]1C(C(F)(F)F)=NN(c2ccc(OC3CCN(c4cc(OC)ccc4F)CC3)cc2)[C@H]1CC(=O)O]

88A. 2,2,2-trifluoro-N'-(4-methoxyphenyl)acetohydrazide: To a stirred suspension of (4-methoxyphenyl)hydrazine (6.0 g, 42.1 mmol) in THF (150 mL) at 0° C. was added 2,2,2-trifluoroacetic anhydride (6.44 mL, 46.3 mmol) dropwise. The resulting mixture was stirred at 0° C. for 2.5 h and then an additional amount of trifluoroacetic anhydride (2.38 mL, 16.9 mmol) was added drowpwise. After stirred for an additional 5 min at 0° C., the mixture was concentrated and purified via silica gel chromatography to give the desired product (6.48 g, 65.7% yield) as an off-white solid: LC-MS [M+Na] 257.

88B. 2,2,2-trifluoro-N'-(4-methoxyphenyl)acetohydrazonoyl chloride: To a stirred solution of 2,2,2-trifluoro-N'-(4-methoxyphenyl)acetohydrazide (6.48 g, 22.14 mmol) in EtOAc (120 mL) was added benzenesulfonyl chloride (3.44 mL, 26.6 mmol) at rt. The solution was cooled to 0° C., and to the solution was added N,N-diisopropylethylamine (5.80 mL, 33.2 mmol) dropwise. The resulting mixture was stirred at 0° C. for 20 min, and then warmed to rt. After stirring at rt overnight, the mixture was diluted with EtOAc and, washed with sat'd $NaHCO_3$ and water. The organic layer was dried ($Na_2SO_4$) and concentrated and the crude was purified via silica gel chromatography (0 to 10% EtOAc) to provide the desired product (4.22 g, 75% yield) as a reddish liquid: LC-MS [M+H] 253, 255.

88C. (4S,5R)- and (4R,5S)-methyl 4-ethyl-1-(4-methoxyphenyl)-3-(trifluoromethyl)-4,5-dihydro-1H-pyrazole-5-carboxylate: A stirred mixture of 2,2,2-trifluoro-N'-(4-methoxyphenyl)acetohydrazonoyl chloride (1.20 g, 4.51 mmol), (E)-methyl pent-2-enoate (1.593 g, 13.54 mmol) and silver carbonate (2.489 g, 9.03 mmol) in dioxane (20 mL) was sonicated under vacuum and refilled with argon three times. The mixture was heated to 65° C. and stirred at this temperature overnight. Then, the mixture was filtered and the filter cake was rinsed with $CH_2Cl_2$. The combined filtrates were concentrated and purified via silica gel chromatography to afford the desired product (910 mg, 61.1% yield) as a reddish oil: LC-MS [M+H] 331.

88D. ((4S,5R) and (4R,5S)-4-ethyl-1-(4-methoxyphenyl)-3-(trifluoromethyl)-4,5-dihydro-1H-pyrazol-5-yl)methanol: To a stirred solution of (4S,5R) and (4R,5S)-methyl 4-ethyl-1-(4-methoxyphenyl)-3-(trifluoromethyl)-4,5-dihydro-1H-pyrazole-5-carboxylate (910 mg, 2.76 mmol) in THF (5.0 mL) and EtOH (10 mL) was added sodium borohydride (208 mg, 5.51 mmol). The reaction mixture was stirred at rt overnight and then quenched with 1M HCl. The aqueous mixture was stirred at rt for 2.5 days. The mixture was concentrated and purified via silica gel chromatography to provide the desired product (705 mg, 85% yield) as a reddish oil: LC-MS [M+H] 303.

88E. ((4S,5R)- and (4R,5S)-4-ethyl-1-(4-methoxyphenyl)-3-(trifluoromethyl)-4,5-dihydro-1H-pyrazol-5-yl)methyl methanesulfonate: To a stirred solution of ((4S,5R) and (4R,5S)-4-ethyl-1-(4-methoxyphenyl)-3-(trifluoromethyl)-4,5-dihydro-1H-pyrazol-5-yl)methanol (705 mg, 2.146 mmol) in $CH_2Cl_2$ (10.0 mL) at 0° C. was added methanesulfonyl chloride (0.251 mL, 3.22 mmol) and then triethylamine (0.748 mL, 5.36 mmol). The resulting mixture was stirred overnight while allowing the temperature to reach rt. The reaction mixture was diluted with $CH_2Cl_2$ and washed with sat'd $NaHCO_3$ and water. The organic layer was dried ($Na_2SO_4$) and concentrated and the crude was purified via silica gel chromatography to give the desired product (678 mg, 83% yield) as a yellowish oil: LC-MS [M+H] 381.

88F. 2-((4S,5S) and (4R,5R)-4-ethyl-1-(4-methoxyphenyl)-3-(trifluoromethyl)-4,5-dihydro-1H-pyrazol-5-yl)acetonitrile: To a stirred solution of ((4S,5R)- and (4R,5S)-4-ethyl-1-(4-methoxyphenyl)-3-(trifluoromethyl)-4,5-dihydro-1H-pyrazol-5-yl)methyl methanesulfonate (678 mg, 1.782 mmol) was added potassium cyanide (239 mg, 3.56 mmol). The resulting mixture was heated to 50° C. and stirred at this temperature for 19 h. After this time, the reaction mixture was cooled to rt, diluted with sat.$NaHCO_3$ and extracted with EtOAc. The organic extract was washed with sat'd NaCl, dried ($Na_2SO_4$) and concentrated. Purification via silica gel chromatography afforded the desired product (512 mg, 91% yield) as an orangish oil: LC-MS [M+H] 312.

88G. 2-((4S,5S)- and (4R,4S)-4-ethyl-1-(4-hydroxyphenyl)-3-(trifluoromethyl)-4,5-dihydro-1H-pyrazol-5-yl)acetonitrile: To a stirred solution of 2-((4S,5S) and (4R,5R)-4-ethyl-1-(4-methoxyphenyl)-3-(trifluoromethyl)-4,5-dihydro-1H-pyrazol-5-yl)acetonitrile (512 mg, 1.628 mmol) in $CH_2Cl_2$ (4.0 mL) at −78° C. under argon was added boron tribromide (0.308 mL, 3.26 mmol) dropwise. The resulting mixture was stirred at −78° C. for 10 min, then allowed to warm up to 0° C. and stirred for 1 h. At this time, the reaction mixture was quenched with MeOH (20 mL), allowed to warm up to rt and stirred for 1 h. The mixture was concentrated and the crude was purified via silica gel chromatography to provide the desired product (427 mg, 82% yield) as a yellowish solid: LC-MS [M+H] 298.

88H. 1-(2-fluoro-5-methoxyphenyl)piperidin-4-yl4-methylbenzenesulfonate: To a stirred solution of 1-(2-fluoro-5-methoxyphenyl)piperidin-4-ol (1.25 g, 5.55 mmol) in $CH_2Cl_2$ (25 mL) at rt was added 4-methylbenzene-1-sulfonyl chloride (1.270 g, 6.66 mmol) followed by pyridine (2.244 mL, 27.7 mmol). The resulting mixture was stirred at rt overnight and then washed with water. The organic layer was dried ($Na_2SO_4$) and concentrated, and the crude was purified via silica gel chromatography to give the desired product (1.38 g, 65.5% yield) as a white solid: LC-MS [M+H] 380.

88I. 2-((4S,5S)- and (4R,5R)-4-ethyl-1-(4-((1-(2-fluoro-5-methoxyphenyl)piperidin-4-yl)oxy)phenyl)-3-(trifluoromethyl)-4,5-dihydro-1H-pyrazol-5-yl)acetonitrile: To a stirred mixture of 1-(2-fluoro-5-methoxyphenyl)piperidin-4-yl4-methylbenzenesulfonate (390 mg, 1.0 mmol) and 2-((4S,5S)- and (4R,5R)-4-ethyl-1-(4-hydroxyphenyl)-3-(trifluoromethyl)-4,5-dihydro-1H-pyrazol-5-yl)acetonitrile (430 mg, 1.4 mmol) in DMF (10 mL) was added cesium carbonate (1.0 g, 3.1 mmol). The resulting mixture was heated to 50° C. and stirred at this temperature overnight. Then, the mixture was diluted with water and extracted with EtOAc. The organic extract was dried ($Na_2SO_4$) and concentrated, and the crude was purified via silica gel chromatography to afford the desired product (206 mg, 36.5% yield) as a yellowish oil: LC-MS [M+H] 505.

88J. methyl 2-((4S,5S)- and (4R,5R)-4-ethyl-1-(4-((1-(2-fluoro-5-methoxyphenyl)piperidin-4-yl)oxy)phenyl)-3-(trifluoromethyl)-4,5-dihydro-1H-pyrazol-5-yl)acetate: 2-(4S,5S)- and (4R,5R)-4-ethyl-1-(4-((1-(2-fluoro-5-methoxyphenyl)piperidin-4-yl)oxy)phenyl)-3-(trifluoromethyl)-4,5-dihydro-1H-pyrazol-5-yl)acetonitrile was dissolved in ~3M HCl/MeOH, MeOAc solution [6.85 mL, prepared by addition of AcCl (1.45 mL) to MeOH (5.4 mL) at 0° C. and then stirring at rt for 30 min]. The resulting solution was allowed to stand at rt for 3.5 days and then evaporated. Purification via silica gel chromatography provided the desired product (102 mg, 46.5% yield) as a colorless oil: LC-MS [M+H] 538.

Example 88 (Isomers 1 2): To a solution of methyl 2-((4S,5S)- and (4R,5R)-4-ethyl-1-(4-((1-(2-fluoro-5-methoxyphenyl)piperidin-4-yl)oxy)phenyl)-3-(trifluoromethyl)-4,5-dihydro-1H-pyrazol-5-yl)acetate (102 mg, 0.190 mmol) in THF (3.0 mL) was added a solution of lithium hydroxide (9.1 mg, 0.38 mmol) in water (0.5 mL). The resulting mixture was stirred at rt overnight. The mixture was diluted with water and the pH of the aqueous mixture was adjusted to 1 by dropwise addition of 1M HCl diluted. The aqueous mixture was extracted with $CH_2Cl_2$ and, the organic extract was dried over ($Na_2SO_4$) and concentrated to give the racemic product as a thick oil. The enantiomers were separated by chiral preparative SFC to afford: Example 88, Isomer 1 (white solid, 42 mg, 41% yield): LC-MS [M+H] 524. $^1$H NMR (500 MHz, $CDCl_3$) δ 7.05 (d, J=8.8 Hz, 2H), 6.96 (m, 1H, overlapped), 6.92 (d, J=8.8 Hz, 2H), 6.70-6.35 (m, 2H), 4.53 (d, J=10.0 Hz, 1H), 4.40 (m, 1H), 3.78 (s, 3H), 3.36 (m, 2H), 3.16 (m, 1H), 3.00 (m, 2H) 2.83 (dd, J=16.0, 3.0 Hz, 1H), 2.46 (dd, J=16.1, 10.3 Hz, 1H), 2.24-1.88 (m, 4H), 1.75 (m, 1H), 1.65 (m, 1H) 1.37 (t, J=7.0 Hz, 3H). Analytical HPLC (Zorbax method, 50% Solvent B start): RT=7.45 min, HI: 96%. hGPR40 $EC_{50}$=78 nM. hGPR40 IP1 $EC_{50}$=18 nM. Example 88, Isomer 2 (white solid, 44 mg, 44% yield): LC-MS [M+H] 524. $^1$H NMR (500 MHz, $CDCl_3$) δ 7.05 (d, J=8.8 Hz, 2H), 6.96 (m, 1H, overlapped), 6.92 (d, J=8.8 Hz, 2H), 6.70-6.35 (m, 2H), 4.53 (d, J=10.0 Hz, 1H), 4.40 (m, 1H), 3.78 (s, 3H), 3.36 (m, 2H), 3.16 (m, 1H), 3.00 (m, 2H) 2.83 (dd, J=16.0, 3.0 Hz, 1H), 2.46 (dd, J=16.1, 10.3 Hz, 1H), 2.24-1.88 (m, 4H), 1.75 (m, 1H), 1.65 (m, 1H) 1.37 (t, J=7.0 Hz, 3H). Analytical HPLC (Orthogonal method, 0% Solvent B start): RT=7.45 min, HI: 98%. hGPR40 $EC_{50}$=7454 nM.

EXAMPLE 89

2-((4S,5S)- and (4R,5R)-1-(4-((1-(2-fluoro-5-methoxyphenyl)piperidin-4-yl)oxy)phenyl)-4-isobutyl-3-(trifluoromethyl)-4,5-dihydro-1H-pyrazol-5-yl) acetic acid (Isomers 1 and 2)

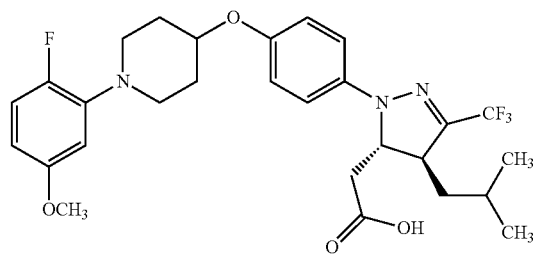 [SMILES: COc1ccc(F)c(N2CCC(Oc3ccc(N4N=C(C(F)(F)F)[C@@H](CC(C)C)[C@@H]4CC(=O)O)cc3)CC2)c1]

Example 89, Isomer 1 (white solid, 15 mg) and Isomer 2 (white solid, 16 mg) were prepared from (E)-methyl 5-methylhex-2-enoate following the procedure for Example 88. Example 89, Isomer 1: LC-MS [M+H] 552. $^1$H NMR (500 MHz, $CDCl_3$) δ 7.06 (d, J=8.9 Hz, 2H), 6.93 (m, 3H), 6.53 (dd, J=7.2, 3.1 Hz, 1H) 6.41 (dt, J=8.8, 3.1 Hz, 1H), 4.52 (d, J=8.7 Hz, 1H), 4.36 (m, 1H), 3.77 (s, 3H), 3.32 (m, 2H), 3.20 (m, 1H), 2.95 (m, 3H) 2.70 (m, 1H), 2.38 (m, 1H), 2.09 (m, 2H), 1.96 (m, 2H), 1.51 (m, 1H), 1.40 (m, 1H) 0.94 (t, J=6.4 Hz, 3H), 0.92 (t, J=6.2 Hz, 3H). Analytical HPLC (Zorbax method, 50% Solvent B start): RT=8.18 min, HI: 96%. hGPR40 $EC_{50}$=7962 nM. Example 89, Isomer 2: LC-MS [M+H] 552. $^1$H NMR (500 MHz, $CDCl_3$) δ 7.06 (d, J=8.9 Hz, 2H), 6.93 (m, 3H), 6.53 (dd, J=7.2, 3.1 Hz, 1H) 6.41 (dt, J=8.8, 3.1 Hz, 1H), 4.52 (d, J=8.7 Hz, 1H), 4.36 (m, 1H), 3.77 (s, 3H), 3.32 (m, 2H), 3.20 (m, 1H), 2.95 (m, 3H) 2.70 (m, 1H), 2.38 (m, 1H), 2.09 (m, 2H), 1.96 (m, 2H), 1.51 (m, 1H), 1.40 (m, 1H) 0.94 (t, J=6.4 Hz, 3H), 0.92 (t, J=6.2 Hz, 3H). Analytical HPLC (Zorbax method, 50% Solvent B start): RT=8.17 min, HI: 98%. hGPR40 $EC_{50}$=390 nM.

EXAMPLE 90

2-((4S,5S)- and (4R,5R)-4-(cyclopropylmethyl)-1-(4-((1-(2-fluoro-5-methoxyphenyl)piperidin-4-yl)oxy)phenyl)-3-(trifluoromethyl)-4,5-dihydro-1H-pyrazol-5-yl)acetic acid (Isomers 1 and 2)

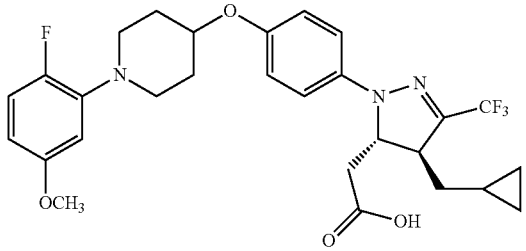 [SMILES: COc1ccc(F)c(N2CCC(Oc3ccc(N4N=C(C(F)(F)F)[C@@H](CC5CC5)[C@@H]4CC(=O)O)cc3)CC2)c1]

90A. (E)-benzyl 4-cyclopropylbut-2-enoate: To a stirred solution of sodium hydride (0.7 g, 18 mmol) in THF (20 mL) at 0° C. under argon was added a solution of benzyl 2-(dimethoxyphosphoryl)acetate (3.8 g, 14 mmol) in THF (5.0 mL), slowly. The mixture was stirred at 0° C. for 15 min until it turned into a clear solution and then, a solution of 2-cyclopropylacetaldehyde (1.0 g, 12 mmol) in THF (5.0 mL) was added dropwise. The resulting mixture was allowed to warm up to rt and was stirred at rt for 6 h. The reaction mixture was quenched with water and extracted with EtOAc. The organic extract was dried (Na$_2$SO$_4$) and concentrated and the crude was purified via silica gel chromatography to provide the desired product (1.3 g, 44% yield) as a colorless oil: LC-MS [M+Na] 239.

Example 90, Isomer 1 (white solid, 39 mg) and Isomer 2 (white solid, 45 mg) were prepared from (E)-benzyl 4-cyclopropylbut-2-enoate following the procedure for Example 88. Example 90, Isomer 1: LC-MS [M+H] 550. $^1$H NMR (500 MHz, CDCl$_3$) δ 7.06 (d, J=9.1 Hz, 2H), 6.92 (m, 3H), 6.54 (dd, J=7.2, 3.0 Hz, 1H), 6.41 (dt, J=8.7, 3.0 Hz, 1H), 4.77 (d, J=9.9 Hz, 1H), 4.37 (m, 1H), 3.77 (s, 3H), 3.34 (m, 2H), 3.28 (m, 1H), 2.98 (m, 2H) 2.82 (dd, J=16.0, 2.5 Hz, 1H), 2.46 (dd, J=16.0, 10.3 Hz, 1H), 2.10 (m, 2H), 1.98 (m, 2H), 1.66 (m, 1H), 1.48 (m, 1H) 0.76 (m, 1H), 052 (m, 1H), 0.44 (m, 1H), 0.19-0.08 (m, 2H). Analytical HPLC (Zorbax method, 50% Solvent B start): RT=7.89 min, HI: 98%. hGPR40 EC$_{50}$=1626 nM. Example 90, Isomer 2: LC-MS [M+H] 550. $^1$H NMR (500 MHz, CDCl$_3$) δ 7.06 (d, J=9.1 Hz, 2H), 6.92 (m, 3H), 6.54 (dd, J=7.2, 3.0 Hz, 1H), 6.41 (dt, J=8.7, 3.0 Hz, 1H), 4.77 (d, J=9.9 Hz, 1H), 4.37 (m, 1H), 3.77 (s, 3H), 3.34 (m, 2H), 3.28 (m, 1H), 2.98 (m, 2H) 2.82 (dd, J=16.0, 2.5 Hz, 1H), 2.46 (dd, J=16.0, 10.3 Hz, 1H), 2.10 (m, 2H), 1.98 (m, 2H), 1.66 (m, 1H), 1.48 (m, 1H) 0.76 (m, 1H), 052 (m, 1H), 0.44 (m, 1H), 0.19-0.08 (m, 2H). Analytical HPLC (Zorbax method, 50% Solvent B start): RT=7.87 min, HI: 97%. hGPR40 EC$_{50}$=156 nM.

EXAMPLE 91

2-((4S,5S)-3-(4-cyanophenyl)-1-(4-((1-(2-fluoro-5-methoxyphenyl)piperidin-4-yl)oxy)phenyl)-4-methyl-4,5-dihydro-1H-pyrazol-5-yl)acetic acid, TFA

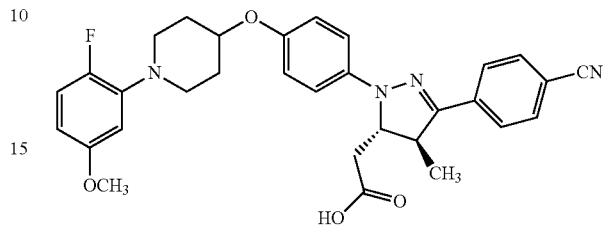

91A. 4-((2-(4-methoxyphenyl)hydrazono)methyl)benzonitrile: To a solution of 4-methoxyphenylhydrazine hydrochloride (626 mg, 3.51 mmol) and 4-cyanobenzaldehyde (421 mg, 3.21 mmol) in DMF (3.5 mL) was added triethylamine (1.0 mL, 7.14 mmol). The mixture was stirred at rt under Ar for 47 h, water (6.8 mL) was added and stirring was continued for 1 h. The solid that resulted was filtered, rinsed with water (6 mL) and dissolved in CH$_2$Cl$_2$ (100 mL). The CH$_2$Cl$_2$ solution was dried (Na$_2$SO$_4$, overnight) and concentrated to provide the desired product (857 mg, 97% yield) as a brownish solid: LC-MS [M+H] 252.

91B. 4-cyano-N'-(4-methoxyphenyl)benzohydrazonoyl bromide: N-Bromosuccinimide (612 mg, 3.41 mmol) was added to a stirred solution of 4-((2-(4-methoxyphenyl)hydrazono)methyl)benzonitrile (855 mg, 3.10 mmol) in THF (5.1 mL) at 0° C. under Ar. The mixture was stirred at 0° C. for 2.5 h and then evaporated under reduced pressure. Purification via silica gel chromatography afforded the desired product (650 mg, 56.6% yield) as a brownish solid: LC-MS [M+H] 330, 332.

91C. 4-((4S,5R)-1-(4-methoxyphenyl)-4-methyl-5-((S)-2-oxo-4-phenyloxazolidine-3-carbonyl)-4,5-dihydro-1H-pyrazol-3-yl)benzonitrile and 4-((4R,5S)-1-(4-methoxyphenyl)-4-methyl-5-((S)-2-oxo-4-phenyloxazolidine-3-carbonyl)-4,5-dihydro-1H-pyrazol-3-yl)benzonitrile: A flask containing a solution of 4-cyano-N'-(4-methoxyphenyl)benzohydrazonoyl bromide (416 mg, 1.121 mmol) and (S,E)-3-(but-2-enoyl)-4-phenyloxazolidin-2-one (300 mg, 1.271 mmol) in dioxane (16 mL) was evacuated and backfilled with Ar. Silver carbonate (877 mg, 3.15 mmol) was added to the solution and the resulting suspension was stirred and heated to 50° C. After stirring at this temperature for 14.5 h, the reaction mixture was cooled to rt and filtered through Celite. The filter cake was rinsed with EtOAc (120 mL) and, the combined filtrate and rinse were concentrated. The crude was chromatographed to afford 4-((4S,5R)-1-(4-methoxyphenyl)-4-methyl-5-((S)-2-oxo-4-phenyloxazolidine-3-carbonyl)-4,5-dihydro-1H-pyrazol-3-yl)benzonitrile (152 mg, 28% yield) as a yellow solid: LC-MS [M+H] 481. Further elution of the silica column gave a mixture of the diastereomers (270 mg, 50% yield) followed by 4-((4R,5S)-1-(4-methoxyphenyl)-4-methyl-5-((S)-2-oxo-4-phenyloxazolidine-3-carbonyl)-4,5-dihydro-1H-pyrazol-3-yl)benzonitrile (18 mg, 3% yield) as a yellow solid: LC-MS [M+H] 481.

91D. 4-((4S,5R)-5-(hydroxymethyl)-1-(4-methoxyphenyl)-4-methyl-4,5-dihydro-1H-pyrazol-3-yl)benzonitrile: To a solution of 4-((4S,5R)-1-(4-methoxyphenyl)-4-methyl-5-((S)-2-oxo-4-phenyloxazolidine-3-carbonyl)-4,5-dihydro- 1H-pyrazol-3-yl)benzonitrile (171 mg, 0.356 mmol) in THF (6.0 mL) at rt was added a solution of sodium borohydride (83 mg, 2.172 mmol) in water (1.2 mL). After stirring at rt for 4.4 h, the reaction mixture was cooled to 0° C. and quenched with 10% $KHSO_4$ (10 mL). The resulting aqueous mixture was allowed to warm up to rt and stirred for 2 h. The organic solvent was mostly evaporated under reduced pressure and the remaining aqueous mixture was extracted with $CH_2Cl_2$ (3×30 mL). The combined organic extracts were dried ($Na_2SO_4$) and concentrated. Chromatography of the crude afforded the desired product (138 mg, 99% yield) as a yellow oil: LC-MS [M+H] 322.

91E. ((4S,5R)-3-(4-cyanophenyl)-1-(4-methoxyphenyl)-4-methyl-4,5-dihydro-1H-pyrazol-5-yl)methyl methanesulfonate: To a solution of 4-((4S,5R)-5-(hydroxymethyl)-1-(4-methoxyphenyl)-4-methyl-4,5-dihydro-1H-pyrazol-3-yl)benzonitrile (138 mg, 0.35 mmol) and methanesulfonyl chloride (0.030 mL, 0.386 mmol) in $CH_2Cl_2$ (3.1 mL) at 0° C. was added triethylamine (0.078 mL, 0.557 mmol). The mixture was stirred for 30 min at 0° C. and for 3.2 h while warming to rt. Then, the mixture was diluted with EtOAc (50 mL) and washed with sat'd $NaHCO_3$ (2×30 mL) and sat'd NaCl (20 mL). The EtOAc solution was dried ($Na_2SO_4$) and evaporated. Drying under vacuum gave the desired product (154 mg, 91% yield) as a yellow oil: LC-MS [M+H] 400.

91F. 4-((4S,5S)-5-(cyanomethyl)-1-(4-methoxyphenyl)-4-methyl-4,5-dihydro-1H-pyrazol-3-yl)benzonitrile: To a solution of ((4S,5R)-3-(4-cyanophenyl)-1-(4-methoxyphenyl)-4-methyl-4,5-dihydro-1H-pyrazol-5-yl)methyl methanesulfonate (154 mg, 0.320 mmol) in DMSO (1.4 mL) was added potassium cyanide (25 mg, 0.372 mmol). The mixture was heated to 40° C. and stirred at this temperature for 12 h, the mixture was cooled to rt, diluted with 4/1 EtOAc/Hex (60 mL) and, washed with sat'd $NaHCO_3$ (2×30 mL), water (2×30 mL) and sat'd NaCl (30 mL). The organic layer was dried ($Na_2SO_4$) and concentrated. Purification via silica gel chromatography gave the desired product (94 mg, 87% yield) as a yellow oil: LC-MS [M+H] 331.

91G. 4-((4S,5S)-5-(cyanomethyl)-1-(4-hydroxyphenyl)-4-methyl-4,5-dihydro-1H-pyrazol-3-yl)benzonitrile: To a solution of 4-((4S,5S)-5-(cyanomethyl)-1-(4-methoxyphenyl)-4-methyl-4,5-dihydro-1H-pyrazol-3-yl)benzonitrile (93 mg, 0.28 mmol) in $CH_2Cl_2$ (0.8 mL) at 0° C. was added boron trifluoride-methyl sulfide complex (0.18 mL, 1.7 mmol). The reaction mixture was stirred at 0° C. for 20 min and then at rt for 2.7 h. The reaction mixture was cooled to 0° C. and the reaction was quenched with MeOH (6.0 mL) followed by AcCl (0.2 mL). The mixture was allowed to warm up to rt, stirred for 1.5 h and evaporated. The residue was taken up in EtOAc (50 mL) and, washed with 5% $NaHCO_3$ (2×25 mL) and sat'd NaCl (20 mL). The organic layer was dried ($Na_2SO_4$) and concentrated. Purification via silica gel chromatography provided the desired product (87 mg, 97% yield) as a yellow oil: LCMS [M+H] 317.

91H. 1-(2-fluoro-5-methoxyphenyl)piperidin-4-yl methanesulfonate: To a solution of 1-(2-fluoro-5-methoxyphenyl)piperidin-4-ol (146 mg, 0.62 mmol) and methanesulfonyl chloride (0.067 mL, 0.86 mmol) in $CH_2Cl_2$ (6.2 mL) at 0° C. was added triethylamine (0.18 mL, 1.285 mmol). The mixture was stirred for 30 min at 0° C. and for 5.0 h while warming to rt. Then, the mixture was diluted with EtOAc (60 mL) and washed with sat'd $NaHCO_3$ (2×30 mL) and sat'd NaCl (20 mL). The EtOAc solution was dried ($Na_2SO_4$) and evaporated. Drying under vacuum gave the desired product (180 mg, 93% yield) as a yellow solid: LC MS [M+H] 304.

91I. 4-((4S,5S)-5-(cyanomethyl)-1-(4-((1-(2-fluoro-5-methoxyphenyl)piperidin-4-yl)oxy)phenyl)-4-methyl-4,5-dihydro-1H-pyrazol-3-yl)benzonitrile: To a solution of 4-((4S,5S)-5-(cyanomethyl)-1-(4-hydroxyphenyl)-4-methyl-4,5-dihydro-1H-pyrazol-3-yl)benzonitrile (41 mg, 0.128 mmol) in DMF (0.25 mL) were added potassium carbonate (powder, 30 mg, 0.215 mmol) and 1-(2-fluoro-5-methoxyphenyl)piperidin-4-yl methanesulfonate (61 mg, 0.195 mmol). The mixture was heated to 85° C. and stirred at this temperature for 24 h. Then, the mixture was cooled to rt, diluted with 1/1 EtOAc/Hex (60 mL) and, washed with 5% NaHCO3 (2×30 mL), water (30 mL) and sat'd NaCl (20 mL). The organic layer was dried ($Na_2SO_4$) and evaporated. Purification by two consecutive chromatographies (SiO2, first 95/5 $CH_2Cl_2$/Ether and then 7/3 Hex/EtOAc) afforded the desired product (23 mg, 32.5% yield) as a yellow oil: LCMS [M+H] 524.

91J. methyl 2-((4S,5S)-3-(4-cyanophenyl)-1-(4-((1-(2-fluoro-5-methoxyphenyl)piperidin-4-yl)oxy)phenyl)-4-methyl-4,5-dihydro-1H-pyrazol-5-yl)acetate and methyl 4-((4S,5S)-1-(4-((1-(2-fluoro-5-methoxyphenyl)piperidin-4-yl)oxy)phenyl)-5-(2-methoxy-2-oxoethyl)-4-methyl-4,5-dihydro-1H-pyrazol-3-yl)benzoate: 4-((4S,5S)-5-(cyanomethyl)-1-(4-((1-(2-fluoro-5-methoxyphenyl)piperidin-4-yl)oxy)phenyl)-4-methyl-4,5-dihydro-1H-pyrazol-3-yl)benzonitrile: (22 mg, 0.040 mmol) was dissolved in ~3M HCl/MeOH, MeOAc, $CH_2Cl_2$ solution [6.3 mL, prepared by addition of AcCl (1.3 mL) to 3/2 $CH_2Cl_2$/MeOH (5.0 mL) at 0° C. and then stirring at rt for 30 min]. The resulting solution was stirred at rt for 12.0 h, then diluted with MeCN (6 mL) and evaporated. The residue was taken up in EtOAc (50 mL) and, washed with 5% $NaHCO_3$ (2×30 mL) and sat'd NaCl (20 mL). The crude was purified by preparative RP-HPLC. Fractions containing the slower moving component were combined, basified with solid $NaHCO_3$ and partially evaporated at rt to remove most of the MeCN. The remaining aqueous mixture was extracted with $CH_2Cl_2$ (3×30 mL) and, the combined extracts were dried ($Na_2SO_4$) and concentrated. Drying under vacuum provided methyl 2-((4S,5S)-3-(4-cyanophenyl)-1-(4-((1-(2-fluoro-5-methoxyphenyl)piperidin-4-yl)oxy)phenyl)-4-methyl-4,5-dihydro-1H-pyrazol-5-yl)acetate (6 mg, 27% yield) as a yellow solid: LC-MS [M+H] 557. Fractions containing the faster moving component were combined, basified with solid $NaHCO_3$ and partially evaporated at rt to remove most of the MeCN. The remaining aqueous mixture was extracted with $CH_2Cl_2$ (3×30 mL) and, the combined extracts were dried ($Na_2SO_4$) and evaporated. The concentrate was dissolved in 1/1 $CH_2Cl_2$/MeOH (4.0 mL) and allowed to stand at rt for 7 days to enable conversion to a slower moving derivative. The solution was concentrated to give methyl 4-((4S,5S)-1-(4-((1-(2-fluoro-5-methoxyphenyl)piperidin-4-yl)oxy)phenyl)-5-(2-methoxy-2-oxoethyl)-4-methyl-4,5-dihydro-1H-pyrazol-3-yl)benzoate (10 mg, 0.015 mmol, 36.3% yield) as a yellow solid: LC-MS [M+H] 590.

Example 91: To a stirred solution of methyl 2-((4S,5S)-3-(4-cyanophenyl)-1-(4-((1-(2-fluoro-5-methoxyphenyl)piperidin-4-yl)oxy)phenyl)-4-methyl-4,5-dihydro-1H-pyrazol-5-yl)acetate (6.0 mg, 10 μmol) in THF (0.4 mL) and water (0.04 mL) at rt was added LOM aqueous lithium hydroxide (0.03 mL, 0.030 mmol). After stirring at rt for 5.0 h, the reaction mixture was partially evaporated to remove most of the THF. The remaining solution was partitioned between water (30 mL) and Hex (10 mL). The aqueous layer was acidified to pH 2 by dropwise addition of 1M HCl, and extracted with $CH_2Cl_2$ (3×30 mL). The combined organic extracts were dried ($Na_2SO_4$) and concentrated. The crude (5.5 mg) was purified by preparative RP-HPLC. Fractions containing the desired acid were combined and partially evaporated at rt to remove most of the MeCN. The remaining aqueous mixture was extracted with $CH_2Cl_2$ (3×30 mL) and, the combined extracts were dried ($Na_2SO_4$) and evaporated. Drying under vacuum afforded the desired product (3.5 mg, 51.5% yield) as a yellow solid: HPLC-50% start B (RT 6.75, Area % 100); LC-MS [M+H] 543. $^1$H NMR (400 MHz, $CD_2Cl_2$) δ 7.82 (d, J=8.0 Hz, 2H), 7.66 (d, J=8.0 Hz, 2H), 7.14 (m, 2H), 6.96 (m, 3H), 6.69 (m, 1H), 6.50 (dt, J=8.9, 3.0 Hz, 1H), 4.44 (m, 2H), 3.77 (s, 3H), 3.43 (m, 3H), 3.05 (m, 2H), 2.83 (d, J=16.2 Hz, 1H), 2.41 (dd, J=16.2, 10.6 Hz, 1H), 2.17 (m, 2H), 1.99 (m, 2H), 1.32 (d, J=7.2 Hz, 3H). Analytical HPLC (Zorbax method, 50% Solvent B start): RT=6.75 min, HI: 100%. hGPR40 $EC_{50}$=62 nM.

EXAMPLE 92

2-((4S,5S)-1-(4-((1-(2-fluoro-5-methoxyphenyl)piperidin-4-yl)oxy)phenyl)-3-(4-(methoxycarbonyl)phenyl)-4-methyl-4,5-dihydro-1H-pyrazol-5-yl)acetic acid, TFA

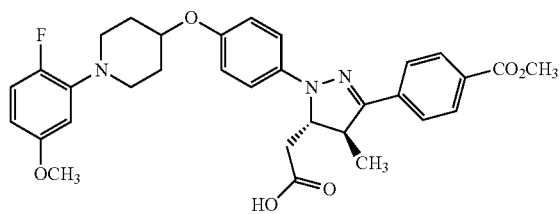 [SMILES: COC(=O)c1ccc(C2=NN(c3ccc(OC4CCN(c5cc(OC)ccc5F)CC4)cc3)[C@@H](CC(=O)O)[C@@H]2C)cc1]

To a stirred solution of methyl 4-((4S,5S)-1-(4-((1-(2-fluoro-5-methoxyphenyl)piperidin-4-yl)oxy)phenyl)-5-(2-methoxy-2-oxoethyl)-4-methyl-4,5-dihydro-1H-pyrazol-3-yl)benzoate (10 mg, 0.015 mmol) in THF (0.5 mL) and water (0.04 mL) at rt was added LOM aqueous lithium hydroxide (0.03 mL, 0.03 mmol). After stirring at rt for 2.4 h, the mixture was cooled to 0° C. and acidified with 1M HCl (0.04 mL). The aqueous mixture was partitioned between $CH_2Cl_2$ (40 mL) and water (15 mL). The aqueous layer pH was adjusted to 2 by dropwise addition of 1M HCl and the biphasic mixture was shaken. The organic layer was collected and the aqueous layer was extracted with $CH_2Cl_2$ (2×20 mL). The combined organic layers were dried ($Na_2SO_4$) and evaporated. The crude (8 mg) was purified by preparative RP-HPLC. Fractions containing the desired acid were combined and partially evaporated at rt to remove most of the MeCN. The remaining aqueous mixture was extracted with $CH_2Cl_2$ (3×30 mL) and, the combined extracts were dried ($Na_2SO_4$) and evaporated. Drying under vacuum afforded 2-((4S,5S)-1-(4-((1-(2-fluoro-5-methoxyphenyl)piperidin-4-yl)oxy)phenyl)-3-(4-(methoxycarbonyl)phenyl)-4-methyl-4,5-dihydro-1H-pyrazol-5-yl)acetic acid, TFA (5.0 mg, 49.0% yield) as a yellow solid: LC-MS [M+H] 576. $^1$H NMR (500 MHz, $CD_2Cl_2$) δ 8.03 (d, J=8.6 Hz, 2H), 7.81 (d, J=8.6 Hz, 2H), 7.15 (d, J=8.9 Hz, 2H), 7.01 (dd, J=12.1, 9.0 Hz, 1H), 6.96 (d, J=8.9 Hz, 2H), 6.81 (m, 1H), 6.58 (dt, J=9.0, 3.0 Hz, 1H), 4.45 (m, 2H), 3.90 (s, 3H), 3.77 (s, 3H), 3.55 (m, 2H), 3.47 (m, 1H), 3.14 (m, 2H), 2.83 (dd, J=16.3, 2.8 Hz, 1H), 2.40 (dd, J=16.3, 10.4 Hz, 1H), 2.23 (m, 2H), 2.03 (m, 2H), 1.33 (d, J=7.1 Hz, 3H). Analytical HPLC (Zorbax method, 50% Solvent B start): RT=7.28 min, HI: 99%. hGPR40 $EC_{50}$=139 nM.

EXAMPLE 93

2-((4S,5S)-3-(4-cyanophenyl)-1-(4-((1-(5-ethoxy-2-fluorophenyl)piperidin-4-yl)oxy)phenyl)-4-methyl-4,5-dihydro-1H-pyrazol-5-yl)acetic acid

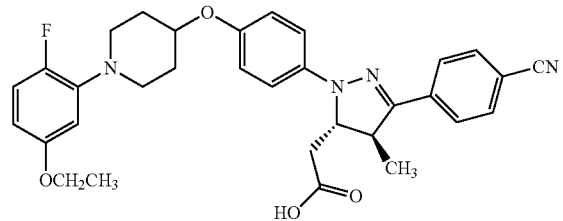 [SMILES: CCOc1ccc(F)c(N2CCC(Oc3ccc(N4N=C(c5ccc(C#N)cc5)[C@@H](C)[C@@H]4CC(=O)O)cc3)CC2)c1]

93A. 1-(5-ethoxy-2-fluorophenyl)piperidin-4-ol: A mixture of piperidin-4-ol (607 mg, 5.88 mmol), 4-ethoxy-1,2-difluorobenzene (0.4 mL, 2.83 mmol), pyridine (0.6 mL) and DMSO (1.2 mL) was heated at 160° C. in a microwave reactor for 20 h. Then, the mixture was partitioned between 1/4 Hex/EtOAc (50 mL) and 2% $NaHCO_3$ (30 mL). The organic layer was washed with 2% $NaHCO_3$ (2×20 mL) and sat'd NaCl (20 mL), dried ($Na_2SO_4$) and evaporated. Purification via silica gel chromatography (3/2 Hex/EtOAc) gave the desired product (222 mg, 32.1% yield) as a colorless oil: LCMS [M+H] 240.

93B. 4-((4S,5S)-5-(cyanomethyl)-1-(4-((1-(5-ethoxy-2-fluorophenyl)piperidin-4-yl)oxy)phenyl)-4-methyl-4,5-dihydro-1H-pyrazol-3-yl)benzonitrile: To a stirred solution of 4-((4S,5S)-5-(cyanomethyl)-1-(4-hydroxyphenyl)-4-methyl-4,5-dihydro-1H-pyrazol-3-yl)benzonitrile (310 mg, 0.970 mmol), 1-(5-ethoxy-2-fluorophenyl)piperidin-4-ol (368 mg, 1.492 mmol) and triphenylphosphine (420 mg, 1.585 mmol) in THF (5.8 mL) at rt was added di-tert-butylazodicarboxylate (375 mg, 1.596 mmol). The resulting solution was stirred at rt for 25 h and then evaporated. The residue was purified by two consecutive chromatographies ($SiO_2$, first 95/5 $CHCl_3$/Ether and then 4/1 to 3/2 Hex/EtOAc) to give the desired product (390 mg, 74.0% yield) as a yellow oil: LC-MS [M+H] 538.

93C. methyl 2-((4S,5S)-3-(4-cyanophenyl)-1-(4-((1-(5-ethoxy-2-fluorophenyl)piperidin-4-yl)oxy)phenyl)-4-methyl-4,5-dihydro-1H-pyrazol-5-yl)acetate: 4-((4S,5S)-5-(cyanomethyl)-1-(4-((1-(5-ethoxy-2-fluorophenyl)piperidin-4-yl)oxy)phenyl)-4-methyl-4,5-dihydro-1H-pyrazol-3-yl)benzonitrile (389 mg, 0.716 mmol) was dissolved in ~2.5M HCl/MeOH, MeOAc, $CH_2Cl_2$ solution [36.6 mL, prepared by addition of AcCl (6.6 mL) to 3/2 $CH_2Cl_2$/MeOH (30.0 mL) at 0° C. and then stirring at rt for 30 min]. The resulting solution was stirred at rt for 6.5 h and then evaporated to a volume of about 5 mL. The oily remnant was stripped from MeOH (2×20 mL), taken up in EtOAc (100 mL) and, washed with 5% $NaHCO_3$ (2×50 mL) and sat'd NaCl (40 mL). The organic layer was dried ($Na_2SO_4$) and concentrated. Purification via silica gel chromatography provided the desired (75 mg, 18% yield) as a yellow oil: LC-MS [M+H] 571.

Example 93: To a stirred solution of methyl 2-((4S,5S)-3-(4-cyanophenyl)-1-(4-((1-(5-ethoxy-2-fluorophenyl)piperidin-4-yl)oxy)phenyl)-4-methyl-4,5-dihydro-1H-pyrazol-5-yl)acetate (17 mg, 0.03 mmol) in THF (0.9 mL) and water (0.09 mL) at rt was added 1.0M aqueous lithium hydroxide (0.09 mL, 0.09 mmol). After stirring at rt for 4.5 h, the reaction mixture was partially evaporated to remove most of the THF. The remaining mixture was partitioned between water (50 mL) and Hex (15 mL). The aqueous layer was acidified to pH 2 by dropwise addition of 1M HCl, and then extracted with $CH_2Cl_2$ (3×30 mL). The combined organic extracts were dried ($Na_2SO_4$) and concentrated. The residue was dried under vacuum to afford the desired product (16.7 mg, 92% yield) as a yellow solid: LC-MS [M+H] 557. $^1$H NMR (500 MHz, $CD_2Cl_2$) δ 7.82 (d, J=8.2 Hz, 2H), 7.66 (d, J=8.2 Hz, 2H), 7.14 (d, J=8.8 Hz, 2H), 6.95 (d, J=8.8 Hz, 2H), 6.91 (dd, J=12.1, 8.8 Hz, 1H), 6.55 (m, 1H), 6.41 (m, 1H), 4.48 (d, J=9.6 Hz, 1H), 4.38 (m, 1H), 3.97 (q, J=7.0 Hz, 2H), 3.44 (m, 1H), 3.35 (m, 2H), 2.96 (m, 2H), 2.85 (dd, J=16.3, 2.8 Hz, 1H), 2.41 (dd, J=16.3, 10.5 Hz, 1H), 2.11 (m, 2H), 1.95 (m, 2H), 1.37 (t, J=7.0 Hz, 3H), 1.32 (d, J=7.2 Hz, 3H). Analytical HPLC (Zorbax method, 0% Solvent B start): RT=8.23 min, HI: 98%. hGPR40 $EC_{50}$=82 nM. hGPR40 IP1 $EC_{50}$=7 nM. Acute oral glucose tolerance: −56% @ 0.3 mg/kg.

EXAMPLE 94

2-((4S,5S)-3-(4-cyano-2-fluorophenyl)-1-(4-((1-(5-ethoxy-2-fluorophenyl)piperidin-4-yl)oxy)phenyl)-4-methyl-4,5-dihydro-1H-pyrazol-5-yl)acetic acid

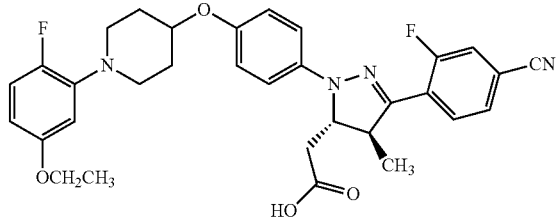 [SMILES: CCOc1ccc(F)c(N2CCC(Oc3ccc(N4N=C(c5ccc(C#N)cc5F)[C@@H](C)[C@@H]4CC(=O)O)cc3)CC2)c1]

94A. 4-((4S,5S)-5-(cyanomethyl)-1-(4-hydroxyphenyl)-4-methyl-4,5-dihydro-1H-pyrazol-3-yl)-3-fluorobenzonitrile was prepared from 3-fluoro-4-formylbenzonitrile following the procedure for the preparation of 4-((4S,5S)-5-(cyanomethyl)-1-(4-hydroxyphenyl)-4-methyl-4,5-dihydro-1H-pyrazol-3-yl)benzonitrile (91G): LC-MS [M+H] 335.

Example 94 (yellow solid, 11.7 mg) was prepared from 4-((4S,5S)-5-(cyanomethyl)-1-(4-hydroxyphenyl)-4-methyl-4,5-dihydro-1H-pyrazol-3-yl)-3-fluorobenzonitrile following the procedure for Example 93 but purification of the final acid was achieved by acidification of the reaction mixture, extraction with $CH_2Cl_2$ and chromatography ($SiO_2$, 95/5 $CHCl_3$/MeOH). LC-MS [M+H] 575. $^1$H NMR (500 MHz, $CD_2Cl_2$) δ 8.16 (t, J=8.0 Hz, 1H), 7.49 (dd, J=8.2, 1.6 Hz, 1H), 7.44 (dd, J=11.2, 1.6 Hz, 1H), 7.18 (d, J=9.0 Hz, 2H), 6.99 (d, J=9.0 Hz, 2H), 6.95 (dd, J=12.4, 8.8 Hz, 1H), 6.55 (dd, J=7.4, 3.0 Hz, 1H), 6.44 (dt, J=8.8, 3.0 Hz, 1H), 4.53 (d, J=10.3, 2.6 Hz, 1H), 4.42 (m, 1H), 4.01 (q, J=7.0 Hz, 2H), 3.58 (m, 1H), 3.37 (m, 2H), 2.99 (m, 2H), 2.89 (dd, J=16.3, 2.9 Hz, 1H), 2.49 (dd, J=16.3, 10.3 Hz, 1H), 2.14 (m, 2H), 1.97 (m, 2H), 1.41 (t, J=7.0 Hz, 3H). 1.32 (d, J=7.2 Hz, 3H). Analytical HPLC (Zorbax method, 0% Solvent B start): RT=8.16 min, HI: 100%. hGPR40 $EC_{50}$=59 nM.

EXAMPLE 95

2-((4S,5S)-1-(4-((1-(5-ethoxy-2-fluorophenyl)piperidin-4-yl)oxy)phenyl)-3-(4-fluorophenyl)-4-methyl-4,5-dihydro-1H-pyrazol-5-yl)acetic acid

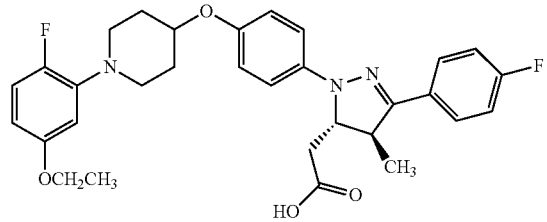 [SMILES: CCOc1ccc(F)c(N2CCC(Oc3ccc(N4N=C(c5ccc(F)cc5)[C@@H](C)[C@@H]4CC(=O)O)cc3)CC2)c1]

95A. 2-((4S,5S)-1-(4-bromophenyl)-3-(4-fluorophenyl)-4-methyl-4,5-dihydro-1H-pyrazol-5-yl)acetonitrile was prepared from 4-fluorobenzaldehyde and (4-bromophenyl)hydrazine following the procedure for the preparation of 4-((4S,5S)-5-(cyanomethyl)-1-(4-methoxyphenyl)-4-methyl-4,5-dihydro-1H-pyrazol-3-yl)benzonitrile (example 91G). LC-MS [M+H] 372, 374.

95B. 2-((4S,5S)-3-(4-fluorophenyl)-4-methyl-1-(4-(4,4,5,5-tetramethyl-1,3,2-dioxaborolan-2-yl)phenyl)-4,5-dihydro-1H-pyrazol-5-yl)acetonitrile: To a stirred solution of 2-((4S,5S)-1-(4-bromophenyl)-3-(4-fluorophenyl)-4-methyl-4,5-dihydro-1H-pyrazol-5-yl)acetonitrile (511 mg, 1.373 mmol) in DMF (15 mL) was added 4,4,4',4',5,5,5',5'-octamethyl-2,2'-bi(1,3,2-dioxaborolane) (558 mg, 2.196 mmol), potassium acetate (404 mg, 4.12 mmol) and 1,1'-bis(diphenylphosphino)ferrocenepalladium(II) dichloride dichloromethane complex, (56.5 mg, 0.069 mmol). The resulting reaction mixture was purged with argon three times and then heated to 80° C. After stirring at this temperature overnight, the reaction mixture was cooled to rt, diluted with water and extracted with $CH_2Cl_2$. The combined organic extracts were washed with sat'd NaCl, dried ($Na_2SO_4$) and purified via silica gel chromatography to afford the desired product (447 mg, 72.2% yield) as a yellowish solid: LC-MS [M+H] 420.

95C. 2-((4S,5S)-3-(4-fluorophenyl)-1-(4-hydroxyphenyl)-4-methyl-4,5-dihydro-1H-pyrazol-5-yl)acetonitrile: To a stirred solution of 2-((4S,5S)-3-(4-fluorophenyl)-4-methyl-1-(4-(4,4,5,5-tetramethyl-1,3,2-dioxaborolan-2-yl)phenyl)-4,5-dihydro-1H-pyrazol-5-yl)acetonitrile (447 mg, 0.991 mmol) in ethyl acetate (10.0 mL) at rt was added 30% hydrogen peroxide (3.04 mL, 29.7 mmol) over 2 min. The resulting solution was stirred at rt for 5 h. At this time, the reaction mixture was cooled to 0° C. and quenched by slow addition of aqueous sodium sulfite solution. The aqueous mixture was diluted with water and extracted with $CH_2Cl_2$. The combined organic extract was dried ($Na_2SO_4$), concentrated and purified via silica gel chromatography (0 to 60% EtOAc/Hex) to provide the desired product (226 mg, 73.7% yield) as a dark solid: LC-MS [M+H] 310.

Example 95 (yellowish solid, 10 mg) was prepared from 2-((4S,5S)-3-(4-fluorophenyl)-1-(4-hydroxyphenyl)-4-methyl-4,5-dihydro-1H-pyrazol-5-yl)acetonitrile following the procedure for Example 93. The resulting TFA salt was treated with an equivalent amount of LiOH, diluted with water and the pH of the aqueous mixture was adjusted to 2 by dropwise addition of 1M HCl. The aqueous mixture was extracted with $CH_2Cl_2$ and, the organic extract was dried ($Na_2SO_4$) and concentrated. LC-MS [M+H] 550. $^1$H NMR (400 MHz, CDCl$_3$) δ 7.72 (m, 2H), 7.09 (m, 4H), 6.92 (m, 3H), 6.55 (m, 1H), 6.40 (m, 1H), 4.38 (m, 2H), 3.99 (q, J=7.0 Hz, 2H), 3.36 (m, 3H), 2.97 (m, 2H), 2.84 (dd, J=16.0, 2.9 Hz, 1H), 2.36 (dd, J=16.0, 10.5 Hz, 1H), 2.11 (m, 2H), 1.98 (m, 2H), 1.40 (t, J=7.0 Hz, 3H), 1.32 (d, J=7.1 Hz, 3H). Analytical HPLC (Zorbax method, 0% Solvent B start): RT=8.81 min, HI: 97%. hGPR40 EC$_{50}$=108 nM.

EXAMPLE 96

2-((4S,5S)-3-(3,4-dicyanophenyl)-1-(4-((1-(5-ethoxy-2-fluorophenyl)piperidin-4-yl)oxy)phenyl)-4-methyl-4,5-dihydro-1H-pyrazol-5-yl)acetic acid

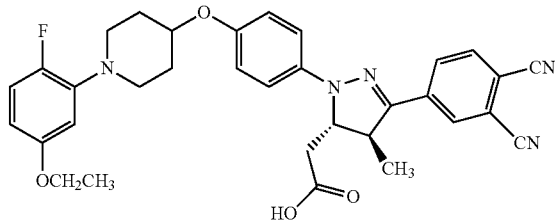 [SMILES: CCOc1ccc(F)c(N2CCC(Oc3ccc(N4N=C(c5ccc(C#N)c(C#N)c5)[C@@H](C)[C@@H]4CC(=O)O)cc3)CC2)c1]

96A. 4-((4S,5S)-1-(4-bromophenyl)-5-(cyanomethyl)-4-methyl-4,5-dihydro-1H-pyrazol-3-yl)phthalonitrile was prepared from 2-fluoro-5-formylbenzonitrile and (4-bromophenyl)hydrazine following the procedure for the preparation of 4-((4S,5S)-5-(cyanomethyl)-1-(4-methoxyphenyl)-4-methyl-4,5-dihydro-1H-pyrazol-3-yl)benzonitrile (example 91G) but 3 equivalents of potassium cyanide were used in the last step. LC-MS [M+H] 404, 406.

96B. methyl 2-((4S,5S)-1-(4-bromophenyl)-3-(3,4-dicyanophenyl)-4-methyl-4,5-dihydro-1H-pyrazol-5-yl)acetate: 4-((4S,5S)-1-(4-bromophenyl)-5-(cyanomethyl)-4-methyl-4,5-dihydro-1H-pyrazol-3-yl)phthalonitrile (2.10 g, 5.19 mmol) was dissolved in ~3.0M HCl/CH$_2$Cl$_2$, MeOH, MeOAc, solution [42 mL, prepared by addition of AcCl (9.0 mL) to 6/5 CH$_2$Cl$_2$/MeOH (33 mL) at 0° C. and then stirring at rt for 30 min]. The resulting solution was stirred at rt overnight and then evaporated. The residue was taken up in EtOAc and, washed with sat'd NaHCO$_3$ and water. The organic layer was dried (Na$_2$SO$_4$) and concentrated. Purification via silica gel chromatography provided the desired product (800 mg, 35% yield) as an orange solid: LC-MS [M+H] 437, 439.

96C. methyl 2-((4S,5S)-3-(3,4-dicyanophenyl)-4-methyl-1-(4-(4,4,5,5-tetramethyl-1,3,2-dioxaborolan-2-yl)phenyl)-4,5-dihydro-1H-pyrazol-5-yl)acetate: To a stirred solution of methyl 2-((4S,5S)-1-(4-bromophenyl)-3-(3,4-dicyanophenyl)-4-methyl-4,5-dihydro-1H-pyrazol-5-yl)acetate (800 mg, 1.829 mmol) in DMF (20 mL) was added 4,4,4',4',5,5,5',5'-octamethyl-2,2'-bi(1,3,2-dioxaborolane) (743 mg, 2.93 mmol), potassium acetate (539 mg, 5.49 mmol) and 1,1'-Bis(diphenylphosphino)ferrocenepalladium(II) dichloride, dichloromethane complex) (151 mg, 0.183 mmol). The resulting reaction mixture was purged with argon three times and then heated to 80° C. After stirring at this temperature overnight, the reaction mixture was cooled to rt, diluted with water and extracted with CH$_2$Cl$_2$. The combined organic extracts were washed with sat'd NaCl, dried (Na$_2$SO$_4$) and purified via silica gel chromatography (0 to 50% EtOAc/Hex) to afford the desired product (777 mg, 88% yield) as an orangish solid: LC-MS [M+H] 485.

96D. methyl 2-((4S,5S)-3-(3,4-dicyanophenyl)-1-(4-hydroxyphenyl)-4-methyl-4,5-dihydro-1H-pyrazol-5-yl)acetate: To a stirred solution of methyl 2-((4S,5S)-3-(3,4-dicyanophenyl)-4-methyl-1-(4-(4,4,5,5-tetramethyl-1,3,2-dioxaborolan-2-yl)phenyl)-4,5-dihydro-1H-pyrazol-5-yl)acetate (820 mg, 1.7 mmol) in ethyl acetate (10 mL) at rt was added 30% hydrogen peroxide (5.2 mL, 51 mmol) over 2 min. The resulting solution was stirred at rt for 3 h. At this time, the reaction mixture was cooled to 0° C. and quenched by slow addition of aqueous sodium sulfite solution. The aqueous mixture was diluted with water and extracted with CH$_2$Cl$_2$. The combined organic extract was dried (Na$_2$SO$_4$), concentrated and purified via silica gel chromatography to provide the desired product (538 mg, 85% yield) as a dark reddish oil: LC-MS [M+H] 375.

96E. methyl 2-((4S,5S)-3-(3,4-dicyanophenyl)-1-(4-((1-(5-ethoxy-2-fluorophenyl)piperidin-4-yl)oxy)phenyl)-4-methyl-4,5-dihydro-1H-pyrazol-5-yl)acetate: To a stirred solution of 1-(5-ethoxy-2-fluorophenyl)piperidin-4-ol (54 mg, 0.22 mmol), methyl 2-((4S,5S)-3-(3,4-dicyanophenyl)-1-(4-hydroxyphenyl)-4-methyl-4,5-dihydro-1H-pyrazol-5-yl)acetate (70 mg, 0.187 mmol) and triphenylphosphine (74 mg, 0.280 mmol) in THF (1.5 mL) at rt was added di-tert-butyl azodicarboxylate (65 mg, 0.280 mmol). The resulting solution was stirred at rt overnight and then evaporated. Purification via silica gel chromatography followed by preparative RP-HPLC. Fractions containing the product were combined and treated with sat'd NaHCO$_3$. The aqueous mixture was extracted with CH$_2$Cl$_2$ and the organic extract was dried (Na$_2$SO$_4$) and concentrated to give the desired product (17 mg, 15% yield) as an orangish solid: LC-MS [M+H] 596.

Example 96: To a solution of methyl 2-((4S,5S)-3-(3,4-dicyanophenyl)-1-(4-((1-(5-ethoxy-2-fluorophenyl)piperidin-4-yl)oxy)phenyl)-4-methyl-4,5-dihydro-1H-pyrazol-5-yl)acetate (62 mg, 0.104 mmol) in THF (2.0 mL) was added 1M lithium hydroxide (0.42 mL, 0.42 mmol). The resulting mixture was stirred at rt overnight and then diluted with water. The pH of the resulting aqueous mixture was adjusted to 2 by dropwise addition of 1M HCl, and the aqueous mixture was extracted with CH$_2$Cl$_2$. The organic extract was dried (Na$_2$SO$_4$), and concentrated to afford the desired product (3 mg, 5% yield) as an orange solid: LC-MS [M+H] 582. $^1$H NMR (400 MHz, CDCl$_3$, selected peaks) δ 8.11 (d, J=1.7 Hz, 1H), 7.93 (dd, J=8.3, 1.7 Hz, 1H), 7.75 (d, J=8.3 Hz, 1H), 7.16 (d, J=9.0 Hz, 2H), 6.98 (m, 1H, overlapped), 6.97 (d, J=9.0 Hz, 2H), 6.81-6.30 (m, 2H) 4.53 (m, 1H), 3.99 (m, 3H), 3.40 (m, 1H), 2.87 (dd, J=16.4, 2.9 Hz, 1H), 2.40 (dd, J=16.4, 10.5 Hz, 1H), 1.40 (t, J=7.0 Hz, 3H), 1.33 (d, J=7.1 Hz, 3H). Analytical HPLC (Zorbax method, 50% Solvent B start): RT=7.54 min, HI: 98%. hGPR40 EC$_{50}$=1575 nM.

EXAMPLE 97

2-((4S,5S)-3-(3,4-difluorophenyl)-1-(4-((1-(5-ethoxy-2,3-difluorophenyl)piperidin-4-yl)oxy)phenyl)-4-methyl-4,5-dihydro-1H-pyrazol-5-yl)acetic acid

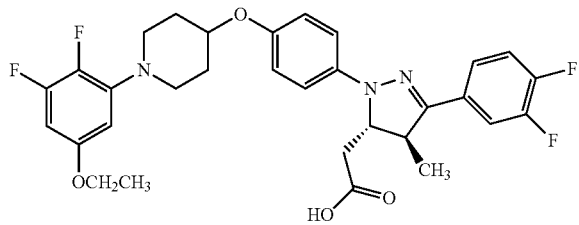 [SMILES: CCOc1cc(F)c(F)c(N2CCC(Oc3ccc(N4N=C(c5ccc(F)c(F)c5)[C@@H](C)[C@@H]4CC(=O)O)cc3)CC2)c1]

97A. 2-((4R,5R)-1-(4-bromophenyl)-3-(3,4-difluorophenyl)-4-methyl-4,5-dihydro-1H-pyrazol-5-yl)acetonitrile was prepared from 3,4-difluorobenzaldehyde and (4-bromophenyl)hydrazine following the procedure for the preparation of 4-((4S,5S)-5-(cyanomethyl)-1-(4-methoxyphenyl)-4-methyl-4,5-dihydro-1H-pyrazol-3-yl)benzonitrile (example 90G). LC-MS [M+H] 390, 392.

97B. 2-((4R,5R)-3-(3,4-difluorophenyl)-1-(4-hydroxyphenyl)-4-methyl-4,5-dihydro-1H-pyrazol-5-yl)acetonitrile was prepared from 2-((4R,5R)-1-(4-bromophenyl)-3-(3,4-difluorophenyl)-4-methyl-4,5-dihydro-1H-pyrazol-5-yl)acetonitrile following the procedure for the preparation of 2-((4S,5S)-3-(4-fluorophenyl)-1-(4-hydroxyphenyl)-4-methyl-4,5-dihydro-1H-pyrazol-5-yl)acetonitrile (example 95B). LC-MS [M+H] 328.

97C. 1-(5-ethoxy-2,3-difluorophenyl)piperidin-4-yl 4-methylbenzenesulfonate: To a stirred solution of 1-(5-ethoxy-2,3-difluorophenyl)piperidin-4-ol (0.911 g, 3.54 mmol) in CH$_2$Cl$_2$ (20 mL) was added 4-methylbenzene-1-sulfonyl chloride (0.81 g, 4.25 mmol) and pyridine (1.43 mL, 17.7 mmol). The resulting reaction mixture was stirred at rt overnight and then, diluted with water and extracted with CH$_2$Cl$_2$. The organic extract was dried (Na$_2$SO$_4$) and concentrated. Purification via silica gel chromatography provided the desired product (1.06 g, 73% yield) as a white solid: LC-MS [M+H] 412, 414.

97D. 2-((4R,5R)-3-(3,4-difluorophenyl)-1-(4-((1-(5-ethoxy-2,3-difluorophenyl)piperidin-4-yl)oxy)phenyl)-4-methyl-4,5-dihydro-1H-pyrazol-5-yl)acetonitrile: To a stirred solution of 2-((4R,5R)-3-(3,4-difluorophenyl)-1-(4-hydroxyphenyl)-4-methyl-4,5-dihydro-1H-pyrazol-5-yl)acetonitrile (84 mg, 0.218 mmol) in DMF (3.0 mL) was added 1-(5-ethoxy-2,3-difluorophenyl)piperidin-4-yl 4-methylbenzenesulfonate (108 mg, 0.262 mmol) and cesium carbonate (213 mg, 0.654 mmol). The mixture was heated to 50° C. and stirred at this temperature overnight. Then, the reaction mixture was cooled to rt, diluted with water and extracted with CH$_2$Cl$_2$. The organic extract was dried (Na$_2$SO$_4$), concentrated and the crude was purified via silica gel chromatography to afford the desired product (62 mg, 48% yield) as a yellow oil: LC-MS [M+H] 567.

97E. methyl 2-((4R,5R)-3-(3,4-difluorophenyl)-1-(4-((1-(5-ethoxy-2,3-difluorophenyl)piperidin-4-yl)oxy)phenyl)-4-methyl-4,5-dihydro-1H-pyrazol-5-yl)acetate: 2-((4R,5R)-3-(3,4-difluorophenyl)-1-(4-((1-(5-ethoxy-2,3-difluorophenyl)piperidin-4-yl)oxy)phenyl)-4-methyl-4,5-dihydro-1H-pyrazol-5-yl)acetonitrile (62 mg, 0.104 mmol) was dissolved in ~3.0M HCl/CH$_2$Cl$_2$, MeOH, MeOAc, solution [6.9 mL, prepared by addition of AcCl (1.4 mL) to 9/2 CH$_2$Cl$_2$/MeOH (5.5 mL) at 0° C. and then stirring at rt for 1 h]. The resulting solution was allowed to stand at rt overnight and then evaporated. The residue was purified via silica gel chromatography to give the desired product (38 mg, 0.056 mmol, 53.6% yield) as a yellow oil: LC-MS [M+H] 600.

Example 97: To a stirred solution of methyl 2-((4R,5R)-3-(3,4-difluorophenyl)-1-(4-((1-(5-ethoxy-2,3-difluorophenyl)piperidin-4-yl)oxy)phenyl)-4-methyl-4,5-dihydro-1H-pyrazol-5-yl)acetate (62 mg, 0.103 mmol) in THF (2.0 mL) was added 0.5M aqueous lithium hydroxide (0.42 mL, 0.21 mmol). The mixture was stirred at rt for 3 h and then diluted with water. The pH of the resulting aqueous mixture was adjusted to 2 by dropwise addition of 1M HCl and extracted with CH$_2$Cl$_2$. The organic extract was concentrated and the residue was purified by preparative RP-HPLC. Fractions containing the desired acid were combined and extracted with CH$_2$Cl$_2$. The organic extract was dried (Na$_2$SO$_4$) and evaporated The resulting TFA salt was treated with an equivalent amount of LiOH, diluted with water and the pH of the aqueous mixture was adjusted to 2 by dropwise addition of 1M HCl. The aqueous mixture was extracted with CH$_2$Cl$_2$ and, the organic extract was dried (Na$_2$SO$_4$) and concentrated to afford 2-((4S,5S)-3-(3,4-difluorophenyl)-1-(4-((1-(5-ethoxy-2,3-difluorophenyl)piperidin-4-yl)oxy)phenyl)-4-methyl-4,5-dihydro-1H-pyrazol-5-yl)acetic acid (5.0 mg, 7.8% yield) as a yellow solid: LC-MS [M+H] 586. $^1$H NMR (400 MHz, CDCl$_3$) δ 7.60 (m, 1H), 7.39 (m, 1H), 7.16 (m, 1H), 7.10 (d, J=9.1 Hz, 2H), 6.93 (d, J=9.1 Hz, 2H), 6.70-6.26 (m, 2H), 4.41 (m, 2H), 3.96 (q, J=7.1 Hz, 2H), 3.48 (m, 2H), 3.35 (m, 1H), 3.09 (m, 2H), 2.84 (dd, J=16.2, 3.0 Hz, 1H), 2.36 (dd, J=16.2, 10.7 Hz, 1H), 2.23 (m, 1H), 2.02 (m, 3H), 1.39 (t, J=7.0 Hz, 3H), 1.32 (d, J=7.1 Hz, 3H). Analytical HPLC (Zorbax method, 0% Solvent B start): RT=9.25 min, HI: 95%. hGPR40 EC$_{50}$=3141 nM.

EXAMPLE 98

2-((4S,5S)-1-(4-(((3R,4R)-1-(5-ethoxy-2-fluorophenyl)-3-methylpiperidin-4-yl)oxy)phenyl)-4-methyl-3-(4-(methylsulfonyl)phenyl)-4,5-dihydro-1H-pyrazol-5-yl)acetic acid

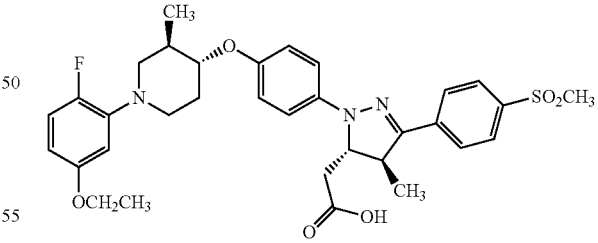

98A. 2-((4S,5S)-1-(4-hydroxyphenyl)-4-methyl-3-(4-(methylsulfonyl)phenyl)-4,5-dihydro-1H-pyrazol-5-yl)acetonitrile was prepared from 4-(methylsulfonyl)benzaldehyde following the procedure for the preparation of 4-((4S,5S)-5-(cyanomethyl)-1-(4-hydroxyphenyl)-4-methyl-4,5-dihydro-1H-pyrazol-3-yl)benzonitrile (example 91G): LC-MS [M+H] 370.

Example 98 (yellow solid, 27 mg) was prepared from 4-((4S,5S)-5-(cyanomethyl)-1-(4-hydroxyphenyl)-4-methyl-4,5-dihydro-1H-pyrazol-3-yl)-3-fluorobenzonitrile and (3R,4S)-1-(5-ethoxy-2-fluorophenyl)-3-methylpiperidin-4-ol following the procedure for Example 93 but no purification by preparative RP-HPLC was required: LC-MS [M+H] 624. $^1$H NMR (400 MHz, CDCl$_3$) δ 7.94 (d, J=8.6 Hz, 2H), 7.89 (d, J=8.6 Hz, 2H), 7.14 (d, J=9.0 Hz, 2H), 6.95 (d, J=9.0 Hz, 2H), 6.91 (m, 1H, overlapped), 6.53 (m, 1H), 6.40 (m, 1H), 4.48 (d, J=10.6 Hz, 1H), 3.98 (q, J=7.1 Hz, 2H), 3.84 (m, 1H), 3.44 (m, 3H), 3.08 (s, 3H), 2.87 (dd, J=16.4, 2.9 Hz, 1H), 2.80 (m, 1H, overlapped), 0.2.58 (t, J=10.7 Hz, 1H) 2.39 (dd, J=16.4, 10.6 Hz, 1H), 2.19 (m, 2H), 1.84 (m, 1H), 1.40 (t, J=7.0 Hz, 3H), 1.34 (d, J=7.2 Hz, 3H), 1.13 (d, J=6.8 Hz, 3H). Analytical HPLC (Zorbax method, 50% Solvent B start): RT=7.22 min, HI: 97%. hGPR40 EC$_{50}$=83 nM. hGPR40 IP1 EC$_{50}$=25 nM.

EXAMPLE 99

2-((4S,5S)-3-(4-cyanophenyl)-1-(4-(((3R,4R)-1-(5-ethoxy-2-fluorophenyl)-3-methylpiperidin-4-yl)oxy)phenyl)-4-ethyl-4,5-dihydro-1H-pyrazol-5-yl)acetic acid

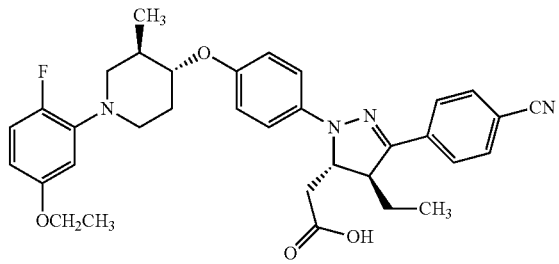 [SMILES: CCOc1ccc(F)c(N2CC[C@@H](Oc3ccc(N4N=C(c5ccc(C#N)cc5)[C@@H](CC)[C@@H]4CC(=O)O)cc3)[C@H](C)C2)c1]

99A. (E)-pent-2-enoic anhydride: To a stirred solution of (E)-pent-2-enoic acid (5 g, 48.9 mmol) in CH$_2$Cl$_2$ (50 mL) was added triethylamine (6.82 mL, 48.9 mmol). The resulting solution was purged with argon and then cooled to 0° C. Triphosgene (2.90 g, 9.79 mmol) was slowly added in portions and after completion of the addition, the resulting mixture was allowed to warm up to rt and stirred under argon overnight. The solvent was removed by blowing nitrogen onto the reaction mixture and the residual white solid was taken up in EtOAc (20 mL). The resulting suspension was filtered and the filter cake was rinsed with Et$_2$O. The combined filtrates were concentrated to afford the desired product (5.10 g, quantitative yield) as an orange liquid: LC-MS [M+Na] 205.

99B. (S,E)-3-(pent-2-enoyl)-4-phenyloxazolidin-2-one: To a light suspension of (S)-4-phenyloxazolidin-2-one (3.8 g, 23 mmol), lithium chloride (1.017 g, 24 mmol) and triethylamine (4.32 mL, 31 mmol) in THF (50 mL) at −20° C. was added (E)-pent-2-enoic anhydride (5.09 g, 27.9 mmol) dropwise. After completion of addition, the cold bath was removed and the mixture was allowed to warm to rt. The mixture was stirred at rt for 2.5 days and the resulting thick suspension was diluted with EtOAc. The mixture was washed sequentially with 0.2M HCl, sat'd NaHCO$_3$, water and sat'd NaCl. The organic layer was dried (Na$_2$SO$_4$) and concentrated to give an orange liquid which was purified via silica gel chromatography to afford (the desired product (4.37 g, 76% yield) as a white solid: LC-MS [M+H] 246.

99C. 4-((4S,5S)-5-(cyanomethyl)-4-ethyl-1-(4-hydroxyphenyl)-4,5-dihydro-1H-pyrazol-3-yl)benzonitrile was prepared from (S,E)-3-(pent-2-enoyl)-4-phenyloxazolidin-2-one following the procedure for the preparation of 4-((4S,5S)-5-(cyanomethyl)-1-(4-hydroxyphenyl)-4-methyl-4,5-dihydro-1H-pyrazol-3-yl)benzonitrile (example 91G): LC-MS [M+H] 331.

Example 99 (yellow solid, 5.0 mg) was prepared from 4-((4S,5S)-5-(cyanomethyl)-4-ethyl-1-(4-hydroxyphenyl)-4,5-dihydro-1H-pyrazol-3-yl)benzonitrile and (3R,4S)-1-(5-ethoxy-2-fluorophenyl)-3-methylpiperidin-4-ol following the procedure for Example 93 but no purification by preparative RP-HPLC was required: LC-MS [M+H] 585. $^1$H NMR (400 MHz, CDCl$_3$, selected peaks) δ 7.80 (d, J=8.5 Hz, 2H), 7.64 (d, J=8.5 Hz, 2H), 7.13 (d, J=8.8 Hz, 2H), 6.94 (d, J=8.8 Hz, 2H), 6.91, 1H, overlapped), 6.53 (m, 1H), 6.40 (m, 1H), 4.58 (m, 1H), 3.98 (q, J=7.0 Hz, 2H), 3.83 (m, 1H), 3.44 (m, 2H), 3.32 (m, 1H), 2.87 (dd, J=15.8, 3.0 Hz, 1H), 2.81 (m, 1H, overlapped), 2.39 (dd, J=15.8, 10.4 Hz, 1H), 1.40 (t, J=7.0 Hz, 3H), 1.13 (d, J=6.7 Hz, 3H), 0.97 (t, J=7.3 Hz, 3H). Analytical HPLC (Zorbax method, 50% Solvent B start): RT=8.47 min, HI: 98%. hGPR40 EC$_{50}$=25 nM. hGPR40 IP1 EC$_{50}$=20 nM.

EXAMPLE 100

2-((4S,5S)-1-(4-((1-(2-fluoro-5-methoxyphenyl)piperidin-4-yl)methyl)phenyl)-4-methyl-3-(trifluoromethyl)-4,5-dihydro-1H-pyrazol-5-yl)acetic acid

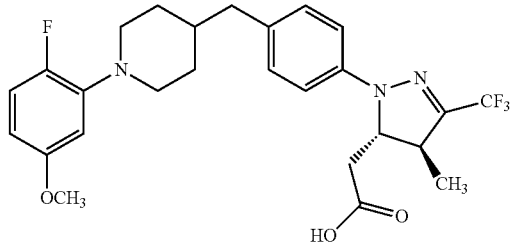 [SMILES: COc1ccc(F)c(N2CCC(Cc3ccc(N4N=C(C(F)(F)F)[C@@H](C)[C@@H]4CC(=O)O)cc3)CC2)c1]

100A. 8-(2-fluoro-5-methoxyphenyl)-1,4-dioxa-8-azaspiro[4.5]decane: A mixture of 3,4-difluoroanisole (0.4 mL, 3.31 mmol), 1,4-dioxa-8-azaspiro[4.5]decane (0.85 mL, 6.50 mmol), potassium carbonate (457 mg, 3.31 mmol) and DMSO (1.8 mL) was heated at 140° C. for 45 h in a microwave reactor. After this time, the mixture was partitioned between 4/1 Hex/EtOAc (60 mL) and 5% NaHCO$_3$ (30 mL). The organic layer was washed with 5% NaHCO$_3$ (2×30 mL) and sat'd NaCl (30 mL), dried (Na$_2$SO$_4$) and evaporated. Purification via silica gel chromatography gave the desired product (261 mg, 26% yield) as a colorless oil: LC-MS [M+H] 268.

100B. 1-(2-fluoro-5-methoxyphenyl)piperidin-4-one: To a stirred solution of 8-(2-fluoro-5-methoxyphenyl)-1,4-dioxa-8-azaspiro[4.5]decane (541 mg, 2.024 mmol) in THF (2.0 mL) at rt was added 1.78M sulfuric acid (5.7 mL, 10.15 mmol) and the resulting solution was heated to 66° C. After stirring at this temperature for 11 h, the reaction mixture was cooled to 0° C. and then quenched by dropwise addition of sat'd NaHCO$_3$ (10 mL) followed by excess sat'd NaHCO$_3$ (30 mL). The mixture was stirred for 15 min and then extracted with CH$_2$Cl$_2$ (3×30 mL). The organic extracts were washed with sat'd NaCl (20 mL), dried (Na$_2$SO$_4$) and concentrated. Purification via silica gel chromatography of the crude gave the desired product (352 mg, 1.42 mmol, 70% yield) as a colorless oil: LC-MS [M+H] 224.

100C. 1-(2-fluoro-5-methoxyphenyl)-4-methylenepiperidine: To a suspension of methyltriphenylphosphonium iodide (970 mg, 2.352 mmol) in THF (9.7 mL) at 0° C. was added 2.5M butyl lithium/toluene (0.94 mL, 2.350 mmol) and the mixture was stirred at 0° C. for 30 min. A solution 1-(2-fluoro-5-methoxyphenyl)piperidin-4-one (434 mg, 1.750 mmol) in THF (2.4 mL) was added dropwise, and the resulting suspension was allowed to warm to rt over 3.0 h. The rxn was quenched with sat'd NH$_4$Cl (20 mL) and diluted with EtOAc (40 mL). The layers were separated and the aqueous layer was extracted with EtOAc (2×20 mL). The combined organic layers were washed with sat'd NaCl (20 mL), dried (Na$_2$SO$_4$) and evaporated. The crude was chromatographed to afford the desired product (269 mg, 1.118 mmol, 63.9% yield) as a colorless oil: LC-MS [M+H] 222.

100D. 2-((4S,5S)-1-(4-((1-(2-fluoro-5-methoxyphenyl)piperidin-4-yl)methyl)phenyl)-4-methyl-3-(trifluoromethyl)-4,5-dihydro-1H-pyrazol-5-yl)acetonitrile: 0.5M 9-Borabicyclo[3.3.1]nonane/THF (1.3 mL, 0.650 mmol) was added to a solution of 1-(2-fluoro-5-methoxyphenyl)-4-methylenepiperidine (118 mg, 0.491 mmol) in THF (1.5 mL) and the resulting solution was heated at 65° C. for 1.5 h. After cooling to rt, the solution was added to a vigorously stirred mixture of 2-((4S,5S)-1-(4-bromophenyl)-4-methyl-3-(trifluoromethyl)-4,5-dihydro-1H-pyrazol-5-yl)acetonitrile (191 mg, 0.546 mmol), [1,1-Bis(diphenylphosphino)ferrocene]dichloropalladium(II), complex with dichloromethane (22 mg, 0.027 mmol), DMF (1.9 mL), water (0.2 mL) and potassium carbonate (153 mg, 1.107 mmol) under Ar. The mixture was heated to 65° C. and stirred at this temperature for 3.5 h, cooled to rt and poured onto water (40 mL). The pH of the resulting aqueous mixture was adjusted to 11 by addition of 1M NaOH and the mixture was extracted with CH$_2$Cl$_2$ (3×40 mL). The combined organic extracts were dried (Na$_2$SO$_4$) and concentrated. Purification by two consecutive chromatographies (SiO$_2$, first 4/1 to 7/3 Hex/EtOAc and then CHCl$_3$ to 97/3 CHCl$_3$/Ether) gave the desired product (31 mg, 11% yield) as a colorless oil: LC-MS [M+H] 489.

100E. methyl 2-((4S,5S)-1-(4-((1-(2-fluoro-5-methoxyphenyl)piperidin-4-yl)methyl)phenyl)-4-methyl-3-(trifluoromethyl)-4,5-dihydro-1H-pyrazol-5-yl)acetate: 2-((4S,5S)-1-(4-((1-(2-Fluoro-5-methoxyphenyl)piperidin-4-yl)methyl)phenyl)-4-methyl-3-(trifluoromethyl)-4,5-dihydro-1H-pyrazol-5-yl)acetonitrile (27 mg, 0.054 mmol) was dissolved in ~3M HCl/MeOH, CH$_2$Cl$_2$, MeOAc solution [6.3 mL, prepared by addition of AcCl (1.3 mL) to a 3/2 CHCl$_2$/MeOH solution (5.0 mL) at 0° C. and then stirring at rt for 20 min]. The resulting solution was allowed to stand at rt for 15 h and then evaporated. The remaining oily material was stripped from MeOH (2×4 mL) and dissolved in ~3M HCl/MeOH, MeOAc solution [6.3 mL, prepared by addition of AcCl (1.3 mL) to MeOH (5 mL) at 0° C. and then stirring at rt for 30 min]. The resulting solution was heated to 38° C. and allowed to stand at this temperature for 22 h. At this time, the solution was cooled to rt, diluted with MeCN (5 mL) and evaporated. The residue was taken up in EtOAc (50 mL) and, washed with 5% NaHCO$_3$ (2×30 mL) and sat'd NaCl (20 mL). The organic layer was dried (Na$_2$SO$_4$) and concentrated. The crude was chromatographed (SiO$_2$, 4/1 Hex/EtOAc) to afford the desired product (26 mg, 91% yield) as a colorless oil: LC-MS [M+H] 522.

Example 100: To a stirred solution of methyl 2-((4S,5S)-1-(4-((1-(2-fluoro-5-methoxyphenyl)piperidin-4-yl)methyl)phenyl)-4-methyl-3-(trifluoromethyl)-4,5-dihydro-1H-pyrazol-5-yl)acetate (26 mg, 0.049 mmol) in THF (1.2 mL) and water (0.12 mL) was added 1.0M aqueous lithium hydroxide (0.12 mL, 0.120 mmol). After stirring at rt for 6.2 h, the reaction mixture was partially evaporated to remove most of the THF. The remaining solution was partitioned between water (40 mL) and hexanes (16 mL). The aqueous layer was acidified to pH 2 by dropwise addition of 1M HCl, and then extracted with CH$_2$Cl$_2$ (3×30 mL). The combined organic extracts were dried (Na$_2$SO$_4$) and concentrated. The residue was dried under vacuum to afford the desired product (26 mg, 97% yield) as a white solid: LC-MS [M+H] 508. $^1$H NMR (500 MHz, CD$_2$Cl$_2$) δ 7.13 (d, J=8.6 Hz, 2H), 7.04 (d, J=8.6 Hz, 2H), 6.89 (dd, J=12.3, 8.9 Hz, 1H), 6.49 (m, 1H), 6.38 (m, 1H), 4.46 (m, 1H), 3.73 (s, 3H), 3.40 (m, 2H), 3.26 (m, 1H), 2.90 (dd, J=16.6, 3.0 Hz, 1H), 2.57 (m, 4H), 2.50 (dd, J=16.6, 10.3 Hz, 1H), 1.72 (m, 2H), 1.62 (m, 1H), 1.45 (m, 2H), 1.34 (d, J=7.2 Hz, 3H). Analytical HPLC (Zorbax method, 0% Solvent B start): RT=8.09 min, HI: 100%. hGPR40 EC$_{50}$=266 nM.

EXAMPLE 101

2-((4S,5S)-3-(4-fluorophenyl)-1-(4-((1-(3-methoxyphenyl)piperidin-4-yl)methyl)phenyl)-4-methyl-4,5-dihydro-1H-pyrazol-5-yl)acetic acid

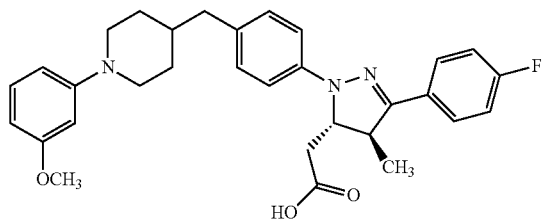 [SMILES: COc1cccc(N2CCC(Cc3ccc(N4N=C(c5ccc(F)cc5)[C@@H](C)[C@@H]4CC(=O)O)cc3)CC2)c1]

101A. tert-butyl 4-(4-((4S,5S)-3-(4-fluorophenyl)-5-(2-methoxy-2-oxoethyl)-4-methyl-4,5-dihydro-1H-pyrazol-1-yl)benzyl)piperidine-1-carboxylate: 0.5M 9-Borabicyclo[3.3.1]nonane/THF (1.04 mL, 0.520 mmol) was added to a solution of N-Boc-4-methylene-piperidine (0.11 mL, 0.541 mmol) in THF (1.7 mL) and the resulting solution was heated at 65° C. for 1.5 h. After cooling to rt, the solution was added to a vigorously stirred mixture of methyl 2-((4S,5S)-1-(4-bromophenyl)-3-(4-fluorophenyl)-4-methyl-4,5-dihydro-1H-pyrazol-5-yl)acetate (220 mg, 0.516 mmol), [1,1-bis(diphenylphosphino)ferrocene]dichloropalladium(II), complex with dichloromethane (22 mg, 0.027 mmol), DMF (1.7 mL), water (0.11 mL) and potassium carbonate (90 mg, 0.651 mmol). The mixture was heated to 65° C. and stirred at this temperature for 3.0 h. After cooling to rt, The mixture was diluted with EtOAc (50 mL) and, washed with water (2×20 mL) and sat'd NaCl (20 mL). The organic layer was dried (Na$_2$SO$_4$) and concentrated. Purification via silica gel chromatography afforded the desired product (116 mg, 42.5% yield) as a yellowish oil: LC-MS [M+H] 524.

101B. methyl 2-((4S,5S)-3-(4-fluorophenyl)-4-methyl-1-(4-(piperidin-4-ylmethyl)phenyl)-4,5-dihydro-1H-pyrazol-5-yl)acetate: tert-Butyl 4-(4-((4S,5S)-3-(4-fluorophenyl)-5-(2-methoxy-2-oxoethyl)-4-methyl-4,5-dihydro-1H-pyrazol-1-yl)benzyl)piperidine-1-carboxylate (115 mg, 0.217 mmol) was dissolved in ~1.1M HCl/MeOH, MeOAc solution [6.5 mL, prepared by addition of AcCl (0.5 mL) to MeOH (6.0 mL) at 0° C. and then stirring at rt for 1.0 h]. The resulting solution was allowed to stand at rt for 11 h and then, diluted with MeCN (6 mL) and evaporated. The residue was taken up in EtOAc (50 mL) and, washed with sat'd NaHCO$_3$ (30 mL), 10% Na$_2$CO$_3$ (30 mL) and sat'd NaCl (20 mL). The organic layer was dried (Na$_2$SO$_4$) and concentrated. Drying under vacuum provided the desired product (92 mg, 100% yield) as a yellowish oil: LC-MS [M+H] 424.

101C. methyl 2-((4S,5S)-3-(4-fluorophenyl)-1-(4-((1-(3-methoxyphenyl)piperidin-4-yl)methyl)phenyl)-4-methyl-4,5-dihydro-1H-pyrazol-5-yl)acetate: A suspension of 3-methoxyphenylboronic acid (55 mg, 0.351 mmol), copper (II) acetate monohydrate (7 mg, 0.035 mmol) and powdered molecular sieves (4 Å, <5 micron, activated, 185 mg) in dichloromethane (1.3 mL) was stirred for 5 min at rt. To this stirring suspension was added a solution of methyl 2-((4S,5S)-3-(4-fluorophenyl)-4-methyl-1-(4-(piperidin-4-ylmethyl)phenyl)-4,5-dihydro-1H-pyrazol-5-yl)acetate (92 mg, 0.217 mmol) in dichloromethane (0.7 mL). The reaction mixture was heated to 30° C. and stirred, at this temperature and under air (balloon), for 24 h. The mixture was filtered through Celite and the filter cake was rinsed with EtOAc (80 mL). The combined filtrate and rinses were concentrated and the residue was chromatographed to provide the desired product (50 mg, 40% yield) as a yellowish oil: LCMS [M+H] 530.

Example 101: To a stirred solution of methyl 2-((4S,5S)-3-(4-fluorophenyl)-1-(4-((1-(3-methoxyphenyl)piperidin-4-yl)methyl)phenyl)-4-methyl-4,5-dihydro-1H-pyrazol-5-yl)acetate (50 mg, 0.094 mmol) in THF (2.2 mL) and water (0.22 mL) at rt was added 1.0M aqueous lithium hydroxide (0.28 mL, 0.280 mmol). After stirring at rt for 5.0 h, the reaction mixture was partially evaporated to remove most of the THF. The remaining solution was partitioned between water (50 mL) and Hex (15 mL). The aqueous layer was acidified to pH 2 by dropwise addition of 1M HCl, and then extracted with $CH_2Cl_2$ (3×30 mL). The combined organic extracts were dried ($Na_2SO_4$) and concentrated. The residue was purified by chromatography followed by precipitation from Ether/Hex to afford the desired product (45 mg, 90% yield) as a yellowish solid: LCMS [M+H] 516. $^1$H NMR (500 MHz, $CD_2Cl_2$) δ 7.76 (m, 2H), 7.14-7.07 (m, 7H), 6.52 (dd, J=8.4, 2.4 Hz, 1H), 6.44 (t, J=2.4 Hz, 1H), 6.34 (dd, J=8.0, 2.4 Hz, 1H), 4.43 (dt, J=10.4, 2.5 Hz, 1H), 3.75 (s, 3H), 3.65 (m, 2H), 3.43 (m, 1H), 2.87 (dd, J=16.6, 3.0 Hz, 1H), 2.64 (dt, J=12.2, 2.4 Hz, 1H), 2.52 (d, J=7.0 Hz, 2H), 2.39 (dd, J=16.3, 10.6 Hz, 1H), 1.74 (m, 2H), 1.65 (m, 1H), 1.36 (m, 2H), 1.30 (d, J=7.2 Hz, 3H). Analytical HPLC (Zorbax method, 0% Solvent B start): RT=6.49 min, HI: 97%. hGPR40 $EC_{50}$=281 nM. hGPR40 IP1 $EC_{50}$=40 nM.

EXAMPLE 102

2-((4S,5S)-1-(4-((1-(2-fluoro-5-hydroxyphenyl)piperidin-4-yl)oxy)phenyl)-4-methyl-3-(trifluoromethyl)-4,5-dihydro-1H-pyrazol-5-yl)acetic acid

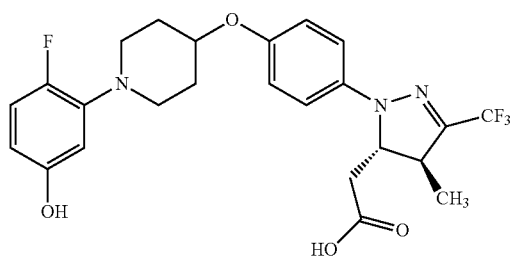 [SMILES: C[C@@H]1C(C(F)(F)F)=NN(c2ccc(OC3CCN(c4cc(O)ccc4F)CC3)cc2)[C@H]1CC(=O)O]

102A. ethyl 2-((4S,5S)-1-(4-((1-(2-fluoro-5-hydroxyphenyl)piperidin-4-yl)oxy)phenyl)-4-methyl-3-(trifluoromethyl)-4,5-dihydro-1H-pyrazol-5-yl)acetate: To a solution of EtOH (0.86 mL) was added acetyl chloride (0.18 mL, 2.6 mmol) to generate anhydrous HCl. After addition, the mixture was warmed to room temp, and 2-((4S,5S)-1-(4-((1-(2-fluoro-5-methoxyphenyl)piperidin-4-yl)oxy)phenyl)-4-methyl-3-(trifluoromethyl)-4,5-dihydro-1H-pyrazol-5-yl) acetic acid (Example 1, 0.044 g, 0.086 mmol) was added. The mixture was stirred at rt for 1.5 h. The reaction mixture was evaporated to dryness. The residue was dissolved in $CH_2Cl_2$ (0.6 mL) and was cooled to −78° C., and $BBr_3$ (0.8 mL, 8.46 mmol) was added. The reaction mixture was stirred for 2h, and was warmed to −40° C. overnight. The reaction solution was poured over ice and, after 30 min agitation, the mixture was extracted with ethyl acetate. The organic layer was washed with brine, dried over $MgSO_4$, filtered and evaporated to give 85 mg of a yellow oil that was purified via silica chromatography to give 25 mg of desired product as a clear oil. Anal. Calc'd for $C_{26}H_{29}F_4N_3O_4$: 523.21, LCMS obs. [M+H]=524.1.

Example 102: To a solution of ethyl 2-((4S,5S)-1-(4-((1-(2-fluoro-5-hydroxyphenyl)piperidin-4-yl)oxy)phenyl)-4-methyl-3-(trifluoromethyl)-4,5-dihydro-1H-pyrazol-5-yl) acetate (0.01 g, 0.019 mmol) in acetonitrile (0.3 mL) and water (0.2 mL) was added lithium hydroxide (3 mg, 0.1 mmol), and the mixture was stirred for 1 h. The reaction mixture was diluted with acetonitrile and 1N HCl and the mixture was purified via preparative reverse-phase HPLC. Product-containing fractions were evaporated to remove acetonitrile. The water layer was extracted 2× with $CH_2Cl_2$. The combined organic layers were dried over $Na_2SO_4$, and the organic layer was decanted. The solution was evaporated to give 8 mg of a white foam that was re-dissolved in acetonitrile and 3M HCl (aq). The mixture was stirred for 5 min, then evaporated and placed on the pump overnight to give 8 mg of 2-((4S,5S)-1-(4-((1-(2-fluoro-5-hydroxyphenyl)piperidin-4-yl)oxy)phenyl)-4-methyl-3-(trifluoromethyl)-4,5-dihydro-1H-pyrazol-5-yl)acetic acid as a white solid. LCMS Anal. Calc'd for $C_{24}H_{25}F_4N_3O_4$: 495.18, found [M+H]=496.1. $^1$H NMR (400 MHz, $CD_3CN$) δ 7.61 (br. s., 1H), 7.12-6.89 (m, 2H), 6.84 (d, J=9.1 Hz, 2H), 6.70 (br. s., 1H), 4.50 (br. s., 1H), 4.28 (d, J=9.6 Hz, 1H), 3.67 (br. s., 2H), 3.33 (br. s., 2H), 3.18 (br. s., 1H), 2.58 (dd, J=16.4, 3.3 Hz, 2H), 2.34 (dd, J=16.4, 9.6 Hz, 4H), 1.15 (d, J=7.3 Hz, 3H). Analytical HPLC (Orthogonal method): RT=10.2 min, HI: 98%. hGPR40 $EC_{50}$=190 nM. hGPR40 IP1 $EC_{50}$=131 nM.

EXAMPLE 103

2-((4S,5S)-1-(6-((1-(5-chloro-2-methoxypyridin-4-yl)-3-methylpiperidin-4-yl)oxy)pyridin-3-yl)-4-methyl-3-(trifluoromethyl)-4,5-dihydro-1H-pyrazol-5-yl)acetic acid, 2HCl. Isomers 1 and Isomer 2

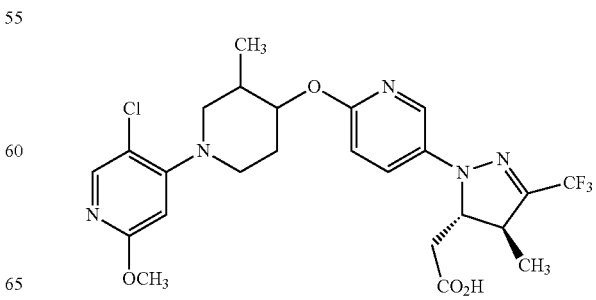

103A. 1-benzyl-3-methylpiperidin-4-ol: Dissolved 1-benzyl-3-methylpiperidin-4-one (9 g, 44 mmol) in MeOH (44 mL) and added sodium borohydride (3.4 g, 89 mmol) slowly into the solution at 23° C. After 55 min, LCMS showed a new more polar peak and no starting material peak. TLC (1:1 EtOAc:Hexanes) showed starting materials were completely consumed. Then, 10% KHSO$_4$ (200 mL) was added slowly to the reaction mixture and organic solvent was removed by rotavap. The mixture was then extracted with EtOAc (2×500 mL), and the combined organic extracts were dried (Na$_2$SO$_4$), filtered, and concentrated, gave 1-benzyl-3-methylpiperidin-4-ol (9 g, 43.8 mmol, 99% yield) as oil. LC-MS Anal. Calc'd for C$_{13}$H$_{19}$NO, 205.15, found [M+H] 206.1.

103B. Rac-1-benzyl-4-((tert-butyldimethylsilyl)oxy)-3-methylpiperidine: To a solution of 1-benzyl-3-methylpiperidin-4-ol (9 g, 44 mmol) in DCM (44 mL) and triethylamine (18 mL, 132 mmol) was added tert-butyldimethylsilyl trifluoromethanesulfonate (12 mL, 53 mmol) at 0° C. After 1 h, TLC (2:1 Hexanes:EtOAc) showed that starting material were completely consumed. Then, sat. aq NaHCO$_3$ (100 mL) was added slowly to the reaction mixture. The mixture was then extracted with EtOAc (2×300 mL), and the combined organic extracts were dried (Na$_2$SO$_4$), filtered, and concentrated. Purification by chromatography gave rac-1-benzyl-4-((tert-butyldimethylsilyl)oxy)-3-methylpiperidine (9 g, 28 mmol, 65% yield) as an oil. LC-MS Anal. Calc'd for C$_{19}$H$_{33}$NOSi, 319.23, found [M+H] 320.3.

103C. Rac-4-((tert-butyldimethylsilyl)oxy)-3-methylpiperidine: To a solution of rac-1-benzyl-4-((tert-butyldimethylsilyl)oxy)-3-methylpiperidine (9.1 g, 28.5 mmol) in MeOH (280 mL) was added Pd on carbon (1.5 g, 1.42 mmol). The reaction mixture was stirred under H$_2$ (1 atm) at rt for 24 h. Then, the mixture was filter through Celite and washed with EtOAc. The combined organic layer was concentrated in vacuo, gave rac-4-((tert-butyldimethylsilyl)oxy)-3-methylpiperidine (5.6 g, 24 mmol, 86% yield) as an oil. LC-MS Anal. Calc'd for C$_{12}$H$_{27}$NOSi, 229.19, found [M+H] 230.2.

103D. Rac-4-(((tert-butyldimethylsilyl)oxy)-3-methylpiperidin-1-yl)-5-chloro-2-methoxypyridine: A mixture of rac-4-((tert-butyldimethylsilyl)oxy)-3-methylpiperidine (500 mg, 2.2 mmol), 4-bromo-5-chloro-2-methoxypyridine (485 mg, 2.2 mmol) and Sphos precatalyst (14 mg, 0.022 mmol) in THF (4.3 mL) was purged with argon and Lithium bis(trimethylsilyl)amide (2.6 mL, 2.6 mmol) was added. The reaction was heated at 70° C. for 2 h. LCMS showed the desired mass of product. Then, sat. aq NaHCO$_3$ (10 mL) was added slowly to the reaction mixture. The mixture was then extracted with EtOAc (2×10 mL), and the combined organic extracts were washed with water (20 mL) and brine (20 mL), and dried (Na$_2$SO$_4$), filtered, and concentrated. Purification by chromatography gave rac-4-(((tert-butyldimethylsilyl)oxy)-3-methylpiperidin-1-yl)-5-chloro-2-methoxypyridine (540 mg, 1.46 mmol, 66% yield) as an oil. LC-MS Anal. Calc'd for C$_{18}$H$_{31}$ClN$_2$O$_2$Si, 370.18, found [M+H] 371.1.

103E. Rac-1-(5-chloro-2-methoxypyridin-4-yl)-3-methylpiperidin-4-ol: To a mixture of rac-4-(((tert-butyldimethylsilyl)oxy)-3-methylpiperidin-1-yl)-5-chloro-2-methoxypyridine (640 mg, 1.73 mmol) in THF (3.4 mL) was added TBAF (2.0 mL, 2.07 mmol). The reaction was stirred at 23° C. for 16 h. LCMS showed the desired mass of product. Then, sat. aq NaHCO$_3$ (10 mL) was added slowly to the reaction mixture. The mixture was then extracted with EtOAc (2×10 mL), and the combined organic extracts were washed with water (20 mL) and brine (20 mL), and dried (Na$_2$SO$_4$), filtered, and concentrated. Purification by chromatography gave rac-1-(5-chloro-2-methoxypyridin-4-yl)-3-methylpiperidin-4-ol (320 mg, 1.25 mmol, 72% yield) as white foam. LC-MS Anal. Calc'd for C$_{12}$H$_{17}$ClN$_2$O$_2$ 256.10, found [M+H] 257.1.

103F. Rac-5-chloro-4-(((5-iodopyridin-2-yl)oxy)-3-methylpiperidin-1-yl)-2-methoxypyridine: To a solution of rac-1-(5-chloro-2-methoxypyridin-4-yl)-3-methylpiperidin-4-ol (470 mg, 1.8 mmol) in DMF (1.8 mL) was added sodium hydride (110 mg, 2.7 mmol) at 0° C. After 10 min, 2-fluoro-5-iodopyridine (612 mg, 2.7 mmol) was added. The mixture was heated at 70° C. for 6 h. LCMS showed the completion of reaction. Then, sat. aq NaHCO$_3$ (10 mL) was added slowly to the reaction mixture. The mixture was then extracted with EtOAc (2×20 mL), and the combined organic extracts were dried (Na$_2$SO$_4$), filtered, and concentrated. Purification by chromatography gave rac-5-chloro-4-((((5-iodopyridin-2-yl)oxy)-3-methylpiperidin-1-yl)-2-methoxypyridine (660 mg, 1.4 mmol, 78% yield) as waxy solid. LC-MS Anal. Calc'd for C$_{17}$H$_{19}$ClN$_3$O$_2$ 459.02, found [M+H] 459.8.

103G. Rac-benzyl 1-(6-((1-(5-chloro-2-methoxypyridin-4-yl)-3-methylpiperidin-4-yl)oxy)pyridin-3-yl)hydrazinecarboxylate: To a suspension of rac-5-chloro-4-((((5-iodopyridin-2-yl)oxy)-3-methylpiperidin-1-yl)-2-methoxypyridine (580 mg, 1.2 mmol) in Toluene (2.5 mL) was added N$_1$,N$_2$-dimethylethane-1,2-diamine (53 µL, 0.5 mmol) and K$_2$CO$_3$ (349 mg, 2.5 mmol)). The mixture was evacuated and refilled with N$_2$ for three times. copper(I) iodide (48 mg, 0.25 mmol) was added and the reaction mixture was heated to 80° C. for 20 h. The mixture was filtered through Celite and concentrated. Purification via silica gel chromatography gave rac-benzyl 1-(6-((1-(5-chloro-2-methoxypyridin-4-yl)-3-methylpiperidin-4-yl)oxy)pyridin-3-yl)hydrazinecarboxylate (530 mg, 1.06 mmol, 84% yield) as waxy solid. LC-MS Anal. Calc'd for C$_{25}$H$_{28}$ClN$_5$O$_4$ 497.18, found [M+H] 498.0.

103H. Rac-benzyl 1-(6-((1-(5-chloro-2-methoxypyridin-4-yl)-3-methylpiperidin-4-yl)oxy)pyridin-3-yl)-2-(2,2,2-trifluoroacetyl)hydrazinecarboxylate: To a stirred suspension of rac-benzyl 1-(6-(((3R,4R)-1-(5-chloro-2-methoxypyridin-4-yl)-3-methylpiperidin-4-yl)oxy)pyridin-3-yl)hydrazinecarboxylate (530 mg, 1.1 mmol) in DCM (11 mL) at 0° C. was added TFAA (0.16 mL, 1.2 mmol) dropwise. The resulting mixture was stirred at 0° C. for 2 h. LCMS showed the completion of the reaction. The mixture was then concentrated and purified by silica gel chromatography gave rac-benzyl 1-(6-((1-(5-chloro-2-methoxypyridin-4-yl)-3-methylpiperidin-4-yl)oxy)pyridin-3-yl)-2-(2,2,2-trifluoroacetyl)hydrazinecarboxylate (630 mg, 1.1 mmol, 100% yield). LC-MS Anal. Calc'd for C$_{27}$H$_{27}$ClF$_3$N$_5$O$_4$ 593.17, found [M+H] 594.1.

103I. Rac-N'-(6-((1-(5-chloro-2-methoxypyridin-4-yl)-3-methylpiperidin-4-yl)oxy)pyridin-3-yl)-2,2,2-trifluoroacetohydrazide: To a solution of rac-benzyl 1-(6-((1-(5-chloro-2-methoxypyridin-4-yl)-3-methylpiperidin-4-yl)oxy)pyridin-3-yl)-2-(2,2,2-trifluoroacetyl)hydrazinecarboxylate (630 mg, 1.1 mmol) in MeOH (10 mL) was added Pd on carbon (56 mg, 0.053 mmol). The reaction mixture was stirred under H$_2$ (1 atm) at rt for 14 h. Then, the mixture was filter through Celite and washed with EtOAc. The combined organic layer was concentrated in vacuo, gave rac-N'-(6-((1-(5-chloro-2-methoxypyridin-4-yl)-3-methylpiperidin-4-yl)oxy)pyridin-3-yl)-2,2,2-trifluoroacetohydrazide (430 mg, 0.94 mmol, 88% yield). LC-MS Anal. Calc'd for C$_{19}$H$_{21}$ClF$_3$N$_5$O$_3$ 459.13, found [M+H] 460.0.

103J. Rac-(Z)—N'-(6-((1-(5-chloro-2-methoxypyridin-4-yl)-3-methylpiperidin-4-yl)oxy)pyridin-3-yl)-2,2,2-trifluoroacetohydrazonoyl chloride: To a stirred solution of rac- N'-(6-((1-(5-chloro-2-methoxypyridin-4-yl)-3-methylpiperidin-4-yl)oxy)pyridin-3-yl)-2,2,2-trifluoroacetohydrazide (430 mg, 0.94 mmol) in EtOAc (20 mL) at 0° C. was added benzenesulfonyl chloride (0.15 mL, 1.1 mmol) followed by N-ethyl-N-isopropylpropan-2-amine (0.20 mL, 1.1 mmol) dropwise. The resulting mixture was then warmed up to rt and stirred at rt for 12 h. LCMS showed the completion of the reaction. Then, sat. aq NaHCO$_3$ (50 mL) was added slowly to the reaction mixture. The mixture was then extracted with EtOAc (2×50 mL), and the combined organic extracts were dried (Na$_2$SO$_4$), filtered, and concentrated. Purification by chromatography gave rac-(Z)—N'-(6-((1-(5-chloro-2-methoxypyridin-4-yl)-3-methylpiperidin-4-yl)oxy)pyridin-3-yl)-2,2,2-trifluoroacetohydrazonoyl chloride (200 mg, 0.42 mmol, 45% yield). LC-MS Anal. Calc'd for C$_{19}$H$_{20}$Cl$_2$F$_3$N$_5$O$_2$ 477.10, found [M+H] 478.0.

103K. (S)-3-((4S,5R)-1-(6-((1-(5-chloro-2-methoxypyridin-4-yl)-3-methylpiperidin-4-yl)oxy)pyridin-3-yl)-4-methyl-3-(trifluoromethyl)-4,5-dihydro-1H-pyrazole-5-carbonyl)-4-phenyloxazolidin-2-one: A flask containing a solution of rac-(Z)—N'-(6-((1-(5-chloro-2-methoxypyridin-4-yl)-3-methylpiperidin-4-yl)oxy)pyridin-3-yl)-2,2,2-trifluoroacetohydrazonoyl chloride (200 mg, 0.42 mmol) and N-acryloyl oxazolidinone (111 mg, 0.48 mmol) in dioxane (0.8 mL) was evacuated and backfilled with Ar. Silver carbonate (288 mg, 1.05 mmol) was added to the solution and the resulting suspension was stirred and heated at 60° C. for 16 h. The rxn mixture was cooled to rt and filtered through Celite. The filter cake was rinsed with EtOAc and, the combined filtrate and rinse were concentrated. Purification by chromatography gave (S)-3-((4S,5R)-1-(6-((1-(5-chloro-2-methoxypyridin-4-yl)-3-methylpiperidin-4-yl)oxy)pyridin-3-yl)-4-methyl-3-(trifluoromethyl)-4,5-dihydro-1H-pyrazole-5-carbonyl)-4-phenyloxazolidin-2-one (80 mg, 0.13 mmol, 28% yield). LC-MS Anal. Calc'd for C$_{32}$H$_{32}$ClF$_3$N$_6$O$_5$ 673.08, found [M+H] 673.1.

103L. (4S,5R)-1-(6-((1-(5-chloro-2-methoxypyridin-4-yl)-3-methylpiperidin-4-yl)oxy)pyridin-3-yl)-4-methyl-3-(trifluoromethyl)-4,5-dihydro-1H-pyrazol-5-yl)methanol: Dissolved (S)-3-(1-(6-((1-(5-chloro-2-methoxypyridin-4-yl)-3-methylpiperidin-4-yl)oxy)pyridin-3-yl)-4-methyl-3-(trifluoromethyl)-4,5-dihydro-1H-pyrazole-5-carbonyl)-4-phenyloxazolidin-2-one (80 mg, 0.12 mmol) in THF (2.5 mL) and Water (0.5 mL) and added NaBH$_4$ (16 mg, 0.71 mmol) slowly into the solution at 23° C. After 55 min, LCMS showed a new more polar peak and no starting material peak. TLC (1:1 EtOAc:Hexanes) showed starting materials were completely consumed. Then, 10% KHSO$_4$ (10 mL) was added slowly to the reaction mixture. The mixture was then extracted with EtOAc (2×30 mL), and the combined organic extracts were dried (Na$_2$SO$_4$), filtered, and concentrated. Purification via silica gel chromatography gave (4S,5R)-1-(6-((1-(5-chloro-2-methoxypyridin-4-yl)-3-methylpiperidin-4-yl)oxy)pyridin-3-yl)-4-methyl-3-(trifluoromethyl)-4,5-dihydro-1H-pyrazol-5-yl)methanol (50 mg, 0.097 mmol, 82% yield). LC-MS Anal. Calc'd for C$_{23}$H$_{27}$ClF$_3$N$_5$O$_3$ 513.18, found [M+H] 514.1.

103M. (4S,5R)-1-(6-((1-(5-chloro-2-methoxypyridin-4-yl)-3-methylpiperidin-4-yl)oxy)pyridin-3-yl)-4-methyl-3-(trifluoromethyl)-4,5-dihydro-1H-pyrazol-5-yl)methyl methanesulfonate: To a solution of (4S,5R)-1-(6-((1-(5-chloro-2-methoxypyridin-4-yl)-3-methylpiperidin-4-yl)oxy)pyridin-3-yl)-4-methyl-3-(trifluoromethyl)-4,5-dihydro-1H-pyrazol-5-yl)methanol (60 mg, 0.12 mmol) in THF (1.2 mL) added triethylamine (80 µL, 0.58 mmol) and methanesulfonyl chloride (27 µL, 0.35 mmol) at 0° C. and stirred for 30 mins. LCMS showed that the reaction was completed. TLC (1:2 EtOAc:Hexanes) showed starting materials were completely consumed. Then, sat. NaHCO$_3$ (10 mL) was added slowly to the reaction mixture. The mixture was then extracted with EtOAc (2×20 mL), and the combined organic extracts were dried (Na$_2$SO$_4$), filtered, and concentrated. Purification via silica gel chromatography gave (4S,5R)-1-(6-((1-(5-chloro-2-methoxypyridin-4-yl)-3-methylpiperidin-4-yl)oxy)pyridin-3-yl)-4-methyl-3-(trifluoromethyl)-4,5-dihydro-1H-pyrazol-5-yl)methyl methanesulfonate (60 mg, 0.10 mmol, 87% yield). LC-MS Anal. Calc'd for C$_{24}$H$_{29}$ClF$_3$N$_5$O$_5$S, 519.15, found [M+H] 592.1.

103N. 2-((4S,5S)-1-(6-((1-(5-chloro-2-methoxypyridin-4-yl)-3-methylpiperidin-4-yl)oxy)pyridin-3-yl)-4-methyl-3-(trifluoromethyl)-4,5-dihydro-1H-pyrazol-5-yl)acetonitrile: A solution of ((4S,5R)-1-(6-((1-(5-chloro-2-methoxypyridin-4-yl)-3-methylpiperidin-4-yl)oxy)pyridin-3-yl)-4-methyl-3-(trifluoromethyl)-4,5-dihydro-1H-pyrazol-5-yl)methyl methanesulfonate (60 mg, 0.10 mmol) in DMSO (200 µl) was treated with cyanopotassium (13 mg, 0.20 mmol) and stirred at 40° C. under Ar. Reaction was monitored by LC/MS. After 16 h, LCMS showed completion. After cooling to rt, it was diluted with NaHCO$_3$ and EtOAc. After separation of the layers, the aqueous layer was then extracted with EtOAc. The combined organic extracts were washed with water (3×), brine, dried (Na$_2$SO$_4$), and concentrated. Purification via silica gel chromatography gave 2-((4S,5S)-1-(6-((1-(5-chloro-2-methoxypyridin-4-yl)-3-methylpiperidin-4-yl)oxy)pyridin-3-yl)-4-methyl-3-(trifluoromethyl)-4,5-dihydro-1H-pyrazol-5-yl)acetonitrile (47 mg, 0.09 mmol, 89% yield). LC-MS Anal. Calc'd for C$_{24}$H$_{26}$ClF$_3$N$_6$O$_2$ 522.18, found [M+H] 523.1.

Example 103 Isomer 1 and Isomer 2: 3.6 M HCl in MeOH/MeOAc (424 µl, 1.55 mmol)) was added to 2-((4S,5S)-1-(6-((1-(5-chloro-2-methoxypyridin-4-yl)-3-methylpiperidin-4-yl)oxy)pyridin-3-yl)-4-methyl-3-(trifluoromethyl)-4,5-dihydro-1H-pyrazol-5-yl)acetonitrile (47 mg, 0.09 mmol) and the reaction stirred at rt for 48 h. The reaction mixture was diluted with acetonitrile and was evaporated to remove methanol and acetonitrile. The residue was dissolved in ethyl acetate and washed with a saturated aqueous NaHCO$_3$, water, and brine. The organic layer was then dried (Na$_2$SO$_4$), filtered, and concentrated. The residue was dissolved in THF (290 µL) and Water (30 µL) at rt was added 2M LiOH (440 µl, 0.90 mmol). The rxn mixture was stirred at rt for 1 h and LCMS showed no starting material. Then, 3N HCl (0.4 mL) was added at 0° C. and warmed up to rt. The solvent was evaporated and the residue was dissolved in CH3CN, filtered. Purification by RP-Prep HPLC afforded a diastereomeric mixture. The diastereomers were separated by chiral Prep. SFC to provide Example 103, Isomer 1 and Isomer 2 as single enantiomers. Example 103 Isomer 1 (white solid, 8 mg), LC-MS Anal. Calc'd for C$_{24}$H$_{27}$ClF$_3$N$_5$O$_4$ 541.17, found [M+H] 542.1. $^1$H NMR (400 MHz, CD$_3$CN) δ ppm 8.02 (s, 1H), 7.94 (br. s., 1H), 7.59 (dd, J=9.0, 2.8 Hz, 1H), 6.81 (d, J=8.8 Hz, 1H), 6.42 (s, 1H), 4.84 (td, J=9.2, 4.3 Hz, 2H), 4.48-4.42 (m, 1H), 3.93 (s, 3H), 3.69 (d, J=12.0 Hz, 2H), 3.14-2.99 (m, 2H), 2.89-2.72 (m, 2H), 2.56 (dd, J=16.6, 9.0 Hz, 1H), 2.38-2.28 (m, 1H), 2.18-2.08 (m, 1H), 1.82-1.64 (m, 1H), 1.35 (d, J=7.3 Hz, 3H), 1.06 (d, J=6.5 Hz, 3H). HPLC (Orthogonal method, 30% Solvent B start): RT=11.1 min, HI: 100%. hGPR40 EC$_{50}$=533 nM. Example 103 Isomer 2 (white solid, 8 mg), LC-MS Anal. Calc'd for C$_{24}$H$_{27}$ClF$_3$N$_5$O$_4$ 541.17, found [M+H] 542.1. $^1$H NMR (400 MHz, CD$_3$CN) δ ppm 8.02 (s, 1H), 7.94 (br. s., 1H), 7.59 (dd, J=9.0, 2.8 Hz, 1H), 6.81 (d, J=8.8 Hz, 1H), 6.42 (s, 1H), 4.84 (td, J=9.2, 4.3 Hz, 1H), 4.48-4.42 (m, 1H), 3.93 (s, 3H), 3.69 (d, J=12.0 Hz, 2H), 3.14-2.99 (m, 2H), 2.89-2.72 (m, 2H), 2.56 (dd, J=16.6, 9.0 Hz, 1H), 2.38-2.28 (m, 1H), 2.18-2.08 (m, 1H), 1.82-1.64 (m, 1H), 1.35 (d, J=7.3 Hz, 3H), 1.06 (d, J=6.5 Hz, 3H). HPLC (Orthogonal method, 30% Solvent B start): RT=11.1 min, HI: 100%. hGPR40 $EC_{50}$=96 nM. hGPR40 IP1 $EC_{50}$=43 nM.

EXAMPLE A1 (ISOMER 1) AND (ISOMER 2)

2-((4S,5S)-1-(4-((1-(5-chloro-2-methoxypyridin-4-yl)-3-fluoropiperidin-4-yl)oxy)phenyl)-4-methyl-3-(trifluoromethyl)-4,5-dihydro-1H-pyrazol-5-yl)acetic acid, HCl

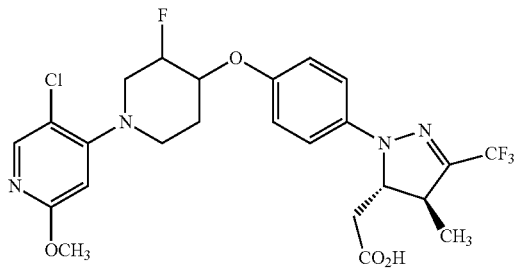 [SMILES: COc1cc(N2CCC(Oc3ccc(N4N=C(C(F)(F)F)[C@@H](C)[C@@H]4CC(=O)O)cc3)C(F)C2)c(Cl)cn1]

A1A. Benzyl 4-((trimethylsilyl)oxy)-5,6-dihydropyridine-1(2H)-carboxylate: To a solution of benzyl 4-oxopiperidine-1-carboxylate (1.3 g, 5.4 mmol) in DMF (4 mL) was added chlorotrimethylsilane (0.8 mL, 6.53 mmol) followed by triethylamine (1.5 mL, 10.89 mmol). The resulting heterogeneous mixture was warmed to 80° C. and stirred for 16 h. The cooled mixture was diluted with hexanes (50 mL), washed with sat. NaHCO$_3$ (30 mL) and brine (30 mL), then dried over MgSO$_4$, filtered and concentrated to afford the title compound (1.5 g, 4.91 mmol, 90% yield) as a clear oil. $^1$H NMR (400 MHz, CDCl$_3$) δ 7.22-7.08 (m, 5H), 4.98-4.94 (m, 2H), 4.60 (br. s., 1H), 3.77 (q, J=2.3 Hz, 2H), 3.42 (t, J=5.6 Hz, 2H), 1.94 (br. s., 2H), 0.04-0.04 (m, 9H).

A1B. Benzyl 3-fluoro-4-oxopiperidine-1-carboxylate: To a solution of benzyl 4-((trimethylsilyl)oxy)-5,6-dihydropyridine-1(2H)-carboxylate (1.5 g, 4.98 mmol) in Acetonitrile (31 mL) at rt was added Selectfluro® (2.1 g, 5.97 mmol) portionwise over 10 min. The mixture was stirred for 2 h, then concentrated to dryness and partitioned between EtOAc and brine. The aq layer was extracted with EtOAc and the combined organic phases were washed with brine, dried over MgSO$_4$, filtered and concentrated to afford the title compound (1.2 g, 4.78 mmol, 96% yield) as a solid. $^1$H NMR (400 MHz, CDCl$_3$) δ 7.51-7.30 (m, 5H), 5.27-5.16 (m, 2H), 4.97-4.70 (m, 1H), 4.47 (br. s., 1H), 4.33-4.18 (m, 1H), 3.59-3.28 (m, 2H), 2.72-2.41 (m, 2H).

A1C. Benzyl 3-fluoro-4-hydroxypiperidine-1-carboxylate: To a solution of benzyl 3-fluoro-4-oxopiperidine-1-carboxylate (880 mg, 3.50 mmol) in MeOH (7 mL) was added sodium borohydride (130 mg, 3.50 mmol) slowly. After 1 h, 10% KHSO$_4$ (10 mL) was added slowly to the reaction mixture. The mixture was extracted with EtOAc (2×30 mL), and the combined organic extracts were dried (Na$_2$SO$_4$), filtered, and concentrated to afford the title compound (870 mg, 3.44 mmol, 98% yield). LC-MS Anal. Calc'd for C13H16FNO3, found [M+H] 253.26 254. $^1$H NMR (400 MHz, CDCl$_3$) δ 7.47-7.27 (m, 5H), 5.13 (s, 2H), 4.75-4.52 (m, 1H), 4.07-3.68 (m, 3H), 3.61-3.04 (m, 2H), 2.22 (d, J=5.0 Hz, 1H), 1.93-1.63 (m, 2H).

A1D. Benzyl 4-((tert-butyldimethylsilyl)oxy)-3-fluoropiperidine-1-carboxylate: To a solution of benzyl 3-fluoro-4-hydroxypiperidine-1-carboxylate (410 mg, 1.62 mmol) in DCM (1.6 mL) and triethylamine (670 µL, 4.86 mmol) was added tert-butyldimethylsilyl trifluoromethanesulfonate (390 µL, 1.70 mmol) at 0° C. After 1 h, sat. aq NaHCO$_3$ (10 mL) was added slowly to the reaction mixture. The mixture was extracted with EtOAc (2×30 mL), and the combined organic extracts were dried (Na$_2$SO$_4$), filtered, and concentrated to afford the title compound (450 mg, 1.224 mmol, 76% yield). $^1$H NMR (400 MHz, CDCl$_3$) δ 7.36-7.20 (m, 5H), 5.05 (s, 2H), 4.43-4.22 (m, 1H), 4.07-3.96 (m, 1H), 3.88-3.62 (m, 2H), 3.59-3.24 (m, 2H), 1.75-1.50 (m, 2H), 0.84 (s, 9H), 0.02-0.05 (m, 6H).

A1E. 4-((tert-Butyldimethylsilyl)oxy)-3-fluoropiperidine: A mixture of benzyl 4-((tert-butyldimethylsilyl)oxy)-3-fluoropiperidine-1-carboxylate (440 mg, 1.20 mmol) and Pd on activated carbon (127 mg, 0.120 mmol) in MeOH (12 mL) was purged with H$_2$ for 30 min and stirred under atm H$_2$ at rt for 1 h. The mixture was filtered through Celite®, washed with EtOAc (30 mL) and MeOH (30 mL) and concentrated to afford the title compound (270 mg, 1.157 mmol, 97% yield) as a clear oil. $^1$H NMR (400 MHz, CDCl$_3$) δ 4.50-4.27 (m, 1H), 3.97-3.77 (m, 1H), 3.19-3.05 (m, 1H), 2.93 (ddd, J=13.1, 6.3, 4.1 Hz, 1H), 2.82-2.65 (m, 2H), 2.62-2.46 (m, 1H), 1.73-1.50 (m, 2H), 0.88 (s, 9H), 0.00 (d, J=3.8 Hz, 6H).

A1F. 4-(4-((tert-Butyldimethylsilyl)oxy)-3-fluoropiperidin-1-yl)-5-chloro-2-methoxypyridine: A mixture of 4-((tert-butyldimethylsilyl)oxy)-3-fluoropiperidine (194 mg, 0.83 mmol), 4-bromo-5-chloro-2-methoxypyridine (185 mg, 0.83 mmol) and Sphos precatalyst (6 mg, 8.3 µmol) in THF (1.7 mL) was purged with argon and lithium bis (trimethylsilyl)amide (1M solution in THF, 1 mL, 1.0 mmol) was added. The reaction was heated at 70° C. for 2 h, and sat. aq NaHCO$_3$ (10 mL) was added slowly to the reaction mixture. The mixture was extracted with EtOAc (2×10 mL), and the combined organic extracts were washed with water (20 mL) and brine (20 mL), and dried (Na$_2$SO$_4$), filtered, and concentrated. Purification by chromatography gave 4-(4-((tert-butyldimethylsilyl)oxy)-3-fluoropiperidin-1-yl)-5-chloro-2-methoxypyridine (182 mg, 0.49 mmol, 58% yield). LC-MS Anal. Calc'd for $C_{17}H_{28}ClFN_2O_2Si$, 374.16, found [M+H] 374.9.

A1G. 1-(5-Chloro-2-methoxypyridin-4-yl)-3-fluoropiperidin-4-ol: To a mixture of 4-(4-((tert-butyldimethylsilyl)oxy)-3-fluoropiperidin-1-yl)-5-chloro-2-methoxypyridine (192 mg, 0.51 mmol) in THF (1.0 mL) was added TBAF (0.6 mL, 0.61 mmol). The reaction mixture was stirred at 23° C. for 2 h and sat. aq NaHCO$_3$ (10 mL) was added slowly to the reaction mixture. The mixture was then extracted with EtOAc (2×10 mL), and the combined organic extracts were washed with water (20 mL) and brine (20 mL), and dried (Na$_2$SO$_4$), filtered, and concentrated. Purification by chromatography gave the title compound (110 mg, 0.42 mmol, 82% yield) as a white foam. LC-MS Anal. Calc'd for $C_{11}H_{24}ClFN_2O_2$ 260.07, found [M+H] 261.0.

A1H. Methyl 2-((4S,5S)-1-(4-((1-(5-chloro-2-methoxypyridin-4-yl)-3-fluoropiperidin-4-yl)oxy)phenyl)-4-methyl-3-(trifluoromethyl)-4,5-dihydro-1H-pyrazol-5-yl)acetate:
To a solution of methyl 2-((4S,5S)-1-(4-hydroxyphenyl)-4-methyl-3-(trifluoromethyl)-4,5-dihydro-1H-pyrazol-5-yl) acetate (86 mg, 0.27 mmol) and 1-(5-chloro-2-methoxypyridin-4-yl)-3-fluoropiperidin-4-ol (47 mg, 0.18 mmol) in toluene (2.2 mL) was added tributylphosphine (75 µL, 0.29 mmol). While stirring, (E)-diazene-1,2-diylbis(piperidin-1- ylmethanone) (73 mg, 0.29 mmol) was added portionwise to the reaction mixture, and the reaction mixture was heated at 50° C. for 120 min. The mixture was cooled to rt and 6 mL hexanes was added to the mixture and white solid was formed. The mixture was filtered, and the filtrate was concentrated. Purification by chromatography yielded methyl 2-((4S,5S)-1-(4-((1-(5-chloro-2-methoxypyridin-4-yl)-3-fluoropiperidin-4-yl)oxy)phenyl)-4-methyl-3-(trifluoromethyl)-4,5-dihydro-1H-pyrazol-5-yl)acetate (20 mg, 0.036 mmol, 20% yield) as a white foam. LC-MS Anal. Calc'd for $C_{25}H_{27}ClF_4N_4O_4$ 558.2, found [M+H] 559.2. $^1H$ NMR (400 MHz, $CDCl_3$) δ 7.97-7.87 (m, 1H), 7.04-6.97 (m, 2H), 6.93-6.86 (m, 2H), 6.23 (s, 1H), 4.86-4.61 (m, 1H), 4.31 (ddd, J=10.6, 7.5, 3.6 Hz, 2H), 3.87-3.79 (m, 3H), 3.70-3.58 (m, 4H), 3.41-3.26 (m, 1H), 3.20-3.09 (m, 2H), 2.95-2.87 (m, 1H), 2.72 (dd, J=16.1, 3.1 Hz, 1H), 2.34 (dd, J=16.1, 10.1 Hz, 1H), 2.25-2.13 (m, 1H), 1.91-1.82 (m, 1H), 1.27 (d, J=7.0 Hz, 3H).

Example A1 (Isomer 1) and (Isomer 2): To a stirred solution of methyl 2-((4S,5S)-1-(4-((1-(5-chloro-2-methoxypyridin-4-yl)-3-fluoropiperidin-4-yl)oxy)phenyl)-4-methyl-3-(trifluoromethyl)-4,5-dihydro-1H-pyrazol-5-yl) acetate (18 mg, 0.032 mmol) in THF (0.3 mL) and water (30 µL) at rt was added 2N LiOH solution (40 µL, 0.081 mmol). The reaction mixture was stirred at rt for 16 h. Then, 1N HCl (80 µL, 0.081 mmol) was added at 0° C. to pH=4-5, followed by warming to rt. The solvent was evaporated and the residue was extracted with EtOAc 3 times. The organic portions were dried over $Na_2SO_4$, filtered and concentrated. The diastereomers were separated by chiral Prep. SFC to provide Example A1, Isomer 1 and Isomer 2 as single stereoisomers. Example A1, Isomer 1: (white solid, 5 mg). LC-MS Anal. Calc'd for $C_{24}H_{25}ClF_4N_4O_4$ 544.2, found [M+H] 545.2. $^1H$ NMR (400 MHz, $CD_3CN$) δ 8.03 (s, 1H), 7.20-6.97 (m, 4H), 6.43 (s, 1H), 4.94-4.73 (m, 1H), 4.58-4.41 (m, 2H), 3.88 (s, 3H), 3.80-3.69 (m, 1H), 3.48-3.30 (m, 2H), 3.19 (dt, J=12.4, 7.3 Hz, 1H), 3.11-3.02 (m, 2H), 2.31-2.22 (m, 2H), 1.91-1.79 (m, 2H), 1.36-1.30 (m, 3H). HPLC (Orthogonal method, 50% Solvent B start): RT=9.2 min, HI: 100%. hGPR40 $EC_{50}$=184 nM. Example A1, Isomer 2: (white solid, 5 mg). LC-MS Anal. Calc'd for $C_{24}H_{25}ClF_4N_4O_4$ 544.2, found [M+H] 545.2. $^1H$ NMR (400 MHz, $CD_3CN$) δ 8.03 (s, 1H), 7.15-6.92 (m, 4H), 6.43 (s, 1H), 4.92-4.58 (m, 1H), 4.47 (br. s., 2H), 3.87 (s, 3H), 3.81-3.66 (m, 1H), 3.46-3.30 (m, 2H), 3.24-3.13 (m, 2H), 3.10-3.00 (m, 2H), 2.08 (d, J=7.0 Hz, 2H), 1.84 (dd, J=8.7, 3.9 Hz, 1H), 1.35-1.30 (m, 3H). HPLC (Orthogonal method, 50% Solvent B start): RT=9.1 min, HI: 100%. hGPR40 $EC_{50}$=218 nM.

EXAMPLE A2

2-((4S,5S)-1-(4-(1-(5-methoxy-2-methylphenyl) piperidin-4-yloxy)phenyl)-4-methyl-3-(trifluoromethyl)-4,5-dihydro-1H-pyrazol-5-yl)acetic acid

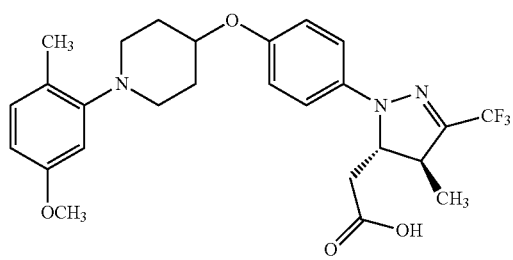 [SMILES: COc1ccc(C)c(N2CCC(Oc3ccc(N4N=C(C(F)(F)F)[C@@H](C)[C@@H]4CC(=O)O)cc3)CC2)c1]

A2A. 1-(5-Methoxy-2-methylphenyl)piperidin-4-one: To a round bottom flask was added 5-methoxy-2-methylaniline (265 mg, 1.93 mmol), $K_2CO_3$ (40 mg, 0.29 mmol) and ethanol (2.5 mL). To this mixture at 100° C. was added a slurry of 1-benzyl-1-methyl-4-oxopiperidin-1-ium, iodide salt (960 mg, 2.9 mmol) in water (1 mL) over 20 min, and stirring and heating were continued for 1 h. The solution was cooled to rt, and then it was extracted with $CH_2Cl_2$ (2×20 mL). The combined organic extracts were washed with brine (20 mL), dried over $MgSO_4$, filtered and concentrated. The residue was purified via silica chromatography to give 1-(5-methoxy-2-methylphenyl)piperidin-4-one (120 mg, 0.55 mmol, 28% yield) as a clear oil. LC-MS Anal. Calc'd for $C_{13}H_{17}NO_2$: 219.1, found [M+H] 220.1. $^1H$ NMR (400 MHz, $CDCl_3$) δ 7.15 (d, J=8.1 Hz, 1H), 6.69-6.54 (m, 2H), 3.81 (s, 3H), 3.23 (t, J=6.1 Hz, 4H), 2.63 (t, J=6.1 Hz, 4H), 2.33 (s, 3H).

A2B. 1-(5-Methoxy-2-methylphenyl)piperidin-4-ol: To a round bottom flask was added 1-(5-methoxy-2-methylphenyl)piperidin-4-one (110 mg, 0.49 mmol), THF (2 mL) and $NaBH_4$ (19 mg, 0.49 mmol), and the solution was stirred at rt for 30 min. The reaction was quenched with water (1 mL), and the mixture was partitioned between EtOAc (30 mL) and water (15 mL). The organic layer was separated, washed with brine (10 ml), dried over $MgSO_4$, filtered and concentrated. The crude product was purified via silica chromatography to give the title compound (95 mg, 0.43 mmol, 87% yield) as a clear oil. LC-MS Anal. Calc'd for $C_{13}H_{19}NO_2$: 221.3, found [M+H] 222.2. $^1H$ NMR (500 MHz, CHLOROFORM-d) δ 7.09 (d, J=8.3 Hz, 1H), 6.62 (d, J=2.8 Hz, 1H), 6.55 (dd, J=8.3, 2.5 Hz, 1H), 3.86 (d, J=3.3 Hz, 1H), 3.18-3.06 (m, 2H), 2.79-2.65 (m, 2H), 2.27-2.23 (m, 3H), 2.10-1.99 (m, 2H), 1.75 (dtd, J=12.7, 9.3, 3.7 Hz, 2H), 1.48 (br. s., 1H).

A2C. Methyl 2-((4S,5S)-1-(4-(1-(5-methoxy-2-methylphenyl)piperidin-4-yloxy)phenyl)-4-methyl-3-(trifluoromethyl)-4,5-dihydro-1H-pyrazol-5-yl)acetate: To a round bottom flask was added 1-(5-methoxy-2-methylphenyl) piperidin-4-ol (35 mg, 0.16 mmol), methyl 2-((4S,5S)-1-(4-hydroxyphenyl)-4-methyl-3-(trifluoromethyl)-4,5-dihydro-1H-pyrazol-5-yl)acetate (50 mg, 0.16 mmol), toluene (1 mL), $Bu_3P$ (0.062 mL, 0.25 mmol) and 1,1'-(azodicarbonyl) dipiperidine (63.8 mg, 0.253 mmol). The mixture was stirred at 65° C. for 1 h. The reaction solution was cooled and diluted with heptane. The mixture was filtered and the filtrate was concentrated. The residue was purified via silica gel chromatography to give methyl 2-((4S,5S)-1-(4-((1-(5-methoxy-2-methylphenyl)piperidin-4-yl)oxy)phenyl)-4-methyl-3-(trifluoromethyl)-4,5-dihydro-1H-pyrazol-5-yl) acetate (45 mg, 0.087 mmol, 55% yield) as a clear oil. LC-MS Anal. Calc'd for $C_{27}H_{32}F_3N_3O_4$: 519.2, found [M+H] 520.2.

Example A2: To a round bottom flask was added methyl 2-((4S,5S)-1-(4-((1-(5-methoxy-2-methylphenyl)piperidin-4-yl)oxy)phenyl)-4-methyl-3-(trifluoromethyl)-4,5-dihydro-1H-pyrazol-5-yl)acetate (45 mg, 0.087 mmol), 2M LiOH (0.26 mL, 0.52 mmol) and THF (1 mL). The reaction solution was stirred at rt for 1.5 h, and the solution was acidified with 1N HCl to pH<4. The mixture was extracted with EtOAc (10 mL). The organic layer was washed with water (10 mL) and brine (10 mL), and then it was dried over $MgSO_4$, filtered and concentrated. The residue was purified by Prep-HPLC to give 2-((4S,5S)-1-(4-(1-(5-methoxy-2-methylphenyl)piperidin-4-yloxy)phenyl)-4-methyl-3-(trifluoromethyl)-4,5-dihydro-1H-pyrazol-5-yl)acetic acid (31 mg, 0.062 mmol, 71% yield). LC-MS Anal. Calc'd for $C_{26}H_{30}F_3N_3O_4$: 505.2, found [M+H] 506.1. $^1H$ NMR (500

MHz, DMSO-$d_6$) δ 7.12-7.03 (m, 3H), 6.99 (d, J=9.1 Hz, 2H), 6.59 (br. s., 1H), 6.55 (dd, J=8.3, 1.9 Hz, 1H), 4.45 (d, J=3.9 Hz, 2H), 3.72 (s, 4H), 3.39-3.33 (m, 2H), 3.05 (d, J=4.4 Hz, 2H), 2.78 (t, J=9.9 Hz, 2H), 2.66 (dd, J=16.2, 3.0 Hz, 1H), 2.18 (s, 3H), 2.05 (br. s., 2H), 1.85-1.72 (m, 2H), 1.27 (d, J=6.9 Hz, 3H). hGPR40 $EC_{50}$=161 nM.

EXAMPLE A3

2-((4S,5S)-1-(2-Bromo-4-(((3R,4R)-1-(5-chloro-2-methoxypyridin-4-yl)-3-methylpiperidin-4-yl)oxy) phenyl)-4-methyl-3-(trifluoromethyl)-4,5-dihydro-1H-pyrazol-5-yl)acetic acid

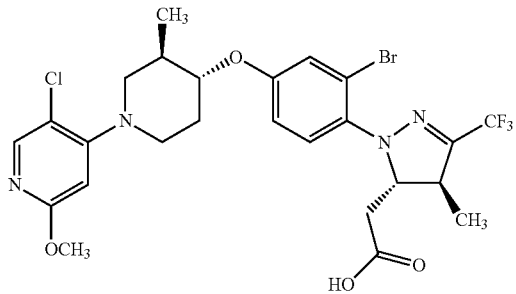 [SMILES: COc1cc(N2CC[C@@H](Oc3ccc(N4N=C(C(F)(F)F)[C@@H](C)[C@@H]4CC(=O)O)c(Br)c3)[C@H](C)C2)c(Cl)cn1]

A3A. (4S,5R)-1-(4-Bromophenyl)-5-(((tert-butyldimethylsilyl)oxy)methyl)-4-methyl-3-(trifluoromethyl)-4,5-dihydro-1H-pyrazole: To a solution of ((4S,5R)-1-(4-bromophenyl)-4-methyl-3-(trifluoromethyl)-4,5-dihydro-1H-pyrazol-5-yl)methanol (1G, 285 mg, 0.845 mmol) and imidazole (151 mg, 2.198 mmol) in dichloromethane (2.7 mL) at rt was added a solution of tert-butyldimethylsilyl chloride (171 mg, 1.10 mmol) in $CH_2Cl_2$ (1.4 mL) dropwise. The reaction mixture was stirred at rt for 19 h. After this time, the mixture was diluted with EtOAc (70 mL) and washed with sat'd $NaHCO_3$ (2×30 mL) and sat'd NaCl (20 mL). The organic layer was dried ($Na_2SO_4$) and evaporated. Chromatography ($SiO_2$, 9/1Hex/Ether) of the crude provided (4S,5R)-1-(4-Bromophenyl)-5-(((tert-butyldimethylsilyl)oxy)methyl)-4-methyl-3-(trifluoromethyl)-4,5-dihydro-1H-pyrazole (351 mg, 92% yield) as a colorless oil: LC-MS [M+H] 451, 453.

A3B. (4S,5R)-5-(((tert-Butyldimethylsilyl)oxy)methyl)-4-methyl-1-(4-(4,4,5,5-tetramethyl-1,3,2-dioxaborolan-2-yl)phenyl)-3-(trifluoromethyl)-4,5-dihydro-1H-pyrazole: A flask containing a suspension of (4S,5R)-1-(4-bromophenyl)-5-(((tert-butyldimethylsilyl)oxy)methyl)-4-methyl-3-(trifluoromethyl)-4,5-dihydro-1H-pyrazole (351 mg, 0.778 mmol), bis(pinacolato)diboron (230 mg, 0.897 mmol) and potassium acetate (232 mg, 2.340 mmol) in DMF (1.4 mL) was evacuated and backfilled with Ar. [1,1-bis(Diphenylphosphino)ferrocene]dichloropalladium(II), complex with dichloromethane (32 mg, 0.039 mmol) was added to the suspension and the mixture was degassed by ultrasound irradiation under Ar for 5 min. The mixture was heated to 80° C. and stirred at this temperature for 6 h. At this time, the reaction mixture was allowed to cool to rt while stirring for an additional 12 h. The reaction mixture was filtered through Celite and the filter cake was rinsed with EtOAc (80 mL). The combined filtrate and rinse were washed with 10% $Na_2CO_3$ (2×40 mL), water (40 mL) and sat'd NaCl (40 mL), dried ($Na_2SO_4$) and evaporated. To a solution of the residue and imidazole (116 mg, 1.69 mmol) in $CH_2Cl_2$ (2.1 mL) at rt was added a solution of tert-butyldimethylsilyl chloride (132 mg, 0.85 mmol) in $CH_2Cl_2$ (1.1 mL) dropwise. The reaction mixture was stirred at rt for 14 h and then, diluted with EtOAc (80 mL) and washed with sat'd $NaHCO_3$ (2×40 mL) and sat'd NaCl (40 mL). The organic layer was dried ($Na_2SO_4$) and evaporated. The crude was chromatographed ($SiO_2$, 95/5 to 9/1 Hex/Ether) to provide (4S,5R)-5-(((tert-Butyldimethylsilyl)oxy)methyl)-4-methyl-1-(4-(4,4,5,5-tetramethyl-1,3,2-dioxaborolan-2-yl)phenyl)-3-(trifluoromethyl)-4,5-dihydro-1H-pyrazole (318 mg, 82% yield) as a colorless oil: LC-MS [M+H] 499.

A3C. 4-((4S,5R)-5-(((tert-butyldimethylsilyl)oxy)methyl)-4-methyl-3-(trifluoromethyl)-4,5-dihydro-1H-pyrazol-1-yl)phenol: To a stirred solution of (4S,5R)-5-(((tert-butyldimethylsilyl)oxy)methyl)-4-methyl-1-(4-(4,4,5,5-tetramethyl-1,3,2-dioxaborolan-2-yl)phenyl)-3-(trifluoromethyl)-4,5-dihydro-1H-pyrazole (227 mg, 0.455 mmol) in EtOAc (2.0 mL) at rt was added 30% hydrogen peroxide (0.7 mL, 6.85 mmol) dropwise. The reaction mixture was stirred at rt for 21 h. After this time, the mixture was cooled to 0° C. and treated with 10% $Na_2S_2O_3$ (11 mL). The resulting aqueous mixture was stirred at rt for 2 h and then extracted with EtOAc (3×40 mL). The organic extracts were washed with sat'd NaCl (20 mL), dried ($Na_2SO_4$) and concentrated. Chromatography ($SiO_2$, 7/3 Hex/EtOAc) of the crude residue afforded 4-((4S,5R)-5-(((tert-butyldimethylsilyl)oxy)methyl)-4-methyl-3-(trifluoromethyl)-4,5-dihydro-1H-pyrazol-1-yl)phenol (156 mg, 88% yield) as a white solid: LC-MS [M+H] 389.

A3D. 3-bromo-4-((4S,5R)-5-(((tert-butyldimethylsilyl)oxy)methyl)-4-methyl-3-(trifluoromethyl)-4,5-dihydro-1H-pyrazol-1-yl)phenol: To a stirred solution of 4-((4S,5R)-5-(((tert-butyldimethylsilyl)oxy)methyl)-4-methyl-3-(trifluoromethyl)-4,5-dihydro-1H-pyrazol-1-yl)phenol (44.5 mg, 0.115 mmol) in $CH_2Cl_2$ (2.3 mL) at 0° C. was added pyridinium bromide perbromide (41 mg, 0.115 mmol) in three portions. The solution turned purple after portion addition and was stirred, until it turned back to clear, before addition of the next portion. After addition of the last portion, the reaction mixture was stirred until decoloration and then quenched with 10% $Na_2S_2O_3$ (4.0 mL). The aqueous mixture was allowed to warm to rt and stirred for 30 min. The final mixture was partitioned between EtOAc (50 mL) and water (10 mL). The organic layer was washed with 5% $NaHCO_3$ (2×30 mL) and sat'd NaCl (20 mL), dried ($Na_2SO_4$) and evaporated. To a solution of the residue in $CH_2Cl_2$ (0.5 mL) at rt was added a solution of tert-butyldimethylsilyl chloride (32 mg, 0.206 mmol) in $CH_2Cl_2$ (0.25 mL), dropwise. The reaction mixture was stirred at rt for 7.3 h. At this time, additional imidazole (28 mg, 0.407 mmol) and solution of tert-butyldimethylsilyl chloride (32 mg, 0.206 mmol) in dichloromethane (0.25 mL) were added and stirring at rt was continued for an additional 11 h. The mixture was diluted with EtOAc (50 mL) and washed with sat'd $NaHCO_3$ (2×20 mL) and sat'd NaCl (20 mL). The organic layer was dried ($Na_2SO_4$) and evaporated. To a solution of the resulting residue in DMF (0.45 mL) was added water (0.05 mL) followed by cesium carbonate (30 mg, 0.092 mmol). The resulting yellow solution was stirred at rt for 26 h. After this time, the solution was diluted with ether (40 mL) and washed with sat'd NaCl (20 mL). The organic layer was dried ($Na_2SO_4$) and evaporated, and the crude was chromatographed ($SiO_2$, 4/1Hex/EtOAc) to give a mixture of isomeric aryl bromides (30 mg). This isomeric mixture was separated by chromatography ($SiO_2$, 96/4 $CHCl_3$/Ether) to afford 3-bromo-4-((4S,5R)-5-(((tert-butyldimethylsilyl)oxy)methyl)-4-methyl-3-(trifluoromethyl)-

4,5-dihydro-1H-pyrazol-1-yl)phenol (11 mg, 14.21% yield) as a colorless oil: LC-MS [M+H] 467, 469.

A3E. 4-((3R,4R)-4-(3-Bromo-4-((4S,5R)-5-(((tert-butyldimethylsilyl)oxy)methyl)-4-methyl-3-(trifluoromethyl)-4,5-dihydro-1H-pyrazol-1-yl)phenoxy)-3-methylpiperidin-1-yl)-5-chloro-2-methoxypyridine: To a stirred solution of 3-bromo-4-((4S,5R)-5-(((tert-butyldimethylsilyl)oxy)methyl)-4-methyl-3-(trifluoromethyl)-4,5-dihydro-1H-pyrazol-1-yl)phenol (10.2 mg, 0.022 mmol), (3R,4S)-1-(5-chloro-2-methoxypyridin-4-yl)-3-methylpiperidin-4-ol (81I, 11 mg, 0.042 mmol) and triphenylphosphine (13 mg, 0.049 mmol) in THF (0.2 mL) at rt was added di-tert-butylazodicarboxylate (11 mg, 0.047 mmol). The resulting solution was stirred at rt for 59 h and then evaporated The residue was chromatographed (SiO$_2$, 96/4 CHCl$_3$/Ether) to afford 4-((3R,4R)-4-(3-Bromo-4-((4S,5R)-5-(((tert-butyldimethylsilyl)oxy)methyl)-4-methyl-3-(trifluoromethyl)-4,5-dihydro-1H-pyrazol-1-yl)phenoxy)-3-methylpiperidin-1-yl)-5-chloro-2-methoxypyridine (14 mg, 66% yield) as a colorless oil: LC-MS [M+H] 705, 707, 709.

A3F. ((4S,5R)-1-(2-Bromo-4-(((3R,4R)-1-(5-chloro-2-methoxypyridin-4-yl)-3-methylpiperidin-4-yl)oxy)phenyl)-4-methyl-3-(trifluoromethyl)-4,5-dihydro-1H-pyrazol-5-yl) methanol: 4-((3R,4R)-4-(3-Bromo-4-((4S,5R)-5-(((tert-butyldimethylsilyl)oxy)methyl)-4-methyl-3-(trifluoromethyl)-4,5-dihydro-1H-pyrazol-1-yl)phenoxy)-3-methylpiperidin-1-yl)-5-chloro-2-methoxypyridine was dissolved in in ~1.1M HCl/MeOH, MeOAc solution [3.25 mL, prepared by addition of AcCl (0.25 mL) to MeOH (3.0 mL) at 0° C. and then stirring at rt for 30 min]. The resulting solution was allowed to stand at rt for 12 h. After this time, the solution was diluted with MeCN (4 mL) and evaporated. The residue was taken up in EtOAc (40 mL) and, washed with 5% NaHCO$_3$ (2×20 mL) and sat'd NaCl (20 mL). The organic layer was dried (Na$_2$SO$_4$) and concentrated. Chromatography (SiO$_2$, 4/1 to 7/3 Hex/EtOAc) of the crude afforded ((4S,5R)-1-(2-bromo-4-(((3R,4R)-1-(5-chloro-2-methoxypyridin-4-yl)-3-methylpiperidin-4-yl)oxy)phenyl)-4-methyl-3-(trifluoromethyl)-4,5-dihydro-1H-pyrazol-5-yl) methanol (9 mg, 82% yield) as a colorless oil: LC-MS [M+H] 591, 593.

A3G. ((4S,5R)-1-(2-Bromo-4-(((3R,4R)-1-(5-chloro-2-methoxypyridin-4-yl)-3-methylpiperidin-4-yl)oxy)phenyl)-4-methyl-3-(trifluoromethyl)-4,5-dihydro-1H-pyrazol-5-yl) methyl methanesulfonate: To a solution of ((4S,5R)-1-(2-bromo-4-(((3R,4R)-1-(5-chloro-2-methoxypyridin-4-yl)-3-methylpiperidin-4-yl)oxy)phenyl)-4-methyl-3-(trifluoromethyl)-4,5-dihydro-1H-pyrazol-5-yl)methanol (9 mg, 0.016 mmol) and methanesulfonyl chloride (2 µL, 0.026 mmol) in CH$_2$Cl$_2$ (0.3 mL) at 0° C. was added triethylamine (5 µL, 0.036 mmol). The mixture was stirred for 30 min at 0° C. and for 3 h while warming to rt. Then, the mixture was diluted with EtOAc (30 mL) and washed with sat'd NaHCO$_3$ (2×15 mL) and sat'd NaCl (15 mL). The EtOAc solution was dried (Na$_2$SO$_4$) and evaporated. Drying under vacuum gave ((4S,5R)-1-(2-bromo-4-(((3R,4R)-1-(5-chloro-2-methoxypyridin-4-yl)-3-methylpiperidin-4-yl)oxy)phenyl)-4-methyl-3-(trifluoromethyl)-4,5-dihydro-1H-pyrazol-5-yl)methyl methanesulfonate (10 mg, 97% yield) as a yellowish oil: LC-MS [M+H] 669, 671.

A3H. 2-((4S,5S)-1-(2-Bromo-4-(((3R,4R)-1-(5-chloro-2-methoxypyridin-4-yl)-3-methylpiperidin-4-yl)oxy)phenyl)-4-methyl-3-(trifluoromethyl)-4,5-dihydro-1H-pyrazol-5-yl)acetonitrile: To a solution of ((4S,5R)-1-(2-bromo-4-(((3R,4R)-1-(5-chloro-2-methoxypyridin-4-yl)-3-methylpiperidin-4-yl)oxy)phenyl)-4-methyl-3-(trifluoromethyl)-4,5-dihydro-1H-pyrazol-5-yl)methyl methanesulfonate (10 mg, 0.015 mmol) in DMSO (0.2 mL) was added potassium cyanide (2.0 mg, 0.030 mmol). The mixture was heated to 40° C. and stirred at this temperature under Ar for 8.5 h. At this time, the mixture was cooled to rt and stirred for an additional 12 h. The mixture was diluted with EtOAc (40 mL) and, washed with sat'd NaHCO$_3$ (2×15 mL), water (2×15 mL) and sat'd NaCl (10 mL). The organic layer was dried (Na$_2$SO$_4$) and concentrated. The crude was chromatographed (SiO$_2$, 7/3 Hex/EtOAc) to give 2-((4S,5S)-1-(2-bromo-4-(((3R,4R)-1-(5-chloro-2-methoxypyridin-4-yl)-3-methylpiperidin-4-yl)oxy)phenyl)-4-methyl-3-(trifluoromethyl)-4,5-dihydro-1H-pyrazol-5-yl)acetonitrile (7 mg, 78% yield) as a colorless oil: LC-MS [M+H] 600, 602.

A3I. Methyl 2-((4S,5S)-1-(2-bromo-4-(((3R,4R)-1-(5-chloro-2-methoxypyridin-4-yl)-3-methylpiperidin-4-yl)oxy)phenyl)-4-methyl-3-(trifluoromethyl)-4,5-dihydro-1H-pyrazol-5-yl)acetate: 2-((4S,5S)-1-(2-Bromo-4-(((3R,4R)-1-(5-chloro-2-methoxypyridin-4-yl)-3-methylpiperidin-4-yl)oxy)phenyl)-4-methyl-3-(trifluoromethyl)-4,5-dihydro-1H-pyrazol-5-yl)acetonitrile (7 mg, 0.012 mmol) was dissolved in ~3M HCl/MeOH, CH$_2$Cl$_2$, MeOAc solution [3.8 mL, prepared by addition of AcCl (0.8 mL) to a 3/2 CH$_2$Cl$_2$/MeOH solution (3.0 mL) at 0° C. and then stirring at rt for 20 min]. The resulting solution was allowed to stand at rt for 29 h. After this time, the solution was evaporated and the remaining oily material was stripped from MeOH (2×4 mL). The residue was dissolved in ~3M HCl/MeOH, MeOAc solution [3.8 mL, prepared by addition of AcCl (0.8 mL) to MeOH (3.0 mL) at 0° C. and then stirring at rt for 30 min] The resulting solution was heated to 40° C. and allowed to stand at this temperature for 23 h. After this time, the solution was cooled to rt, diluted with MeCN (4 mL) and evaporated. The residue was taken up in EtOAc (40 mL) and, washed with sat'd NaHCO$_3$ (2×35 mL) and sat'd NaCl (30 mL). The organic layer was dried (Na$_2$SO$_4$) and concentrated. The crude was chromatographed (SiO$_2$, 4/1 Hex/EtOAc) to afford methyl 2-((4S,5S)-1-(2-bromo-4-(((3R,4R)-1-(5-chloro-2-methoxypyridin-4-yl)-3-methylpiperidin-4-yl)oxy)phenyl)-4-methyl-3-(trifluoromethyl)-4,5-dihydro-1H-pyrazol-5-yl)acetate (7 mg, 89% yield) as a colorless oil: LC-MS [M+H] 633, 635.

Example A3: To a stirred solution of methyl 2-((4S,5S)-1-(2-bromo-4-(((3R,4R)-1-(5-chloro-2-methoxypyridin-4-yl)-3-methylpiperidin-4-yl)oxy)phenyl)-4-methyl-3-(trifluoromethyl)-4,5-dihydro-1H-pyrazol-5-yl)acetate (6.5 mg, 10.25 µmol) in THF (0.5 mL) and water (0.04 mL) at rt was added 1.0M aqueous lithium hydroxide (0.04 mL, 0.040 mmol). The mixture was stirred at rt for 13.5 h and then partially evaporated to remove most of the THF. The remaining solution was partitioned between water (40 mL) and Hex (15 mL). The aqueous layer was acidified to pH 2 by dropwise addition of 1M HCl, and then extracted with CH$_2$Cl$_2$ (3×30 mL). The combined organic extracts were dried (Na$_2$SO$_4$) and concentrated. The residue was dried under vacuum to afford 2-((4S,5S)-1-(2-bromo-4-(((3R,4R)-1-(5-chloro-2-methoxypyridin-4-yl)-3-methylpiperidin-4-yl)oxy)phenyl)-4-methyl-3-(trifluoromethyl)-4,5-dihydro-1H-pyrazol-5-yl)acetic acid (6 mg, 89% yield) as a white solid: LC-MS [M+H] 619, 621. $^1$H NMR (400 MHz, CD$_2$Cl$_2$) δ 7.96 (s, 1H), 7.21 (d, J=8.8 Hz, 1H), 7.19 (d, J=8.8 Hz, 1H), 6.91 (dd, J=8.8, 2.8 Hz, 1H), 6.29 (s, 1H), 4.63 (m, 1H), 3.99 (dt, J=4.1, 8.8 Hz, 1H), 3.86 (s, 3H), 3.52 (m, 2H), 3.27 (m, 1H), 2.89 (m, 1H), 2.66 (dd, J=12.2, 9.3 Hz, 1H), 2.41 (m, 2H), 2.18 (m, 2H), 1.79 (m, 1H), 1.41 (d, J=7.1 Hz, 3H), 1.10 (d, J=6.8 Hz, 3H). Analytical HPLC (Zorbax method, 0% Solvent B start): RT=8.69 min, HI: 97%. hGPR40 $EC_{50}$=844 nM.

EXAMPLE A4

2-((4S,5S)-1-(3-Bromo-4-(((3R,4R)-1-(5-chloro-2-methoxypyridin-4-yl)-3-methylpiperidin-4-yl)oxy)phenyl)-4-methyl-3-(trifluoromethyl)-4,5-dihydro-1H-pyrazol-5-yl)acetic acid

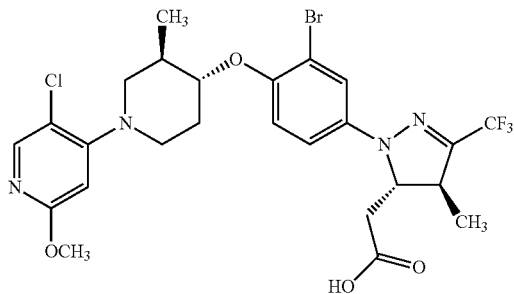 [SMILES: COc1cc(N2CC[C@@H](Oc3ccc(N4N=C(C(F)(F)F)[C@@H](C)[C@@H]4CC(=O)O)cc3Br)[C@H](C)C2)c(Cl)cn1]

A4A. 2-((4S,5S)-4-methyl-1-(4-(4,4,5,5-tetramethyl-1,3,2-dioxaborolan-2-yl)phenyl)-3-(trifluoromethyl)-4,5-dihydro-1H-pyrazol-5-yl)acetonitrile: A flask containing a suspension of 2-((4S,5S)-1-(4-bromophenyl)-4-methyl-3-(trifluoromethyl)-4,5-dihydro-1H-pyrazol-5-yl)acetonitrile (1I, 645 mg, 1.863 mmol), bis(pinacolato)diboron (560 mg, 2.183 mmol) and potassium acetate (573 mg, 5.78 mmol) in DMF (3.4 mL) was evacuated and backfilled with Ar. [1,1-Bis(diphenylphosphino)ferrocene]dichloropalladium (II), complex with dichloromethane (76 mg, 0.093 mmol) was added to the suspension and the mixture was degassed by ultrasound irradiation under Ar for 5 min. The mixture was heated to 78° C. and stirred at this temperature for 10.8 h. After this time, the reaction mixture was filtered through Celite and the filter cake was rinsed with EtOAc (130 mL). The combined filtrate and rinse were washed with 10% $Na_2CO_3$ (50 mL), sat'd $NaHCO_3$ (70 ml), water (70 mL) and sat'd NaCl (50 mL). The organic layer was dried ($Na_2SO_4$) and evaporated. The crude was chromatographed ($SiO_2$, 4/1 to 7/3 Hex/EtOAc) to provide 2-((4S,5S)-4-methyl-1-(4-(4,4,5,5-tetramethyl-1,3,2-dioxaborolan-2-yl)phenyl)-3-(trifluoromethyl)-4,5-dihydro-1H-pyrazol-5-yl)acetonitrile (642 mg, 88% yield) as a colorless oil: LC-MS [M+H] 394.

A4B. 2-((4S,5S)-1-(4-hydroxyphenyl)-4-methyl-3-(trifluoromethyl)-4,5-dihydro-1H-pyrazol-5-yl)acetonitrile: To a stirred solution of the 2-((4S,5S)-4-methyl-1-(4-(4,4,5,5-tetramethyl-1,3,2-dioxaborolan-2-yl)phenyl)-3-(trifluoromethyl)-4,5-dihydro-1H-pyrazol-5-yl)acetonitrile (572 mg, 1.455 mmol) in EtOAc (6.4 mL) at rt was added 30% hydrogen peroxide (2.3 mL, 22.52 mmol) dropwise. The reaction mixture was stirred at rt for 22 h. After this time, the mixture was cooled to 0° C. and treated with 10% $Na_2S_2O_3$ (35 mL). The resulting aqueous mixture was stirred at rt for 2 h and then extracted with EtOAc (3×50 mL). The organic extracts were washed with sat'd NaCl (40 mL), dried ($Na_2SO_4$) and concentrated. Chromatography ($SiO_2$, 3/2 Hex/EtOAc) of the crude afforded 2-((4S,5S)-1-(4-hydroxyphenyl)-4-methyl-3-(trifluoromethyl)-4,5-dihydro-1H-pyrazol-5-yl)acetonitrile (391 mg, 94% yield) as a yellowish oil: LC-MS [M+H] 284.

A4C. 2-((4S,5S)-1-(3-bromo-4-(((3R,4R)-1-(5-chloro-2-methoxypyridin-4-yl)-3-methylpiperidin-4-yl)oxy)phenyl)-4-methyl-3-(trifluoromethyl)-4,5-dihydro-1H-pyrazol-5-yl)acetonitrile: To a stirred solution of the 2-((4S,5S)-1-(4-hydroxyphenyl)-4-methyl-3-(trifluoromethyl)-4,5-dihydro-1H-pyrazol-5-yl)acetonitrile (179 mg, 0.489 mmol), (3R,4S)-1-(5-chloro-2-methoxypyridin-4-yl)-3-methylpiperidin-4-ol (81I, 228 mg, 0.881 mmol) and triphenylphosphine (262 mg, 0.988 mmol) in THF (2.9 mL) at rt was added di-tert-butylazodicarboxylate (231 mg, 0.984 mmol). The resulting solution was stirred at rt for 24 h and then evaporated. The residue was chromatographed ($SiO_2$ 230-400 mesh, 96/4 $CHCl_3$/Ether) to afford 2-((4S,5S)-1-(3-bromo-4-(((3R,4R)-1-(5-chloro-2-methoxypyridin-4-yl)-3-methylpiperidin-4-yl)oxy)phenyl)-4-methyl-3-(trifluoromethyl)-4,5-dihydro-1H-pyrazol-5-yl)acetonitrile (257 mg, 87% yield) as a colorless oil: LC-MS [M+H] 600, 602.

A4D. Methyl 2-((4S,5S)-1-(3-bromo-4-(((3R,4R)-1-(5-chloro-2-methoxypyridin-4-yl)-3-methylpiperidin-4-yl)oxy)phenyl)-4-methyl-3-(trifluoromethyl)-4,5-dihydro-1H-pyrazol-5-yl)acetate: 2-((4S,5S)-1-(3-Bromo-4-(((3R,4R)-1-(5-chloro-2-methoxypyridin-4-yl)-3-methylpiperidin-4-yl)oxy)phenyl)-4-methyl-3-(trifluoromethyl)-4,5-dihydro-1H-pyrazol-5-yl)acetonitrile (258 mg, 0.425 mmol) was dissolved in ~3M HCl/MeOH, $CH_2Cl_2$, MeOAc solution [12.6 mL, prepared by addition of AcCl (2.6 mL) to a 3/2 $CH_2Cl_2$/MeOH solution (10.0 mL) at 0° C. and then stirring at rt for 20 min]. The resulting solution was allowed to stand at rt for 18 h. The solution was evaporated and the remaining oily material was stripped from MeOH (2×10 mL). The residue was dissolved in ~3M HCl/MeOH, MeOAc solution [12.6 mL, prepared by addition of AcCl (2.6 mL) to MeOH (10.0 mL) at 0° C. and then stirring at rt for 30 min]. The resulting solution was heated to 40° C. and allowed to stand at this temperature. for 23.0 h. After this time, the solution was cooled to rt, diluted with MeCN (10 mL) and evaporated. The residue was taken up in EtOAc (60 mL) and, washed with sat'd $NaHCO_3$ (2×35 mL) and sat'd NaCl (30 mL). The organic layer was dried ($Na_2SO_4$) and concentrated. The crude was chromatographed ($SiO_2$, 4/1 Hex/EtOAc) to afford methyl 2-((4S,5S)-1-(3-bromo-4-(((3R,4R)-1-(5-chloro-2-methoxypyridin-4-yl)-3-methylpiperidin-4-yl)oxy)phenyl)-4-methyl-3-(trifluoromethyl)-4,5-dihydro-1H-pyrazol-5-yl)acetate: 2-((4S,5S)-1-(3-Bromo-4-(((3R,4R)-1-(5-chloro-2-methoxypyridin-4-yl)-3-methylpiperidin-4-yl)oxy)phenyl)-4-methyl-3-(trifluoromethyl)-4,5-dihydro-1H-pyrazol-5-yl)acetonitrile (247 mg, 92% yield) as a white solid: LC-MS [M+H] 633, 635.

EXAMPLE A4

To a stirred solution of methyl 2-((4S,5S)-1-(3-bromo-4-(((3R,4R)-1-(5-chloro-2-methoxypyridin-4-yl)-3-methylpiperidin-4-yl)oxy)phenyl)-4-methyl-3-(trifluoromethyl)-4,5-dihydro-1H-pyrazol-5-yl)acetate (44 mg, 0.069 mmol) in THF (2.0 mL) and water (0.2 mL) at rt was added 1.0M aqueous lithium hydroxide (0.2 mL, 0.200 mmol). After stirring at rt for 4.5 h, the reaction mixture was partially evaporated to remove most of the THF. The remaining solution was partitioned between water (50 mL) and Hex (15 mL). The aqueous layer was acidified to pH 2 by dropwise addition of 1M HCl, and then extracted with $CH_2Cl_2$ (3×30 mL). The combined organic extracts were dried ($Na_2SO_4$) and concentrated. The residue was dried under vacuum to afford 2-((4S,5S)-1-(3-bromo-4-(((3R,4R)-1-(5-chloro-2-methoxypyridin-4-yl)-3-methylpiperidin-4-yl)oxy)phenyl)-4-methyl-3-(trifluoromethyl)-4,5-dihydro-1H-pyrazol-5-yl)acetic acid (43 mg, 100% yield) as a white solid: LC-MS

[M+H] 619, 621. $^1$H NMR (500 MHz, $CD_2Cl_2$) δ 7.97 (s, 1H), 7.36 (d, J=2.8 Hz, 1H), 7.02 (dd, J=9.0, 2.8 Hz, 1H), 6.95 (d, J=9.0 Hz, 1H), 6.30 (s, 1H), 4.41 (m, 1H), 4.02 (dt, J=3.9, 8.3 Hz, 1H), 3.86 (s, 3H), 3.54 (m, 2H), 3.28 (m, 1H), 2.90 (m, 1H), 2.84 (dd, J=16.5, 3.1 Hz, 1H), 2.18 (m, 2H), 1.86 (m, 2H), 1.35 (d, J=7.1 Hz, 3H), 1.17 (d, J=6.7 Hz, 3H). Analytical HPLC (Zorbax method, 50% Solvent B start): RT=8.55 min, HI: 100%. hGPR40 $EC_{50}$=45 nM.

EXAMPLE B1

2-((4S,5S)-1-(4-(((3S,4R)-1-(5-chloro-2-methoxy-pyridin-4-yl)-3-(hydroxymethyl)piperidin-4-yl)oxy)phenyl)-4-methyl-3-(trifluoromethyl)-4,5-dihydro-1H-pyrazol-5-yl)acetic acid

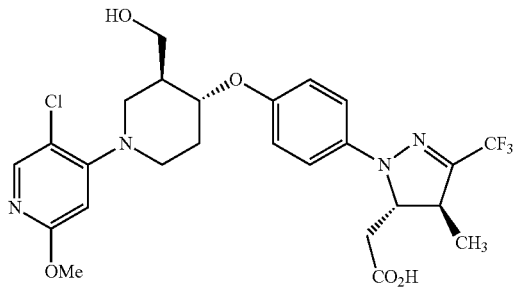 [SMILES: COc1cc(N2CC[C@@H](Oc3ccc(N4N=C(C(F)(F)F)[C@@H](C)[C@@H]4CC(=O)O)cc3)[C@H](CO)C2)c(Cl)cn1]

B1A. (3R,4S)-1-tert-butyl 3-ethyl 4-hydroxypiperidine-1,3-dicarboxylate: To a 1 liter flask with tap water (240 mL) was added sucrose (24 g, 11 mmol) and Baker's yeast (24 g, 11.06 mmol). The mixture was stirred at 32° C. for 30 min and 1-tert-butyl 3-ethyl 4-oxopiperidine-1,3-dicarboxylate (3 g, 11.06 mmol) was added. The reaction mixture was stirred at 32° C. for 60 h, and it was filtered through celite. The solids were washed with $CH_2Cl_2$ (3×). The filtrate was extracted with $CH_2Cl_2$ (3×) and the organic layers were successively washed with water, dried and concentrated. Purification via silica gel chromatography gave the title compound as a white solid (2.22 g, 8.12 mmol, 73.5% yield). $^1$H NMR (400 MHz, $CDCl_3$-d) δ 4.32-4.25 (m, 1H), 4.19 (d, J=7.3 Hz, 2H), 3.77-3.61 (m, 1H), 3.48-3.36 (m, 1H), 3.33-3.22 (m, 1H), 3.15-3.04 (m, 1H), 2.68-2.58 (m, 1H), 1.89-1.74 (m, 1H), 1.65 (s, 1H), 1.28 (t, J=7.2 Hz, 3H).

B1B. (3 S,4S)-tert-butyl 4-hydroxy-3-(hydroxymethyl)piperidine-1-carboxylate: To a solution of (3R,4S)-1-tert-butyl 3-ethyl 4-hydroxypiperidine-1,3-dicarboxylate (1.48 g, 5.41 mmol) in THF (54.1 mL) at 0° C. was added LAH (0.247 g, 6.50 mmol) in portions, and the mixture was subsequently warmed to rt. The reaction mixture was stirred for 7 h, then it was cooled to 0° C. To this mixture was added 0.2 mL water, 0.2 mL 15% NaOH, and three portions of 0.2 mL water. After stirring for 0.5 h, the mixture was filtered through Celite®. The filtrate was concentrated and re-dissolved in EtOAc. The organic solution was washed with brine, dried and concentrated. Purification via silica gel chromatography gave the title compound as a colorless oil (1.0 g, 4.3 mmol, 80% yield). $^1$H NMR (400 MHz, $CDCl_3$) δ 4.27-4.15 (m, 1H), 3.79 (d, J=5.7 Hz, 2H), 3.64-3.48 (m, 2H), 3.41 (d, J=9.2 Hz, 2H), 3.27-3.15 (m, 1H), 1.93-1.78 (m, 1H), 1.75-1.61 (m, 2H).

B1C. (3S,4S)-3-(hydroxymethyl)piperidin-4-ol, TFA salt: To a solution of (3S,4S)-tert-butyl 4-hydroxy-3-(hydroxymethyl)piperidine-1-carboxylate (1.0 g, 4.3 mmol) in DCM (22 mL) was added TFA (3.33 mL, 43.2 mmol). The reaction solution was stirred for 2 h and was evaporated to dryness to give (3S,4S)-3-(hydroxymethyl)piperidin-4-ol, TFA salt as a colorless foam (1.7 g, 4.73 mmol, 100% yield). LC-MS Anal. Calc'd for $C_6H_{13}NO_2$: 131.1, found: [M+H] 132.0.

B1D. (3S,4S)-1-(5-chloro-2-methoxypyridin-4-yl)-3-(hydroxymethyl)piperidin-4-ol: To a solution of (3S,4S)-3-(hydroxymethyl)piperidin-4-ol, TFA salt (1.55 g, 4.32 mmol) and $K_2CO_3$ (2.69 g, 19.4 mmol) in DMSO (14.4 mL) was added 4-bromo-5-chloro-2-methoxypyridine (1.01 g, 4.54 mmol). The reaction mixture was stirred at 110° C. for 16 h. The reaction mixture was diluted with EtOAc and the organic layer was washed with water, brine, dried over $Na_2SO_4$, and concentrated. Purification via silica gel chromatography gave the title compound as a colorless oil (0.68 g, 2.49 mmol, 57.7% yield). LC-MS Anal. Calc'd for $C_{12}H_{17}ClN_2O_3$: 272.1, found: [M+H] 273.1.

B1E. (3S,4S)-3-(((tert-butyldiphenylsilyl)oxy)methyl)-1-(5-chloro-2-methoxypyridin-4-yl)piperidin-4-ol: To a solution of (3S,4S)-1-(5-chloro-2-methoxypyridin-4-yl)-3-(hydroxymethyl)piperidin-4-ol (0.68 g, 2.493 mmol) in DMF (12.47 mL) was added imidazole (0.25 g, 3.7 mmol) and TBDPS-Cl (0.71 mL, 2.7 mmol). The reaction mixture was stirred at room temperature for 2 h. The mixture was diluted with EtOAc and the organic layer was washed with water, brine, dried over $Na_2SO_4$, and concentrated. Purification via silica gel chromatography gave 3-(((tert-butyldiphenylsilyl)oxy)methyl)-1-(5-chloro-2-methoxypyridin-4-yl)piperidin-4-ol as a colorless oil (0.9 g, 1.76 mmol, 70.6% yield). The cis-isomers were submitted for SFC for chiral separation. The desired isomer as peak 1 was obtained as (3S,4S)-3-(((tert-butyldiphenylsilyl)oxy)methyl)-1-(5-chloro-2-methoxypyridin-4-yl)piperidin-4-ol (0.34 g, 0.67 mmol, 27% yield). LC-MS Anal. Calc'd for $C_{28}H_{35}ClN_2O_3Si$: 510.2, found: [M+H] 511.1.

B1F. Methyl 2-((4S,5S)-1-(4-(((3S,4R)-3-(((tert-butyldiphenylsilyl)oxy)methyl)-1-(5-chloro-2-methoxypyridin-4-yl)piperidin-4-yl)oxy)phenyl)-4-methyl-3-(trifluoromethyl)-4,5-dihydro-1H-pyrazol-5-yl)acetate: To a solution of (3S,4S)-3-(((tert-butyldiphenylsilyl)oxy)methyl)-1-(5-chloro-2-methoxypyridin-4-yl)piperidin-4-ol (129 mg, 0.25 mmol), methyl 2-((4S,5S)-1-(4-hydroxyphenyl)-4-methyl-3-(trifluoromethyl)-4,5-dihydro-1H-pyrazol-5-yl)acetate (80 mg, 0.25 mmol), and $Bu_3P$ (100 µL, 0.40 mmol) in toluene (3.16 mL) was added (E)-diazene-1,2-diylbis(piperidin-1-ylmethanone) (102 mg, 0.40 mmol). The reaction mixture was sonicated for 2 h, and then it was poured into hexanes (5 mL). The resulting mixture was filtered and concentrated. Purification via silica gel chromatography gave the title compound (143 mg, 0.177 mmol, 70% yield) as a colorless oil. LC-MS Anal. Calc'd for $C_{42}H_{48}ClF_3N_4O_5Si$: 808.3, found: [M+H] 809.2. $^1$H NMR (400 MHz, CDCl3-d) δ 7.96 (s, 1H), 7.69-7.61 (m, 2H), 7.58-7.49 (m, 2H), 7.46-7.32 (m, 4H), 7.27 (s, 2H), 7.05-6.98 (m, 2H), 6.90-6.85 (m, 2H), 6.27-6.22 (m, 1H), 4.43-4.32 (m, 2H), 3.97-3.79 (m, 5H), 3.69 (s, 3H), 3.61-3.53 (m, 1H), 3.52-3.39 (m, 1H), 3.25-3.06 (m, 1H), 2.98-2.69 (m, 3H), 2.40 (dd, J=16.2, 10.2 Hz, 1H), 2.31-2.09 (m, 2H), 1.77 (s, 1H), 1.33 (d, J=7.0 Hz, 3H), 1.09-1.00 (m, 9H).

B1G. methyl 2-((4S,5S)-1-(4-(((3S,4R)-1-(5-chloro-2-methoxypyridin-4-yl)-3-(hydroxymethyl)piperidin-4-yl)oxy)phenyl)-4-methyl-3-(trifluoromethyl)-4,5-dihydro-1H-pyrazol-5-yl)acetate: To a solution of methyl 2-((4S,5S)-1-(4-(((3S,4R)-3-(((tert-butyldiphenylsilyl)oxy)methyl)-1-(5-chloro-2-methoxypyridin-4-yl)piperidin-4-yl)oxy)phenyl)-4-methyl-3-(trifluoromethyl)-4,5-dihydro-1H-pyrazol-5-yl)acetate (130 mg, 0.161 mmol) in THF (803 µL) was added 1M TBAF/THF (201 µL, 0.201 mmol). The reaction was stirred for 2.5 h and the reaction mixture was diluted with EtOAc. The organic layer was washed with water, brine, dried over Na$_2$SO$_4$, and concentrated. Purification via silica gel chromatography gave the title compound as a colorless oil (65 mg, 0.114 mmol, 70.9% yield). LC-MS Anal. Calc'd for C$_{26}$H$_{30}$ClF$_3$N$_4$O$_5$: 570.2, found: [M+H] 571.2. $^1$H NMR (400 MHz, CDCl3-d) δ 7.98 (s, 1H), 7.10-7.00 (m, 2H), 6.96-6.85 (m, 2H), 6.31 (s, 1H), 4.46-4.35 (m, 1H), 4.31 (td, J=7.9, 4.2 Hz, 1H), 3.98-3.79 (m, 5H), 3.76-3.67 (m, 3H), 3.57 (dt, J=12.2, 1.8 Hz, 1H), 3.50-3.40 (m, 1H), 3.19 (ddd, J=7.0, 3.8, 1.3 Hz, 1H), 2.97-2.84 (m, 2H), 2.79 (dd, J=16.3, 3.1 Hz, 1H), 2.41 (dd, J=16.2, 10.2 Hz, 1H), 2.31-2.11 (m, 3H), 1.89 (dd, J=8.6, 4.2 Hz, 1H), 1.34 (d, J=7.0 Hz, 3H).

Example B1 was synthesized from B1G according to the method of Example 1. LC-MS Anal. Calc'd for C$_{25}$H$_{28}$ClF$_3$N$_4$O$_5$: 556.2, found: [M+H] 557.2. $^1$H NMR (400 MHz, CD$_3$CN) δ 7.98 (s, 1H), 7.17-7.05 (m, 2H), 7.02-6.86 (m, 2H), 6.45 (s, 1H), 4.50-4.28 (m, 2H), 3.95 (s, 3H), 3.89-3.81 (m, 1H), 3.76 (d, J=4.2 Hz, 3H), 3.29 (m, 1H), 3.18 (m, 2H), 2.71 (d, J=3.1 Hz, 1H), 2.56-2.41 (m, 1H), 2.27-2.16 (m, 1H), 2.09 (s, 1H), 1.82-1.69 (m, 1H), 1.31 (d, J=7.3 Hz, 3H). hGPR40 EC$_{50}$=2483 nM.

EXAMPLE B2

2-((4S,5S)-1-(4-(((3R,4R)-1-(5-chloro-2-methoxy-pyridin-4-yl)-3-(cyanomethyl)piperidin-4-yl)oxy)phenyl)-4-methyl-3-(trifluoromethyl)-4,5-dihydro-1H-pyrazol-5-yl)acetic acid

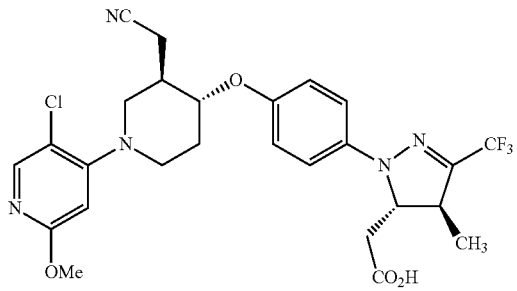 [SMILES: COc1cc(N2CC[C@@H](Oc3ccc(N4N=C(C(F)(F)F)[C@@H](C)[C@@H]4CC(=O)O)cc3)[C@H](CC#N)C2)c(Cl)cn1]

B2A. Methyl 2-((4S,5S)-1-(4-(((3R,4R)-1-(5-chloro-2-methoxypyridin-4-yl)-3-(cyanomethyl)piperidin-4-yl)oxy)phenyl)-4-methyl-3-(trifluoromethyl)-4,5-dihydro-1H-pyrazol-5-yl)acetate: To a cooled (0° C.) solution of methyl 2-((4S,5S)-1-(4-(((3S,4R)-1-(5-chloro-2-methoxypyridin-4-yl)-3-(hydroxymethyl)piperidin-4-yl)oxy)phenyl)-4-methyl-3-(trifluoromethyl)-4,5-dihydro-1H-pyrazol-5-yl)acetate (21 mg, 0.037 mmol) in CH$_2$Cl$_2$ (306 μL) was added TEA (15.38 μL, 0.110 mmol), and Ms-Cl (5.73 μl, 0.074 mmol). The reaction mixture was stirred for 30 mins, then quenched with water, diluted with CH$_2$Cl$_2$, washed with 1N HCl, NaHCO$_3$, brine, dried over Na$_2$SO$_4$/MgSO$_4$, and concentrated via vacuum to give methyl 2-((4S,5S)-1-(4-(((3 S,4R)-1-(5-chloro-2-methoxypyridin-4-yl)-3-(((methylsulfonyl)oxy)methyl)piperidin-4-yl)oxy)phenyl)-4-methyl-3-(trifluoromethyl)-4,5-dihydro-1H-pyrazol-5-yl)acetate as a clear foam (23 mg, 0.035 mmol, 96% yield). To the intermediate, dissolved in DMSO (153 μL), was added sodium cyanide (7 mg, 0.15 mmol). The reaction mixture was stirred at 50° C. for overnight and quenched with water. The solution was diluted with EtOAc and the layers were separated. The organic layer was washed successively with water, and brine, then it was dried over Na$_2$SO$_4$, and concentrated. Purification via silica gel chromatography gave the title compound as a colorless oil (23 mg, 0.040 mmol, 108% yield). LC-MS Anal. Calc'd for C$_{27}$H$_{29}$ClF$_3$N$_5$O$_4$: 579.2, found: [M+H] 580.2.

Example B2 (6.5 mg, 35.8% yield) was synthesized from B2B via the method of Example 1. LC-MS Anal. Calc'd for C$_{26}$H$_{27}$ClF$_3$N$_5$O$_4$: 565.1, found: [M+H] 565.8. $^1$H NMR (400 MHz, CD$_3$CN) δ 8.01 (s, 1H), 7.17-7.04 (m, 2H), 7.03-6.92 (m, 2H), 6.45 (s, 1H), 4.54-4.36 (m, 1H), 4.31-4.15 (m, 1H), 4.01-3.85 (m, 4H), 3.80-3.65 (m, 1H), 3.43-3.27 (m, 1H), 3.19-2.96 (m, 2H), 2.80-2.64 (m, 3H), 2.50 (dd, J=16.5, 9.7 Hz, 1H), 2.40-2.29 (m, 1H), 2.25 (dd, J=13.4, 2.9 Hz, 1H), 1.76 (d, J=10.8 Hz, 1H), 1.30 (d, J=7.0 Hz, 3H). Analytical HPLC (Orthogonal method): RT=11.39 min, HI: 96.8%. hGPR40 EC$_{50}$=586 nM. hGPR40 IP1 EC$_{50}$=362 nM.

EXAMPLE B3, ISOMER 1, ISOMER 2 AND ISOMER 3

Methyl 2-((4S,5S)-1-(4-((1-(5-chloro-2-methoxy-pyridin-4-yl)-3-(methoxymethyl)piperidin-4-yl)oxy)phenyl)-4-methyl-3-(trifluoromethyl)-4,5-dihydro-1H-pyrazol-5-yl)acetate

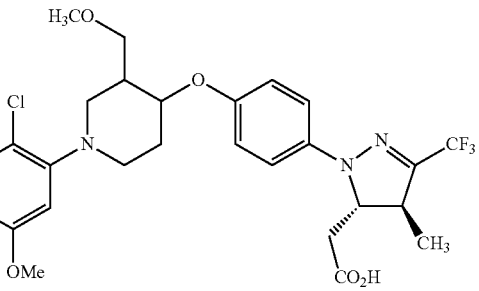

B3A. tert-Butyl 4-hydroxy-3-(methoxymethyl)piperidine-1-carboxylate: To a solution of tert-butyl 4-hydroxy-3-(hydroxymethyl)piperidine-1-carboxylate (230 mg, 1.0 mmol) in THF (3.3 mL) in ice bath was added NaH (56 mg, 1.4 mmol). After 10 min, MeI (75 μL, 1.2 mmol) was added. After stirring for 2 h, the reaction was quenched with water and diluted with EtOAc. The organic layer was washed with water, brine, dried over Na$_2$SO$_4$, and concentrated. Purification via silica gel chromatography gave the title compound as a colorless oil (140 mg, 0.571 mmol, 57.4% yield).

B3B. 3-(methoxymethyl)piperidin-4-ol, TFA salt: tert-butyl 4-hydroxy-3-(methoxymethyl)piperidine-1-carboxylate (140 mg, 0.57 mmol) in DCM (2.85 mL) was added TFA (440 μL, 5.7 mmol). After stirring for 3 h, the mixture was evaporated to give 3-(methoxymethyl)piperidin-4-ol, TFA salt as a beige oil (235 mg, 0.630 mmol, 110% yield). LC-MS Anal. Calc'd for C$_7$H$_{15}$NO$_2$: 145.1, found: [M+H] 146.0.

B3C. 1-(5-Chloro-2-methoxypyridin-4-yl)-3-(methoxymethyl)piperidin-4-ol: To a solution of 3-(methoxymethyl)piperidin-4-ol, TFA salt (235 mg, 0.630 mmol) and K$_2$CO$_3$ (348 mg, 2.52 mmol) in DMSO (2.1 mL) was added 4-bromo-5-chloro-2-methoxypyridine (140 mg, 0.630 mmol). The mixture was stirred at 110° C. over night. The reaction mixture was diluted with EtOAc and the organic layer was washed successively with water and brine. The combined organic layers were dried over Na$_2$SO$_4$, filtered, and concentrated. Purification via silica gel chromatography gave the title compound as a colorless oil (120 mg, 0.418 mmol, 66.5% yield). LC-MS Anal. Calc'd for $C_{13}H_{19}ClN_2O_3$: 286.1, found: [M+H] 287.1.

Example B3: The title compound was synthesized from B3C according to the method of Example B1 to give, after SFC chiral separation: Isomer 1: (16.5 mg, 24.2%). LC-MS Anal. Calc'd for $C_{26}H_{30}ClF_3N_4O_5$: 570.2, found: [M+H] 571.2. $^1$H NMR (500 MHz, $CD_3CN$) δ 7.97 (s, 1H), 7.06 (d, J=9.1 Hz, 2H), 6.94 (d, J=9.1 Hz, 2H), 6.35 (s, 1H), 4.51-4.35 (m, 1H), 4.29-4.20 (m, 1H), 3.83 (s, 3H), 3.65-3.47 (m, 3H), 3.47-3.42 (m, 1H), 3.36-3.30 (m, 1H), 3.26 (s, 3H), 2.90 (m, 2H), 2.68-2.57 (m, 1H), 2.33-2.23 (m, 1H), 2.22-2.11 (m, 2H), 1.84-1.68 (m, 2H), 1.30-1.20 (m, 3H). hGPR40 $EC_{50}$=352 nM. Isomer 2: (13.7 mg, 20%). LC-MS Anal. Calc'd for $C_{26}H_{30}ClF_3N_4O_5$: 570.2, found: [M+H] 571.2. $^1$H NMR (400 MHz, $CD_3CN$) δ 7.98 (s, 1H), 7.14-7.03 (m, 2H), 7.00-6.91 (m, 2H), 6.38 (s, 1H), 4.51-4.38 (m, 1H), 4.29 (d, J=4.2 Hz, 1H), 3.88 (s, 3H), 3.75-3.64 (m, 1H), 3.61-3.48 (m, 3H), 3.39-3.30 (m, 1H), 3.29-3.19 (s, 3H), 3.09-2.88 (m, 3H), 2.72 (dd, J=16.6, 3.2 Hz, 1H), 2.49 (dd, J=16.5, 9.5 Hz, 1H), 2.18 (dd, J=8.3, 3.9 Hz, 2H), 1.77 (m, 1H), 1.30 (d, J=7.0 Hz, 3H). hGPR40 $EC_{50}$=768 nM. Isomer 3: (16.2 mg, 23.7%). LC-MS Anal. Calc'd for $C_{26}H_{30}ClF_3N_4O_5$: 570.2, found: [M+H] 571.2. $^1$H NMR (500 MHz, DMSO-$d_6$) δ 7.98 (s, 1H), 7.05 (d, J=8.8 Hz, 2H), 6.91 (d, J=8.8 Hz, 2H), 6.41 (s, 1H), 4.43 (br. s., 1H), 4.08-3.91 (m, 2H), 3.83-3.71 (m, 3H), 3.63 (br. s., 2H), 3.41-3.24 (s, 3H), 3.18-2.99 (m, 4H), 2.62 (d, J=15.4 Hz, 1H), 2.47-2.27 (m, 2H), 1.92 (br. s., 1H), 1.81-1.62 (m, 1H), 1.25 (d, J=6.3 Hz, 3H). hGPR40 $EC_{50}$=1997 nM.

EXAMPLE B4

4-((4S,5S)-5-(carboxymethyl)-1-(4-((1-(5-ethoxy-2-fluorophenyl)piperidin-4-yl)oxy)phenyl)-4-methyl-4,5-dihydro-1H-pyrazol-3-yl)-3-fluorobenzoic acid

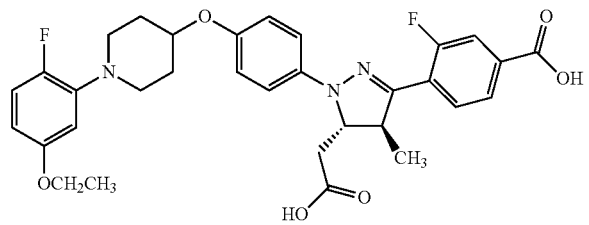 [SMILES: CCOc1ccc(F)c(N2CCC(Oc3ccc(N4N=C(c5ccc(C(=O)O)cc5F)[C@@H](C)[C@@H]4CC(=O)O)cc3)CC2)c1]

B4A. 4-((4S,5S)-5-(Cyanomethyl)-1-(4-((1-(5-ethoxy-2-fluorophenyl)piperidin-4-yl)oxy)phenyl)-4-methyl-4,5-dihydro-1H-pyrazol-3-yl)-3-fluorobenzonitrile: B4A was prepared from 4-((4S,5S)-5-(cyanomethyl)-1-(4-hydroxyphenyl)-4-methyl-4,5-dihydro-1H-pyrazol-3-yl)-3-fluorobenzonitrile (94A) following the procedure for the preparation of 4-((4S,5S)-5-(cyanomethyl)-1-(4-((1-(5-ethoxy-2-fluorophenyl)piperidin-4-yl)oxy)phenyl)-4-methyl-4,5-dihydro-1H-pyrazol-3-yl)benzonitrile (93B): LC-MS [M+H] 556.

B4B. Methyl 4-((4S,5S)-1-(4-((1-(5-ethoxy-2-fluorophenyl)piperidin-4-yl)oxy)phenyl)-5-(2-methoxy-2-oxoethyl)-4-methyl-4,5-dihydro-1H-pyrazol-3-yl)-3-fluorobenzoate: B4A (7 mg, 0.012 mmol) was dissolved in ~3M HCl/MeOH, $CH_2Cl_2$, MeOAc solution [6.3 mL, prepared by addition of AcCl (1.3 mL) to a 3/2 $CHCl_2$/MeOH solution (5.0 mL) at 0° C. and then stirring at rt for 30 min]. The resulting solution was allowed to stand at rt for 25 h and then evaporated. The remaining oily material was stripped from MeOH (2×4 mL) and dissolved in ~3M HCl/MeOH, MeOAc solution [6.3 mL, prepared by addition of AcCl (1.3 mL) to MeOH (5 mL) at 0° C. and then stirring at rt for 30 min]. The resulting solution was heated to 40° C. and allowed to stand at this temperature for 23.5 h. At this time, the solution was cooled to rt, diluted with MeCN (4 mL) and evaporated. The residue was taken up in EtOAc (40 mL) and, washed with sat'd $NaHCO_3$ (2×20 mL) and sat'd NaCl (20 mL). The organic layer was dried ($Na_2SO_4$) and concentrated. The crude was chromatographed ($SiO_2$, 9/1 to 4/1 Hex/EtOAc) to afford the title compound (5.5 mg, 76% yield) as a yellow oil: LC-MS [M+H] 622.

Example B4: To a stirred solution of methyl 4-((4S,5S)-1-(4-((1-(5-ethoxy-2-fluorophenyl)piperidin-4-yl)oxy)phenyl)-5-(2-methoxy-2-oxoethyl)-4-methyl-4,5-dihydro-1H-pyrazol-3-yl)-3-fluorobenzoate (5.5 mg, 8.76 µmol) in THF (0.5 mL) and water (0.04 mL) at rt was added 1.0M aqueous lithium hydroxide (0.04 mL, 0.040 mmol). After stirring at rt for 6.7 h, the reaction mixture was partially evaporated to remove most of the THF. The remaining solution was partitioned between water (40 mL) and Hex (15 mL). The aqueous layer was acidified to pH 2 by dropwise addition of 1M HCl, and then extracted with $CH_2Cl_2$ (3×30 mL). The combined organic extracts were dried ($Na_2SO_4$) and concentrated. The residue was dried under vacuum to afford the desired product (5.3 mg, 99% yield) as a yellow solid: LC-MS [M+H] 594. $^1$H NMR (500 MHz, $CD_3OD$) δ 8.09 (t, J=7.9 Hz, 1H), 7.77 (d, J=8.4 Hz, 1H), 7.73 (d, J=12.2 Hz, 1H), 7.17 (d, J=9.0 Hz, 2H), 6.97 (d, J=9.0 Hz, 2H), 6.91 (dd, J=12.2, 9.0 Hz, 1H), 6.56 (br. s, 1H), 6.41 (m, 1H), 4.50 (m, 1H), 4.39 (br. s, 1H), 3.97 (q, J=6.8 Hz, 2H), 3.69 (m, 1H), 3.35 (m, 2H), 2.98 (m, 2H), 2.75 (dd, J=15.2, 3.0 Hz, 1H), 2.56 (dd, J=15.2, 8.5 Hz, 1H), 2.12 (m, 2H), 1.96 (m, 2H), 1.37 (t, J=6.9 Hz, 3H). 1.30 (d, J=7.0 Hz, 3H). Analytical HPLC (Zorbax method, 0% Solvent B start): RT=8.04 min, HI: 97%. hGPR40 $EC_{50}$=4952 nM.

EXAMPLE B5, ISOMER 1 AND ISOMER 2

2-(3-cyano-1-(4-((1-(5-ethoxy-2-fluorophenyl)piperidin-4-yl)oxy)phenyl)-4-methyl-4,5-dihydro-1H-pyrazol-5-yl)acetic acid

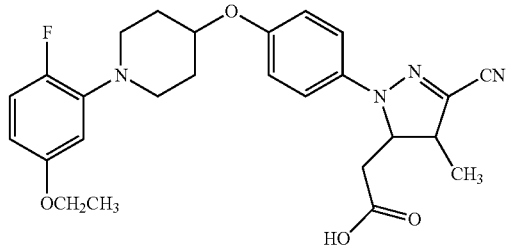 [SMILES: CCOc1ccc(F)c(N2CCC(Oc3ccc(N4N=C(C#N)C(C)C4CC(=O)O)cc3)CC2)c1]

B5A. (4-Bromophenyl)carbonocyanidohydrazonic chloride: A solution of sodium nitrite (3.53 g, 49.6 mmol) in water (21.9 mL) was added to a stirred mixture of 4-bromoaniline (8.35 g, 47.1 mmol), hydrochloric acid, 37% (14.6 mL) and water (36.5 mL) cooled at −5° C. The resulting mixture was stirred for 25 min while warming up to 0° C. and then, 2-chloro-3-oxobutanenitrile (6.34 g, 53.9 mmol, was prepared as described in WO2007122241), EtOH (36.5 mL), sodium acetate (11.7 g, 141 mmol) and water (146 mL) were added in this order. The reaction mixture was allowed to warm up to rt and stirred for an additional 8.5 h. After this time, the mixture was filtered and the collected solid was thoroughly rinsed with water. The solid was dried by suction followed by storage under vacuum. The solid was kept under vacuum for 48 h to give the desired product (8.76 g, 66.2% yield) as a brownish solid: LC-MS [M+H] 258, 260.

B5B. Methyl 1-(4-bromophenyl)-3-cyano-4-methyl-4,5-dihydro-1H-pyrazole-5-carboxylate: A flask containing a solution of (4-bromophenyl) carbonocyanidohydrazonic chloride (753 mg, 2.68 mmol) in dioxane (13.0 mL) was evacuated and backfilled with Ar. Methyl crotonate (0.48 mL, 4.44 mmol) and silver carbonate (1780 mg, 6.39 mmol) were added to the solution and the resulting suspension was degassed by ultrasound irradiation under Ar for 5 min. The reaction mixture heated to 43° C. and stirred at this temperature for 14 h. After this time, the reaction was cooled to rt and filtered through Celite. The filter cake was rinsed with EtOAc (100 mL) and, the combined filtrate and rinse were concentrated. The crude was chromatographed ($SiO_2$, 4/1 Hex/EtOAc) to afford the desired product (837 mg, 81% yield) as a yellowish oil: LC-MS [M+H] 320, 322.

B5C. 1-(4-Bromophenyl)-3-cyano-4-methyl-4,5-dihydro-1H-pyrazole-5-carboxylic acid: To a stirred solution of methyl 1-(4-bromophenyl)-3-cyano-4-methyl-4,5-dihydro-1H-pyrazole-5-carboxylate (837 mg, 2.60 mmol) in THF (40 mL) and water (4.0 mL) at rt was added 1M aqueous lithium hydroxide (5.7 mL, 5.70 mmol). After stirring at rt for 3.5 h, most of the THF was evaporated and the remaining mixture was partitioned between water (90 mL) and Hex (40 mL). The aqueous layer was acidified to pH 2 by dropwise addition of 1M HCl, and then extracted with $CH_2Cl_2$ (3×50 mL). The combined organic extracts were dried ($Na_2SO_4$) and concentrated. The crude was passed through a $SiO_2$ column eluting with 9/1 $CH_2Cl_2$/MeOH to give the title compound (657 mg, 70.3% yield) as a yellowish oil: LC-MS [M+H] 306, 308.

B5D. Methyl 2-(1-(4-bromophenyl)-3-cyano-4-methyl-4,5-dihydro-1H-pyrazol-5-yl)acetate: To a stirred solution of 1-(4-bromophenyl)-3-cyano-4-methyl-4,5-dihydro-1H-pyrazole-5-carboxylic acid (657 mg, 1.535 mmol) in $CH_2Cl_2$ (6.5 mL) at 0° C. were added 2M oxalyl chloride/$CH_2Cl_2$ (1.64 mL, 3.28 mmol) and DMF (3 drops). The reaction mixture was stirred at 0° C. for 15 min and then, at rt for 1.5 h. The final mixture was evaporated in vacuo and the residue was stripped from $CH_2Cl_2$ (2×10 mL) to give the crude acyl chloride. 2M Trimethylsilyldiazomethane/Ether (3.1 mL, 6.20 mmol) was added dropwise to a solution of the above crude acyl chloride in MeCN (6.0 mL) and THF (6.0 mL) at 0° C. under Ar. The mixture was stirred for 4.0 h, while slowly warming up to 6° C., and then for 1.8 h at rt. At this time, the mixture was evaporated in vacuo to provide the crude diazoketone. To a solution of the crude diazoketone in MeOH (25.0 mL) under Ar was added a solution of silver benzoate (126 mg, 0.545 mmol) in triethylamine (1.52 mL, 10.85 mmol), over 5 min while the mixture was sonicated in an ultrasound bath. After sonicating for 2.0 h at rt, the resulting mixture was stirred at rt overnight. The mixture was filtered through Celite and the filter cake was rinsed with EtOAc (100 mL). The filtrate and rinse were combined and evaporated to about 5 mL volume. The residue was taken up in EtOAc (100 mL) and washed with sat'd $NaHCO_3$ (70 mL), water (50 mL), 0.5M HCl (2×25 mL), water (50 mL) and sat'd NaCl (30 mL), dried ($Na_2SO_4$) and concentrated. The crude was chromatographed ($SiO_2$, 4/1 Hex/EtOAc) to give the desired methyl ester contaminated with starting acid methyl ester. The esters were separated by RF-HPLC (MeOH—$H_2O$-TFA). Fractions containing the desired ester were combined, basified with solid $NaHCO_3$ and partially evaporated at rt to remove most of the MeOH. The remaining aqueous mixture was extracted with $CH_2Cl_2$ (3×50 mL) and, the combined extracts were dried ($Na_2SO_4$) and concentrated. Drying under vacuum provided the title compound (220 mg, 43% yield) as a colorless oil: LC-MS [M+Na] 358, 360.

B5E. Methyl 2-((4S,5S)- and ((4R,5R)-3-cyano-4-methyl-1-(4-(4,4,5,5-tetramethyl-1,3,2-dioxaborolan-2-yl)phenyl)-4,5-dihydro-1H-pyrazol-5-yl)acetate: A flask containing a suspension of methyl 2-(1-(4-bromophenyl)-3-cyano-4-methyl-4,5-dihydro-1H-pyrazol-5-yl)acetate (212 mg, 0.631 mmol), bis(pinacolato)diboron (184 mg, 0.717 mmol) and potassium acetate (216 mg, 2.179 mmol) in DMF (1.4 mL) was evacuated and backfilled with Ar and then sonicated in an ultrasound bath for 5 min while under Ar. [1,1-Bis(diphenylphosphino)ferrocene]dichloropalladium (II), complex with dichloromethane (26 mg, 0.032 mmol) was added and the mixture was heated to 80° C. The reaction mixture was stirred at this temperature for 5.5 h and then allowed to cool down to rt. Sat'd $NaHCO_3$ (4 mL) was added dropwise followed by EtOAc (10 mL). The mixture was filtered through Celite and the filter cake was rinsed with EtOAc (40 mL). The resulting biphasic mixture was diluted with 5% $NaHCO_3$ (10 mL) and shaken. The organic layer was washed with water (50 mL) and sat'd NaCl (50 mL), dried ($Na_2SO_4$) and evaporated. Chromatography ($SiO_2$, 4/1 Hex/EtOAc) of the crude afforded the title compound (117 mg, 48.4% yield) as a colorless oil: LC-MS [M+H] 384.

B5F. Methyl 2-(3-cyano-1-(4-hydroxyphenyl)-4-methyl-4,5-dihydro-1H-pyrazol-5-yl)acetate: To a stirred solution of methyl 2-(3-cyano-4-methyl-1-(4-(4,4,5,5-tetramethyl-1,3,2-dioxaborolan-2-yl)phenyl)-4,5-dihydro-1H-pyrazol-5-yl) acetate (117 mg, 0.305 mmol) in EtOAc (1.4 mL) at rt was added 30% hydrogen peroxide (0.47 mL, 4.60 mmol) dropwise. After stirring at rt for 13.0 h, the reaction mixture was cooled to 0° C. and treated with 10% $Na_2S_2O_3$ (8 mL). The resulting aqueous mixture was stirred at rt for 7.0 h and then extracted with EtOAc (3×30 mL). The organic extracts were washed with sat'd NaCl (20 mL), dried ($Na_2SO_4$) and concentrated. Chromatography ($SiO_2$, 3/2 Hex/EtOAc) of the crude afforded the title compound (76.6 mg, 92% yield) as a yellowish oil: LC-MS [M+H] 274.

B5G. Methyl 2-(3-cyano-1-(4-((1-(5-ethoxy-2-fluorophenyl)piperidin-4-yl)oxy)phenyl)-4-methyl-4,5-dihydro-1H-pyrazol-5-yl)acetate: To a stirred solution of methyl 2-(3-cyano-1-(4-hydroxyphenyl)-4-methyl-4,5-dihydro-1H-pyrazol-5-yl)acetate (29 mg, 0.106 mmol), 1-(5-ethoxy-2-fluorophenyl)piperidin-4-ol (93A) (38 mg, 0.157 mmol) and triphenylphosphine (47 mg, 0.177 mmol) in THF (0.65 mL) at rt was added di-tert-butylazodicarboxylate (41 mg, 0.174 mmol). The resulting solution was stirred at rt for 18 h and then evaporated. The residue was chromatographed ($SiO_2$, 4/1 Hex/EtOAc) to give the desired alkyl aryl ether contaminated with DBAD reduction byproduct. Further purification by chromatography ($SiO_2$, 96/4 $CHCl_3$/Ether) afforded the racemic product. The enantiomers were separated by chiral preparative SFC to afford:

Isomer 1 (yellowish solid, 15.0 mg, 29% yield): LC-MS [M+H] 495.

Isomer 2 (yellowish solid, 16.6 mg, 32% yield): LC-MS [M+H] 495.

Example B5 Isomer 1: To a stirred solution of methyl 3-cyano-1-(4-((1-(5-ethoxy-2-fluorophenyl)piperidin-4-yl)oxy)phenyl)-4-methyl-4,5-dihydro-1H-pyrazol-5-yl)acetate (B5G isomer 1, 15.0 mg, 0.030 mmol) in THF (0.9 mL) and water (0.09 mL) at rt was added 1.0M aqueous lithium hydroxide (0.09 mL, 0.090 mmol). After stirring at rt for 4.5 h, the reaction mixture was partially evaporated to remove most of the THF. The remaining solution was partitioned between water (40 mL) and Hex (15 mL). The aqueous layer was collected, acidified to pH 2 by dropwise addition of 1M HCl and extracted with $CH_2Cl_2$ (3×30 mL). The combined organic extracts were dried ($Na_2SO_4$) and concentrated. The residue was dried under vacuum to give the title compound (14.5 mg, 0.030 mmol, 98% yield) as a yellowish solid: LC-MS [M+H] 481. $^1$H NMR (500 MHz, $CD_2Cl_2$) δ 7.10 (d, J=9.1 Hz, 2H), 6.94 (d, J=9.1 Hz, 2H), 6.96 (dd, J=12.4, 9.1 Hz, 1H, overlapped), 6.54 (m, 1H) 6.41 (m, 1H), 4.40 (dt, J=10.2, 3.6 Hz, 1H), 4.40 (m, 1H), 3.97 (q, J=6.9 Hz, 2H), 3.33 (m, 2H), 3.22 (m, 1H), 2.96 (m, 2H) 2.89 (dd, J=16.6, 2.9 Hz, 1H), 2.53 (dd, J=16.6, 10.2 Hz, 1H), 2.10 (m, 2H), 1.93 (m, 2H), 1.37 (t, J=7.0 Hz, 3H, overlapped), 1.35 (d, J=6.9 Hz, 3H). Analytical HPLC (Zorbax method, 0% Solvent B start): RT=7.56 min, HI: 99%. hGPR40 $EC_{50}$=389 nM.

Example B5, Isomer 2: To a stirred solution of the methyl 3-cyano-1-(4-((1-(5-ethoxy-2-fluorophenyl)piperidin-4-yl)oxy)phenyl)-4-methyl-4,5-dihydro-1H-pyrazol-5-yl)acetate (B5G Isomer 2, 16.4 mg, 0.033 mmol) in THF (1.0 mL) and water (0.1 mL) at rt was added 1.0M aqueous lithium hydroxide (0.1 mL, 0.100 mmol). After stirring at rt for 5.0 h, the reaction mixture was partially evaporated to remove most of the THF. The remaining solution was partitioned between water (40 mL) and Hex (15 mL). The aqueous layer was collected, acidified to pH 2 by dropwise addition of 1M HCl and extracted with $CH_2Cl_2$ (3×30 mL). The combined organic extracts were dried ($Na_2SO_4$) and concentrated. The residue was dried under vacuum to afford the title compound (15.9 mg, 98% yield) as a yellowish solid: LC-MS [M+H] 481. $^1$H NMR (500 MHz, $CD_2Cl_2$) δ 7.10 (d, J=9.1 Hz, 2H), 6.94 (d, J=9.1 Hz, 2H), 6.96 (dd, J=12.4, 9.1 Hz, 1H, overlapped), 6.54 (m, 1H) 6.41 (m, 1H), 4.40 (dt, J=10.2, 3.6 Hz, 1H), 4.40 (m, 1H), 3.97 (q, J=6.9 Hz, 2H), 3.33 (m, 2H), 3.22 (m, 1H), 2.96 (m, 2H), 2.89 (dd, J=16.6, 2.9 Hz, 1H), 2.53 (dd, J=16.6, 10.2 Hz, 1H), 2.10 (m, 2H), 1.93 (m, 2H), 1.37 (t, J=7.0 Hz, 3H, overlapped), 1.35 (d, J=6.9 Hz, 3H). Analytical HPLC (Zorbax method, 0% Solvent B start): RT=7.56 min, HI: 98%. hGPR40 $EC_{50}$=4952 nM.

EXAMPLE B6 (ISOMER 1) AND (ISOMER 2)

2-(1-(4-((1-(5-chloro-2-methoxypyridin-4-yl)-3-methylpiperidin-4-yl)oxy)phenyl)-3-cyano-4-methyl-4,5-dihydro-1H-pyrazol-5-yl)acetic acid

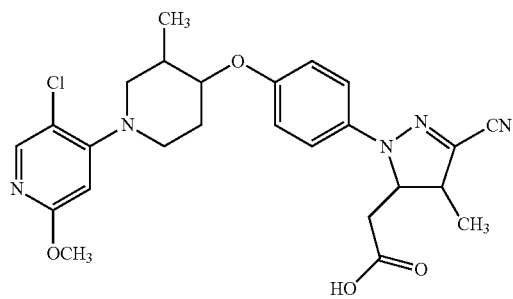 [SMILES: COc1cc(N2CCC(Oc3ccc(N4N=C(C#N)C(C)C4CC(=O)O)cc3)C(C)C2)c(Cl)cn1]

Example B6 Isomer 1 (yellowish solid, 8.3 mg) and Isomer 2 (yellowish solid, 9.6 mg) were prepared from 1-(5-chloro-2-methoxypyridin-4-yl)-3-methylpiperidin-4-ol (8I) following the procedure for Example B5. Example B6, Isomer 1: LC-MS [M+H] 498, 500. $^1$H NMR (500 MHz, $CD_2Cl_2$) δ 7.97 (s, 1H), 7.10 (d, J=9.0 Hz, 2H), 6.94 (d, J=9.0 Hz, 2H), 6.30 (s, 1H), 4.48 (dt, J=10.3, 3.4 Hz, 1H), 3.94 (m, 1H), 3.87 (s, 3H), 3.53 (m, 2H), 3.23 (m, 1H), 2.89 (m, 2H) 2.66 (m, 1H), 2.52 (dd, J=16.6, 10.3 Hz, 1H), 2.16 (m, 2H), 1.79 (m, 1H), 1.35 (d, J=7.2 Hz, 3H), 1.12 (d, J=6.8 Hz, 3H). Analytical HPLC (Zorbax method, 0% Solvent B start): RT=7.81 min, HI: 99%. hGPR40 $EC_{50}$=303 nM. Example B6, Isomer 2: LC-MS [M+H] 498, 500. $^1$H NMR (500 MHz, $CD_2Cl_2$) δ 7.97 (s, 1H), 7.10 (d, J=9.0 Hz, 2H), 6.94 (d, J=9.0 Hz, 2H), 6.30 (s, 1H), 4.48 (dt, J=10.2, 3.5 Hz, 1H), 3.94 (m, 1H), 3.86 (s, 3H), 3.53 (m, 2H), 3.23 (m, 1H), 2.89 (m, 2H) 2.66 (m, 1H), 2.52 (dd, J=16.6, 10.3 Hz, 1H), 2.16 (m, 2H), 1.79 (m, 1H), 1.35 (d, J=7.0 Hz, 3H), 1.12 (d, J=6.8 Hz, 3H). Analytical HPLC (Zorbax method, 0% Solvent B start): RT=7.82 min, HI: 98%. hGPR40 $EC_{50}$=4854 nM.

EXAMPLE B7, ISOMER 1 AND ISOMER 2

2-(3-Cyano-1-(4-((1-(5-ethoxy-2-fluorophenyl)-3-methylpiperidin-4-yl)oxy)phenyl)-4-methyl-4,5-dihydro-1H-pyrazol-5-yl)acetic acid

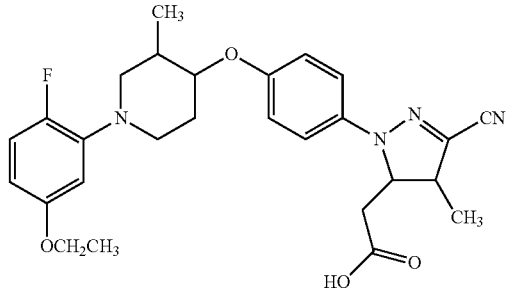 [SMILES: CCOc1ccc(F)c(N2CCC(Oc3ccc(N4N=C(C#N)C(C)C4CC(=O)O)cc3)C(C)C2)c1]

Example B7 Isomer 1 (yellowish solid, 16.0 mg) and Isomer 2 (yellowish solid, 15.2 mg) were prepared from 1-(5-ethoxy-2-fluorophenyl)-3-methylpiperidin-4-ol (29E) following the procedure for Example B5. Example B7, Isomer 1: LC-MS [M+H] 495. $^1$H NMR (500 MHz, $CD_2Cl_2$) δ 7.09 (d, J=9.0 Hz, 2H), 6.94 (d, J=9.0 Hz, 2H), 6.91 (dd, J=12.4, 8.8 Hz, 1H), 6.51 (dd, J=7.3, 3.0 Hz, 1H) 6.41 (dt, J=8.8, 3.0 Hz, 1H), 4.48 (m, 1H), 3.97 (q, J=6.9 Hz, 2H), 3.88 (dt, J=4.2, 9.0 Hz, 1H), 3.42 (m, 2H), 3.23 (m, 1H), 2.89 (dd, J=16.6, 3.0 Hz, 1H), 2.80 (m, 1H), 2.55 (m, 2H), 2.15 (m, 2H), 1.79 (m, 1H), 1.37 (t, J=6.9 Hz, 3H), 1.35 (d, J=7.1 Hz, 3H), 1.10 (d, J=6.7 Hz, 3H). Analytical HPLC (Zorbax method, 0% Solvent B start): RT=7.90 min, HI: 99%. hGPR40 $EC_{50}$=394 nM. Example B7, Isomer 2: LC-MS [M+H] 495. $^1$H NMR (500 MHz, $CD_2Cl_2$) δ 7.10 (d, J=9.0 Hz, 2H), 6.94 (d, J=9.0 Hz, 2H), 6.91 (dd, J=12.4, 8.8 Hz, 1H), 6.52 (dd, J=7.3, 3.0 Hz, 1H) 6.40 (dt, J=8.8, 3.0 Hz, 1H), 4.48 (m, 1H), 3.97 (q, J=6.9 Hz, 2H), 3.88 (dt, J=4.2, 9.0 Hz, 1H), 3.42 (m, 2H), 3.23 (m, 1H), 2.90 (d, J=16.3 Hz, 1H), 2.81 (m, 1H), 2.56 (m, 2H), 2.14 (m, 2H), 1.79 (m, 1H), 1.37 (t, J=6.8 Hz, 3H), 1.35 (d, J=6.9 Hz, 3H), 1.10 (d, J=6.7 Hz, 3H). Analytical HPLC (Zorbax method, 0% Solvent B start): RT=7.90 min, HI: 99%. hGPR40 $EC_{50}$=5787 nM.

EXAMPLE B8

2-((4S,5S)-1-(4-((1-(3-methoxyphenyl)piperidin-4-yl)methyl)phenyl)-4-methyl-3-(trifluoromethyl)-4,5-dihydro-1H-pyrazol-5-yl)acetic acid

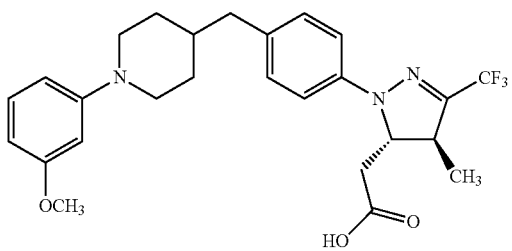 [SMILES: COc1cccc(N2CCC(Cc3ccc(N4N=C(C(F)(F)F)[C@@H](C)[C@@H]4CC(=O)O)cc3)CC2)c1]

B8A. Methyl 2-((4S,5S)-4-methyl-1-(4-(piperidin-4-ylmethyl)phenyl)-3-(trifluoromethyl)-4,5-dihydro-1H-pyrazol-5-yl)acetate: B8A was prepared by following the procedure for methyl 2-((4S,5S)-1-(4-((1-(2-fluoro-5-methoxyphenyl)piperidin-4-yl)methyl)phenyl)-4-methyl-3-(trifluoromethyl)-4,5-dihydro-1H-pyrazol-5-yl)acetate (100E) but replacing 1-(2-fluoro-5-methoxyphenyl)-4-methylenepiperidine (100C) by N-Boc-4-methylene-piperidine: LC-MS [M+H] 398.

B8B. Methyl 2-((4S,5S)-1-(4-((1-(3-methoxyphenyl)piperidin-4-yl)methyl)phenyl)-4-methyl-3-(trifluoromethyl)-4,5-dihydro-1H-pyrazol-5-yl)acetate: A suspension of 3-methoxyphenylboronic acid (26 mg, 0.166 mmol), copper (II) acetate monohydrate (5.0 mg, 0.025 mmol) and powdered molecular sieves (4A, <5 micron, activated, 96 mg) in $CH_2Cl_2$ (0.6 mL) was stirred for 6 min at rt. To this stirring suspension was added a solution of methyl 2-((4S,5S)-4-methyl-1-(4-(piperidin-4-ylmethyl)phenyl)-3-(trifluoromethyl)-4,5-dihydro-1H-pyrazol-5-yl)acetate (41 mg, 0.097 mmol) in $CH_2Cl_2$ (0.3 mL). The reaction mixture was heated to 30° C. and stirred under air (balloon) for 28 h. After this time, the mixture was filtered through Celite and the filter cake was rinsed with EtOAc (80 mL). The combined filtrate and rinse were concentrated and the residue was chromatographed ($SiO_2$, 7/3 Hex/EtOAc) to give 20 mg of contaminated product which was further purified by RP-HPLC (MeOH—$H_2O$-TFA). Fractions containing the title compound were combined, basified with solid $NaHCO_3$ and partially evaporated at to remove most of the MeOH. The remaining aqueous mixture was extracted with $CH_2Cl_2$ (3×30 mL) and, the combined extracts were dried ($Na_2SO_4$) and concentrated. Drying under vacuum provided the title compound (14.0 mg, 28.7% yield) as a colorless oil: LC-MS [M+H] 504.

Example B8: To a stirred solution of methyl 2-((4S,5S)-1-(4-((1-(3-methoxyphenyl)piperidin-4-yl)methyl)phenyl)-4-methyl-3-(trifluoromethyl)-4,5-dihydro-1H-pyrazol-5-yl)acetate (13.6 mg, 0.027 mmol) in THF (0.8 mL) and water (0.08 mL) at rt was added 1.0M aqueous lithium hydroxide (0.08 mL, 0.080 mmol). After stirring at rt for 5.0 h, the reaction mixture was partially evaporated to remove most of the THF. The remaining solution was partitioned between water (40 mL) and Hex (15 mL). The aqueous layer was collected, acidified to pH 2 by dropwise addition of 1M HCl and extracted with $CH_2Cl_2$ (3×30 mL). The combined organic extracts were dried ($Na_2SO_4$) and concentrated. The residue was dried under vacuum to afford the title compound (13.0 mg, 98% yield) as a white solid: LC-MS [M+H] 490.

$^1$H NMR (500 MHz, $CD_2Cl_2$) δ 7.13 (m, 3H), 7.04 (d, J=8.5 Hz, 2H), 6.56 (d, J=7.3 Hz, 1H), 6.50 (s, 1H), 6.39 (d, J=7.3 Hz, 1H), 4.45 (m, 1H), 3.77 (s, 3H), 3.64 (m, 2H), 3.26 (m, 1H), 2.89 (dd, J=16.6, 2.7 Hz, 1H), 2.67 (t, J=11.8 Hz, 2H), 2.54 (d, J=7.1 Hz, 2H), 2.48 (dd, J=16.5, 10.4 Hz, 1H), 1.73 (m, 2H), 1.66 (m, 1H), 1.42 (m, 2H), 1.34 (d, J=7.0 Hz, 3H). Analytical HPLC (Zorbax method, 0% Solvent B start): RT=5.90 min, HI: 100%. hGPR40 $EC_{50}$=761 nM.

EXAMPLE B9

2-((4S,5S)-1-(4-((1-(2-methoxypyridin-4-yl)piperidin-4-yl)methyl)phenyl)-4-methyl-3-(trifluoromethyl)-4,5-dihydro-1H-pyrazol-5-yl)acetic acid

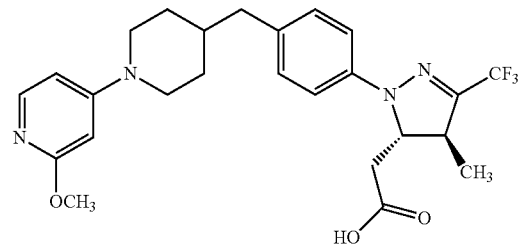 [SMILES: COc1cc(N2CCC(Cc3ccc(N4N=C(C(F)(F)F)[C@@H](C)[C@@H]4CC(=O)O)cc3)CC2)ccn1]

B9A. Methyl 2-((4S,5S)-1-(4-((1-(2-methoxypyridin-4-yl)piperidin-4-yl)methyl)phenyl)-4-methyl-3-(trifluoromethyl)-4,5-dihydro-1H-pyrazol-5-yl)acetate: To a stirred solution of 4-bromo-2-methoxypyridine (20 mg, 0.106 mmol) and methyl 2-((4S,5S)-4-methyl-1-(4-(piperidin-4-ylmethyl)phenyl)-3-(trifluoromethyl)-4,5-dihydro-1H-pyrazol-5-yl)acetate (24.2 mg, 0.057 mmol) in DMSO (0.2 mL) was added potassium carbonate (31 mg, 0.222 mmol). The mixture was heated to 93° C. and stirred at this temperature for 20.8 h. After this time, the mixture was cooled to rt and treated with ~1.1M HCl/MeOH, MeOAc solution [6.5 mL, prepared by addition of AcCl (0.5 mL) to MeOH (6.0 mL) at 0° C. and then stirring at rt for 20 min]. The resulting solution was allowed to stand at rt for 16 h, and then diluted with MeCN (6 mL) and evaporated. The residue was taken up in EtOAc (50 mL) and, washed with sat'd $NaHCO_3$ (2×30 mL), water (2×40 mL) and sat'd NaCl (30 mL). The organic layer was dried ($Na_2SO_4$) and concentrated, and the resulting crude was purified by RP-HPLC (MeOH—$H_2O$-TFA). Fractions containing the desired product were combined, basified with solid $NaHCO_3$ and partially evaporated at rt to remove most of the MeOH. The remaining aqueous mixture was extracted with $CH_2Cl_2$ (3×30 mL) and, the combined extracts were dried ($Na_2SO_4$) and concentrated. Drying under vacuum provided the title compound (7.0 mg, 24.24% yield) as a colorless oil: LC-MS [M+H] 505.

Example B9: To a stirred solution of methyl 2-((4S,5S)-1-(4-((1-(2-methoxypyridin-4-yl)piperidin-4-yl)oxy)phenyl)-4-methyl-3-(trifluoromethyl)-4,5-dihydro-1H-pyrazol-5-yl)acetate (6.5 mg, 0.013 mmol) in THF (0.6 mL) and water (0.05 mL) at rt was added LOM aqueous lithium hydroxide (0.05 mL, 0.050 mmol). After stirring at rt for 5.5 h, the reaction mixture was partially evaporated to remove most of the THF. The remaining solution was partitioned between water (40 mL) and Hex (15 mL). The aqueous layer was acidified to pH 2 by dropwise addition of 1M HCl, and then extracted with $CH_2Cl_2$ (3×30 mL). The combined organic extracts were dried ($Na_2SO_4$) and concentrated. The residue was dried under vacuum to afford the title compound (6.2 mg, 93% yield) as a white solid: LC-MS [M+H] 491. $^1$H NMR (500 MHz, CD$_2$Cl$_2$) δ 7.92 (d, J=7.3 Hz, 1H), 7.09 (d, J=8.5 Hz, 2H), 7.04 (d, J=8.5 Hz, 2H), 6.41 (dd, J=7.1, 2.1 Hz, 1H), 6.39 (d, J=2.1 Hz, 1H), 4.44 (m, 1H), 4.29 (m, 2H) 3.93 (s, 3H), 3.21 (m, 1H), 3.10 (m, 2H), 2.79 (dd, J=16.6, 3.4 Hz, 1H), 2.54 (m, 2H), 2.40 (dd, J=16.6, 9.6 Hz, 1H), 1.83 (m, 3H), 1.33 (m, 2H, overlapped), 1.31 (d, J=7.0 Hz, 3H). Analytical HPLC (Orthogonal method, 10% Solvent B start): RT=8.05 min, HI: 95%. hGPR40 EC$_{50}$=2660 nM

EXAMPLE B10

2-((4S,5S)-1-(4-((1-(5-chloro-2-methoxypyridin-4-yl)piperidin-4-yl)methyl)phenyl)-4-methyl-3-(trifluoromethyl)-4,5-dihydro-1H-pyrazol-5-yl)acetic acid

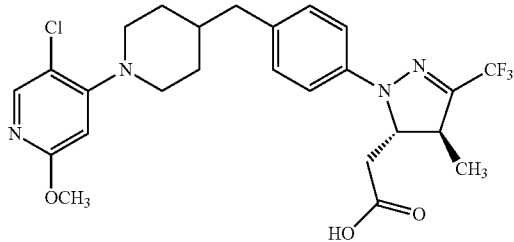 [SMILES: COc1cc(N2CCC(Cc3ccc(N4N=C(C(F)(F)F)[C@@H](C)[C@@H]4CC(=O)O)cc3)CC2)c(Cl)cn1]

B10A. Methyl 2-((4S,5S)-1-(4-((1-(5-chloro-2-methoxypyridin-4-yl)piperidin-4-yl)methyl)phenyl)-4-methyl-3-(trifluoromethyl)-4,5-dihydro-1H-pyrazol-5-yl)acetate: To a stirred solution of methyl 2-((4S,5S)-4-methyl-1-(4-(piperidin-4-ylmethyl)phenyl)-3-(trifluoromethyl)-4,5-dihydro-1H-pyrazol-5-yl)acetate (25 mg, 0.059 mmol) and 4-bromo-5-chloro-2-methoxypyridine (81B, 20 mg, 0.090 mmol) in DMSO (0.3 mL) under Ar was added N,N-diisopropylethylamine (0.041 mL, 0.237 mmol) dropwise. The mixture was heated to 92° C. and stirred at this temperature for 19.5 h. After this time, the mixture was cooled to rt and treated with ~1.1M HCl/MeOH, MeOAc solution [6.5 mL, prepared by addition of AcCl (0.5 mL) to MeOH (6.0 mL) at 0° C. and then stirring at rt for 20 min]. The resulting solution was allowed to stand at rt for 7.5 h, and then diluted with MeCN (10 mL) and evaporated. The residue was taken up in EtOAc (50 mL) and, washed with sat'd NaHCO$_3$ (2×30 mL), water (2×40 mL) and sat'd NaCl (30 mL). The organic layer was dried (Na$_2$SO$_4$) and concentrated. The crude (38.3 mg) was purified by chromatography (SiO$_2$, 9/1 to 4/1 Hex/EtOAc) to give the title compound (10.8 mg, 33.2% yield) as a colorless oil: LC-MS [M+H] 539, 541.

Example B10: To a stirred solution of the methyl 2-((4S,5S)-1-(4-((1-(5-chloro-2-methoxypyridin-4-yl)piperidin-4-yl)oxy)phenyl)-4-methyl-3-(trifluoromethyl)-4,5-dihydro-1H-pyrazol-5-yl)acetate (10.8 mg, 0.020 mmol) in THF (0.8 mL) and water (0.08 mL) at rt was added 1.0M aqueous lithium hydroxide (0.08 mL, 0.080 mmol). After stirring at rt for 6.3 h, the rxn mixture was partially evaporated to remove most of the THF. The remaining solution was partitioned between water (50 mL) and Hex (15 mL). The aqueous layer was acidified to pH 2 by dropwise addition of 1M HCl, and then extracted with CH$_2$Cl$_2$ (3×30 mL). The combined organic extracts were dried (Na$_2$SO$_4$) and concentrated. The residue was dried under vacuum to give the title compound (10.3 mg, 100% yield) as a white solid: LC-MS [M+H] 525, 527. $^1$H NMR (500 MHz, CD$_2$Cl$_2$) δ 7.94 (s, 1H), 7.13 (d, J=8.5 Hz, 2H), 7.05 (d, J=8.5 Hz, 2H), 6.25 (s, 1H), 4.46 (m, 1H), 3.84 (s, 3H), 3.56 (m, 2H), 3.25 (m, 1H), 2.90 (dd, J=16.5, 2.8 Hz, 1H), 2.61 (m, 2H), 2.56 (m, 2H), 2.50 (dd, J=16.5, 10.3 Hz, 1H), 1.74 (m, 2H), 1.67 (m, 1H), 1.42 (m, 2H), 1.34 (d, J=7.1 Hz, 3H). Analytical HPLC (Zorbax method, 50% Solvent B start): RT=8.29 min, HI: 100%. hGPR40 EC$_{50}$=517 nM.

EXAMPLE B11

2-((4S,5S)-1-(4-(((1R,5S,8S)-3-((benzyloxy)carbonyl)-3-azabicyclo[3.2.1]octan-8-yl)methyl)phenyl)-4-methyl-3-(trifluoromethyl)-4,5-dihydro-1H-pyrazol-5-yl)acetic acid

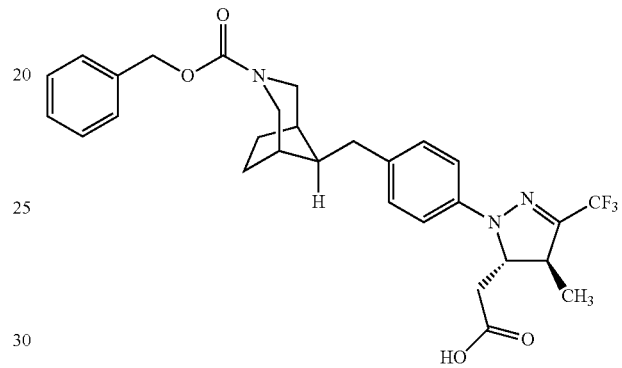

B11A. 3-Benzyl-8-methylene-3-azabicyclo[3.2.1]octane: To a suspension of methyltriphenylphosphonium bromide (774 mg, 2.145 mmol) in THF (8.7 mL) at 0° C. was added 2.5M butyl lithium/toluene (0.83 mL, 2.075 mmol) and the mixture was stirred at 0° C. for 35 min. A solution of 3-benzyl-3-azabicyclo[3.2.1]octan-8-one (300 mg, 1.393 mmol) in THF (2.90 mL) was added dropwise and the resulting suspension was allowed to warm up to rt over 3.5 h while stirring. The reaction was stirred for an additional 1.0 h at rt and then quenched with sat'd NH$_4$Cl (20 mL). The aqueous mixture was extracted with EtOAc (1×50 mL and then 2×30 mL). The combined organic layers were washed with sat'd NaCl (30 mL), dried (Na$_2$SO$_4$) and evaporated. The crude was chromatographed (SiO$_2$, 95/5 to 9/1 CH$_2$Cl$_2$/Ether) to afford the title compound (302 mg, 98% yield) as a colorless liquid: LC-MS [M+H] 214.

B11B. N-Cbz 8-methylene-3-azabicyclo[3.2.1]octane: To a solution of the 3-benzyl-8-methylene-3-azabicyclo[3.2.1]octane (301 mg, 1.355 mmol) in 1,2-DCE (5.4 mL) was added benzyl chloroformate (0.41 mL, 2.73 mmol) and the resulting solution was stirred at rt for 24 h. After this time, the mixture was heated to 45° C. and stirred at this temperature for 19 h. The reaction temperature was increased to 64° C. and stirring was continued for 28 h. Additional benzyl chloroformate (0.15 mL, 0.998 mmol) was added and the mixture was stirred at 64° C. for an additional 14 h. At this time, the reaction mixture was evaporated and the residue was chromatographed (SiO$_2$, 9/1 Hex/EtOAc) to provide the title compound (333 mg, 94% yield) as a colorless liquid: LC-MS [M+H] 258.

B11C. (1R,5S,8S)-benzyl 8-(4-((4S,5S)-5-(2-methoxy-2-oxoethyl)-4-methyl-3-(trifluoromethyl)-4,5-dihydro-1H-pyrazol-1-yl)benzyl)-3-azabicyclo[3.2.1]octane-3-carboxylate (colorless oil, 11% yield) and methyl 2-((4S,5S)-1-(4-((1R,5S,8s)-3-azabicyclo[3.2.1]octan-8-ylmethyl)phenyl)-

4-methyl-3-(trifluoromethyl)-4,5-dihydro-1H-pyrazol-5-yl) acetate (yellowish oil, 64% yield) were prepared by following the procedure for methyl 2-((4S,5S)-1-(4-(((1-(2-fluoro-5-methoxyphenyl)piperidin-4-yl)methyl)phenyl)-4-methyl-3-(trifluoromethyl)-4,5-dihydro-1H-pyrazol-5-yl) acetate (100E) but replacing 1-(2-fluoro-5-methoxyphenyl)-4-methylenepiperidine (Example 100C) by N-Cbz 8-methylene-3-azabicyclo[3.2.1]octane. Purification and separation of products were accomplished by RP-HPLC (MeOH—H$_2$O-TFA). Fractions containing the products were basified with solid Na$_2$CO$_3$ and partially evaporated at rt to remove most of the MeOH. The remaining aqueous mixtures were each extracted with CH$_2$Cl$_2$ (3×30 mL) and, the extracts were dried (Na$_2$SO$_4$) and concentrated: LC-MS [M+H] 558 and LC-MS [M+H] 424 respectively.

Example B11: To a stirred solution of (1R,5S,8S)-benzyl 8-(4-((4S,5S)-5-(2-methoxy-2-oxoethyl)-4-methyl-3-(trifluoromethyl)-4,5-dihydro-1H-pyrazol-1-yl)benzyl)-3-azabicyclo[3.2.1]octane-3-carboxylate (17.5 mg, 0.031 mmol) in THF (1.0 mL) and water (0.1 mL) at rt was added 1.0M aqueous lithium hydroxide (0.1 mL, 0.100 mmol). After stirring at rt for 6.0 h, the reaction mixture was partially evaporated to remove most of the THF. The remaining solution was partitioned between water (40 mL) and Hex (15 mL). The aqueous layer was acidified to pH 2 by dropwise addition of 1M HCl, and then extracted with CH$_2$Cl$_2$ (3×30 mL). The combined organic extracts were dried (Na$_2$SO$_4$) and concentrated. The residue was dried under vacuum to afford the title compound (15.4 mg, 90% yield) as a white solid: LC-MS [M+H] 544. $^1$H NMR (400 MHz, CD$_2$Cl$_2$) δ 7.40-7.28 (m, 5H), 7.17 (d, J=8.4 Hz, 2H), 7.04 (d, J=8.4 Hz, 2H), 5.12 (s, 2H), 4.45 (m, 1H), 3.64 (m, 2H), 3.32 (m, 3H), 2.87 (m, 3H), 2.49 (dd, J=16.5, 10.3 Hz, 1H), 1.98 (m, 3H), 1.72 (m, 2H), 1.57 (m, 2H), 1.34 (d, J=7.1 Hz, 3H). Analytical HPLC (Zorbax method, 0% Solvent B start): RT=8.67 min, HI: 100%. hGPR40 EC$_{50}$=7379 nM.

EXAMPLE B12

2-((4S,5S)-1-(4-(((1R,5S,8S)-3-(3-methoxyphenyl)-3-azabicyclo[3.2.1]octan-8-yl)methyl)phenyl)-4-methyl-3-(trifluoromethyl)-4,5-dihydro-1H-pyrazol-5-yl)acetic acid

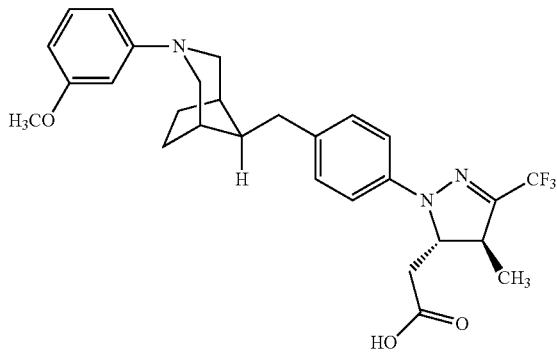 [SMILES: COc1cccc(N2CC3CCC(C2)C3Cc2ccc(N3N=C(C(F)(F)F)[C@@H](C)[C@@H]3CC(=O)O)cc2)c1]

Example B12 (white solid, 11.0 mg) was prepared from methyl 2-((4S,5S)-1-(4-((1R,5S,8s)-3-azabicyclo[3.2.1]octan-8-ylmethyl)phenyl)-4-methyl-3-(trifluoromethyl)-4,5-dihydro-1H-pyrazol-5-yl)acetate by following the procedure for Example B8. LC-MS [M+H] 516. $^1$H NMR (500 MHz, CD$_2$Cl$_2$) δ 7.19 (d, J=8.5 Hz, 2H), 7.13 (t, J=8.2 Hz, 1H), 7.04 (d, J=8.5 Hz, 2H), 6.45 (dd, J=8.2, 2.3 Hz, 1H), 6.36 (t, J=2.3 Hz, 1H), 6.30 (dd, J=8.2, 2.3 Hz, 1H), 4.46 (m, 1H), 3.78 (s, 3H), 3.33 (dd, J=11.3, 2.9 Hz, 2H), 3.26 (m, 1H), 3.22 (d, J=11.3 Hz, 2H), 2.91 (dd, J=16.5, 2.8 Hz, 1H), 2.82 (d, J=7.9 Hz, 2H), 2.51 (dd, J=16.5, 10.1 Hz, 1H), 2.16 (br. s, 2H), 2.01 (m, 1H), 1.79 (m, 2H), 1.69 (m, 2H), 1.34 (d, J=7.1 Hz, 3H). Analytical HPLC (Zorbax method, 50% Solvent B start): RT=8.64 min, HI: 97%. hGPR40 EC$_{50}$=5720 nM.

EXAMPLE B13

2-((4S,5S)-1-(4-(((1R,5S,8S)-3-(5-chloro-2-methoxypyridin-4-yl)-3-azabicyclo[3.2.1]octan-8-yl) methyl)phenyl)-4-methyl-3-(trifluoromethyl)-4,5-dihydro-1H-pyrazol-5-yl)acetic acid

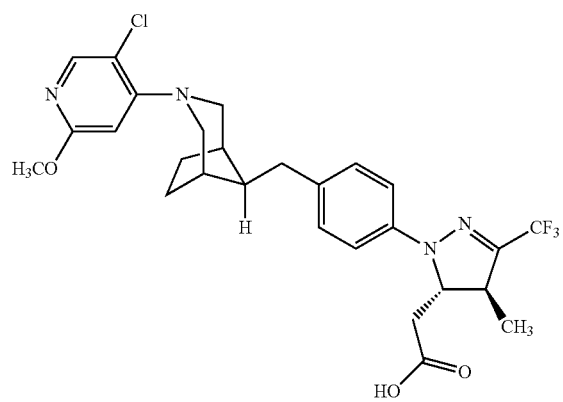 [SMILES: COc1cc(N2CC3CCC(C2)C3Cc2ccc(N3N=C(C(F)(F)F)[C@@H](C)[C@@H]3CC(=O)O)cc2)c(Cl)cn1]

B13A. Methyl 2-((4S,5S)-1-(4-(((1R,5S,8S)-3-(5-chloro-2-methoxypyridin-4-yl)-3-azabicyclo[3.2.1]octan-8-yl) methyl)phenyl)-4-methyl-3-(trifluoromethyl)-4,5-dihydro-1H-pyrazol-5-yl)acetate: To a stirred solution of methyl 2-((4S,5S)-1-(4-((1R,5S,8S)-3-azabicyclo[3.2.1]octan-8-ylmethyl)phenyl)-4-methyl-3-(trifluoromethyl)-4,5-dihydro-1H-pyrazol-5-yl)acetate (24 mg, 0.057 mmol) and 4-bromo-5-chloro-2-methoxypyridine (18 mg, 0.081 mmol) in n-BuOH (0.4 mL) was added N,N-diisopropylethylamine (30 μL, 0.173 mmol). The mixture was heated to 88° C. and stirred at this temperature for 23.5 h. At this time, the reaction temperature was increased to 98° C. and stirring was continued for an additional 10 h. The mixture was cooled to rt, diluted with EtOAc (40 mL) and washed with sat'd NaHCO$_3$ (3×20 mL), water (20 mL) and sat'd NaCl (20 mL). The organic layer was dried (Na$_2$SO$_4$) and evaporated. The residue was dissolved in ~3M HCl/MeOH, CH$_2$Cl$_2$, MeOAc solution [6.3 mL, prepared by addition of AcCl (1.3 mL) to a 3/2 CH$_2$Cl$_2$/MeOH solution (5.0 mL) at 0° C. and then stirring at rt for 20 min]. The resulting solution was allowed to stand at rt for 16 h. After this time, the solution was evaporated and the remaining oily material was stripped from MeOH (2×6 mL). The residue was taken up in EtOAc (40 mL) and, washed with sat'd NaHCO$_3$ (2×20 mL) and sat'd NaCl (20 mL). The organic layer was dried (Na$_2$SO$_4$) and concentrated. The crude (39 mg) was dissolved in CH$_2$Cl$_2$ (0.5 mL) and Et$_3$N (16 μL, 0.11 mmol) and BOC$_2$O (12 mg, 0.055 mmol) were added. The resulting solution was stirred at rt for 18 h. The final solution was diluted with EtOAc (40 mL) and washed with sat'd NaHCO$_3$ (2×20 mL) and sat'd NaCl (20 mL). The organic layer was dried (Na$_2$SO$_4$) and concentrated. This last crude (42.2 mg) was chromatographed (SiO$_2$, 7/3 Hex/Ether) to give the title compound (8.0 mg, 23.7% yield) as a white solid: LC-MS [M+H] 565, 567.

Example B13: To a stirred solution of methyl 2-((4S,5S)-1-(4-(((1R,5S,8R)-3-(5-chloro-2-methoxypyridin-4-yl)-3-azabicyclo[3.2.1]octan-8-yl)methyl)phenyl)-4-methyl-3-(trifluoromethyl)-4,5-dihydro-1H-pyrazol-5-yl)acetate (8 mg, 0.013 mmol) in THF (0.7 mL) and water (0.06 mL) at rt was added 1.0M aqueous lithium hydroxide (0.06 mL, 0.060 mmol). After stirring at rt for 5.8 h, the reaction mixture was partially evaporated to remove most of the THF. The remaining solution was partitioned between water (40 mL) and Hex (15 mL). The aqueous layer was acidified to pH 2 by dropwise addition of 1M HCl, and then extracted with CH$_2$Cl$_2$ (3×30 mL). The combined organic extracts were dried (Na$_2$SO$_4$) and concentrated. The residue was dried under vacuum to afford the title compound (6.5 mg, 83% yield) as a white solid: LC-MS [M+H] 551, 553. $^1$H NMR (500 MHz, CD$_2$Cl$_2$) δ 7.93 (s, 1H), 7.18 (d, J=8.5 Hz, 2H), 7.04 (d, J=8.5 Hz, 2H), 6.34 (s, 1H), 4.46 (m, 1H), 3.87 (s, 3H), 3.33 (dd, J=11.6, 3.5 Hz, 2H), 3.27 (m, 1H, overlapped), 3.23 (d, J=11.6 Hz, 2H), 2.88 (m, 3H), 2.50 (m, 1H), 2.08 (br. s, 2H), 1.94 (m, 3H), 1.73 (m, 2H), 1.34 (d, J=7.1 Hz, 3H). Analytical HPLC (Zorbax method, 50% Solvent B start): RT=8.70 min, HI: 95%. hGPR40 EC$_{50}$=2201 nM.

EXAMPLE B14

2-((4S,5S)-1-(4-((1-(6-Chlorobenzo[d][1,3]dioxol-5-yl)piperidin-4-yl)oxy)phenyl)-4-methyl-3-(trifluoromethyl)-4,5-dihydro-1H-pyrazol-5-yl)acetic acid, HCl

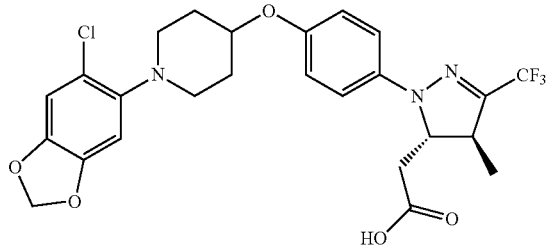 [SMILES: C[C@@H]1C(C(F)(F)F)=NN(c2ccc(OC3CCN(c4cc5c(cc4Cl)OCO5)CC3)cc2)[C@H]1CC(=O)O]

B14A. 5-Bromo-6-chlorobenzo[d][1,3]dioxole: To 5-bromobenzo[d][1,3]dioxole (2.01 g, 10.0 mmol) in acetonitrile (25.0 mL) at rt, trifluoroacetic acid (0.23 mL, 3.0 mmol) and N-chlorosuccinimide (1.40 g, 10.5 mmol) were added. The reaction was stirred at room temperature overnight. The reaction mixture was concentrated, diluted with EtOAc, washed with sat. NaHCO$_3$, water, brine, dried (MgSO$_4$) and concentrated. Purification via silica gel chromatography gave 5-bromo-6-chlorobenzo[d][1,3]dioxole as a white solid (2.22 g, 94% yield). $^1$H NMR (500 MHz, CDCl$_3$) δ ppm 7.04 (s, 1H), 6.92 (s, 1H), 6.00 (s, 2H).

Example B14 was prepared from B14A following the procedure for Example 4. LC-MS Anal. Calc'd for C$_{25}$H$_{25}$ClF$_3$N$_3$O$_5$ 539.14, found [M+H] 540.10. $^1$H NMR (500 MHz, CD$_3$CN) δ ppm 7.88 (s, 1H), 7.13-7.02 (m, 5H), 6.13 (s, 2H), 5.48 (s, 1H), 4.69 (s, 1H), 4.46-4.45 (m, 1H), 4.03 (s, br, 2H), 3.52-3.35 (m, 3H), 2.78-2.52 (m, 4H), 2.27-2.24 (m, 2H), 1.34-1.31 (m, 3H). Analytical HPLC (Orthogonal method, 0% Solvent B start): RT=11.04 min, HI: 98%. hGPR40 EC$_{50}$=569 nM.

EXAMPLE B15

2-((4S,5S)-1-(4-((1-(7-Chloro-2,3-dihydrobenzo[b][1,4]dioxin-6-yl)piperidin-4-yl)oxy)phenyl)-4-methyl-3-(trifluoromethyl)-4,5-dihydro-1H-pyrazol-5-yl)acetic acid, TFA

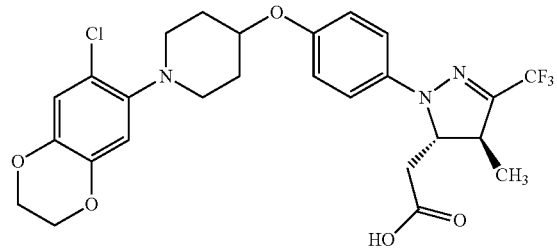 [SMILES: C[C@@H]1C(C(F)(F)F)=NN(c2ccc(OC3CCN(c4cc5c(cc4Cl)OCCO5)CC3)cc2)[C@H]1CC(=O)O]

Example B15 (light yellow solid, 31 mg) was prepared from 6-bromo-2,3-dihydrobenzo[b][1,4]dioxine following the procedure for B14A and Example 4. LC-MS Anal. Calc'd for C$_{26}$H$_{27}$ClF$_3$N$_3$O$_5$ 553.16, found [M+H] 554.0. $^1$H NMR (500 MHz, DMSO-d$_6$) δ ppm 7.95 (s, 1H), 7.06 (d, J=9.1 Hz, 2H), 6.97 (d, J=9.1 Hz, 2H) 6.94 (s, 1H), 6.68 (s, 1H), 4.48-4.36 (m, 2H), 4.26-4.16 (m, 4H), 3.11-3.03 (m, 2H), 2.82-2.71 (m, 4H), 2.68-2.59 (m, 1H), 2.01 (br. s, 2H), 1.81-1.69 (m, 2H), 1.26 (d, J=7.2 Hz, 3H). hGPR40 EC$_{50}$=325 nM.

EXAMPLE B16

2-((4S,5S)-1-(4-((1-(2,4-Dimethylthiazol-5-yl)piperidin-4-yl)oxy)phenyl)-4-methyl-3-(trifluoromethyl)-4,5-dihydro-1H-pyrazol-5-yl)acetic acid

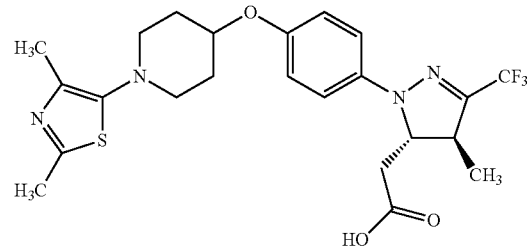 [SMILES: Cc1nc(C)c(N2CCC(Oc3ccc(N4N=C(C(F)(F)F)[C@@H](C)[C@@H]4CC(=O)O)cc3)CC2)s1]

B16A. 8-(2,4-Dimethylthiazol-5-yl)-1,4-dioxa-8-azaspiro[4.5]decane: To 5-bromo-2,4-dimethylthiazole (100 mg, 0.52 mmol) and 1,4-dioxa-8-azaspiro[4.5]decane (224 mg, 1.56 mmol) in DMF (0.52 mL), cesium carbonate (339 mg, 1.04 mmol) was added. The reaction was heated at 55° C. overnight. Additional 1,4-dioxa-8-azaspiro[4.5]decane (224 mg, 1.56 mmol) and diisopropylethylamine (0.1 mL) were added. The reaction was heated at 120° C. for one day and at 130° C. for 1 h. The reaction mixture was diluted with EtOAc, washed with water, brine, dried (MgSO$_4$) and concentrated. Purification via silica gel chromatography gave the title compound (55 mg, 42% yield). LC-MS Anal. Calc'd for C$_{12}$H$_{18}$SN$_2$O$_2$ 254.109, found [M+H] 255.1.

Example B16 was prepared from B16A following the procedure for Example 4. LC-MS Anal. Calc'd for $C_{23}H_{27}SF_3N_4O_3$ 496.176, found [M+H] 497.2. $^1$H NMR (500 MHz, DMSO-$d_6$) δ ppm 7.97 (s, 1H), 7.14-7.03 (m, 2H), 7.00-6.96 (m, 2H), 4.45-4.42 (m, 2H), 3.00-2.93 (m, 2H), 2.90 (s, 1H), 2.77-2.60 (m, 5H), 2.44-2.41 (m, 1H), 2.18 (s, 3H), 2.02 (m, 2H), 1.78 (m, 2H), 1.26 (d, J=6.9 Hz, 3H). hGPR40 $EC_{50}$=1100 nM.

EXAMPLE B17

2-((4S,5S)-1-(4-((1-(2-Fluoro-5-(oxazol-2-yl)phenyl)piperidin-4-yl)oxy)phenyl)-4-methyl-3-(trifluoromethyl)-4,5-dihydro-1H-pyrazol-5-yl)acetic acid

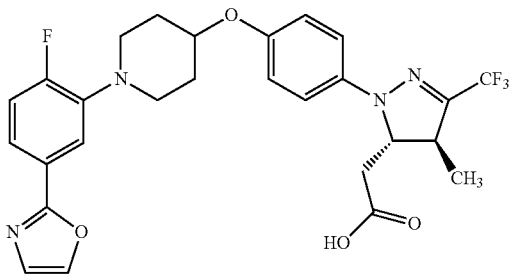 [SMILES: C[C@@H]1C(C(F)(F)F)=NN(c2ccc(OC3CCN(c4cc(-c5ncco5)ccc4F)CC3)cc2)[C@H]1CC(=O)O]

B17A. 3-Bromo-N-(2,2-dimethoxyethyl)-4-fluorobenzamide: To aminoacetaldehyde dimethylacetal (1.62 mL, 15.0 mmol) and triethylamine (2.09 mL, 15.00 mmol) in dichloromethane (16.67 mL) at 0° C., a solution of 3-bromo-4-fluorobenzoyl chloride (2.97 g, 12.5 mmol) in dichloromethane (8.33 mL) was added dropwise. The reaction was stirred at 0° C. for 1 h and at rt overnight. Solvent was evaporated. The reaction mixture was diluted with EtOAc, washed with water, brine dried (MgSO$_4$) and concentrated. Purification via silica gel chromatography gave an oil (3.7 g, yield 97%). LC-MS Anal. Calc'd for $C_{11}H_{13}BrFNO_3$ 306.128, found [M+H] 307.1.

B17B. 2-(3-Bromo-4-fluorophenyl)oxazole: To 3-bromo-N-(2,2-dimethoxyethyl)-4-fluorobenzamide (2 g, 6.53 mmol) in methanesulfonic acid (15.02 mL, 231 mmol) under argon, phosphorus pentoxide (4.64 g, 32.7 mmol) was added portions. The reaction was heated at 140° C. for 3 h. The mixture was poured into ice, extracted with EtOAc (3×). The extracts were washed with water (3×), brine, dried (MgSO$_4$) and concentrated. Purification via silica gel chromatography gave an oil (790 mg, 50% yield). LC-MS Anal. Calc'd for $C_9H_5BrFNO$, 242.045, found [M+H] 243.8.

Example B17 was prepared from B17B following the procedure for Example 4. LC-MS Anal. Calc'd for $C_{27}H_{26}F_4N_4O_4$ 546.189, found [M+H] 547.0. $^1$H NMR (500 MHz, METHANOL-$d_4$) δ ppm 7.85 (s, 1H), 7.71 (dd, J=8.4, 2.0 Hz, 1H), 7.65-7.59 (m, 2H), 7.23 (s, 1H), 7.15 (dd, J=12.4, 8.4 Hz, 1H), 7.08 (d, J=8.9 Hz, 1H), 6.96 (d, J=8.9 Hz, 2H), 4.48-4.40 (m, 2H), 3.42 (t, J=7.7 Hz, 2H), 3.25 (br. s., 1H), 3.11-3.04 (m, 2H), 2.78 (m, 1H), 2.40-2.32 (m, 1H), 2.16 (m, 2H), 2.01 (m, 1H), 1.34 (d, J=7.4 Hz, 3H). hGPR40 $EC_{50}$=2487 nM.

EXAMPLE B18

2-((4S,5S)-4-Methyl-1-(4-((1-(2-methylbenzo[d]oxazol-6-yl)piperidin-4-yl)oxy)phenyl)-3-(trifluoromethyl)-4,5-dihydro-1H-pyrazol-5-yl)acetic acid

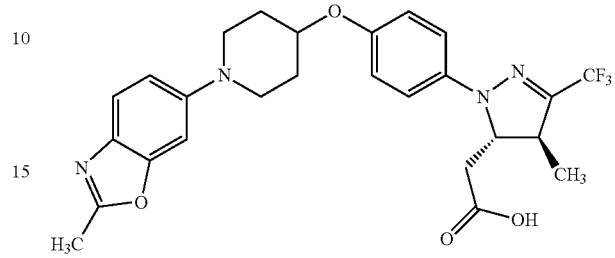

B18A. 1-(2-Methylbenzo[d]oxazol-6-yl)piperidin-4-one: To 2-methylbenzo[d]oxazol-6-amine (200 mg, 1.350 mmol) and 1-benzyl-1-methyl-4-oxopiperidin-1-ium iodide (894 mg, 2.70 mmol) in EtOH (3.4 mL) and water (1.13 mL), potassium carbonate (37 mg, 0.27 mmol) was added. The reaction was heated at 90° C. for 1.5 h. 10 mL water was added. The mixture was extracted with dichloromethane. The extract was dried (MgSO$_4$) and concentrated. Purification via silica gel chromatography gave a light brown solid (240 mg, 77% yield). LC-MS Anal. Calc'd for $C_{13}H_{14}N_2O_2$ 230.106, found [M+H] 231.0.

Example B18 was prepared from B18A following the procedure for Example 4. LC-MS Anal. Calc'd for $C_{26}H_{27}F_3N_4O_4$ 516.198, found [M+H] 517.2. $^1$H NMR (500 MHz, DMSO-$d_6$) δ ppm 7.95 (br. s., 1H), 7.44 (d, J=8.5 Hz, 1H), 7.20 (br. s., 1H), 7.06 (d, J=8.0 Hz, 2H), 7.02-6.94 (m, 3H), 4.45 (br. s., 2H), 3.50 (br. s., 3H), 3.07 (t, J=10.3 Hz, 2H), 2.89 (s, 1H), 2.73 (s, 1H), 2.63 (d, J=16.2 Hz, 1H), 2.53 (s, 1H), 2.48-2.41 (m, 1H), 2.02 (br. s., 2H), 1.73 (d, J=8.8 Hz, 2H), 1.25 (d, J=6.3 Hz, 3H). hGPR40 $EC_{50}$=5200 nM.

EXAMPLE B19

2-((4S,5S)-1-(4-((1-(2,3-Dihydrobenzo[b][1,4]dioxin-5-yl)piperidin-4-yl)oxy)phenyl)-4-methyl-3-(trifluoromethyl)-4,5-dihydro-1H-pyrazol-5-yl)acetic acid

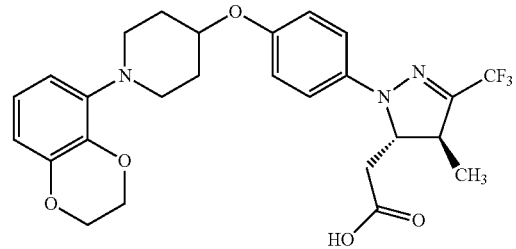 [SMILES: C[C@@H]1C(C(F)(F)F)=NN(c2ccc(OC3CCN(c4cccc5c4OCCO5)CC3)cc2)[C@H]1CC(=O)O]

B19A. 1-(2,3-Dihydrobenzo[b][1,4]dioxin-5-yl)piperidin-4-one was prepared following the procedure for B18A. LC-MS Anal. Calc'd for $C_{13}H_{15}NO_3$ 233.105, found [M+H] 234.0.

Example B19 was prepared from B19A following the procedure for Example 4. LC-MS Anal. Calc'd for $C_{26}H_{28}F_3N_3O_5$ 519.198, found [M+H] 518.3. $^1$H NMR (500

MHz, DMSO-$d_6$) δ ppm 7.96 (s, 1H), 7.07 (d, J=8.8 Hz, 2H), 6.97 (d, J=8.8 Hz, 2H), 6.76-6.68 (m, 1H), 6.51 (dd, J=8.0, 3.3 Hz, 2H), 4.48-4.37 (m, 2H), 4.23 (dd, J=18.2, 3.9 Hz, 4H), 2.90-2.62 (m, 6H), 2.46-2.43 (m, 1H), 2.02 (br. s., 2H), 1.80-1.69 (m, 2H), 1.27 (d, J=7.2 Hz, 3H). hGPR40 $EC_{50}$=6200 nM.

EXAMPLE B20

2-((4S,5S)-1-(4-((1-(2-Fluoro-5-(1H-pyrazol-1-yl)phenyl)piperidin-4-yl)oxy)phenyl)-4-methyl-3-(trifluoromethyl)-4,5-dihydro-1H-pyrazol-5-yl)acetic acid

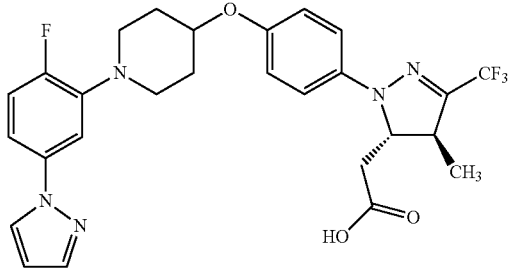 [SMILES: C[C@@H]1C(C(F)(F)F)=NN(c2ccc(OC3CCN(c4cc(-n5cccn5)ccc4F)CC3)cc2)[C@H]1CC(=O)O]

B20A. 1-(3-Bromo-4-fluorophenyl)-1H-pyrazole: A mixture of 2-bromo-1-fluoro-4-iodobenzene (602 mg, 2.0 mmol), 1H-pyrazole (150 mg, 2.2 mmol), sym-2-pyridinealdoxime (48.9 mg, 0.40 mmol), cesium carbonate (1.63 g, 5.0 mmol) and cuprous oxide (28.6 mg, 0.20 mmol) in acetonitrile (4 mL) was purged with argon. The reaction vial was sealed and heated at 80° C. for 51 h. After cooling, the mixture was diluted with EtOAc, filtered. The filtrate was washed with water, brine, dried (MgSO$_4$) and concentrated. Purification via silica gel chromatography gave a grey solid (273 mg, 57% yield). LC-MS Anal. Calc'd for $C_9H_6BrFN_2$ 241.06, found [M+H] 242.8.

Example B20 was prepared from B20A following the procedure for Example 4. LC-MS Anal. Calc'd for $C_{27}H_{27}F_4N_5O_3$ 545.205, found [M+H] 546.1. $^1$H NMR (500 MHz, DMSO-$d_6$) δ ppm 8.48 (d, J=2.5 Hz, 1H), 7.95 (s, 1H), 7.71 (d, J=0.8 Hz, 1H), 7.52-7.43 (m, J=7.7, 2.2 Hz, 1H), 7.25 (dd, J=12.1, 8.8 Hz, 1H), 7.12-7.02 (m, 2H), 6.98 (d, J=9.1 Hz, 2H), 6.52 (d, J=1.7 Hz, 1H), 4.53-4.38 (m, 2H), 3.02-2.43 (m, 8H), 2.07 (br. s., 2H), 1.84-1.74 (m, 2H), 1.25 (d, J=6.9 Hz, 3H). hGPR40 $EC_{50}$=4590 nM.

EXAMPLE B21

2-((4S,5S)-1-(4-((1-(2-Cyanophenyl)sulfonyl)piperidin-4-yl)oxy)phenyl)-4-methyl-3-(trifluoromethyl)-4,5-dihydro-1H-pyrazol-5-yl)acetic acid

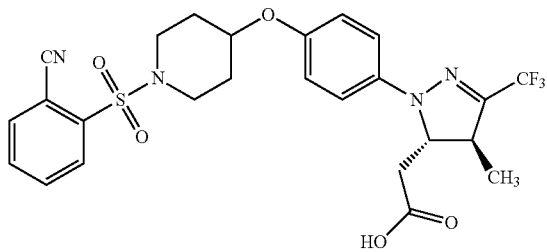 [SMILES: C[C@@H]1C(C(F)(F)F)=NN(c2ccc(OC3CCN(S(=O)(=O)c4ccccc4C#N)CC3)cc2)[C@H]1CC(=O)O]

B21A. 2-((4-Hydroxypiperidin-1-yl)sulfonyl)benzonitrile: To piperidin-4-ol (890 mg, 8.80 mmol), dichloromethane (10 mL), and triethylamine (3.01 mL, 21.60 mmol) at 0° C. under nitrogen was added 2-cyanobenzene-1-sulfonyl chloride (1613 mg, 8 mmol) over 2-3 minutes to produce an off-white suspension. The ice bath was removed and the mixture was then allowed to warm to rt. After 8 days at rt the reaction mixture was added to 10 mL of CH$_2$Cl$_2$ and 10 mL of 4 N aqueous HCl, mixed, and allowed to settle. The lower organic layer was with 2×10 mL additional 4 N HCl then 3×5 mL of water, dried with MgSO4, filtered, and concentrated in vacuo to provide the title compound (pale amber oily foam, 430 mg, 20%). LC-MS Anal. Calc'd for $C_{12}H_{14}N_2O_3S$: 266.07, found [M+Na] 267.1.

B21B. Methyl 2-((4S,5S)-1-(4-((1-((2-cyanophenyl)sulfonyl)piperidin-4-yl)oxy)phenyl)-4-methyl-3-(trifluoromethyl)-4,5-dihydro-1H-pyrazol-5-yl)acetate: To a solution of triphenylphosphine (29.0 mg, 0.111 mmol) and DMF (0.5 mL) added (E)-diethyl diazene-1,2-dicarboxylate (0.015 mL, 0.095 mmol). After stirring for 5 min this mixture was added to the thick 2-((4S,5S)-1-(4-hydroxyphenyl)-4-methyl-3-(trifluoromethyl)-4,5-dihydro-1H-pyrazol-5-yl)acetate (25 mg, 0.079 mmol) and stirred for 5 min. To this amber solution was then added 2-((4-hydroxypiperidin-1-yl)sulfonyl)benzonitrile (21.05 mg, 0.079 mmol) and the mixture capped under nitrogen. The mixture was placed in a 100° C. oil bath for 2 h. After cooling to rt, 1 mL of water plus 1 mL of brine and 2 mL of EtOAc were added to the reaction mixture, mixed, and allowed settle. The lower aqueous layer was removed and then the organic was washed with two more 2 mL of 50% brine/water then 2 mL of water. The EtOAc was concentrated to an oil and purified by prep LC using the system below to provide product (yellow oil, 12 mg, 26.9%). LC-MS Anal. Calc'd for $C_{26}H_{27}F_3N_4O_5S$: 564.17, found [M+Na] 565.1.

Example B21: To methyl 2-((4S,5S)-1-(4-((1-(2-cyanophenyl)sulfonyl)piperidin-4-yl)oxy)phenyl)-4-methyl-3-(trifluoromethyl)-4,5-dihydro-1H-pyrazol-5-yl)acetate (12 mg, 0.021 mmol) was added THF (0.3 mL) and Water (0.030 mL). To this mixture was dded lithium hydroxide (2 M aqueous) (0.032 mL, 0.064 mmol). After stirring overnight the reaction mixture was added to 1 mL of water and 1 mL of CH$_2$Cl$_2$. The mixture was shaken and then allowed to settle. An emulsion had formed. To this mixture was added 3 drops of 2 N aqueous HCl, causing the emulsion to break. The lower CH$_2$Cl$_2$ layer was removed. The aqueous layer was extracted with an additional 2×1 mL of CH$_2$Cl$_2$ and the combined extracts dried with Na$_2$SO$_4$, filtered, and concentrated in vacuo to provide product (pale yellow oil, 9 mg, 73%). LC-MS Anal. Calc'd for $C_{26}H_{27}F_3N_4O_5S$: 550.15, found [M+Na] 551.0. $^1$H NMR (500 MHz, CDCl$_3$) δ 8.08 (d, J=7.7 Hz, 1H), 7.91 (d, J=7.7 Hz, 1H), 7.80-7.76 (m, 1H), 7.72 (s, 1H), 7.08-6.99 (m, 2H), 6.89-6.75 (m, 2H), 4.51-4.27 (m, 2H), 3.85-3.71 (m, 2H), 3.21 (br. s., 1H), 2.82 (d, J=16.2 Hz, 1H), 2.43 (dd, J=16.4, 10.3 Hz, 1H), 2.09-1.90 (m, 4H), 1.34 (d, J=6.6 Hz, 3H). hGPR40 $EC_{50}$=7952 nM.

Examples B22-B25 were prepared using the same procedure described in Example B21.

EXAMPLE B22

2-((4S,5S)-1-(4-((1-(cyclohexylsulfonyl)piperidin-4-yl)oxy)phenyl)-4-methyl-3-(trifluoromethyl)-4,5-dihydro-1H-pyrazol-5-yl)acetic acid

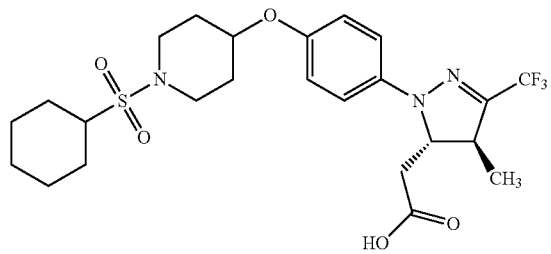 [SMILES: C[C@@H]1C(C(F)(F)F)=NN(c2ccc(OC3CCN(S(=O)(=O)C4CCCCC4)CC3)cc2)[C@H]1CC(=O)O]

LC-MS Anal. Calc'd for $C_{24}H_{32}F_3N_3O_5S$: 531.20, found [M+Na] 532.2. $^1$H NMR (500 MHz, CDCl$_3$) δ 7.06 (d, J=7.2 Hz, 2H), 6.95-6.85 (m, 2H), 4.53-4.28 (m, 2H), 3.77 (d, J=1.9 Hz, 1H), 3.62-3.51 (m, 2H), 3.43-3.35 (m, 2H), 3.23 (br. s., 1H), 3.00-2.89 (m, 1H), 2.85 (d, J=16.2 Hz, 1H), 2.55-2.38 (m, 1H), 2.14 (d, J=12.4 Hz, 2H), 1.97 (d, J=8.8 Hz, 2H), 1.93-1.83 (m, 4H), 1.72 (d, J=11.6 Hz, 1H), 1.52 (q, J=12.3 Hz, 2H), 1.36 (d, J=6.6 Hz, 2H), 1.33-1.12 (m, 3H). hGPR40 EC$_{50}$=1328 nM.

EXAMPLE B23

2-((4S,5S)-1-(4-((1-(isobutylsulfonyl)piperidin-4-yl)oxy)phenyl)-4-methyl-3-(trifluoromethyl)-4,5-dihydro-1H-pyrazol-5-yl)acetic acid

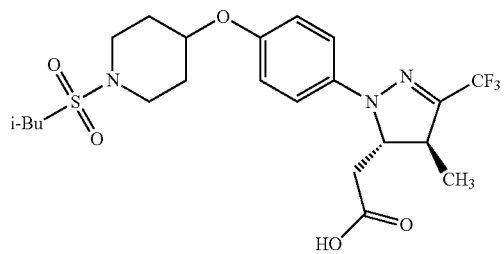

LC-MS Anal. Calc'd for $C_{22}H_{30}F_3N_3O_5S$: 505.19, found [M+Na] 506.2. $^1$H NMR (500 MHz, CDCl$_3$) δ 7.05 (d, J=8.8 Hz, 2H), 6.88 (d, J=8.8 Hz, 2H), 4.49-4.28 (m, 2H), 3.77 (t, J=6.3 Hz, 2H), 3.46-3.39 (m, 1H), 3.36-3.29 (m, 2H), 3.21 (br. s., 1H), 2.83-2.73 (m, 3H), 2.42 (dd, J=16.4, 10.3 Hz, 1H), 2.31 (dt, J=13.4, 6.6 Hz, 1H), 2.08-1.94 (m, 3H), 1.90-1.77 (m, 2H), 1.33 (d, J=7.2 Hz, 3H), 1.13 (d, J=6.9 Hz, 6H). hGPR40 EC$_{50}$=1995 nM.

EXAMPLE B24

2-((4S,5S)-1-(4-((1-(Cyclopentylsulfonyl)piperidin-4-yl)oxy)phenyl)-4-methyl-3-(trifluoromethyl)-4,5-dihydro-1H-pyrazol-5-yl)acetic acid

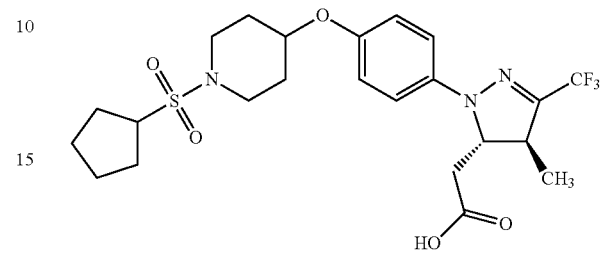

LC-MS Anal. Calc'd for $C_{23}H_{30}F_3N_3O_5S$: 517.19, found [M+Na] 518.2. $^1$H NMR (500 MHz, CDCl$_3$) δ 7.06 (d, J=9.1 Hz, 2H), 6.93-6.65 (m, 2H), 4.58-4.36 (m, 2H), 3.76 (t, J=6.5 Hz, 1H), 3.59-3.45 (m, 3H), 3.43-3.30 (m, 2H), 3.27-3.18 (m, 1H), 2.85 (dd, J=16.5, 2.8 Hz, 1H), 2.45 (dd, J=16.4, 10.3 Hz, 1H), 2.07-1.95 (m, 6H), 1.92-1.79 (m, 4H), 1.70-1.57 (m, 3H), 1.40-1.32 (m, 4H), 1.29-1.17 (m, 3H). hGPR40 EC$_{50}$=3600 nM.

EXAMPLE B25

2-((4S,5S)-4-Methyl-3-(trifluoromethyl)-1-(4-((1-((2-(trifluoromethyl)phenyl)sulfonyl)piperidin-4-yl)oxy)phenyl)-4,5-dihydro-1H-pyrazol-5-yl)acetic acid

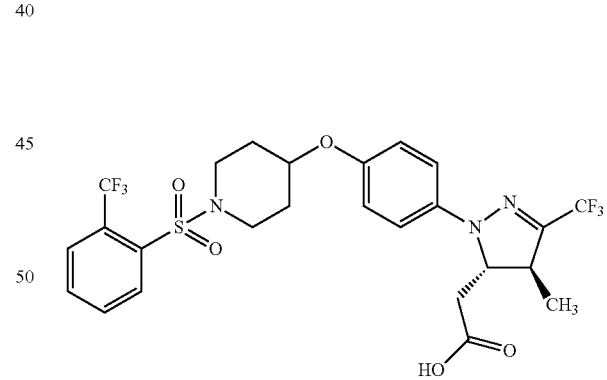

LC-MS Anal. Calc'd for $C_{25}H_{25}F_6N_3O_5S$: 593.14, found [M+Na] 594.0. $^1$H NMR (500 MHz, CDCl$_3$) δ 8.16 (d, J=7.2 Hz, 1H), 7.91 (d, J=7.2 Hz, 1H), 7.72 (td, J=3.6, 1.7 Hz, 2H), 7.03 (d, J=7.4 Hz, 2H), 6.95-6.78 (m, 2H), 4.49-4.30 (m, 2H), 3.51-3.41 (m, 2H), 3.40-3.32 (m, 2H), 3.22 (br. s., 1H), 2.83 (d, J=16.2 Hz, 1H), 2.05-1.95 (m, 2H), 1.94-1.80 (m, 4H), 1.35 (d, J=6.9 Hz, 3H). hGPR40 EC$_{50}$=4421 nM.

EXAMPLE B26

2-((4S,5S)-1-(4-((1-(2-fluoro-5-methoxyphenyl)piperidin-3-yl)oxy)phenyl)-4-methyl-3-(trifluoromethyl)-4,5-dihydro-1H-pyrazol-5-yl)acetic acid, TFA

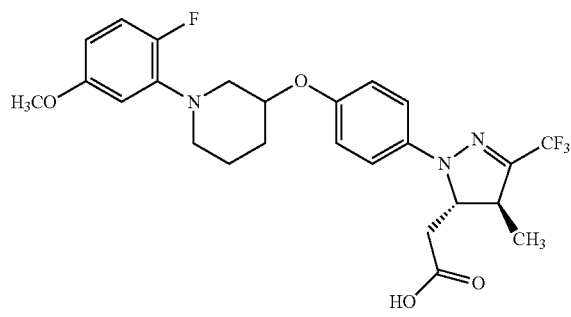 [SMILES: COc1ccc(F)c(N2CCCC(Oc3ccc(N4N=C(C(F)(F)F)[C@@H](C)[C@@H]4CC(=O)O)cc3)C2)c1]

Example B26 (isomeric mixture) was synthesized according to the method of Example 1 using piperidin-3-ol instead of piperidi-4-ol. LC-MS Anal. Calc'd for $C_{25}H_{27}F_4N_3O_4$ 509.19, found [M+H] 510.0. $^1$H NMR (500 MHz, CDCl$_3$) δ 6.87-7.11 (m, 6H), 6.80 (d, J=8.53 Hz, 1H), 4.27-4.44 (m, 2H), 3.72-3.84 (m, 5H), 3.64 (d, J=7.98 Hz, 1H), 3.15-3.38 (m, 3H), 2.74-2.89 (m, 3H), 2.36-2.50 (m, 1H), 2.14-2.25 (m, 2H), 2.10 (d, J=10.73 Hz, 1H), 1.78-2.00 (m, 2H), 1.53-1.68 (m, 1H), 1.31-1.38 (m, 6H), 0.81-0.97 (m, 7H). Analytical HPLC (Orthogonal method, 10% Solvent B start): RT=10.67 and 10.87 min, hGPR40 EC$_{50}$=4233 nM.

EXAMPLE B27

2-((4S,5S)-4-Methyl-1-(4-((1-(o-tolylsulfonyl)piperidin-4-yl)oxy)phenyl)-3-(trifluoromethyl)-4,5-dihydro-1H-pyrazol-5-yl)acetic acid

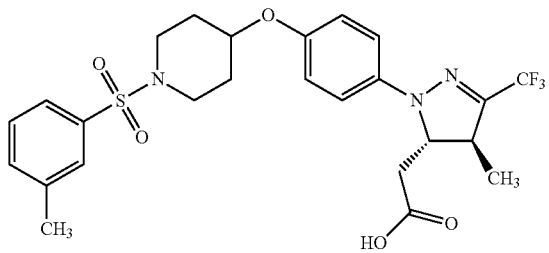 [SMILES: Cc1cccc(S(=O)(=O)N2CCC(Oc3ccc(N4N=C(C(F)(F)F)[C@@H](C)[C@@H]4CC(=O)O)cc3)CC2)c1]

B27A. Methyl 2-((4S,5S)-4-methyl-1-(4-((1-(o-tolylsulfonyl)piperidin-4-yl)oxy)phenyl)-3-(trifluoromethyl)-4,5-dihydro-1H-pyrazol-5-yl)acetate: To a mixture of methyl 2-((4S,5S)-4-methyl-1-(4-(piperidin-4-yloxy)phenyl)-3-(trifluoromethyl)-4,5-dihydro-1H-pyrazol-5-yl)acetate (50 mg, 0.088 mmol) and N-ethyl-N-isopropylpropan-2-amine (0.045 mL, 0.263 mmol) in CH$_2$Cl$_2$ (0.3 mL) was added 2-methylbenzene-1-sulfonyl chloride (33.4 mg, 0.175 mmol) and stirred at rt overnight. The reaction was quenched with saturated aqueous NaHCO$_3$, diluted with CH$_2$Cl$_2$ (5 mL) and the organic was separated and washed with H$_2$O followed by saturated aqueous NaCl. The organic was dried over Na$_2$SO$_4$ and concentrated. Purification via silica gel chromatography with 0-70% EtOAc in hexane gave the title compound as an white oil (13 mg, 26.8% yield). LC-MS Anal. Calc'd for $C_{26}H_{30}F_3N_3O_5S$, 553.19, found [M+H] 554.0.

Example B27 was prepared following the procedure in Example 1. LC-MS Anal. Calc'd for $C_{25}H_{28}F_3N_3O_5S$, 539.19, found [M+H] 540.1. $^1$H NMR (500 MHz, CHLOROFORM-d) δ 7.92 (d, J=8.25 Hz, 1H), 7.43-7.53 (m, 1H), 7.29-7.39 (m, 2H), 7.02 (d, J=9.08 Hz, 2H), 6.84 (d, J=9.08 Hz, 2H), 4.37 (dd, J=3.16, 6.46 Hz, 2H), 3.39 (ddd, J=3.16, 8.73, 12.31 Hz, 2H), 3.14-3.30 (m, 3H), 2.82 (dd, J=2.75, 16.51 Hz, 1H), 2.64 (s, 3H), 2.43 (dd, J=10.18, 16.51 Hz, 1H), 1.94-2.03 (m, 2H), 1.80-1.92 (m, 2H), 1.33 (d, J=7.15 Hz, 3H). Analytical HPLC (Orthogonal method, 10% Solvent B start): RT=11.8 min., hGPR40 EC$_{50}$=4850 nM.

EXAMPLE B28

2-((4S,5S)-1-(4-((1-(4-methoxypyrimidin-2-yl)piperidin-4-yl)oxy)phenyl)-4-methyl-3-(trifluoromethyl)-4,5-dihydro-1H-pyrazol-5-yl)acetic acid

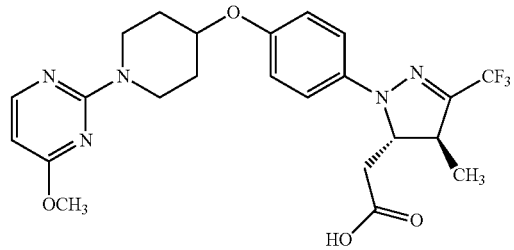 [SMILES: COc1ccnc(N2CCC(Oc3ccc(N4N=C(C(F)(F)F)[C@@H](C)[C@@H]4CC(=O)O)cc3)CC2)n1]

Example B28 (white solid) was prepared following the same procedure in Example 5. LC-MS Anal. Calc'd for $C_{23}H_{26}F_3N_5O_4$ 493.4, found [M+H] 494.0. $^1$H NMR (500 MHz, CHLOROFORM-d) δ 8.06-8.23 (m, 1H), 7.06 (s, 2H), 6.90 (s, 2H), 6.23 (s, 3H), 4.53-4.64 (m, 1H), 4.33-4.46 (m, 1H), 4.04 (s, 3H), 3.87-3.98 (m, 2H), 3.15-3.28 (m, 1H), 2.72-2.86 (m, 1H), 2.35-2.51 (m, 1H), 1.95-2.13 (m, 4H), 1.34 (d, J=7.15 Hz, 3H). Analytical HPLC (Orthogonal method, 10% Solvent B start): RT=6.99 min., hGPR40 EC$_{50}$=5269 nM.

EXAMPLE B29

2-((4S,5S)-1-(4-((1-(5-Fluoro-4-methoxypyrimidin-2-yl)piperidin-4-yl)oxy)phenyl)-4-methyl-3-(trifluoromethyl)-4,5-dihydro-1H-pyrazol-5-yl)acetic acid

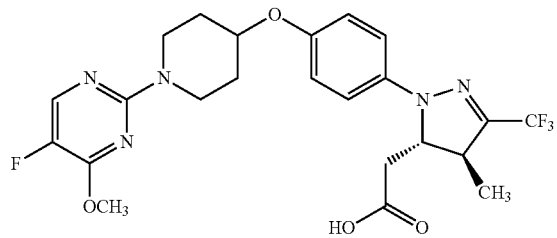 [SMILES: COc1nc(N2CCC(Oc3ccc(N4N=C(C(F)(F)F)[C@@H](C)[C@@H]4CC(=O)O)cc3)CC2)ncc1F]

Example B29 was prepared following the procedure of Example 5. LC-MS Anal. Calc'd for $C_{23}H_{25}F_4N_5O$, 511.1, found [M+H] 512.0. $^1$H NMR (500 MHz, CHLOROFORM-d) δ 8.15 (d, J=3.58 Hz, 1H), 7.01-7.13 (m, 2H), 6.83-6.97

(m, 2H), 4.53 (br. s., 1H), 4.40 (d, J=9.90 Hz, 1H), 4.10 (s, 3H), 3.80-4.02 (m, 4H), 3.14-3.30 (m, 1H), 2.83 (dd, J=3.30, 16.51 Hz, 1H), 2.44 (dd, J=9.90, 16.51 Hz, 2H), 1.98 (br. s., 4H), 1.35 (d, J=6.88 Hz, 3H). Analytical HPLC (Orthogonal method, 10% Solvent B start): RT=10.57 min., hGPR40 $EC_{50}$=3676 nM.

EXAMPLE B30

2-((4S,5S)-1-(4-((1-(tert-Butoxycarbonyl)azetidin-3-yl)methoxy)phenyl)-4-methyl-3-(trifluoromethyl)-4,5-dihydro-1H-pyrazol-5-yl)acetic acid

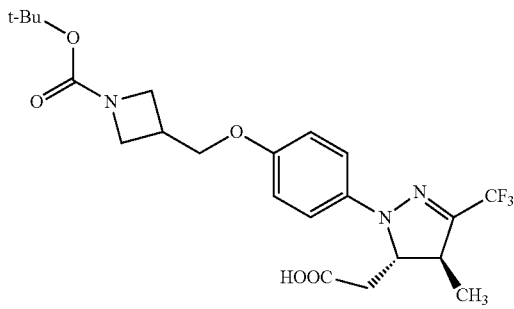 [SMILES: C[C@@H]1C(C(F)(F)F)=NN(c2ccc(OCC3CN(C(=O)OC(C)(C)C)C3)cc2)[C@H]1CC(=O)O]

B30A. tert-Butyl 3-((4-((4S,5S)-5-(2-methoxy-2-oxoethyl)-4-methyl-3-(trifluoromethyl)-4,5-dihydro-1H-pyrazol-1-yl)phenoxy)methyl)azetidine-1-carboxylate: To a mixture of triphenylphosphine (59.7 mg, 0.228 mmol) and (E)-di-tert-butyl diazene-1,2-dicarboxylate (52.4 mg, 0.228 mmol) in THF (0.3 mL) was added methyl 2-((4S,5S)-1-(4-hydroxyphenyl)-4-methyl-3-(trifluoromethyl)-4,5-dihydro-1H-pyrazol-5-yl)acetate (60 mg, 0.190 mmol) and tert-butyl 3-(hydroxymethyl)azetidine-1-carboxylate (35.5 mg, 0.190 mmol) and then the resulting mixture was stirred at rt for 16 h. The reaction was quenched with saturated aqueous $NaHCO_3$ (1 mL), extracted with EtOAc (5 mL) and the organic was separated and washed $H_2O$ 1× followed by saturated aq. NaCl. The organic layer was dried over $Na_2SO_4$ and concentrated to give the crude product. Purification via silica gel chromatography with 0-100% EtOAc in hexane gave the title compound as an white solid (30 mg, 32.6% yield). LC-MS Anal. Calc'd for $C_{23}H_{30}F_3N_3O_5$ 485.2, found [M+H] 486.0.

Example B30 was prepared following the procedure of Example 1. LC-MS Anal. Calc'd for $C_{22}H_{28}F_3N_3O_5$ 471.4, found [M+H] 472.0. $^1$H NMR (500 MHz, DMSO-$d_6$) δ 6.97-7.07 (m, 2H), 6.86-6.94 (m, 2H), 4.29-4.39 (m, 1H), 4.03-4.11 (m, 3H), 3.89-3.99 (m, 2H), 3.57-3.71 (m, 2H), 3.20-3.26 (m, 1H), 2.85-2.96 (m, 1H), 2.21-2.31 (m, 1H), 1.77 (d, J=3.03 Hz, 1H), 1.38 (s, 9H), 1.18-1.23 (m, 3H).) Analytical HPLC(Orthogonal method, 10% Solvent B start): RT=11.48 min. hGPR40 $EC_{50}$=2768 nM.

EXAMPLE B31

2-((4S,5S)-1-(4-((1-(Cyclohexylsulfonyl)azetidin-3-yl)methoxy)phenyl)-4-methyl-3-(trifluoromethyl)-4,5-dihydro-1H-pyrazol-5-yl)acetic acid

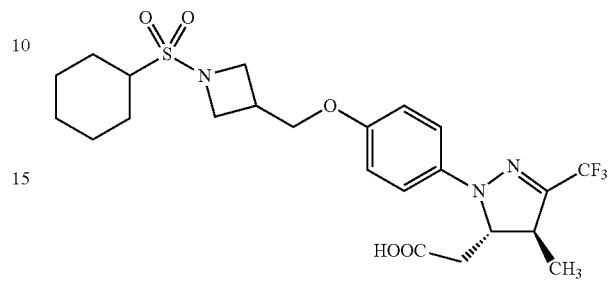

Example B31 was prepared following the procedure of Example B27 using of methyl 2-((4S,5S)-1-(4-(azetidin-3-ylmethoxy)phenyl)-4-methyl-3-(trifluoromethyl)-4,5-dihydro-1H-pyrazol-5-yl)acetate instead of methyl 2-((4S,5S)-4-methyl-1-(4-(piperidin-4-yloxy)phenyl)-3-(trifluoromethyl)-4,5-dihydro-1H-pyrazol-5-yl)acetate and cyclohexanesulfonyl chloride instead of 2-methylbenzene-1-sulfonyl chloride. LC-MS Anal. Calc'd for $C_{23}H_{30}F_3N_3O_5S$, 517.1, found [M+H] 518.0. $^1$H NMR (500 MHz, CHLOROFORM-d) δ 7.05 (d, J=8.80 Hz, 2H), 6.88 (d, J=8.80 Hz, 2H), 4.35-4.43 (m, 1H), 4.04-4.14 (m, 3H), 3.83-3.92 (m, 2H), 3.22 (d, J=3.30 Hz, 1H), 2.96-3.07 (m, 1H), 2.76-2.88 (m, 2H), 2.39-2.49 (m, 2H), 2.16 (d, J=11.83 Hz, 2H), 1.88 (d, J=12.93 Hz, 2H), 1.65-1.80 (m, 2H), 1.48 (dq, J=3.16, 12.43 Hz, 2H), 1.35 (d, J=7.15 Hz, 3H), 1.16-1.31 (m, 3H). Analytical HPLC (Orthogonal method, 10% Solvent B start): RT=6.04 min. hGPR40 $EC_{50}$=3772 nM.

EXAMPLE B32

2-((4S,5S)-1-(4-((1-(3-Methoxyphenyl)azetidin-3-yl)methoxy)phenyl)-4-methyl-3-(trifluoromethyl)-4,5-dihydro-1H-pyrazol-5-yl)acetic acid, TFA

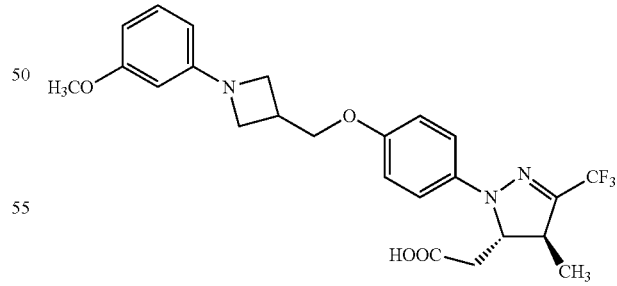

B32A. Methyl 2-((4S,5S)-1-(4-((1-(3-methoxyphenyl)azetidin-3-yl)methoxy)phenyl)-4-methyl-3-(trifluoromethyl)-4,5-dihydro-1H-pyrazol-5-yl)acetate: The mixture of (3-methoxyphenyl)boronic acid (26.8 mg, 0.176 mmol), diacetoxycopper hydrate (4.14 mg, 0.021 mmol) and 4 A° molecular sieve stirred 5 min in $CH_2Cl_2$ (0.5 mL) before methyl 2-((4S,5S)-1-(4-(azetidin-3-ylmethoxy)phenyl)-4-methyl-3-(trifluoromethyl)-4,5-dihydro-1H-pyrazol-5-yl)

acetate (40 mg, 0.104 mmol) was added and was stirred at 30° C. for 14 h. The reaction was quenched with saturated aq. NaHCO$_3$ and diluted with CH$_2$Cl$_2$ (5 mL). The organic was washed H$_2$O 3× followed by saturated aq. NaCl, dried over Na$_2$SO$_4$ and concentrated. Purification via silica gel chromatography with 0-70% EtOAc/hexanes gave the title compound as a white oil (18 mg, 35% yield). LC-MS Anal. Calc'd for C$_{25}$H$_{28}$F$_3$N$_3$O$_4$ 491.2, found [M+H] 492.0.

Example B32 was prepared following the procedure in Example 1. LC-MS Anal. Calc'd for C$_{24}$H$_{26}$F$_3$N$_3$O$_4$ 477.1, found [M+H] 478.0. $^1$H NMR (500 MHz, CHLOROFORM-d) δ 7.33 (t, J=8.12 Hz, 1H), 7.04-7.14 (m, 2H), 6.88-6.99 (m, 2H), 6.66-6.79 (m, 2H), 4.47 (t, J=8.80 Hz, 2H), 4.25 (t, J=8.12 Hz, 2H), 4.15 (d, J=5.23 Hz, 2H), 3.85 (s, 4H), 3.74-3.81 (m, 2H), 3.41-3.50 (m, 1H), 3.15-3.30 (m, 1H), 2.83 (dd, J=3.30, 16.23 Hz, 1H), 2.47 (dd, J=9.90, 16.23 Hz, 1H), 1.38 (d, J=7.15 Hz, 3H). Analytical HPLC(Orthogonal method, 10% Solvent B start): RT=11.0 min. hGPR40 EC$_{50}$=1086 nM.

EXAMPLE B33

2-((4S,5S)-1-(4-((1-(5-chloro-2-methoxypyridin-4-yl)azetidin-3-yl)methoxy)phenyl)-4-methyl-3-(trifluoromethyl)-4,5-dihydro-1H-pyrazol-5-yl)acetic acid

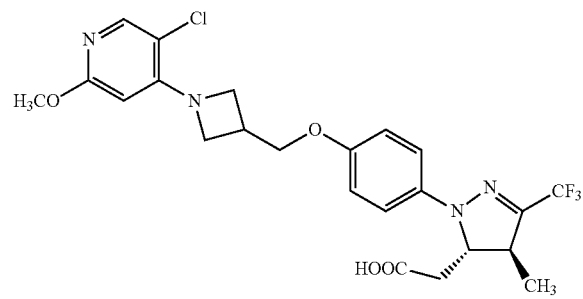 [SMILES: COc1cc(N2CC(COc3ccc(N4N=C(C(F)(F)F)[C@@H](C)[C@@H]4CC(=O)O)cc3)C2)c(Cl)cn1]

Example B33 was synthesized according to the method of Example B32. LC-MS Anal. Calc'd for C$_{23}$H$_{24}$ClF$_3$N$_4$O$_4$ 512.1, found [M+H] 513.0. $^1$H NMR (500 MHz, DMSO-d$_6$) δ 7.79 (s, 1H), 6.88-7.16 (m, 4H), 5.80 (s, 1H), 4.38-4.49 (m, 1H), 4.07-4.33 (m, 5H), 3.97 (dd, J=5.64, 8.12 Hz, 2H), 3.76 (s, 3H), 2.99-3.14 (m, 1H), 2.89 (s, 1H), 2.73 (s, 1H), 2.50 (s, 1H), 1.25 (d, J=6.88 Hz, 3H). hGPR40 EC$_{50}$=713 nM.

EXAMPLE B34

2-((4S,5S)-1-(4-((1-(benzo[d][1,3]dioxol-5-yl)azetidin-3-yl)methoxy)phenyl)-4-methyl-3-(trifluoromethyl)-4,5-dihydro-1H-pyrazol-5-yl)acetic acid

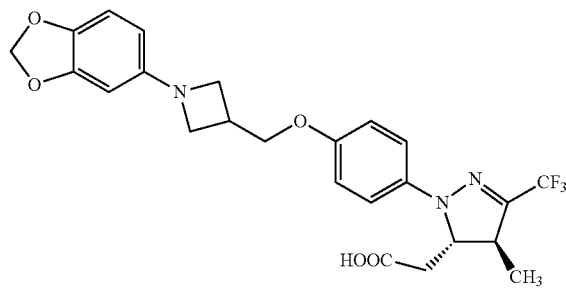 [SMILES: C[C@@H]1C(C(F)(F)F)=NN(c2ccc(OCC3CN(c4ccc5c(c4)OCO5)C3)cc2)[C@H]1CC(=O)O]

Example B34 was synthesized according to the method of Example B32. LC-MS Anal. Calc'd for C$_{24}$H$_{24}$F$_3$N$_3$O$_5$ 491.6, found [M+H] 492.0. $^1$H NMR (500 MHz, DMSO-d$_6$) δ 7.95 (s, 1H), 7.05 (s, 2H), 6.93 (d, J=8.80 Hz, 2H), 6.63-6.77 (m, 1H), 6.09-6.22 (m, 1H), 4.35-4.49 (m, 1H), 4.13 (d, J=6.88 Hz, 2H), 3.85 (s, 2H), 3.55 (s, 2H), 2.98-3.14 (m, 1H), 2.89 (s, 4H), 2.73 (s, 2H), 1.25 (d, J=7.15 Hz, 3H). hGPR40 EC$_{50}$=4763 nM.

EXAMPLE B35

2-((4S,5S)-1-(4-((1-(2-fluoro-5-methoxyphenyl)azetidin-3-yl)methoxy)phenyl)-4-methyl-3-(trifluoromethyl)-4,5-dihydro-1H-pyrazol-5-yl)acetic acid

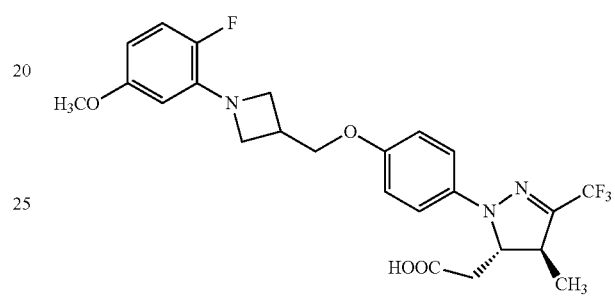

Example B35 was synthesized according to the method of Example B32. Calc'd for C$_{24}$H$_{25}$F$_4$N$_3$O$_4$ 495.1, found [M+H] 496.0. $^1$H NMR (500 MHz, DMSO-d$_6$) δ 7.04 (d, J=8.80 Hz, 2H), 6.84-6.96 (m, 3H), 6.18-6.27 (m, 1H), 5.98-6.11 (m, 1H), 4.31-4.46 (m, 1H), 4.15 (d, J=6.88 Hz, 2H), 4.03 (d, J=1.93 Hz, 2H), 3.74 (s, 2H), 3.69 (s, 3H), 3.02-3.14 (m, 1H), 1.96-2.07 (m, 1H), 1.23 (d, J=7.15 Hz, 6H). hGPR40 EC$_{50}$=4763 nM.

EXAMPLE B36

2-((4S,5S)-1-(4-(2-(1-(5-chloro-2-methoxypyridin-4-yl)azetidin-3-yl)ethyl)phenyl)-4-methyl-3-(trifluoromethyl)-4,5-dihydro-1H-pyrazol-5-yl)acetic acid, TFA

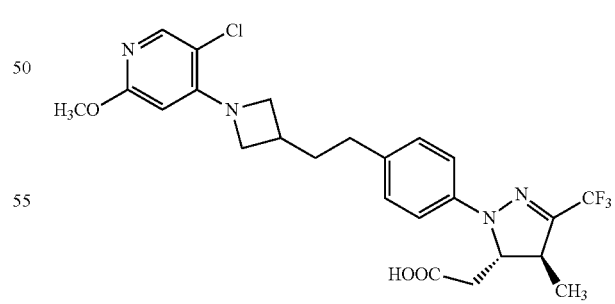

B36A. tert-Butyl 3-vinylazetidine-1-carboxylateTo a solution of methyltriphenylphosphonium bromide (3.86 g, 10.80 mmol) in THF (6 mL) at −78° C. was added butyllithium (1.080 mL, 10.80 mmol) and stirred for 20 min before being warmed up to 0° C. and stirred 1 h before tert-butyl 3-formylazetidine-1-carboxylate (1 g, 5.40 mmol) in THF (3 mL) was added. The reaction continued stirring at 0° C. for 2 h and then at rt for 3 h. After quenched with NH$_4$Cl (sat.), the reaction was extracted with EtOAc (3×), washed with saturated aqueous NaCl. The organic was dried and concentrated. Purification via silica gel chromatography with 0-70% EtOAc/hexanes gave the title compound as a white oil (0.5 g, 50% yield). LC-MS Anal. Calc'd for C$_{10}$H$_{17}$NO$_2$ 183.1, found [M+H] 184.0.

B36B. tert-Butyl 3-(4-((4S,5S)-5-(cyanomethyl)-4-methyl-3-(trifluoromethyl)-4,5-dihydro-1H-pyrazol-1-yl)phenethyl)azetidine-1-carboxylate: To a solution of tert-butyl 3-vinylazetidine-1-carboxylate (300 mg, 1.637 mmol) in THF (0.6 mL) was added 9-BBN (3.27 mL, 1.637 mmol) under argon and stirred at 68° C. for 1.5 h. Cooled to rt, the resulting mixture was added into vigously stirred mixture of 2-((4S,5S)-1-(4-bromophenyl)-4-methyl-3-(trifluoromethyl)-4,5-dihydro-1H-pyrazol-5-yl)acetonitrile (584 mg, 1.686 mmol), (1,1-bis(diphenylphosphino)ferrocene}dichloropalladium(II), complex with dichloromethane (66.8 mg, 0.082 mmol) and potassium carbonate (453 mg, 3.27 mmol) in DMF (2 mL) and H$_2$O (0.2 mL) and then stirred at 65° C. for 3 h. The reaction was poured into water and its pH was adjusted >11, then was extracted with CH$_2$Cl$_2$ (3×). The organic was dried over MgSO$_4$ and concentrated. Purification via silica gel chromatography with 0-50% EtOAc/hexanes gave the title compound as white oil (400 mg, 54.2%). LC-MS Anal. Calc'd for C$_{23}$H$_{29}$F$_3$N$_4$O$_2$ 450.4, found [M+H] 451.0.

Example B36 was synthesized following the procedure of Example 1. LC-MS Anal. Calc'd for C$_{24}$H$_{26}$ClF$_3$N$_4$O$_3$ 510.1, found [M+H] 511.0. $^1$H NMR (400 MHz, CD$_2$Cl$_2$) δ 7.90 (s, 1H), 7.10-7.19 (m, 2H), 6.96-7.08 (m, 2H), 5.47 (s, 1H), 4.45 (d, J=9.90 Hz, 2H), 3.97 (s, 3H), 3.19-3.32 (m, 2H), 2.76-2.90 (m, 2H), 2.63 (t, J=7.26 Hz, 2H), 2.47 (dd, J=10.12, 16.51 Hz, 1H), 1.91-2.07 (m, 2H), 1.34 (d, J=7.04 Hz, 3H). Analytical HPLC(Orthogonal method, 10% Solvent B start): RT=7.93 min. hGPR40 EC$_{50}$=591 nM.

EXAMPLE B37

2-((4S,5S)-1-(4-((5-(5-chloro-2-methoxypyridin-4-yl)-5-azaspiro[2.5]octan-8-yl)oxy)phenyl)-4-methyl-3-(trifluoromethyl)-4,5-dihydro-1H-pyrazol-5-yl)acetic acid

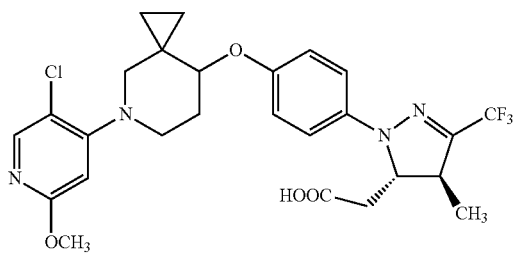 [SMILES: COc1cc(N2CCC(Oc3ccc(N4N=C(C(F)(F)F)[C@@H](C)[C@@H]4CC(=O)O)cc3)C3(CC3)C2)c(Cl)cn1]

B37A. tert-Butyl 8-oxo-5-azaspiro[2.5]octane-5-carboxylate: To a suspension of potassium 2-methylpropan-2-olate (0.732 g, 6.52 mmol) in tert-butyl alcohol (5 mL) was added tert-butyl 4-oxopiperidine-1-carboxylate (1.3 g, 6.52 mmol) and stirred for 15 min. before (2-chloroethyl)dimethylsulfonium iodide (1.483 g, 5.87 mmol) was added in portions over 1 h period. After stirred 1 h, added another 1 eq (0.338 g, 3.01 mmol) and t-BuOH (3 mL), continued stirring at rt overnight. The reaction was poured onto water and extracted by EtOAc (2×30 mL). The combined organics were derived over Na$_2$SO$_4$ and concentrated in vaccuo. Purification via flash chromatography (0-40% EtOAc/hexanes) afforded the title compound as a white oil (360 mg, 19.5% yield). LC-MS Anal. Calc'd for C$_{12}$H$_{19}$NO$_3$ 225.1, found [M+H] 226.1. $^1$H NMR (500 MHz, CHLOROFORM-d) δ 3.71-3.85 (m, 2H), 3.56 (br. s., 2H), 2.59 (t, J=6.60 Hz, 2H), 1.45-1.53 (m, 9H), 1.26-1.32 (m, 2H), 0.71-0.93 (m, 2H).

B37B. tert-Butyl 8-hydroxy-5-azaspiro[2.5]octane-5-carboxylate To a suspension of tert-butyl 8-oxo-5-azaspiro[2.5]octane-5-carboxylate (260 mg, 0.808 mmol) in ethyl alcohol (3 mL) at 0° C. was added sodium borohydride (32.2 mg, 0.808 mmol) and stirred at rt for 16 h. After concentration in vacuo, CH$_2$Cl$_2$ (5 mL) was added and then quenched with 5 mL H$_2$O. The organic layer was collected and the aqueous layer was back extracted with CH$_2$Cl$_2$ (2×5 mL). The combined extract was dried over Na$_2$SO$_4$ and concentrated. Purification via flash chromatography (0-70% EtOAc/hexanes) afforded the title compound as white oil (149 mg, 81% yield).

B37C. tert-Butyl 8-(4-((4S,5S)-5-(2-methoxy-2-oxoethyl)-4-methyl-3-(trifluoromethyl)-4,5-dihydro-1H-pyrazol-1-yl)phenoxy)-5-azaspiro[2.5]octane-5-carboxylate: The intermediate was prepared following the procedure of Example B30.

B37D. Methyl 2-((4S,5S)-1-(4-(5-azaspiro[2.5]octan-8-yloxy)phenyl)-4-methyl-3-(trifluoromethyl)-4,5-dihydro-1H-pyrazol-5-yl)acetate: To a solution of tert-butyl 8-(4-((4S,5S)-5-(2-methoxy-2-oxoethyl)-4-methyl-3-(trifluoromethyl)-4,5-dihydro-1H-pyrazol-1-yl)phenoxy)-5-azaspiro[2.5]octane-5-carboxylate (34 mg, 0.065 mmol) in CH$_2$Cl$_2$ (0.6 mL) was added hydrogen chloride (0.065 mL, 0.065 mmol) and stirred at rt for 16 h. After neutralized with saturated aqueous NaHCO$_3$, the organic layer was collected, dried over Na$_2$SO$_4$ and concentrated. Used for next step reaction without further purification. LC-MS Anal. Calc'd for C$_{21}$H$_{26}$F$_3$N$_3$O$_3$ 425.19, found [M+H] 426.0.

B37E. Methyl 2-((4S,5S)-1-(4-((5-(5-chloro-2-methoxypyridin-4-yl)-5-azaspiro[2.5]octan-8-yl)oxy)phenyl)-4-methyl-3-(trifluoromethyl)-4,5-dihydro-1H-pyrazol-5-yl)acetate: The intermediate was prepared following the procedure of Example 5A. LC-MS Anal. Calc'd for C$_{27}$H$_{30}$ClF$_3$N$_4$O$_4$ 566, [M+H] 567.1.

Example B37 was prepared following the procedure in Example 1. LC-MS Anal. Calc'd for C$_{26}$H$_{28}$ClF$_3$N$_4$O$_4$ 552, [M+H] 553.2. $^1$H NMR (500 MHz, DMSO-d$_6$) δ 8.00 (s, 1H), 6.85-7.11 (m, 4H), 6.41 (s, 1H), 4.31-4.48 (m, 1H), 3.94 (br. s., 1H), 3.80 (s, 3H), 3.16 (br. s., 2H), 2.68-2.93 (m, 3H), 2.12-2.27 (m, 1H), 1.90 (s, 3H), 1.23 (d, J=6.88 Hz, 3H), 0.58 (d, J=11.55 Hz, 4H). hGPR40 EC$_{50}$=774 nM.

What is claimed is:
1. A compound of Formula (I):

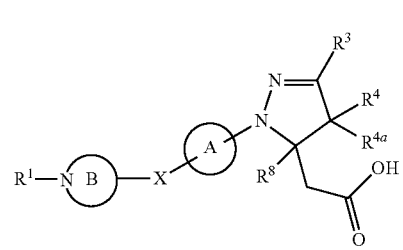

or a stereoisomer, a tautomer, or a pharmaceutically acceptable salt thereof, wherein:

X is independently selected from: a bond, O, S, NH, N($C_{1-4}$ alkyl), $CH_2$, $CH_2CH_2$, CH($C_{1-4}$ alkyl), $OCH_2$, $CH_2O$, $OCH_2CH_2$, and $CH_2CH_2O$;

ring A is independently

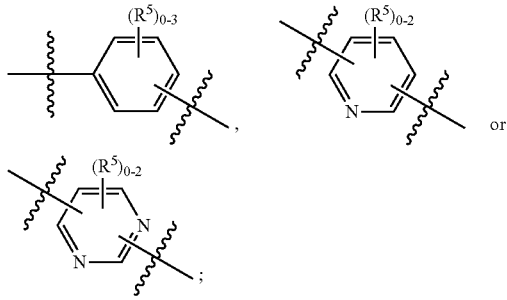

,   or   ;

ring B is independently a 4- to 7-membered saturated heterocycle containing carbon atoms, the nitrogen atom shown in the ring B and 0-1 additional heteroatom selected from N, O, and S; and ring B is substituted with 0-4 $R^2$;

$R^1$ is independently $CO_2R^9$, $SO_2R^9$,

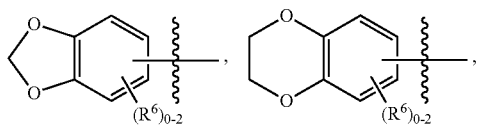

,   , phenyl, benzyl, naphthyl or a 5- to 10-membered heteroaryl containing carbon atoms and 1-4 heteroatoms selected from N, $NR^{11}$, O, and S; wherein said phenyl, benzyl, naphthyl and heteroaryl are each substituted with 0-3 $R^6$;

$R^2$, at each occurrence, is independently selected from: =O, OH, halogen, $C_{1-6}$ alkyl substituted with 0-1 $R^{12}$, $C_{1-6}$ alkoxy substituted with 0-1 $R^{12}$, $C_{1-4}$ haloalkyl substituted with 0-1 $R^{12}$, $C_{1-4}$ haloalkoxy substituted with 0-1 $R^{12}$, —$(CH_2)_m$—$C_{3-6}$ carbocycle substituted with 0-1 $R^{12}$, and —$(CH_2)_m$-(5- to 10-membered heteroaryl containing carbon atoms and 1-4 heteroatoms selected from N, $NR^{11}$, O, and S); wherein said heteroaryl is substituted with 0-1 $R^{12}$;

when two $R^2$ groups are attached to two different carbon atoms, they may combine to form a 1- to 3-membered carbon atom bridge over ring B;

when two $R^2$ groups are attached to the same carbon, they may combine, together with the carbon atom to which they are attached, to form a 3- to 6-membered carbon atom containing spiro ring;

$R^3$ is independently selected from: H, halogen, CN, OH, $CO_2H$, $C_{1-6}$ alkyl, $C_{2-6}$ alkenyl, $C_{2-6}$ alkynyl, $C_{1-6}$ haloalkyl, —N($C_{1-4}$ alkyl)$SO_2Ph$, $OR^9$, $SR^9$, $C(O)OR^9$, $CO_2R^9$, $S(O)R^9$, $SO_2R^9$, $CONHR^9$, $CON(C_{1-4}$ alkyl)$_2$, —$(O)_n$—$(CH_2)_m$-(phenyl substituted with 0-2 $R^{10}$), —$(O)_n$—$(CH_2)_m$-(5- to 10-membered heteroaryl containing carbon atoms and 1-4 heteroatoms selected from N, $NR^{11}$, O, and S; wherein said heteroaryl is substituted with 0-2 $R^{10}$);

$R^4$ is independently selected from: H, $C_{1-6}$ alkyl substituted with 0-1 $R^c$, $C_{1-6}$ alkoxy, and —$(CH_2)_m$—$C_{3-6}$ carbocycle substituted with 0-2 $R^c$;

$R^{4a}$ is independently selected from: H, halogen, $C_{1-6}$ alkyl, $C_{1-6}$ alkoxy, and —$(CH_2)_m$—$C_{3-6}$ carbocycle;

$R^5$, at each occurrence, is independently selected from: halogen, $C_{1-6}$ alkyl, and $C_{1-6}$ alkoxy;

$R^6$, at each occurrence, is independently selected from: halogen, OH, $C_{1-4}$ alkylthio, CN, $SO_2(C_{1-2}$ alkyl), $N(C_{1-4}$ alkyl)$_2$, $C_{1-4}$ haloalkyl, $C_{1-4}$ haloalkoxy, $C_{1-8}$ alkyl substituted with 0-1 $R^7$, $C_{1-6}$ alkoxy substituted with 0-1 $R^7$, —$(O)_n$—$(CH_2)_m$—$(C_{3-10}$ carbocycle substituted with 0-2 $R^7$), and —$(CH_2)_m$-(5- to 10-membered heteroaryl containing carbon atoms and 1-4 heteroatoms selected from N, $NR^{11}$, O, and S; wherein said heteroaryl is substituted with 0-2 $R^7$;

$R^7$, at each occurrence, is independently selected from: halogen, OH, $C_{1-4}$ alkyl, $C_{2-4}$ alkenyl, $C_{1-4}$ alkoxy, $C_{1-4}$ alkylthio, $C_{1-4}$ haloalkyl, $C_{1-4}$ haloalkoxy, $SCF_3$, CN, $NO_2$, $NH_2$, $NH(C_{1-4}$ alkyl), $N(C_{1-4}$ alkyl)$_2$, $SO_2(C_{1-2}$ alkyl), and phenyl;

$R^8$ is independently selected from: H and $C_{1-4}$ alkyl;

$R^9$, at each occurrence, is independently selected from: $C_{1-6}$ alkyl, $C_{1-4}$ haloalkyl, —$(CH_2)_m$—$(C_{3-6}$ cycloalkyl substituted with 0-2 $R^{10}$), and —$(CH_2)_m$-(phenyl substituted with 0-2 $R^{10}$);

$R^{10}$ and $R^{12}$, at each occurrence, is independently selected from: OH, halogen, CN, $C_{1-4}$ alkyl, $C_{1-4}$ alkoxy, $C_{1-4}$ haloalkyl, $C_{1-4}$ haloalkoxy, $SCF_3$, $NO_2$, $CO_2(C_{1-4}$ alkyl), $SO_2(C_{1-4}$ alkyl), and tetrazolyl;

$R^{11}$, at each occurrence, is independently selected from: H, $C_{1-4}$ alkyl and benzyl; $R^c$, at each occurrence, is independently selected from: OH, $C_{1-4}$ alkoxy, halogen, $CF_3$, $OCF_3$, and CN;

m, at each occurrence, is independently 0, 1, or 2; and n, at each occurrence, is independently 0 or 1;

provided that the compound is other than a compound of Formula (1a):

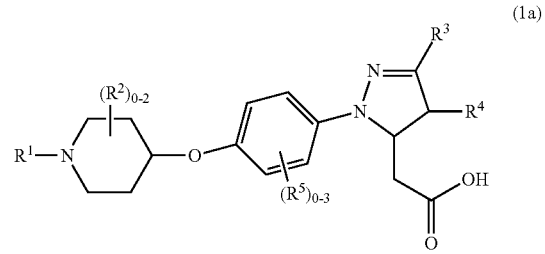

(1a)

wherein:

$R^1$ is independently phenyl substituted with 0-3 $R^6$ or pyridinyl substituted with 0-3 $R^6$;

$R^2$ is, at each occurrence, independently halogen or $C_{1-4}$ alkyl;

$R^3$ is independently selected from: $CF_3$, 4-halo-Ph, 4-CN-Ph, 4-$CO_2(C_{1-2}$ alkyl)-Ph, 2-halo-4-CN-Ph, and pyrimidin-2-yl;

$R^4$ is independently $C_{1-4}$ alkyl or cyclopropylmethyl;

$R^5$ is, at each occurrence, independently halogen; and $R^6$, at each occurrence, is independently selected from: OH, halogen, CN, $C_{1-4}$ alkyl, and $C_{1-4}$ alkoxy.

2. A compound according to claim 1, wherein the compound is of Formula (II):

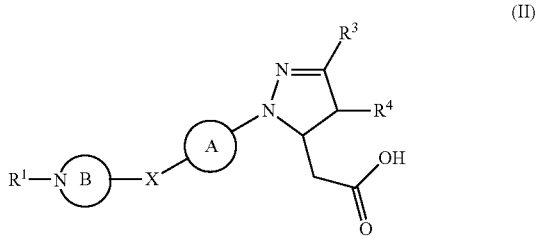

(II)

or a stereoisomer, a tautomer, or a pharmaceutically acceptable salt thereof, wherein:

X is independently selected from: a bond, O, S, NH, $N(C_{1-4}$ alkyl), $CH_2$, $CH_2CH_2$, $CH(C_{1-4}$ alkyl), $OCH_2$, $CH_2O$, $OCH_2CH_2$, and $CH_2CH_2O$;

ring A is independently

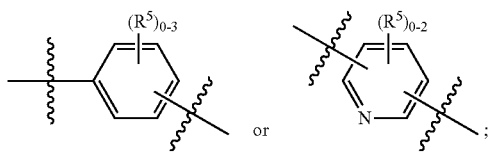

ring B is independently a 4- to 7-membered saturated heterocycle containing carbon atoms and the nitrogen atom shown in ring B; and ring B is substituted with 0-4 $R^2$;

$R^1$ is independently $CO_2(C_{1-4}$ alkyl), $CO_2Bn$,

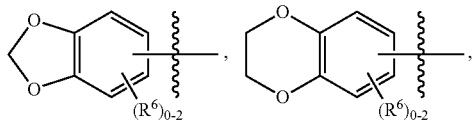

phenyl, benzyl, naphthyl or a 5- to 10-membered hetcroaryl containing carbon atoms and 1-4 heteroatoms selected from N, $NR^{11}$, O, and S; wherein said phenyl, benzyl, naphthyl and heteroaryl are each substituted with 0-3 $R^6$;

$R^2$, at each occurrence, is independently selected from: =O, OH, halogen, $C_{1-6}$ alkyl substituted with 0-1 $R^{12}$, $C_{1-6}$ alkoxy substituted with 0-1 $R^{12}$, $C_{1-4}$ haloalkyl, $C_{1-4}$ haloalkoxy, and benzyl;

when two $R^2$ groups are attached to two different carbon atoms, they may combine to form a 1- to 3-membered carbon atom bridge over ring B;

when two $R^2$ groups are attached to the same carbon, they may combine, together with the carbon atom to which they are attached, to form a 3- to 6-membered carbon atom containing spiro ring;

$R^3$ is independently selected from: H, halogen, CN, $SO_2(C_{1-4}$ alkyl), $CONH(C_{1-4}$ alkyl), $CON(C_{1-4}$ alkyl)$_2$, $C_{1-4}$ alkyl, $C_{1-4}$ alkoxy, $C_{1-4}$ alkylthio, $C_{1-4}$ haloalkyl, $C_{1-4}$ haloalkoxy, $-N(C_{1-4}$ alkyl)$SO_2Ph$, $-(O)_n-(CH_2)_m-$ (phenyl substituted with 0-2 $R^{10}$), and $-(O)_n-(CH_2)_m-$(a 5- to 10-membered heteroaryl containing carbon atoms and 1-4 heteroatoms selected from N, $NR^{11}$, O, and S wherein said heteroaryl is substituted with 0-2 $R^{10}$);

$R^4$ is independently selected from: H, halogen, $C_{1-4}$ alkyl, $C_{1-4}$ alkoxy, and $-(CH_2)_m-C_{3-6}$ carbocycle;

$R^5$, at each occurrence, is independently selected from: halogen, $C_{1-6}$ alkyl, and $C_{1-6}$ alkoxy;

$R^6$, at each occurrence, is independently selected from halogen, OH, $C_{1-4}$ alkylthio, CN, $SO_2(C_{1-2}$ alkyl), $N(C_{1-4}$ alkyl)$_2$, $C_{1-4}$ haloalkyl, $C_{1-4}$ haloalkoxy, $C_{1-6}$ alkyl substituted with 0-1 $R^7$, $C_{1-4}$ alkoxy substituted with 0-1 $R^7$, $-(O)_n-(CH_2)_m-(C_{3-6}$ carbocycle substituted with 0-2 $R^7$), $-(CH_2)_m-$(naphthyl substituted with 0-2 $R^7$), and $-(CH_2)_m-$(5- to 10-membered heteroaryl containing carbon atoms and 1-4 heteroatoms selected from N, $NR^{11}$, O, and S; wherein said heteroaryl is substituted with 0-2 $R^7$;

$R^7$, at each occurrence, is independently selected from: halogen, OH, $C_{1-4}$ alkyl, $C_{2-4}$ alkenyl, $C_{1-4}$ alkoxy, $C_{1-4}$ alkylthio, $C_{1-4}$ haloalkyl, $C_{1-4}$ haloalkoxy, $SCF_3$, CN, $NO_2$, $NH_2$, $NH(C_{1-4}$ alkyl), $N(C_{1-4}$ alkyl)$_2$, $SO_2(C_{1-2}$ alkyl), and phenyl;

$R^{10}$ and $R^{12}$, at each occurrence, are independently selected from: OH, halogen, CN, $C_{1-4}$ alkyl, $C_{1-4}$ alkoxy, $C_{1-4}$ haloalkyl, $C_{1-4}$ haloalkoxy, $SCF_3$, $NO_2$, $CO_2(C_{1-4}$ alkyl), $SO_2(C_{1-4}$ alkyl), and tetrazolyl;

$R^{11}$, at each occurrence, is independently selected from: H, $C_{1-4}$ alkyl and benzyl; m, at each occurrence, is independently 0, 1, or 2; and n, at each occurrence, is independently 0 or 1;

provided that the compound is other than a compound of Formula (1a):

wherein:

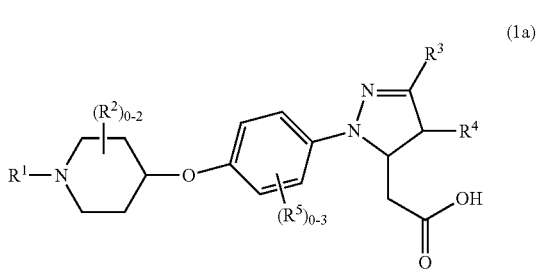

(1a)

$R^1$ is independently phenyl substitute with 0-3 $R^6$ or pyridinyl substituted with 0-3 $R^6$;

$R^2$ is, at each occurrence, independently halogen or $C_{1-4}$ alkyl;

$R^3$ is independently selected from: $CF_3$, 4-halo-Ph, 4-CN-Ph, 4-$CO_2(C_{1-2}$ alkyl)-Ph, 2-halo-4-CN-Ph, and pyrimidin-2-yl;

$R^4$ is independently $C_{1-4}$ alkyl or cyclopropylmethyl;

$R^5$ is, at each occurrence, independently halogen; and $R^6$, at each occurrence, is independently selected from: OH, halogen, CN, $C_{1-4}$ alkyl, and $C_{1-4}$ alkoxy.

3. A compound according to claim 1, wherein:

X is independently selected from: a bond, O, NH, $N(CH_3)$, $CH_2$, $CH_2CH_2$, $CH(CH_3)$, $OCH_2$, $CH_2O$, $OCH_2CH_2$, and $CH_2CH_2O$;

ring A is independently

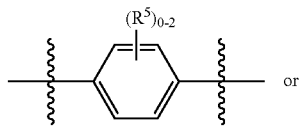 or

-continued

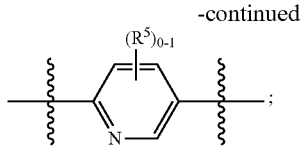

ring B is independently selected from:

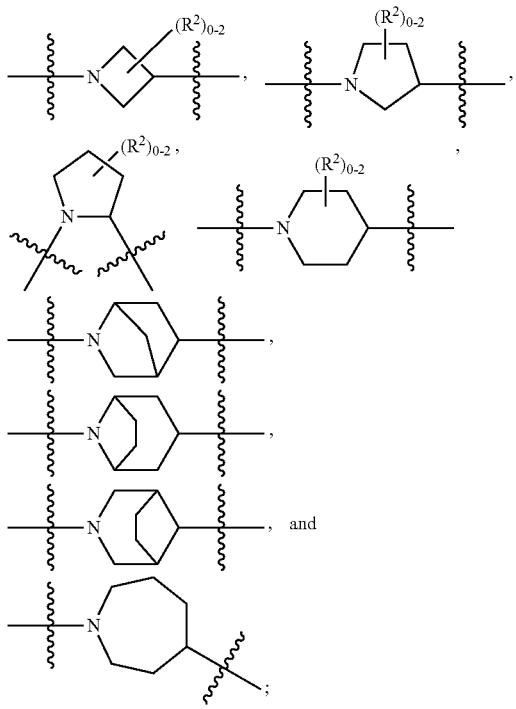

$R^1$ is independently $CO_2(C_{1-4}$ alkyl), $CO_2Bn$,

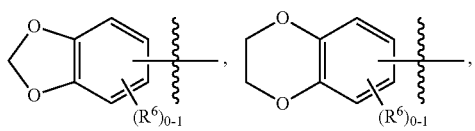

phenyl substituted with 0-3 $R^6$ or a heteroaryl substituted with 0-2 $R^6$; wherein said heteroaryl is selected from: furanyl, oxazolyl, thiazolyl, pyrazolyl, oxadiazolyl, pyridinyl, pyrazinyl,

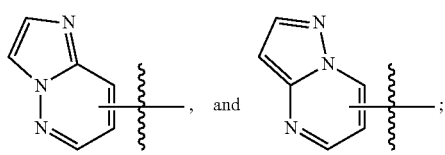

$R^2$, at each occurrence, is independently selected from: =O, OH, halogen, $C_{1-4}$ alkyl substituted with 0-1 $R^{12}$; $C_{1-4}$ alkoxy substituted 0-1 $R^{12}$, and benzyl;
$R^3$ is independently selected from: H, halogen, CN, $SO_2(C_{1-4}$ alkyl), $CONH(C_{1-4}$ alkyl), $CON(C_{1-4}$ alkyl)$_2$, —N($C_{1-4}$ alkyl)$SO_2$Ph, $C_{1-6}$ alkyl, $C_{1-6}$ alkoxy, $C_{1-4}$ haloalkyl, $C_{1-4}$ haloalkoxy, phenyl, benzyl, phenoxy, benzoxy, oxazolyl, 1-$C_{1-4}$ alkyl-pyrazolyl, triazolyl, tetrazolyl, pyridinyl, —O-pyridinyl, pyrimidinyl, —O-pyrimidinyl, and

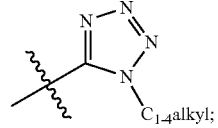

wherein each said ring moiety is each substituted with 0-2 $R^{10}$;
$R^4$ is independently selected from: H, halogen, $C_{1-4}$ alkyl, and —$(CH_2)_m$—$C_{3-6}$ carbocycle; and
$R^6$, at each occurrence, is independently selected from: halogen, OH, $C_{1-6}$ alkyl substituted with 0-1 OH, $C_{1-4}$ alkoxy, $C_{1-4}$ alkylthio, $C_{1-4}$ haloalkyl, $C_{1-4}$ haloalkoxy, CN, $SO_2(C_{1-2}$ alkyl), $N(C_{1-4}$ alkyl)$_2$, $C_{3-6}$ cycloalkyl, —O—$C_{3-6}$ cycloalkyl, benzyl, and oxazolyl;
provided that the compound is other than a compound of Formula(1b):

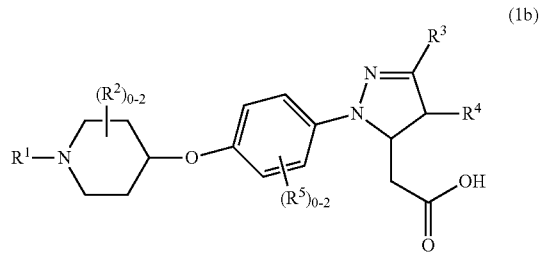

wherein:
$R^1$ is independently phenyl substituted with 0-3 $R^6$ or pyridinyl substituted with 0-3 $R^6$;
$R^2$ is, at each occurrence, independently halogen or $C_{1-4}$ alkyl;
$R^3$ is independently selected from: $CF_3$, 4-halo-Ph, 4-CN-Ph, 4-$CO_2(C_{1-2}$ alkyl)-Ph, 2-halo-4-CN-Ph, and pyrimidin-2-yl;
$R^4$ is independently $C_{1-4}$ alkyl or cyclopropylmethyl;
$R^5$ is, at each occurrence, independently halogen;
$R^6$, at each occurrence, is independently selected from: OH, halogen, CN, $C_{1-4}$ alkyl, and $C_{1-4}$ alkoxy.

4. A compound according to claim 3, wherein:
$R^1$ is independently

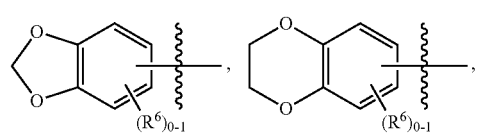

phenyl substituted with 0-3 $R^6$ or a heteroaryl substituted with 0-2 $R^6$; wherein said heteroaryl is selected from: thiazolyl, pyridinyl, pyrimidinyl, pyrazinyl,

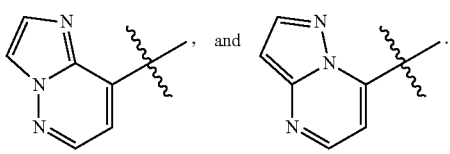 [SMILES: *c1ccnn2ccnc12 ; *c1ccnc2ccnn12]

5. A compound according to claim 4, wherein:
X is independently selected from: O, N(CH$_3$), CH$_2$, CH$_2$O, and CH$_2$CH$_2$O;
ring A is

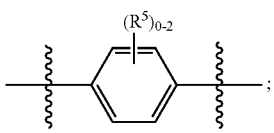

ring B is independently selected from:

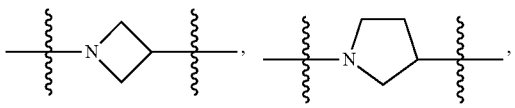

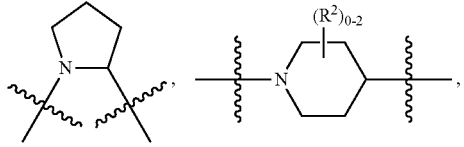

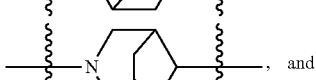, and

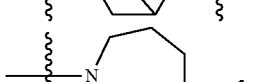

$R^1$ is independently phenyl substituted with 0-3 $R^6$, pyridinyl substituted with 0-2 $R^6$, pyrazinyl substituted with 0-2 $R^6$, pyrimidinyl substituted with 0-2 $R^6$, thiazolyl substituted with 0-2 $R^6$,

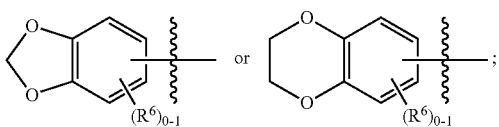

$R^2$, at each occurrence, is independently selected from: OH, halogen, C$_{1-4}$ alkyl substituted with 0-1 $R^{12}$, C$_{1-4}$ alkoxy substituted with 0-1 C$_{1-4}$ alkoxy, benzyl, and tetrazolylmethyl;
$R^3$ is independently selected from: H, halogen, CN, C$_{1-4}$ alkyl, C$_{1-4}$ alkoxy, C$_{1-4}$ haloalkyl, C$_{1-4}$ haoalkoxy, phe-nyl, benzyl, phenoxy, benzoxy, —N(C$_{1-4}$ alkyl)SO$_2$Ph, 1-C$_{1-4}$ alkyl-pyrazolyl, triazolyl, tetrazolyl, pyridinyl, —O-pyridinyl, pyrimidinyl, and —O-pyrimidinyl; wherein said phenyl, benzyl, phenoxy and pyridinyl are each substituted with 0-2 $R^{10}$;
$R^4$ is independently C$_{1-4}$ alkyl or —CH$_2$—C$_{3-6}$ cycloalkyl;
$R^6$, at each occurrence, is independently selected from: halogen, CN, C$_{1-4}$ alkyl, C$_{1-4}$ alkoxy, C$_{1-4}$ haoalkyl, C$_{1-4}$ haoalkoxy, C$_{3-6}$ cycloalkyl, —O—C$_{3-6}$ cycloalkyl, benzyl, and oxazolyl;
$R^{10}$, at each occurrence, is independently selected from: halogen, CN, C$_{1-4}$ alkyl, C$_{1-4}$ alkoxy, C$_{1-4}$ haoalkyl, C$_{1-4}$ haoalkoxy, and CO$_2$(C$_{1-2}$ alkyl); and
$R^{12}$ is independently selected from: OH, CN, and C$_{1-4}$ alkoxy.

6. A compound according to claim 5, wherein:
X is O;
ring A is

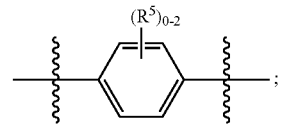

ring B is independently selected from:

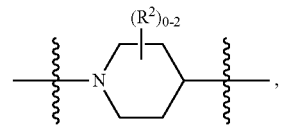

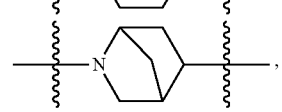

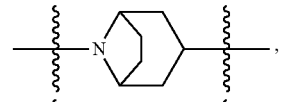

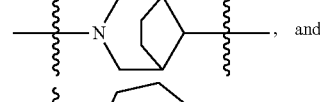, and

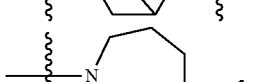

$R^2$, at each occurrence, is independently selected from: halogen, C$_{1-4}$ alkyl substituted with 0-1 $R^{12}$, C$_{1-4}$ alkoxy, and benzyl;
$R^3$ is independently selected from: CN, C$_{1-4}$ haloalkyl, 4-halo-Ph, 4-CN-Ph, 4-CO$_2$(C$_{1-2}$ alkyl)-Ph, 2-halo-4-CN-Ph, 3-CN-4-CN-Ph, and pyrimidinyl;
$R^4$ is independently C$_{1-4}$ alkyl or —CH$_2$—C$_{3-6}$ cycloalkyl;
$R^5$ is independently halogen or C$_{1-4}$ alkyl;
$R^6$, at each occurrence, is independently selected from: halogen, CN, C$_{1-4}$ alkyl, C$_{1-4}$ alkoxy, cyclopentoxy, and oxazolyl; and
$R^{12}$ is independently selected from; OH, CN, and C$_{1-4}$ alkoxy.

7. A pharmaceutical composition, comprising: a pharmaceutically acceptable carrier and a compound of claim 1, or a stereoisomer, a tautomer, or a pharmaceutically acceptable salt thereof.

8. The pharmaceutical composition according to claim 7, further comprising one or more other therapeutic agents selected from the group consisting of anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, and anti-inflammatory agents.

9. The pharmaceutical composition according to claim 7, further comprising a dipeptidyl peptidase-IV inhibitor and/or a sodium-glucose transporter-2 inhibitor.

10. A method for treating or modulating a disease or disorder associated with the activity of GPR40, comprising administering to a patient in need of such treatment a therapeutically effective amount of at least one of the compounds of claim 1, or a stereoisomer, a tautomer, or a pharmaceutically acceptable salt thereof, wherein the disease or disorder is selected from the group consisting of diabetes, hyperglycemia, impaired glucose tolerance, gestational diabetes, insulin resistance, hyperinsulinemia, retinopathy, neuropathy, nephropathy, diabetic kidney disease, acute kidney injury, cardiorenal syndrome, acute coronary syndrome, delayed wound healing, atherosclerosis and its sequelae, abnormal heart function, congestive heart failure, myocardial ischemia, stroke, Metabolic Syndrome, hypertension, obesity, fatty liver disease, dislipidemia, dyslipidemia, hyperlipidemia, hypertriglyceridemia, hypercholesterolemia, low high-density lipoprotein (HDL), high low-density lipoprotein (LDL), non-cardiac ischemia, pancreatitis, lipid disorders, neurodegenerative disease, cognitive impairment, dementia, liver diseases, NASH (Non-Alcoholic SteatoHepatitis), NAFLD (Non-Alcoholic Fatty Liver Disease) and liver cirrhosis.

11. The method according to claim 10, wherein the compound is administered simultaneously, separately or sequentially with an additional therapeutic agent.

12. A compound according to claim 1, which selected from the group consisting of

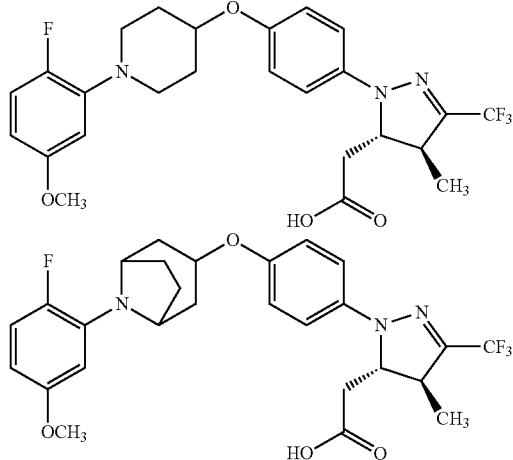

-continued

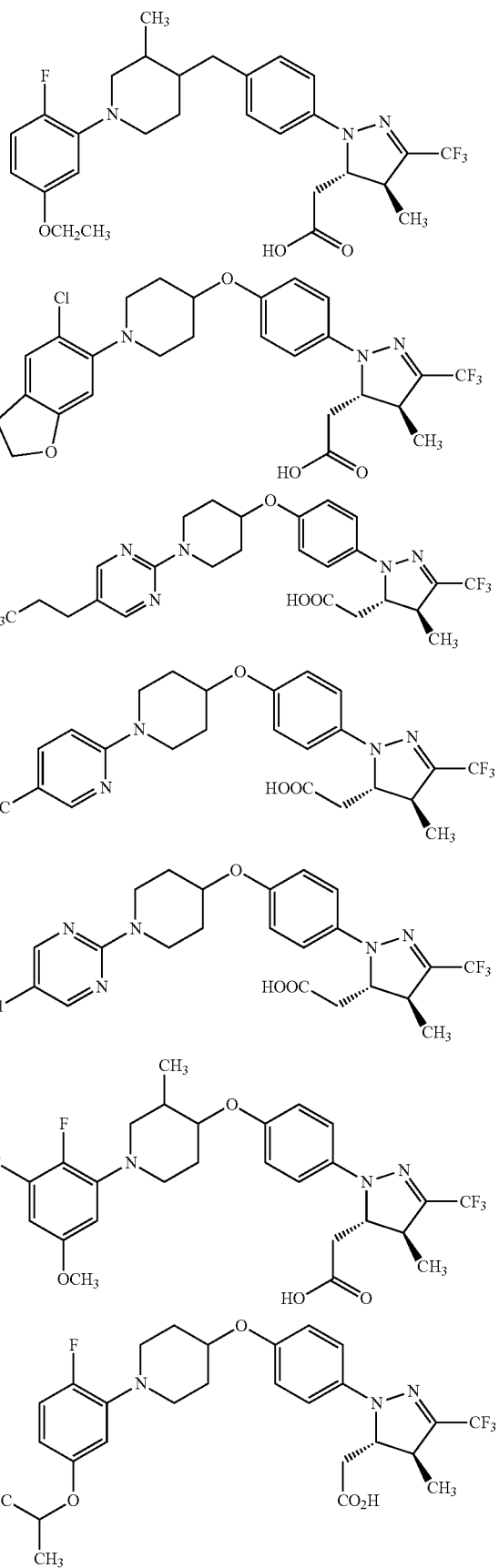

205
-continued
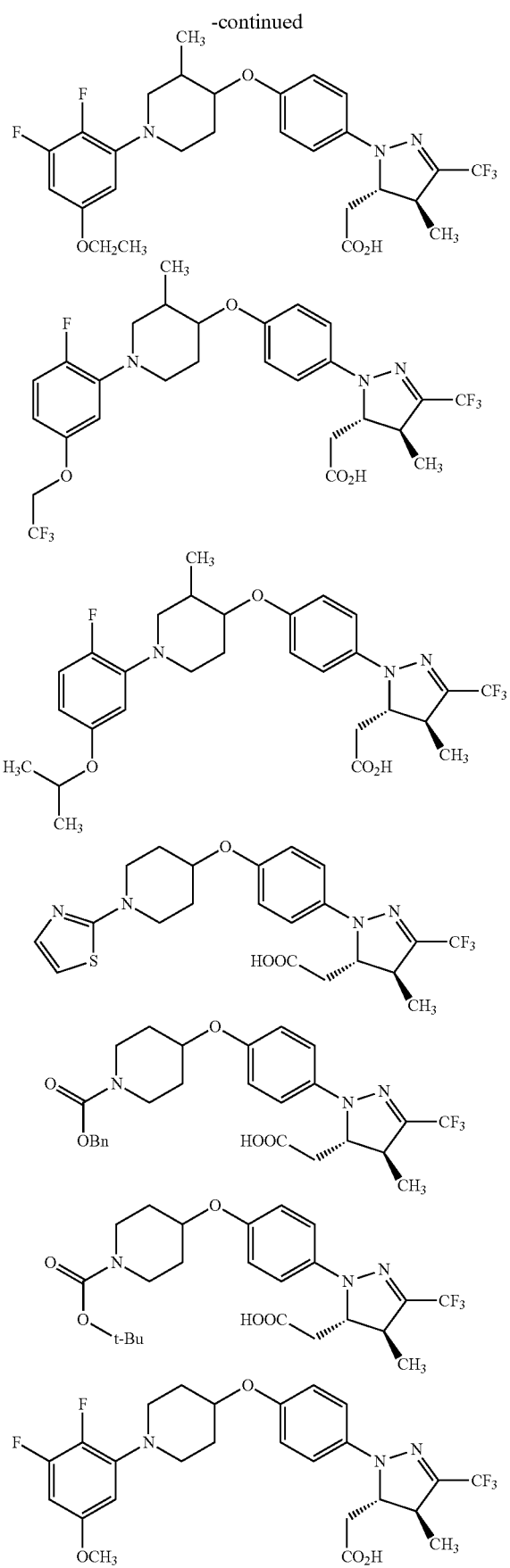
206
-continued
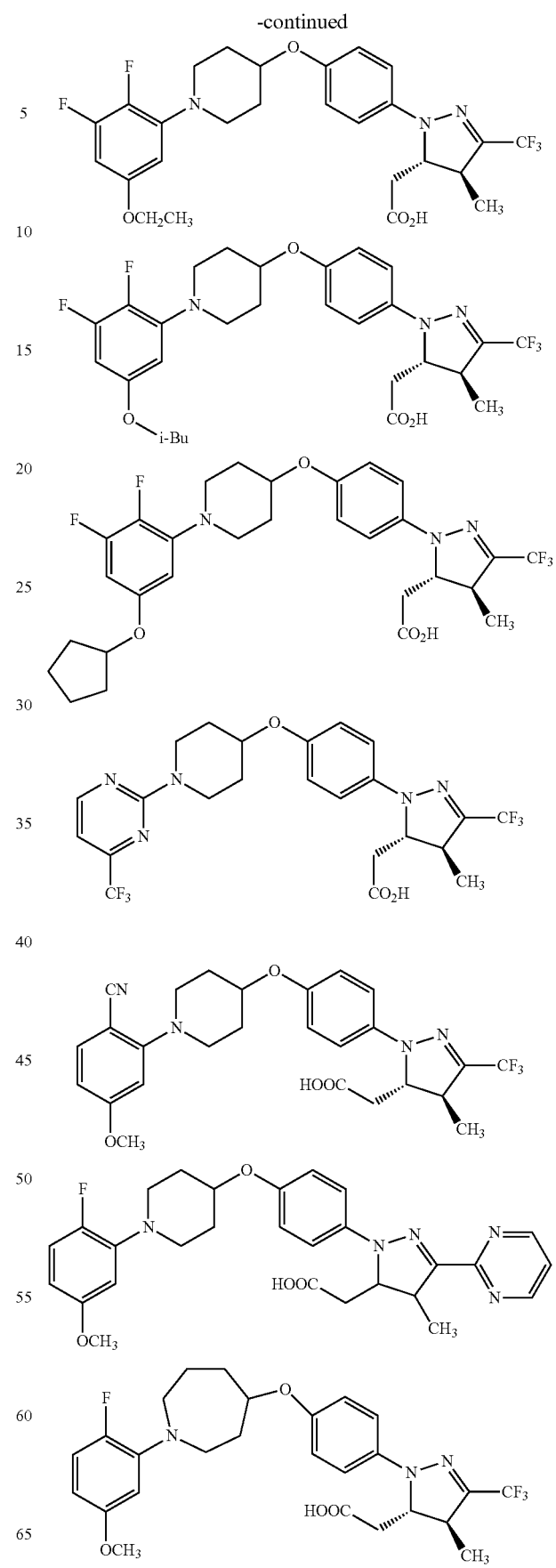

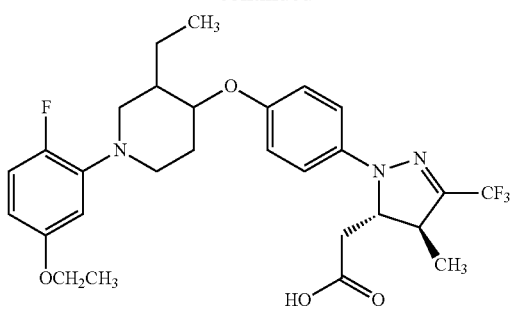
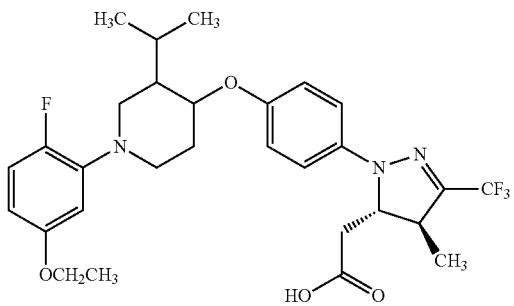
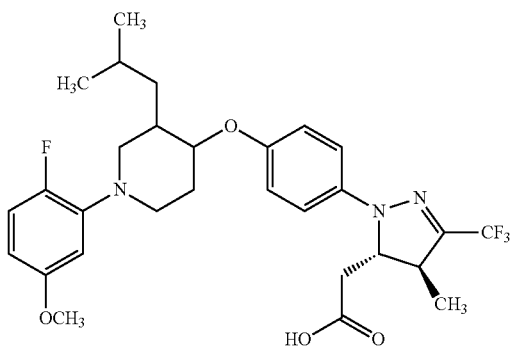
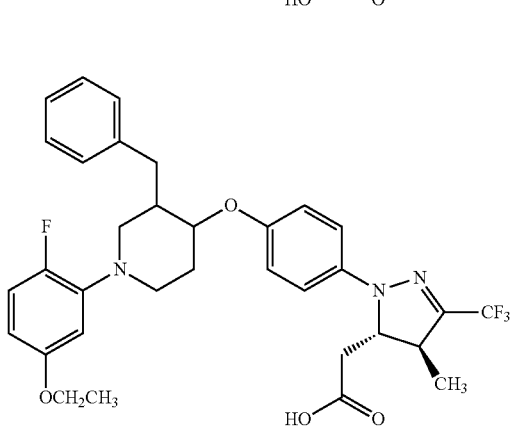
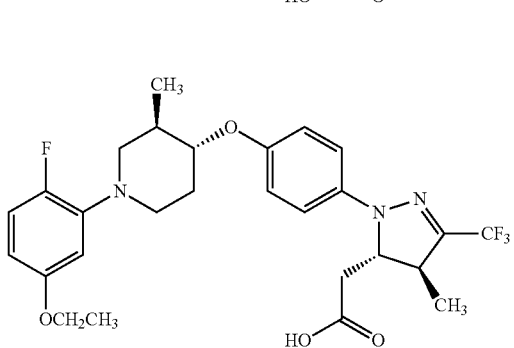
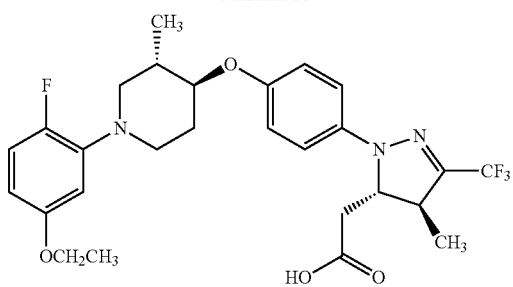
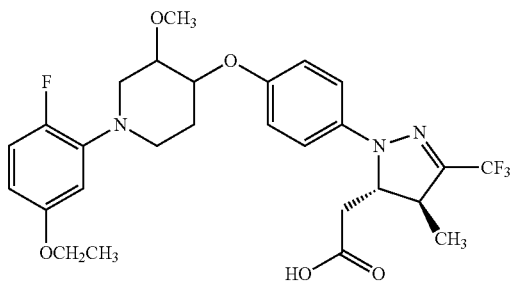
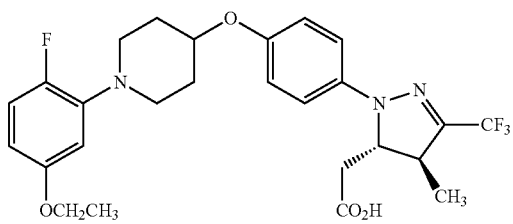
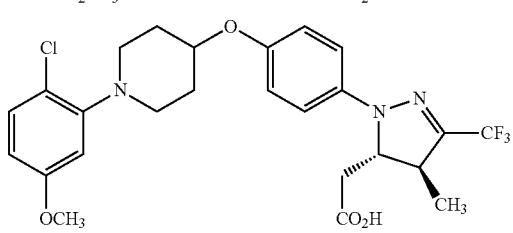
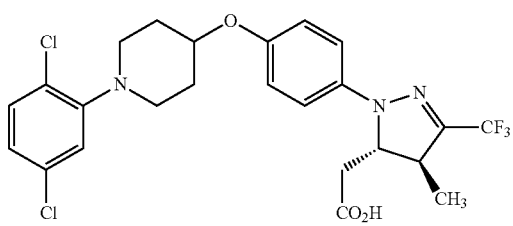
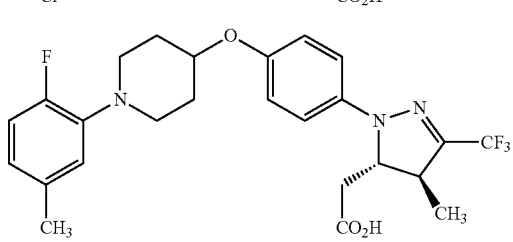
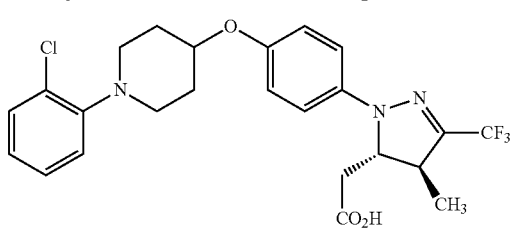

-continued
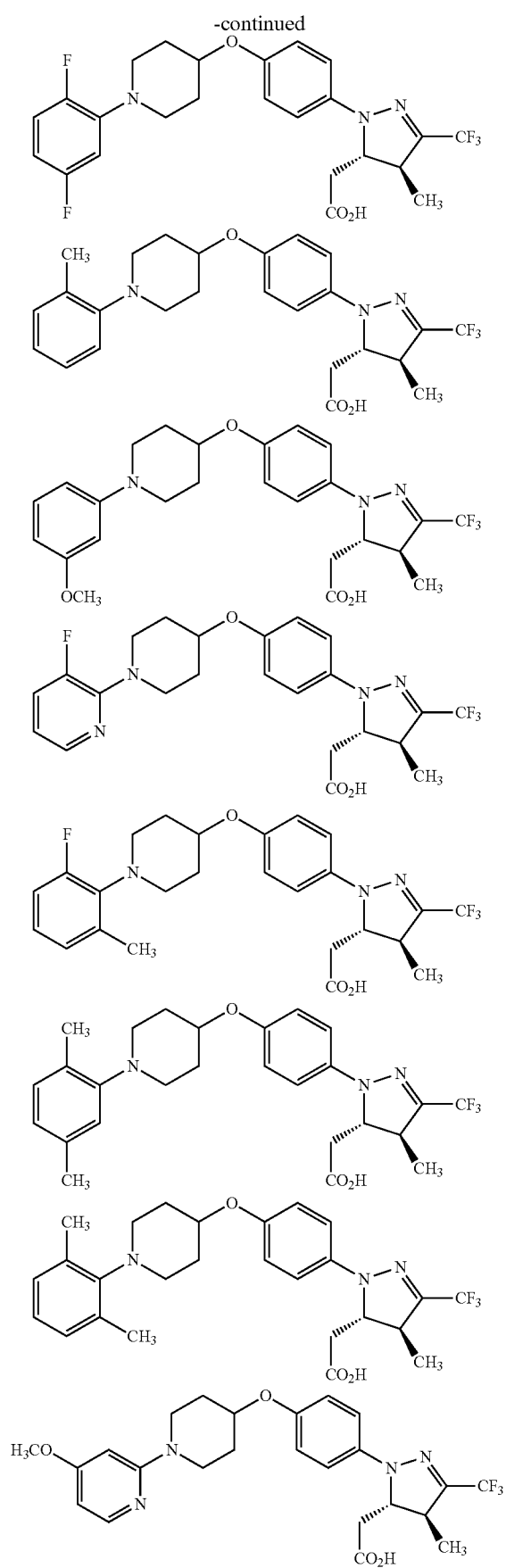
-continued
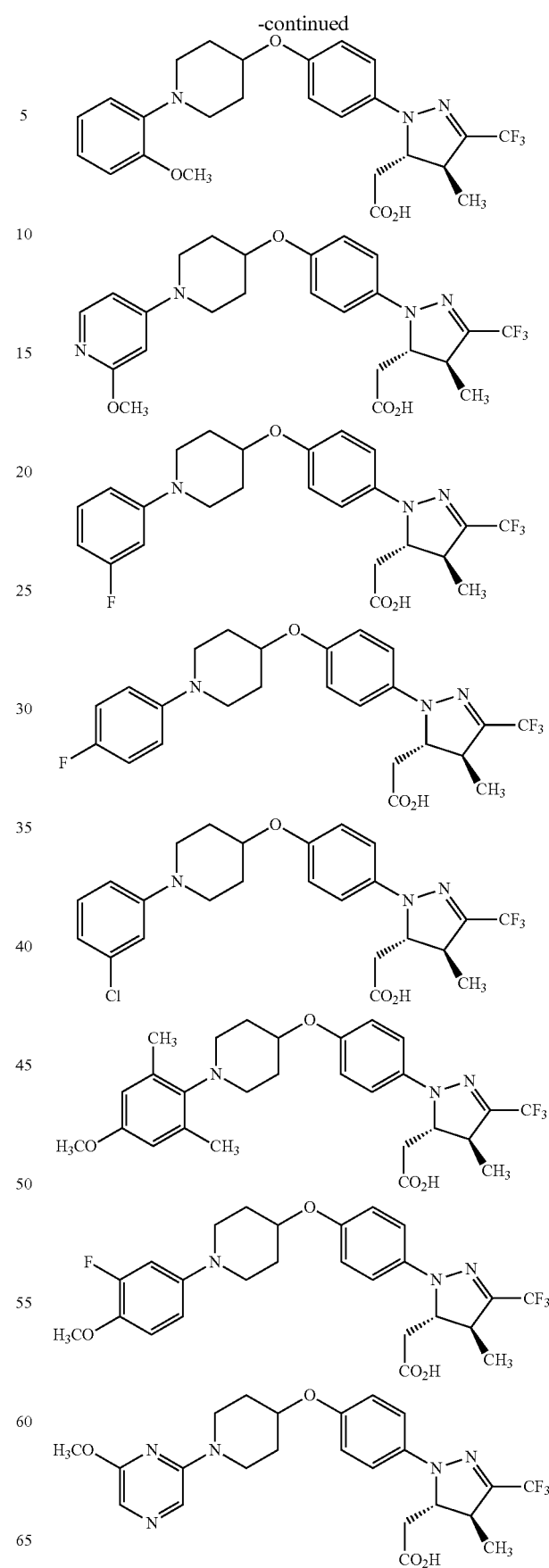

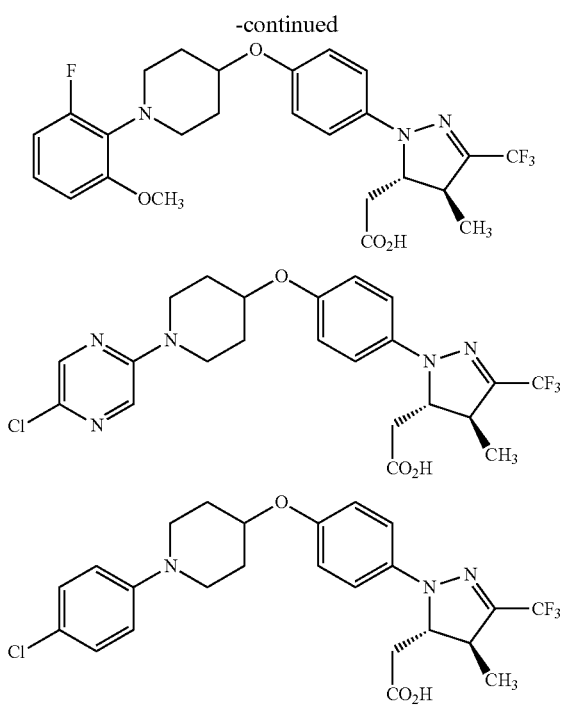
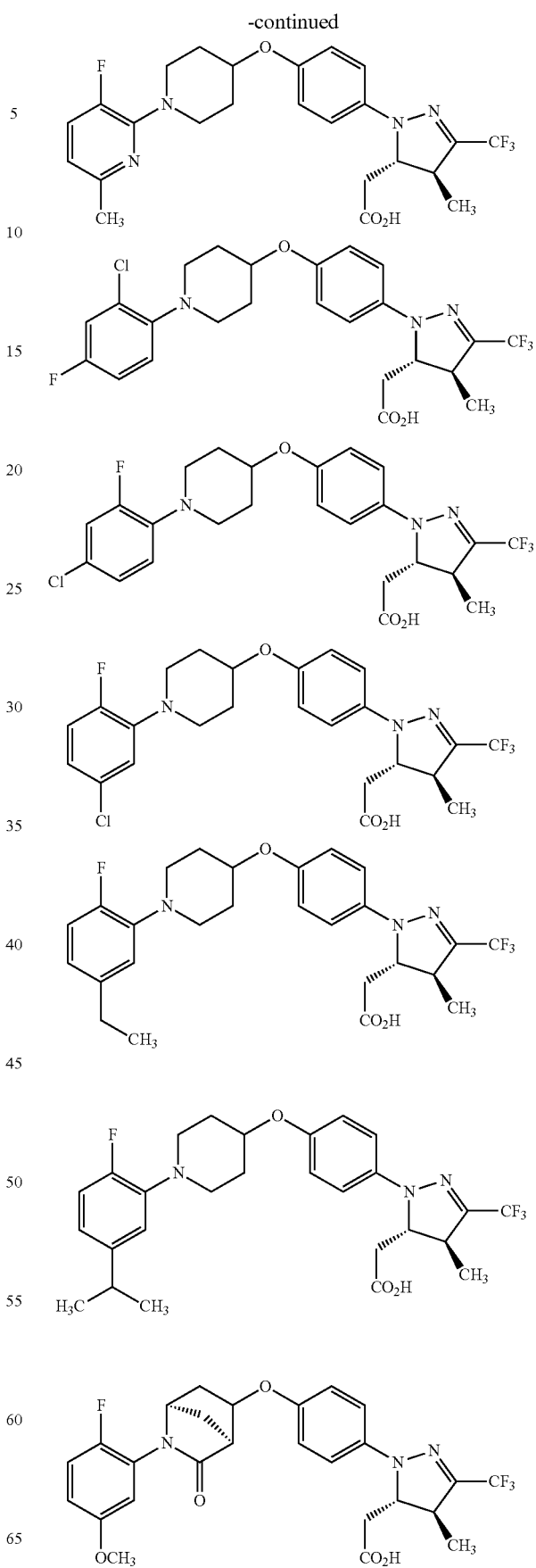

213
-continued
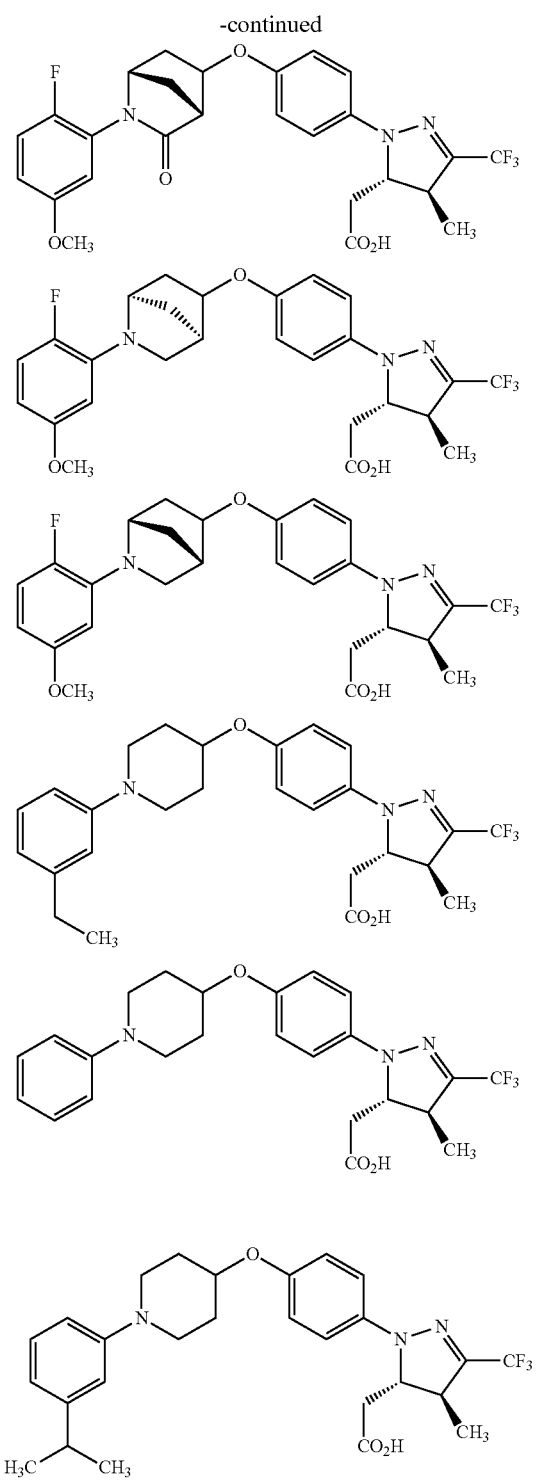
214
-continued
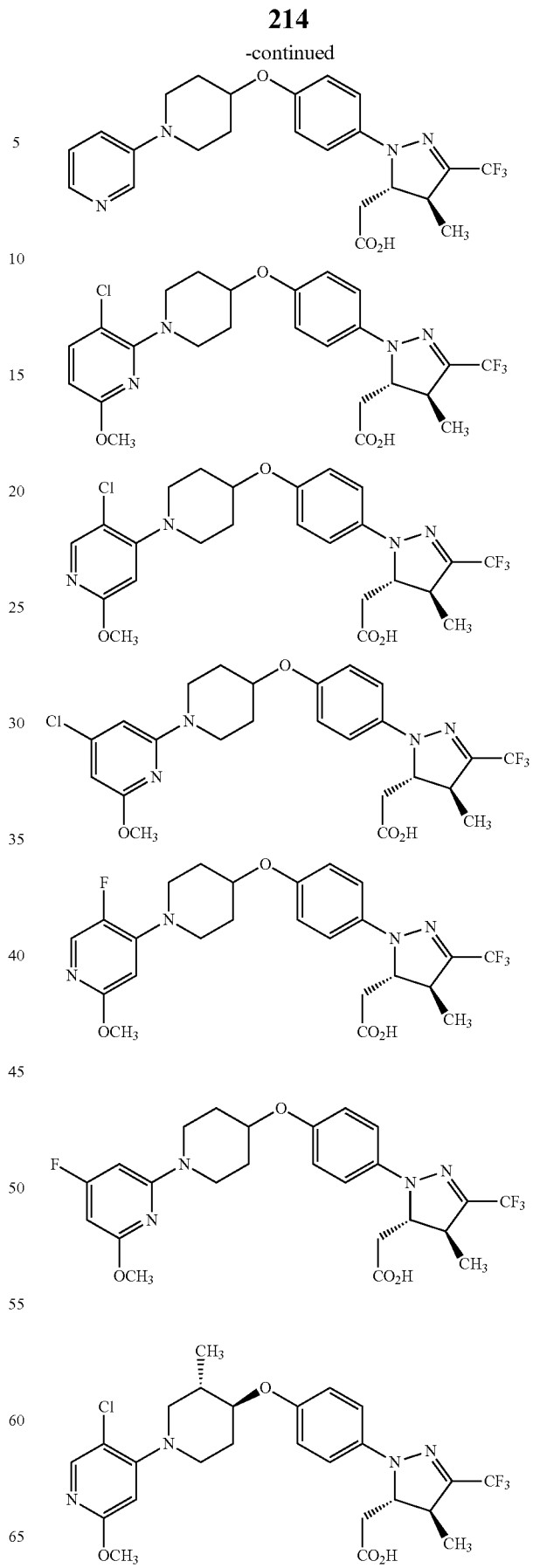

215
-continued
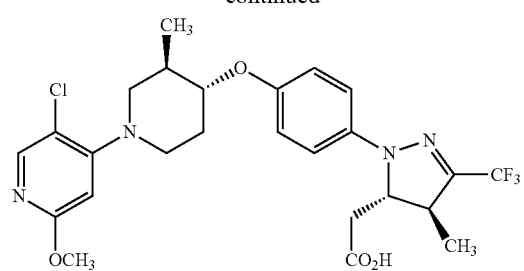
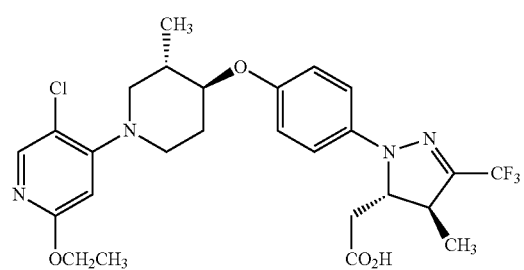
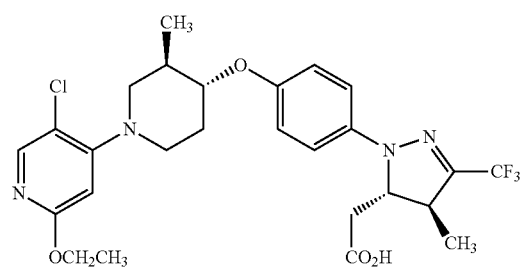
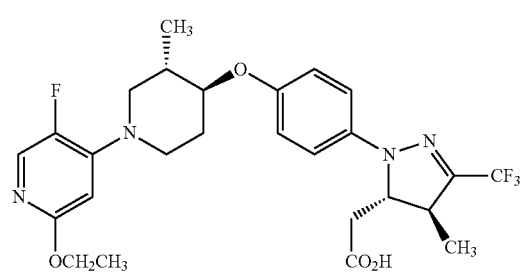
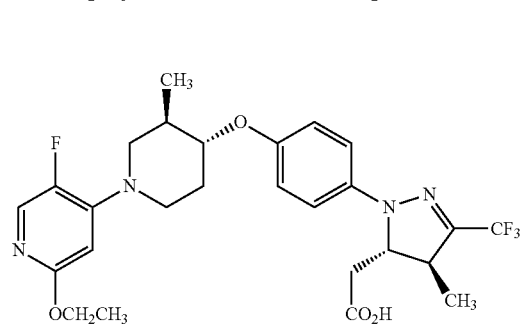
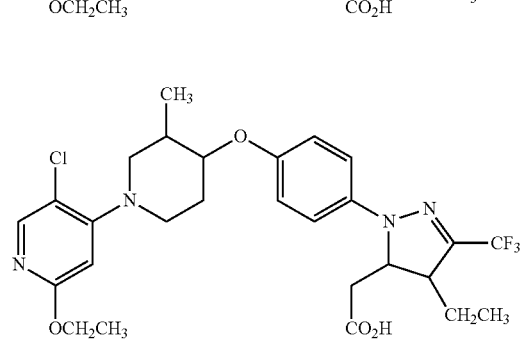
216
-continued
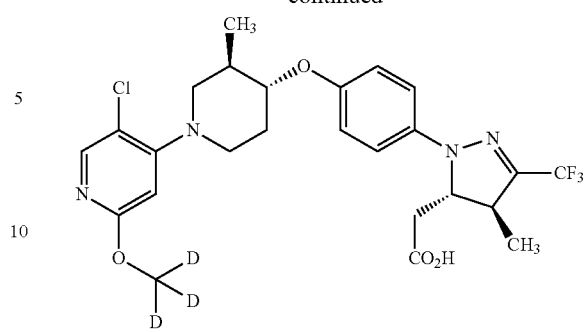
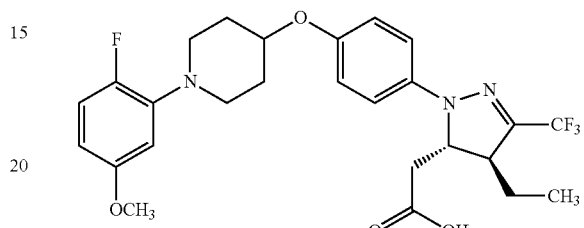
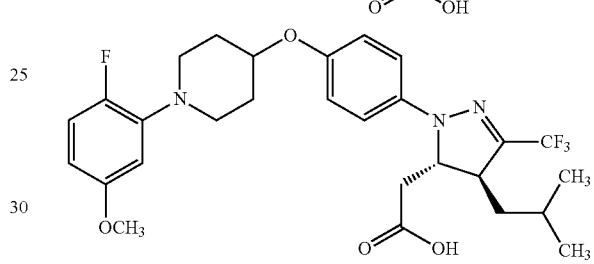
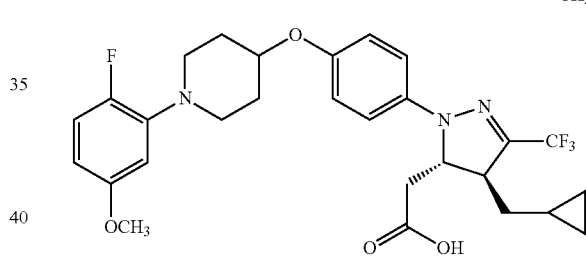
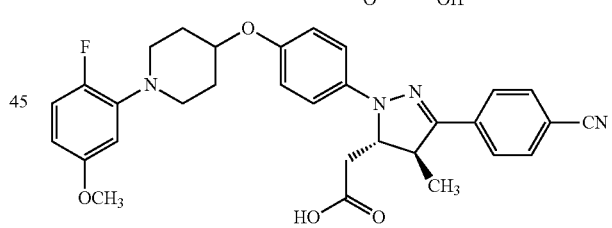
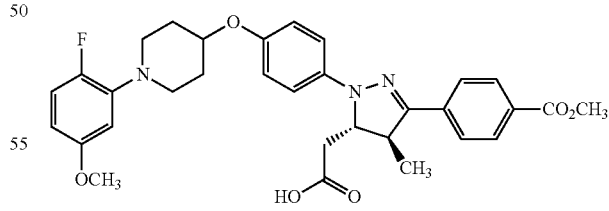
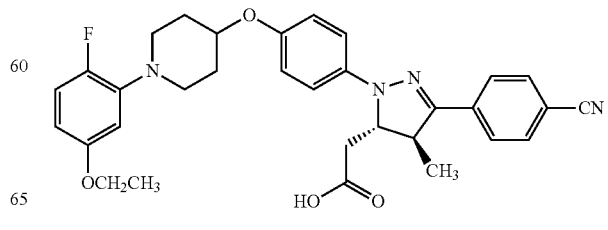

-continued
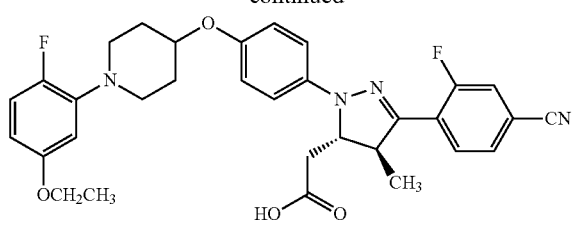
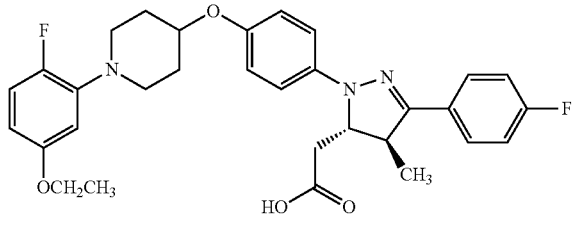
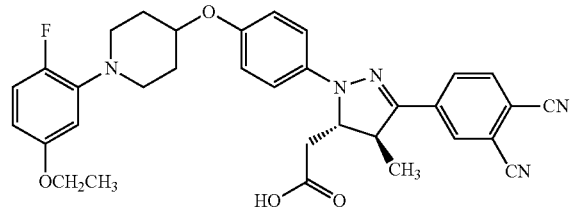
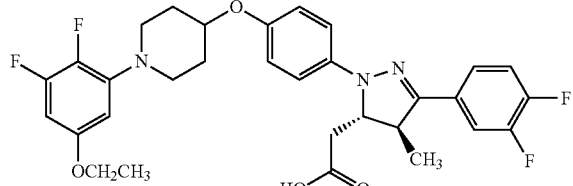
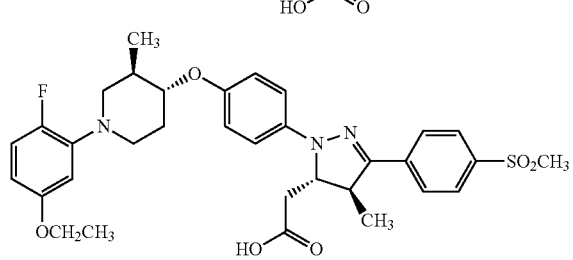
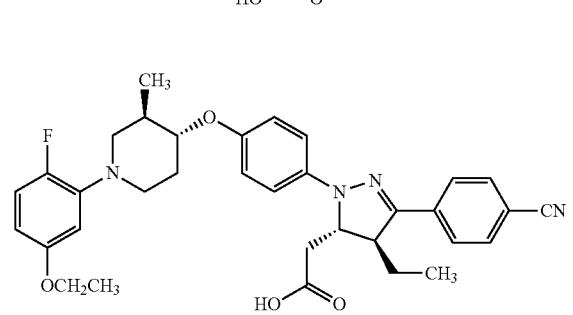
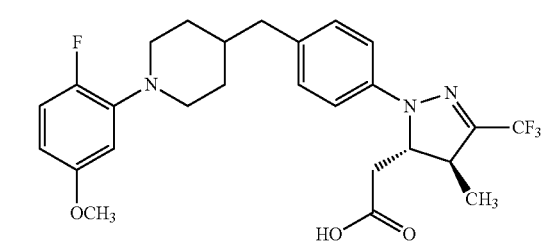
-continued
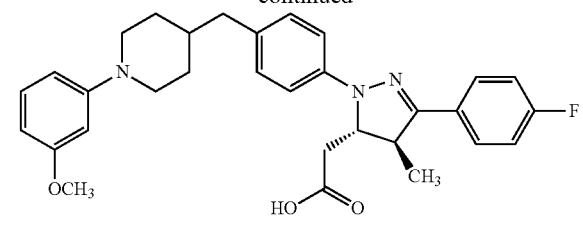
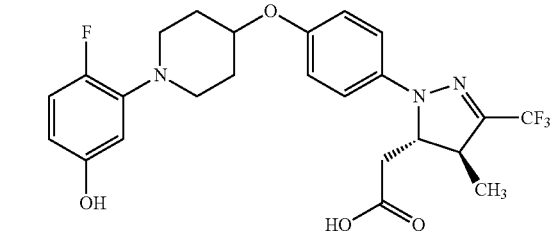
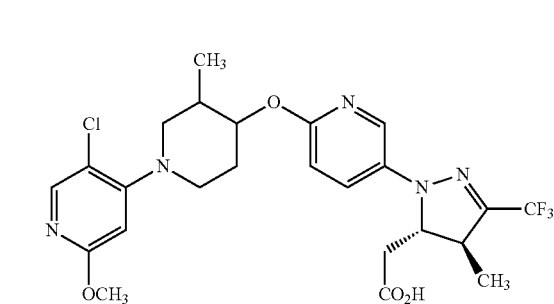
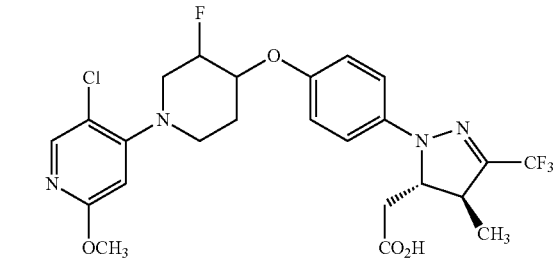
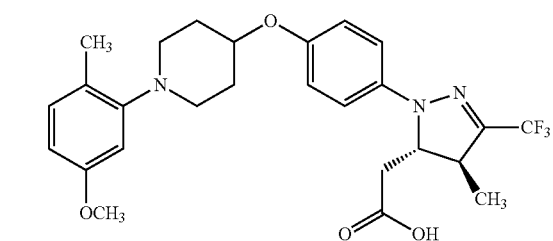
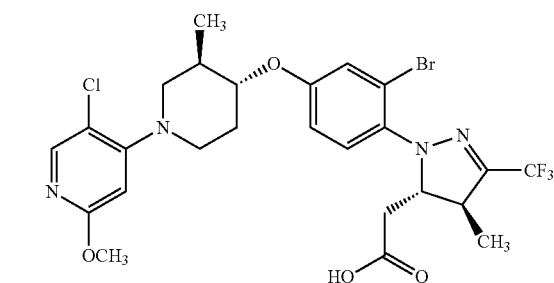

219
-continued
220
-continued
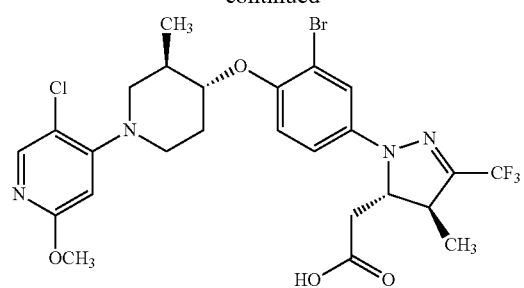
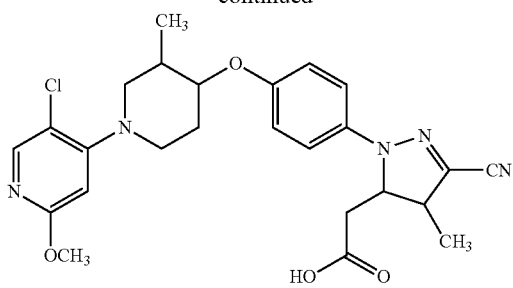
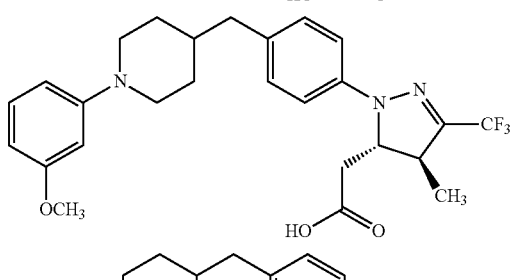
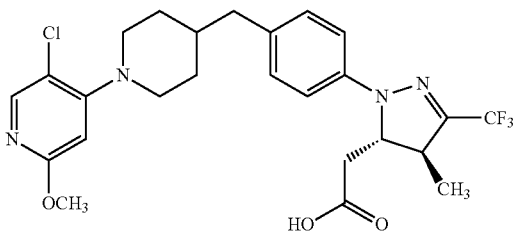
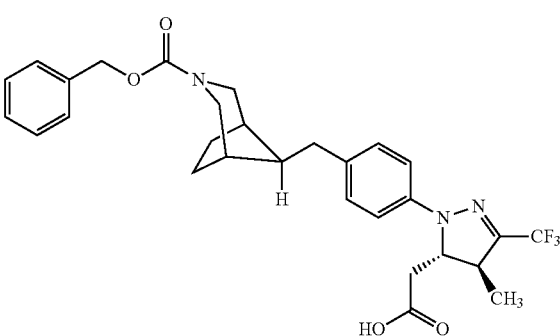

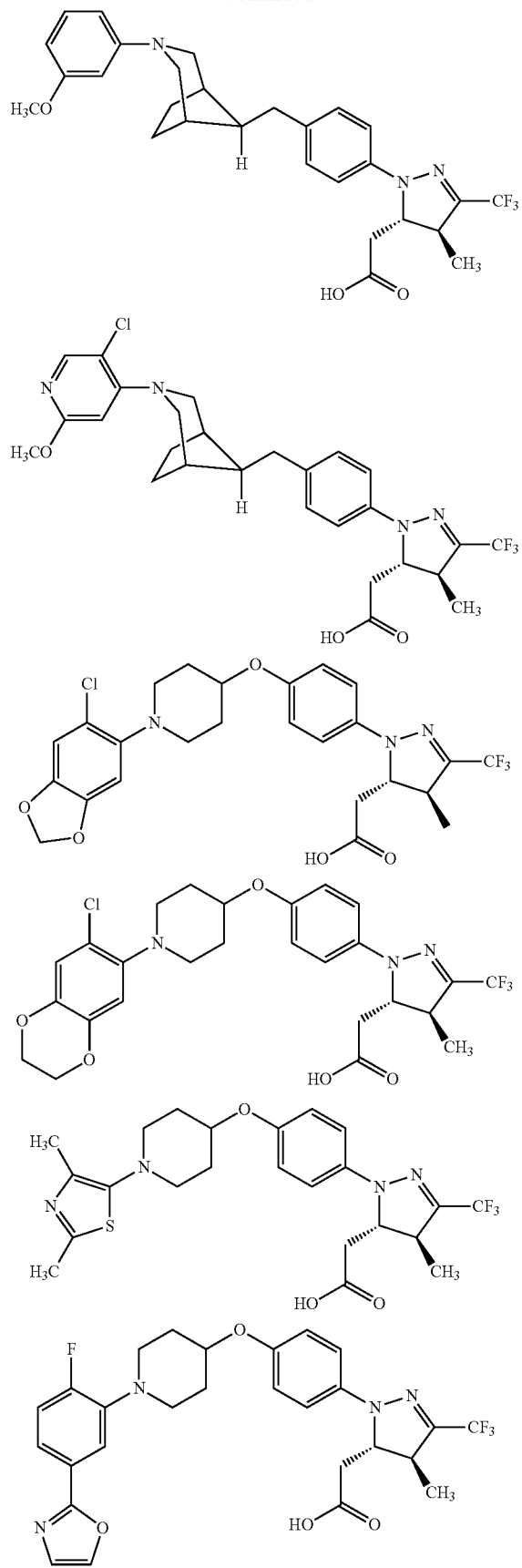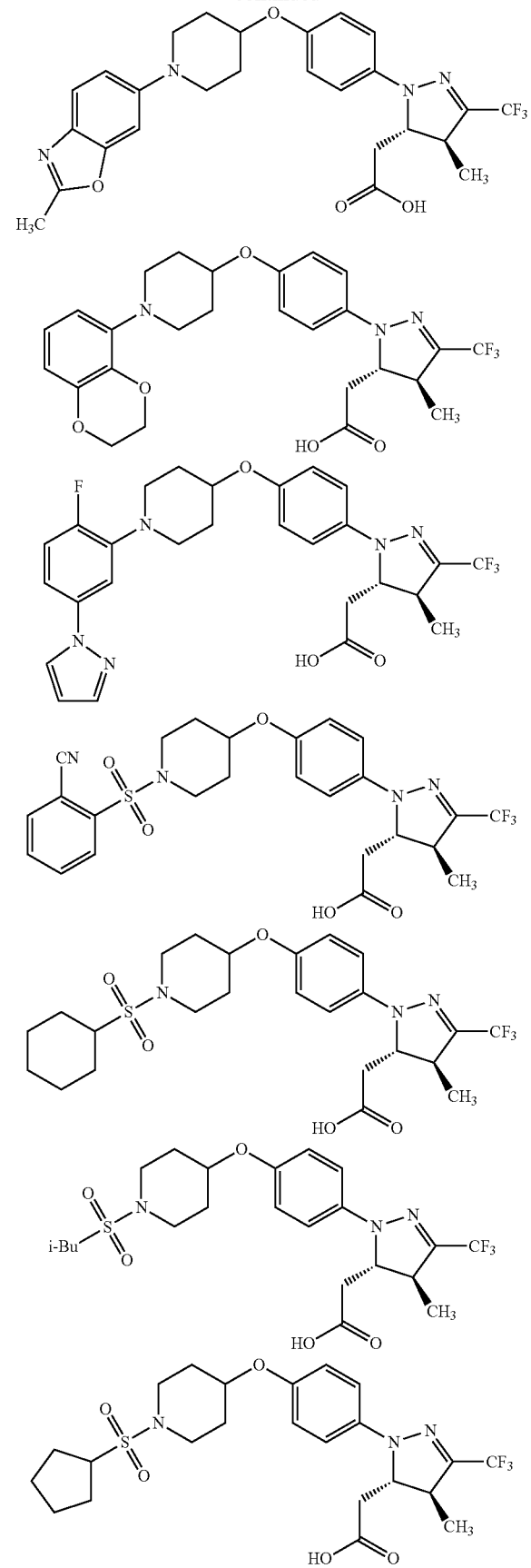

223
-continued
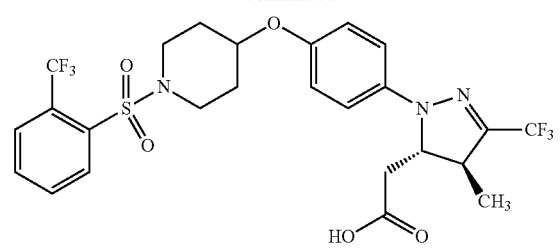
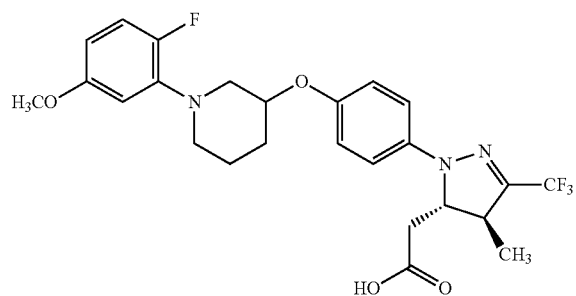
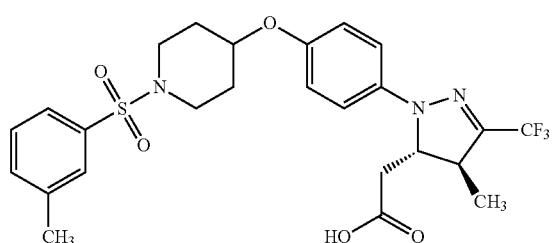
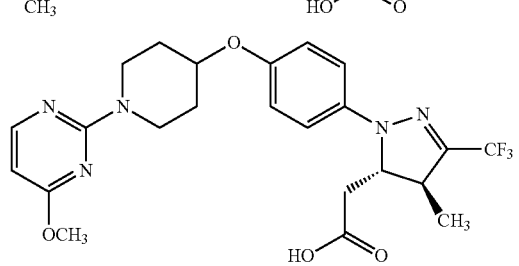
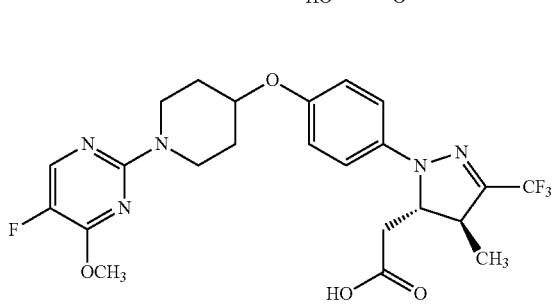
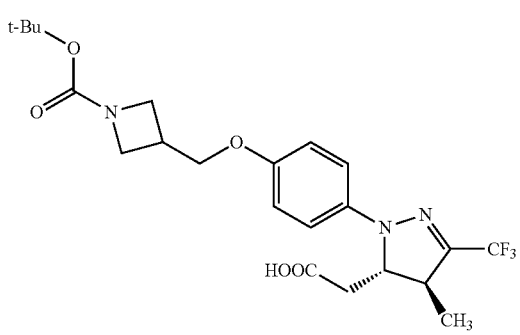
224
-continued
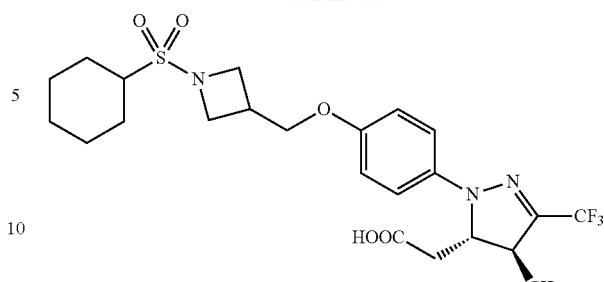
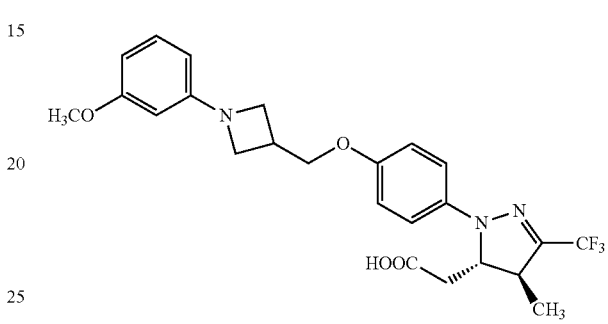
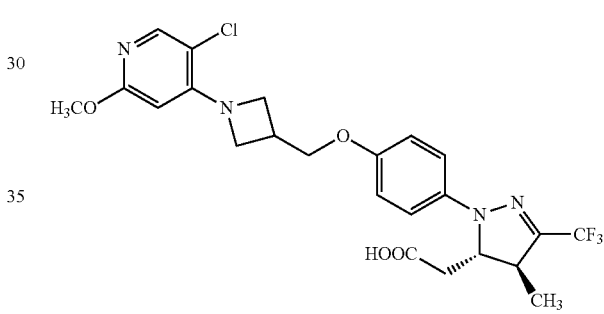
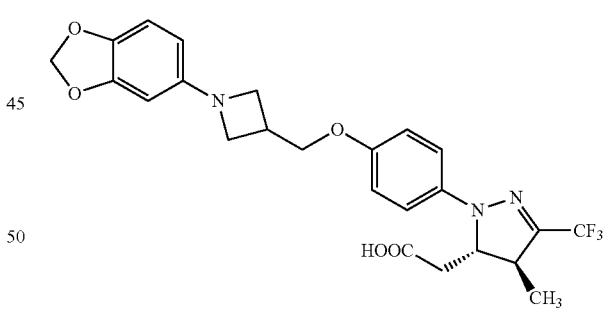
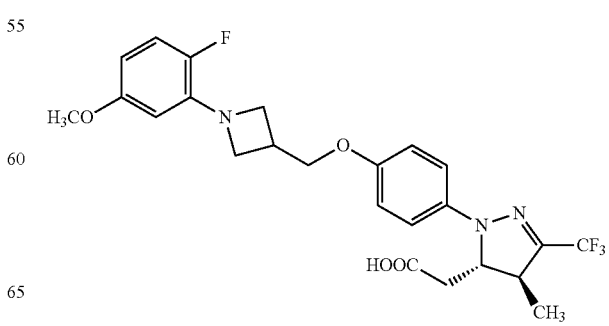

-continued
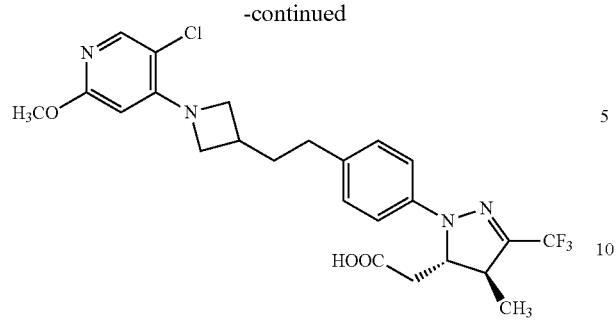
and
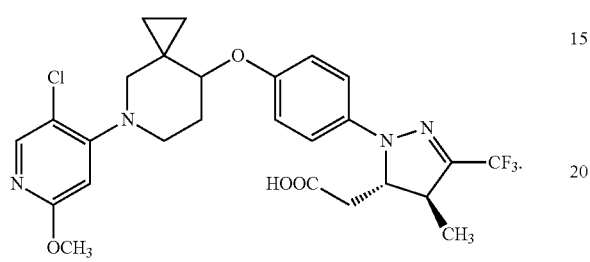
* * * * *